(12) United States Patent
Vandyck et al.

(10) Patent No.: US 10,457,638 B2
(45) Date of Patent: *Oct. 29, 2019

(54) SULPHAMOYLPYRROLAMIDE DERIVATIVES AND THE USE THEREOF AS MEDICAMENTS FOR THE TREATMENT OF HEPATITIS B

(71) Applicant: Janssen Sciences Ireland UC, County Cork (IE)

(72) Inventors: Koen Vandyck, Paal-Beringen (BE); Geerwin Yvonne Paul Haché, Kapellen (BE); Stefaan Julien Last, Lint (BE); David Craig McGowan, Brussels (BE); Geert Rombouts, Borsbeek (BE); Wim Gaston Verschueren, Berchem (BE); Pierre Jean-Marie Bernard Raboisson, Rosieres (BE)

(73) Assignee: Janssen Sciences Ireland UC, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,929

(22) Filed: Jan. 19, 2018

(65) Prior Publication Data
US 2018/0141905 A1    May 24, 2018

Related U.S. Application Data

(63) Continuation of application No. 14/891,864, filed as application No. PCT/EP2014/060102 on May 16, 2014, now Pat. No. 9,884,818.

(30) Foreign Application Priority Data

May 17, 2013 (EP) .................. 13168291
Jul. 4, 2013 (EP) .................. 13175181
Aug. 29, 2013 (EP) .................. 13182281
Oct. 31, 2013 (EP) .................. 13191209
Dec. 18, 2013 (EP) .................. 13198160
Mar. 5, 2014 (EP) .................. 14157900

(51) Int. Cl.
| | | |
|---|---|---|
| C07D 207/36 | (2006.01) | |
| C07D 403/12 | (2006.01) | |
| C07D 405/12 | (2006.01) | |
| C07D 207/40 | (2006.01) | |
| A61K 45/06 | (2006.01) | |
| A61K 31/401 | (2006.01) | |

(52) U.S. Cl.
CPC .......... *C07D 207/36* (2013.01); *A61K 31/401* (2013.01); *A61K 45/06* (2013.01); *C07D 207/40* (2013.01); *C07D 403/12* (2013.01); *C07D 405/12* (2013.01)

(58) Field of Classification Search
None
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |

(Continued)

FOREIGN PATENT DOCUMENTS

| | | |
|---|---|---|
| CA | 2950807 A1 | 12/2013 |
| CN | 101039919 A | 9/2007 |

(Continued)

OTHER PUBLICATIONS

Mohebbi et al., An Overview of Hepatitis B Virus Surface Antigen Secretion Inhibitors. Frontier in Microbiology, 2018, 9, 1-9.*
Schafer, S., Kolkhof, P. Failure is an option: learning from unsuccessful proof-of-concept trials. Drug Discovery Today. Nov. 2008, 13, 913-916.*
Honig, H., Pullman, W. From bench to clinic and back: Perspective on the 1st IQPC Translational Research conference. Journal of Translational Medicine. Dec. 2004, 2, 44.*
Online Registry via STN Dec. 22, 2008, RN 1088200-12-7.
Online Registry via STN, Feb. 3, 2007, RN 924514-21-6.
Online Registry via STN, Sep. 2, 2003, RN 577752-12-6.
Bennes, et al., "Recognition-induced control and acceleration of a pyroole Diels-Alder reaction", Tetrahedron Letters, vol. 42 : pp. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.

(Continued)

*Primary Examiner* — Po-Chih Chen

(57) ABSTRACT

Inhibitors of HBV replication of Formula (ID)

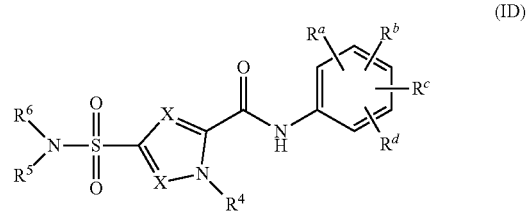

(ID)

including stereochemically isomeric forms, and salts, hydrates, solvates thereof, wherein X, $R^a$ to $R^d$ and $R^4$ to $R^6$ have the meaning as defined herein.

The present invention also relates to processes for preparing said compounds, pharmaceutical compositions containing them and their use, alone or in combination with other HBV inhibitors, in HBV therapy.

18 Claims, No Drawings

(56) References Cited

U.S. PATENT DOCUMENTS

| | | |
|---|---|---|
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,071,961 B2 | 9/2018 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |
| JP | 2008525406 A | 7/2008 |
| JP | 2010535172 A | 11/2010 |
| JP | 2015531773 A | 11/2015 |

(56) References Cited

FOREIGN PATENT DOCUMENTS

| | | |
|---|---|---|
| JP | 2015533782 A1 | 11/2015 |
| WO | 198403281 A1 | 8/1984 |
| WO | 199207835 A1 | 5/1992 |
| WO | 1998023285 A1 | 6/1998 |
| WO | 199909022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001025200 A1 | 4/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | 2008054605 A2 | 7/2008 |
| WO | 2008054605 A3 | 7/2008 |
| WO | 2008093614 A1 | 8/2008 |
| WO | 2008137794 A1 | 11/2008 |
| WO | 2008154819 A1 | 12/2008 |
| WO | 2009016088 A1 | 2/2009 |
| WO | 2009018219 A2 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A1 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | WO2013006394 A1 | 1/2013 |
| WO | 2013096744 A1 | 6/2013 |
| WO | 2013102655 A1 | 7/2013 |
| WO | 2013130703 A2 | 9/2013 |
| WO | 2013144129 A1 | 10/2013 |
| WO | 2013174962 | 11/2013 |
| WO | 2013181584 A2 | 12/2013 |
| WO | 2013184757 A1 | 12/2013 |
| WO | 2014033167 A1 | 3/2014 |
| WO | 2014033170 A1 | 3/2014 |
| WO | 2014033176 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2019011323 A1 | 1/2019 |

OTHER PUBLICATIONS

Brahmania, et al., "New Therapeutic Agents for Chronic Hepatitis B", Lancet Infec Dis, vol. 16: pp. e10-21 (Feb. 2016).

Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).

Cai, et al., "Identification of disubstituted sulfonamide compounds as specific inhibitors of hepatitis B virus covalently closed circular DNA formuation, Antimicrobial agents and chemotherapy", pp. vol. 56(8): pp. 4277-4288 (May 29, 2012).

Campagna et al., "Sulfamoylbenzamide Derivatives Inhibit the Assembly of Hepatitis B Virus Nucleocapsids", Journal of Virology, ),vol. 87 (12): pp. 6931-6942 (Jun. 2013).

Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).

Carver, et al., Polyfunctionalisation of Imidazole via Sequential Imidazolyl Anion Formation, Tetrahedron, 1997, pp. 14481-14496, vol. 53 Issue 42

Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).

Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).

(56) References Cited

OTHER PUBLICATIONS

Cowie, et al., "Mortality due to viral hepatitis in the Global Burden of Disease Study 2010: new evidence of an urgent global public health priority demanding action", Antiviral Therapy,vol. 18: pp. 953-954 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6 , Bioorganic & Medicinal Chemistry Letter, vol. 19: pp. 2777-2779 (2009).
EL-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
EL-Sharief, et al., "Synthesis of Different Types of Chlorinated Sulphonamides with Expected Insecticidal and Bactencidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Effecient Synthesis of 2-Chloro-3-carboethoxy or 2-Chloro-3-cyano- 4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geies, et al., Synthesis of some Thiazolo[3,2-a]Pyrimidines, Phosphorus, Sulfur and Silicon, vol. 56: pp. 87-93 (1991).
Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al, "Discovery of potent, selective sulfonylfuran urea endothelial lipase inhibitors", Bioorganic & Medicinal Chemistry Letters, vol. 19:pp. 27-30 (2009).
Guo, et al., "HBc binds to the CpG island of HBV cccDNA and promotes an epigenetic permissive state", Epigenetics, vol. 6 (6): pp. 720-726 (Jun. 2011).
Hogan, et al., "Aqueous Process Chemistry: The Preparation of Aryl Sulfonyl Chlorides", Organic Process Research & Development, vol. 13: pp. 875-879 (2009).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, ( Oct. 2016).
Hughes, et al., "Hepatitis Delta Virus", The Lancet, vol. 378: pp. 73-85, (Jul. 2, 2011).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).

Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009.
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Online Registr via STN, Dec. 28, 2008, RN 1090750-88-1.
Online Registry via STN , Aug. 13, 2012, RN 1390589-54-4.
Online Registry via STN Feb. 2, 2007, RN 919040-39-4.
Online Registry via STN Feb. 2, 2007, RN 919040-53-2.
Online Registry via STN Feb. 2, 2007, RN 919040-55-4.
Online Registry via STN Aug. 6, 2012. RN 1386725-02-5.
Online Registry via STN Jun. 7, 2012, RN 1375909-37-7.
Online Registry via STN Dec. 8, 2012, RN 1389720-57-3.
Online Registry via STN Oct. 10, 2001, RN 361373-90-2.
Online Registry via STN Dec. 11, 2007, RN 957487-45-5.
Online Registry via STN Dec. 11, 2007, RN 957487-49-9.
Online Registry via STN Aug. 12, 2012, RN 1389686-79-6.
Online Registry via STN Aug. 13, 2012, RN 1390500-09-0.
Online Registry via STN Jan. 16, 2001, RN 314043-17-9.
Online Registry via STN Mar. 17, 2013, RN 1424462-66-7.
Online Registry via STN Sep. 18, 2012, RN 1394742-82-5.
Online Registry via STN 2010, RN 1253220-91-5.
Online Registry via STN Aug. 30, 2011, RN 1325664-90-1.
Online Registry via STN, Jan. 24, 2008, RN 296790-26-6.
Online Registry via STN, Feb. 2, 2007, RN 9019040-48-5.
Online Registry via STN, Feb. 2, 2007, RN 919040-37-2.
Online Registry via STN, May 6, 2011, RN 1291044-81-9.
Online Registry via STN, Sep. 6, 2011, RN 1328738-57-3.
Online Registry via STN, Oct. 7, 2008, RN 1057788-44-9.

(56) References Cited

OTHER PUBLICATIONS

Online Registry via STN, Oct. 7, 2008, RN 1057871-39-2.
Online Registry via STN, Jan. 9, 2001, RN 313253-89-3.
Online Registry via STN, Mar. 10, 2010, RN 1208400-27-4.
Online Registry via STN, Feb. 15, 2007, RN 921179-95-5.
Online Registry via STN, Aug. 15, 2011, RN 1317923-24-2.
Online Registry via STN, Aug. 15, 2011, RN 1318022-74-0.
Online Registry via STN, Mar. 17, 2003, RN 499189-09-2.
Online Registry via STN, May 18, 2011, RN 1296380-95-4.
Online Registry via STN, Oct. 18, 2000, RN 296894-70-7.
Online Registry via STN, Sep. 20, 2013, RN 1452780-00-5.
Online Registry via STN, Apr. 24, 2002, RN 406926-60-1.
Online Registry via STN, Apr. 28, 2011, RN 1286906-97-5.
Online Registry via STN. Apr. 19, 2008, RN 930914-71-9.
Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qidong You et al, Pharmaceutical Chemistry, Chemical Industry Press, Jan. 31, 2014, pp. 32-33, /.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schroder, et al., "Arzneimittelchemie Passage", Arzneimittelchemei Grundlagen Nerven Musklen und Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41-4109 has multiple effects on Hepatitis B virus capsid assembly", Journal of Molecular Recognition,vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).

Wang, et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber et al., "Inhibition of Human Hepatitis B Virus (HBV) by a Novel Non-Nucleosidic Compound in a Transgenic Mouse Model", Antiviral Research, vol. 54: pp. 69-78 (2002).
Weber, et al, "Inhibition of human hepatitis B virus (HBV) by a novel non-nucleosidic compound in a transgenic mouse model", Antiviral Research, vol. 54 (2): pp. 69-78 (Jan. 1, 2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), in treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 82-93 (2015).
Zoulim, et al., "Current Treatments for Chronic Hepatitis B Virus Infections", Current Opinion in Virology, vol. 18: pp. 109-116 (2016).
Online Registry via STN Feb. 3, 2012, RN 1359583-56-4.
Online Registry via STN Feb. 3, 2012, RN 1359596_55_6.
Njampatnam et al., "Recent advances in the development of HBV capsid assembly modulators", Current Opinion in Chemical Biology, vol. 50; pp. 73-79 (2019).

* cited by examiner

SULPHAMOYLPYRROLAMIDE DERIVATIVES AND THE USE THEREOF AS MEDICAMENTS FOR THE TREATMENT OF HEPATITIS B

CROSS-REFERENCE TO RELATED APPLICATIONS

This application is a Continuation of U.S. patent application Ser. No. 14/891,864 filed Nov. 17, 2015, which is a national stage filing under USC 371 of international application PCT/EP2014/060102 filed on May 16, 2014, which claims priority to European Patent Application No. 13168291.6 filed May 17, 2013, European Patent Application No. 13175181.0 filed Jul. 4, 2013, European Patent Application No. 13182281.9 filed Aug. 29, 2013, European Patent Application No. 13191209.9 filed Oct. 31, 2013, European Patent Application No. 13198160.7 filed Dec. 18, 2013, and European Patent Application No. 14157900.3 filed Mar. 5, 2014, the complete disclosures of which are hereby incorporated herein by reference for all purposes.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development of cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013, relates to a subclass of Sulphamoyl-arylamides active against HBV. WO2013/096744, published on Jun. 26, 2013 relates to compounds active against HBV.

In addition, WO2014/033170 and WO2014/033176, published on Mar. 6, 2014 relate further compounds active against HBV.

Amongst the problems which HBV direct antivirals may encounter are toxicity, mutagenicity, lack of selectivity, poor efficacy, poor bioavailability, and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to a compound of Formula (ID)

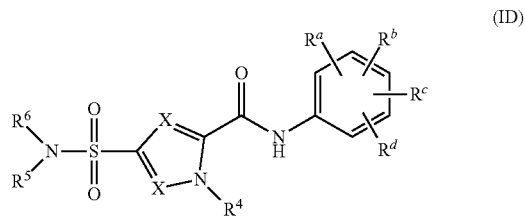

or a stereoisomer or tautomeric form thereof, wherein:
Each X independently represents $CR^7$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_1$-$C_3$alkyl and $C_3$-$C_4$cycloalkyl;
$R^d$ is Hydrogen or Fluoro;
$R^4$ is Hydrogen, $C_1$-$C_3$alkyl or $C_3$-$C_4$cycloalkyl;
$R^5$ is Hydrogen;
$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^{10}$;
$R^7$ represents hydrogen, —CN, Fluoro, Chloro, Bromo, —$CHF_2$, —$CF_2$-methyl, —$CH_2F$, —$CF_3$, $C_1$-$C_3$alkyl optionally substituted with methoxy, $C_2$-$C_3$alkenyl or $C_3$-$C_4$cycloalkyl;
$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;
$R^9$ represents, $C_1$-$C_4$alkyloxy, —$SO_2$-methyl, —C(=O)—$OR^{11}$ or —C(=O)—$N(R^{11})_2$;
$R^{10}$ represents —CN, —OH, Fluoro, —$CHF_2$, —$CH_2F$ or —$CF_3$;
$R^{11}$ represents hydrogen or $C_1$-$C_3$alkyl;
or a pharmaceutically acceptable salt or a solvate thereof wherein such compound is not

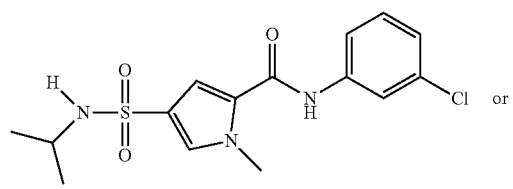

-continued

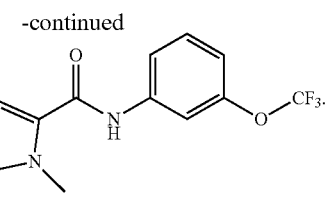

The invention further relates to a pharmaceutical composition comprising a compound of Formula (ID), and a pharmaceutically acceptable carrier.

The invention also relates to the compounds of Formula (ID) for use as a medicament, preferably for use in the prevention or treatment of an HBV infection in a mammal.

In a further aspect, the invention relates to a combination of a compound of Formula (ID), and another HBV inhibitor.

The pharmaceutical composition, use and combination of compounds of Formula (ID) as provided according to the present invention includes the pharmaceutical composition, use and combination of

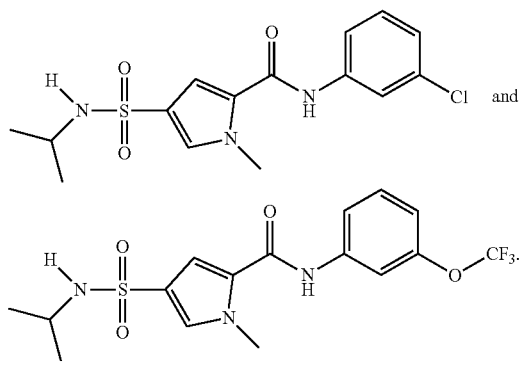

Definitions

The terms "$C_{1-x}$alkyl" and $C_1$-$C_x$alkyl can be used interchangeably.

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radicals having from 1 to 4 carbon atoms such as the group defined for $C_{1-3}$alkyl and butyl and the like.

$C_{1-6}$alkyl and $C_{2-6}$alkyl as a group or part of a group defines straight or branched chain saturated hydrocarbon radicals having from 1 to 6 carbon atoms, or from 2 to 6 carbon atoms such as the groups defined for $C_{1-4}$alkyl and pentyl, hexyl, 2-methylbutyl and the like.

The term "$C_{2-3}$alkenyl" as a group or part of a group refers to a hydrocarbon radical comprising 2 or 3 carbon atoms having at least one double bond therein, and thus includes such as for example, ethenyl (vinyl), 1-propenyl, and 2-propenyl.

The term "$C_{1-3}$alkyloxy" as a group or part of a group refers to a radical having the Formula —$OR^c$ wherein $R^c$ is $C_{1-3}$alkyl. Non-limiting examples of suitable $C_{1-3}$alkyloxy include methyloxy (also methoxy), ethyloxy (also ethoxy), propyloxy and isopropyloxy.

As used herein, the term "3-7 membered mono or polycyclic saturated ring" means saturated cyclic hydrocarbon with 3, 4, 5, 6 or 7 carbon atoms and is generic to cyclopropyl, cyclobutyl, cyclopentyl, cyclohexyl and cycloheptyl (monocyclic) and fused or spiro ring systems with 2 or more saturated rings with at most 7 carbon atoms (polycyclic).

Such saturated ring optionally contains one or more heteroatoms, such that at least one carbon atom is replaced by a heteroatom selected from N, O and S, in particular from N and O.

Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbon with 3 or 4 carbon atoms and 1 oxygen atom. Examples include oxetane, and tetrahydrofuranyl.

It should be noted that different isomers of the various heterocycles may exist within the definitions as used throughout the specification. For example, if not structurally specified according to the chemical name or structure, pyrrolyl may be 1H-pyrrolyl or 2H-pyrrolyl.

The term halo and halogen are generic to Fluoro, Chloro, Bromo or Iodo. Preferred halogens are Bromo, Fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

Positions indicated on phenyl (e.g. ortho, meta and/or para) are indicated relative to the bond connecting the phenyl to the main structure. An example with regard to the position of para $R^2$, location is indicated relative to the nitrogen (*) connected to the main structure:

(I)

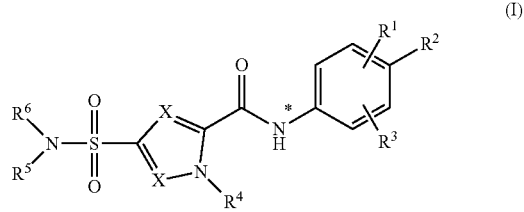

When any variable (e.g. halogen or $C_{1-4}$alkyl) occurs more than one time in any constituent, each definition is independent.

For therapeutic use, the salts of the compounds of Formula (ID) are those wherein the counter ion is pharmaceutically or physiologically acceptable. However, salts having a pharmaceutically unacceptable counter ion may also find use, for example, in the preparation or purification of a pharmaceutically acceptable compound of Formula (ID). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric forms of Formula (ID) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of Hydrogen include tritium and deuterium. Isotopes of carbon include C-13 and C-14.

DETAILED DESCRIPTION OF THE INVENTION

Whenever used hereinafter, the term "compounds of formula (ID)",

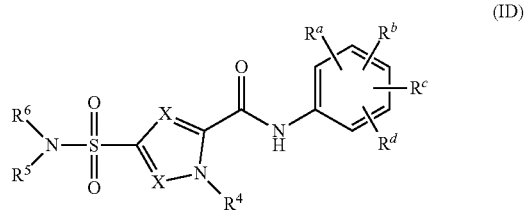

(ID)

or "the present compounds" "compounds of the present invention" or similar term is meant to include the compounds of general formula (ID), (IA), (IB), (IC), (I), (Ia), (II), (III) salts, stereoisomeric forms and racemic mixtures or any subgroups thereof.

In a first aspect, the present invention relates to a compound of Formula (ID)

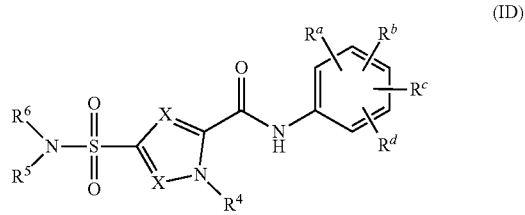

(ID)

or a stereoisomer or tautomeric form thereof, wherein:
Each X independently represents $CR^7$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_1$-$C_3$alkyl and $C_3$-$C_4$cycloalkyl;
$R^d$ is Hydrogen or Fluoro;
$R^4$ is Hydrogen, $C_1$-$C_3$alkyl or $C_3$-$C_4$cycloalkyl;
$R^5$ is Hydrogen;
$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^H$);

$R^7$ represents hydrogen, —CN, Fluoro, Chloro, Bromo, —$CHF_2$, —$CF_2$-methyl, —$CH_2F$, —$CF_3$, $C_1$-$C_3$alkyl optionally substituted with methoxy, $C_2$-$C_3$alkenyl or $C_3$-$C_4$cycloalkyl;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —$SO_2$-methyl, —C(=O)—$OR^{11}$ or —C(=O)—$N(R^{11})_2$;

$R^{10}$ represents —CN, —OH, Fluoro, —$CHF_2$, —$CH_2F$ or —$CF_3$;

$R^{11}$ represents hydrogen or $C_1$-$C_3$alkyl;

or a pharmaceutically acceptable salt or a solvate thereof wherein such compound is not

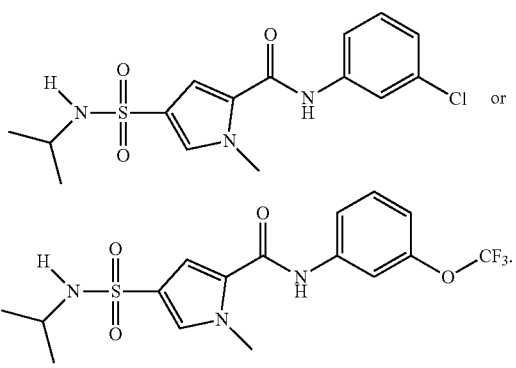

In a further aspect, aspect, the present invention relates to a compound of Formula (IA)

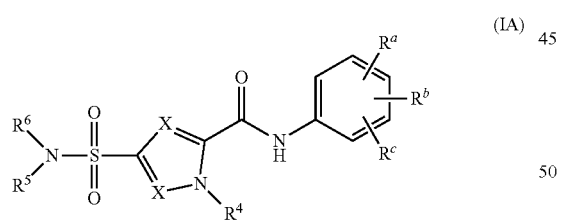

or a stereoisomer or tautomeric form thereof, wherein:
Each X independently represents $CR^7$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, $C_1$-$C_3$alkyl and $C_3$-$C_4$cycloalkyl;
$R^4$ is Hydrogen, $C_1$-$C_3$alkyl or $C_3$-$C_4$cycloalkyl;
$R^5$ is Hydrogen;
$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^{10}$;

$R^7$ represents hydrogen, —CN, Fluoro, Chloro, Bromo, —$CHF_2$, —$CF_2$-methyl, —$CH_2F$, —$CF_3$, $C_1$-$C_3$alkyl or $C_3$-$C_4$cycloalkyl;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —$SO_2$-methyl, —C(=O)—$OR^{11}$ or —C(=O)—$N(R^{11})_2$;

$R^{10}$ represents —CN, —OH, Fluoro, —$CHF_2$, —$CH_2F$ or —$CF_3$;

$R^{11}$ represents hydrogen or $C_1$-$C_3$alkyl;

or a pharmaceutically acceptable salt or a solvate thereof, wherein such compound is not

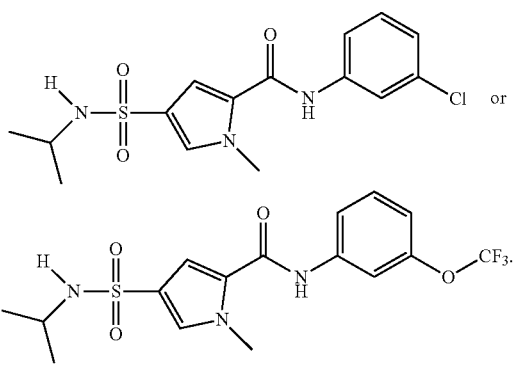

In one embodiment, the present invention relates to a compound Formula (IC)

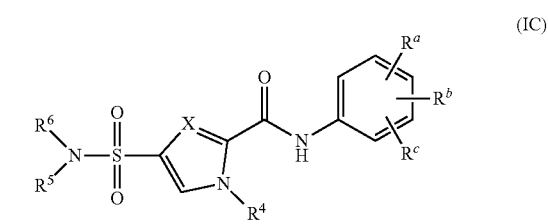

or a stereoisomer or tautomeric form thereof, wherein:
X represents $CR^7$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, $C_1$-$C_3$alkyl and $C_3$-$C_4$cycloalkyl;
$R^4$ is Hydrogen, $C_1$-$C_3$alkyl or $C_3$-$C_4$cycloalkyl;
$R^5$ is Hydrogen;
$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^{10}$;

$R^7$ represents hydrogen, —CN, Fluoro, Chloro, Bromo, —CHF$_2$, —CF$_2$-methyl, —CH$_2$F, —CF$_3$, $C_1$-$C_3$alkyl or $C_3$-$C_4$cycloalkyl;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —SO$_2$-methyl, —C(=O)—OR$^{11}$ or —C(=O)—N(R$^{11}$)$_2$;

$R^{10}$ represents —CN, —OH, Fluoro, —CHF$_2$, —CH$_2$F or —CF$_3$;

$R^{11}$ represents hydrogen or $C_1$-$C_3$alkyl;

or a pharmaceutically acceptable salt or a solvate thereof, wherein such compound is not

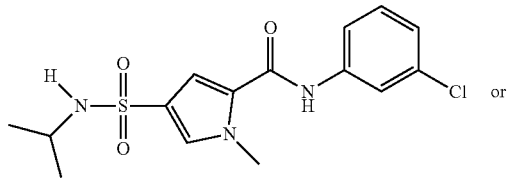

or

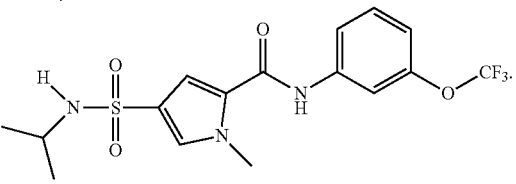

Of interest are compounds of the present invention wherein:

$R^a$, $R^b$ and $R^c$ are independently selected from the group consisting of Hydrogen, Fluoro, Bromo, Chloro, —CHF$_2$, —CF$_2$-methyl, —CH$_2$F, —CF$_3$, —OCF$_3$, —CN, and $C_1$-$C_3$alkyl;

$R^4$ is Hydrogen, or methyl;

$R^5$ is Hydrogen;

$R^6$ is selected from the group consisting of $C_2$-$C_6$alkyl and a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^{10}$;

$R^7$ represents hydrogen, —CN, Fluoro, Chloro, Bromo, —CHF$_2$, —CF$_2$-methyl, —CH$_2$F, —CF$_3$ or methyl;

$R^9$ represents, $C_1$-$C_4$alkyloxy, —SO$_2$-methyl, —C(=O)—OR$^{11}$ or —C(=O)—N(R$^{11}$)$_2$ $R^{10}$ represents —CN, —OH, Fluoro, —CHF$_2$, —CH$_2$F or —CF$_3$;

$R^{11}$ represents hydrogen or $C_1$-$C_3$alkyl.

Another embodiment of the present invention relates to those compounds of Formula (ID), (IA) or any subgroup thereof as mentioned in any of the other embodiments wherein one or more of the following restrictions apply:

(a) $R^4$ is $C_1$-$C_3$alkyl, preferably methyl; $R^6$ is selected from the group consisting of $C_2$-$C_6$alkyl optionally being substituted with one or more Fluoro; and $R^7$ represents hydrogen Fluoro, Chloro or $C_1$-$C_3$alkyl, preferably hydrogen Fluoro, Chloro or methyl.

(b) $R^b$ is Hydrogen or Fluoro.

(c) $R^a$ and $R^c$ are independently selected from the group consisting of Hydrogen, Fluoro, Chloro —CN and methyl.

(d) $R^b$ is Hydrogen or Fluoro and W and $R^c$ are independently selected from the group consisting of Hydrogen, Fluoro, Chloro and CN.

(e) $R^6$ contains a 3-7 membered saturated ring optionally containing one oxygen, more specifically $R^6$ is a 4 or 5 membered saturated ring containing one oxygen, such 4 or 5 membered saturated ring optionally substituted with $C_1$-$C_4$alkyl optionally substituted with $R^{10}$.

(f) $R^6$ comprises a branched $C_3$-$C_6$alkyl optionally substituted with one or more Fluoro, or wherein $R^6$ comprises a $C_3$-$C_6$cycloalkyl wherein such $C_3$-$C_6$cycloalkyl is substituted with one or more Fluoro or substituted with $C_1$-$C_4$alkyl substituted with one or more Fluoro, or wherein $R^6$ comprises a $C_3$-$C_6$cycloalkyl optionally substituted with one or more Fluoro and/or substituted with $C_1$-$C_4$alkyl optionally substituted with one or more Fluoro.

(g) $R^6$ comprises a branched $C_3$-$C_6$alkyl optionally substituted with one or more Fluoro, or $R^6$ comprises a $C_3$-$C_6$cycloalkyl wherein such $C_3$-$C_6$cycloalkyl is substituted with one or more Fluoro or substituted with $C_1$-$C_4$ substituted with one or more Fluoro. More specifically, $R^6$ is a branched $C_3$-$C_6$alkyl substituted with one or more Fluoro.

(h) $R^4$ is $C_1$-$C_3$alkyl, preferably methyl; $R^6$ is selected from the group consisting of $C_2$-$C_6$alkyl optionally being substituted with one or more Fluoro; and $R^7$ represents hydrogen, Fluoro, Chloro or $C_1$-$C_3$alkyl, preferably hydrogen Fluoro, Chloro or methyl.

In one aspect, the present invention relates to a compound of Formula (IA)

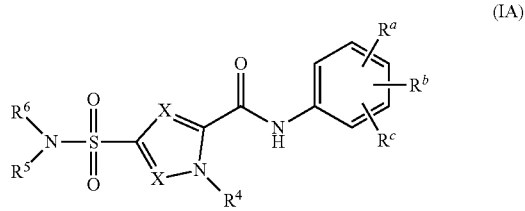

or a stereoisomer or tautomeric form thereof, wherein:

Each X independently represents CR$^7$;

$R^a$, $R^b$ and $R^c$ are independently selected from the group consisting of Hydrogen, Fluoro, Bromo, Chloro, —CHF$_2$, —CF$_2$-methyl, —CH$_2$F, —CF$_3$, —OCF$_3$, —CN and methyl;

$R^4$ is Hydrogen or $C_1$-$C_3$alkyl;

$R^5$ is Hydrogen;

$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^H$);

$R^7$ represents hydrogen, methyl, CN, Fluoro or Chloro;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —$SO_2$-methyl, —C(=O)—$OR^{11}$ or —C(=O)—$N(R^{11})_2$;

$R^{10}$ represents —CN, —OH, Fluoro, —$CHF_2$, —$CH_2F$ or —$CF_3$;

$R^{11}$ represents hydrogen or $C_1$-$C_3$alkyl;

or a pharmaceutically acceptable salt or a solvate thereof, wherein such compound is not

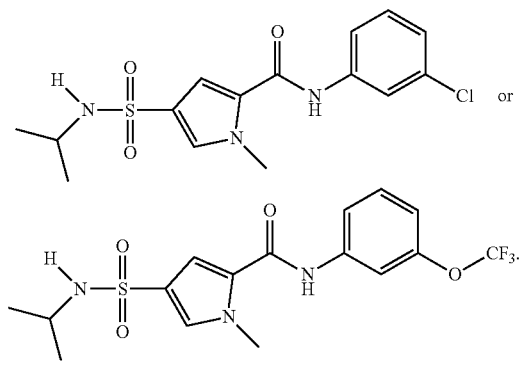

In a further aspect, the present invention relates to a compound of Formula (IA)

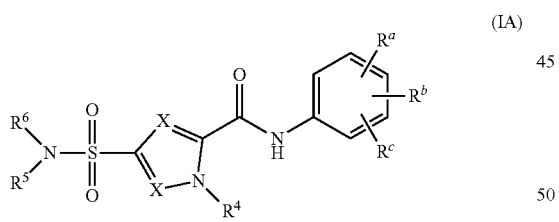

or a stereoisomer or tautomeric form thereof, wherein:
Each X independently represents $CR^7$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN and methyl;
$R^4$ is Hydrogen or $C_1$-$C_3$alkyl;
$R^5$ is Hydrogen;
$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^{10}$);

$R^7$ represents hydrogen, methyl, Fluoro or Chloro;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —$SO_2$-methyl, —C(=O)—$OR^{11}$ or —C(=O)—$N(R^{11})_2$;

$R^{10}$ represents —CN, —OH, Fluoro, —$CHF_2$, —$CH_2F$ or —$CF_3$;

$R^{11}$ represents hydrogen or $C_1$-$C_3$alkyl;

or a pharmaceutically acceptable salt or a solvate thereof, wherein such compound is not

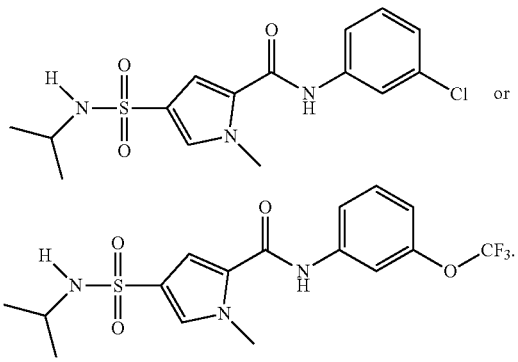

In a further aspect, the invention relates to compound of Formula

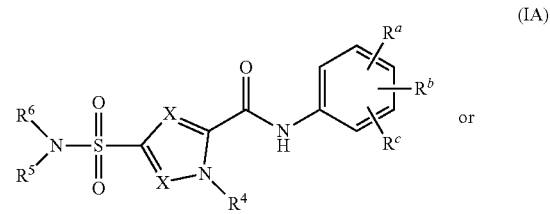

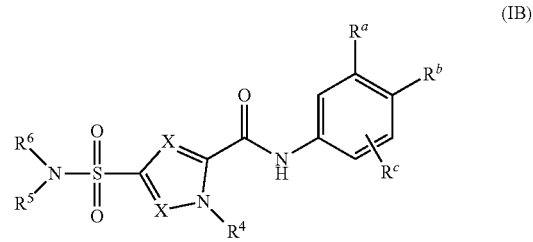

or a stereoisomer or tautomeric form thereof, wherein:
Each X independently represents $CR^7$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN and methyl;
$R^4$ is Hydrogen or $C_1$-$C_3$alkyl;
$R^5$ is Hydrogen;

$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $R^{10}$ and $C_1$-$C_4$alkyl optionally substituted with $R^{10}$;

$R^7$ represents hydrogen, methyl, Fluoro or Chloro;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —$SO_2$-methyl, —C(=O)—$OR^{11}$ or —C(=O)—$N(R^{11})_2$ $R^{10}$ represents —CN, —OH, Fluoro, —$CHF_2$, —$CH_2F$ or —$CF_3$;

$R^{11}$ represents hydrogen or $C_1$-$C_3$alkyl;

or a pharmaceutically acceptable salt or a solvate thereof, wherein such compound is not

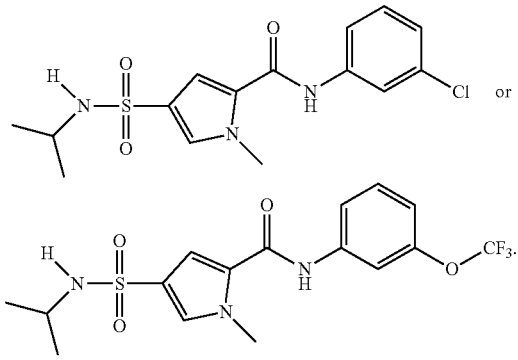

In one embodiment of compounds of the present invention, $R^4$ is methyl.

In a further embodiment of compounds of the present invention, $R^b$ is Hydrogen or Fluoro. Furthermore, compounds according to the invention are described wherein $R^a$ and $R^c$ are independently selected from the group consisting of Hydrogen, Fluoro, Chloro —CN and methyl. Preferably, $R^b$ is Hydrogen or Fluoro and $R^a$ and $R^c$ are independently selected from the group consisting of Hydrogen, Fluoro, Chloro and —CN.

In one embodiment of compounds of the present invention, $R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, $R^9$, $W^o$ and $C_1$-$C_4$alkyl optionally substituted with $R^{10}$. In a further embodiment, $R^6$ contains a 3-7 membered saturated ring optionally containing one oxygen, more specifically $R^6$ is a 5 membered saturated ring containing one oxygen, such 5 membered saturated ring optionally substituted with $C_1$-$C_4$alkyl optionally substituted with $R^{10}$.

In one embodiment of compounds of the present invention, $R^6$ comprises a branched $C_3$-$C_6$alkyl optionally substituted with one or more Fluoro, or $R^6$ comprises a $C_3$-$C_6$cycloalkyl wherein such $C_3$-$C_6$cycloalkyl is substituted with one or more Fluoro or substituted with $C_1$-$C_4$ substituted with one or more Fluoro. More specifically, $R^6$ is a branched $C_3$-$C_6$alkyl substituted with one or more Fluoro.

In a further aspect, the invention provides compound of Formula (I)

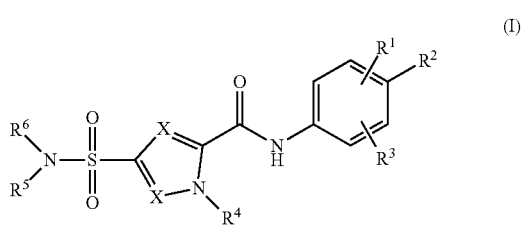

or a stereoisomer or tautomeric form thereof, wherein:

Each X independently represents $CR^7$;

$R^2$ is Hydrogen, CN, Chloro or Fluoro;

$R^1$ and $R^3$ are independently selected from the group consisting of Hydrogen, Fluoro, Bromo, Chloro, —$CHF_2$, —$CH_2F$, —$CF_3$, —$OCF_3$, —CN and methyl, wherein at maximum one of $R^1$ $R^2$ and $R^3$ is Hydrogen if one of $R^1$ and $R^3$ is Chloro or —$OCF_3$;

$R^4$ is Hydrogen or $C_1$-$C_3$alkyl;

$R^5$ is Hydrogen;

$R^6$ is selected from the group consisting of $C_2$-$C_6$alkyl, $C_1$-$C_4$alkyl-$R^8$ optionally substituted with one or more Fluoro, $C_1$-$C_4$alkyl-$R^9$ optionally substituted with one or more Fluoro, and a 3-7 membered saturated ring optionally containing one or more heteroatoms each independently selected from the group consisting of O, S and N, such 3-7 membered saturated ring or —$C_2$-$C_6$alkyl optionally being substituted with one or more substituents each independently selected from the group consisting of Hydrogen, —OH, Fluoro, oxo and $C_1$-$C_4$alkyl optionally substituted with $R^{10}$;

$R^7$ represents hydrogen, methyl, Fluoro or Chloro;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents, $C_1$-$C_4$alkyloxy, —$SO_2$-methyl, —C(=O)—$OR^{11}$ or —C(=O)—$N(R^{11})_2$ $R^{10}$ represents —CN, —OH, Fluoro, —$CHF_2$, —$CH_2F$ or —$CF_3$;

$R^{11}$ represents hydrogen or $C_1$-$C_3$alkyl;

or a pharmaceutically acceptable salt or a solvate thereof.

In one embodiment, compounds of Formula (I) are disclosed wherein:

Each X independently represents $CR^7$;

$R^2$ is Hydrogen, CN, or Fluoro;

$R^1$ and $R^3$ are independently selected from the group consisting of Hydrogen, Fluoro, Bromo, Chloro, —$CHF_2$, —$CH_2F$, —$CF_3$, —CN and methyl, wherein at maximum one of $R^1$ $R^2$ and $R^3$ is Hydrogen if one of $R^1$ and $R^3$ is Chloro;

$R^4$ is Hydrogen or $C_1$-$C_3$alkyl;

$R^5$ is Hydrogen;

$R^6$ is selected from the group consisting of $C_2$-$C_6$alkyl, $C_1$-$C_4$alkyl-$R^8$, $C_1$-$C_4$alkyl-$R^9$ and a 3-7 membered saturated ring optionally containing one or more heteroatoms each independently selected from the group consisting of O, S and N, such 3-7 membered saturated ring or —$C_2$-$C_6$alkyl optionally being substituted with one or more substituents each independently selected from the group consisting of Hydrogen, —OH, Fluoro, oxo and $C_1$-$C_4$alkyl optionally substituted with $R^{10}$;

$R^7$ represents hydrogen, methyl, Fluoro or Chloro;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with RE);

$R^9$ represents —C(=O)—$OR^{11}$ or —C(=O)—$N(R^{11})_2$;

$R^{10}$ represents —CN, —OH, Fluoro, —$CHF_2$, —$CH_2F$ or —$CF_3$; and $R^{11}$ represents hydrogen or $C_1$-$C_3$alkyl.

In one further embodiment, compounds of Formula (I) are disclosed wherein:

Each X independently represents $CR^7$;

$R^2$ is Hydrogen or Fluoro;

$R^1$ and $R^3$ are independently selected from the group consisting of Hydrogen, Fluoro, Bromo, Chloro, $CHF_2$, $CH_2F$, $CF_3$ and methyl, wherein at maximum one of $R^1$, $R^2$ and $R^3$ is Hydrogen;

$R^4$ is Hydrogen or methyl;

$R^5$ is Hydrogen;

$R^6$ is selected from the group consisting of $C_2$-$C_6$alkyl, $C_1$-$C_3$alkyl-$R^8$ and a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, OH, Fluoro, and $C_1$-$C_4$alkyl;

$R^7$ represents Hydrogen, methyl, Fluoro or Chloro;

$R^8$ represents 3-7 membered saturated ring optionally containing one or more heteroatoms each independently selected from the group consisting of O, S and N.

In one embodiment, for compounds according to Formula (I), at least one X represents CH.

In a further aspect, the invention provides compounds of Formula (Ia)

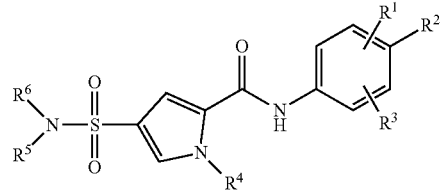

(Ia)

or a stereoisomer or tautomeric form thereof, wherein:

$R^2$ is Hydrogen, CN or Fluoro;

$R^1$ and $R^3$ are independently selected from the group consisting of Hydrogen, Fluoro, Bromo, Chloro, —$CHF_2$, —$CH_2F$, —$CF_3$, —CN and methyl, wherein at maximum one of $R^1$, $R^2$ and $R^3$ is Hydrogen if one of $R^1$ and $R^3$ is Chloro;

$R^4$ is Hydrogen or $C_1$-$C_3$alkyl;

$R^5$ is Hydrogen;

$R^6$ is selected from the group consisting of $C_2$-$C_6$alkyl, $C_1$-$C_4$alkyl-$R^8$, $C_1$-$C_4$alkyl-$R^9$ and a 3-7 membered saturated ring optionally containing one or more heteroatoms each independently selected from the group consisting of O, S and N, such 3-7 membered saturated ring or —$C_2$-$C_6$alkyl optionally being substituted with one or more substituents each independently selected from the group consisting of Hydrogen, —OH, Fluoro, oxo and $C_1$-$C_4$alkyl optionally substituted with $R^{10}$;

$R^7$ represents hydrogen, methyl, Fluoro or Chloro;

$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;

$R^9$ represents —C(=O)—$OR^{11}$ or —C(=O)—$N(R^{11})_2$ $R^{10}$ represents —CN, —OH, Fluoro, —$CHF_2$, —$CH_2F$ or —$CF_3$, $R^{11}$ represents hydrogen or $C_1$-$C_3$alkyl;

or a pharmaceutically acceptable salts or a solvate thereof.

In a sub-embodiment, compounds of Formula (I) are disclosed wherein:

$R^2$ is Hydrogen or Fluoro;

$R^1$ and $R^3$ are independently selected from the group consisting of Hydrogen, Fluoro, $CHF_2$, $CH_2F$, $CF_3$ and methyl, wherein at maximum one of $R^1$, $R^2$ and $R^3$ is Hydrogen;

$R^4$ is Hydrogen or methyl;

$R^5$ is Hydrogen;

$R^6$ is selected from the group consisting of $C_2$-$C_6$alkyl and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of Hydrogen, OH and $C_1$-$C_4$alkyl.

In another embodiment, compounds of the invention are represented by Formula (II)

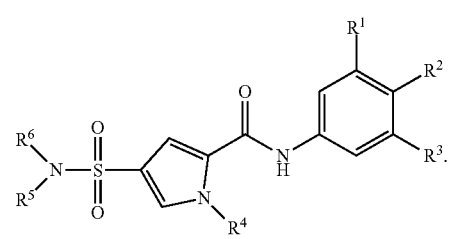

(II)

In yet another embodiment, compounds of the invention are represented by Formula (III)

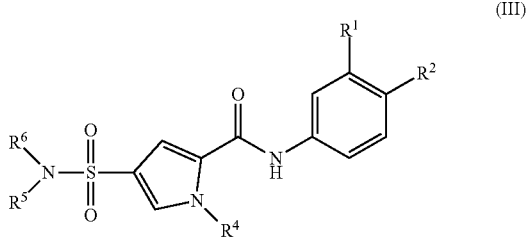

(III)

For both compounds of Formula (II) and (III):
$R^2$ is Hydrogen, CN or Fluoro;
$R^1$ is independently selected from the group consisting of Fluoro, Bromo, Chloro, —$CHF_2$, —$CH_2F$, —$CF_3$, —CN and methyl, wherein if $R^1$ is Chloro, $R^2$ is not Hydrogen;
$R^4$ is Hydrogen or $C_1$-$C_3$alkyl;
$R^5$ is Hydrogen;
$R^6$ is selected from the group consisting of $C_2$-$C_6$alkyl, $C_1$-$C_4$alkyl-$R^8$, $C_1$-$C_4$alkyl-$R^9$ and a 3-7 membered saturated ring optionally containing one or more heteroatoms each independently selected from the group consisting of O, S and N, such 3-7 membered saturated ring or —$C_2$-$C_6$alkyl optionally being substituted with one or more substituents each independently selected from the group consisting of Hydrogen, —OH, Fluoro, oxo and $C_1$-$C_4$alkyl optionally substituted with $R^{10}$;
$R^7$ represents hydrogen, methyl, Fluoro or Chloro;
$R^8$ represents 3-7 membered saturated ring optionally containing one or more heteroatoms each independently selected from the group consisting of O, S and N, such 3-7 membered saturated ring optionally being substituted with one or more $C_1$-$C_4$alkyl optionally substituted with $R^{10}$;
$R^9$ represents —C(=O)—$OR^{11}$ or —C(=O)—$N(R^{11})_2$
$R^{10}$ represents —CN, —OH, Fluoro, —$CHF_2$, —$CH_2F$ or —$CF_3$;
$R^{11}$ represents hydrogen or $C_1$-$C_3$alkyl.

In one embodiment, compounds of the present invention are disclosed wherein $R^1$ is selected from either Bromo, Chloro, Fluoro or methyl, or Fluoro or methyl. In another embodiment, $R^1$ is selected from either Fluoro or methyl and at least one of $R^1$ and $R^3$ is Fluoro. In yet a further embodiment, $R^1$ is selected from either Fluoro or methyl and at least one of $R^1$ and $R^3$ is Fluoro, and the other $R^1$ or $R^3$ is selected from methyl, Fluoro, $CHF_2$, $CH_2F$, $CF_3$ and methyl. In another embodiment, at least two of $R^1$, $R^2$ and $R^3$ are halogens, preferably Bromo, Fluoro or Chloro, even more preferably Fluoro or Chloro. In a further embodiment, each of $R^1$, $R^2$ and $R^3$ are halogen, preferably Bromo, Fluoro or Chloro, even more preferably Fluoro or Chloro.

In yet another embodiment, compounds of the present invention are disclosed wherein $R^4$ is methyl or ethyl, preferably methyl.

In a further embodiment, compounds of the present invention are disclosed wherein $R^6$ contains a 3-7 membered saturated ring optionally containing one oxygen, preferably $R^6$ is a 5 membered saturated ring containing one oxygen.

In another embodiment, compounds of the present invention are disclosed wherein $R^6$ comprises a $C_1$-$C_4$alkyl substituted with one or more Fluoro. In addition, compounds of the present invention are disclosed wherein $R^6$ comprises a branched $C_3$-$C_6$alkyl substituted with one or more Fluoro, or wherein $R^6$ comprises a $C_3$-$C_6$cycloalkyl wherein such $C_3$-$C_6$cycloalkyl is substituted with one or more Fluoro or substituted with $C_1$-$C_4$ substituted with one or more Fluoro.

In yet another embodiment, compounds of the invention are disclosed wherein $R^6$ comprises a carbon atom without hydrogen substituent. Preferably, carbon without hydrogen substituent is directly attached to the Nitrogen of the —N—$SO_1$~ moiety.

Further combinations of any of the embodiments are also envisioned to be in the scope of the present invention.

Preferred compounds according to the invention are compound or a stereoisomer or tautomeric form thereof with a formula as represented in the synthesis of compounds section and of which the activity is displayed in Table 1.

In a further aspect, the present invention concerns a pharmaceutical composition comprising a therapeutically or prophylactically effective amount of a compound of Formula (ID) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (ID), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (ID) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (ID) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (ID).

The compounds of Formula (ID), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of Formula (ID) or any subgroup thereof, as specified herein with other anti-HBV agents. The term "combination" may relate to a product or kit containing (a) a compound of Formula (ID), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of Formula (ID) or any subgroup thereof with at least one anti-HBV agent. In a particular embodiment, the invention concerns combination of a compound of Formula (ID) or any subgroup thereof with at least two anti-HBV agents. In a particular embodiment, the invention concerns combination of a compound of Formula (ID) or any subgroup thereof with at least three anti-HBV agents. In a particular embodiment, the invention concerns combination of a compound of Formula (ID) or any subgroup thereof with at least four anti-HBV agents.

The term anti-HBV agent also includes compounds capable of treating HBV infection via immunomodulation. Examples of immunomodulators are interferon-α (IFN-α), pegylated interferon-α or stimulants of the innate immune system such as Toll-like receptor 7 and/or 8 agonists. One embodiment of the present invention relates to combinations of a compound of Formula (ID) or any subgroup thereof, as specified herein with an immunomodulating compound, more specifically a Toll-like receptor 7 and/or 8 agonist.

The combination of previously known anti-HBV agents, such as interferon-α (IFN-α), pegylated interferon-α, 3TC, adefovir or a combination thereof, and, a compound of Formula (ID) or any subgroup thereof can be used as a medicine in a combination therapy.

Generic Synthesis:

The substituents represented in this general synthesis section are meant to include any substituent or reactive species that is suitable for transformation into any substituent according to the present invention without undue burden for the person skilled in the art.

A possible synthesis of compound of general formula (I) is described in schemes 1 and 2. Similarly, the synthesis of compounds of general formula (IA) are described in schemes 1a, 2a. Also similarly, the synthesis of compounds of general formula ID is described in scheme 1b and scheme 2b. A carboxylic acid chloride of general formula (IV) (for example prepared according to the synthesis described for compound 2) can be selectively reacted with an aniline of general formula (V), for example by slow addition of aniline (V) to a refluxing solution of compound (IV) in toluene, resulting in compound (VI). The remaining sulfonic acid chloride functionality in compound (VI) is further reacted with an amine of general formula (VII), resulting in a compound of general formula (I), for example in a solvent like acetonitrile in the presence of an inorganic base like sodium bicarbonate or as further exemplified in the experimental synthetic description of compounds.

Scheme 1

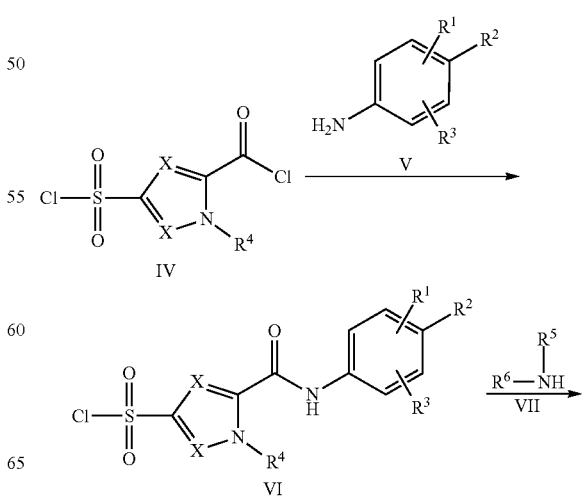

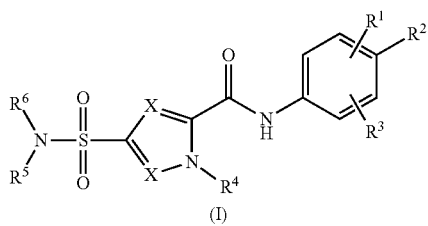

(I)

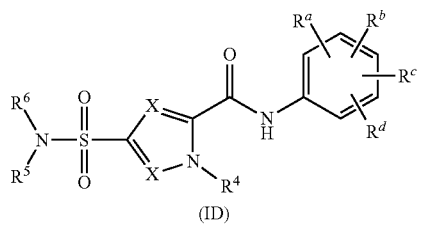

(ID)

Alternatively a compound of general formula (I) might be obtained as described in scheme 2. This time the sulfonic acid chloride (VIII) (for example prepared according to the synthesis described for compound 2) is reacted with an amine of general formula (VII), for example in an organic solvent like $CH_2Cl_2$ in the presence of an organic base like triethylamine or DIPEA. The formed compound (IX) is coupled with aniline of general formula (V) in the presence of an activating reagent like for example HATU and an organic base like triethylamine or DIPEA.

Scheme 1a

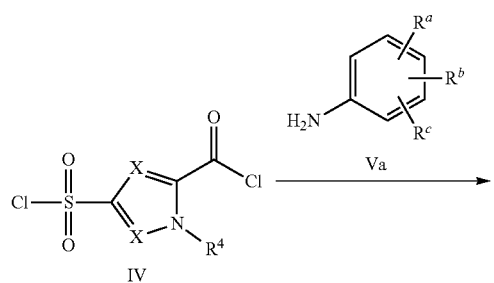

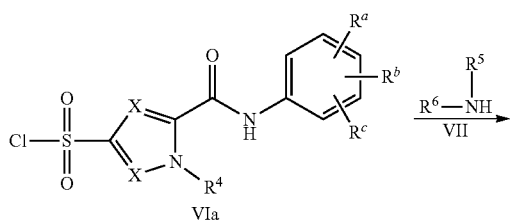

Scheme 1b

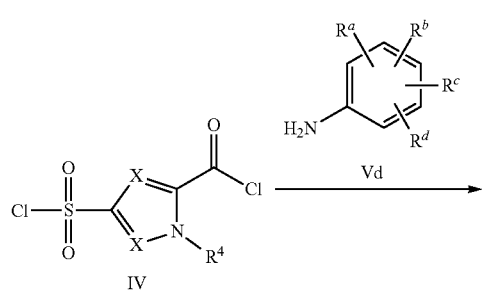

Scheme 2

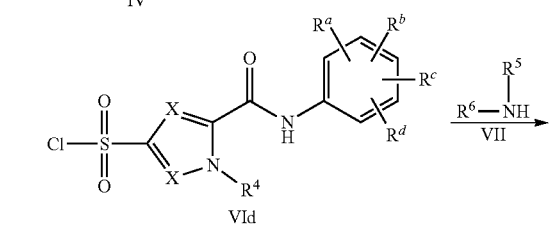

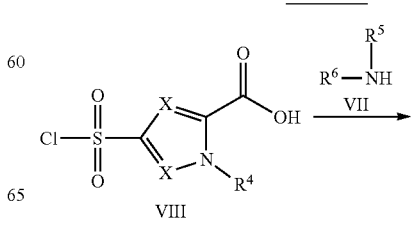

Scheme 2a

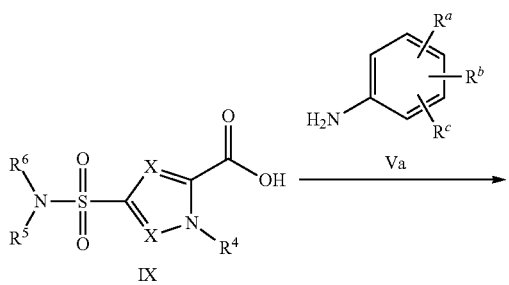

(IA)

Scheme 2b

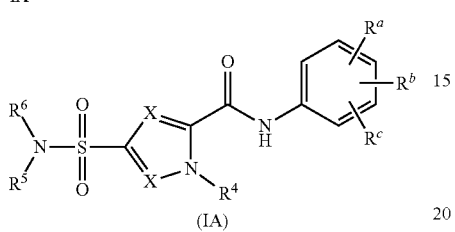

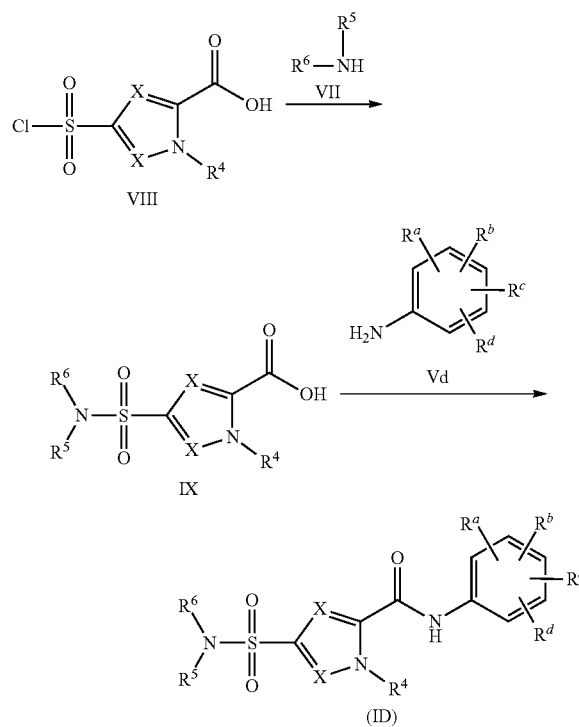

Scheme 3

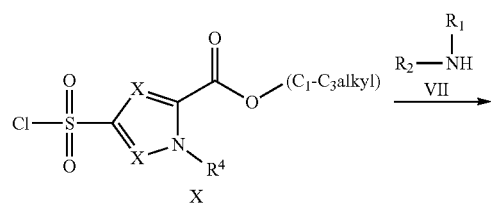

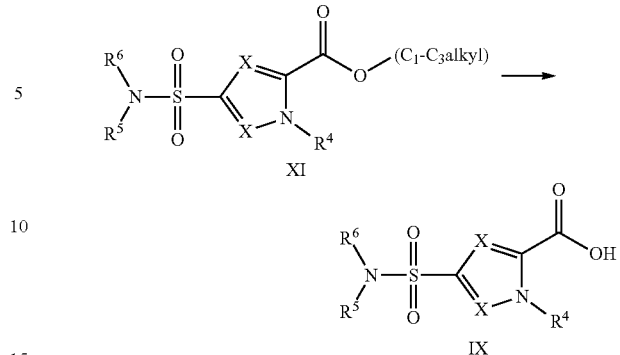

An alternative method for the synthesis of compounds of general formula IX, is via ester X as described in scheme 3. Reaction of X with amine VII, for example in an organic solvent like acetonitrile in the presence of an organic base like for example triethylamine or DIPEA, or an inorganic base like for example sodium bicarbonate, resulting in a compound of general formula XI, followed by hydrolysis of the ester, for example with LiOH in THF/$H_2O$, followed by acidification, results in a compound of general formula IX.

A compound of general formula VIII can be converted to a compound of general formula IV, for example by treatment with oxalyl chloride in $CH_2Cl_2$.

Scheme 4

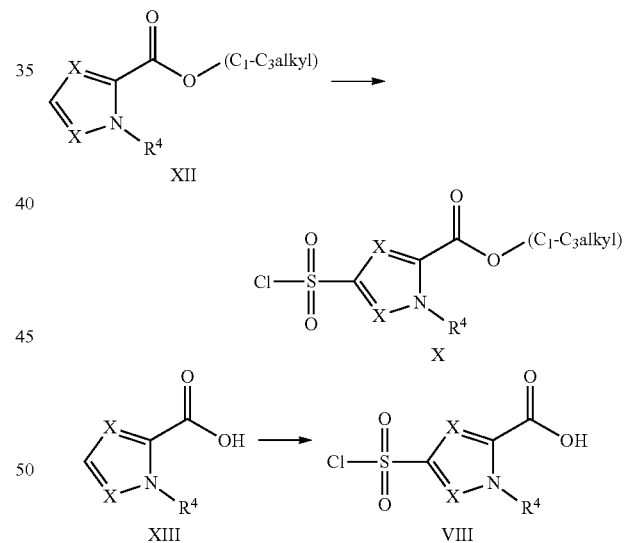

Possible synthetic routes, for compounds of general formula X and VIII are described in scheme 4, and further exemplified in the experimental section. Chlorosulfonation of carboxylic ester XII or carboxylic acid XIII, can results in compounds of general formula X or VIII respectively, for example by treatment with chlorosulfonic acid at for example 0° C., if necessary, followed by quenching with water. Alternatively, compound XII can be treated with chlorosulfonic acid, resulting in a sulfonic acid derivative, for example by treatment of compound XII with 1-1.2 equiv chlorosulfonic acid in $CH_2Cl_2$, the resulting sulfonic acid derivative can be converted the sulfonyl chloride compound X, for example by treatment with $SOCl_2$ at 80° C.

Scheme 5

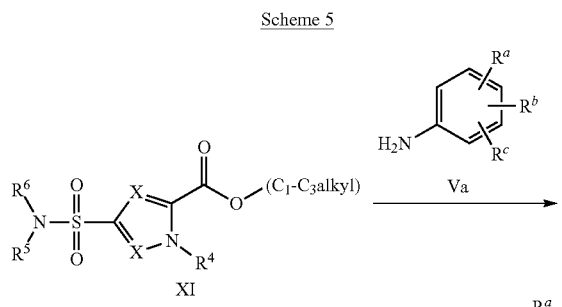

Scheme 5a

Alternatively a compound of general formula (IA) might be obtained as described in scheme 5. A compound of general formula XI can be coupled with a compound of general formula Va in the presence of a base like for example lithium bis(trimethylsilyl)amide, in a solvent like for example THF, resulting in the formation of a compound of general formula (IA). Similarly, a compound of general formula ID can be prepared as described in scheme 5a.

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]+ (protonated molecule) and/or [M−H]− (deprotonated molecule). In case the compound was not directly ionizable the type of adduct is specified (i.e. [M+NH$_4$]$^+$, [M+HCOO]$^-$, etc.). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector, LCMS Methods (Flow expressed in mL/min; column temperature (T) in ° C.; Run time in minutes).

| Method code | Instrument | Column | Mobile phase | Gradient | Flow Col T | Run time |
|---|---|---|---|---|---|---|
| A | Waters: Acquity® UPLC® - DAD and SQD | Waters: HSS T3 (1.8 µm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.8 55 | 3.5 |
| B | Waters: Acquity® UPLC® - DAD and SQD | Waters: BEH C18 (1.7 µm, 2.1 * 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 55 | 2 |
| C | Waters: Acquity® UPLC® - DAD and SQD | Waters: HSS T3 (1.8 µm, 2.1 * 100 mm) | A: 10 mM CH$_3$COONH$_4$ in 95% H$_2$O + 5% CH$_3$CN B: CH$_3$CN | From 95% A to 0% A in 2.5 min, to 5% A in 0.5 min | 0.8 55 | 3 |

| Method code | Instrument | Column | Mobile phase | Gradient | Flow Col T | Run time |
|---|---|---|---|---|---|---|
| D | Waters: Acquity ® UPLC ® - DAD and SQD | Waters: HSS T3 (1.8 μm, 2.1 * 100 mm) | A: 10 mM CH₃COONH₄ in 95% H₂O + 5% CH₃CN B: CH₃CN | From 100% A to 5% A in 2.10 min, to 0% A in 0.90 min, to 5% A in 0.5 min | 0.7 55 | 3.5 |

Synthesis of Compounds

Compound 1: N-(4-fluoro-3-methyl-phenyl)-4-(isopropylsulfamoyl)-1H-pyrrole-2-carboxamide

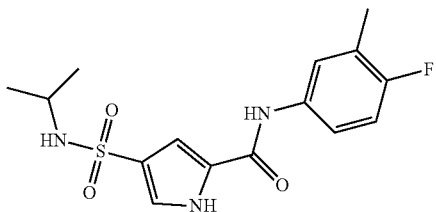 [SMILES: Cc1cc(NC(=O)c2cc(S(=O)(=O)NC(C)C)c[nH]2)ccc1F]

4-(isopropylsulfamoyl)-1H-Pyrrole-2-carboxylic acid (857 mg, 3.69 mmol), 4-Fluoro-3-Methylaniline (461.8 mg, 369 mmol), COMU ((1-Cyano-2-ethoxy-2-oxoethylidenaminooxy)dimethylamino-morpholino-carbenium hexafluorophosphate; CAS Number 1075198-30-9; 1738 mg, 4.06 mmol) and triethylamine (2.0 mL, 4.06 mmol) in dichloromethane (43 mL) was stirred for 3 hours. The reaction mixture was treated with 1M HCl (50 mL). The precipitate was filtered off and was recrystallized from hot acetonitrile (50 mL). The solid was filtered and dried overnight in vacuo yielding a beige powder (58 mg). $^1$H NMR (400 MHz, DMSO-d$_6$) δ ppm 1.00 (d, J=6.4 Hz, 6H), 2.23 (d, J=1.5 Hz, 3H), 3.20-3.31 (m, 1H), 7.05-7.20 (m, 2H), 7.31-7.34 (m, 1H), 7.34-7.38 (m, 1H), 7.54-7.60 (m, 1H), 7.62 (dd, J=7.2, 2.3 Hz, 1H), 10.01 (s, 1H), 12.33 (br. s., 1H). Method A; Rt: 1.51 min. m/z: 338.0 (M−H)⁻ Exact mass: 339.1.

Compound 2: N-(4-fluoro-3-methyl-phenyl)-4-(isopropylsulfamoyl)-1-methyl-pyrrole-2-carboxamide

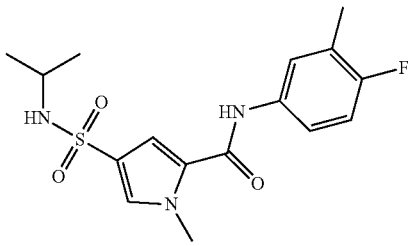 [SMILES: Cc1cc(NC(=O)c2cc(S(=O)(=O)NC(C)C)cn2C)ccc1F]

A mixture of 4-(isopropylsulfamoyl)-1-methyl-pyrrole-2-carboxylic acid (Commercial from enamine, EN300-30498, 954 mg, 3.87 mmol) 4-Fluoro-3-Methylaniline (485 mg, 3.87 mmol), COMU (1825 mg, 4.261 mmol) and triethylamine (2.15 mL, 4.26 mmol) in dichloromethane (50 mL) was stirred for 3 hours. The reaction mixture was washed with 1M HCl (50 mL), water and NaHCO₃ solution, dried over sodium sulphate, filtered and concentrated. The obtained residue was purified by Preparative HPLC (Stationary phase: RP Vydac Denali C18—10 μm, 200 g, 5 cm), Mobile phase: 0.25% NH₄HCO₃ solution in water, CH₃CN). The product fractions were concentrated yielding a white powder which was dried overnight in vacuo at 50° C. (30 mg). Method A; Rt: 1.73 min. m/z: 354.0 (M+H)⁺ Exact mass: 353.1. $^1$H NMR (400 MHz, DMSO-d$_6$) δ ppm 1.02 (d, J=6.6 Hz, 6H), 2.23 (d, J=1.8 Hz, 3H), 3.21-3.30 (m, 1H), 3.91 (s, 3H), 7.09 (t, J=9.2 Hz, 1H), 7.17 (d, J=6.8 Hz, 1H), 7.30 (d, J=2.0 Hz, 1H), 7.45-7.57 (m, 2H), 7.64 (dd, J=7.0, 2.4 Hz, 1H), 10.01 (s, 1H).

Synthesis of 4-chlorosulfonyl-1-methyl-pyrrole-2-carbonyl chloride and 5-[(4-fluoro-3-methyl-phenyl)carbamoyl]-1-methyl-pyrrole-3-sulfonyl chloride 1-Methyl-1H-pyrrole-2-carboxylic acid (5520 mg, 44.1 mmol) was dissolved portion wise in chlorosulfonic acid (25 mL) in an ice bath. The mixture was stirred for 70 minutes. The mixture was added drop wise to ice/water (200 mL) and stirred for 5 minutes. The precipitate was filtered, rinsed with water and dried overnight in vacuo at 50° C. resulting in 4-chlorosulfonyl-1-methyl-pyrrole-2-carboxylic acid as a powder (5632 mg). Oxalyl chloride (22.4 g, 176.8 mmol) was added portion wise to 4-chlorosulfonyl-1-methyl-pyrrole-2-carboxylic acid (obtained as described above, 7.9 g, 35.37 mmol) and DMF (0.14 mL) in CH₂Cl₂ (200 mL) and the mixture was stirred over weekend at room temperature. The reaction mixture was concentrated yielding 4-chlorosulfonyl-1-methyl-pyrrole-2-carbonyl chloride as a brown solid (8.6 g) which was used as such. 4-fluoro-3-methylaniline (2049 mg, 16.37 mmol) was dissolved in toluene (20 mL) and added drop wise to a solution of 4-chlorosulfonyl-1-methyl-pyrrole-2-carbonyl chloride (3963 mg, 16.37 mmol) in toluene (200 mL) at reflux. The reaction mixture was refluxed 1 hour and allowed to cool to room temperature overnight. The formed precipitate was filtered and dried in vacuo at 50° C. resulting in 5-[(4-fluoro-3-methyl-phenyl)carbamoyl]-1-methyl-pyrrole-3-sulfonyl chloride (3.14 g) as a powder. Method A; Rt: 1.96 min. m/z: 328.9 (M−H)⁻ Exact mass: 330.0. $^1$H NMR (400 MHz, CHLOROFORM-d) δ ppm 2.29 (d, J=1.8 Hz, 3H), 4.05 (s, 3H), 7.00 (t, J=9.0 Hz, 1H), 7.15 (d, J=1.8 Hz, 1H), 7.27-7.32 (m, 1H), 7.42 (dd, J=6.6, 2.6 Hz, 1H), 7.50 (d, J=1.8 Hz, 1H), 7.63 (br. s., 1H).

Compound 3: N-(4-fluoro-3-methyl-phenyl)-4-[[(1R)-2-hydroxy-1-methyl-ethyl]sulfamoyl]-1-methyl-pyrrole-2-carboxamide

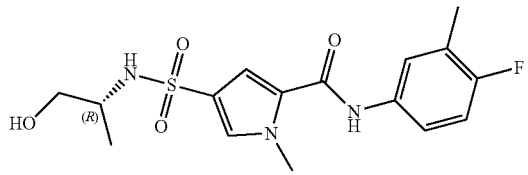

A mixture of D-alaninol (696 mg, 9.08 mmol) and DIPEA (1.3 mL, 7.57 mmol) dissolved in dichloromethane (25 mL) was added to a solution of 5-[(4-fluoro-3-methyl-phenyl)carbamoyl]-1-methyl-pyrrole-3-sulfonyl chloride (2250 mg). The reaction mixture was stirred 15 minutes. More D-alaninol (1.5 eq) and DIPEA (2 eq) were added and the reaction mixture was stirred 15 minutes more. The reaction mixture was washed with 1M HCl (3×), water and NaHCO$_3$ solution. The organic layer was dried over MgSO$_4$, filtered and concentrated. The obtained residue was purified by column chromatography on silica using a gradient from 10 to 100% EtOAc in heptane. The product fractions were concentrated and the obtained residue was crystallized from warm EtOAc (50 mL) by slowly adding heptane. Compound 3 was filtered off as white crystals and dried in vacuo at 50° C. (342 mg). Method A; Rt: 1.47 min. m/z: 370.2 (M+H)$^+$ Exact mass: 369.1. $^1$H NMR (400 MHz, DMSO-d$_6$) δ ppm 0.98 (d, J=6.2 Hz, 3H), 2.23 (d, J=1.5 Hz, 3H), 3.07-3.18 (m, 2H), 3.32-3.39 (m, 1H), 3.91 (s, 3H), 4.65 (t, J=5.5 Hz, 1H), 7.03-7.15 (m, 2H), 7.30 (d, J=1.8 Hz, 1H), 7.47-7.57 (m, 2H), 7.64 (dd, J=7.0, 2.4 Hz, 1H), 10.02 (s, 1H).

Compound 4: N-(4-fluoro-3-methyl-phenyl)-1-methyl-4-[[(3S)-tetrahydrofuran-3-yl]-sulfamoyl]pyrrole-2-carboxamide

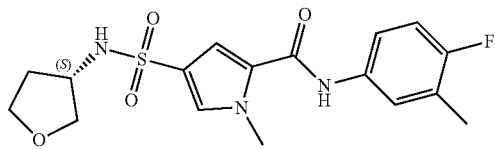

A mixture of (S)-Tetrahydro-3-furylamine p-toluenesulfonate salt (822 mg, 3.17 mmol) and DIPEA (1.09 mL, 6.34 mmol) in dichloromethane (25 mL), was added to a solution of 5-[(4-fluoro-3-methyl-phenyl)carbamoyl]-1-methyl-pyrrole-3-sulfonyl chloride (785 mg) in dichloromethane (50 mL) and stirred overnight. The reaction mixture was washed with 1M HCl (3×), water and NaHCO$_3$ solution. The organic layer was dried over MgSO$_4$, filtered and concentrated. The residue was purified by column chromatography on silica using a gradient from 10 to 100% EtOAc in heptane. The product fractions were concentrated yielding compound 4 as a beige solid which was dried overnight in vacuo at 50° C. (696 mg). Method A; Rt: 1.57 min. m/z: 382.0 (M+H)$^+$ Exact mass: 381.1. $^1$H NMR (400 MHz, DMSO-d$_6$) δ ppm 1.66-1.77 (m, 1H), 1.91-2.04 (m, 1H), 2.23 (d, J=1.5 Hz, 3H), 3.39-3.47 (m, 1H), 3.61 (td, J=8.0, 5.9 Hz, 1H), 3.66-3.76 (m, 3H), 3.92 (s, 3H), 7.09 (t, J=9.1 Hz, 1H), 7.31 (d, J=2.0 Hz, 1H), 7.47-7.59 (m, 3H), 7.64 (dd, J=7.2, 2.3 Hz, 1H), 10.03 (s, 1H).

Compound 5: N-(4-fluoro-3-methyl-phenyl)-1-methyl-4-[(3-methyloxetan-3-yl)-sulfamoyl]pyrrole-2-carboxamide

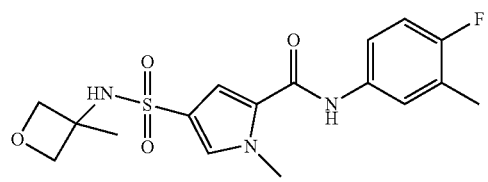 [SMILES: Cc1cc(NC(=O)c2cc(S(=O)(=O)NC3(C)COC3)cn2C)ccc1F]

A mixture of 3-methyl-3-oxetanamine hydrochloride (1:1) (391.5 mg, 3.17 mmol) and DIPEA (1.09 mL, 6.34 mmol) in dichloromethane (25 mL) was added to a solution of 5-[(4-fluoro-3-methyl-phenyl)carbamoyl]-1-methyl-pyrrole-3-sulfonyl chloride (785 mg) in dichloromethane (50 mL) and stirred overnight. The reaction mixture was washed with 1M HCl (3×), water and NaHCO$_3$ solution. The organic layer was dried over MgSO$_4$, filtered and concentrated. The obtained residue was purified by silica gel column chromatography using a gradient from 10 to 100% EtOAc in heptane. The product fractions were concentrated yielding compound 5 as a beige solid which was dried overnight in vacuo at 50° C. (584 mg). Method A; Rt: 1.57 min. m/z: 399.2 (M+NH$_4$)$^+$ Exact mass: 381.1. $^1$H NMR (400 MHz, DMSO-d$_6$) δ ppm 1.55 (s, 3H), 2.23 (d, J=1.5 Hz, 3H), 3.91 (s, 3H), 4.13 (d, J=6.0 Hz, 2H), 4.60 (d, J=6.0 Hz, 2H), 7.09 (t, J=9.1 Hz, 1H), 7.32 (d, J=2.0 Hz, 1H), 7.48-7.54 (m, 1H), 7.56 (d, J=1.8 Hz, 1H), 7.63 (dd, J=7.0, 2.4 Hz, 1H), 7.94 (s, 1H), 10.02 (s, 1H).

Compound 6: N-(4-fluoro-3-methyl-phenyl)-1-methyl-4-[[(1R)-1-methylpropyl]-sulfamoyl]pyrrole-2-carboxamide

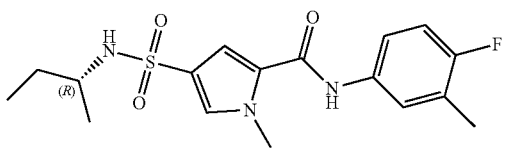

A mixture of (R)-(−)-2-aminobutane (231.7 mg, 3.17 mmol) and DIPEA (1.09 mL, 6.34 mmol) in dichloromethane (25 mL) was added to a solution of 5-[(4-fluoro-3-methyl-phenyl)carbamoyl]-1-methyl-pyrrole-3-sulfonyl chloride (785 mg) in dichloromethane (50 mL) and stirred overnight. The reaction mixture was washed with 1M HCl (3×), water and NaHCO$_3$ solution. The organic layer was dried over MgSO$_4$, filtered and concentrated. The obtained residue was purified by column chromatography on silica using a gradient from 10 to 100% EtOAc in heptane. The product fractions were concentrated yielding compound 6 as a beige solid which was dried overnight in vacuo at 50° C. (540 mg). Method A; Rt: 1.78 min. m/z: 368.1 (M+H)$^+$ Exact mass: 367.1. $^1$H NMR (400 MHz, DMSO-d$_6$) δ ppm 0.77 (t, J=7.4 Hz, 3H), 0.96 (d, J=6.4 Hz, 3H), 1.29-1.41 (m, 2H), 2.23 (d, J=1.5 Hz, 3H), 3.01-3.12 (m, 1H), 3.91 (s, 3H), 7.04-7.16 (m, 2H), 7.30 (d, J=2.0 Hz, 1H), 7.46-7.57 (m, 2H), 7.64 (dd, J=7.0, 2.4 Hz, 1H), 10.00 (s, 1H).

Alternative Synthesis of Compound 2:

A solution of isopropylamine (499 mg, 8.45 mmol) in dichloromethane (25 mL) was added to a solution of 5-[(4-fluoro-3-methyl-phenyl)carbamoyl]-1-methyl-pyrrole-3-sulfonyl chloride (785 mg). The reaction mixture was stirred overnight. The reaction mixture was washed with 1M HCl (3×), water and NaHCO₃ solution. The organic layer was dried over MgSO₄, filtered and concentrated. The obtained residue was recrystallized by slowly adding heptanes to warm EtOAc (50 mL) solution of compound 2. Compound 2 was filtered off as white solid and dried in vacuo at 50° C. (357 mg).

Compound 7: N-(4-fluoro-3-methyl-phenyl)-1-methyl-4-[(3-methyloxetan-3-yl)methyl-sulfamoyl] pyrrole-2-carboxamide

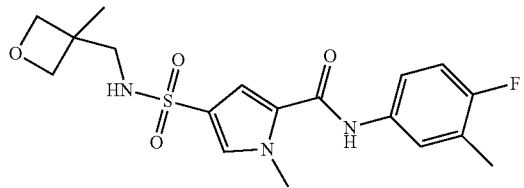 [SMILES: Cc1cc(NC(=O)c2cc(S(=O)(=O)NCC3(C)COC3)cn2C)ccc1F]

A solution of 4-chlorosulfonyl-1-methyl-pyrrole-2-carbonyl chloride (5.05 g, 0.021 mol) in toluene (225 mL) was stirred at reflux under N₂-flow. A solution of 4-fluoro-3-methyl-aniline (2.56 g, 0.020 mol) in toluene (25 mL) was added dropwise over 35 minutes. After addition, the reaction mixture was stirred and refluxed for 1 hour. The reaction mixture was cooled to −50° C. and the solvent was removed in vacuo resulting in crude 5-[(4-fluoro-3-methyl-phenyl)carbamoyl]-1-methyl-pyrrole-3-sulfonyl chloride. Part of this crude 5-[(4-fluoro-3-methyl-phenyl)carbamoyl]-1-methyl-pyrrole-3-sulfonyl chloride (0.63 g, 1.9 mmol) and 3-methyloxetan-3-yl)methanamine (212 mg, 2.1 mmol) were dissolved in dichloromethane (10 mL). Then diisopropylethylamine (820 μL, 4.8 mmol) was added and the resulting mixture was stirred for two hours. HCl (5 mL, aq/1M) was added to the mixture and the organic layer was separated and loaded directly on a silica plug purified by silica gel column chromatography using gradient elution from heptane to EtOAc (100:0 to 0:100). The desired fractions were concentrated in vacuo and dried in vacuo resulting in compound 7 (586 mg) as a white powder. Method A; Rt: 1.60 min. m/z: 394.0 (M−H)⁻ Exact mass: 395.1. ¹H NMR (400 MHz, DMSO-d₆) δ ppm 1.18-1.24 (s, 3H), 2.23 (d, J=1.8 Hz, 3H), 2.96 (s, 2H), 3.92 (s, 3H), 4.17 (d, J=5.8 Hz, 2H), 4.34 (d, J=5.8 Hz, 2H), 7.10 (t, J=9.2 Hz, 1H), 7.32 (d, J=1.8 Hz, 1H), 7.41-7.54 (m, 2H), 7.57 (d, J=1.8 Hz, 1H), 7.64 (dd, J=6.6, 2.2 Hz, 1H), 10.04 (s, 1H).

Compound 8: N-(4-fluoro-3-methyl-phenyl)-1-methyl-4-[[(1S)-2,2,2-trifluoro-1-methyl-ethyl]sulfamoyl]pyrrole-2-carboxamide

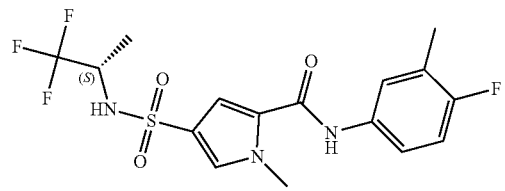

Crude 5-[(4-fluoro-3-methyl-phenyl)carbamoyl]-1-methyl-pyrrole-3-sulfonyl chloride (obtained as described in the synthesis of compound 7, 0.5 g, 1.51 mmol) and (S)-1,1,1-trifluoro-2-propylamine (0.38 g, 3.33 mmol) were dissolved in of acetonitrile (9 mL). Then diisopropylethylamine (0.78 mL, 4.53 mmol) was added and the resulting mixture was stirred for two hours. HCl (5 mL, aq/1M) was added and the mixture was extracted using dichloromethane (3×25 mL) The combined extracts were dried on sodium sulphate, filtered and concentrated in vacuo. The residue was purified by silica gel column chromatography using gradient elution from heptane to EtOAc (100:0 to 0:100). The desired fractions were concentrated in vacuo and dried in vacuo resulting in compound 8 (557 mg) as a white powder. Method B; Rt: 1.03 min. m/z: 406.1 (M−H)⁻ Exact mass: 407.1. ¹H NMR (400 MHz, DMSO-d₆) δ ppm 1.08 (d, J=7.0 Hz, 3H), 2.23 (d, J=1.5 Hz, 3H), 3.83-4.01 (m, 4H), 7.10 (t, J=9.1 Hz, 1H), 7.33 (d, J=2.0 Hz, 1H), 7.47-7.55 (m, 1H), 7.57-7.69 (m, 2H), 8.15 (br. s., 1H), 9.90-10.13 (br. s., 1H). Columns: AD-H (250 mm×4.6 mm), Flow: 5 ml/min, Mobile phase: 25% MeOH (containing 0.2% iPrNH₂) hold 4.00 min, up to 50% in 1 min and hold 2.00 min at 50%, Temperature: 40° C. Rt (compound 8): 1.2 min.

Compound 9: N-(4-fluoro-3-methyl-phenyl)-1-methyl-4-[[(1R)-2,2,2-trifluoro-1-methyl-ethyl]sulfamoyl]pyrrole-2-carboxamide

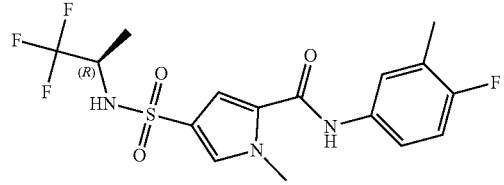

Crude 5-[(4-fluoro-3-methyl-phenyl)carbamoyl]-1-methyl-pyrrole-3-sulfonyl chloride (obtained as described in the synthesis of compound 7, 0.69 g, 2.09 mmol), (R)-1,1,1-trifluoro-2-propylamine (472 mg, 4.2 mmol) and DIPEA (0.72 mL, 4.2 mmol) where stirred in a sealed tube at 55° C. for 16 hours. The reaction mixture was allowed to reach room temperature, and left for 4 hours. The solid was filtered off and washed with CH₃CN (2×). The solvent of the filtrate was evaporated and the obtained residue was dissolved in CH₂Cl₂-heptane and then purified by silica gel column chromatography (heptane-EtOAc 100/0 to 0/100]. The desired fractions were combined and the solvent removed in vacuo. The obtained residue was stirred in CH₂Cl₂ (5 mL), filtered and washed with CH₂Cl₂ (2×) resulting in compound 9 (0.244 g). Method A; Rt: 1.78 min. m/z: 408.1 (M+H)⁺ Exact mass: 407.1. ¹H NMR (400 MHz, DMSO-d₆) δ ppm 1.08 (d, J=7.0 Hz, 3H), 2.23 (d, J=1.5 Hz, 3H), 3.87-3.96 (m, 4H), 7.10 (dd, J=9.2 Hz, 1H), 7.33 (d, J=1.8 Hz, 1H), 7.47-7.55 (m, 1H), 7.59-7.66 (m, 2H), 8.15 (br. s., 1H), 10.03 (s, 1H).

Columns: AD-H (250 mm×4.6 mm), Flow: 5 ml/min, Mobile phase: 25% MeOH (containing 0.2% iPrNH2) hold 4.00 min, up to 50% in 1 min and hold 2.00 min at 50%, Temperature: 40° C. Rt (compound 9): 1.6 min.

Compound 10: N-(4-fluoro-3-methyl-phenyl)-4-[[3-(hydroxymethyl)oxetan-3-yl]sulfamoyl]-1-methyl-pyrrole-2-carboxamide

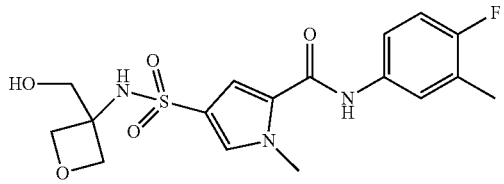 [SMILES: Cc1cc(NC(=O)c2cc(S(=O)(=O)NC3(CO)COC3)cn2C)ccc1F]

DIPEA (1.44 mL, 0.008 mol) was added to a stirring mixture of crude 5-[(4-fluoro-3-methyl-phenyl)carbamoyl]-1-methyl-pyrrole-3-sulfonyl chloride (obtained as described in the synthesis of compound 7, 1.38 g, 0.0042 mol) and CH$_2$Cl$_2$ (45 mL). (3-aminooxetan-3-yl)methanol, 0.47 g, 0.0046 mol) was added, and the reaction mixture was stirred at room temperature for 16 hours. The volatiles were evaporated. The residue was stirred in EtOAc (50 mL) and washed with HCl 1M (25 mL). The separated organic layer was dried with Na$_2$SO$_4$, filtered off and evaporated. The obtained residue was dissolved in EtOAc (3 mL), and heptane (2 mL) was added. The resulting solution was left standing overnight. The formed precipitate was filtered off, washed with a minimum amount EtOAc (3×) and dried in vacuo. The obtained solid was recrystallized from CH$_3$CN (20 mL) filtered off, washed with CH$_3$CN (3×), and dried in vacuo, resulting in compound 10 (767 mg). Method A; Rt: 1.41 min. m/z: 395.9 (M−H)$^-$ Exact mass: 397.1. $^1$H NMR (400 MHz, DMSO-d$_6$) δ ppm 2.23 (d, J=1.8 Hz, 3H), 3.61 (d, J=5.7 Hz, 2H), 3.91 (s, 3H), 4.39 (d, J=6.4 Hz, 2H), 4.56 (d, J=6.4 Hz, 2H), 5.08 (t, J=5.6 Hz, 1H), 7.10 (t, J=9.2 Hz, 1H), 7.33 (d, J=2.0 Hz, 1H), 7.49-7.54 (m, 1H), 7.57 (d, J=1.8 Hz, 1H), 7.64 (dd=7.2, 2.3 Hz, 1H), 7.88 (s, 1H), 10.02 (s, 1H).

Compound 11: N-(4-fluoro-3-methyl-phenyl)-1-methyl-4-[(3-methyltetrahydrofuran-3-yl)sulfamoyl]pyrrole-2-carboxamide

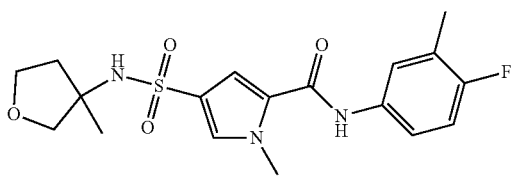 [SMILES: Cc1cc(NC(=O)c2cc(S(=O)(=O)NC3(C)CCOC3)cn2C)ccc1F]

Crude 5-[(4-fluoro-3-methyl-phenyl)carbamoyl]-1-methyl-pyrrole-3-sulfonyl chloride (obtained as described in the synthesis of compound 7, 690 mg) was stirred in CH$_2$Cl$_2$ (25 mL), 3-methyloxolan-3-amine hydrochloride (316 mg, 2.3 mmol) and DIPEA (0.9 mL, 5.2 mmol) were added and the mixture was stirred at room temperature for 17 hours. Ethylacetate (300 mL) was added and the mixture was washed with 0.5 M HCl (1×100 mL). The organic layer was dried with Na$_2$SO$_4$ and the solvent was evaporated. The obtained residue was purified by silica gel column chromatography Methanol/Dichloromethane 2/98 to 4/96]. The desired fractions were combined and the solvent was evaporated. The mixture was repurified by silica gel column chromatography using EtOAc/Heptane 50/50 to 100/0]. The desired fractions were combined and the solvent was evaporated. The obtained residue was recrystallized from 2-Propanol (7 mL). The obtained white solid was filtered off, washed with 2-Propanol (2×2 mL) and dried in vacuo, resulting in compound 11 (211 mg). Method A; Rt: 1.62 min. m/z: 394.1 (M−H)$^-$ Exact mass: 395.1. $^1$H NMR (400 MHz, DMSO-d$_6$) δ ppm 1.29 (s, 3H), 1.73 (dt, J=12.7, 7.3 Hz, 1H), 2.11-2.28 (m, 4H), 3.39 (d, J=8.6 Hz, 1H), 3.66-3.79 (m, 3H), 3.91 (s, 3H), 7.09 (t, J=9.2 Hz, 1H), 7.31 (d, J=1.8 Hz, 1H), 7.46-7.56 (m, 3H), 7.64 (dd, J=7.0, 2.2 Hz, 1H), 10.02 (s, 1H).

Compound 12: N-(4-fluoro-3-methyl-phenyl)-4-[[1-(hydroxymethyl)cyclopropyl]sulfamoyl]-1-methyl-pyrrole-2-carboxamide

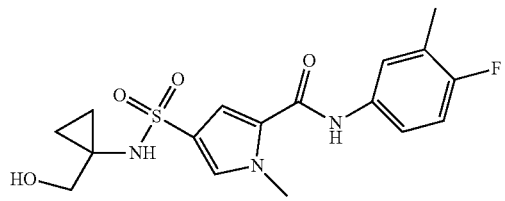 [SMILES: Cc1cc(NC(=O)c2cc(S(=O)(=O)NC3(CO)CC3)cn2C)ccc1F]

Compound 12 was prepared similarly as described for compound 11, using 1-amino-cyclopropanemethanol instead of 3-methyloxolan-3-amine hydrochloride. After work up, the obtained solid was stirred in boiling CH$_2$Cl$_2$ and filtered off. The obtained white solid was recrystallized from Acetonitrile, resulting in compound 12 (1.021 g). Method B; Rt: 0.84 min. m/z: 380.1 (M−H)$^-$ Exact mass: 381.1. $^1$H NMR (360 MHz, DMSO-d$_6$) δ ppm 0.54-0.65 (m, 4H), 2.23 (d, J=1.8 Hz, 3H), 3.37 (d, J=5.9 Hz, 2H), 3.90 (s, 3H), 4.59 (t, J=5.9 Hz, 1H), 7.10 (t, J=9.1 Hz, 1H), 7.27 (d, J=1.8 Hz, 1H), 7.49-7.55 (m, 2H), 7.65 (dd, J=7.1, 2.4 Hz, 1H), 7.75 (s, 1H), 10.03 (s, 1H).

Compound 13: N-(4-fluoro-3-methyl-phenyl)-1-methyl-4-[(1-methyl-5-oxo-pyrrolidin-3-yl)sulfamoyl]pyrrole-2-carboxamide

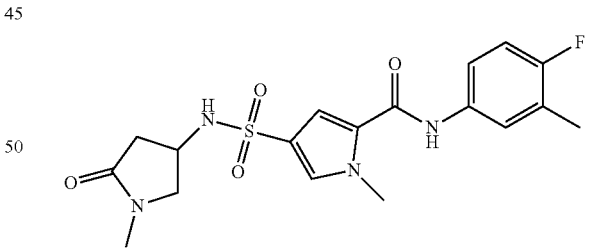

Compound 13 was prepared similarly as described for compound 7, using 4-amino-1-methyl-pyrrolidin-2-one hydrochloride instead of 3-methyloxetan-3-yl)methanamine. Method B; Rt: 0.81 min. m/z: 409.1 (M+H)$^+$ Exact mass: 408.1. $^1$H NMR (400 MHz, DMSO-d$_6$) δ ppm 2.07-2.15 (m, 1H), 2.23 (d, J=1.8 Hz, 3H), 2.35-2.50 (m, 1H), 2.67 (s, 3H), 3.18 (dd, J=10.1, 4.6 Hz, 1H), 3.52 (dd, J=10.1, 7.3 Hz, 1H), 3.76-3.85 (m, 1H), 3.92 (s, 3H), 7.10 (t, J=9.2 Hz, 1H), 7.31 (d, J=2.0 Hz, 1H), 7.46-7.55 (m, 1H), 7.58 (d, J=1.8 Hz, 1H), 7.64 (dd, J=7.0, 2.6 Hz, 1H), 7.72 (br. s, 1H), 10.03 (s, 1H). Compound 13, was separated in it's enantiomers compound 13a and compound 13b by preparative SFC (Stationary phase: Chiralpak Daicel IC 20×250 mm), Mobile phase: $CO_2$, MeOH with 0.4% $iPrNH_2$) The desired fractions were concentrated in vacuo and dried in vacuo yielding compound 13a (192 mg) and compound 13b (200 mg) as white powders. Columns: ID-H (diacel) 250 mm×4.6 mm, Flow: 5 mL/min. Mobile phase: 30% MeOH (containing 0.2% $iPrNH_2$) hold 4.00 min, up to 50% in 1 min and hold 2.00 min at 50%. Temperature: 40° C. Rt: 13a: 2.2 min; 13b 2.5 min.

Compound 14: N-(4-fluoro-3-methyl-phenyl)-4-[[3-(2-hydroxyethyl)oxetan-3-yl]sulfamoyl]-1-methyl-pyrrole-2-carboxamide

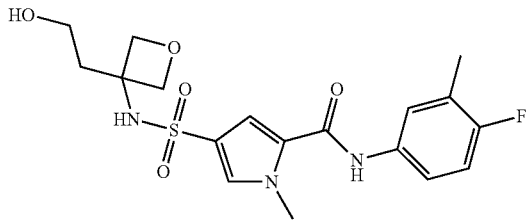 [SMILES: Cc1cc(NC(=O)c2cc(S(=O)(=O)NC3(CCO)COC3)cn2C)ccc1F]

Compound 14 was prepared similarly as described for compound 7, using 2-(3-aminooxetan-3-yl)ethanol instead of 3-methyloxetan-3-yl)methanamine, resulting in compound 14 (1.09 g) as a white powder. Method B; Rt: 0.80 min. m/z: 410.1 (M−H)⁻ Exact mass: 411.1. ¹H NMR (400 MHz, DMSO-$d_6$) δ ppm 2.14 (t, J=6.6 Hz, 2H), 2.23 (d, J=1.5 Hz, 3H), 3.42-3.50 (m, 2H), 3.91 (s, 3H), 4.32 (d, J=6.4 Hz, 2H), 4.45 (br. s, 1H), 4.56 (d, J=6.4 Hz, 2H), 7.10 (t, J=9.1 Hz, 1H), 7.33 (d, J=1.8 Hz, 1H), 7.46-7.54 (m, 1H), 7.56 (d, J=1.8 Hz, 1H), 7.63 (dd, J=7.0, 2.4 Hz, 1H), 7.84 (br. s., 1H), 10.02 (s, 1H).

Compound 15: N-(4-fluoro-3-methyl-phenyl)-4-[(3-hydroxycyclobutyl)sulfamoyl]-1-methyl-pyrrole-2-carboxamide

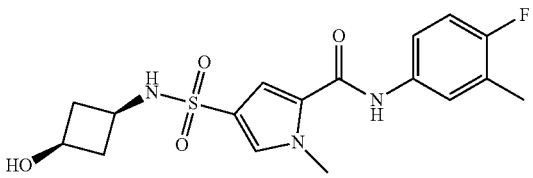 [SMILES: Cc1cc(NC(=O)c2cc(S(=O)(=O)N[C@H]3C[C@@H](O)C3)cn2C)ccc1F]

5-[(4-fluoro-3-methyl-phenyl)carbamoyl]-1-methyl-pyrrole-3-sulfonyl chloride (0.56 g, 1.7 mmol) was stirred in $CH_2Cl_2$ (15 mL). cis-3-aminocyclobutanol hydrochloride (0.23 g, 1.9 mmol) and DIPEA (1.5 mL, 8.5 mmol) were added at room temperature and the mixture was stirred for 60 hour. The solvent was evaporated and the obtained residue was purified by silica gel column chromatography (Methanol/Dichloromethane 2/98 to 4/96). The pure fractions were combined and the solvent was evaporated and the obtained residue was crystallized from dichloromethane, resulting in compound 15 (273 mg) as a white solid after filtration and drying in vacuo. Method B; Rt: 0.81 min. m/z: 380.1 (M−H)⁻ Exact mass: 381.1 ¹H NMR (360 MHz, DMSO-$d_6$) δ ppm 1.59-1.71 (m, 2H), 2.22 (d, J=1.5 Hz, 3H), 2.28-2.38 (m, 2H), 3.02-3.16 (m, 1H), 3.63-3.75 (m, 1H), 3.90 (s, 3H), 5.02 (d, J=5.9 Hz, 1H), 7.10 (dd, J=9.1 Hz, 1H), 7.28 (d, J=1.8 Hz, 1H), 7.47-7.55 (m, 3H), 7.65 (dd, J=7.1, 2.4 Hz, 1H), 10.03 (s, 1H).

Compound 16: 4-(tert-butylsulfamoyl)-N-(4-fluoro-3-methyl-phenyl)-1-methyl-pyrrole-2-carboxamide

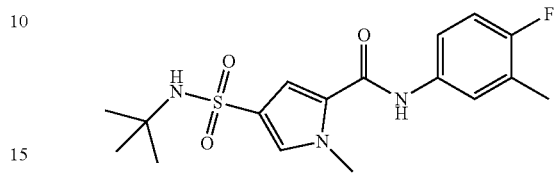

5-[(4-fluoro-3-methyl-phenyl)carbamoyl]-1-methyl-pyrrole-3-sulfonyl chloride (0.60 g, 1.8 mmol) was stirred in $CH_2Cl_2$ (15 mL). tert-butylamine (0.23 g, 1.9 mmol) and DIPEA (0.8 mL, 4.5 mmol) were added at room temperature and the mixture was stirred for 18 hours. The solvent was evaporated and EtOAc (50 mL) was added. After washing with 1M HCl (20 mL), the organic layer was dried with $Na_2SO_4$ and the solvent was evaporated. The obtained solid was dissolved in dichloromethane (10 mL) and the solvent was slowly evaporated at 50° C. The evaporation was stopped when precipitation commenced, and stirring was continued at room temperature for 15 minutes. The precipitate was filtered off, washed with dichloromethane (1 mL) and dried in vacuo at 50° C., resulting in compound 16 (136 mg). Method A; Rt: 1.79 min. m/z: 366.1 (M−H)⁻ Exact mass: 367.1. ¹H NMR (400 MHz, DMSO-$d_6$) δ ppm 1.17 (s, 9H), 2.23 (d, J=1.5 Hz, 3H), 3.90 (s, 3H), 7.05-7.13 (m, 2H), 7.29 (d, J=1.8 Hz, 1H), 7.45-7.55 (m, 2H), 7.64 (dd, J=7.0, 2.2 Hz, 1H), 10.00 (s, 1H).

Compound 17: 4-[[3-(cyanomethyl)oxetan-3-yl]sulfamoyl]-N-(4-fluoro-3-methyl-phenyl)-1-methyl-pyrrole-2-carboxamide

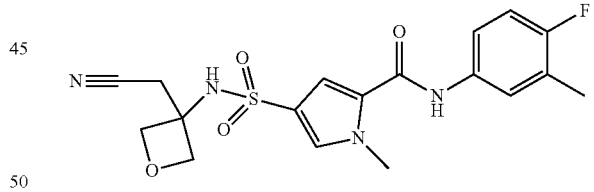

Compound 10 (0.46 g, 1.2 mmol) was dissolved in dry dichloromethane (30 mL) and dry DIPEA (0.31 mL, 1.8 mmol) was added. This mixture was cooled in an ice bath and stirred for 20 minutes. Then Methanesulfonyl Chloride (0.10 mL, 1.3 mmol) in dry dichloromethane (10 mL) was added dropwise over 10 minutes, after stirring 30 minutes more at 0° C., the mixture was washed with 0.5 M HCl (50 mL) and saturated aqueous $NaHCO_3$ (5 mL). The water layer was extracted with EtOAc (200 mL) and the combined organic layers were dried with $Na_2SO_4$. The solvent was removed in vacuo and the obtained residue was dissolved in dry DMSO. This solution was added dropwise to a solution of sodium cyanide (0.12 g, 2.4 mmol) in dry DMSO (25 mL) at 40° C. The mixture was stirred 2.5 hour at 40° C. After cooling to room temperature water (50 mL) was added. This mixture was extracted with diethylether (3×100 mL) and EtOAc (3×150 mL). The combined organic layer were dried on Na₂SO₄ and the solvent was evaporated. The obtained residue was purified by silica gel column chromatography by gradient elution with EtOAc/Heptane 0/100 to 100/0]. The desired fractions were combined and the solvent was removed, resulting compound 17 (264 mg) as a beige solid after drying in vacuo. Method B; Rt: 0.86 min. m/z: 405.2 (M−H)⁻ Exact mass: 406.1 ¹H NMR (360 MHz, DMSO-d₆) δ ppm 2.23 (d, J=1.8 Hz, 3H), 3.28 (s, 2H), 3.91 (s, 3H), 4.28 (d, J=7.0 Hz, 2H), 4.55 (d, J=7.0 Hz, 2H), 7.11 (t, J=9.3 Hz, 1H), 7.35 (d, J=2.2 Hz, 1H), 7.47-7.55 (m, 1H), 7.61-7.67 (m, 2H), 8.46-8.53 (m, 1H), 10.05 (s, 1H).

Compound 18: 4-[[1-(cyanomethyl)cyclopropyl]sulfamoyl]-N-(4-fluoro-3-methyl-phenyl)-1-methyl-pyrrole-2-carboxamide

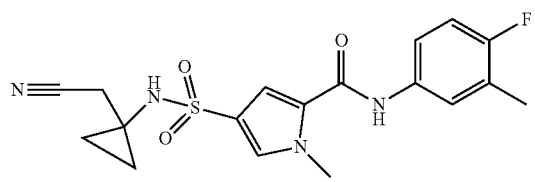 [SMILES: Cc1cc(NC(=O)c2cc(S(=O)(=O)NC3(CC#N)CC3)cn2C)ccc1F]

Prepared similarly as described for compound 17, starting from compound 12 instead of compound 10. Method C; Rt: 1.69 min. m/z: 389.1 (M−H)⁻ Exact mass: 390.1.

¹H NMR (360 MHz, CHLOROFORM-d) δ ppm 0.63-0.74 (m, 4H), 2.23 (d, J=1.8 Hz, 3H), 2.81 (s, 2H), 3.92 (s, 3H), 7.07-7.15 (m, 1H), 7.26-7.31 (m, 1H), 7.49-7.59 (m, 2H), 7.62-7.68 (m, 1H), 8.13-8.20 (m, 1H), 10.02-10.09 (m, 1H).

Compound 19: 4-(tert-butylsulfamoyl)-N-(3,4-difluorophenyl)-1-methyl-pyrrole-2-carboxamide

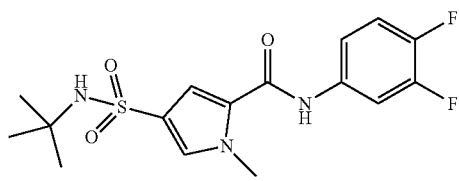 [SMILES: Cn1cc(S(=O)(=O)NC(C)(C)C)cc1C(=O)Nc1ccc(F)c(F)c1]

A solution of 3,4-difluoroaniline (1.9 mL, 19.2 mmol) in toluene (20 mL) was added dropwise (over 15 minutes) to a refluxing solution of 4-chlorosulfonyl-1-methyl-pyrrole-2-carbonylchloride in toluene (250 mL). After the addition, the reaction mixture was left to stir at reflux for 1 hour. The reaction mixture was left to cool to room temperature under nitrogen atmosphere while stirring. The grey suspension was concentrated and the obtained residue containing 5-[(3,4-difluorophenyl)carbamoyl]-1-methyl-pyrrole-3-sulfonyl chloride was dried in vacuo and further used without further purification. Tert-butylamine (0.3 mL, 2.8 mmol) was added to a suspension of crude 5-[(3,4-difluorophenyl)carbamoyl]-1-methyl-pyrrole-3-sulfonyl chloride (1.2 g, 2.55 mmol) in dry dichloromethane (20 mL) at room temperature. Next, NEt₃ (0.9 mL, 6.4 mmol) was added dropwise and the reaction mixture was stirred at room temperature for 1 hour and at 50° C. for 1.5 hour. The reaction mixture was diluted with EtOAc (250 mL). 0.5 N HCl (30 mL) was added to the reaction mixture and the layers were separated. The organic layer was washed again with 0.5 N NaOH (30 mL), followed by water. The organic layer was dried on MgSO₄, filtered and evaporated. The obtained residue was purified by silica gel column chromatography (eluent: CH₂Cl₂:MeOH 100:0→95:5). The obtained white solid was triturated in a small amount of CH₂Cl₂. After filtration, washing with CH₂Cl₂ and drying in vacuo, compound 19 (310 mg) was obtained as a white solid. Method B; Rt: 1.02 min. m/z: 370.1 (M−H)⁻ Exact mass: 371.1. ¹H NMR (360 MHz, DMSO-d₆) δ ppm 1.16 (s, 9H) 3.90 (s, 3H) 7.16 (s, 1H) 7.31 (d, J=1.8 Hz, 1H) 7.35-7.46 (m, 1H) 7.45-7.53 (m, 1H) 7.54 (d, J=1.5 Hz, 1H) 7.88 (ddd, J=13.5, 7.8, 2.2 Hz, 1H) 10.24 (s, 1H).

Compound 20: N-(3,4-difluorophenyl)-1-methyl-4-[(3-methyloxetan-3-yl)sulfamoyl]pyrrole-2-carboxamide

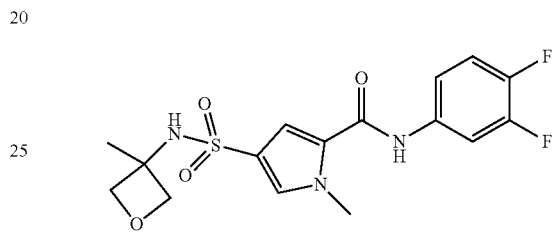

Compound 20 was prepared similarly as described for compound 19, using 3-methyl-3-oxetanamine hydrochloride instead of tert-butylamine. After work-up the obtained residue was triturated in a small amount of CH₂Cl₂ and filtered resulting in a white powder. The powder was triturated in EtOAc (1 mL), filtered and rinsed with a small amount of CH₂Cl₂ resulting in compound 20 (421 mg) as a white powder after drying in vacuo. Method B; Rt: 0.86 min. m/z: 384.1 (M−H)⁻ Exact mass: 385.1. ¹H NMR (360 MHz, DMSO-d₆) δ ppm 1.54 (s, 3H) 3.91 (s, 3H) 4.13 (d, J=6.2 Hz, 2H) 4.59 (d, J=6.2 Hz, 2H) 7.33 (d, J=1.8 Hz, 1H) 7.37-7.46 (m, 1H) 7.46-7.52 (m, 1H) 7.61 (d, J=1.8 Hz, 1H) 7.87 (ddd, J=13.5, 7.4, 2.6 Hz, 1H) 8.00 (s, 1H) 10.25 (s, 1H).

Compound 21: N-(3,4-difluorophenyl)-1-methyl-4-[[(3S)-tetrahydrofuran-3-yl]-sulfamoyl]pyrrole-2-carboxamide

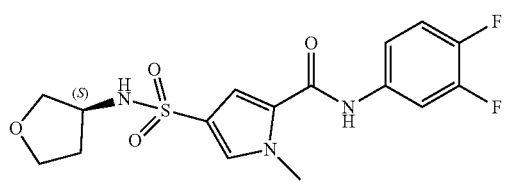

A solution of 3,4-difluoroaniline in toluene (50 mL) was slowly added (over 1 hour) to a refluxing solution of 4-chlorosulfonyl-1-methyl-pyrrole-2-carbonylchloride in toluene (200 mL). After addition, the reaction mixture was left to stir at reflux for 45 minutes.

The reaction mixture was left to cool to room temperature under nitrogen atmosphere while stirring and was then cooled with an ice bath. The precipitate was filtered and the filtrate was concentrated and dried in vacuo, resulting in a residue containing 5-[(3,4-difluorophenyl)carbamoyl]-1-methyl-pyrrole-3-sulfonyl chloride. (S)-3-aminotetrahydrofuran tosylate (0.59 g, 2.3 mmol) was added to a suspension of 5-[(3,4-difluorophenyl)carbamoyl]-1-methyl-pyrrole-3-sulfonyl chloride (1.0 g of the above obtained crude) in dry dichloromethane (50 mL) at room temperature. NEt$_3$ (0.72 mL, 5.2 mmol) was added dropwise and the mixture was further stirred at room temperature for 1 hour. 0.5 N HCl (30 mL) was added to the reaction mixture and the layers were separated. The organic layer was washed again with 0.5 N NaOH (30 mL) followed by water. The organic layer was dried on MgSO$_4$ and was evaporated.

The obtained residue was triturated in a small amount of CH$_2$Cl$_2$, filtered, and washed with a small amount of CH$_2$Cl$_2$, resulting in compound 21 (408 mg) as a white solid, after drying in vacuo. Method B; Rt: 0.84 min m/z: 384.0 (M−H)$^-$ Exact mass: 385.1. $^1$H NMR (360 MHz, DMSO-d$_6$) δ ppm 1.66-1.76 (m, 1H) 1.91-2.03 (m, 1H) 3.40-3.47 (m, 1H) 3.61 (td, J=8.1, 5.9 Hz, 1H) 3.65-3.75 (m, 3H) 3.92 (s, 3H) 7.33 (d, J=1.83 Hz, 1H) 7.37-7.46 (m, 1H) 7.46-7.52 (m, 1H) 7.57-7.62 (m, 2H) 7.88 (ddd, J=13.5, 7.6, 2.4 Hz, 1H) 10.26 (s, 1H).

Compound 22: N-(3,4-difluorophenyl)-4-(isopropylsulfamoyl)-1-methyl-pyrrole-2-carboxamide

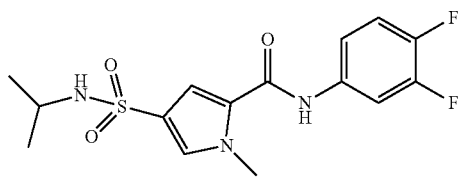 [SMILES: CC(C)NS(=O)(=O)c1cc(C(=O)Nc2ccc(F)c(F)c2)n(C)c1]

Compound 22 was prepared similarly as described for compound 21, using isopropylamine instead of (S)-3-aminotetrahydrofuran tosylate. After work-up (only 0.5 N HCl was used for washing) the obtained residue was purified by silica gel column chromatography (CH$_2$Cl$_2$:MeOH 100:0→95:5) resulting in compound 22 (534 mg) as a white solid after drying in vacuo. Method B; Rt: 0.94 min. m/z: 356.1 (M−H)$^-$ Exact mass: 357.1. $^1$H NMR (360 MHz, DMSO-d$_6$) δ ppm 1.01 (d, J=6.2 Hz, 6H) 3.18-3.28 (m, 1H) 3.91 (s, 3H) 7.23 (d, J=7.0 Hz, 1H) 7.32 (d, J=1.8 Hz, 1H) 7.36-7.46 (m, 1H) 7.46-7.53 (m, 1H) 7.56 (d, J=1.8 Hz, 1H) 7.88 (ddd, J=13.4, 7.5, 2.6 Hz, 1H) 10.25 (s, 1H).

Compound 23: N-(3,4-difluorophenyl)-1-methyl-4-[[(1R)-1-methylpropyl]sulfamoyl]pyrrole-2-carboxamide

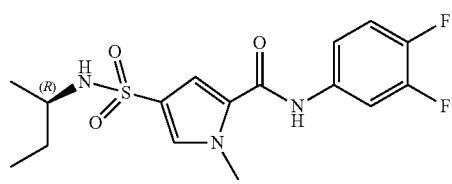

Compound 23 was prepared similarly as described for compound 22, using (R)-(−)-2-aminobutane instead of isopropylamine. After work up, the obtained residue was triturated in a small amount of CH$_2$Cl$_2$, filtered and washed with a small amount of CH$_2$Cl$_2$. The obtained solid was triturated with 0.5 N NaOH and filtered. The white solid was washed with water resulting in compound 23 (499 mg) as a white solid, after drying in vacuo. Method B; Rt: 1.00 min. m/z: 370.1 (M−H)$^-$ Exact mass: 371.1. $^1$H NMR (360 MHz, DMSO-d$_6$) δ ppm 0.76 (t, J=7.5 Hz, 3H) 0.95 (d, J=6.6 Hz, 3H) 1.28-1.41 (m, 2H) 3.00-3.13 (m, 1H) 3.91 (s, 3H) 7.18 (d, J=7.7 Hz, 1H) 7.32 (d, J=1.8 Hz, 1H) 7.36-7.46 (m, 1H) 7.46-7.53 (m, 1H) 7.56 (d, J=1.8 Hz, 1H) 7.88 (ddd, J=13.4, 7.7, 2.4 Hz, 1H) 10.25 (s, 1H).

Compound 24: N-(3,4-difluorophenyl)-4-[[(1R)-2-hydroxy-1-methyl-ethyl]sulfamoyl]-1-methyl-pyrrole-2-carboxamide

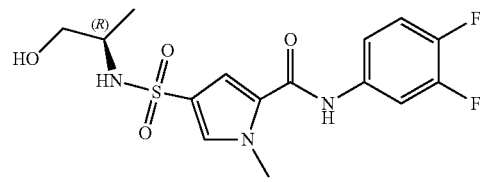

Compound 24 was prepared similarly as described for compound 19, using D-alaninol instead of tert-butylamine, using 5 equiv of NEt$_3$ and 1.5 hour stirring at room temperature. The reaction mixture was diluted with EtOAc (250 mL), 0.5 N HCl (30 mL) was added to the reaction mixture and the layers were separated. The organic layer was washed again with 0.5 N NaOH (30 mL) followed by water. The organic layer was dried on MgSO$_4$, filtered and evaporated. The obtained residue was triturated in a small amount of CH$_2$Cl$_2$, filtered and washed with a small amount of CH$_2$Cl$_2$ resulting in compound 24 (717 mg) as a white powder, after drying in vacuo. Method B; Rt: 0.81 min. m/z: 372.0 (M−H)$^-$ Exact mass: 373.1 $^1$H NMR (360 MHz, DMSO-d$_6$) δ ppm 0.97 (d, J=5.9 Hz, 3H) 3.06-3.17 (m, 2H) 3.32-3.39 (m, 1H), 3.91 (s, 3H) 4.69 (t, J=5.3 Hz, 1H) 7.14 (d, J=6.6 Hz, 1H) 7.32 (d, J=1.5 Hz, 1H) 7.36-7.46 (m, 1H) 7.46-7.53 (m, 1H) 7.57 (d, J=1.5 Hz, 1H) 7.88 (ddd, J=13.5, 7.6, 2.4 Hz, 1H) 10.25 (s, 1H).

Compound 25: N-(3,4-difluorophenyl)-4-[(3-hydroxycyclobutyl)sulfamoyl]-1-methyl-pyrrole-2-carboxamide

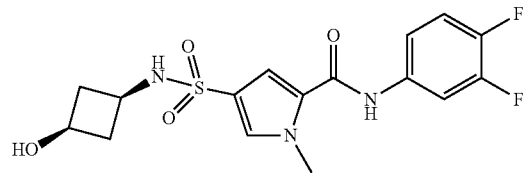 [SMILES: Cn1cc(S(=O)(=O)N[C@H]2C[C@@H](O)C2)cc1C(=O)Nc1ccc(F)c(F)c1]

Compound 25 was prepared similarly as described for compound 19, using cis-3-amino-cyclobutanol hydrochloride instead of tert-butylamine and adding 2.5 equiv more NEt$_3$ before heating to 50° C.

The residue obtained after work up was triturated in a small amount of CH$_2$Cl$_2$, filtered and washed with a small amount of CH$_2$Cl$_2$ resulting in a white powder, which was further triturated in MeOH/CH$_2$Cl$_2$ 5/95. After filtration, washing and drying in vacuo, compound 25 (150 mg) was obtained as a white powder. Method A; Rt: 0.80 min. m/z: 384.0 (M–H)⁻ Exact mass: 385.1. ¹H NMR (360 MHz, DMSO-d₆) δ ppm 1.59-1.71 (m, 2H) 2.27-2.39 (m, 2H) 3.03-3.15 (m, 1H) 3.64-3.76 (m, 1H) 3.91 (s, 3H) 5.02 (d, J=5.5 Hz, 1H) 7.28-7.33 (m, 1H) 7.36-7.46 (m, 1H) 7.46-7.57 (m, 2H) 7.88 (ddd, J=13.5, 7.6, 2.0 Hz, 1H) 10.24 (s, 1H).

Compound 91: N-(3,4-Difluorophenyl)-1-methyl-4-[(3-methyltetrahydrofuran-3-yl)sulfamoyl]-1H-pyrrole-2-carboxamide

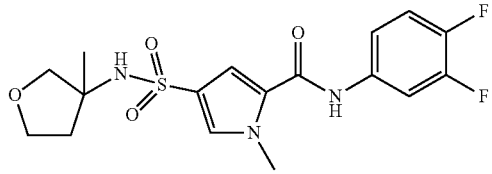 [SMILES: Cn1cc(S(=O)(=O)NC2(C)CCOC2)cc1C(=O)Nc1ccc(F)c(F)c1]

Compound 91 was prepared similarly as described for compound 19 using 3-methyloxolan-3-amine hydrochloride instead of tert-butylamine. Compound 91 (206 mg) was obtained as a white solid. Method B; Rt: 0.91 min. m/z: 398.1 (M–H)⁻ Exact mass: 399.1. ¹H NMR (360 MHz, DMSO-d₆) ppm 1.28 (s, 3H) 1.72 (dt, J=12.5, 7.5 Hz, 1H) 2.12-2.21 (m, 1H) 3.38 (d, J=8.8 Hz, 1H) 3.69-3.75 (m, 3H) 3.91 (s, 3H) 7.33 (d, J=2.2 Hz, 1H) 7.36-7.46 (m, 1H) 7.46-7.52 (m, 1H) 7.55-7.59 (m, 2H) 7.88 (ddd, J=13.4, 7.6, 2.4 Hz, 1H) 10.25 (s, 1H).

Compound 92: N-(3,4-Difluorophenyl)-1-methyl-4-{[(1R)-2,2,2-trifluoro-1-methylethyl]-sulfamoyl}-1H-pyrrole-2-carboxamide

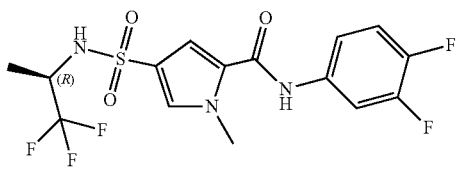

Compound 92 was prepared similarly as described for compound 19 using (R)-1,1,1-trifluoro-2-propylamine instead of tert-butylamine. Compound 92 precipitated from the basic 0.5 N NaOH water layer upon neutralization. Compound 92 was further purified by Preparative HPLC (Stationary phase: Uptisphere C₁₈ ODB—10 μm, 200 g, 5 cm), Mobile phase: 0.5% NH₄OAc solution in water+10% CH₃CN, CH₃CN). The collected fractions were concentrated (to the aqueous phase). The aqueous phase was acidified with HCl 1N and was extracted with EtOAc. The organic layer was dried on MgSO₄, filtered, and evaporated resulting in compound 92 (49 mg) as a white solid after drying in vacuo at 50° C. Method B; Rt: 1.03 min. m/z: 410.1 (M–H)⁻ Exact mass: 411.1.

¹H (360 MHz, DMSO-d₆) δ ppm 1.06 (d, J=7.0 Hz, 3H) 3.92 (s, 3H) 3.87-4.00 (m, 1H) 7.35 (d, J=1.8 Hz, 1H) 7.37-7.52 (m, 2H) 7.66 (d, J=1.8 Hz, 1H) 7.88 (ddd, J=13.4, 7.6, 2.4 Hz, 1H) 8.18 (d, J=8.8 Hz, 1H) 10.27 (s, 1H).

Compound 93: N-(3,4-Difluorophenyl)-1-methyl-4-{[(1S)-2,2,2-trifluoro-1-methyl-ethyl]sulfamoyl}-1H-pyrrole-2-carboxamide

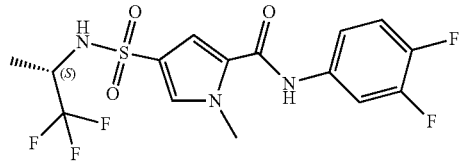

Compound 93 was prepared similarly as described for compound 92 using (S)-1,1,1-trifluoro-2-propylamine instead of (R)-1,1,1-trifluoro-2-propylamine. Method B; Rt: 1.03 min. m/z: 410.1 (M–H)⁻ Exact mass: 411.1.

Alternative Synthesis of Compound 92:

Methyl 1-methyl-4-[[(1R)-2,2,2-trifluoro-1-methyl-ethyl]sulfamoyl]pyrrole-2-carboxylate (6.61 g, 21.0 mmol) and 3,4-difluoroaniline (3.26 g, 25.24 mmol) were dissolved in tetrahydrofuran (150 mL) and this was stirred and cooled in an ice-water bath. Lithium bis(trimethylsilyl)amide in toluene (63.1 mL, 1 M, 63.1 mmol) was added dropwise over a period of 5 minutes. The resulting mixture was stirred for 1 h while cooling was continued. Another two equivalents of lithium bis(trimethylsilyl)amide in toluene (42.06 mL, 1 M, 42.06 mmol) were added and the resulting mixture was stirred for 2 hours at room temperature. The resulting mixture was quenched using ammonium chloride (sat./200 mL). The resulting mixture was extracted using EtOAc (3×250 mL). The combined extracts were washed with brine (250 mL), dried on Na₂SO₄, filtered and concentrated in vacuo yielding a brown powder. This was crystallised twice out of methanol/water. The precipitation was collected on a glass filter. The obtained powder was purified by silica gel column chromatography using gradient elution from heptane to EtOAc. (100:0 to 0:100) and next by silica gel column chromatography using gradient elution from dichloromethane to MeOH (100:0 to 99:1). The desired fractions were concentrated in vacuo yielding a powder. The obtained residue was crystallized out of methanol/water. The white crystals were collected on a glass filter and dried in a vacuum oven at 55° C. for 24 hours yielding compound 92 (4.32 g) as white needles. [α]₃₆₅²⁰=−11.6° (c 0.85 w/v %, MeOH). Differential scanning calorimetry: From 30 to 300° C. at 10° C./min: peak at 219.6° C.

Compound 95: N-(3,4-Difluorophenyl)-1-methyl-4-[(2,2,2-trifluoro-1,1-dimethylethyl)-sulfamoyl]-1H-pyrrole-2-carboxamide

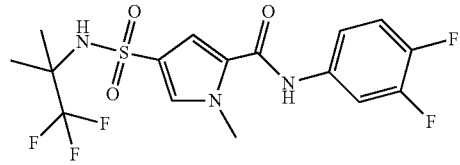 [SMILES: Cn1cc(S(=O)(=O)NC(C)(C)C(F)(F)F)cc1C(=O)Nc1ccc(F)c(F)c1]

5-[(3,4-difluorophenyl)carbamoyl]-1-methyl-pyrrole-3-sulfonyl chloride (648 mg, 1.374 mmol), 2,2,2-trifluoro-1,1-dimethyl-ethylamine (262 mg), DIPEA (0.296 mL, 1.72 mmol) in acetonitrile (65 mL) was refluxed overnight. 2,2,2-trifluoro-1,1-dimethyl-ethylamine (349 mg) were added and the reaction mixture was refluxed over weekend. The reaction mixture was concentrated. The residue was dissolved in EtOAc (100 mL), washed with 1M HCl, dried over sodium sulphate, filtered and concentrated. The obtained residue was subjected to silica gel column chromatography using a gradient from 10 to 100% EtOAc in heptane. The pure fractions were collected, concentrated and dried in vacuo at 50° C. yielding compound 95 as a white powder (162 mg). Method A; Rt: 1.78 min. m/z: 424.1 (M−H)⁻ Exact mass: 425.1. ¹H NMR (400 MHz, DMSO-d₆) δ ppm 1.36 (s, 6H), 3.92 (s, 3H), 7.32 (d, J=1.8 Hz, 1H), 7.36-7.45 (m, 1H), 7.46-7.52 (m, 1H), 7.58 (d, J=1.8 Hz, 1H), 7.87 (ddd, J=13.4, 7.6, 2.5 Hz, 1H), 8.04 (s, 1H), 10.25 (s, 1H).

Compound 26: 1-methyl-4-[[(3S)-tetrahydrofuran-3-yl]sulfamoyl]-N-(3,4,5-trifluoro-phenyl)pyrrole-2-carboxamide

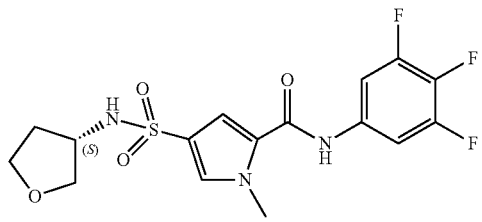

A solution of 3,4,5-trifluoroaniline (0.99 g, 6.7 mmol) in toluene (20 mL) was added dropwise to a refluxing solution of 4-chlorosulfonyl-1-methyl-pyrrole-2-carbonylchloride in toluene (80 mL). After the addition, the reaction mixture was left to stir at reflux for 1 hour. The mixture was cooled and concentrated in vacuo. The obtained crude containing 1-methyl-5-[(3,4,5-trifluorophenyl)carbamoyl]pyrrole-3-sulfonyl chloride was used a such. A solution of (S)-(−)-3-aminotetrahydrofuran p-toluenesulfonate (647 mg, 2.5 mmol) and DIPEA (0.98 mL, 5.7 mmol) in CH₂Cl₂ (10 mL) was added to crude 1-methyl-5-[(3,4,5-trifluorophenyl)carbamoyl]pyrrole-3-sulfonyl chloride (800 mg) in CH₂Cl₂ (150 mL) and stirred for 1 hour. The mixture was diluted with dichloromethane (400 mL) and washed with 1M HCl (2×), water and saturated NaHCO₃ solution. The organic layer was dried over magnesium sulphate, filtered and concentrated. The obtained residue was dissolved in hot MeOH (100 mL) and water was added. The formed white precipitate was filtered off, dried in vacuo and purified by silica gel column chromatography using a gradient from 20 to 100% EtOAc in heptane. The product fractions were concentrated and dried in vacuo resulting in compound 26 (286 mg) as a white powder. Method A; Rt: 1.67 min. m/z: 401.9 (M−H)⁻ Exact mass: 403.1. ¹H NMR (400 MHz, DMSO-d₆) δ ppm 1.66-1.76 (m, 1H), 1.91-2.03 (m, 1H), 3.39-3.47 (m, 1H), 3.55-3.65 (m, 1H), 3.65-3.75 (m, 3H), 3.92 (s, 3H), 7.33 (d, J=2.0 Hz, 1H), 7.58 (d, J=5.5 Hz, 1H), 7.61 (d, J=1.5 Hz, 1H), 7.63-7.71 (m, 2H), 10.33 (s, 1H).

Compound 27: 1-methyl-4-[(3-methyloxetan-3-yl)sulfamoyl]-N-(3,4,5-trifluorophenyl)pyrrole-2-carboxamide

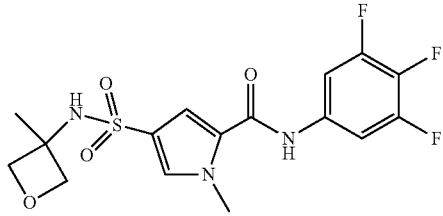 [SMILES: Cn1cc(S(=O)(=O)NC2(C)COC2)cc1C(=O)Nc1cc(F)c(F)c(F)c1]

3-methyl-3-oxetanamine hydrochloride (526 mg, 4.3 mmol) and DIPEA (1.8 mL) were dissolved in CH₂Cl₂ (5 mL). Crude 1-methyl-5-[(3,4,5-trifluorophenyl)carbamoyl]pyrrole-3-sulfonyl chloride (1.2 g, obtained as described for compound 26) was added and the reaction mixture was stirred for 30 minutes. The reaction mixture was directly loaded on silica gel column and purified by gradient elution from heptane to EtOAc, yielding compound 27 (758 mg) as a white powder after trituration in CH₂Cl₂ and drying in vacuo. Method A; Rt: 1.68 min. m/z: 401.9 (M−H)⁻ Exact mass: 403.1. ¹H NMR (400 MHz, DMSO-d₆) δ ppm 1.54 (s, 3H), 3.92 (s, 3H), 4.14 (d, J=6.5 Hz, 2H), 4.60 (d, J=6.1 Hz, 2H), 7.34 (d, J=1.6 Hz, 1H), 7.62 (d, J=2.0 Hz, 1H), 7.66 (dd, J=10.3, 6.7 Hz, 2H), 7.98 (s, 1H), 10.32 (s, 1H).

DSC: From 30 to 300° C. at 10° C./min, Peak: 218° C.

Compound 28: 1-methyl-4-[(3-methyloxetan-3-yl)sulfamoyl]-N-[3-(trifluoromethyl)-phenyl]pyrrole-2-carboxamide

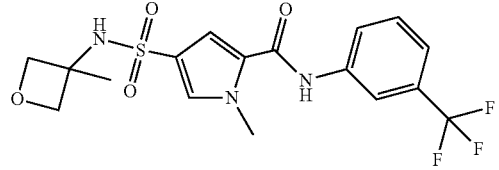 [SMILES: Cn1cc(S(=O)(=O)NC2(C)COC2)cc1C(=O)Nc1cccc(C(F)(F)F)c1]

3-(trifluoromethyl)aniline (0.41 mL, 3.3 mmol) was added dropwise to a refluxing solution of 4-chlorosulfonyl-1-methyl-pyrrole-2-carbonylchloride in toluene (25 mL). After the addition, the reaction mixture was left to stir at reflux for 4 hours. The mixture was cooled to room temperature and a solution of 3-methyl-3-oxetanamine hydrochloride (408 mg, 3.3 mmol) and DIPEA (0.57 mL) in CH₂Cl₂ (2 mL) was added. The mixture was stirred overnight at room temperature. More 3-methyl-3-oxetanamine hydrochloride (0.5 equiv) and DIPEA (0.5 equiv) in CH₂Cl₂ (2 mL) were added and the mixture was stirred for 2 hours at room temperature and 2 hours more at 50° C. The reaction mixture was allowed to reach room temperature and the formed precipitate was filtered off, triturated in MeOH (12 mL), filtered and dried in vacuo, resulting in compound 28 as a white powder. Method B; Rt: 0.99 min. m/z: 416.1 (M−H)⁻ Exact mass: 417.1. ¹H NMR (400 MHz, DMSO-d₆) δ ppm 1.55 (s, 3H), 3.93 (s, 3H), 4.14 (d, J=6.4 Hz, 2H), 4.60 (d, J=5.9 Hz, 2H), 7.39 (d, J=2.0 Hz, 1H), 7.43 (d, J=7.7 Hz, 1H), 7.58 (t, J=8.0 Hz, 1H), 7.61 (d, J=1.8 Hz, 1H), 7.95-8.02 (m, 2H), 8.19 (s, 1H), 10.32 (s, 1H).

Compound 29: 1-ethyl-N-(4-fluoro-3-methyl-phenyl)-4-(isopropylsulfamoyl)pyrrole-2-carboxamide

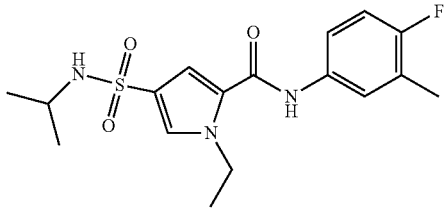 [SMILES: CCn1cc(S(=O)(=O)NC(C)C)cc1C(=O)Nc1ccc(F)c(C)c1]

To 4-chlorosulfonyl-1-ethyl-pyrrole-2-carboxylic acid (1 g, commercial from enamine, EN300-43738, 4.2 mmol) in CH$_2$Cl$_2$, (10 mL) at room temperature under N$_2$-atmosphere, DMF (1 drop) was added followed by dropwise addition of a solution of oxalyl chloride (1.44 mL, 0.0168 mol) in CH$_2$Cl$_2$ (5 mL) over 10 minutes. After addition, the reaction mixture as stirred at room temperature for 24 hours. The volatiles were evaporated, and co-evaporated with dry toluene (2×). The obtained residue containing 4-chlorosulfonyl-1-ethyl-pyrrole-2-carbonyl chloride was used as such in the next step.

A solution of 4-fluoro-3-methylaniline (527 mg, 4.2 mmol) in toluene was added dropwise to a solution of the above obtained crude 4-chlorosulfonyl-1-ethyl-pyrrole-2-carbonyl chloride in toluene at reflux over 5 minutes. The reaction mixture was refluxed 30 minutes and next allowed to reach room temperature. After stirring at room temperature for 2 hours the volatiles were removed in vacuo resulting in a residue containing 1-ethyl-5-[(4-fluoro-3-methyl-phenyl)carbamoyl]pyrrole-3-sulfonyl chloride that was used as such in the next step. Part of the as such obtained crude 1-ethyl-5-[(4-fluoro-3-methyl-phenyl)carbamoyl]pyrrole-3-sulfonyl chloride (708 mg) was dissolved in CH$_2$Cl$_2$ (5 mL) and isopropylamine (0.13 mL, 1.6 mmol) and DIPEA (0.72 mL, 4.2 mmol) were added and the reaction mixture stirred at room temperature for 30 minutes. The mixture was diluted with EtOAc (100 mL) and washed with 1 M HCl (2×10 mL). The organic layer was dried on Na$_2$SO$_4$, filtered and concentrated resulting in a residue that was purified using silica gel column chromatography (ethyl acetate in heptane from 10 to 100%) resulting in compound 29 (270 mg). Method B; Rt: 1.02 min. m/z: 366.2 (M–H)$^-$ Exact mass: 367.1. $^1$H NMR (400 MHz, DMSO-d$_6$) δ ppm 1.01 (d, J=6.6 Hz, 6H), 1.31 (t, J=7.0 Hz, 3H), 2.23 (d, J=1.5 Hz, 3H), 3.20-3.33 (m, 1H), 4.38 (q, J=7.0 Hz, 2H), 7.09 (t, J=9.1 Hz, 1H), 7.16 (d, J=7.0 Hz, 1H), 7.29 (d, J=1.8 Hz, 1H), 7.48-7.54 (m, 1H), 7.57 (d, J=1.8 Hz, 1H), 7.64 (dd, J=7.0, 2.4 Hz, 1H), 10.03 (br. s, 1H).

Compound 30: 1-ethyl-N-(4-fluoro-3-methyl-phenyl)-4-[[(3S)-tetrahydrofuran-3-yl]-sulfamoyl]pyrrole-2-carboxamide

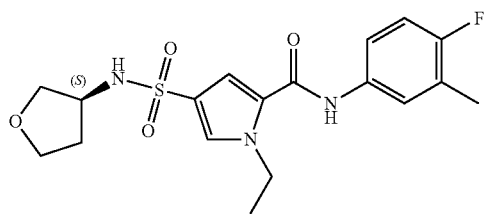

Crude 1-ethyl-5-[(4-fluoro-3-methyl-phenyl)carbamoyl]pyrrole-3-sulfonyl chloride (obtained as described for compound 29) was dissolved in CH$_2$Cl$_2$ (5 mL) and (S)-(−)-3-aminotetrahydrofuran p-toluenesulfonate (410 mg, 1.6 mmol)) and DIPEA (0.7 mL, 4.2 mmol) were added and the reaction mixture stirred at room temperature for 30 minutes. The mixture was diluted with EtOAc (100 mL) and washed with 1M HCl (2×10 mL). The organic layer was dried (Na$_2$SO$_4$), filtered and concentrated in vacuo to afford a residue that was purified using silica gel column chromatography (ethyl acetate in heptane from 10 to 100%) resulting in compound 30 (282 mg) as white powder after drying in vacuo. Method B; Rt: 0.92 min. m/z: 394.1 (M–H)$^-$ Exact mass: 395.1. $^1$H NMR (400 MHz, DMSO-d$_6$) δ ppm 1.32 (t, J=7.0 Hz, 3H), 1.64-1.75 (m, 1H), 1.90-2.02 (m, 1H), 2.23 (d, J=1.5 Hz, 3H), 3.36-3.45 (m, 1H), 3.61 (td, J=8.0, 5.9 Hz, 1H), 3.66-3.78 (m, 3H), 4.39 (q, J=7.1 Hz, 2H), 7.09 (t, J=9.1 Hz, 1H), 7.30 (d, J=1.8 Hz, 1H), 7.46-7.56 (m, 2H), 7.61 (d, J=1.8 Hz, 1H), 7.64 (dd, J=7.0, 2.4 Hz, 1H), 10.04 (br. s, 1H).

Compound 31: N-(4-fluoro-3,5-dimethyl-phenyl)-1-methyl-4-[[(3S)-tetrahydrofuran-3-yl]-sulfamoyl]pyrrole-2-carboxamide

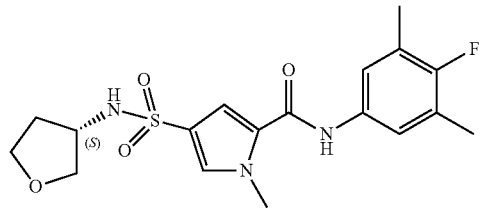

4-fluoro-3,5-dimethyl-benzenamine (995 mg, 7.1 mmol) dissolved in toluene (20 mL) was added dropwise to a solution of 4-chlorosulfonyl-1-methyl-pyrrole-2-carbonyl-chloride (1.7 g) in toluene (100 mL) at reflux. The reaction mixture was refluxed 1 hour and next allowed to cool to room temperature. (S)-(−)-3-aminotetrahydrofuran p-toluenesulfonate (2.0 g, 7.9 mmol) and DIPEA (3.1 mL, 17.9 mmol) dissolved in CH$_2$Cl$_2$ (50 mL) was added, the reaction mixture was stirred for 1 hour and then concentrated in vacuo. The obtained residue was dissolved in EtOAc (300 mL), washed with 1 M HCl (2×), water and saturated NaHCO$_3$. The solution was dried over magnesium sulphate, filtered and concentrated. The obtained residue was purified by silica gel column chromatography (gradient from 20 till 100% EtOAc in heptanes). The product fractions were concentrated and the obtained residue was recrystallized from hot EtOAc (100 mL) upon addition of heptane. The white crystals were filtered off and dried in vacuo resulting in compound 31 (1.7 g) as a white powder. Method A; Rt: 1.68 min. m/z: 393.9 (M–H)$^-$ Exact mass: 395.1. $^1$H NMR (400 MHz, DMSO-d$_6$) δ ppm 1.66-1.77 (m, 1H), 1.92-2.03 (m, 1H), 2.21 (d, J=2.0 Hz, 6H), 3.40-3.47 (m, 1H), 3.61 (td, J=8.1, 5.9 Hz, 1H), 3.66-3.76 (m, 3H), 3.91 (s, 3H), 7.31 (d, J=2.0 Hz, 1H), 7.43 (d, J=6.8 Hz, 2H), 7.50-7.58 (m, 2H), 9.94 (s, 1H).

Compound 32: N-(3-fluoro-5-methyl-phenyl)-1-methyl-4-[[(3S)-tetrahydrofuran-3-yl]-sulfamoyl]pyrrole-2-carboxamide

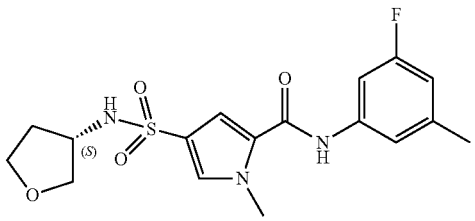

Compound 32 was prepared similarly as described for compound 31, using 3-fluoro-5-methylaniline instead of 4-fluoro-3,5-dimethyl-benzenamine. After silica gel column chromatography (EtOAc in heptanes 20% to 100%), compound 32 (2.2 g) was obtained as a white powder. Method A; Rt: 1.62 min. m/z: 379.9 (M−H)⁻ Exact mass: 381.1. ¹H NMR (400 MHz, DMSO-d₆) δ ppm 1.66-1.77 (m, 1H), 1.92-2.03 (m, 1H), 2.30 (s, 3H), 3.40-3.47 (m, 1H), 3.61 (td, J=8.0, 5.9 Hz, 1H), 3.66-3.76 (m, 3H), 3.92 (s, 3H), 6.75 (d, J=9.7 Hz, 1H), 7.34 (d, J=1.8 Hz, 1H), 7.35-7.38 (m, 1H), 7.47 (d, J=11.7 Hz, 1H), 7.55 (d, J=5.5 Hz, 1H), 7.58 (d, J=1.8 Hz, 1H), 10.12 (s, 1H).

Compound 33: N-(3,4-difluoro-5-methyl-phenyl)-4-(isopropylsulfamoyl)-1-methyl-pyrrole-2-carboxamide

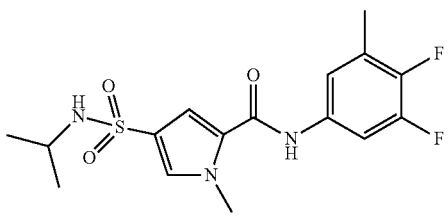 [SMILES: Cc1cc(NC(=O)c2cc(S(=O)(=O)NC(C)C)cn2C)cc(F)c1F]

3,4-difluoro-5-methylbenzoic acid (Alfa Aesar, H32313-03, 4.8 g, 26.9 mmol) was dissolved in t-BuOH (100 mL). NEt₃ (4.1 mL, 29.6 mmol) was added followed by diphenylphosphoryl azide (7.5 g, 27.4 mmol) and the reaction mixture was refluxed overnight. The mixture was concentrated and the obtained residue was purified by silica gel column chromatography using a gradient from 30 till 100% EtOAc in heptane. The product fractions were concentrated in vacuo yielding tert-butyl N-(3,4-difluoro-5-methyl-phenyl)carbamate (4.15 g) as a white powder. ¹H NMR (400 MHz, DMSO-d₆) δ ppm 1.47 (s, 9H), 2.22 (d, J=1.8 Hz, 3H), 7.11 (d, J=5.1 Hz, 1H), 7.26-7.38 (m, 1H), 9.47 (br. s., 1H). To a tert-butyl N-(3,4-difluoro-5-methyl-phenyl)carbamate (4.15 g) in CH₂Cl₂ (100 mL), HCl (6M in iPrOH, 13.7 mL) was added and the mixture was stirred for 3 hours. The reaction mixture was concentrated in vacuo. The white solid residue was dissolved in water (100 mL), alkalinized with 1M NaOH and extracted with ether. The organic layer was dried over MgSO₄, filtered and concentrated yielding 3,4-difluoro-5-methyl-aniline as a colorless oil which was stored under nitrogen in the dark and used a such. ¹H NMR (400 MHz, DMSO-d₆) δ ppm 2.13 (d, J=2.2 Hz, 3H), 5.11 (s, 2H), 6.16-6.23 (m, 1H), 6.31 (ddd, J=12.9, 6.5, 2.8 Hz, 1H).

3,4-difluoro-5-methyl-aniline (209 mg, 1.5 mmol) dissolved in toluene (20 mL) was added dropwise to a solution of 4-chlorosulfonyl-1-methyl-pyrrole-2-carbonylchloride (353 mg) in toluene (30 mL) at reflux. The reaction mixture was refluxed 2 hours, allowed to cool to room temperature and concentrated in vacuo. Isopropylamine (216 mg, 3.7 mmol) dissolved in CH₂Cl₂ (50 mL) was added and the reaction mixture was stirred overnight and next concentrated in vacuo. The obtained residue was dissolved in hot methanol (100 mL) and H₂O was added. The formed precipitate was filtered off and dried in vacuo, resulting in compound 33 (385 mg). Method A; Rt: 1.83 min. m/z: 370.0 (M−H)⁻ Exact mass: 371.1. ¹H NMR (400 MHz, DMSO-d₆) δ ppm 1.02 (d, J=6.4 Hz, 6H), 2.28 (d, J=2.0 Hz, 3H), 3.21-3.30 (m, 1H), 3.91 (s, 3H), 7.19 (d, J=7.0 Hz, 1H), 7.31 (d, J=1.8 Hz, 1H), 7.41 (d, J=5.9 Hz, 1H), 7.54 (d, J=1.8 Hz, 1H), 7.66 (ddd, J=12.9, 7.1, 2.4 Hz, 1H), 10.13 (s, 1H).

Compound 34: N-(3,4-difluoro-5-methyl-phenyl)-1-methyl-4-[[(1R)-1-methylpropyl]-sulfamoyl]pyrrole-2-carboxamide

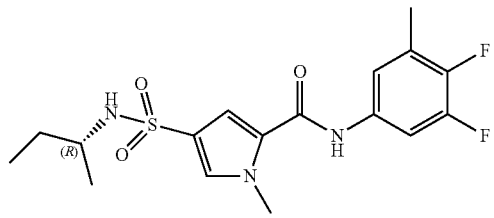

Compound 34 (1.18 g) was prepared similarly as described for compound 33, using (R)-(−)-2-aminobutane instead of iPrNH₂. Method A; Rt: 1.87 min. m/z: 384.1 (M−H)⁻ Exact mass: 385.1. ¹H NMR (400 MHz, DMSO-d₆) δ ppm 0.76 (t, J=7.4 Hz, 3H), 0.96 (d, J=6.6 Hz, 3H), 1.29-1.42 (m, 2H), 2.28 (d, J=1.8 Hz, 3H), 3.00-3.12 (m, 1H), 3.91 (s, 3H), 7.15 (d, J=7.7 Hz, 1H), 7.32 (d, J=2.0 Hz, 1H), 7.42 (d, J=5.7 Hz, 1H), 7.54 (d, J=1.8 Hz, 1H), 7.67 (ddd, J=13.0, 7.0, 2.4 Hz, 1H), 10.11 (s, 1H).

Compound 35: N-(3,4-difluoro-5-methyl-phenyl)-1-methyl-4-[(3-methyloxetan-3-yl)-sulfamoyl]pyrrole-2-carboxamide

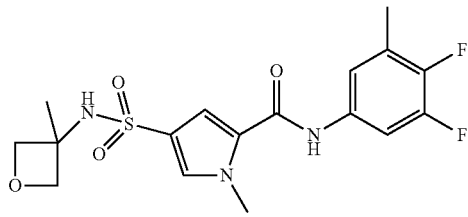 [SMILES: Cc1cc(NC(=O)c2cc(S(=O)(=O)NC3(C)COC3)cn2C)cc(F)c1F]

3,4-difluoro-5-methyl-aniline (600 mg, 4.2 mmol) dissolved in toluene (20 mL) was added dropwise to a solution of 4-chlorosulfonyl-1-methyl-pyrrole-2-carbonylchloride (1.0 g) in toluene (50 mL) at reflux. The reaction mixture was refluxed 2 hour, allowed to cool to room temperature and concentrated in vacuo. A mixture of 3-methyl-3-oxetanamine hydrochloride (570 mg, 4.6 mmol) and DIPEA (1.8 mL, 10.5 mmol) dissolved in CH₂Cl₂ (100 mL) was added and the reaction mixture was stirred overnight and next concentrated in vacuo. The obtained residue was dissolved in hot methanol (200 mL) and H$_2$O was added. The formed precipitate was filtered off and dried in vacuo, resulting in compound 35 (1.1 g) as a white powder. Method A; Rt: 1.66 min. m/z: 398.1 (M−H)$^-$ Exact mass: 399.1. $^1$H NMR (400 MHz, DMSO-d$_6$) δ ppm 1.54 (s, 3H), 2.28 (d, J=2.0 Hz, 3H), 3.91 (s, 3H), 4.14 (d, J=6.4 Hz, 2H), 4.60 (d, J=5.9 Hz, 2H), 7.33 (d, J=1.8 Hz, 1H), 7.41 (d, J=5.9 Hz, 1H), 7.59 (d, J=1.8 Hz, 1H), 7.66 (ddd, J=12.9, 7.0, 2.5 Hz, 1H), 7.96 (s, 1H), 10.13 (s, 1H).

Compound 36: N-(3,4-difluoro-5-methyl-phenyl)-4-[[(1R)-2-hydroxy-1-methyl-ethyl]-sulfamoyl]-1-methyl-pyrrole-2-carboxamide

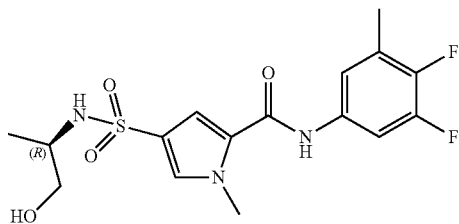

3,4-difluoro-5-methyl-aniline (600 mg, 4.2 mmol) dissolved in toluene (20 mL) was added dropwise to a solution of 4-chlorosulfonyl-1-methyl-pyrrole-2-carbonylchloride (353 mg) in toluene (100 mL) at reflux. The reaction mixture was refluxed 2 hours, allowed to cool to room temperature and concentrated in vacuo. D-alaninol (787 mg, 10.5 mmol) in CH$_2$Cl$_2$ (100 mL) was added, followed by CH$_3$CN (50 mL) and the reaction mixture was stirred overnight and next concentrated in vacuo. The obtained residue was dissolved in warm methanol (50 mL) and H$_2$O was added. The formed precipitate was filtered off and dried in vacuo, resulting in compound 36 (1.16 g).

Method A; Rt: 1.57 min. m/z: 386.0 (M−H)$^-$ Exact mass: 387.1. $^1$H NMR (400 MHz, DMSO-d$_6$) δ ppm 0.98 (d, J=6.2 Hz, 3H), 2.28 (d, J=2.0 Hz, 3H), 3.07-3.20 (m, 2H), 3.32-3.39 (m, 1H), 3.91 (s, 3H), 4.65 (t, J=5.5 Hz, 1H), 7.10 (d, J=6.8 Hz, 1H), 7.32 (d, J=2.0 Hz, 1H), 7.42 (d, J=5.9 Hz, 1H), 7.55 (d, J=1.8 Hz, 1H), 7.66 (ddd, J=12.9, 7.0, 2.5 Hz, 1H), 10.13 (s, 1H).

Compound 37: N-(3,4-difluoro-5-methyl-phenyl)-1-methyl-4-[[(3S)-tetrahydrofuran-3-yl]-sulfamoyl]pyrrole-2-carboxamide

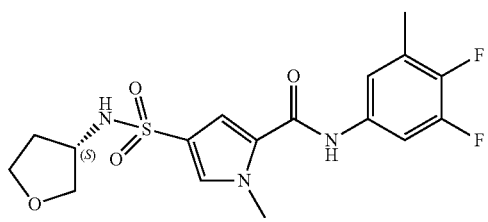

Compound 37 was prepared similarly as described for compound 35, using (S)-(−)-3-aminotetrahydrofuran p-toluenesulfonate instead of 3-methyl-3-oxetanamine hydrochloride. After reaction, the obtained residue was dissolved in EtOAc (300 mL), washed with 1M HCl (2×), water and saturated NaHCO$_3$. The solution was dried over magnesium sulphate, filtered and concentrated. The obtained residue was recrystallized from hot methanol (50 mL) upon addition of water. Compound 37 (464 mg) was obtained as white fluffy crystals after drying in vacuo. Method A; Rt: 1.65 min. m/z: 398.1 (M−H)$^-$ Exact mass: 399.1. $^1$H NMR (400 MHz, DMSO-d$_6$) δ ppm 1.66-1.77 (m, 1H), 1.90-2.03 (m, 1H), 2.28 (d, J=1.8 Hz, 3H), 3.40-3.47 (m, 1H), 3.61 (td, J=8.0, 5.9 Hz, 1H), 3.66-3.76 (m, 3H), 3.92 (s, 3H), 7.33 (d, J=2.0 Hz, 1H), 7.41 (d, J=5.9 Hz, 1H), 7.56 (d, J=5.5 Hz, 1H), 7.58 (d, J=1.8 Hz, 1H), 7.66 (ddd, J=12.9, 7.0, 2.5 Hz, 1H), 10.14 (s, 1H).

Compound 38: 4-(tert-butylsulfamoyl)-N-(3,4-difluoro-5-methyl-phenyl)-1-methyl-pyrrole-2-carboxamide

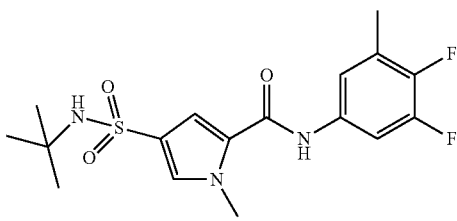 [SMILES: Cc1cc(NC(=O)c2cc(S(=O)(=O)NC(C)(C)C)cn2C)cc(F)c1F]

Compound 38 (399 mg) was prepared similarly as described for compound 33, using tert-butylamine instead of iPrNH$_2$. Method A; Rt: 1.86 min. m/z: 384.1 (M−H)$^-$ Exact mass: 385.1. $^1$H NMR (400 MHz, DMSO-d$_6$) δ ppm 1.17 (s, 9H), 2.28 (d, J=2.0 Hz, 3H), 3.90 (s, 3H), 7.11 (s, 1H), 7.31 (d, J=1.8 Hz, 1H), 7.38-7.44 (m, 1H), 7.52 (d, J=1.5 Hz, 1H), 7.66 (ddd, J=1.0 Hz, 1H), 10.11 (s, 1H).

Compound 39: N-[3-(difluoromethyl)-4-fluoro-phenyl]-1-methyl-4-[(3-methyloxetan-3-yl)sulfamoyl]pyrrole-2-carboxamide

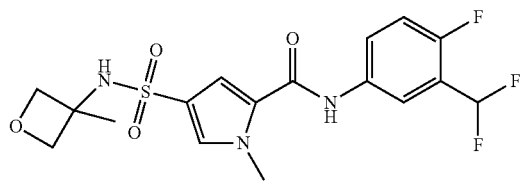 [SMILES: Cn1cc(S(=O)(=O)NC2(C)COC2)cc1C(=O)Nc1ccc(F)c(C(F)F)c1]

To 4-chlorosulfonyl-1-methyl-pyrrole-2-carbonylchloride (1.6 g) in toluene (100 mL) at reflux, 3-(difluoromethyl)-4-fluoro-aniline (1 equiv) was added dropwise (0.1 mL/min). After addition, the mixture was further refluxed for 15 minutes. The reaction mixture, containing 5-[[3-(difluoromethyl)-4-fluoro-phenyl]carbamoyl]-1-methyl-pyrrole-3-sulfonyl chloride was allowed to reach room temperature and was used as such in the next step. To half of the above obtained solution containing 5-[[3-(difluoromethyl)-4-fluoro-phenyl]carbamoyl]-1-methyl-pyrrole-3-sulfonyl chloride, 3-methyl-3-oxetanamine hydrochloride (449 mg, 3.6 mmol) and DIPEA (1.14 mL, 6.6 mmol) dissolved in CH$_2$Cl$_2$ (5 mL) were added and the reaction mixture was stirred overnight. More DIPEA (1.14 mL, 6.6 mmol) was added and the mixture was stirred over weekend. The volatiles were removed under reduced pressure and the residue was purified on silica using a heptane to EtOAc gradient yielding compound 39 (681 mg) as a white powder. Method C; Rt: 1.60 min. m/z: 416.1 (M–H)⁻ Exact mass: 417.1. ¹H NMR (400 MHz, DMSO-d$_6$) δ ppm 1.55 (s, 3H), 3.92 (s, 3H), 4.14 (d, J=6.4 Hz, 2H), 4.60 (d, J=5.9 Hz, 2H), 7.22 (t, J=54.4 Hz, 1H), 7.32-7.40 (m, 2H), 7.59 (d, J=1.8 Hz, 1H), 7.84-7.93 (m, 1H), 7.96 (s, 1H), 8.05 (dd, J=6.3, 2.5 Hz, 1H), 10.25 (s, 1H).

Compound 40: N-[3-(difluoromethyl)-4-fluoro-phenyl]-4-[[(1R)-2-hydroxy-1-methyl-ethyl]sulfamoyl]-1-methyl-pyrrole-2-carboxamide

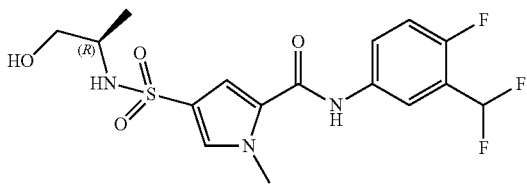

Compound 40 (670 mg) was prepared similarly as described for compound 39 using D-alaninol instead of 3-methyl-3-oxetanamine hydrochloride. Method C; Rt: 1.50 min. m/z: 404.0 (M–H)⁻ Exact mass: 405.1. ¹H NMR (400 MHz, DMSO-d$_6$) δ ppm 0.98 (d, J=6.2 Hz, 3H), 3.05-3.21 (m, 2H), 3.33-3.38 (m, 1H), 3.92 (s, 3H), 4.66 (t, J=5.5 Hz, 1H), 7.10 (d, J=6.8 Hz, 1H), 7.22 (t, J=54.4 Hz, 1H), 7.34 (d, J=2.0 Hz, 1H), 7.36 (t, J=9.5 Hz, 1H), 7.56 (d, J=1.5 Hz, 1H), 7.89 (dd, J=8.8, 3.3 Hz, 1H), 8.06 (dd, J=6.3, 2.5 Hz, 1H), 10.26 (s, 1H).

Compound 41: N-[4-fluoro-3-(trifluoromethyl)phenyl]-4-[[(1R)-2-hydroxy-1-methyl-ethyl]sulfamoyl]-1-methyl-pyrrole-2-carboxamide

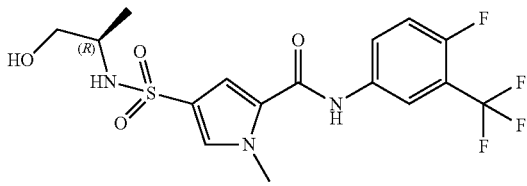

Compound 41 (376 mg) was prepared similarly as described for compound 40 using 4-fluoro-3-(trifluoromethyl)aniline instead of 3-(difluoromethyl)-4-fluoro-aniline.

Method B; Rt: 0.93 min. m/z: (M–H)⁻ Exact mass: 423.1. ¹H NMR (400 MHz, DMSO-d$_6$) δ ppm 0.98 (d, J=6.2 Hz, 3H), 3.07-3.20 (m, 2H), 3.34-3.39 (m, 1H), 3.92 (s, 3H), 4.66 (t, J=5.5 Hz, 1H), 7.11 (d, J=6.8 Hz, 1H), 7.35 (d, J=1.8 Hz, 1H), 7.50 (t, J=9.9 Hz, 1H), 7.57 (d, J=1.8 Hz, 1H), 7.99-8.08 (m, 1H), 8.20 (dd, J=6.6, 2.6 Hz, 1H), 10.34 (s, 1H).

Compound 42: N-[4-fluoro-3-(trifluoromethyl)phenyl]-1-methyl-4-[[(3S)-tetrahydrofuran-3-yl]sulfamoyl]pyrrole-2-carboxamide

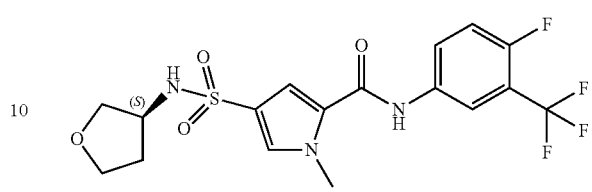

Compound 42 (569 mg) was prepared similarly as described for compound 41, using (S)-(−)-3-aminotetrahydrofuran-4-toluene-sulfonate instead of D-alaninol. Method C; Rt: 1.77 min. m/z: 434.1 (M–H)⁻ Exact mass: 435.1. ¹H NMR (400 MHz, DMSO-d$_6$) δ ppm 1.67-1.77 (m, 1H), 1.91-2.04 (m, 1H), 3.40-3.48 (m, 1H), 3.61 (td, J=8.0, 5.9 Hz, 1H), 3.66-3.77 (m, 3H), 3.93 (s, 3H), 7.36 (d, J=2.0 Hz, 1H), 7.50 (t, J=9.8 Hz, 1H), 7.57 (d, J=5.7 Hz, 1H), 7.60 (d, J=1.8 Hz, 1H), 7.99-8.07 (m, 1H), 8.20 (dd, J=6.4, 2.6 Hz, 1H), 10.35 (s, 1H).

Compound 43: N-[4-fluoro-3-(trifluoromethyl)phenyl]-1-methyl-4-[(3-methyloxetan-3-yl)-sulfamoyl]pyrrole-2-carboxamide

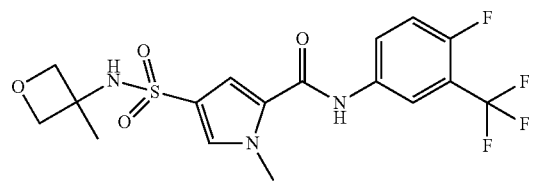 [SMILES: Cn1cc(S(=O)(=O)NC2(C)COC2)cc1C(=O)Nc1ccc(F)c(C(F)(F)F)c1]

Compound 43 (164 mg) was prepared similarly as described for compound 41, using 3-methyl-3-oxetanamine hydrochloride instead of D-alaninol. After silica gel column chromatography, the compound was recrystallized from MeOH. Method A; Rt: 1.73 min. m/z: 434.0 (M–H)⁻ Exact mass: 435.1. ¹H NMR (400 MHz, DMSO-d$_6$) δ ppm 1.55 (s, 3H), 3.92 (s, 3H), 4.14 (d, J=6.2 Hz, 2H), 4.60 (d, J=5.9 Hz, 2H), 7.36 (d, J=2.0 Hz, 1H), 7.50 (t, J=9.8 Hz, 1H), 7.61 (d, J=1.8 Hz, 1H), 7.97 (s, 1H), 7.99-8.07 (m, 1H), 8.20 (dd, J=6.5, 2.5 Hz, 1H), 10.34 (s, 1H).

Compound 44: N-[4-fluoro-3-(trifluoromethyl)phenyl]-4-(isopropylsulfamoyl)-1-methyl-pyrrole-2-carboxamide

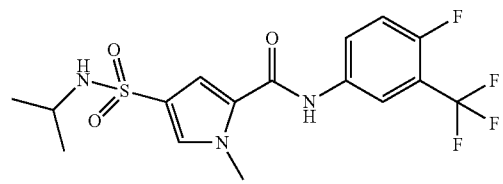 [SMILES: CC(C)NS(=O)(=O)c1cc(C(=O)Nc2ccc(F)c(C(F)(F)F)c2)n(C)c1]

Compound 44 (146 mg) was prepared similarly as described for compound 41, using isopropylamine instead of D-alaninol. After silica gel column chromatography, the compound triturated with MeOH and diisopropylether, resulting in compound 44 as a white solid. Method B; Rt: 1.06 min. m/z: 406.1 (M−H)⁻ Exact mass: 407.1. ¹H NMR (400 MHz, DMSO-d₆) δ ppm 1.02 (d, J=6.6 Hz, 6H), 3.22-3.29 (m, 1H), 3.92 (s, 3H), 7.20 (d, J=7.0 Hz, 1H), 7.35 (d, J=2.0 Hz, 1H), 7.50 (t, J=9.8 Hz, 1H), 7.56 (d, J=1.5 Hz, 1H), 7.98-8.07 (m, 1H), 8.20 (dd, J=6.4, 2.6 Hz, 1H), 10.33 (s, 1H).

Compound 45: N-[3-fluoro-5-(trifluoromethyl)phenyl]-1-methyl-4-[(3-methyloxetan-3-yl)sulfamoyl]pyrrole-2-carboxamide

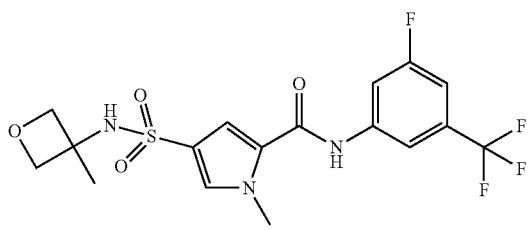 [SMILES: Cn1cc(S(=O)(=O)NC2(C)COC2)cc1C(=O)Nc1cc(F)cc(C(F)(F)F)c1]

4-chlorosulfonyl-1-methyl-pyrrole-2-carbonylchloride (800 mg) was dissolved in toluene (25 mL) and brought to reflux. 3-amino-5-fluorobenzotrifluoride (592 mg, 3.3 mmol) was added dropwise. After addition the reaction was refluxed for 4 hours. The reaction mixture was allowed to reach room temperature and 3-methyl-3-oxetanamine hydrochloride (408 mg, 3.3 mmol) and DIPEA (1.4 mL, 8.3 mmol) dissolved in CH₂Cl₂ (2 mL) were added and the reaction mixture was stirred overnight. More 3-methyl-3-oxetanamine hydrochloride (0.5 equiv) and DIPEA (0.5 equiv) in CH₂Cl₂ (2 mL) was added and the reaction mixture was stirred 2 hours more. The reaction mixture was brought to 50° C. and stirred for 2 hours. The volatiles were removed under reduced pressure and the residue was redissolved in EtOAc (30 mL). The formed precipitates were filtered off and the filtrate was evaporated to dryness. The obtained residue was triturated in MeOH (15 mL), filtered and dried in vacuo, yielding compound 45 (704 mg) as a white powder. Method B; Rt: 1.05 min. m/z: 434.2 (M−H) Exact mass: 435.1. ¹H NMR (400 MHz, DMSO-d₆) δ ppm 1.55 (s, 3H), 3.93 (s, 3H), 4.14 (d, J=6.4 Hz, 2H), 4.60 (d, J=6.2 Hz, 2H), 7.37 (d, J=8.6 Hz, 1H), 7.40 (d, J=2.0 Hz, 1H), 7.64 (d, J=1.8 Hz, 1H), 7.91-8.02 (m, 3H), 10.46 (s, 1H).

Compound 46: N-(3-bromo-4,5-difluoro-phenyl)-4-(isopropylsulfamoyl)-1-methyl-pyrrole-2-carboxamide

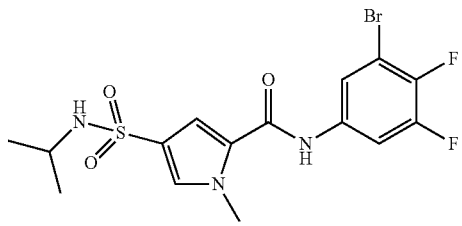 [SMILES: CC(C)NS(=O)(=O)c1cc(C(=O)Nc2cc(F)c(F)c(Br)c2)n(C)c1]

3-bromo-4,5-difluoroaniline (2.6 g, 12.8 mmol) in toluene (20 mL) was added dropwise to a solution of 4-chlorosulfonyl-1-methyl-pyrrole-2-carbonylchloride (3100 mg, 12.8 mmol) in toluene (160 mL) at reflux. The reaction mixture was refluxed 2 hours and next allowed to cool to room temperature. To one third of the above mixture containing 5-[(3-bromo-4,5-difluoro-phenyl)carbamoyl]-1-methyl-pyrrole-3-sulfonyl chloride, Isopropylamine (7.3 mL, 85.4 mmol) and DIPEA (2.2 mL, 12.8 mmol) in CH₂Cl₂ (70 mL) was added. The reaction mixture was stirred at room temperature. After a few seconds the homogeneous mixture became a suspension.

The solids were filtered, washed with CH₂Cl₂ (4 mL) and dried overnight in vacuo resulting in compound 46 (1.02 g) as an off white powder. Method B; Rt: 1.10 min. m/z: 436.1 (M−H)⁻ Exact mass: 437.0. ¹H NMR (400 MHz, DMSO-d₆) δ ppm 1.02 (d, J=6.6 Hz, 6H), 3.14-3.30 (m, 1H), 3.92 (s, 3H), 7.22 (d, J=7.0 Hz, 1H), 7.33 (d, J=1.8 Hz, 1H), 7.57 (d, J=1.8 Hz, 1H), 7.74-7.95 (m, 2H), 10.27 (s, 1H).

Compound 47: N-(3-bromo-4,5-difluoro-phenyl)-1-methyl-4-[[(1R)-1-methylpropyl]-sulfamoyl]pyrrole-2-carboxamide

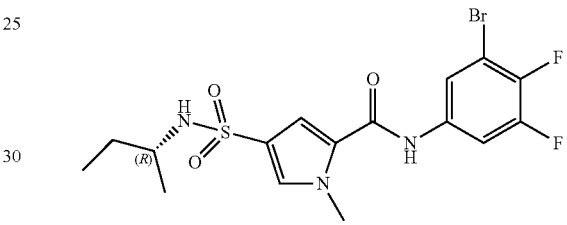

Compound 47 was prepared similarly as described for compound 46 using (R)-(−)-2-aminobutane (4 equiv) instead of isopropylamine. After addition of (R)-(−)-2-aminobutane, the mixture was stirred overnight. The solid was filtered, washed with CH₂Cl₂ and dried in vacuo, resulting in compound 47 (1.17 g) as an off-white solid. Method B; Rt: 1.15 min. m/z: 448.0 (M−H)⁻ Exact mass: 449.0. ¹H NMR (400 MHz, DMSO-d₆) δ ppm 0.76 (t, J=7.5 Hz, 3H), 0.96 (d, J=6.6 Hz, 3H), 1.24-1.46 (m, 2H), 3.07 (spt, J=6.7 Hz, 1H), 3.91 (s, 3H), 7.17 (d, J=7.5 Hz, 1H), 7.33 (d, J=1.8 Hz, 1H), 7.57 (d, J=1.8 Hz, 1H), 7.78-7.95 (m, 2H), 10.26 (s, 1H).

Compound 48: N-(3-bromo-4,5-difluoro-phenyl)-1-methyl-4-[(3-methyloxetan-3-yl)-sulfamoyl]pyrrole-2-carboxamide

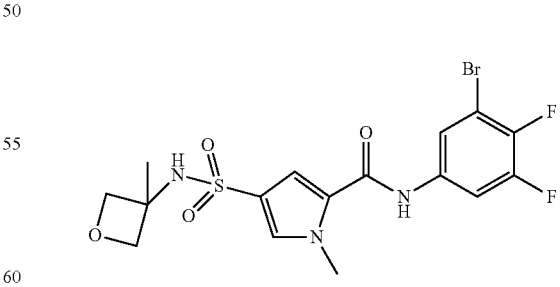

Compound 48 was prepared similarly as described for compound 46 using 3-methyl-3-oxetanamine (4 equiv) instead of isopropylamine. After addition of 3-methyl-3-oxetanamine, the mixture was stirred for 5 days. The formed precipitate was filtered, washed with CH₂Cl₂ and dried in vacuo, resulting in compound 48 (707 mg) as an off white powder. Method B; Rt: 1.00 min. m/z: 464.0 (M−H)⁻ Exact mass: 465.0. ¹H NMR (400 MHz, DMSO-d₆) δ ppm 1.54 (s, 3H), 3.92 (s, 3H), 4.14 (d, J=6.4 Hz, 2H), 4.59 (d, J=6.2 Hz, 2H), 7.35 (d, J=2.0 Hz, 1H), 7.62 (d, J=1.8 Hz, 1H), 7.84 (td, J=6.3, 2.5 Hz, 1H), 7.89 (ddd, J=7.7, 5.1, 2.4 Hz, 1H), 7.98 (br. s., 1H), 10.28 (br. s., 1H).

Compound 49: methyl 2-[[5-[(4-fluoro-3-methyl-phenyl)carbamoyl]-1-methyl-pyrrol-3-yl]sulfonylamino]-2-methyl-propanoate

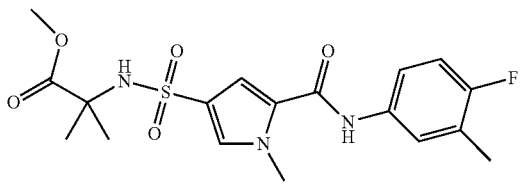 [SMILES: COC(=O)C(C)(C)NS(=O)(=O)c1cc(C(=O)Nc2ccc(F)c(C)c2)n(C)c1]

5-[(4-fluoro-3-methyl-phenyl)carbamoyl]-1-methyl-pyrrole-3-sulfonyl chloride (1.96 g) was stirred in CH₂Cl₂ (90 mL). DIPEA (1.0 mL, 5.9 mmol) and alpha-aminoisobutyric acid methyl ester hydrochloride (1 g, 6.5 mmol) were added under N₂-atmosphere at room temperature. The reaction mixture was stirred for 3 hour. More DIPEA (2 mL) was added and the reaction mixture was stirred for 80 hours. Next, the reaction mixture was washed with 1M HCl (100 mL). The organic layer was dried on Na₂SO₄. After evaporation of the solvent, the residue was purified by silica gel column chromatography (EtOAc/Heptane 0/100 to 100/0). The desired fractions were combined, the solvent was evaporated and the obtained solid dried in vacuo. Compound 49 (1.6 g) was obtained as a white solid. Method A; Rt: 1.70 min. m/z: 410.1 (M−H)⁻ Exact mass: 411.1. ¹H NMR (360 MHz, DMSO-d₆) δ ppm 1.35 (s, 6H), 2.23 (d, J=1.1 Hz, 3H), 3.54 (s, 3H), 3.90 (s, 3H), 7.10 (t, J=9.1 Hz, 1H), 7.29 (d, J=1.5 Hz, 1H), 7.48-7.56 (m, 2H), 7.65 (dd, J=7.0, 2.6 Hz, 1H), 7.85 (s, 1H), 10.04 (s, 1H).

Synthesis of 1-methyl-4-[(3-methyloxetan-3-yl)sulfamoyl]-1H-pyrrole-2-carboxylic acid

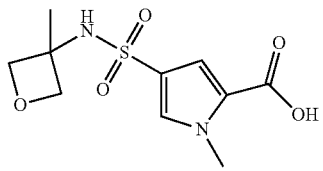 [SMILES: Cn1cc(S(=O)(=O)NC2(C)COC2)cc1C(=O)O]

Chlorosulfonic acid (80 mL) was cooled to 0° C. and methyl 1-methylpyrrole-2-carboxylate (20 g, 143.73 mmol) was added dropwise. After addition, the mixture was allowed to reach room temperature and stirred for another hour. The resulting mixture was added drop wise to a mechanically stirred, temperature controlled, ice-water mixture (1500 mL) keeping the temperature under 5° C. A white precipitation was formed. The obtained aqueous mixture was extracted using dichloromethane (3×500 mL). The combined extracts were dried on sodium sulphate, filtered and concentrated in vacuo yielding methyl 4-(chlorosulfonyl)-1-methyl-1H-pyrrole-2-carboxylate (29.4 g) as a white powder which was used as such. Methyl 4-(chlorosulfonyl)-1-methyl-1H-pyrrole-2-carboxylate (5 g, 1.04 mmol) was dissolved in acetonitrile (50 mL). diisopropylethylamine (9.06 mL, 52.6 mmol) was added, followed by 3-methyl-3-oxetanamine (1.92 g, 22.1 mmol) and the resulting mixture was refluxed for 2 hours. Then, the mixture was cooled to room temperature and concentrated in vacuo. The resulting residue was dissolved in dichloromethane (250 mL) and this was washed with HCl (2×150 mL). The organics were dried on sodium sulphate, filtered and concentrated in vacuo yielding methyl 1-methyl-4-[(3-methyloxetan-3-yl)sulfamoyl]-1H-pyrrole-2-carboxylate (6.07 g) as a beige powder which was used as such. Method B; Rt: 0.63 min. m/z: 287.1 (M−H)⁻ Exact mass: 288.1. Methyl 1-methyl-4-[(3-methyl-oxetan-3-yl)sulfamoyl]-1H-pyrrole-2-carboxylate (6.07 g, 21.05 mmol) was dissolved in tetrahydrofuran (60 mL). Lithium hydroxide (0.76 g, 31.58 mmol) in distilled water (8 mL) was added, followed by methanol (3 mL). The resulting mixture was stirred for 72 hours. Next, it was concentrated until only water remained and extra distilled water (15 mL) was added. After neutralization with hydrochloric acid (1M/aq/31.6 mL, 31.58 mmol). The resulting mixture was extracted using 2-methyltetrahydrofuran (3×20 mL). The combined extracts were dried on sodium sulphate, filtered and concentrated in vacuo yielding 1-methyl-4-[(3-methyl-oxetan-3-yl)sulfamoyl]-1H-pyrrole-2-carboxylic acid (5.77 g) as a bright white powder which was used as such. Method B; Rt: 0.26 min. m/z: 273.1 (M−H)⁻ Exact mass: 274.1

Compound 50: N-(3-cyano-4-fluorophenyl)-1-methyl-4-[(3-methyloxetan-3-yl)sulfamoyl]-1H-pyrrole-2-carboxamide

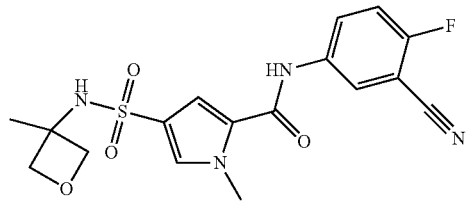 [SMILES: Cn1cc(S(=O)(=O)NC2(C)COC2)cc1C(=O)Nc1ccc(F)c(C#N)c1]

A tube was charged with 1-methyl-4-[(3-methyloxetan-3-yl)sulfamoyl]-1H-pyrrole-2-carboxylic acid (0.25 g, 0.91 mmol) and HATU (0.36 g, 0.96 mmol). N,N-dimethylformamide (1 mL) and diisopropylethylamine (0.47 mL, 2.73 mmol) were added and the mixture was stirred for 30 minutes. Next, 5-amino-2-fluorobenzonitrile (0.26 g, 1.82 mmol) was added at once and the resulting mixture was stirred at room temperature for 2 hours. The resulting mixture was added to distilled water (10 mL) under stirring and the mixture was allowed to stir for 1 hour. A precipitation was formed which was collected on a filter and dried in vacuo, yielding compound 50 (0.25 g) as a white powder. Method B; Rt: 0.83 min. m/z: 391.1 (M−H)⁻ Exact mass: 392.1. ¹H NMR (400 MHz, DMSO-d₆) δ ppm 1.54 (s, 3H), 3.92 (s, 3H), 4.14 (d, J=6.2 Hz, 2H), 4.60 (d, J=5.9 Hz, 2H), 7.35 (d, J=1.5 Hz, 1H), 7.53 (t, J=9.1 Hz, 1H), 7.61 (d, J=1.5 Hz, 1H), 7.93-8.07 (m, 2H), 8.21 (dd, J=5.7, 2.6 Hz, 1H), 10.36 (s, 1H).

Compound 51: N-[4-cyano-3-(trifluoromethyl)phenyl]-1-methyl-4-[(3-methyloxetan-3-yl)-sulfamoyl]-1H-pyrrole-2-carboxamide

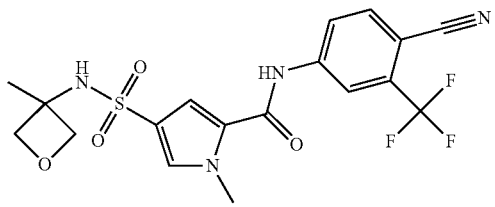 [SMILES: Cn1cc(S(=O)(=O)NC2(C)COC2)cc1C(=O)Nc1ccc(C#N)c(C(F)(F)F)c1]

A tube was charged with 1-methyl-4-[(3-methyloxetan-3-yl)sulfamoyl]-1H-pyrrole-2-carboxylic acid (0.2 g, 0.73 mmol) and HATU (0.29 g, 0.77 mmol). N,N-dimethylformamide (1 mL) and diisopropylethylamine 0.38 mL, 2.19 mmol) were added and the mixture was stirred for 30 minutes. To this was added 4-amino-2-(trifluoromethyl)benzonitrile (0.27 g, 1.46 mmol) at once and the resulting mixture was stirred at room temperature for 2 hours. The resulting mixture was added to distilled water (10 mL) under stirring. The resulting mixture was allowed to stir for 1 hour and then it was extracted using 2-methyl tetrahydrofuran (3×20 mL). The combined extracts were dried on sodium sulphate, filtered and concentrated in vacuo. The obtained crude was dissolved in dichloromethane (3 mL) and loaded directly on a silica plug. This was purified using column chromatography (gradient elution EtOAc/heptane 0:100 to 100:0) The desired fractions were concentrated in vacuo and dried in vacuo, resulting in compound 51 (18.1 mg) as a bright white powder. Method A; Rt: 1.67 min. m/z: 440.9 (M−H)⁻ Exact mass: 442.1 $^1$H NMR (400 MHz, DMSO-d$_6$) δ ppm 1.54 (s, 3H), 3.94 (s, 3H), 4.14 (d, J=6.4 Hz, 2H), 4.60 (d, J=5.9 Hz, 2H), 7.41-7.46 (m, 1H), 7.62-7.68 (m, 1H), 8.00 (br. s., 1H), 8.07-8.14 (m, 1H), 8.16-8.23 (m, 1H), 8.34-8.45 (m, 1H), 10.69 (br. s., 1H).

Compound 52: N-(3-cyano-4,5-difluoro-phenyl)-4-(isopropylsulfamoyl)-1-methyl-pyrrole-2-carboxamide

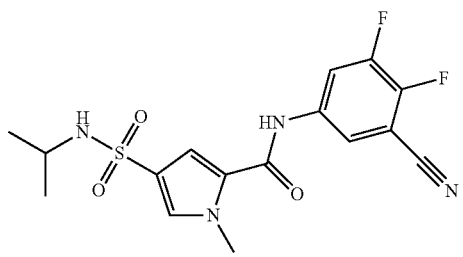 [SMILES: CC(C)NS(=O)(=O)c1cc(C(=O)Nc2cc(F)c(F)c(C#N)c2)n(C)c1]

A degassed suspension of compound 46 (400 mg, 0.917 mmol), Zn(CN)$_2$ (93.0 mg, 0.79 mmol) and tetrakis(triphenylphosphine)palladium (57.3 mg, 0.050 mmol) in DMF (3 mL) was stirred at 75° C. overnight. The mixture was cooled to room temperature and the solids were filtered off and washed with DMF (2 mL). The filtrate was then poured into water (50 mL). The precipitates were filtered and washed with water to afford an off white powder. This solid was purified using silica gel column chromatography (ethyl acetate in heptane from 0 to 50%) to afford a white powder (310 mg). This white powder is purified using Prep. LCMS. (Hypersyl C18 BDS-3 µm, 100×4.6 mm) Mobile phase (NH$_4$HCO$_3$ 0.2% in water, methanol) the desired fractions were combined and evaporated to dryness, dissolved in methanol again and evaporated to dryness and dried in vacuo to afford compound 52 (27.8 mg) as a white powder. Method B; Rt: 1.01 min. m/z: 381.1 (M−H)⁻ Exact mass: 382.1. $^1$H NMR (400 MHz, DMSO-d$_6$) δ ppm 1.02 (d, J=6.6 Hz, 6H), 3.20-3.30 (m, 1H), 3.92 (s, 3H), 7.23 (br. s., 1H), 7.34 (d, J=1.8 Hz, 1H), 7.59 (d, J=1.8 Hz, 1H), 7.98 (dt, J=4.6, 2.2 Hz, 1H), 8.14 (ddd, J=12.9, 7.5, 2.5 Hz, 1H), 10.47 (br. s., 1H).

Compound 53: 4-(tert-butylsulfamoyl)-N-(3-cyano-5-fluoro-phenyl)-1-methyl-pyrrole-2-carboxamide

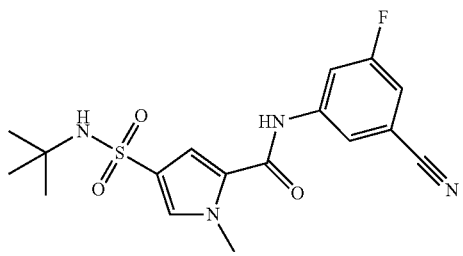 [SMILES: Cn1cc(S(=O)(=O)NC(C)(C)C)cc1C(=O)Nc1cc(F)cc(C#N)c1]

5-amino-3-fluorobenzonitrile (1034 mg, 7.6 mmol) dissolved in toluene (10 mL) was added dropwise during 5 minutes to a solution of 4-chlorosulfonyl-1-methyl-pyrrole-2-carbonyl chloride (1839 mg, 7.6 mmol) in toluene (190 mL) at reflux. The reaction mixture was refluxed 3 hours and concentrated in vacuo yielding crude 5-[(3-cyano-5-fluoro-phenyl)carbamoyl]-1-methyl-pyrrole-3-sulfonyl chloride as a brown powder which was used as such. (2.74 g). $^1$H NMR (400 MHz, acetonitrile-d$_3$) δ ppm 3.97 (s, 3H), 7.24-7.29 (m, 1H), 7.42 (d, J=2.0 Hz, 1H), 7.75 (d, J=1.8 Hz, 1H), 7.79-7.86 (m, 2H), 8.93 (br. s, 1H). A solution of 5-[(3-cyano-5-fluoro-phenyl)carbamoyl]-1-methyl-pyrrole-3-sulfonyl chloride (892 mg, 2.48 mmol) and tert-butylamine (544 mg, 7.44 mmol) in acetonitrile (100 mL) were stirred overnight. Water was added until crystallisation started. The crystals were filtered of and dried overnight in vacuo at 50° C., resulting in compound 53 (631 mg) Method A, Rt: 1.74 min m/z: 377.1 (M−H)⁻ Exact mass: 378.1. $^1$H NMR (400 MHz, DMSO-d$_6$) δ ppm 1.17 (s, 9H), 3.92 (s, 3H), 7.15 (s, 1H), 7.37 (d, J=2.0 Hz, 1H), 7.52-7.56 (m, 1H), 7.57 (d, J=1.8 Hz, 1H), 7.96 (d, J=11.2 Hz, 1H), 7.99-8.01 (m, 1H), 10.44 (s, 1H).

Compound 54: N-(3-cyano-5-fluoro-phenyl)-1-methyl-4-[(3-methyloxetan-3-yl)-sulfamoyl]pyrrole-2-carboxamide

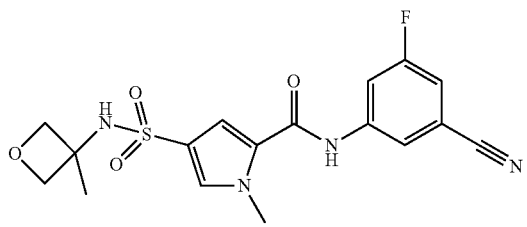 [SMILES: Cn1cc(S(=O)(=O)NC2(C)COC2)cc1C(=O)Nc1cc(F)cc(C#N)c1]

A solution of 5-[(3-cyano-5-fluoro-phenyl)carbamoyl]-1-methyl-pyrrole-3-sulfonyl chloride (924 mg, 2.57 mmol) and 3-methyl-3-oxetanamine (559 mg, 6.4 mmol) in acetonitrile (100 mL) was stirred overnight. Water was added until crystallisation started. The crystals were filtered of and dried overnight in vacuo at 50° C., resulting in compound 54 (630 mg) Method A, Rt: 1.52 min m/z: 391.1 (M−H)⁻ Exact mass: 392.1

¹H NMR (400 MHz, DMSO-d₆) δ ppm 1.54 (s, 3H), 3.93 (s, 3H), 4.14 (d, J=6.4 Hz, 2H), 4.60 (d, J=5.9 Hz, 2H), 7.38 (d, J=2.0 Hz, 1H), 7.52-7.58 (m, 1H), 7.64 (d, J=1.5 Hz, 1H), 7.93-7.98 (m, 1H), 7.98-8.01 (m, 2H), 10.46 (s, 1H).

Compound 55: N-(3-cyanophenyl)-1-methyl-4-[(3-methyloxetan-3-yl)sulfamoyl]pyrrole-2-carboxamide

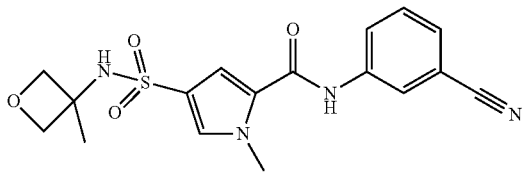 [SMILES: Cn1cc(S(=O)(=O)NC2(C)COC2)cc1C(=O)Nc1cccc(C#N)c1]

3-aminobenzonitrile (360 mg, 3.0 mmol) dissolved in toluene (10 mL) was added dropwise to a solution of 4-chlorosulfonyl-1-methyl-pyrrole-2-carbonyl chloride (752 mg, 3.1 mmol) in toluene (90 mL) at reflux. The reaction mixture was refluxed 2.5 hours, decanted hot and concentrated in vacuo yielding crude 5-[(3-cyanophenyl)carbamoyl]-1-methyl-pyrrole-3-sulfonyl chloride. A solution of 3-methyloxetan-3-amine (0.271 g, 3.11 mmol) in CH₃CN (10 mL, p.a. dried on molecular sieves) was added to a stirring solution of 5-[(3-cyanophenyl)carbamoyl]-1-methyl-pyrrole-3-sulfonyl chloride (1.00 g, 3.11 mmol) in CH₃CN (40 mL, p.a. dried on molecular sieves). DIPEA (1.07 mL, 6.21 mol) was added, and the reaction mixture was stirred at room temperature for 18 hours. The volatiles were evaporated. The residue was purified by silica gel column chromatography using EtOAc-heptane 0/100 to 100/0 as eluent. The desired fractions were combined and evaporated. The residue was stirred in CH₂Cl₂ (4 mL), filtered off, washed with CH₂Cl₂ (3×), and dried in vacuo at 50° C., resulting in compound 55 (0.43 g). Method A; Rt: 1.42 min. m/z: 373.0 (M−H)⁻ Exact mass: 374.1. ¹H NMR (400 MHz, DMSO-d₆) δ ppm 1.55 (s, 3H), 3.93 (s, 3H), 4.14 (d, J=6.4 Hz, 2H), 4.60 (d, J=5.9 Hz, 2H), 7.38 (d, J=2.0 Hz, 1H), 7.50-7.59 (m, 2H), 7.61 (d, J=1.5 Hz, 1H), 7.85-8.10 (m, 2H), 8.16-8.24 (m, 1H), 10.00-10.67 (m, 1H).

Compound 56: N-(2,6-dideuterio-4-fluoro-3-methyl-phenyl)-1-methyl-4-[(3-methyloxetan-3-yl)sulfamoyl]pyrrole-2-carboxamide

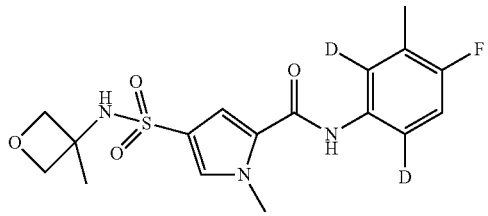 [SMILES: [2H]c1cc(F)c(C)c([2H])c1NC(=O)c1cc(S(=O)(=O)NC2(C)COC2)cn1C]

4-fluoro-3-methyl-aniline (1386 mg, 11.075 mmol), 1M DCl (2075 mg, 11.075 mmol) in 11 mL D₂O was heated in the microwave at 180° C. during 30 minutes. The reaction mixture was diluted with distilled water (50 mL), alkalanised with 1M NaOH, diluted with brine until product separates as oil and extracted with Et₂O. The organic layer was dried over magnesium sulphate, filtered and concentrated yielding 2,6-dideuterio-4-fluoro-3-methyl-aniline (1068 mg) as a light brown colored oil which used as such.

¹H NMR (400 MHz, DMSO-d₆) δ ppm 2.09 (d, J=2.0 Hz, 3H), 4.79 (br. s., 2H), 6.75 (d, J=9.9 Hz, 1H). 2,6-dideuterio-4-fluoro-3-methyl-aniline (1068 mg, 8.40 mmol) dissolved in toluene (10 mL) was added dropwise during 5 minutes to a solution of 4-chlorosulfonyl-1-methyl-pyrrole-2-carbonyl chloride (2033 mg, 8.40 mmol) in toluene (210 mL) at reflux. The reaction mixture was refluxed 90 minutes and concentrated in vacuo yielding crude 5-[(2,6-dideuterio-4-fluoro-3-methyl-phenyl)carbamoyl]-1-methyl-pyrrole-3-sulfonyl chloride as a grey powder which was used as such. (2810 mg). Method A; Rt: 1.91 min m/z: 331.0 (M−H)⁻ Exact mass: 332.0. ¹H NMR (400 MHz, CHLOROFORM-d) δ ppm 2.30 (d, J=2.0 Hz, 3H), 4.05 (s, 3H), 7.01 (d, J=9.2 Hz, 1H), 7.14 (d, J=1.8 Hz, 1H), 7.50 (d, J=1.5 Hz, 1H), 7.57 (br. s., 1H). 3-methyl-3-oxetanamine (491 mg, 5.63 mmol) and DIPEA (0.97 mL, 5.63 mmol) were added to a solution of 5-[(2,6-dideuterio-4-fluoro-3-methyl-phenyl)carbamoyl]-1-methyl-pyrrole-3-sulfonyl chloride (750 mg, 2.25 mmol) in dichloromethane (100 mL) and stirred overnight and concentrated in vacuo at 50° C. The residue was dissolved in EtOAc (150 mL), washed twice with 1M HCl, water and saturated NaHCO₃ solution. The solution was dried over sodium sulphate, filtered and concentrated. The residue was dissolved in warm EtOAc (75 mL) and the product crystallized upon addition of heptane (350 mL) The white crystals were filtered off and dried overnight in vacuo at 50° C., resulting in compound 56 (532 mg). Method A, Rt: 1.56 min m/z: 382.1 (M−H)⁻ Exact mass: 383.1. ¹H NMR (400 MHz, DMSO-d₆) δ ppm 1.55 (s, 3H), 2.23 (d, J=2.0 Hz, 3H), 3.91 (s, 3H), 4.13 (d, J=6.4 Hz, 2H), 4.60 (d, J=5.9 Hz, 2H), 7.09 (d, J=9.5 Hz, 1H), 7.32 (d, J=2.0 Hz, 1H), 7.56 (d, J=1.8 Hz, 1H), 7.94 (s, 1H), 10.02 (s, 1H).

Compound 57: N-(3-chloro-4,5-difluoro-phenyl)-4-(isopropylsulfamoyl)-1-methyl-pyrrole-2-carboxamide

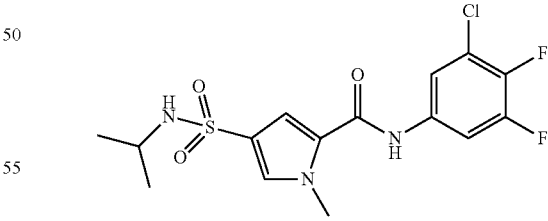

3-chloro-4,5-difluorobenzoic acid (1011 mg, 52.5 mmol) was dissolved in tert-butyl alcohol (200 mL). Triethylamine (8 mL, 57.8 mmol) was added followed by diphenylphosphoryl azide (14.74 g, 53.6 mmol) and the reaction mixture was refluxed overnight. The reaction mixture was concentrated and purified by column chromatography on silica using a gradient from 10 till 100% EtOAc in heptane and again with 10% CH₂Cl₂ in heptane till 100% CH₂Cl₂. The product fractions were concentrated in vacuo yielding tert-butyl N-(3-chloro-4,5-difluoro-phenyl)carbamate as a white powder (10.68 g). Method A. Rt: 2.09 min m/z: 262.0 (M−H)⁻ Exact mass: 263.1. ¹H NMR (400 MHz, DMSO-d₆) δ ppm 1.48 (s, 9H), 7.37-7.57 (m, 2H), 9.74 (s, 1H). HCl (6 M in iPrOH) (20 mL, 120 mmol) was added to tert-butyl N-(3-chloro-4,5-difluoro-phenyl)carbamate (10.68 g, 40.5 mmol) dissolved in dichloromethane (200 mL) and stirred overnight. The reaction mixture was concentrated. The white solid residue was dissolved in water (100 mL), alkalinized with NaOH 1M and extracted with ether. The organic layer was dried over MgSO₄, filtered and concentrated yielding 3-chloro-4,5-difluoro-aniline (6.53 g) as a colorless oil which was stored under nitrogen in the dark. ¹H NMR (400 MHz, DMSO-d₆) δ ppm 5.53 (s, 2H), 6.34-6.61 (m, 2H).

3-chloro-4,5-difluoro-aniline (3.43 g, 20.95 mmol) dissolved in toluene (10 mL) was added dropwise during 5 minutes to a solution of 4-chlorosulfonyl-1-methyl-pyrrole-2-carbonyl chloride (5.07 g, 20.95 mmol) in toluene (525 mL) at reflux. The reaction mixture was refluxed 90 minutes and then concentrated in vacuo yielding crude 5-[(3-chloro-4,5-difluoro-phenyl)carbamoyl]-1-methyl-pyrrole-3-sulfonyl chloride (7.83 g) as a brown powder which was used as such. A mixture of 5-[(3-chloro-4,5-difluorophenyl)carbamoyl]-1-methyl-pyrrole-3-sulfonyl chloride (1002 mg, 2.58 mmol) and isopropylamine (457 mg, 7.73 mmol) in acetonitrile (100 mL) was stirred 60 minutes. Water was added until crystallisation began. The beige crystals were filtered off and dried in vacuo overnight at 50° C., resulting in compound 57 (706 mg). Method A, Rt: 1.88 min m/z: 390.0 (M−H)⁻ Exact mass: 391.1. ¹H NMR (400 MHz, DMSO-d₆) δ ppm 1.02 (d, J=6.6 Hz, 6H), 3.20-3.30 (m, 1H), 3.92 (s, 3H), 7.22 (d, J=6.8 Hz, 1H), 7.33 (d, J=2.0 Hz, 1H), 7.57 (d, J=1.8 Hz, 1H), 7.75-7.87 (m, 2H), 10.29 (s, 1H).

Compound 58: 4-(tert-butylsulfamoyl)-N-(3-chloro-4,5-difluoro-phenyl)-1-methyl-pyrrole-2-carboxamide

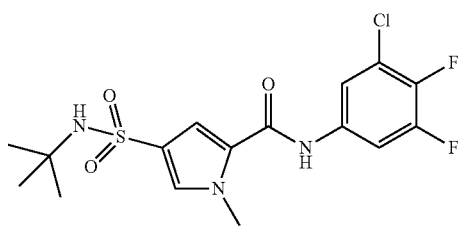 [SMILES: Cn1cc(S(=O)(=O)NC(C)(C)C)cc1C(=O)Nc1cc(F)c(F)c(Cl)c1]

A mixture of 5-[(3-chloro-4,5-difluoro-phenyl)carbamoyl]-1-methyl-pyrrole-3-sulfonyl chloride (1008 mg, 2.59 mmol), tert-butylamine (569 mg, 7.78 mmol) in acetonitrile (100 mL) was stirred 60 minutes. Water was added until crystallisation began. The beige crystals were filtered off and dried in vacuo overnight at 50° C., resulting in compound 58 (773 mg) Method A: Rt: 1.95 min m/z: 404.0 (M−H)⁻ Exact mass: 405.1 ¹H NMR (400 MHz, DMSO-d₆) δ ppm 1.17 (s, 9H), 3.91 (s, 3H), 7.14 (s, 1H), 7.33 (d, J=1.8 Hz, 1H), 7.55 (d, J=1.8 Hz, 1H), 7.76-7.86 (m, 2H), 10.28 (s, 1H).

Compound 59: N-(3-chloro-4,5-difluoro-phenyl)-1-methyl-4-[(3-methyloxetan-3-yl)-sulfamoyl]pyrrole-2-carboxamide

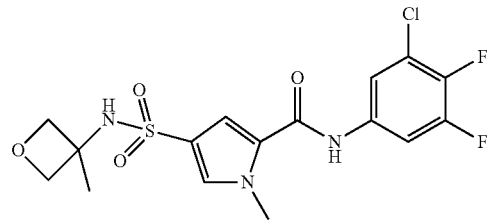 [SMILES: Cn1cc(S(=O)(=O)NC2(C)COC2)cc1C(=O)Nc1cc(F)c(F)c(Cl)c1]

A mixture of 5-[(3-chloro-4,5-difluoro-phenyl)carbamoyl]-1-methyl-pyrrole-3-sulfonyl chloride (1.0 g, 2.57 mmol) 3-methyl-3-oxetanamine (560 mg, 6.43 mmol) and acetonitrile (100 mL) was refluxed 30 minutes. The reaction mixture was cooled to 20° C. and diluted with water (350 mL). The product crystallized, was filtered off and dried in vacuo overnight yielding compound 59 as a beige powder (677 mg). Method A, Rt: 1.77 min m/z: 418.0 (M−H)⁻ Exact mass: 419.1. ¹H NMR (400 MHz, DMSO-d₆) δ ppm 1.54 (s, 3H), 3.92 (s, 3H), 4.14 (d, J=6.4 Hz, 2H), 4.60 (d, J=6.2 Hz, 2H), 7.34 (d, J=2.0 Hz, 1H), 7.62 (d, J=1.8 Hz, 1H), 7.74-7.87 (m, 2H), 7.98 (s, 1H), 10.30 (s, 1H).

Compound 60: N-(3-chloro-4,5-difluoro-phenyl)-1-methyl-4-[[(1R)-2,2,2-trifluoro-1-methyl-ethyl]sulfamoyl]pyrrole-2-carboxamide

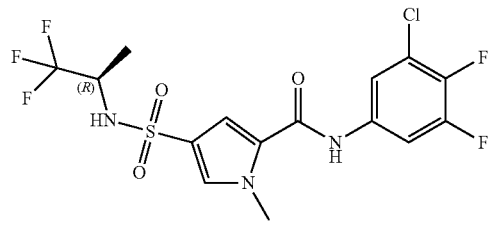

A mixture of 5-[(3-chloro-4,5-difluoro-phenyl)carbamoyl]-1-methyl-pyrrole-3-sulfonyl chloride (1008 mg, 2.59 mmol), (R)-1,1,1-trifluoro-2-propylamine (1026 mg, 9.07 mmol) in acetonitrile (100 mL) was refluxed overnight. Water was added until crystallisation started. The beige crystals were filtered of and dried overnight in vacuo at 50° C., resulting in compound 60 (673 mg). Method A Rt: 1.92 min m/z: 444.0 (M−H)⁻ Exact mass: 445.0. ¹H NMR (400 MHz, DMSO-d₆) δ ppm 1.08 (d, J=7.0 Hz, 3H), 3.83-4.01 (m, 4H), 7.36 (d, J=1.8 Hz, 1H), 7.67 (d, J=1.8 Hz, 1H), 7.75-7.87 (m, 2H), 8.19 (d, J=8.8 Hz, 1H), 10.32 (s, 1H).

Alternative Synthesis of Compound 60:
1-methyl-4-[[(1R)-2,2,2-trifluoro-1-methyl-ethyl]sulfamoyl]pyrrole-2-carboxylic acid (8.0 g, 26.7 mmol), HATU (12.7 g, 33.3 mmol), Et₃N (9.3 mL, 66.6 mmol) and 3-chloro-4,5-difluoro-aniline (5.44 g, 33.3 mmol) in DMF (30 mL) was stirred overnight at room temperature. The solution was subjected directly to column chromatography on a 330 g Reveleris cartridge in a Biotage system using a gradient from 10 till 100% EtOAc in heptane. The product fractions were concentrated and purified again in the same way. The product fractions were concentrated, dissolved in warm EtOAc en the product crystallized upon addition of heptane. The white crystals were filtered off and dried over weekend in vacuo at 50° C. The crystals (7.97 g) were dissolved in warm methanol (150 mL) and the product crystallized upon addition of water. The product was filtered off and dried in vacuo at 50° C. overnight, resulting in compound 60 (7.44 g). [α]$_{365}^{20}$=−9.5° (c 1.30 w/v %, MeOH). Differential scanning calorimetry: From 30 to 300° C. at 10° C./min: peak at 204.6° C.

Compound 65: N-(3-chloro-4,5-difluoro-phenyl)-4-[(3,3-difluoro-1-methyl-cyclo-butyl)sulfamoyl]-1-methyl-pyrrole-2-carboxamide

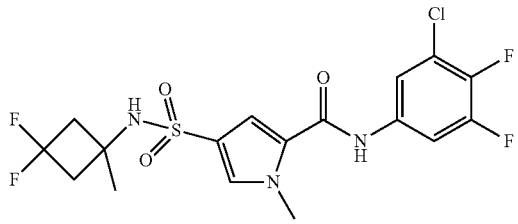 [SMILES: Cn1cc(S(=O)(=O)NC2(C)CC(F)(F)C2)cc1C(=O)Nc1cc(F)c(F)c(Cl)c1]

A mixture of 5-[(3-chloro-4,5-difluoro-phenyl)carbamoyl]-1-methyl-pyrrole-3-sulfonyl chloride (622 mg, 1.69 mmol) 3,3-difluoro-1-methyl-cyclobutanamine hydrochloride (306 mg, 2.527 mmol), DIPEA (0.87 mL, 5.06 mmol) and acetonitrile (100 mL) was refluxed 60 minutes. The reaction mixture was concentrated and the obtained residue was dissolved in EtOAc (100 mL), washed with 1M HCl, dried over sodium sulphate, filtered and concentrated. The obtained residue was dissolved in acetonitrile (50 mL). Water was added until precipitation was observed. The mixture was allowed to triturate further overnight. The beige crystals were filtered off and dried in vacuo at 50° C., resulting in compound 65 (473 mg). Method A; Rt: 1.89 min. m/z: 452.0 (M−H)$^-$ Exact mass: 453.0. $^1$H NMR (400 MHz, acetonitrile-d$_3$) δ ppm 1.46 (s, 3H), 2.44-2.59 (m, 2H), 2.78-2.94 (m, 2H), 3.92 (s, 3H), 5.89 (s, 1H), 7.14 (d, J=2.0 Hz, 1H), 7.36 (d, J=2.0 Hz, 1H), 7.59 (dt, J=5.8, 2.4 Hz, 1H), 7.65 (ddd, J=12.4, 6.8, 2.6 Hz, 1H), 8.64 (br. s., 1H).

Compound 66: N-(3-chloro-4,5-difluoro-phenyl)-4-(1,1-dimethylpropylsulfamoyl)-1-methyl-pyrrole-2-carboxamide

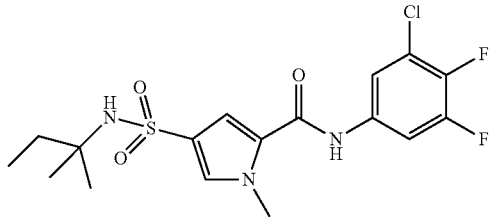 [SMILES: CCC(C)(C)NS(=O)(=O)c1cc(C(=O)Nc2cc(F)c(F)c(Cl)c2)n(C)c1]

A mixture of 5-[(3-chloro-4,5-difluoro-phenyl)carbamoyl]-1-methyl-pyrrole-3-sulfonyl chloride (572 mg, 1.472 mmol), tert-amylamine (327 mg, 3.68 mmol) in acetonitrile (75 mL) was stirred 48 hours. Water was added until crystallisation began. The crystals were filtered off and dried in vacuo at 50° C., resulting in compound 66 (356 mg).

Method A; Rt: 2.09 min. m/z: 418.1 (M−H)$^-$ Exact mass: 419.1. $^1$H NMR (400 MHz, DMSO-d$_6$) δ ppm 0.78 (t, J=7.4 Hz, 3H), 1.12 (s, 6H), 1.49 (q, J=1.0 Hz, 2H), 3.91 (s, 3H), 7.01 (s, 1H), 7.33 (d, J=2.0 Hz, 1H), 7.54 (d, J=1.8 Hz, 1H), 7.75-7.87 (m, 2H), 10.28 (s, 1H).

Compound 72: N-(3-chloro-4,5-difluoro-phenyl)-1-methyl-4-[[1-(trifluoromethyl)-cyclopropyl]sulfamoyl]pyrrole-2-carboxamide

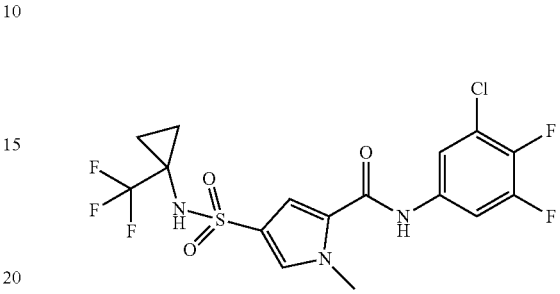

A mixture of 5-[(3-chloro-4,5-difluoro-phenyl)carbamoyl]-1-methyl-pyrrole-3-sulfonyl chloride (1274 mg, 3.28 mmol), 1-(trifluoromethyl)cyclopropanamine (1000 mg, 7.99 mmol) and triethylamine (0.57 mL, 4.1 mmol) in acetonitrile (100 mL) was refluxed overnight. An equal amount of 1-(trifluoromethyl)cyclopropanamine was added and the reaction mixture was further refluxed overnight. The reaction mixture was concentrated. The residue was dissolved in EtOAc (100 mL), washed with 1M HCl, dried over sodium sulphate, filtered and concentrated. The residue was purified by column chromatography on silica using a gradient from 10 to 100% EtOAc in heptane. The pure fractions were concentrated yielding compound 72 (42.4 mg) as a powder. Method A; Rt: 1.95 min. m/z: 456.0 (M−H)$^-$ Exact mass: 457.0. $^1$H NMR (400 MHz, DMSO-d$_6$) δ ppm 1.10-1.22 (m, 4H), 3.91 (s, 3H), 7.31 (d, J=1.8 Hz, 1H), 7.59 (d, J=1.8 Hz, 1H), 7.74-7.86 (m, 2H), 8.74 (s, 1H), 10.30 (s, 1H).

Compound 73: N-(3-chloro-4,5-difluoro-phenyl)-1-methyl-4-[[2,2,2-trifluoro-1-(methoxymethyl)-1-methyl-ethyl]sulfamoyl]pyrrole-2-carboxamide

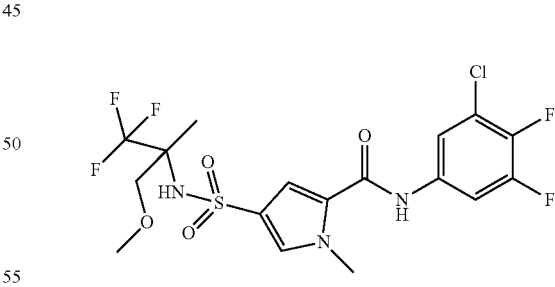

A mixture of 5-[(3-chloro-4,5-difluoro-phenyl)carbamoyl]-1-methyl-pyrrole-3-sulfonyl chloride (318 mg, 0.817 mmol), 1,1,1-trifluoro-3-methoxy-2-methyl-propan-2-amine hydrochloride (237 mg, 1.23 mmol) and triethylamine (0.34 mL, 1.45 mmol) in acetonitrile (7 mL) was heated in a microwave oven at 150° C. during 30 minutes. The reaction mixture was concentrated. The residue was dissolved in water (50 mL) and washed with 1M HCl. The organic layer was dried over sodium sulphate, filtered and concentrated. The residue was subjected to column chromatography on silica using a gradient from 10 to 100% EtOAc in heptane. The product fractions were concentrated and the residue was crystallized by dissolving in methanol (5 mL) upon addition of water. The crystals were filtered off and dried overnight in vacuo at 50° C., resulting in compound 73 (17.8 mg). Method A; Rt: 1.97 min. m/z: 488.0 (M−H)⁻ Exact mass: 489.0. $^1$H NMR (360 MHz, DMSO-$d_6$) δ ppm 1.41 (s, 3H), 3.23 (s, 3H), 3.46 (s, 2H), 3.92 (s, 3H), 7.34 (d, J=1.8 Hz, 1H), 7.60 (d, J=1.8 Hz, 1H), 7.74-7.89 (m, 2H), 8.04 (s, 1H), 10.34 (s, 1H).

Compound 96: N-(3-Chloro-4,5-difluorophenyl)-1-methyl-4-[(2,2,2-trifluoro-1,1-dimethylethyl)sulfamoyl]-1H-pyrrole-2-carboxamide

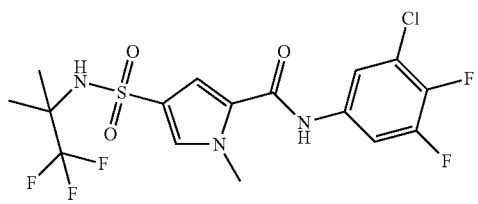 [SMILES: Cn1cc(S(=O)(=O)NC(C)(C)C(F)(F)F)cc1C(=O)Nc1cc(F)c(F)c(Cl)c1]

2,2,2-trifluoro-1,1-dimethyl-ethylamine (0.344 g, 2.71 mmol) was dissolved in pyridine (10 mL, dried on molecular sieves) under $N_2$-atm. 5-[(3-chloro-4,5-difluoro-phenyl)carbamoyl]-1-methyl-pyrrole-3-sulfonyl chloride (0.5 g, 1.35 mmol) was added. The reaction mixture was stirred at room temperature for 20 hours. The reaction mixture was treated with HCl 1M (100 mL) and extracted with EtOAc. The combined organic layer was washed with water followed by saturated $NaHCO_3$, dried with $Na_2SO_4$ and the solvent was evaporated. The residue was dissolved in $CH_2Cl_2$ (5 mL) and the formed precipitate was filtered off and washed with $CH_2Cl_2$ (2×5 mL). The filtrate was concentrated and the obtained residue was purified by silica gel chromatography (EtOAc-heptane 0/100 to 100/0) and further purified by reverse phase column chromatography, resulting in compound 96 (45 mg) as a white solid. Method A; Rt: 2.03 min. m/z: 457.9 (M−H)⁻ Exact mass: 459.0. $^1$H NMR (400 MHz, DMSO-$d_6$) δ ppm 1.35 (s, 6H), 3.92 (s, 3H), 7.34 (d, J=2.0 Hz, 1H), 7.59 (s, 1H), 7.75-7.89 (m, 2H), 8.08 (br. s., 1H), 10.33 (br. s., 1H).

Compound 61: 2-[[5-[(4-fluoro-3-methyl-phenyl)carbamoyl]-1-methyl-pyrrol-3-yl]-sulfonylamino]-2-methyl-propanoic acid

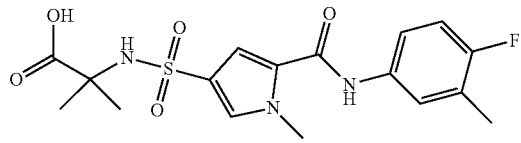 [SMILES: Cc1cc(NC(=O)c2cc(S(=O)(=O)NC(C)(C)C(=O)O)cn2C)ccc1F]

LiOH (0.567 g, 13.5 mmol) was dissolved in water (20 mL) and added dropwise to a mixture of compound 49 (1.39 g, 3.38 mmol) in MeOH (40 mL). The reaction mixture was stirred at 50° C. for 7 hour. Then HCl 1N (15 mL, 15.2 mmol) was added dropwise After 16 hour without stirring the white precipitate was filtered off, washed with Methanol/Water (2:1; 2×60 mL). The white solid was dried in vacuo at 50° C. resulting in compound 61 (1.09 g). Method A; Rt:

1.19 min. m/z: 396.0 (M−H)⁻ Exact mass: 397.1. $^1$H NMR (400 MHz, DMSO-$d_6$) δ ppm 1.32 (s, 6H), 2.22 (d, J=1.5 Hz, 3H), 3.89 (s, 3H), 7.05-7.13 (m, 1H), 7.30 (d, J=1.8 Hz, 1H), 7.45-7.55 (m, 2H), 7.57-7.68 (m, 2H), 10.01 (s, 1H), 12.42-12.58 (m, 1H).

Compound 62: 4-[[1,1-dimethyl-2-(methylamino)-2-oxo-ethyl]sulfamoyl]-N-(4-fluoro-3-methyl-phenyl)-1-methyl-pyrrole-2-carboxamide

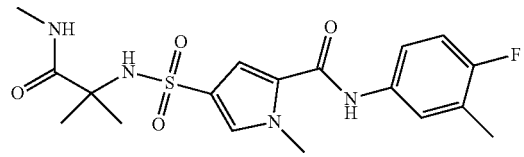 [SMILES: CNC(=O)C(C)(C)NS(=O)(=O)c1cc(C(=O)Nc2ccc(F)c(C)c2)n(C)c1]

1,1'-carbonyldiimidazole (CDI, 0.326 g, 2.013 mmol) was added to a stirring solution of compound 61 (0.32 g, 0.805 mmol) in acetonitrile dried on molecular sieves (10 mL). The reaction mixture was stirred in a sealed tube at room temperature for 2 hour. Next, methylamine (2M in Methanol, 4.0 mL, 8.1 mmol) was added. The reaction mixture was stirred for 2.5 hour at room temperature. The solvent and the excess of methylamine were removed and the mixture was purified by silica gel column chromatography (EtOAc/Heptane 0/100 to 100/0). The desired fractions were combined and the solvent was evaporated and dried in vacuo resulting in compound 62 (221 mg) as a white solid. Method A; Rt: 1.49 min. m/z: 409.0 (M−H)⁻ Exact mass: 410.1. $^1$H NMR (400 MHz, DMSO-$d_6$) δ ppm 1.30 (s, 6H), 2.23 (d, J=1.5 Hz, 3H), 2.53 (d, J=4.6 Hz, 3H), 3.89 (s, 3H), 7.06-7.13 (m, 1H), 7.27-7.30 (m, 1H), 7.32-7.36 (m, 1H), 7.43-7.48 (m, 1H), 7.50-7.54 (m, 2H), 7.61-7.66 (m, 1H), 9.97-10.04 (m, 1H).

Compound 63: 4-[[2-(dimethylamino)-1,1-dimethyl-2-oxo-ethyl]sulfamoyl]-N-(4-fluoro-3-methyl-phenyl)-1-methyl-pyrrole-2-carboxamide

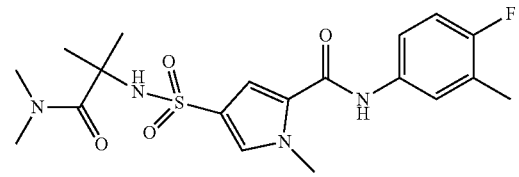

1,1'-carbonyldiimidazole (CDI, 0.149 g, 0.921 mmol) was added to a stirring mixture of compound 61 (0.366 g, 0.921 mmol) in acetonitrile in a sealed tube under $N_2$ atmosphere. The resultant solution was stirred at room temperature for 18 hours. Then, more (CDI, 0.224 g, 1.381 mmol) was added and the mixture was further stirred for 2 hours. An excess of dimethylamine was added (10 drops out of a pressure bottle). The reaction mixture was stirred at room temperature for 5 h. The precipitate was filtered off, washed with AcCN (1×2 mL) and the solid was dried at 50° C. in vacuo yielding compound 63 (323 mg) as a white powder. Method A; Rt: 1.51 min. m/z: 423.2 (M−H)⁻ Exact mass: 424.2. $^1$H NMR (400 MHz, DMSO-$d_6$, 100° C.) δ ppm 1.39 (s, 6H), 2.22 (d, J=1.8 Hz, 3H), 2.97 (s, 6H), 3.91 (s, 3H), 7.02 (t, J=9.2 Hz, 1H), 7.25 (d, J=1.8 Hz, 2H), 7.37 (d, J=1.8 Hz, 1H), 7.45-7.52 (m, 1H), 7.58 (dd, J=7.0, 2.4 Hz, 1H), 9.74 (br. s., 1H).

Compound 64: 4-[(2-amino-1,1-dimethyl-2-oxo-ethyl)sulfamoyl]-N-(4-fluoro-3-methyl-phenyl)-1-methyl-pyrrole-2-carboxamide

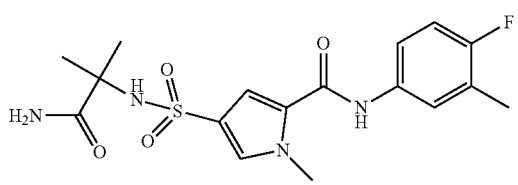 [SMILES: Cc1cc(NC(=O)c2cc(S(=O)(=O)NC(C)(C)C(N)=O)cn2C)ccc1F]

1,1'-carbonyldiimidazole (CDI, 0.295 g, 1.820 mmol) was added to a stirring mixture of compound 61 (0.289 g, 0.727 mmol) in acetonitrile in a sealed tube under $N_2$ atmosphere and stirred 3 hours. The reaction mixture was added dropwise to 7M $NH_3$ in methanol (25 mL). The solvent was evaporated leaving a yellow oil which was purified by silica gel column chromatography (EtOAc/Heptane 0/100 to 100/0). The desired fractions were combined and the solvent was evaporated and dried in vacuo resulting in compound 64 (123 mg) as a solid. Method A; Rt: 1.44 min. m/z: 395.0 (M–H)⁻ Exact mass: 396.1. ¹H NMR (400 MHz, DMSO-d₆, 60° C.) δ ppm 1.35 (s, 6H), 2.22 (d, J=1.8 Hz, 3H), 3.90 (s, 3H), 6.91 (br. s., 2H), 7.02-7.08 (m, 1H), 7.11 (br. s., 1H), 7.30 (d, J=2.0 Hz, 1H), 7.47-7.54 (m, 2H), 7.61 (dd, J=7.4, 2.3 Hz, 1H), 9.86 (br. s., 1H).

Compound 67: 4-(tert-butylsulfamoyl)-N-(2,6-dideuterio-4-fluoro-3-methyl-phenyl)-1-methyl-pyrrole-2-carboxamide

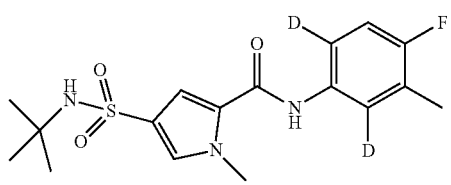 [SMILES: [2H]c1cc(F)c(C)c([2H])c1NC(=O)c1cc(S(=O)(=O)NC(C)(C)C)cn1C]

t-Butylamine (245 mg, 3.35 mmol) was added to a solution of 5-[(2,6-dideuterio-4-fluoro-3-methyl-phenyl)carbamoyl]-1-methyl-pyrrole-3-sulfonyl chloride (372 mg, 1.116 mmol) in acetonitrile (25 mL) and stirred overnight. Water was added until crystallization began. The precipitate was filtered off and dried in vacuo at 50° C., resulting in compound 67 (260 mg) Method A; Rt: 1.76 min. m/z: 368.1 (M–H)⁻ Exact mass: 369.2. ¹H NMR (400 MHz, DMSO-d₆) δ ppm 1.17 (s, 9H), 2.22 (d, J=2.0 Hz, 3H), 3.90 (s, 3H), 7.06-7.11 (m, 2H), 7.29 (d, J=2.0 Hz, 1H), 7.49 (d, J=1.5 Hz, 1H), 10.00 (s, 1H).

Compound 68: 4-(tert-butylsulfamoyl)-1-methyl-N-(3,4,5-trifluorophenyl)pyrrole-2-carboxamide

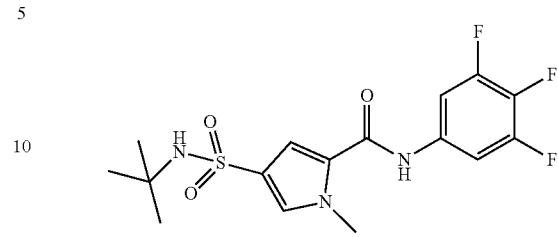

t-Butylamine (498 mg, 6.806 mmol) was added to a solution of 1-methyl-5-[(3,4,5-trifluorophenyl)carbamoyl] pyrrole-3-sulfonyl chloride (800 mg, 2.269 mmol) in acetonitrile (50 mL) and stirred 3 hours. Water was added until crystallization began. The precipitate was filtered off and dried in vacuo at 50° C. Method A; Rt: 1.91 min. m/z: 388.1 (M–H)⁻ Exact mass: 389.1. ¹H NMR (400 MHz, DMSO-d₆) δ ppm 1.17 (s, 9H), 3.91 (s, 3H), 7.14 (s, 1H), 7.32 (d, J=2.0 Hz, 1H), 7.55 (d, J=1.5 Hz, 1H), 7.67 (dd, J=10.6, 6.6 Hz, 2H), 10.30 (s, 1H).

Compound 69: N-(4-fluoro-3-methyl-phenyl)-1-methyl-4-[[2,2,2-trideuterio-1,1-bis(trideuteriomethyl)ethyl]sulfamoyl]pyrrole-2-carboxamide

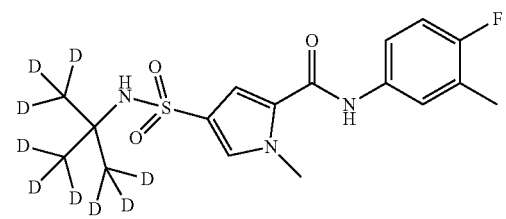 [SMILES: [2H]C([2H])([2H])C(NS(=O)(=O)c1cc(C(=O)Nc2ccc(F)c(C)c2)n(C)c1)(C([2H])([2H])[2H])C([2H])([2H])[2H]]

1,1,1,3,3,3-hexadeuterio-2-(trideuteriomethyl)propan-2-amine (473 mg, 5.76 mmol) was added to a solution of 5-[(4-fluoro-3-methyl-phenyl)carbamoyl]-1-methyl-pyrrole-3-sulfonyl chloride (635 mg, 1.92 mmol) in acetonitrile (43 mL) and stirred overnight. Water was added until crystallization began. The precipitate was filtered off and dried in vacuo at 50° C. Method A; Rt: 1.74 min. m/z: 375.1 (M–H)⁻ Exact mass: 376.2. ¹H NMR (400 MHz, DMSO-d₆) δ ppm 2.23 (d, J=1.5 Hz, 3H), 3.90 (s, 3H), 7.04-7.13 (m, 2H), 7.29 (d, J=1.8 Hz, 1H), 7.47-7.56 (m, 2H), 7.64 (dd, J=7.2, 2.5 Hz, 1H), 10.00 (s, 1H).

Compound 70: N-(2,6-dideuterio-4-fluoro-3-methyl-phenyl)-1-methyl-4-[[2,2,2-trideuterio-1,1-bis(trideuteriomethyl)ethyl]sulfamoyl]pyrrole-2-carboxamide

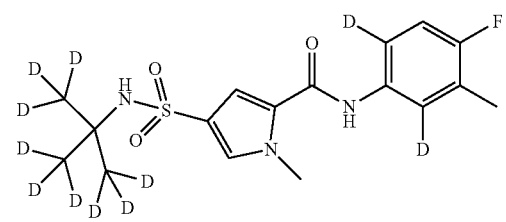 [SMILES: [2H]c1cc(F)c(C)c([2H])c1NC(=O)c1cc(S(=O)(=O)NC(C([2H])([2H])[2H])(C([2H])([2H])[2H])C([2H])([2H])[2H])cn1C]

1,1,1,3,3,3-hexadeuterio-2-(trideuteriomethyl)propan-2-amine (377 mg, 4.59 mmol) was added to a solution of 5-[(2,6-dideuterio-4-fluoro-3-methyl-phenyl)carbamoyl]-1-methyl-pyrrole-3-sulfonyl chloride (611 mg, 1.84 mmol) in acetonitrile (41 mL) and stirred overnight. Water was added until crystallization began. The precipitate was filtered off and dried in vacuo at 50° C. Method A; Rt: 1.82 min. m/z: 377.1 (M–H)⁻ Exact mass: 378.2. $^1$H NMR (400 MHz, DMSO-$d_6$) δ ppm 2.23 (d, J=2.0 Hz, 3H), 3.90 (s, 3H), 7.05-7.12 (m, 2H), 7.29 (d, J=2.0 Hz, 1H), 7.49 (d, J=1.8 Hz, 1H), 10.00 (s, 1H).

Compound 71: 4-(tert-butylsulfamoyl)-N-(2,6-dideuterio-3,4,5-trifluoro-phenyl)-1-methyl-pyrrole-2-carboxamide

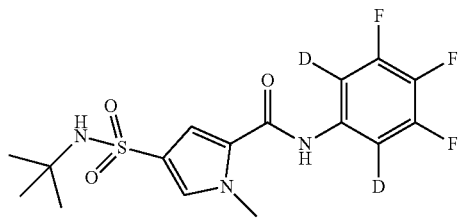 [SMILES: [2H]c1c(F)c(F)c(F)c([2H])c1NC(=O)c1cc(S(=O)(=O)NC(C)(C)C)cn1C]

t-Butylamine (331 mg, 4.53 mmol) was added to a solution of 5-[(2,6-dideuterio-3,4,5-trifluoro-phenyl)carbamoyl]-1-methyl-pyrrole-3-sulfonyl chloride (666 mg, 1.51 mmol) (obtained similarly as described in the synthesis for compound 56, starting from 3,4,5-trifluoroaniline instead of 4-fluoro-3-methyl-aniline, via 2,6-dideuterio-3,4,5-trifluoro-aniline) in acetonitrile (30 mL) and stirred 1 hour. Water was added until crystallization began. The precipitate was filtered off and dried overnight in vacuo at 50° C. Method A; Rt: 1.89 min. m/z: 389.9 (M–H)⁻ Exact mass: 391.1. $^1$H NMR (400 MHz, DMSO-$d_6$) δ ppm 1.17 (s, 9H), 3.91 (s, 3H), 7.14 (s, 1H), 7.32 (d, J=2.0 Hz, 1H), 7.55 (d, J=1.5 Hz, 1H), 10.30 (s, 1H).

Synthesis of 3-fluoro-1-methyl-4-[(3-methyloxetan-3-yl)sulfamoyl]pyrrole-2-carboxylic acid Sodium hydride (914 mg, 23.87 mmol) was added to a solution of ethyl 3-fluoro-1H-pyrrole-2-carboxylate (2885 mg, 18.36 mmol) and iodomethane (3888 mg, 23.9 mmol) in dry DMF (43 mL) and the mixture was stirred for 17 hours. The reaction mixture was acidified with 1M HCl and concentrated. The residue was dissolved in water/EtOAc. The organic layer was dried over sodium sulphate, filtered and concentrated. The obtained residue was dissolved in acetonitrile (50 mL), washed with heptane and concentrated yielding a brown liquid of crude ethyl 3-fluoro-1-methyl-pyrrole-2-carboxylate, which was used as such. Chlorosulfonic acid (1344 mg, 11.53 mmol) was dissolved in dichloromethane (50 mL) and cooled in an icebath. Crude ethyl 3-fluoro-1-methyl-pyrrole-2-carboxylate (1880 mg) was added and the reaction mixture was stirred 90 minutes. The reaction mixture was concentrated and the brown residual powder was dried for 17 hours in vacuo at 50° C. (5-ethoxycarbonyl-4-fluoro-1-methyl-pyrrole-3-sulfonic acid, 2477 mg) Method A; Rt: 0.76 min. m/z: 250.0 (M–H)⁻ Exact mass: 251.0. A mixture of crude 5-ethoxycarbonyl-4-fluoro-1-methyl-pyrrole-3-sulfonic acid (2318 mg) in thionylchloride (20 mL) was heated at 80° C. during 30 minutes. The solution was concentrated and the residue (containing ethyl 4-chlorosulfonyl-3-fluoro-1-methyl-pyrrole-2-carboxylate) dissolved in acetonitrile (25 mL). 3-methyloxetan-3-amine (3035 mg, 34.84 mmol) dissolved in acetonitrile (20 mL) was added and the reaction mixture was stirred 1 hour at room temperature. The reaction mixture was concentrated. The obtained residue was dissolved in dichloromethane (200 mL), washed with water, dried over sodium sulphate, filtered and concentrated. The residue was purified by column chromatography on silica using a gradient from 5 to 100% EtOAc in heptane. The product fractions were concentrated in vacuo yielding ethyl 3-fluoro-1-methyl-4-[(3-methyloxetan-3-yl)sulfamoyl]pyrrole-2-carboxylate (1900 mg) as a white powder. $^1$H NMR (400 MHz, DMSO-$d_6$) δ ppm 1.28 (t, J=7.2 Hz, 3H), 1.52 (s, 3H), 3.83 (s, 3H), 4.15 (d, J=6.4 Hz, 2H), 4.27 (q, J=7.0 Hz, 2H), 4.61 (d, J=5.9 Hz, 2H), 7.57 (d, J=4.6 Hz, 1H), 8.28 (s, 1H). A mixture of ethyl 3-fluoro-1-methyl-4-[(3-methyloxetan-3-yl)sulfamoyl]pyrrole-2-carboxylate (1900 mg, 5.93 mmol), lithium hydroxide (426 mg, 17.8 mmol), THF (20 mL) and distilled water (5 mL) was stirred 210 minutes at room temperature. THF was distilled off and the mixture neutralized with 1M HCl (5.9 mL, 5.9 mmol). The mixture was extracted with 2-methyltetrahydrofuran (3×100 mL). The combined organic layers were dried over sodium sulphate, filtered and concentrated. The resulting white powder was dried overnight in vacuo at 50° C. (3-fluoro-1-methyl-4-[(3-methyloxetan-3-yl)sulfamoyl]pyrrole-2-carboxylic acid, 1710 mg) Method A; Rt: 0.68 min. m/z: 290.9 (M–H)⁻ Exact mass: 292.1. $^1$H NMR (400 MHz, DMSO-$d_6$) δ ppm 1.52 (s, 3H), 3.82 (s, 3H), 4.15 (d, J=6.6 Hz, 2H), 4.61 (d, J=5.9 Hz, 2H), 7.52 (d, J=4.6 Hz, 1H), 8.26 (s, 1H), 13.11 (br. s, 1H).

Compound 74: N-(3,4-difluorophenyl)-3-fluoro-1-methyl-4-[(3-methyloxetan-3-yl)-sulfamoyl]pyrrole-2-carboxamide

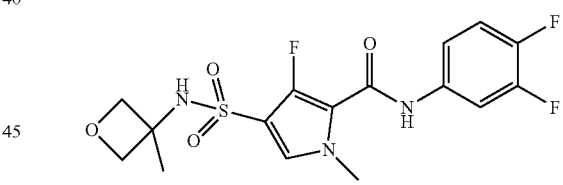

Triethylamine (0.19 mL, 1.36 mmol) was added to a solution of 3-fluoro-1-methyl-4-[(3-methyloxetan-3-yl)sulfamoyl]pyrrole-2-carboxylic acid (133 mg, 0.57 mmol) in DMF (1 mL) followed by HATU (216 mg, 0.57 mmol) and stirred 20 minutes. Then 3,4-difluoroaniline (117 mg, 0.91 mmol) was added and the reaction mixture stirred overnight. The mixture was concentrated in vacuo. The residue was mixed with water (10 mL) and extracted with EtOAc (2×30 mL). The organic layer was dried over sodium sulphate, filtered and concentrated. The obtained residue was purified by column chromatography on silica using a gradient from 10 to 100% EtOAc in heptane. The product fractions were concentrated and the remaining white powder was dissolved in warm EtOAc (10 mL) and upon addition of heptane the compound crystallized. The white crystals were filtered off and dried in vacuo, resulting in compound 74 (102 mg) Method A; Rt: 1.62 min. m/z: 401.9 (M–H)⁻ Exact mass: 403.1. $^1$H NMR (400 MHz, DMSO-$d_6$) δ ppm 1.56 (s, 3H), 3.80 (s, 3H), 4.17 (d, J=6.4 Hz, 2H), 4.64 (d, J=6.2 Hz, 2H), 7.35-7.47 (m, 2H), 7.51 (d, J=4.6 Hz, 1H), 7.75-7.87 (m, 1H), 8.30 (s, 1H), 10.24 (s, 1H).

Compound 75: N-(3,5-Dichloro-4-fluorophenyl)-1-methyl-4-[(3-methyloxetan-3-yl)sulfamoyl]-1H-pyrrole-2-carboxamide

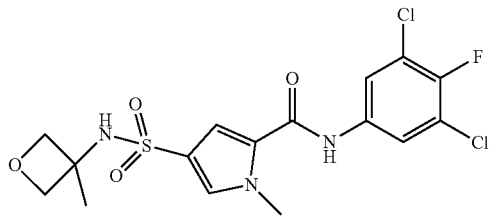 [SMILES: Cn1cc(S(=O)(=O)NC2(C)COC2)cc1C(=O)Nc1cc(Cl)c(F)c(Cl)c1]

3,5-dichloro-4-fluoroaniline (1534 mg, 8.5 mmol) dissolved in toluene (10 mL) was added to 4-chlorosulfonyl-1-methyl-pyrrole-2-carbonyl chloride (2063 mg, 8.52 mmol) in toluene (115 mL) at reflux and refluxed 2 hours. The reaction mixture was filtered while still hot and the filtrate was concentrated, yielding crude 5-[(3,5-dichloro-4-fluorophenyl)carbamoyl]-1-methyl-pyrrole-3-sulfonyl chloride as a crude beige powder which was used as such. $^1$H NMR (400 MHz, acetonitrile-d$_3$) δ ppm 3.96 (s, 3H), 7.39 (d, J=2.0 Hz, 1H), 7.71-7.77 (m, 3H), 8.78 (br. s., 1H). 3-methyl-3-oxetanamine (407.3 mg, 4.68 mmol) was added to crude 5-[(3,5-dichloro-4-fluoro-phenyl)carbamoyl]-1-methyl-pyrrole-3-sulfonyl chloride (601 mg) in acetonitrile (57 mL) and stirred overnight. Water was added until crystallisation began. The formed white crystals were filtered off and dried in vacuo at 50° C. during 4 hours. Compound 75 was recrystallized from EtOAc upon addition of heptane. The white crystals (346 mg) were filtered off and dried in vacuo at 50° C. over weekend. $^1$H NMR (400 MHz, DMSO-d$_6$) δ ppm 1.54 (s, 3H), 3.92 (s, 3H), 4.14 (d, J=6.4 Hz, 2H), 4.60 (d, J=5.9 Hz, 2H), 7.35 (d, J=2.0 Hz, 1H), 7.62 (d, J=1.8 Hz, 1H), 7.95 (d, J=6.2 Hz, 2H), 7.99 (s, 1H), 10.27 (s, 1H). Method A; Rt: 1.77 min. m/z: 434.0 (M–H)$^-$ Exact mass: 435.0.

Compound 76: 4-(tert-Butylsulfamoyl)-N-(3,5-dichloro-4-fluorophenyl)-1-methyl-1H-pyrrole-2-carboxamide

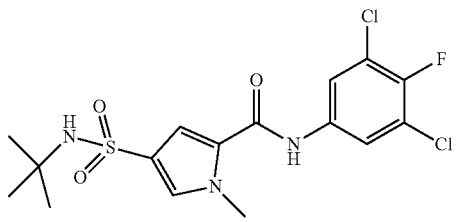 [SMILES: Cn1cc(S(=O)(=O)NC(C)(C)C)cc1C(=O)Nc1cc(Cl)c(F)c(Cl)c1]

tert-butylamine (450.6 mg, 6.16 mmol) was added to crude 5-[(3,5-dichloro-4-fluoro-phenyl)carbamoyl]-1-methyl-pyrrole-3-sulfonyl chloride (792 mg) in acetonitrile (75 mL) and stirred 2 hours. Water was added until crystallisation began. The white crystals were filtered off and dried overnight in vacuo at 50° C., resulting in compound 76 (517 mg). $^1$H NMR (400 MHz, DMSO-d$_6$) δ ppm 1.17 (s, 9H), 3.91 (s, 3H), 7.14 (s, 1H), 7.33 (d, J=1.8 Hz, 1H), 7.55 (d, J=1.5 Hz, 1H), 7.95 (d, J=6.2 Hz, 2H), 10.26 (s, 1H). Method A; Rt: 1.99 min. m/z: 420.0 (M–H)$^-$ Exact mass: 421.0.

Compound 77: N-(4-Chloro-3-methylphenyl)-1-methyl-4-[(3-methyloxetan-3-yl)sulfamoyl]-1H-pyrrole-2-carboxamide

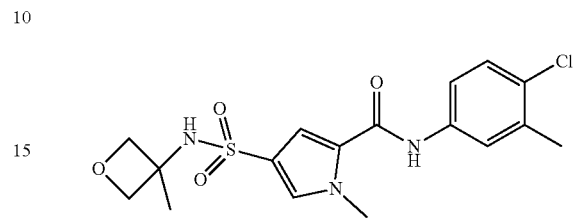

DIPEA (0.471 mL, 2.73 mol) was added to a stirring mixture of 1-methyl-4-[(3-methyloxetan-3-yl)sulfamoyl]pyrrole-2-carboxylic acid (0.25 g, 0.000911 mol) and CH$_3$CN (5 mL) under N$_2$-atmosphere. To the resulting solution was added 4-chloro-3-methylaniline (0.142 g, 1 mmol), then HATU (364 mg, 0.957 mmol). The reaction mixture was stirred at room temperature for 3 hours and left standing for 2 hours. The product was filtered off, washed with CH$_3$CN (5×), and dried at 50° C. in vacuo, resulting in compound 77 (190 mg). $^1$H NMR (400 MHz, DMSO-d$_6$) δ ppm 1.55 (s, 3H), 2.32 (s, 3H), 3.92 (s, 3H), 4.13 (d, J=6.2 Hz, 2H), 4.60 (d, J=6.2 Hz, 2H), 7.31-7.40 (m, 2H), 7.54-6 7.62 (m, 2H), 7.73 (d, J=2.2 Hz, 1H), 7.95 (s, 1H), 10.08 (s, 1H). Method A; Rt: 1.70 min. m/z: 396.0 (M–H)$^-$ Exact mass: 397.1.

Compound 78: N-(3-Chloro-4-fluorophenyl)-1-methyl-4-[(3-methyloxetan-3-yl)sulfamoyl]-1H-pyrrole-2-carboxamide

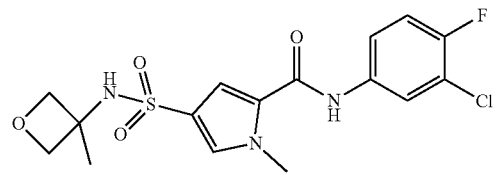 [SMILES: Cn1cc(S(=O)(=O)NC2(C)COC2)cc1C(=O)Nc1ccc(F)c(Cl)c1]

1-methyl-4-[(3-methyloxetan-3-yl)sulfamoyl]pyrrole-2-carboxylic acid (250 mg, 0.911 mmol) and HATU (433 mg, 1.14 mmol) were dissolved in DMF (5 mL) and stirred for 10 minutes. 3-chloro-4-fluoroaniline (265 mg, 1.8 mmol) and DIPEA (0.471 mL, 2.73 mmol) were added and the reaction mixture was stirred overnight at room temperature. The volatiles were removed under reduced pressure and the residue was purified on silica using a heptane to EtOac gradient yielding compound 78 as a white powder after trituration in MeOH. Method B; Rt: 0.93 min. m/z: 400.0 (M–H)$^-$ Exact mass: 401.1. $^1$H NMR (400 MHz, DMSO-d$_6$) δ ppm 1.54 (s, 3H), 3.92 (s, 3H), 4.13 (d, J=6.4 Hz, 2H), 4.60 (d, J=5.9 Hz, 2H), 7.34 (d, J=2.0 Hz, 1H), 7.40 (t, J=9.1 Hz, 1H), 7.60 (d, J=1.8 Hz, 1H), 7.66 (ddd, J=9.1, 4.3, 2.6 Hz, 1H), 7.96 (br. s., 1H), 8.01 (dd, J=6.9, 2.5 Hz, 1H), 10.21 (s, 1H).

Compound 79: N-[4-Fluoro-3-methyl-5-(trifluoromethyl)phenyl]-1-methyl-4-[(3-methyloxetan-3-yl)sulfamoyl]-1H-pyrrole-2-carboxamide

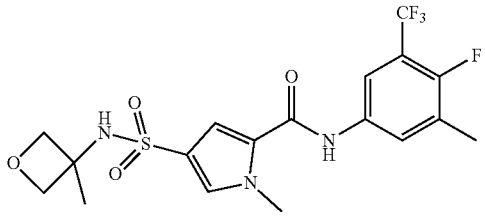 [SMILES: Cc1cc(NC(=O)c2cc(S(=O)(=O)NC3(C)COC3)cn2C)cc(C(F)(F)F)c1F]

Compound 79 (1.9 g) was prepared similarly as described for compound 75, using 4-fluoro-3-methyl-5-(trifluoromethyl)aniline instead of 3,5-dichloro-4-fluoroaniline $^1$H NMR (400 MHz, DMSO-$d_6$) δ ppm 1.55 (s, 3H), 2.31 (d, J=2.0 Hz, 3H), 3.92 (s, 3H), 4.14 (d, J=6.4 Hz, 2H), 4.60 (d, J=5.9 Hz, 2H), 7.36 (d, J=2.0 Hz, 1H), 7.60 (d, J=1.8 Hz, 1H), 7.92-8.03 (m, 3H), 10.25 (br. s, 1H). Method B; Rt: 1.04 min. m/z: 448.1 (M–H)$^-$ Exact mass: 449.1. Differential scanning calorimetry: From 30 to 300° C. at 10° C./min: peak at 192.0° C.

Compound 80: N-(4-Fluoro-3,5-dimethylphenyl)-1-methyl-4-[(3-methyloxetan-3-yl)sulfamoyl]-1H-pyrrole-2-carboxamide

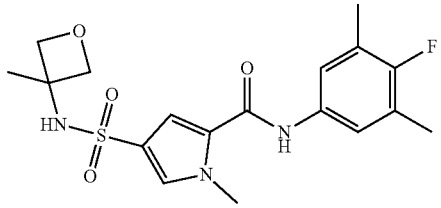

1-methyl-4-[(3-methyloxetan-3-yl)sulfamoyl]pyrrole-2-carboxylic acid (200 mg, 0.73 mmol) was dissolved in N,N-dimethylformamide (2 mL). HATU (0.35 g, 0.91 mmol) was added followed by diisopropylethylamine (0.38 mL, 2.19 mmol). The resulting mixture was stirred for 30 minutes at room temperature. Then, 4-fluoro-3,5-dimethylaniline (0.2 g, 1.46 mmol) was added. The resulting mixture was stirred for 24 hours and next poured onto 10 mL of ice. The mixture was extracted using 2-Me-THF (3×10 mL). The combined organics were washed with brine, dried on Na$_2$SO$_4$, filtered and concentrated in vacuo. The obtained residue was purified by silica gel column chromatography using gradient elution from heptane to EtOAc. (100:0 to 0:100). The desired fractions were concentrated in vacuo and dried in a vacuum oven at 55° C. for 24 hours yielding compound 80 (130 mg): Method B; Rt: 0.93 min. m/z: 394.2 (M–H)$^-$ Exact mass: 395.1. $^1$H NMR (400 MHz, DMSO-$d_6$) δ ppm 1.55 (s, 3H), 2.21 (d, J=1.8 Hz, 6H), 3.91 (s, 3H), 4.13 (d, J=5.7 Hz, 2H), 4.60 (d, J=5.9 Hz, 2H), 7.31 (d, J=1.8 Hz, 1H), 7.43 (d, J=6.6 Hz, 2H), 7.56 (d, J=1.8 Hz, 1H), 7.94 (br. s., 1H), 9.94 (br. s, 1H).

Compound 81: N-(3-Bromo-4-fluorophenyl)-1-methyl-4-[(3-methyloxetan-3-yl)sulfamoyl]-1H-pyrrole-2-carboxamide

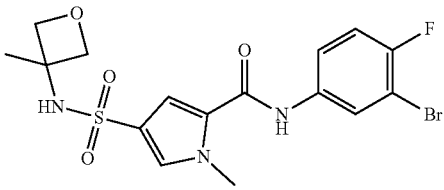 [SMILES: Cn1cc(S(=O)(=O)NC2(C)COC2)cc1C(=O)Nc1ccc(F)c(Br)c1]

Compound 81 (129 mg) was prepared as described for compound 80 using 3-bromo-4-fluoroaniline instead of 4-fluoro-3,5-dimethylaniline. Method B; Rt: 0.93 min. m/z: 444.1 (M–H)$^-$ Exact mass: 445.0. $^1$H NMR (400 MHz, DMSO-$d_6$) δ ppm 1.47-1.60 (m, 3H), 3.83-3.99 (m, 3H), 4.13 (d, J=6.4 Hz, 2H), 4.60 (d, J=5.9 Hz, 2H), 7.28-7.44 (m, 2H), 7.59 (d, J=1.8 Hz, 1H), 7.71 (ddd, J=9.0, 4.4, 2.4 Hz, 1H), 7.97 (br. s., 1H), 8.13 (dd, J=6.5, 2.5 Hz, 1H), 10.20 (br. s., 1H).

Compound 82: 1-Methyl-4-[(3-methyloxetan-3-yl)sulfamoyl]-N-[3-methyl-5-(trifluoro-methyl)phenyl]-1H-pyrrole-2-carboxamide

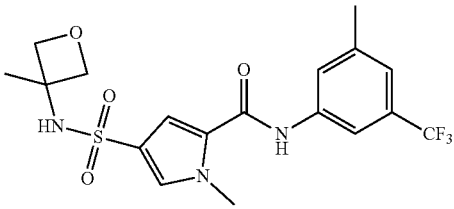 [SMILES: Cc1cc(NC(=O)c2cc(S(=O)(=O)NC3(C)COC3)cn2C)cc(C(F)(F)F)c1]

Compound 82 (167 mg) was prepared as described for compound 80 using 3-methyl-5-trifluoromethylaniline instead of 4-fluoro-3,5-dimethylaniline. Method B; Rt: 1.01 min. m/z: 430.2 (M–H)$^-$ Exact mass: 431.1. $^1$H NMR (400 MHz, DMSO-$d_6$) δ ppm 1.55 (s, 3H), 2.39 (s, 3H), 3.92 (s, 3H), 4.14 (d, J=6.4 Hz, 2H), 4.60 (d, J=5.9 Hz, 2H), 7.26 (s, 1H), 7.39 (d, J=2.0 Hz, 1H), 7.60 (d, J=1.8 Hz, 1H), 7.84 (s, 1H), 7.90-8.08 (m, 2H), 10.24 (br. s., 1H).

Compound 83: N-(4-Cyano-3-methylphenyl)-1-methyl-4-[(3-methyloxetan-3-ylsulfamoyl]-1H-pyrrole-2-carboxamide

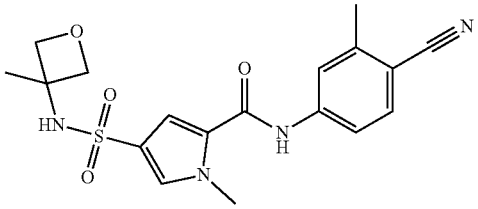 [SMILES: Cc1cc(NC(=O)c2cc(S(=O)(=O)NC3(C)COC3)cn2C)ccc1C#N]

Compound 83 (76 mg) was prepared as described for compound 80 using 4-amino-2-methyl-benzonitrile instead of 4-fluoro-3,5-dimethylaniline. Method B; Rt: 0.81 min.

m/z: 387.1 (M−H)⁻ Exact mass: 388.1. ¹H NMR (400 MHz, DMSO-d₆) δ ppm 1.48-1.59 (m, 3H), 2.46 (s, 3H), 3.87-3.98 (m, 3H), 4.14 (d, J=6.4 Hz, 2H), 4.60 (d, J=5.9 Hz, 2H), 7.40 (d, J=2.0 6 Hz, 1H), 7.62 (d, J=1.8 Hz, 1H), 7.69-7.77 (m, 2H), 7.86 (s, 1H), 7.98 (br. s., 1H), 10.32 (br. s., 1H).

Compound 84: N-(4-Chloro-3-fluorophenyl)-1-methyl-4-[(3-methyloxetan-3-yl)sulfamoyl]-1H-pyrrole-2-carboxamide

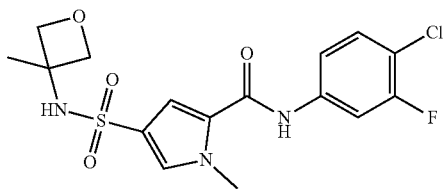 [SMILES: Cn1cc(S(=O)(=O)NC2(C)COC2)cc1C(=O)Nc1ccc(Cl)c(F)c1]

1-methyl-4-[(3-methyloxetan-3-yl)sulfamoyl]pyrrole-2-carboxylic acid (200 mg, 0.729 mmol) was dissolved in DMF (5 mL) and triethylamine (0.405 mL, 2.92 mmol) and HATU (360 mg, 0.95 mmol) were added. After 10 minutes, 4-chloro-3-fluoroaniline (212 mg, 1.46 mmol) was added. The reaction mixture was stirred at room temperature for 1 hour and heated at 50° C. for 1 hour. More 4-chloro-3-fluoroaniline (424 mg, 2.92 mmol) was added to the reaction mixture. The reaction mixture was stirred at 60° C. for 1 hour. The mixture was poured into water (50 mL) and filtered. The formed precipitate was filtered and the solid was washed with water. The filtrate was stored for 42 hours and the formed precipitate was filtered and washed with water. The solids were combined, and further purified using silica gel column chromatography (ethyl acetate in heptane from 0 to 100%) resulting in compound 84 as a white solid. The white solid was triturated in methanol (5 mL), filtered and dried in vacuum oven overnight resulting in compound 84 (119 mg) as a white powder. ¹H NMR (400 MHz, DMSO-d₆) δ ppm 1.54 (s, 3H), 3.92 (s, 3H), 4.14 (d, J=6.4 Hz, 2H), 4.60 (d, J=5.9 Hz, 2H), 7.36 (d, J=1.8 Hz, 1H), 7.45-7.67 (m, 1H), 7.68-8.56 (m, 2H), 10.30 (br. s., 1H). Method B; Rt: 0.96 min. m/z: 400.1 (M−H)⁻ Exact mass: 401.1.

Compound 85: N-(2,4-Difluoro-3-methylphenyl)-1-methyl-4-[(3-methyloxetan-3-yl)sulfamoyl]-1H-pyrrole-2-carboxamide

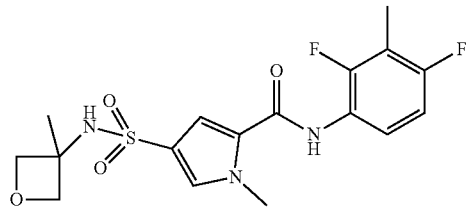 [SMILES: Cc1c(F)ccc(NC(=O)c2cc(S(=O)(=O)NC3(C)COC3)cn2C)c1F]

2,4-difluoro-3-methyl-aniline (0.306 g, 2.14 mol) was dissolved in acetonitrile (50 mL, 0.957 mol), 1-methyl-4-[(3-methyloxetan-3-yl)sulfamoyl]pyrrole-2-carboxylic acid (0.645 g, 2.35 mmol) and Et₃N (0.891 mL, 6.41 mmol) were added. HATU (0.975 g, 2.57 mmol) was added at once. The reaction mixture was stirred at room temperature for 1 hour. Then the reaction mixture was stirred at 40° C. for 80 hours. The solvent was removed, water (1×50 mL) was added and the mixture was washed with brine (1×5 mL) and extracted with EtOAc (2×50 mL). The combined organic layers were dried with Na₂SO₄ and the solvent was removed by evaporation. The crude mixture was purified by silica gel chromatography (EtOAc-heptane 0/100 to 100/0). The desired fractions were combined and evaporated. The obtained solid was crystallized by evaporation of a acetonitrile/H₂O solution, the precipitate was filtered off, washed with water (2 mL) and dried at 50° C. in vacuo, resulting in compound 85. Method A; Rt: 1.55 min. m/z: 398.1 (M−H)⁻ Exact mass: 399.1. ¹H NMR (360 MHz, DMSO-d₆) δ ppm 1.55 (s, 3H), 2.18 (s, 3H), 3.89 (s, 3H), 4.13 (s, 2H), 4.59 (s, 2H), 7.07 (td, J=9.0, 1.8 Hz, 1H), 7.28-7.39 (m, 2H), 7.59 (d, J=1.8 Hz, 1H), 8.00 (br. s., 1H), 9.95 (br. s., 1H).

Compound 86: N-[4-Fluoro-3-(trifluoromethoxy)phenyl]-1-methyl-4-[(3-methyloxetan-3-yl)sulfamoyl]-1H-pyrrole-2-carboxamide

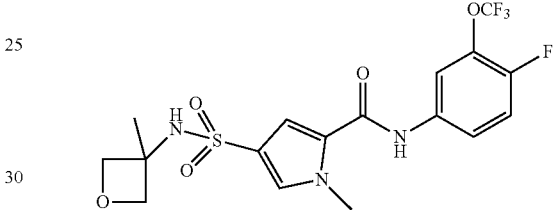

Compound 86 (127 mg) was prepared similar as described for compound 80 using 4-fluoro-3-(trifluoromethoxy)aniline instead of 4-fluoro-3,5-dimethylaniline. Method B, Rt: 1.01 min. m/z: 450.2 (M−H)⁻ Exact mass: 451.1. ¹H NMR (400 MHz, DMSO-d₆) δ ppm 1.54 (s, 3H), 3.92 (s, 3H), 4.14 (d, J=6.2 Hz, 2H), 4.60 (d, J=5.9 Hz, 2H), 7.35 (d, J=2.0 Hz, 1H), 7.45-7.53 (m, 1H), 7.60 (d, J=1.8 Hz, 1H), 7.68-7.77 (m, 1H), 7.97 (s, 1H), 7.99-8.07 (m, 1H), 10.29 (br. s, 1H).

Compound 87: N-(3-Chloro-5-cyanophenyl)-1-methyl-4-[(3-methyloxetan-3-yl)sulfamoyl]-1H-pyrrole-2-carboxamide

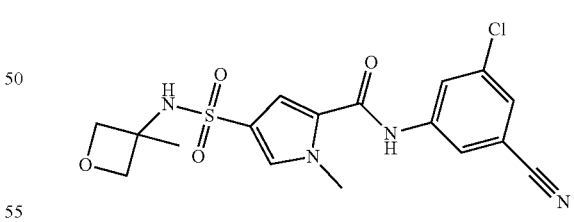

Compound 87 was prepared similar as described for compound 75 using 3-amino-5-chlorobenzonitrile instead of 3,5-dichloro-4-fluoroaniline. The reaction mixture was filtered and the solids were washed with water. The grey powder was dissolved in ethyl acetate (300 mL) and washed with aqueous HCl (1 N, 50 mL), saturated aqueous sodium bicarbonate (30 mL) and brine, dried (Na₂SO₄), and evaporated to dryness and dried overnight in vacuum oven at 50° C., resulting in compound 87 (867 mg) as a white powder. Method B; Rt: 0.91 min. m/z: 407.1 (M−H)⁻ Exact mass: 408.1. ¹H NMR (400 MHz, DMSO-d₆) δ ppm 1.54 (s, 3H), 3.93 (s, 3H), 4.14 (d, J=6.4 Hz, 2H), 4.60 (d, J=5.9 Hz, 2H), 7.38 (d, J=1.8 Hz, 1H), 7.64 (d, J=1.5 Hz, 1H), 7.74 (dd, J=2.0, 1.3 Hz, 1H), 8.00 (s, 1H), 8.10-8.13 (m, 1H), 8.15 (t, J=2.0 Hz, 1H), 10.42 (s, 1H). Differential scanning calorimetry: From 30 to 300° C. at 10° C./min: peak at 209.4° C.

Compound 88: N-(4-Fluoro-3-methylphenyl)-1,3,5-trimethyl-4-[(3-methyloxetan-3-yl)sulfamoyl]-1H-pyrrole-2-carboxamide

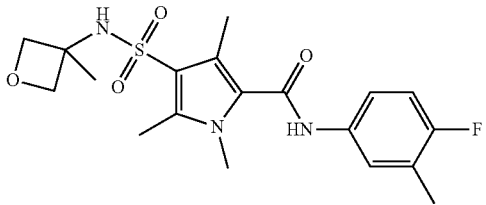 [SMILES: Cc1cc(NC(=O)c2c(C)c(S(=O)(=O)NC3(C)COC3)c(C)n2C)ccc1F]

Ethyl 1,3,5-trimethylpyrrole-2-carboxylate (1000 mg, 5.52 mmol) was added in 5 portions to chlorosulfonic acid (5 mL) at 0° C. under nitrogen atmosphere. The reaction mixture was warmed to room temperature and allowed to stir overnight. The reaction mixture was slowly added to ice cold water (50 mL), followed by extraction with $CH_2Cl_2$ (3×50 mL). The combined organic extracts were dried ($Na_2SO_4$) and concentrated resulting in crude ethyl 4-chlorosulfonyl-1,3,5-trimethyl-pyrrole-2-carboxylate (510 mg) as brown oil which solidified on standing. Crude ethyl 4-chlorosulfonyl-1,3,5-trimethyl-pyrrole-2-carboxylate (500 mg) was dissolved in acetonitrile (50 mL) and 3-methyl-3-oxetanamine (622.9 mg, 7.15 mmol) was added. The reaction mixture was stirred at room temperature for 2 hours. Water (100 mL) was added and the mixture was extracted with $CH_2Cl_2$ (3×50 mL) and the combined organic layers were washed with brine, dried and evaporated to afford a brown sticky oil. The oil was purified using silica gel column chromatography (ethyl acetate in heptane from 0 to 100%) resulting in ethyl 1,3,5-trimethyl-4-[(3-methyloxetan-3-yl)sulfamoyl]pyrrole-2-carboxylate (100 mg) as a white solid. Method B; Rt: 0.83 min. m/z: 329.1 (M−H)⁻ Exact mass: 330.1. Ethyl 1,3,5-trimethyl-4-[(3-methyloxetan-3-yl)sulfamoyl]pyrrole-2-carboxylate was dissolved in ethanol (10 mL) and NaOH (1M in $H_2O$, 0.61 mL) was added. The resulting solution was stirred at room temperature for 42 hours. The reaction mixture was stirred at 70° C. for 20 hours. NaOH (1 M in $H_2O$, 0.61 mL) was added to the reaction mixture which was stirred at 80° C. for 64 hours. The reaction mixture was allowed to reach room temperature. Triethylamine hydrochloride (222 mg, 1.61 mmol) was added, the reaction mixture was evaporated to dryness and co evaporated with toluene (2×20 mL) to afford a residue which was used as such. The obtained residue was dissolved in DMF (5 mL). Triethylamine (0.23 mL, 1.654 mmol) and HATU (150.9 mg, 0.397 mmol) were added and the reaction mixture was stirred at room temperature for 10 minutes. 4-fluoro-3-methylaniline (124 mg, 0.99 mmol) was added to the reaction mixture which was stirred at room temperature for 42 hours. The reaction mixture was poured into water. The dark brown precipitate was filtered and washed with water. The filtrate was extracted with Me-THF (2×20 mL) and EtOAc (2×30 mL). The combined organic layers were washed with brine, combined with the dark brown precipitate, dried ($Na_2SO_4$) and evaporated. The obtained residue was purified using silica gel column chromatography (ethyl acetate in heptane from 0 to 100% and methanol in $CH_2Cl_2$ from 0 to 2%) to afford compound 88 (17.2 mg) as a powder. ¹H NMR (400 MHz, DMSO-$d_6$) δ ppm 1.49 (s, 3H), 2.23 (d, J=1.8 Hz, 3H), 2.28 (s, 3H), 2.43 (s, 3H), 3.56 (s, 3H), 4.12 (d, J=6.4 Hz, 2H), 4.60 (d, J=5.9 Hz, 2H), 7.10 (t, J=9.2 Hz, 1H), 7.46-7.54 (m, 1H), 7.61 (dd, J=7.0, 2.2 Hz, 1H), 7.78 (br. s, 1H), 10.09 (s, 1H). Method B; Rt: 0.90 min. m/z: 408.2 (M−H)⁻ Exact mass: 409.1.

Compound 89: N-(4-Fluoro-3-methylphenyl)-1,5-dimethyl-4-[(3-methyloxetan-3-yl)sulfamoyl]-1H-pyrrole-2-carboxamide

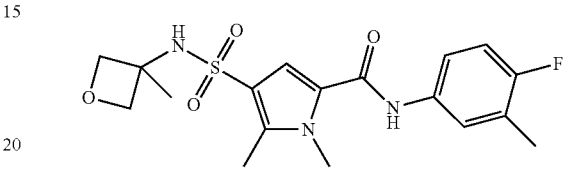

Ethyl 1,5-dimethyl-1H-pyrrole-2-carboxylate (2.5 g, 14.95 mmol) was added drop wise to chlorosulfonic acid (10 mL) at 0° C. under nitrogen atmosphere. The reaction mixture was warmed to room temperature and allowed to stir overnight. The reaction mixture was slowly added to ice cold water, followed by extraction with $CH_2Cl_2$. The combined organic extracts were dried ($Na_2SO_4$) and concentrated resulting in crude ethyl 4-chlorosulfonyl-1,5-dimethyl-pyrrole-2-carboxylate (2.9 g) as light purple powder. ¹H NMR (400 MHz, acetonitrile-$d_3$) δ ppm 1.32 (t, J=7.0 Hz, 3H), 2.54 (s, 3H), 3.86 (s, 3H), 4.28 (q, J=7.2 Hz, 2H), 7.30 (s, 1H). Crude ethyl 4-chlorosulfonyl-1,5-dimethyl-pyrrole-2-carboxylate (1500 mg, 5.65 mmol was dissolved in acetonitrile (15 mL). Hunig's base (2.4 mL, 14.1 mmol) and 3-methyl-3-oxetanamine (639 mg, 7.33 mmol) were added to the reaction mixture. The reaction mixture was stirred at room temperature for 42 hours. Water was added and the mixture was extracted with $CH_2Cl_2$ (2×50 mL) and EtOAc (2×50 mL). The combined organic layers were dried ($Na_2SO_4$) and evaporated to dryness. The obtained crude ethyl 1,5-dimethyl-4-[(3-methyloxetan-3-yl)sulfamoyl]pyrrole-2-carboxylate (1.8 g) was used as such. Method B; Rt: 0.77 min. m/z: 315.1 (M−H)⁻ Exact mass: 316.1. Crude ethyl 1,5-dimethyl-4-[(3-methyloxetan-3-yl)sulfamoyl]pyrrole-2-carboxylate (1800 mg, 5.689 mmol) was dissolved in methanol (8 mL), LiOH (720 mg, 30.1 mmol) in water (2 mL) was added and the reaction mixture was heated at 50° C. for 2 hours. The reaction mixture was evaporated to dryness and coevaporated with toluene (2×50 mL) to afford a beige powder. Half of the above obtained powder was dissolved in DMF (10 mL). Triethylamine hydrochloride (2349 mg, 17.1 mmol), triethylamine (1.19 mL) and HATU (1298 mg, 3.41 mmol), were added and the reaction mixture was stirred at room temperature for 10 minutes. 4-Fluoro-3-methylaniline (712 mg, 5.688 mmol), was added to the reaction mixture which was stirred at room temperature for 3 hours. The reaction mixture was poured into water and the solids were filtered and washed with water to afford a beige solid which was purified using silica gel column chromatography (ethylacetate in heptane from 0 to 100%) to afford compound 89 as a white powder. Method B; Rt: 0.92 min. m/z: 394.1 (M−H)⁻ Exact mass: 395.1.

¹H NMR (400 MHz, DMSO-$d_6$) δ ppm 1.50 (s, 3H), 2.22 (d, J=1.6 Hz, 3H), 2.43 (s, 3H), 3.83 (s, 3H), 4.11 (d, J=6.5 Hz, 2H), 4.59 (d, J=6.1 Hz, 2H), 6 7.08 (t, J=9.3 Hz, 1H), 7.29 (s, 1H), 7.49-7.54 (m, 1H), 7.63 (dd, J=7.3, 2.4 Hz, 1H), 7.92 (s, 1H), 9.94 (s, 1H). Differential scanning calorimetry: From 30 to 300° C. at 10° C./min: peak at 186.6° C.

Compound 90: N-(4-Fluoro-3-methylphenyl)-1,3-dimethyl-4-[(3-methyloxetan-3-yl)sulfamoyl]-1H-pyrrole-2-carboxamide

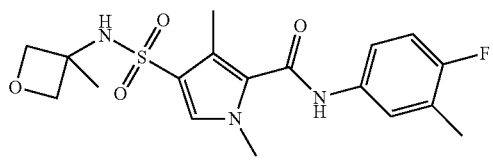 [SMILES: Cc1cc(NC(=O)c2c(C)c(S(=O)(=O)NC3(C)COC3)cn2C)ccc1F]

Ethyl 1,3-dimethylpyrrole-2-carboxylate (1.3 g, 7.78 mmol) was added drop wise to chlorosulfonic acid (5.2 mL) at 0° C. under nitrogen atmosphere. The reaction mixture was warmed to room temperature and allowed to stir 1.5 hours. The reaction mixture was slowly added to ice cold water, followed by extraction with CH₂Cl₂. The combined organic extracts were dried (Na₂SO₄) and concentrated in crude ethyl 4-chlorosulfonyl-1,3-dimethyl-pyrrole-2-carboxylate (1300 mg) as a brown oil. Crude ethyl 4-chlorosulfonyl-1,3-dimethyl-pyrrole-2-carboxylate (1.3 g, 4.89 mmol) was dissolved in acetonitrile (5 mL) and 3-methyl-3-oxetanamine (852 mg, 9.79 mmol) was added followed by Hunig's base (2.11 mL, 12.23 mmol). The reaction mixture was stirred at room temperature for 1 hour. The reaction mixture was filtered. The solids were washed with CH₂Cl₂ and discarded. The filtrate was evaporated and the residue was purified using silica gel column chromatography ethyl acetate in heptane from 0 to 100% resulting in ethyl 1,3-dimethyl-4-[(3-methyloxetan-3-yl)sulfamoyl]pyrrole-2-carboxylate (302 mg) as sticky oil. Method B; Rt: 0.79 min. m/z: 315.1 (M−H)⁻ Exact mass: 316.1. Ethyl 1,3-dimethyl-4-[(3-methyloxetan-3-yl)sulfamoyl]pyrrole-2-carboxylate (302 mg, 0.955 mmol) was dissolved in THF (40 mL) and LiOH (114.3 mg, 4.77 mmol) in water (10 mL) was added. The reaction mixture was stirred at room temperature. Methanol (20 mL) was added to the reaction mixture. The reaction mixture was stirred at room temperature overnight. More LiOH (5 equiv.) in water was added and the reaction mixture was heated at 60° C. for 42 hours. The reaction mixture was evaporated to dryness and coevaporated with toluene (2×50 mL). The residue was used as such in next step. The obtained residue was dissolved in DMF (10 mL). triethylamine hydrochloride (1575 mg, 11.4 mmol), triethylamine (0.663 mL, 4.7 mmol) and HATU (435 mg, 1.15 mmol) were added and the reaction mixture was stirred at room temperature for 10 minutes. 4-fluoro-3-methylaniline (239 mg, 1.91 mmol) was added to the reaction mixture which was stirred at room temperature for 2 hours. The reaction mixture was stirred at 50° C. for 2 hours. Water was added to the reaction mixture and the mixture was extracted with 2-Methyl THF. The combined organic layers were washed with brine, dried (Na₂SO₄) and evaporated to afford a brown oil. The oil was purified using silica gel column chromatography (ethylacetate in heptane from 0 to 100%) to afford a sticky light brown oil. Compound 90 was purified using Preparative LC (Hypersyl C₁₈ BDS-3 μm, 100×4.6 mm) Mobile phase (NH₄HCO₃ 0.2% in water, methanol) the desired fractions were combined and evaporated to dryness, dissolved in methanol and evaporated to dryness. After drying in vacuo compound 90 was obtained as a white powder. ¹H NMR (400 MHz, DMSO-d₆) δ ppm 1.53 (s, 3H), 2.23 (d, J=1.6 Hz, 3H), 2.31 (s, 3H), 3.70 (s, 3H), 4.11 (d, J=6.5 Hz, 2H), 4.61 (d, J=5.7 Hz, 2H), 6 7.11 (t, J=9.3 Hz, 1H), 7.44 (s, 1H), 7.47-7.53 (m, 1H), 7.62 (dd, J=6.9, 2.4 Hz, 1H), 7.88 (br. s., 1H), 10.09 (s, 1H). Method B; Rt: 0.88 min. m/z: 394.2 (M−H)⁻ Exact mass: 395.1. Differential scanning calorimetry: From 30 to 300° C. at 10° C./min: peak at 160.5° C.

Compound 97: N-(4-Fluoro-3-methylphenyl)-1-methyl-4-{[(1R)-1-methyl-2-(methyl-sulfonyl)ethyl]sulfamoyl}-1H-pyrrole-2-carboxamide

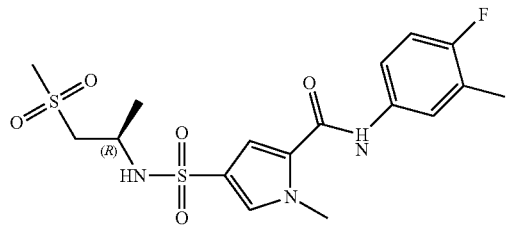

5-[(4-fluoro-3-methyl-phenyl)carbamoyl]-1-methyl-pyrrole-3-sulfonyl chloride (0.269 g, 0.813 mmol) was stirred in acetonitrile (50 mL). Et₃N (0.339 mL, 2.44 mmol) and (2R)-1-methylsulfonylpropan-2-amine (0.123 g, 0.895 mmol) were added under N₂-atmosphere at room temperature. The reaction mixture was stirred for 22 hours and next concentrated. The compound was precipitated from CH₂Cl₂/MeOH (4 mL, 3:1). The precipitate was filtered off, washed with CH₂Cl₂ (2×3 mL) and dried in vacuo at 50° C., resulting in compound 97 (123 mg). Method A; Rt: 1.47 min. m/z: 430.1 (M−H)⁻ Exact mass: 431.1. ¹H NMR (400 MHz, DMSO-d₆, 80° C.) δ ppm 1.20 (d, J=6.6 Hz, 3H), 2.22 (d, J=1.8 Hz, 3H), 2.94 (s, 3H), 3.10-3.17 (m, 1H), 3.27-3.34 (m, 1H), 3.71-3.81 (m, 1H), 3.92 (s, 3H), 7.04 (t, J=9.2 Hz, 1H), 7.30 (d, J=1.8 Hz, 2H), 7.46-7.52 (m, 2H), 7.59 (dd, J=7.3, 2.6 Hz, 1H), 9.80 (br. s., 1H).

Compound 98: 4-(tert-Butylsulfamoyl)-N-[4-fluoro-3-(trifluoromethoxy)phenyl]-1-methyl-1H-pyrrole-2-carboxamide

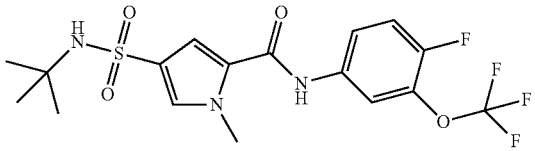 [SMILES: Cn1cc(S(=O)(=O)NC(C)(C)C)cc1C(=O)Nc1ccc(F)c(OC(F)(F)F)c1]

4-fluoro-3-(trifluoromethoxy)aniline (991 mg, 5.08 mmol) dissolved in toluene (10 mL) was added to 4-chlorosulfonyl-1-methyl-pyrrole-2-carbonyl chloride (1.23 g, 5.079 mmol) in toluene (65 mL) at reflux and refluxed 2 hours. The reaction mixture was filtered while still hot and concentrated yielding crude 5-[[4-fluoro-3-(trifluoromethoxy)phenyl]carbamoyl]-1-methyl-pyrrole-3-sulfonyl chloride as a beige powder which was used as such. ¹H NMR (400 MHz, acetonitrile-d₃) δ ppm 3.97 (s, 3H), 7.27-7.35 (m, 1H), 7.38 (d, J=2.0 Hz, 1H), 7.57 (ddd, J=9.0, 4.0, 2.6 Hz, 1H), 7.73 (d, J=1.5 Hz, 1H), 7.87-7.94 (m, 1H), 8.79 (br. s., 1H). Tert-butylamine (342.7 mg, 4.69 mmol) was added to crude 5-[[4-fluoro-3-(trifluoromethoxy)phenyl]carbamoyl]-1-methyl-pyrrole-3-sulfonyl chloride (626 mg) in acetonitrile (52 mL) and stirred 2 hours. Water was added until crystallisation began. The white crystals were filtered off and dried in vacuo at 50° C. during 4 hours. Method A; Rt: 1.90 min. m/z: 436.1 (M–H)⁻ Exact mass: 437.1. $^1$H NMR (400 MHz, DMSO-$d_6$) δ ppm 1.17 (s, 9H), 3.91 (s, 3H), 7.12 (s, 1H), 7.33 (d, J=1.8 Hz, 1H), 7.48 (s, 1H), 7.54 (d, J=1.5 Hz, 1H), 7.69-7.77 (m, 1H), 7.98-8.07 (m, 1H), 10.28 (s, 1H).

Compound 99: N-(2,4-Difluoro-3-methylphenyl)-1-methyl-4-[(1-methylethyl)sulfamoyl]-1H-pyrrole-2-carboxamide

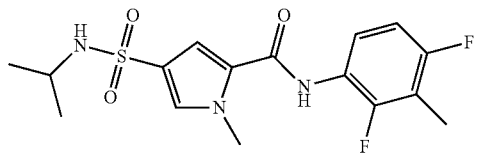 [SMILES: Cc1c(F)ccc(NC(=O)c2cc(S(=O)(=O)NC(C)C)cn2C)c1F]

4-(isopropylsulfamoyl)-1-methyl-pyrrole-2-carboxylic acid (0.426 g, 1.73 mol) was dissolved in acetonitrile (40 mL). Et$_3$N (0.962 mL, 6.92 mmol) and 2,4-difluoro-3-methyl-aniline (0.342 g, 1.9 mmol) were added. HATU (0.789 g, 2.08 mmol) was next added at once. The reaction mixture was stirred at room temperature for 1 hour. Then the solution was stirred at 50° C. for 80 hours. The solution was allowed to cool and water (2×50 mL) and brine (5 mL) were added. The solution was extracted with EtOAc (2×100 mL) and dried with Na$_2$SO$_4$. The solvent was evaporated leaving yellow oil which purified by silica gel chromatography (EtOAc-heptane 0/100 to 100/0). The obtained solid was dissolved in boiling 2-propanol (1.5 mL) and water was added dropwise (1.5 mL) when still boiling. The solution was allowed to cool down After 90 min the white precipitate was filtered off, washed with 2-Propanol/water (2×1 mL) and dried at 50° C. in vacuo yielding compound 99 as white crystals. Method A; Rt: 1.72 min. m/z: 370.0 (M–H)⁻ Exact mass: 371.1. $^1$H NMR (400 MHz, DMSO-$d_6$, 80° C.) δ ppm 1.06 (d, J=6.4 Hz, 6H), 2.18 (t, J=1.9 Hz, 3H), 3.33 (dt, J=13.0, 6.6 Hz, 1H), 3.89 (s, 3H), 6.85 (br. s., 1H), 7.00 (td, J=8.9, 1.8 Hz, 1H), 7.25 (s, 1H), 7.37 (m, J=8.8, 8.8, 6.2 Hz, 1H), 7.43 (d, J=1.8 Hz, 1H), 9.62 (br. s., 1H)

Synthesis of 1-methyl-4-[[(1S)-2,2,2-trifluoro-1-methyl-ethyl]sulfamoyl]pyrrole-2-carboxylic acid Methyl 4-chlorosulfonyl-1-methyl-pyrrole-2-carboxylate (5 g, 21.04 mmol) was dissolved in acetonitrile (50 mL). To this was added diisopropylethylamine (9.06 mL, 52.6 mmol) followed by (S)-1,1,1-trifluoro-2-propylamine (3.57 g, 31.6 mmol) and the resulting mixture was refluxed overnight. Then the mixture was cooled to room temperature and concentrated in vacuo. The resulting residue was dissolved in dichloromethane (250 mL) and this was washed with HCl (2×150 mL). The organics were dried on sodium sulphate, filtered and concentrated in vacuo yielding crude methyl 1-methyl-4-[[(1S)-2,2,2-trifluoro-1-methyl-ethyl]sulfamoyl]pyrrole-2-carboxylate (6.6 g) which was used as such. Methyl 1-methyl-4-[[(1S)-2,2,2-trifluoro-1-methyl-ethyl]sulfamoyl]pyrrole-2-carboxylate (6.6 g, 19.7 mmol) was dissolved in tetrahydrofuran (56 mL). To this was added lithium hydroxide (1.655 g, 69.1 mmol) in distilled water (7.5 mL) followed by methanol (3 mL). The resulting mixture was stirred overnight. The mixture was concentrated until only water remained and extra distilled water (15 mL) was added. The mixture was neutralised with hydrochloric acid (1M, aq). The resulting mixture was extracted using 2-methyltetrahydrofuran (3×20 mL). The combined extracts were dried on sodium sulphate, filtered and concentrated in vacuo yielding 1-methyl-4-[[(1S)-2,2,2-trifluoro-1-methyl-ethyl]sulfamoyl]pyrrole-2-carboxylic acid (5.34 g).

Compound 100 to 105 were prepared similarly as described for compound 80, using 1-methyl-4-[[(1S)-2,2,2-trifluoro-1-methyl-ethyl]sulfamoyl]pyrrole-2-carboxylic acid instead of 1-methyl-4-[(3-methyloxetan-3-yl)sulfamoyl]pyrrole-2-carboxylic acid and the corresponding aniline instead of 4-fluoro-3,5-dimethylaniline. After addition of the aniline, the mixture was stirred at 50° C. for 6 hours instead of 24 hours at room temperature.

Compound 100: N-(3-Bromo-4,5-difluorophenyl)-1-methyl-4-{[(1S)-2,2,2-trifluoro-1-methylethyl]sulfamoyl}-1H-pyrrole-2-carboxamide

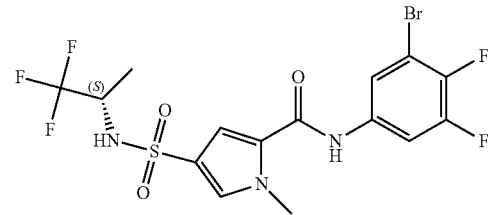

Crude compound 100 was purified by silica gel chromatography heptane-EtOAc 100/0 to 0/100. The product was crystallized from diisopropylether (15 mL)/iPrOH (3.5 mL). The product was filtered off, washed with diisopropylether (3×), and dried at 50° C. in vacuo, resulting in compound 100 (251 mg). Method A; Rt: 1.98 min. m/z: 489.8 (M–H)⁻ Exact mass: 491.0. $^1$H NMR (400 MHz, DMSO-$d_6$) δ ppm 1.08 (d, J=6.8 Hz, 3H), 3.84-4.00 (m, 4H), 7.36 (d, J=2.0 Hz, 1H), 7.66 (d, J=1.8 Hz, 1H), 7.80-7.93 (m, 2H), 8.20 (br. s., 1H), 10.31 (br. s., 1H). $^{19}$F NMR (377 MHz, DMSO-$d_6$) δ ppm –138.51--138.34 (m, 1 F), –133.99--133.81 (m, 1 F), –76.07 (d, J=7.9 Hz, 3 F). Differential scanning calorimetry: From 30 to 300° C. at 10° C./min: peak at 199.0° C.

Compound 101: N-(3-Bromo-4-fluorophenyl)-1-methyl-4-{[(1S)-2,2,2-trifluoro-1-methylethyl]sulfamoyl}-1H-pyrrole-2-carboxamide

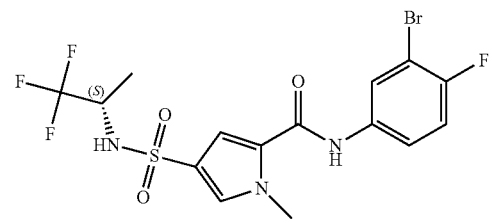

Crude compound 101 was stirred in CH$_2$Cl$_2$ (5 mL), filtered off, and washed with CH$_2$Cl$_2$ (1×). The product (0.289 g) was crystallized from iPrOH—H$_2$O 3/1 (6 mL), filtered off, washed with iPrOH—H$_2$O 3/1 (3×), and dried at 50° C. in vacuo, resulting in compound 101 (70 mg). Method B; Rt: 1.07 min. m/z: 470.0 (M–H)$^-$ Exact mass: 471.0. $^1$H NMR (400 MHz, DMSO-d$_6$) δ ppm 1.08 (d, J=7.0 Hz, 3H), 3.88-3.96 (m, 4H), 7.33-7.41 (m, 2H), 7.63 (d, J=1.5 Hz, 1H), 7.71 (ddd, J=9.0, 4.4, 2.6 Hz, 1H), 8.11-8.28 (m, 2H), 10.21 (s, 1H).

Compound 102: N-(3-Cyano-4-fluorophenyl)-1-methyl-4-{[(1S)-2,2,2-trifluoro-1-methylethyl]sulfamoyl}-1H-pyrrole-2-carboxamide

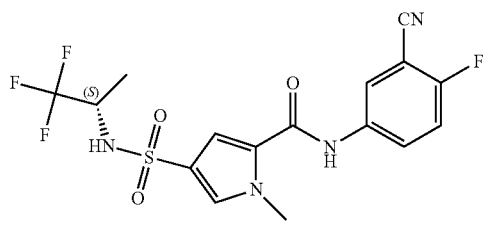

Crude compound 102 was stirred in CH$_2$Cl$_2$ (5 mL), filtered off, and washed with CH$_2$Cl$_2$ (2×). The product was crystallized from iPrOH (12.5 mL)+H$_2$O (2.5 mL), filtered off, washed with iPrOH—H$_2$O 4/1 (2×) and iPrOH, and dried at 50° C. in vacuo, resulting in compound 102 (93 mg). Method B; Rt: 0.97 min. m/z: 417.1 (M–H)$^-$ Exact mass: 418.1. $^1$H NMR (400 MHz, DMSO-d$_6$) δ ppm 1.07 (d, J=7.0 Hz, 3H), 3.84-3.99 (m, 4H), 7.36 (d, J=2.0 Hz, 1H), 7.53 (t, J=9.1 Hz, 1H), 7.64 (br. s., 1H), 7.97-8.04 (m, 1H), 8.22 (dd+br. s., J=5.7, 2.6 Hz, 2H), 10.38 (br. s., 1H).

Alternative Synthesis of Compound 102:

Methyl 1-methyl-4-[[(1S)-2,2,2-trifluoro-1-methyl-ethyl]sulfamoyl]pyrrole-2-carboxylate (5 g, 15.9 mmol) was dissolved in of dry tetrahydrofuran (50 mL) under a blanket of nitrogen. 5-amino-2-fluorobenzonitrile (2.82 g, 20.68 mmol) was added and the mixture was cooled in an ice-water bath while stirring under nitrogen. Lithium bis(trimethylsilyl)amide (1M in toluene, 47.73 mL, 47.73 mmol) was added drop wise over a period of 10 minutes. The resulting mixture was stirred for 1 hour while cooling was continued.

An extra 2 equivalents of lithium bis(trimethylsilyl)amide (1M in toluene, 31.82 mL, 31.82 mmol) were added drop wise over a period of 10 minutes. The resulting mixture was stirred for 1 hour while cooling was continued. An extra equivalent of lithium bis(trimethylsilyl)amide (1M in toluene, 15.9 mL, 15.9 mmol) was added drop wise over a period of 5 minutes. Next, the mixture was quenched with saturated ammonium chloride (150 mL/aq) and the resulting mixture was extracted using EtOAc (3×150 mL). The combined extracts were washed with brine (200 mL), dried on Na$_2$SO$_4$, filtered and concentrated in vacuo. The obtained residue was dissolved in dichloromethane (10 mL) and this was loaded on a dry silica plug (330 g). This was purified by column chromatography using gradient elution from heptane to EtOAc. (100:0 to 0:100). The desired fractions were collected and concentrated in vacuo yielding a slightly red powder. This powder was recrystallized out of MeOH/water. The obtained crystals were collected on a filter, rinsed with water and diisopropylether and dried in a vacuum oven at 55° C. for 24 hours yielding compound 102 (3.92 g) as a bright white powder. [α]$_{589}^{20}$=+2.7° (c 0.96 w/v %, MeOH). [α]$_{589}^{20}$=+21.8° (c 0.37 w/v %, DMF). Differential scanning calorimetry: From 30 to 300° C. at 10° C./min: peak at 213.4° C. SFC analysis: AD-H 250 mm×4.6 mm, Flow: 5 mL/min Mobile phase: 10-55% MeOH (containing 0.2% iPrNH$_2$) @ 14.5% rate, down to 50% and hold for 2.55 min @ 50%, Temperature: 40° C.: Compound 102 (first eluding), containing no detectable compound 157 (second eluding). $^1$H NMR (600 MHz, DMSO-d$_6$) δ ppm 1.08 (d, J=7.0 Hz, 3H), 3.88-3.97 (m, 1H), 3.93 (s, 3H), 7.37 (d, J=1.9 Hz, 1H), 7.53 (t, J=9.2 Hz, 1H), 7.67 (d, J=1.9 Hz, 1H), 8.01 (ddd, J=9.2, 4.8, 2.7 Hz, 1H), 8.19 (br. s., 1H), 8.22 (dd, J=5.8, 2.7 Hz, 1H), 10.39 (br. s., 1H).

Compound 103: N-(3-Chloro-4,5-difluorophenyl)-1-methyl-4-{[(1S)-2,2,2-trifluoro-1-methylethyl]sulfamoyl}-1H-pyrrole-2-carboxamide

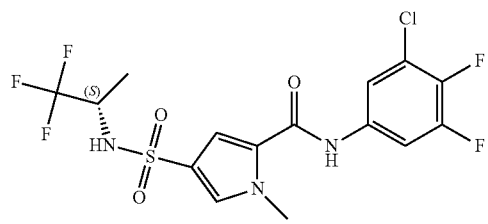

Crude compound 103 was triturated from refluxing CH$_2$Cl$_2$ (10 mL). The suspension was cooled to room temperature, the solids were filtered and washed with CH$_2$Cl$_2$ (2 mL) resulting in compound 103 (308 mg) as white solid after drying in vacuo at 50° C. Method B; Rt: 1.13 min. m/z: 444.0 (M–H)$^-$ Exact mass: 445.0. III NMR (400 MHz, DMSO-d$_6$) δ ppm 1.08 (d, J=6.8 Hz, 3H), 3.85-3.98 (m, 4H), 7.36 (d, J=1.5 Hz, 1H), 7.65 (d, J=1.3 Hz, 1H), 7.75-7.87 (m, 2H), 8.19 (br. s, 1H), 10.33 (br. s., 1H).

Compound 104: N-(3,4-Difluoro-5-methylphenyl)-1-methyl-4-{[(1S)-2,2,2-trifluoro-1-methylethyl]sulfamoyl}-1H-pyrrole-2-carboxamide

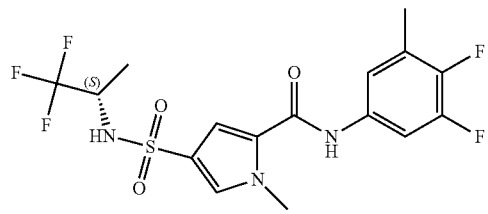

Crude compound 104 was triturated from refluxing CH$_2$Cl$_2$ (10 mL). The suspension was cooled to room temperature, the solids were filtered and washed with CH$_2$Cl$_2$ (2 mL) resulting in compound 104 (481 mg) as white solid after drying in vacuo at 50° C. Method B; Rt: 1.08 min. m/z: 424.0 (M–H)$^-$ Exact mass: 425.1. III NMR (400 MHz, DMSO-d$_6$) δ ppm 1.07 (d, J=7.0 Hz, 3H), 2.28 (d, J=2.0 Hz, 3H), 3.86-3.98 (m, 4H), 7.34 (d, J=2.0 Hz, 1H), 7.38-7.44 (m, 1H), 7.62 (d, J=1.3 Hz, 1H), 7.66 (ddd, J=12.9, 7.1, 2.4 Hz, 1H), 8.16 (br. s., 1H), 10.15 (s, 1H).

Compound 105: N-(3-Chloro-4-fluorophenyl)-1-methyl-4-{[(1S)-2,2,2-trifluoro-1-methylethyl]sulfamoyl}-1H-pyrrole-2-carboxamide

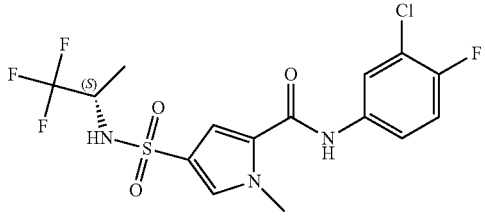

Crude compound 105 was triturated from refluxing CH$_2$Cl$_2$ (10 mL). The suspension was cooled to room temperature, the solids were filtered and washed with CH$_2$Cl$_2$ (2 mL). The obtained solid was triturated with warm acetonitrile, the mixture was cooled to room temperature. The solids were filtered and to the obtained filtrate, water (3 mL) was added to form a white solid which was filtered and washed with water, resulting in compound 105 as white powder. Method B; Rt: 1.08 min. m/z: 426.0 (M−H)⁻ Exact mass: 427.0. $^1$H NMR (400 MHz, DMSO-d$_6$) δ ppm 1.08 (d, J=7.0 Hz, 3H), 3.87-3.98 (m, 4H), 7.35 (d, J=2.0 Hz, 1H), 7.40 (t, J=9.1 Hz, 1H), 7.60-7.70 (m, 2H), 8.01 (dd, J=6.9, 2.5 Hz, 1H), 8.16 (br. s., 1H), 10.23 (s, 1H).

Compound 94: 3-Fluoro-N-(4-fluoro-3-methylphenyl)-1-methyl-4-[(3-methyloxetan-3-yl)sulfamoyl]-1H-pyrrole-2-carboxamide

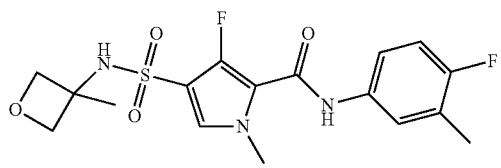 [SMILES: Cc1cc(NC(=O)c2c(F)c(S(=O)(=O)NC3(C)COC3)cn2C)ccc1F]

A solution of Et$_3$N (0.179 mL, 1.29 mmol) in DMF (1.9 mL) was added to 3-fluoro-1-methyl-4-[(3-methyloxetan-3-yl)sulfamoyl]pyrrole-2-carboxylic acid 1125 mg, 0.428 mmol), HATU (204 mg, 0.535 mmol), 4-fluoro-3-methylaniline (107 mg, 0.857 mmol) and stirred overnight. The solution was subjected to column chromatography using a gradient from 10 till 100% EtOAc in heptane. The product fractions were combined and concentrated. Compound 94 (78 mg) was obtained as a white powder after drying in vacuo at 50° C. Method A; Rt: 1.66 min. m/z: 397.9 (M−H)⁻ Exact mass: 399.1. $^1$H NMR (400 MHz, DMSO-d$_6$) δ ppm 1.56 (s, 3H), 2.23 (d, J=1.5 Hz, 3H), 3.79 (s, 3H), 4.17 (d, J=6.4 Hz, 2H), 4.65 (d, J=6.2 Hz, 2H), 7.10 (t, J=9.2 Hz, 1H), 7.43-7.51 (m, 2H), 7.59 (dd, J=7.0, 2.4 Hz, 1H), 8.28 (s, 1H), 10.01 (s, 1H).

Compound 106: N-(3-Bromo-4-fluorophenyl)-3-fluoro-1-methyl-4-[(3-methyloxetan-3-yl)sulfamoyl]-1H-pyrrole-2-carboxamide

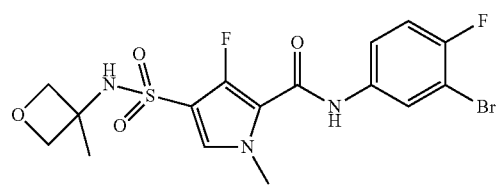 [SMILES: Cn1cc(S(=O)(=O)NC2(C)COC2)c(F)c1C(=O)Nc1ccc(F)c(Br)c1]

Compound 106 (131 mg) was prepared similarly as described for compound 94, using 3-bromo-4-fluoroaniline instead of 4-fluoro-3-methylaniline. Method A; Rt: 1.73 min. m/z: 463.8 (M−H)⁻ Exact mass: 465.0. $^1$H NMR (400 MHz, DMSO-d$_6$) δ ppm 1.56 (s, 3H), 3.80 (s, 3H), 4.17 (d, J=6.4 Hz, 2H), 4.64 (d, J=5.9 Hz, 2H), 7.37 (t, J=8.8 Hz, 1H), 7.51 (d, J=4.4 Hz, 1H), 7.64 (ddd, J=9.0, 4.4, 2.6 Hz, 1H), 8.08 (dd, J=6.4, 2.6 Hz, 1H), 8.30 (s, 1H), 10.20 (s, 1H).

Compound 107: N-[3-(Difluoromethyl)-4-fluorophenyl]-3-fluoro-1-methyl-4-[(3-methyloxetan-3-yl)sulfamoyl]-1H-pyrrole-2-carboxamide

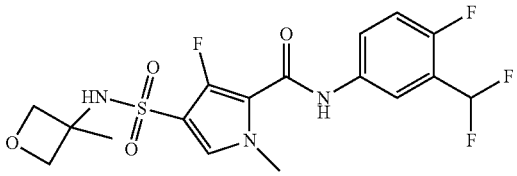 [SMILES: Cn1cc(S(=O)(=O)NC2(C)COC2)c(F)c1C(=O)Nc1ccc(F)c(C(F)F)c1]

Compound 107 (149 mg) was prepared similarly as described for compound 94, using 3-(difluoromethyl)-4-fluoro-aniline instead of 4-fluoro-3-methylaniline. Method A; Rt: 1.63 min. m/z: 334.0 (M−H)⁻ Exact mass: 435.1. $^1$H NMR (400 MHz, DMSO-d$_6$) δ ppm 1.56 (s, 3H), 3.80 (s, 3H), 4.18 (d, J=6.6 Hz, 2H), 4.65 (d, J=5.9 Hz, 2H), 7.04-7.43 (m, 2H), 7.51 (d, J=4.6 Hz, 1H), 7.76-7.86 (m, 1H), 8.01 (dd, J=6.3, 2.5 Hz, 1H), 8.30 (s, 1H), 10.26 (s, 1H).

Compound 108: N-(3-Chloro-4-fluorophenyl)-3-fluoro-1-methyl-4-[(3-methyloxetan-3-yl)sulfamoyl]-1H-pyrrole-2-carboxamide

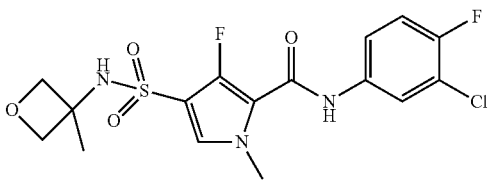 [SMILES: Cn1cc(S(=O)(=O)NC2(C)COC2)c(F)c1C(=O)Nc1ccc(F)c(Cl)c1]

Compound 108 (149 mg) was prepared similarly as described for compound 94, using 3-chloro-4-fluoroaniline instead of 4-fluoro-3-methylaniline. Method A; Rt: 1.70 min. m/z: 417.9 (M−H)⁻ Exact mass: 419.1. $^1$H NMR (400 MHz, DMSO-d$_6$) δ ppm 1.56 (s, 3H), 3.80 (s, 3H), 4.17 (d, J=6.4 Hz, 2H), 4.64 (d, J=6.2 Hz, 2H), 7.41 (t, J=9.1 Hz, 1H), 7.51 (d, J=4.4 Hz, 1H), 7.60 (ddd, J=9.1, 4.3, 2.6 Hz, 1H), 7.96 (dd, J=6.8, 2.4 Hz, 1H), 8.30 (s, 1H), 10.22 (s, 1H).

Compound 109: 3-Fluoro-1-methyl-4-[(3-methyloxetan-3-yl)sulfamoyl]-N-(2,4,5-trifluorophenyl)-1H-pyrrole-2-carboxamide

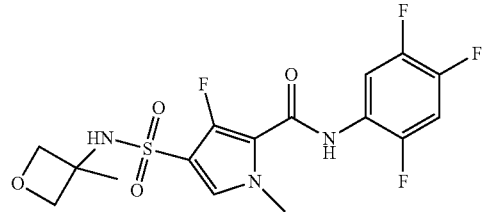 [SMILES: Cn1cc(S(=O)(=O)NC2(C)COC2)c(F)c1C(=O)Nc1cc(F)c(F)cc1F]

Compound 109 (35 mg) was prepared similarly as described for compound 94, using 2,4,5-trifluoroaniline instead of 4-fluoro-3-methylaniline. After overnight stirring at room temperature, the mixture was stirred at 60° C. for 3 hours. Method A; Rt: 1.56 min. m/z: 420.1 (M–H)⁻ Exact mass: 421.1. ¹H NMR (400 MHz, DMSO-d₆) δ ppm 1.55 (s, 3H), 3.81 (s, 3H), 4.17 (d, J=6.4 Hz, 2H), 4.64 (d, J=5.9 Hz, 2H), 7.53 (d, J=4.6 Hz, 1H), 7.67 (td, J=10.6, 7.3 Hz, 1H), 7.80-7.90 (m, 1H), 8.32 (s, 1H), 9.79 (s, 1H).

Compound 110: N-(2,4-Difluoro-3-methylphenyl)-3-fluoro-1-methyl-4-[(3-methyloxetan-3-yl)sulfamoyl]-1H-pyrrole-2-carboxamide

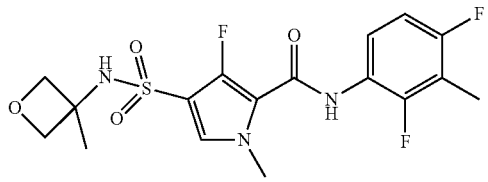 [SMILES: Cc1c(F)ccc(NC(=O)c2c(F)c(S(=O)(=O)NC3(C)COC3)cn2C)c1F]

Compound 110 (90 mg) was prepared similarly as described for compound 94, using 2,4-difluoro-3-methylaniline instead of 4-fluoro-3-methylaniline. Method A; Rt: 1.68 min. m/z: 415.9 (M–H)⁻ Exact mass: 417.1. ¹H NMR (400 MHz, DMSO-d₆) δ ppm 1.56 (s, 3H), 2.15-2.22 (m, 3H), 3.80 (s, 3H), 4.17 (d, J=6.4 Hz, 2H), 4.65 (d, J=6.2 Hz, 2H), 7.06 (td, J=9.0, 1.5 Hz, 1H), 7.46-7.56 (m, 2H), 8.30 (s, 1H), 9.63 (s, 1H).

Compound 111: N-(3-Chloro-4,5-difluorophenyl)-3-fluoro-1-methyl-4-[(3-methyloxetan-3-yl)sulfamoyl]-1H-pyrrole-2-carboxamide

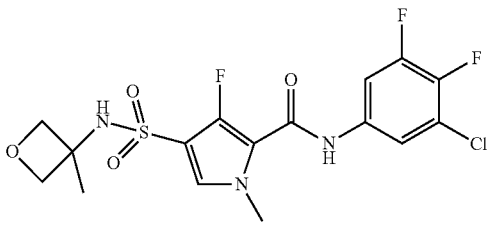 [SMILES: Cn1cc(S(=O)(=O)NC2(C)COC2)c(F)c1C(=O)Nc1cc(F)c(F)c(Cl)c1]

Compound 111 (46 mg) was prepared similarly as described for compound 94, using 3-chloro-4,5-difluoroaniline instead of 4-fluoro-3-methylaniline. The mixture was stirred at 65° C. overnight instead of room temperature. Method A; Rt: 1.80 min. m/z: 435.9 (M–H)⁻ Exact mass: 437.0. ¹H NMR (400 MHz, DMSO-d₆) δ ppm 1.55 (s, 3H), 3.80 (s, 3H), 4.17 (d, J=6.4 Hz, 2H), 4.64 (d, J=6.2 Hz, 2H), 7.54 (d, J=4.4 Hz, 1H), 7.70-7.80 (m, 2H), 8.32 (s, 1H), 10.30 (s, 1H).

Compound 112: 4-(tert-butylsulfamoyl)-N-(2,4-difluoro-3-methyl-phenyl)-1-methyl-pyrrole-2-carboxamide

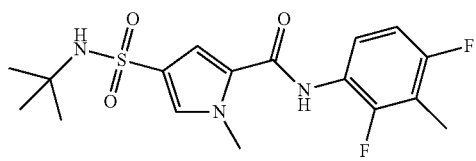 [SMILES: Cc1c(F)ccc(NC(=O)c2cc(S(=O)(=O)NC(C)(C)C)cn2C)c1F]

5-[(2,4-difluoro-3-methyl-phenyl)carbamoyl]-1-methyl-pyrrole-3-sulfonyl chloride (prepared similarly as described for 5-[(3,4-difluorophenyl)carbamoyl]-1-methyl-pyrrole-3-sulfonyl chloride, using 2,4-difluoro-3-methyl-aniline instead of 3,4-difluoroaniline; 0.25 g, 0.72 mmol) was stirred in acetonitrile (20 mL). DIPEA (0.494 mL, 2.87 mmol) and tert-butylamine (0.152 mL, 1.43 mmol) were added under N₂-atmosphere at room temperature. The reaction mixture was stirred in a sealed tube at 80° C. for 5 hours and further at room temperature for more than 80 hours. The solvent was evaporated and the residue was dissolved in (CH₂Cl₂/MeOH (5 mL, 90:10) and purified by silica gel chromatography [EtOAc-heptane 0/100 to 100/0] and further purified by reverse phase column chromatography. The resulting solid was triturated from Heptane/diisopropyl ether (4:1, 2.5 mL). The formed suspension was filtered. The filtercake was washed with heptane/diisopropylether (4:1, 5 mL) and dried at 50° C. in vacuo yielding compound 112 (120 mg) as a white solid. Method A; Rt: 1.71 min. m/z: 384.1 (M–H)⁻ Exact mass: 385.1. ¹H NMR (400 MHz, DMSO-d₆) δ ppm 1.18 (s, 9H), 2.18 (s, 3H), 3.88 (s, 3H), 7.05 (td, J=8.9, 1.5 Hz, 1H), 7.12 (s, 1H), 7.29 (s, 1H), 7.34 (td, J=8.7, 6.3 Hz, 1H), 7.50 (d, J=1.8 Hz, 1H), 9.89 (s, 1H).

Compound 113: N-(3-cyano-4-fluoro-phenyl)-3-fluoro-1-methyl-4-[(3-methyloxetan-3-yl)sulfamoyl]pyrrole-2-carboxamide

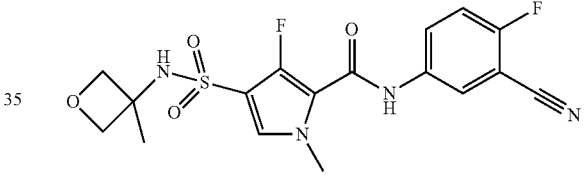

Compound 113 (43 mg) was prepared similarly as described for compound 94, using 5-amino-2-fluoro-benzonitrile instead of 4-fluoro-3-methylaniline but stirred 24 hours at 65° C. and 48 hours at 100° C. The residue after column was crystallized from acetonitrile (10 mL) upon addition of water. The crystals were dried overnight at 50° C. in vacuo. Method A; Rt: 1.44 min. m/z: 409.0 (M–H)⁻ Exact mass: 410.1. ¹H NMR (400 MHz, DMSO-d₆) δ ppm 1.56 (s, 3H), 3.80 (s, 3H), 4.18 (d, J=6.4 Hz, 2H), 4.64 (d, J=5.9 Hz, 2H), 7.48-7.58 (m, 2H), 7.96 (ddd, J=9.2, 4.8, 2.6 Hz, 1H), 8.16 (dd, J=5.7, 2.6 Hz, 1H), 8.32 (s, 1H), 10.34 (s, 1H).

Compound 114: 4-[(1-Carbamoylcyclopropyl)sulfamoyl]-N-(3-chloro-4,5-difluorophenyl)-1-methyl-1H-pyrrole-2-carboxamide

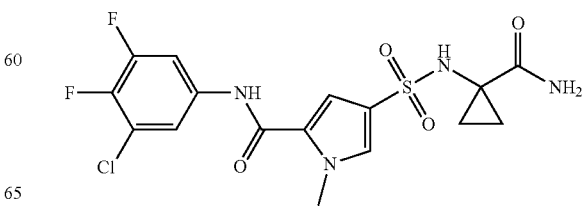

Methyl 1-aminocyclopropanecarboxylate (1.016 g, 6.7 mmol) was dissolved in dry dichloromethane (50 ml) and dry DIPEA (3.08 ml) under N$_2$-atm. 5-[(3-chloro-4,5-difluoro-phenyl)carbamoyl]-1-methyl-pyrrole-3-sulfonyl chloride (prepared similarly as described for compound 57, 1.65 g, 4.47 mmol) was added. The reaction mixture was stirred at room temperature for 3 h. Dry DMF (1 mL) was added and the reaction mixture was stirred for 22 h. Then the mixture was washed with HCl 1M (50 mL). The layers were separated, precipitate 1 was filtered off and washed with CH$_2$Cl$_2$ (10 mL). The organic layer was dried with Na$_2$SO$_4$ and the filtrate was evaporated resulting in residue 1. The water layer was extracted with EtOAc (100 mL). The layers were separated and the organic layer was dried with Na$_2$SO$_4$ and the filtrate was evaporated resulting in residue 2. Residue 1, 2 and precipitate 1 were combined giving methyl 1-[[5-[(3-chloro-4,5-difluoro-phenyl)carbamoyl]-1-methyl-pyrrol-3-yl]sulfonylamino]-cyclopropanecarboxylate (2.0 g) This material was dissolved in methanol (20 mL) and NaOH 1M (13.4 mL, 13.4 mmol) was added. The reaction mixture was stirred for 20 h. After 8 h, THF (6 mL) was added and the mixture was stirred further for 18 h. Then the mixture was successively stirred at 50° C. for 9 h, room temperature for 80 h, 50° C. for 8 h and 18 h at room temperature. The methanol/THF was distilled off and the mixture was extracted with Et$_2$O. The layers were separated and HCl 1M (14 mL) was added to the water layer. The water layer was extracted with MeTHF. The organic layer was evaporated resulting in 1-[[5-[(3-chloro-4,5-difluoro-phenyl)carbamoyl]-1-methyl-pyrrol-3-yl]sulfonylamino]cyclopropanecarboxylic acid as a yellow residue (1164 mg) which was used as such. This material (700 mg, 16.1 mmol) was stirred in CH$_3$CN (50 mL), CDI (654 mg, 40.3 mmol) was added and the resulting solution was stirred at room temperature in a sealed tube for 2.5 h [white precipitation was observed]. Then, NH$_3$ (0.4 M in THF, 80.7 mL, 32.3 mmol) was added at once. The mixture was stirred at room temperature for more than 80 h. The solvent was evaporated and the yellow residue was dissolved in EtOAc (80 mL). The solution was washed with HCl 1M (50 mL) and saturated NaCl solution (5 mL). The layers were separated and the organic was dried with Na$_2$SO$_4$. The solvent was evaporated and the beige residue was stirred in warm CH$_3$CN. The suspension was filtered off leaving a white filtercake. The filtercake was washed with CH$_3$CN and dried in vacuo at 50° C., resulting in compound 114 (319 mg) Method A; Rt: 1.56 min. m/z: 431.0 (M−H)$^-$ Exact mass: 432.05. $^1$H NMR (400 MHz, DMSO-d$_6$) δ ppm 0.94-0.99 (m, 2H), 1.10-1.18 (m, 2H), 3.91 (s, 3H), 6.87 (br. s., 1H), 7.21 (br. s., 1H), 7.32 (d, J=1.8 Hz, 1H), 7.59 (d, J=1.8 Hz, 1H), 7.76-7.87 (m, 2H), 8.20 (br. s., 1H), 10.29 (br. s., 1H).

Compound 115: N-(3-Chloro-4,5-difluorophenyl)-1-methyl-4-{[1-(methylcarbamoyl)cyclopropyl]sulfamoyl}-1H-pyrrole-2-carboxamide

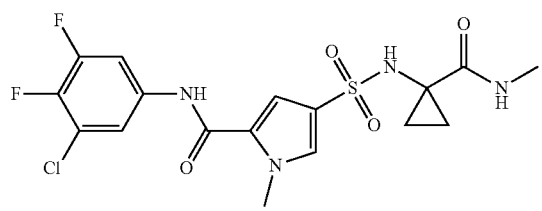 [SMILES: CNC(=O)C1(NS(=O)(=O)c2cc(C(=O)Nc3cc(F)c(F)c(Cl)c3)n(C)c2)CC1]

1-[[5-[(3-chloro-4,5-difluoro-phenyl)carbamoyl]-1-methyl-pyrrol-3-yl]sulfonylamino]-cyclopropanecarboxylic acid (364 mg, 0.839 mmol) was stirred in dry CH$_3$CN (30 mL). After addition of CDI (340 mg, 2.1 mmol) the mixture became a solution. The reaction mixture was stirred at room temperature in a sealed tube for 2.5 h. Then Methylamine (2 M in THF, 12 mL, 24 mmol) was added at once. The mixture was stirred at room temperature for 2 h. The reaction was stirred during 80 h. The solvent was distilled off and the residue dissolved in 5 mL CH$_2$Cl$_2$/MeOH (90:10) and purified by flash chromatography on silica using a gradient EtOAc-heptane 0/100 to 100/0. The desired fractions were combined and the solvent was evaporated, resulting in compound 115 (199 mg) Method A; Rt: 1.60 min. m/z: 445.0 (M−H)$^-$ 447.0 (M+H)$^+$ Exact mass: 446.10. $^1$H NMR (400 MHz, DMSO-d$_6$) δ ppm 0.91-0.98 (m, 2H), 1.08-1.15 (m, 2H), 2.55 (d, J=4.6 Hz, 3H), 3.91 (s, 3H), 7.31 (d, J=2.0 Hz, 1H), 7.41 (d, J=4.6 Hz, 1H), 7.58 (d, J=1.5 Hz, 1H), 7.76-7.86 (m, 2H), 8.14 (br. s., 1H), 10.31 (br. s., 1H).

Compound 116: N-(2,4-Difluoro-3-methylphenyl)-1-methyl-4-{[(1R)-2,2,2-trifluoro-1-methylethyl]sulfamoyl}-1H-pyrrole-2-carboxamide

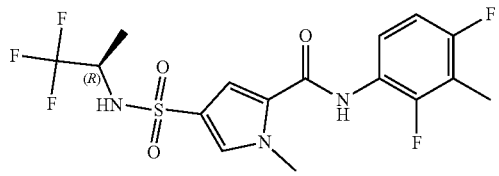

5-[(2,4-difluoro-3-methyl-phenyl)carbamoyl]-1-methyl-pyrrole-3-sulfonyl chloride (310 mg, 0.89 mmol) prepared similarly as described in the synthesis for compound 57 using 2,4-difluoro-3-methyl-aniline (251 mg, 2.22 mmol) was stirred in dry CH$_3$CN (25 mL). (2R)-1,1,1-trifluoropropan-2-amine (251 mg, 2.22 mmol) was added under N$_2$-atm at room temperature. The mixture was stirred in a sealed tube at 75° C. for 42 hours. Then the reaction mixture was concentrated, water was added (8 mL) and the formed precipitate was filtered off and washed with water/CH$_3$CN (10 mL 5:1). The obtained red solid was suspended in boiling diisopropyl ether (3 mL) and 2-propanol (2 mL) was added dropwise. The mixture was left standing for 90 min and then filtered. The precipitate was washed with diisopropyl ether/2-propanol (4:1, 6 mL) and dried in vacuo at 50° C. yielding compound 116 as a slightly red-purple solid (240 mg) Method A; Rt: 1.71 min. m/z: 424.0 (M−H)$^-$ 426.0 (M+H)$^+$ Exact mass: 425.08. $^1$H NMR (360 MHz, DMSO-d$_6$) δ ppm 1.08 (d, J=7.0 Hz, 3H), 2.18 (s, 3H), 3.87-3.97 (m, 4H), 7.07 (td, J=9.0, 1.5 Hz, 1H), 7.31-7.39 (m, 2H), 7.64 (d, J=1.8 Hz, 1H), 8.18 (br. s., 1H), 9.95 (s, 1H) Differential scanning calorimetry: From 30 to 300° C. at 10° C./min: peak at 206.64° C.

Compound 117: N-(2,4-Difluoro-3-methylphenyl)-1-methyl-4-{[1-(trifluoromethyl)-cyclopropyl]sulfamoyl}-1H-pyrrole-2-carboxamide

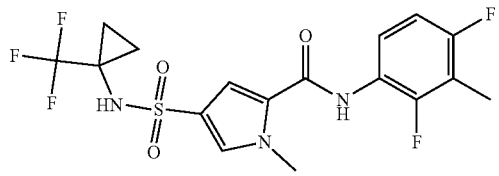 [SMILES: Cc1c(F)ccc(NC(=O)c2cc(S(=O)(=O)NC3(C(F)(F)F)CC3)cn2C)c1F]

5-[(2,4-difluoro-3-methyl-phenyl)carbamoyl]-1-methyl-pyrrole-3-sulfonyl chloride (310 mg, 0.89 mmol) was stirred in dry acetonitrile (25 mL) and dry DIPEA (0.61 mL, 3.56 mmol). 1-(trifluoromethyl)cyclopropanamine (222 mg, 1.78 mmol) was added under $N_2$-atm at room temperature. The reaction mixture was stirred in a sealed tube at 75° C. for 24 h and 110 h at 95° C. Then 1 eq of 1-(trifluoromethyl)cyclopropanamine was added and the mixture was stirred at 95° for 24 h. The solvent was evaporated leaving yellow oil which was dissolved in $CH_2Cl_2$/Methanol (80/20; 5 mL) and purified by Flash Chromatography [Biotage Isolera 1//GraceResolve Silica 12 g//EtOAc-heptane 0/100 to 100/0]. The desired fractions were combined and the solvent was evaporated leaving a red colored solid, which was dissolved in a boiling mixture of 2 mL of diisopropyl ether and 3 mL of $CH_3CN$. The solution was allowed to cool while stirring. After 45 min the formed precipitate was filtered off and was washed once with its own filtrate and at the end with 2 mL of diisopropyl ether. The white solid was dried in vacuo at 50° C. Method B; Rt: 1.01 min. m/z: 436.0 (M−H)⁻ Exact mass: 437.08. $^1$H NMR (360 MHz, DMSO-$d_6$) δ ppm 1.08-1.22 (m, 4H), 2.18 (s, 3H), 3.88 (s, 3H), 7.07 (td, J=9.0, 1.5 Hz, 1H), 7.27 (d, J=1.8 Hz, 1H), 7.34 (td, J=8.8, 6 6.2 Hz, 1H), 7.56 (d, J=1.8 Hz, 1H), 8.76 (br. s., 1H), 9.95 (s, 1H).

Compound 118: N-(2,4-Difluoro-3-methylphenyl)-1-methyl-4-[(2,2,2-trifluoro-1,1-dimethylethyl)sulfamoyl]-1H-pyrrole-2-carboxamide

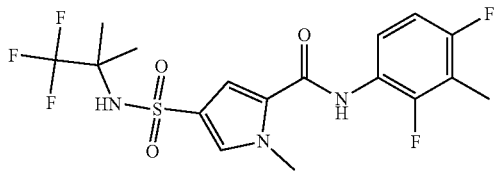 [SMILES: Cc1c(F)ccc(NC(=O)c2cc(S(=O)(=O)NC(C)(C)C(F)(F)F)cn2C)c1F]

The compound was prepared similarly as compound 117 using 2.5 eq of 1,1,1-trifluoro-2-methyl-propan-2-amine instead of 1-(trifluoromethyl)cyclopropanamine. The reaction mixture was stirred in a sealed tube at 75° C. for 18 h and for 80 h at 95° C. Method B; Rt: 1.01 min. m/z: 438.0 (M−H)⁻ Exact mass: 439.10. $^1$H NMR (400 MHz, DMSO-$d_6$) δ ppm 1.37 (s, 6H), 2.19 (s, 3H), 3.90 (s, 3H), 7.06 (td, J=9.0, 1.4 Hz, 1H), 7.28-7.39 (m, 2H), 7.56 (d, J=1.8 Hz, 1H), 6 8.05 (br. s., 1H), 9.94 (s, 1H) Differential scanning calorimetry: From 30 to 300° C. at 10° C./min: peak at 164.23° C.

Compound 119: N-(2,4-Difluoro-3-methylphenyl)-1-methyl-4-{[(1S)-2,2,2-trifluoro-1-methylethyl]sulfamoyl}-1H-pyrrole-2-carboxamide

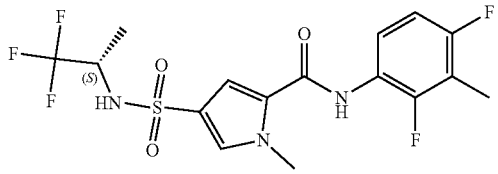

The compound was prepared similarly as compound 117 using (2S)-1,1,1-trifluoropropan-2-amine instead of 1-(trifluoromethyl)cyclopropanamine, the reaction mixture was stirred in a sealed tube for 42 h at 95° C. Then the reaction mixture was concentrated and water was added (8 mL) and the formed precipitate was filtered off and dried in vacuo at 50° C. yielding compound 119 as a powder. Method A; Rt: 1.71 min. m/z: 424.0 (M−H)⁻ Exact mass: 425.08. $^1$H NMR (400 MHz, DMSO-$d_6$) δ ppm 1.09 (d, J=7.0 Hz, 3H), 2.18 (s, 3H), 3.87-3.98 (m, 4H), 7.06 (td, J=8.9, 1.5 Hz, 1H), 7.30-7.40 (m, 2H), 7.63 (d, J=1.8 Hz, 1H), 8.16 (d, J=8.6 Hz, 1H), 9.92 (s, 1H) Differential scanning calorimetry: From 30 to 300° C. at 10° C./min: peak at 207.52.

Compound 120: N-(3-Chloro-2,4-difluorophenyl)-1-methyl-4-{[(1R)-2,2,2-trifluoro-1-methylethyl]sulfamoyl}-1H-pyrrole-2-carboxamide

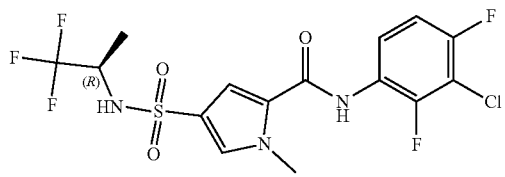

5-[(3-chloro-2,4-difluoro-phenyl)carbamoyl]-1-methyl-pyrrole-3-sulfonyl chloride (900 mg, 2.44 mmol) prepared similarly as in the synthesis for compound 57 using 3-chloro-2,4-difluoro-aniline (3.5 g, 14.46 mmol) was stirred in dry $CH_3CN$ (10 mL). (2R)-1,1,1-trifluoropropan-2-amine (689 mg, 6.1 mmol) was added under $N_2$-atm at room temperature. The reaction mixture was stirred in a sealed tube at 85° C. for 6 h and left standing for 18 h. The solvent was evaporated and the red residue was suspended in DCM. The formed precipitate was filtered off and dried under vacuum at 50° C. The filtrate was concentrated till precipitation took place. The formed precipitate was filtered off. The combined precipitates were recrystallized in DIPE/ACN (1:1; 6 mL), left stirring for 2 h then left standing for 18 h, filtered off and dried under vacuum at 50° C. The filtrate was left standing for 18 h. The formed precipitate was filtered off and dried under vacuum at 50° C. The obtained white solid was recrystallized in DIPE/ACN (1:1; 4 mL), left stirring for 2 h then left standing for 18 h, filtered off and dried under vacuum at 50° C. The 2 solids were combined (394 mg). Method A; Rt: 1.85 min. m/z: 444.0 (M−H)⁻ Exact mass: 445.03. $^1$H NMR (400 MHz, DMSO-$d_6$) δ ppm 1.10 (d, J=7.0 Hz, 3H), 3.85-4.00 (m, 4H), 7.30-7.41 (m, 2H), 7.53 (td, J=8.7, 5.8 Hz, 1H), 7.65 (d, J=1.5 Hz, 1H), 7.97 (br. s., 1H), 10.14 (br. s., 1H).

Alternative Synthesis of Compound 120:

Methyl 1-methyl-4-[[(1R)-2,2,2-trifluoro-1-methyl-ethyl]sulfamoyl]pyrrole-2-carboxylate (6.61 g, 21.03 mmol) and 3-chloro-2,4-difluoroaniline (4.13 g, 25.2 mmol) were dissolved in tetrahydrofuran (150 mL) and this was stirred and cooled in an ice-water bath. Over a period of 5 minutes lithium bis(trimethylsilyl)amide in toluene (63.1 mL, 1 M, 63.1 mmol) was added dropwise. The resulting mixture was stirred for 1 h while cooling was continued. Another 2 eq of lithium bis(trimethylsilyl)amide in toluene (42.1 mL, 1 M, 42.1 mmol) were added and the resulting mixture was stirred for 1 hour at room temperature. The resulting mixture was quenched using ammonium chloride (sat./200 mL). The resulting mixture was extracted using EtOAc (3×250 mL).

The combined extracts were washed with brine (250 mL), dried on Na$_2$SO$_4$, filtered and concentrated in vacuo yielding a brown powder. This powder was crystallized twice out of methanol/water. The precipitation was collected on a glass filter. The obtained powder was purified by silica gel column chromatography using gradient elution from heptane to EtOAc (100:0 to 0:100). The obtained residue was crystallized again out of methanol/water. The white crystals were collected on a glass filter and dried in a vacuum oven at 55° C. for 24 hours yielding compound 120 (3.03 g) as a white powder. Differential scanning calorimetry: From 30 to 300° C. at 10° C./min: peak at 217.6° C.

Compound 121: N-(3-Chloro-2,4-difluorophenyl)-1-methyl-4-[(3-methyloxetan-3-yl)sulfamoyl]-1H-pyrrole-2-carboxamide

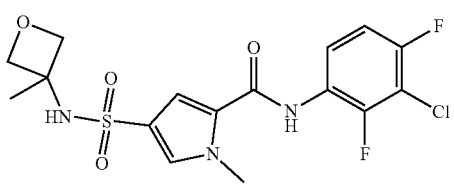 [SMILES: Cn1cc(S(=O)(=O)NC2(C)COC2)cc1C(=O)Nc1ccc(F)c(Cl)c1F]

5-[(3-chloro-2,4-difluoro-phenyl)carbamoyl]-1-methyl-pyrrole-3-sulfonyl chloride (900 mg, 2.44 mmol) prepared similarly as in the synthesis for compound 57 3-chloro-2,4-difluoro-aniline (3.5 g, 14.46 mmol) was stirred in dry CH$_3$CN (10 mL). 3-methyloxetan-3-amine (255 mg, 2.93 mmol) was added under N$_2$-atm. The reaction mixture was stirred in a sealed tube at room temperature for 18 h. The solvent was evaporated. The residue was stirred in CH$_2$Cl$_2$. The formed precipitate was filtered off [fraction 1]. The filtrate was evaporated and the residue was dissolved in CH$_2$Cl$_2$/MeOH (9/1, 5 mL) and purified by Flash Chromatography [Biotage Isolera 1//GraceResolve Silica 12 g//EtOAc-heptane 0/100 to 100/0]. The desired fractions were combined and the solvent was evaporated leaving a white solid which was recrystallized in diisopropyl ether/CH$_3$CN (1:1; 6 mL), left stirring for 2 h then left standing for 18 h, filtered off and dried in vacuo at 50° C. yielding white powder which was combined with fraction 1. Method B; Rt: 0.88 min. m/z: 418.0 (M−H)$^-$ Exact mass: 419.05. 1H NMR (400 MHz, DMSO-d$_6$) δ ppm 1.55 (s, 3H), 3.89 (s, 3H), 4.14 (d, J=6.4 Hz, 2H), 4.60 (d, J=5.9 Hz, 2H), 7.31-7.38 (m, 2H), 7.53 (td, J=8.7, 5.8 6 Hz, 1H), 7.60 (d, J=1.8 Hz, 1H), 7.98 (br. s., 1H), 10.14 (br. s., 1H).

Synthesis of methyl 4-chlorosulfonyl-1-methyl-pyrrole-2-carboxylate

Chlorosulfonic acid (200 mL, 3.01 mol) was cooled to 0° C. and to this stirring liquid was added methyl 1-methyl-pyrrole-2-carboxylate (75 g, 538.97 mmol) drop wise. After addition the mixture was allowed to reach room temperature. Then it was stirred for another hour. The resulting mixture was added drop wise to a mechanically stirred, temperature controlled ice-water mixture (2500 mL) keeping the temperature under 5° C. A white precipitation was formed. This precipitate was collected on a glass filter and this was washed with cold water (1000 mL). The obtained white powder was dried in a vacuum oven at 55° C. for 24 hours yielding methyl 4-chlorosulfonyl-1-methyl-pyrrole-2-carboxylate (99 g) as a bright white powder.

Synthesis of methyl 1-methyl-4-[[(1R)-2,2,2-trifluoro-1-methyl-ethyl]sulfamoyl]pyrrole-2-carboxylate Methyl 4-chlorosulfonyl-1-methyl-pyrrole-2-carboxylate (15 g, 63.11 mmol) was loaded in a pressure tube and this was dissolved in acetonitrile (150 mL). To this solution was added diisopropylethylamine (27.2 mL, 157.8 mmol) followed by (R)-1,1,1-trifluoro-2-propylamine (10.7 g, 94.7 mmol). The pressure tube was flushed with nitrogen and closed. Then it was stirred in a pre-heated oil bath at 80° C. for 6 hours. The mixture was cooled to room temperature and concentrated in vacuo. The residue was dissolved in dichloromethane (500 mL) and this was washed with HCl (1M/aq/2×250 mL). The organics were dried on Na$_2$SO$_4$, filtered and concentrated in vacuo. The obtained residue was dried in a vacuum oven at 55° C. for 24 hours yielding methyl 1-methyl-4-[[(1R)-2,2,2-trifluoro-1-methyl-ethyl]sulfamoyl]pyrrole-2-carboxylate as a yellowish powder (18 g).

Compound 122: 1-methyl-4-[[(1R)-2,2,2-trifluoro-1-methyl-ethyl]sulfamoyl]-N-[3-(trifluoromethyl)phenyl]pyrrole-2-carboxamide

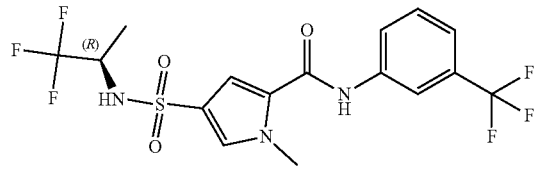

Into a 100 mL round bottom flask equipped with a magnetic stir bar was placed methyl 1-methyl-4-[[(1R)-2,2,2-trifluoro-1-methyl-ethyl]sulfamoyl]pyrrole-2-carboxylate (1 g, 3.18 mmol), anhydrous THF (40 mL), and 3-aminobenzotrifluoride (666 mg, 4.14 mmol). The vial was sealed and placed into an ice-water bath and to it was added LHMDS (9.6 mL of a 1 M solution in THF) slowly via syringe (approx rate of 2 mL/min). Conversion to product seen after 30 min at 0° C. Sat. aq. ammonium chloride was added to quench the reaction. This was diluted with ethyl acetate (100 mL) and the mixture partitioned with ethyl acetate (3×100 mL). The organic layers were combined, dried (magnesium sulfate), the solids were removed by filtration and the solvents of the filtrate were removed under reduced pressure. The crude was partially purified via silica column chromatography using a dichloromethane to ethylacetate gradient. The solvent of the best fractions were removed under reduced pressure and the crude was recrystallized in ethanol/water. (1228 mg) Method B; Rt: 1.92 min. m/z: 442.0 (M−H)$^-$ Exact mass: 443.10. $^1$H NMR (400 MHz, DMSO-d$_6$) δ ppm 1.08 (d, J=7.0 Hz, 3H), 3.86-3.92 (m, 1H), 3.94 (s, 3H), 7.33-7.47 (m, 2H), 7.58 (t, J=8.0 Hz, 1H), 7.66 (d, J=1.8 Hz, 1H), 7.99 (d, J=8.8 Hz, 1H), 8.11-8.24 (m, 2H), 10.34 (s, 1H).

Compound 123: N-(3-Chloro-4-fluorophenyl)-1-methyl-4-{[(1R)-2,2,2-trifluoro-1-methylethyl]sulfamoyl}-1H-pyrrole-2-carboxamide

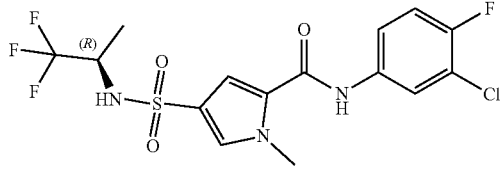

Into a 100 mL round bottom flask, equipped with a magnetic stir bars was placed methyl 1-methyl-4-[[(1R)-2,2,2-trifluoro-1-methyl-ethyl]sulfamoyl]pyrrole-2-carboxylate (1 g, 3.18 mmol), anhydrous THF (40 mL), and 3-chloro-4-fluoro-aniline (602.1 mg, 4.136 mmol). The flask was sealed and placed into an ice-water bath and to it was added LHMDS (9.6 mL of a 1M solution in THF/ethylbenzene) slowly via syringe (approx rate of 2 mL/min). Conversion to product seen after 30 min at 0° C. Sat. aq. ammonium chloride was added to quench the reaction. This was diluted with ethyl acetate (100 mL) and the mixture partitioned with ethyl acetate (3×100 mL). The organic layers were combined, dried (magnesium sulfate), the solids were removed by filtration and the solvents of the filtrate were removed under reduced pressure. The crudes were partially purified via silica column chromatography using a dichloromethane to ethylacetate gradient. The solvent of the best fractions were removed under reduced pressure. The residue was recrystallized from iPrOH (772 mg) Method A; Rt: 1.79 min. m/z: 426.0 (M−H)⁻ Exact mass: 427.04. $^1$H NMR (400 MHz, DMSO-$d_6$) δ ppm 1.09 (d, J=7.0 Hz, 3H), 3.85-4.01 (m, 1H), 3.94 (s, 3H), 7.38 (d, J=2.0 Hz, 1H), 7.51 (t, J=9.8 Hz, 1H), 7.66 (d, J=1.8 Hz, 1H), 7.99-8.09 (m, 1H), 8.14-8.24 (m, 2H), 10.36 (s, 1H).

Compound 124: N-(3-Bromo-4-fluorophenyl)-1-methyl-4-[(1R)-2,2,2-trifluoro-1-methylethyl]sulfamoyl-1H-pyrrole-2-carboxamide

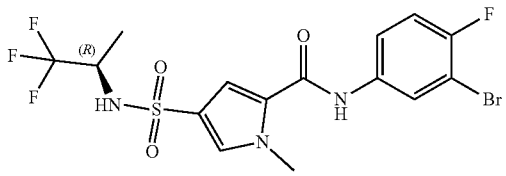

Compound 124 (598 mg) was prepared similarly as described for compound 123, using 3-bromo-4-fluoro-aniline instead of 3-chloro-4-fluoro-aniline. Method B; Rt: 1.07 min. m/z: 472.0 (M−H)⁻ 960 (2M+18) Exact mass: 471.0. $^1$H NMR (400 MHz, DMSO-$d_6$) δ ppm 1.08 (d, J=7.0 Hz, 3H), 3.84-3.99 (m, 1H), 3.92 (s, 3H), 7.32-7.41 (m, 2H), 7.64 (d, J=1.8 Hz, 1H), 7.70 (ddd, 6 J=9.0, 4.4, 2.6 Hz, 1H), 8.11-8.20 (m, 2H), 10.21 (s, 1H).

Compound 125: N-[4-Fluoro-3-(trifluoromethyl)phenyl]-1-methyl-4-{[(1R)-2,2,2-trifluoro-1-methylethyl]sulfamoyl}-1H-pyrrole-2-carboxamide

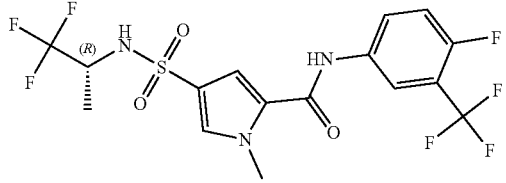

Compound 125 (664 mg) was prepared similarly as compound 123 using 4-fluoro-3-(trifluoromethyl)aniline (740.9 mg, 4.136 mmol) 3-chloro-4-fluoro-aniline. Method B; Rt: 1.96 min. m/z: 460.0 (M−H)⁻ 479.2 (M+18) Exact mass: 461.06. $^1$H NMR (400 MHz, DMSO-$d_6$) δ ppm 1.08 (d, J=7.04 Hz, 3H) 3.87-3.98 (m, 1H) 3.93 (s, 3H) 7.40 (t, J=9.13 Hz, 1H) 7.38 (d, J=1.76 Hz, 1H) 7.65 (d, J=1.76 Hz, 1H) 7.68 (ddd, J=9.02, 4.40, 2.64 Hz, 1H) 8.03 (dd, J=6.82, 2.64 Hz, 1H) 8.17 (d, J=8.80 Hz, 1H) 10.28 (s, 1H).

Compound 126: N-(3-Cyano-4-fluorophenyl)-4-[(2,2-difluoroethyl)sulfamoyl]-1-methyl-1H-pyrrole-2-carboxamide

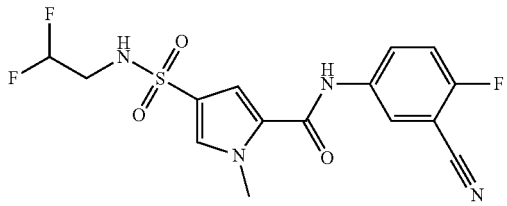 [SMILES: Cn1cc(S(=O)(=O)NCC(F)F)cc1C(=O)Nc1ccc(F)c(C#N)c1]

4-(chlorosulfonyl)-1-methyl-1H-pyrrole-2-carboxylate (made by the procedure described in the synthesis of 1-methyl-4-[(3-methyloxetan-3-yl)sulfamoyl]-1H-pyrrole-2-carboxylic acid) (5.0 g, 21.0 mmol) was dissolved in acetonitrile (50 mL). To this was added diisopropylethylamine (9.06 mL, 52.6 mmol) followed by 2,2-difluoroethylamine (1.93 g, 23.1 mmol) and the resulting mixture was refluxed for 2 hours. Then the mixture was cooled to room temperature and concentrated in vacuo. The resulting residue was dissolved in dichloromethane (250 mL) and this was washed with aqueous hydrochloric acid (2×150 mL, 1N). The organics were dried on sodium sulphate, filtered and concentrated in vacuo yielding methyl 4-(2,2-difluoroethylsulfamoyl)-1-methyl-pyrrole-2-carboxylate (5.4 g) as light brown oil which solidified while standing and was used as such. Methyl 4-(2,2-difluoroethylsulfamoyl)-1-methyl-pyrrole-2-carboxylate (5.4 g, 19.1 mmol) was dissolved in tetrahydrofuran (50 mL). To this was added an aqueous solution of lithium hydroxide (0.69 g, 28.7 mmol) in distilled water (7 mL) and a turbid mixture was obtained. Then methanol (3 mL) was added. The resulting mixture was stirred for 24 hours at room temperature and at 60° C. for 1 hour. To this was added lithium hydroxide (0.458 g, 19.1 mmol). The reaction mixture was further heated at 60° C. for 3 hours. Then it was concentrated to keep~5 mL aqueous solution and extra 15 mL of distilled water was added. Then this was neutralized using an exact amount of hydrochloric acid (47.8 mL, 47.83 mmol/1M/aq/). The resulting mixture was extracted using methyltetrahydrofuran (3×20 mL). The combined extracts were dried on sodium sulphate, filtered and concentrated in vacuo yielding of 4-(2,2-difluoroethylsulfamoyl)-1-methyl-pyrrole-2-carboxylic acid (4.88 g) as white powder which was used as such. $^1$H NMR (400 MHz, DMSO-d$_6$) δ ppm 3.15 (tdd, J=15.4, 15.4, 6.4, 4.0 Hz, 2H), 3.88 (s, 3H), 5.99 (tt, J=55.7, 4.2 Hz, 1H), 6.98 (d, J=2.0 Hz, 1H), 7.61 (d, J=2.0 Hz, 1H), 7.84 (t, J=6.4 Hz, 1H). 4-(2,2-difluoroethylsulfamoyl)-1-methyl-pyrrole-2-carboxylic acid (500 mg, 1.77 mmol) and 5-amino-2-fluorobenzonitrile (0.5 g, 3.54 mmol) and HATU (0.81 g, 2.12 mmol) were dissolved in DMF (2.5 mL) containing diisopropylethylamine (1.22 mL, 7.08 mmol). The reaction mixture was stirred at room temperature for 66 hours. The reaction mixture was directly loaded on column and purified using silica gel column chromatography (ethyl acetate in heptane from 20 to 80%). The desired fractions were combined and evaporated to keep ~50 mL of the solvent and 20 mL of diethyl ether was added. The formed precipitate was filtered and washed with diethyl ether to afford compound 126 (412 mg) as white solid. Method B; Rt: 0.88 min. m/z: 385 (M–H)$^-$ Exact mass: 386.07. $^1$H NMR (400 MHz, DMSO-d$_6$) δ ppm 3.20 (td, J=15.3, 4.0 Hz, 2H), 3.92 (s, 3H), 6.02 (tt, J=55.7, 4.0 Hz, 1H), 7.37 (d, J=2.0 Hz, 1H), 7.53 (t, J=9.1 Hz, 1H), 7.65 (d, J=1.5 Hz, 1H), 7.93 (br. s, 1H), 8.01 (ddd, J=9.2, 5.0, 2.8 Hz, 1H), 8.21 (dd, J=5.7, 2.6 Hz, 1H), 10.36 (br. s., 1H).

Compound 127: N-(3-Bromo-4-fluorophenyl)-4-[(2,2-difluoroethyl)sulfamoyl]-1-methyl-1H-pyrrole-2-carboxamide

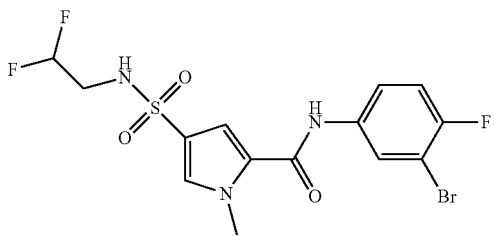 [SMILES: Cn1cc(S(=O)(=O)NCC(F)F)cc1C(=O)Nc1ccc(F)c(Br)c1]

Compound 127 (452 mg) as white powder was synthesized similarly as described for compound 126 using 3-bromo-4-fluoroaniline instead of 5-amino-2-fluorobenzonitrile in the last step. Method B; Rt: 1.00 min. m/z: 438 (M–H)$^-$ Exact mass: 438.98. $^1$H NMR (400 MHz, DMSO-d$_6$) δ ppm 3.20 (td, J=15.3, 4.0 Hz, 2H), 3.92 (s, 3H), 6.02 (tt, J=55.5, 4.0 Hz, 1H), 7.34-7.39 (m, 2H), 7.63 (d, J=1.5 Hz, 1H), 7.70 (ddd, J=9.0, 4.4, 2.6 Hz, 1H), 7.88 (br. s., 1H), 8.14 (dd, J=6.5, 2.5 Hz, 1H), 10.21 (br. s., 1H).

Compound 128: N-(3-Chloro-4-fluorophenyl)-4-[(2,2-difluoroethyl)sulfamoyl]-1-methyl-1H-pyrrole-2-carboxamide

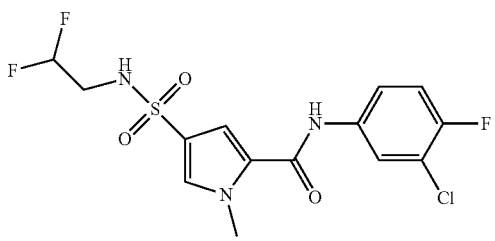

Compound 128 (372 mg) as white powder was synthesized similarly as described for compound 126 using 3-chloro-4-fluoroaniline instead of 5-amino-2-fluorobenzonitrile in the last step. Method B; Rt: 0.99 min. m/z: 394 (M–H)$^-$ Exact mass: 395.03. $^1$H NMR (400 MHz, DMSO-d$_6$) δ ppm 3.20 (td, J=15.3, 4.0 Hz, 2H), 3.92 (s, 3H), 6.02 (tt, J=55.7, 4.0 Hz, 1H), 7.35 (d, J=1.8 Hz, 1H), 7.40 (t, J=9.1 Hz, 1H), 7.61-7.69 (m, 2H), 7.89 (br. s., 1H), 8.02 (dd, J=6.9, 2.5 Hz, 1H), 10.22 (br. s., 1H).

Compound 129: 4-[(2,2-Difluoroethyl)sulfamoyl]-N-(3,4-difluorophenyl)-1-methyl-1H-pyrrole-2-carboxamide

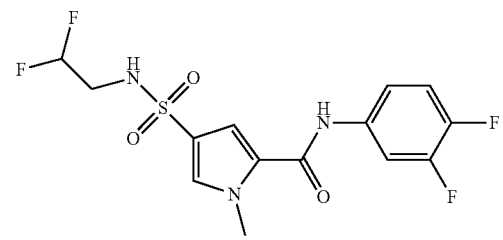 [SMILES: Cn1cc(S(=O)(=O)NCC(F)F)cc1C(=O)Nc1ccc(F)c(F)c1]

Compound 129 (371 mg) as white powder was synthesized similarly as described for compound 126 using 3,4-difluoroaniline instead of 5-amino-2-fluorobenzonitrile in the last step. Method B; Rt: 0.94 min. m/z: 378 (M–H)$^-$ Exact mass: 379.06. $^1$H NMR (400 MHz, DMSO-d$_6$) δ ppm 3.20 (td, J=15.2, 4.1 Hz, 2H), 3.92 (s, 3H), 6.02 (tt, J=55.5, 4.0 Hz, 1H), 7.34 (d, J=2.0 Hz, 1H), 7.41 (dt, J=10.3, 9.0 Hz, 1H), 7.46-7.53 (m, 1H), 7.64 (d, J=1.8 Hz, 1H), 7.79-7.94 (m, 2H), 10.24 (br. s., 1H).

Compound 130: N-(3-Chloro-4,5-difluorophenyl)-4-[(2,2-difluoroethyl)sulfamoyl]-1-methyl-1H-pyrrole-2-carboxamide

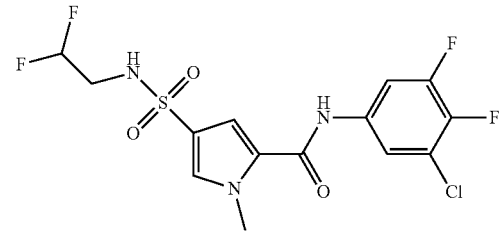 [SMILES: Cn1cc(S(=O)(=O)NCC(F)F)cc1C(=O)Nc1cc(F)c(F)c(Cl)c1]

Compound 130 was synthesized similarly as described for compound 126. In the last step, 3-chloro-4,5-difluoroaniline hydrochloride (synthesis described in synthesis for compound 57) instead of 5-amino-2-fluorobenzonitrile was used and the reaction time was 18 hours instead of 66 hours. The reaction mixture was purified using silica gel column chromatography (gradient elution: ethyl acetate in heptane from 0 to 100% and from 30 to 50%). The purest fractions were combined and stored as such for 66 hours. White precipitates were filtered and washed with heptane to afford a white solid. The solids were dissolved in methanol and concentrated to dryness to afford a white powder which was warm triturated in methanol (3 mL) and cooled to room temperature. The white solids were filtered and washed with methanol to afford compound 130 (131 mg) as white powder. Method B; Rt: 0.94 min. m/z: 412 (M–H)⁻ Exact mass: 413.02.

¹H NMR (400 MHz, DMSO-d₆) δ ppm 3.20 (td, J=15.3, 4.0 Hz, 2H), 3.91 (s, 3H), 6.02 (tt, J=55.7, 4.0 Hz, 1H), 7.35 (d, J=2.0 Hz, 1H), 7.49-8.27 (m, 4H), 10.31 (br. s., 1H).

Compound 131: N-(3-Chloro-4-fluorophenyl)-1-methyl-4-[(2,2,2-trifluoroethyl)sulfamoyl]-1H-pyrrole-2-carboxamide

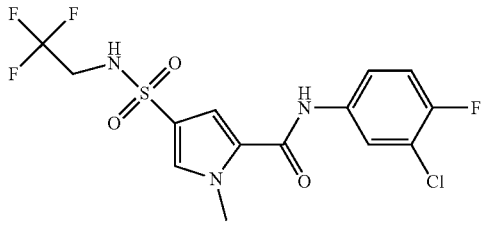 [SMILES: Cn1cc(S(=O)(=O)NCC(F)(F)F)cc1C(=O)Nc1ccc(F)c(Cl)c1]

4-(chlorosulfonyl)-1-methyl-1H-pyrrole-2-carboxylate (made by the procedure described in the synthesis of 1-methyl-4-[(3-methyloxetan-3-yl)sulfamoyl]-1H-pyrrole-2-carboxylic acid) (5.0 g, 21.0 mmol) was dissolved in acetonitrile (50 mL). To this was added DIPEA (9.06 mL, 52.6 mmol) followed by 2,2,2-trifluoroethylamine (2.29 g, 23.1 mmol) and the resulting mixture was refluxed for 2 hours. Then the mixture was cooled to room temperature and concentrated in vacuo. The resulting residue was dissolved in dichloromethane (250 mL) and this was washed with aqueous hydrochloric acid (2×150 mL, 1N). The organics were dried on sodium sulphate, filtered and concentrated in vacuo yielding methyl 1-methyl-4-(2,2,2-trifluoroethyl-sulfamoyl)pyrrole-2-carboxylate (5.3 g) as light brown oil which solidified while standing and was used as such. Methyl 1-methyl-4-(2,2,2-trifluoroethylsulfamoyl)pyrrole-2-carboxylate (5.3 g, 17.65 mmol) was dissolved in tetrahydrofuran (50 mL) and a solution of lithium hydroxide (0.634 g, 26.5 mmol) in distilled water (7 mL) was added and a turbid mixture was obtained. Then methanol (3 mL) was added and the mixture became clear. The resulting mixture was stirred at room temperature for 24 hours and at 60° C. for 1 hour. To this was added lithium hydroxide (0.423 g, 17.7 mmol). The reaction mixture was further heated at 60° C. for 3 hours. Then the reaction mixture was concentrated to keep ~5 mL and distilled water (15 mL) was added. The mixture was neutralized using an exact amount of hydrochloric acid (1M/aq/31.6 mL, 31.58 mmol). The resulting mixture was extracted using methyltetrahydrofuran (3×20 mL). The combined extracts were dried on sodium sulphate, filtered and concentrated in vacuo yielding 1-methyl-4-(2,2,2-trifluoroethylsulfamoyl)pyrrole-2-carboxylic acid (4.62 g) as beige powder which was used as such. 1-methyl-4-(2,2,2-trifluoroethylsulfamoyl)pyrrole-2-carboxylic acid (500 mg, 1.66 mmol) and 3-chloro-4-fluoroaniline (0.48 g, 3.32 mmol) and HATU (0.76 g, 1.99 mmol) were dissolved in DMF (2 mL) containing diisopropylethylamine (1.14 mL, 6.64 mmol). The reaction mixture was stirred at room temperature for 66 hours. The reaction mixture was directly loaded on column and purified using silica gel column chromatography (ethyl acetate in heptane from 20 to 80%). The desired fractions were combined and evaporated to keep ~50 mL of the solvent and 20 mL of diethyl ether was added. The formed precipitate was filtered and washed with diethyl ether to afford an off white solid which was recrystallized from acetonitrile (5 mL) to afford compound 131 (117 mg) as white solid. Method B; Rt: 1.03 min. m/z: 412 (M–H)⁻ 431 (M+18) Exact mass: 413.02 ¹H NMR (400 MHz, DMSO-d₆) δ ppm 3.62 (q, J=9.5 Hz, 2H), 3.91 (s, 3H), 7.31-7.45 (m, 2H), 7.61-7.70 (m, 2H), 8.02 (dd, J=6.8, 2.6 Hz, 1H), 8.27 (br. s., 1H), 10.23 (br. s, 1H).

Compound 132: N-(3,4-Difluorophenyl)-1-methyl-4-[(2,2,2-trifluoroethyl)sulfamoyl]-1H-pyrrole-2-carboxamide

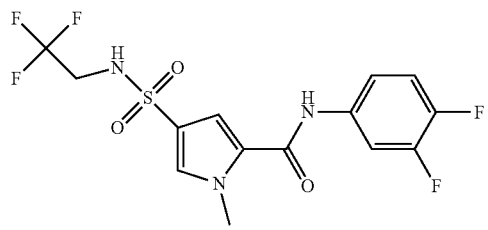

Compound 132 was synthesized similarly as described for compound 131 using 3,4-difluoroaniline (433 mg, 3.32 mmol) instead of 3-chloro-4-fluoroaniline in the last step. The off white solid was recrystallized from methanol to afford compound 132 (208 mg) as white powder. Method B; Rt: 0.98 min. m/z: 396 (M–H)⁻ Exact mass: 397.05. ¹H NMR (400 MHz, DMSO-d₆) δ ppm 3.62 (q, J=9.6 Hz, 2H), 3.91 (s, 3H), 7.35 (d, J=1.8 Hz, 1H), 7.41 (dt, J=10.5, 9.1 Hz, 1H), 7.45-7.52 (m, 1H), 7.65 (d, J=1.8 Hz, 1H), 7.87 (ddd, J=13.4, 7.5, 2.4 Hz, 1H), 8.26 (br. s., 1H), 10.24 (s, 1H).

Compound 133: N-(3-Chloro-4,5-difluorophenyl)-1-methyl-4-[(2,2,2-trifluoroethyl)sulfamoyl]-1H-pyrrole-2-carboxamide

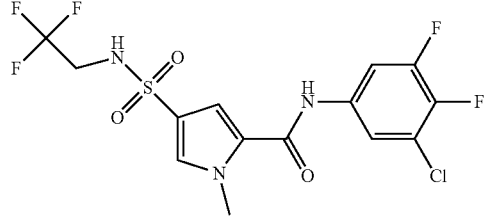 [SMILES: Cn1cc(S(=O)(=O)NCC(F)(F)F)cc1C(=O)Nc1cc(F)c(F)c(Cl)c1]

Compound 133 was synthesized similarly as described for compound 131. 3-chloro-4,5-difluoroaniline hydrochloride (664 mg, 332 mmol) (synthesis described in synthesis for compound 57) was used instead of 3-chloro-4-fluoroaniline in the last step. The reaction mixture was directly loaded on column and purified using silica gel column chromatography (ethyl acetate in heptane from 0 to 100%) The purest fractions were combined and stored as such for 66 hours. Off white crystals were formed and filtered and washed with heptane to afford a beige solid. The solid was triturated in diethyl ether (15 mL) and filtered and washed with diethyl ether to afford a white powder. The white powder was purified using silica gel column chromatography (methanol in CH₂Cl₂ from 0 to 2%) The purest fractions were combined and concentrated to dryness to afford compound 133 (41 mg) as white powder. Method B; Rt: 1.09 min. m/z: 430

(M−H)⁻ 863 (2M+H) Exact mass: 431.01. ¹H NMR (400 MHz, DMSO-d₆) δ ppm 3.62 (q, J=9.6 Hz, 2H), 3.91 (s, 3H), 7.36 (d, J=1.8 Hz, 1H), 7.67 (d, J=1.8 Hz, 1H), 7.77-7.85 (m, 2H), 8.29 (br. s., 1H), 10.32 (br. s., 1H).

Compound 134: N-(3-Cyano-4-fluorophenyl)-1-methyl-4-[(2,2,2-trifluoroethyl)sulfamoyl]-1H-pyrrole-2-carboxamide

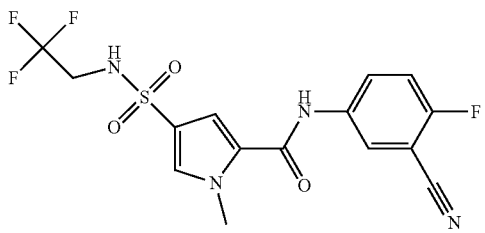 [SMILES: Cn1cc(S(=O)(=O)NCC(F)(F)F)cc1C(=O)Nc1ccc(F)c(C#N)c1]

Compound 134 was synthesized similarly as described for compound 131 using 5-amino-2-fluorobenzonitrile (466 mg, 3.32 mmol) instead of 3-chloro-4-fluoroaniline in the last step. The reaction mixture was directly loaded on column and purified using silica gel column chromatography (ethyl acetate in heptane from 20 to 80%). The desired fractions were combined and evaporated to keep ~50 mL of the solvent and 20 mL of diethyl ether was added. The formed precipitate was filtered and washed with diethyl ether to afford an off white solid which was purified using Prep. LCMS. (Hypersyl C18 BDS-3 μm, 100×4.6 mm) Mobile phase (NH₄HCO₃ 0.2% in water, acetonitrile) the desired fractions were combined and evaporated to dryness, dissolved in methanol again and evaporated to dryness and dried in vacuum oven overnight to afford compound 134 (147 mg) as white powder. Method B; Rt: 0.93 min. m/z: 403 (M−H)⁻ Exact mass: 404.06. ¹H NMR (400 MHz, DMSO-d₆) δ ppm 3.61 (q, J=9.5 Hz, 2H), 3.92 (s, 3H), 7.37 (d, J=2.0 Hz, 1H), 7.53 (t, J=9.1 Hz, 1H), 7.66 (d, J=1.5 Hz, 1H), 8.00 (ddd, J=9.2, 4.9, 2.9 Hz, 1H), 8.33 (br. s, 1H), 8.22 (dd, J=5.9, 2.6 Hz, 1H), 10.38 (br. s., 1H).

Compound 135: N-(3-Bromo-4-fluorophenyl)-1-methyl-4-[(2,2,2-trifluoroethyl)sulfamoyl]-1H-pyrrole-2-carboxamide

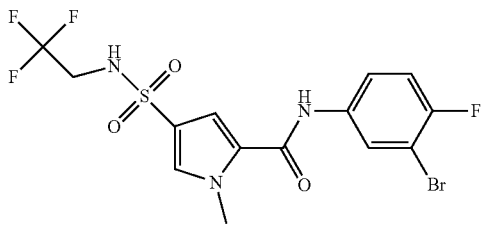

Compound 135 was synthesized similarly as described for compound 134 using 3-bromo-4-fluoroaniline (631 mg, 3.32 mmol) instead of 5-amino-2-fluorobenzonitrile in the last step. Method B; Rt: 1.04 min. m/z: 456 (M−H)⁻ Exact mass: 456.97. ¹H NMR (400 MHz, DMSO-d₆) δ ppm 3.62 (q, J=9.5 Hz, 2H), 3.91 (s, 3H), 7.34-7.40 (m, 2H), 7.65 (d, J=1.8 Hz, 1H), 7.70 (ddd, J=9.1, 4.3, 2.4 Hz, 1H), 8.14 (dd, J=6.4, 2.6 Hz, 1H), 8.26 (br. s., 1H), 10.21 (br. s, 1H).

Compound 136: N-(3-Chloro-4,5-difluorophenyl)-1,5-dimethyl-4-[(3-methyloxetan-3-yl)sulfamoyl]-1H-pyrrole-2-carboxamide

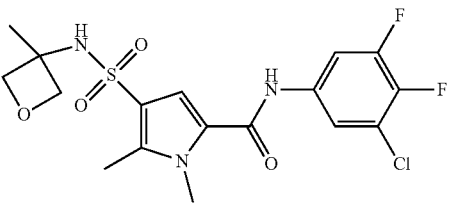 [SMILES: Cc1c(S(=O)(=O)NC2(C)COC2)cc(C(=O)Nc2cc(F)c(F)c(Cl)c2)n1C]

Crude ethyl 1,5-dimethyl-4-[(3-methyloxetan-3-yl)sulfamoyl]pyrrole-2-carboxylate (described in synthesis of compound 89)(1800 mg, 5.689 mmol) was dissolved in methanol (8 mL), lithium hydroxide (720 mg, 30.1 mmol) in water (2 mL) was added and the reaction mixture was heated at 50° C. for 2 hours. The reaction mixture was evaporated to dryness and co evaporated with toluene (2×50 mL) to afford a beige powder. Half of the above obtained powder was dissolved in water (5 mL), and HCl (1M in water, 15.02 mL) was added. The water layer was extracted with Me-THF (3×20 mL). The combined organic layers were washed with Brine, dried (Na₂SO₄) and concentrated to dryness to afford 1,5-dimethyl-4-(N-(3-methyloxetan-3-yl)sulfamoyl)-1H-pyrrole-2-carboxylic acid (600 mg). 1,5-dimethyl-4-(N-(3-methyloxetan-3-yl)-sulfamoyl)-1H-pyrrole-2-carboxylic acid (600 mg, 2.08 mmol) was dissolved in DMF (3 mL). diisopropylethylamine (1.08 mL, 6.24 mmol), HATU (950 mg, 2.50 mmol), and 3-chloro-4,5-difluoroaniline hydrochloride (described in the synthesis of compound 57) were added and the reaction mixture was stirred at room temperature for 68 hours and at 60° C. for 2 hours. The reaction mixture was directly loaded on column. The reaction mixture was purified using silica gel column chromatography (ethyl acetate in heptane from 20 to 80%). The desired fraction were combined and concentrated to keep ~100 mL of solvent. The white precipitate was filtered and washed with petroleum ether and dried in vacuum oven overnight to afford compound 136 (604 mg) as white powder. Method B; Rt: 1.03 min. m/z: 432 (M−H)⁻ Exact mass: 433.07. ¹H NMR (400 MHz, DMSO-d₆) δ ppm 1.49 (s, 3H), 2.44 (s, 3H), 3.83 (s, 3H), 4.11 (d, J=6.4 Hz, 2H), 4.59 (d, J=5.9 Hz, 2H), 7.35 (s, 1H), 7.77-7.86 (m, 2H), 7.97 (s, 1H), 10.20 (s, 1H).

Compound 137: N-(3-Chloro-4,5-difluorophenyl)-1,5-dimethyl-4-{[(1R)-2,2,2-trifluoro-1-methylethyl]sulfamoyl}-1H-pyrrole-2-carboxamide

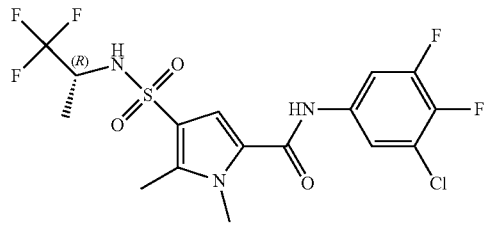

In a pressure tube, crude ethyl 4-chlorosulfonyl-1,5-dimethyl-pyrrole-2-carboxylate (3.03 g, 11.4 mmol) (synthesis described in synthesis for compound 89) was dissolved in acetonitrile (30 mL). To this was added diisopropylethylamine (4.91 mL, 28.5 mmol) followed by (R)-1,1,1-trifluoro-2-propylamine (3.22 g, 28.5 mmol) and the tube was closed and resulting mixture was heated at 80° C. for 2 hours. The reaction mixture was concentrated and the resulting orange sticky oil was dissolved in dichloromethane (50 mL) and this was washed with aqueous hydrochloric acid (1N, 2×20 mL). The organics were dried on sodium sulphate, filtered and concentrated in vacuo yielding orange oil (3.41 g) which was purified using silica gel column chromatography (ethyl acetate in heptane from 0 to 80%). The desired fractions were combined and evaporated to dryness to afford (R)-ethyl 1,5-dimethyl-4-(N-(1,1,1-trifluoropropan-2-yl)sulfamoyl)-1H-pyrrole-2-carboxylate (2.3 g) as white powder which was used as such. (R)-ethyl 1,5-dimethyl-4-(N-(1,1,1-trifluoropropan-2-yl)sulfamoyl)-1H-pyrrole-2-carboxylate (2.3 g, 6.72 mmol) was dissolved in ethanol (30 mL) and sodium hydroxide in water (13.4 mL, 13.4 mmol, 1 M) was added and the reaction mixture was stirred at 40° C. for 2 hours and at room temperature for 66 hours. The reaction mixture was heated at 70° C. for 2 hours. Sodium hydroxide in water (6.72 mL, 6.72-mmol, 1 M) was added to the reaction mixture which was heated at 70° C. for 2 hours more. The reaction mixture was allowed to reach room temperature and was concentrated to keep ~20 mL. HCl (20.15 mL, 20.15 mmol, 1M) was added. The water layer was extracted with Me-THF (3×20 mL). The combined organic layers were washed with Brine, dried (Na$_2$SO$_4$) and concentrated to dryness to afford (R)-1,5-dimethyl-4-(N-(1,1,1-trifluoropropan-2-yl)sulfamoyl)-1H-pyrrole-2-carboxylic acid (2.05 g). (R)-1,5-dimethyl-4-(N-(1,1,1-trifluoropropan-2-yl)sulfamoyl)-1H-pyrrole-2-carboxylic acid (450 mg, 1.43 mmol) and 3-chloro-4,5-difluoroaniline hydrochloride (0.57 g, 2.86 mmol) (synthesis described in synthesis for compound 57) and HATU (0.73 g, 1.91 mmol) were dissolved in DMF (2 mL) containing diisopropylethylamine (0.82 mL, 4.77 mmol). The reaction mixture was stirred at 40° C. for 66 hours. The reaction mixture was directly loaded on column. The reaction mixture was purified using silica gel column chromatography (ethyl acetate in heptane from 20 to 80%). The desired fractions were combined and evaporated to keep ~50 mL of solvent. The precipitates were filtered and washed with petroleum ether and dried in vacuum oven at 50° C. overnight to afford compound 137 (490 mg) as white powder. Method B; Rt: 1.16 min. m/z: 458 (M–H)$^-$ 460 (M+H)$^+$ Exact mass: 459.04. $^1$H NMR (400 MHz, DMSO-d$_6$) δ ppm 1.07 (d, J=6.8 Hz, 3H), 2.44 (s, 3H), 3.69-3.95 (m, 4H), 7.37 (s, 1H), 7.76-7.86 (m, 2H), 8.21 (br. s., 1H), 10.24 (br. s., 1H).

Compound 138: N-(3-Chloro-4-fluorophenyl)-1,5-dimethyl-4-{[(1R)-2,2,2-trifluoro-1-methylethyl]sulfamoyl}-1H-pyrrole-2-carboxamide

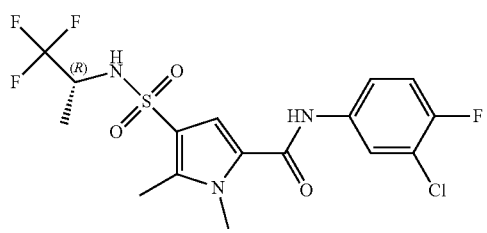

Compound 138 (510 mg) as white powder was synthesized similarly as described for compound 137 using 3-chloro-4-fluoroaniline instead of 3-chloro-4,5-difluoroaniline hydrochloride in the last step. Method B; Rt: 1.10 min. m/z: 440 (M–H)$^-$ Exact mass: 441.05. $^1$H NMR (400 MHz, DMSO-d$_6$) δ ppm 1.07 (d, J=7.0 Hz, 3H), 2.44 (s, 3H), 3.75-3.87 (m, 4H), 7.36 (s, 1H), 7.39 (t, J=9.1 Hz, 1H), 7.66 (ddd, J=9.1, 4.3, 2.6 Hz, 1H), 8.02 (dd, J=6.9, 2.5 Hz, 1H), 8.19 (br. s, 1H), 10.15 (s, 1H).

Compound 139: N-(3,4-Difluorophenyl)-1,5-dimethyl-4-{[(1R)-2,2,2-trifluoro-1-methylethyl]sulfamoyl}-1H-pyrrole-2-carboxamide

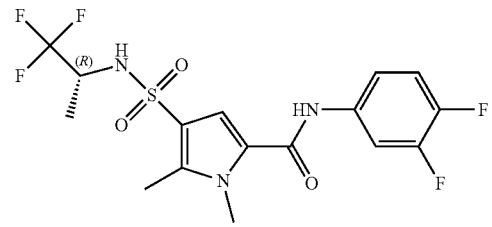

Compound 139 (462 mg) as white powder was synthesized similarly as described for compound 137 using 3,4-difluoroaniline instead of 3-chloro-4,5-difluoroaniline hydrochloride in the last step. Method B; Rt: 1.06 min. m/z: 424 (M–H)$^-$ 426 (M+H)$^+$ Exact mass: 425.08. $^1$H NMR (400 MHz, DMSO-d$_6$) δ ppm 1.07 (d, J=6.8 Hz, 3H), 2.44 (s, 3H), 3.75-3.88 (m, 4H), 7.35 (s, 1H), 7.40 (dt, J=10.5, 9.2 Hz, 1H), 7.45-7.54 (m, 1H), 7.87 (ddd, J=13.4, 7.6, 2.5 Hz, 1H), 8.19 (br. s., 1H), 10.17 (s, 1H).

Compound 140: N-(3-Cyano-4-fluorophenyl)-1,5-dimethyl-4-{[(1R)-2,2,2-trifluoro-1-methylethyl]sulfamoyl}-1H-pyrrole-2-carboxamide

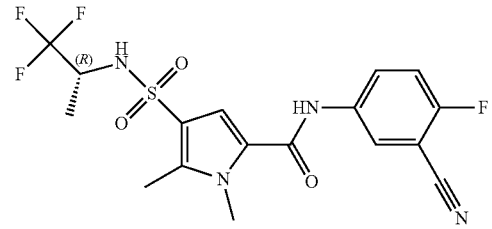

(R)-1,5-dimethyl-4-(N-(1,1,1-trifluoropropan-2-yl)sulfamoyl)-1H-pyrrole-2-carboxylic acid (168 mg, 0.53 mmol) (synthesis described in synthesis for compound 137) 5-amino-2-fluorobenzonitrile (0.15 g, 1.07 mmol) and HATU (0.24 g, 0.64 mmol) were dissolved in DMF (1 mL) containing diisopropylethylamine (0.23 mL, 1.34 mmol). The reaction mixture was stirred at 50° C. for 1 hour. The reaction mixture was purified using silica gel column chromatography (ethyl acetate in heptane from 20 to 80%). The desired fractions were combined and evaporated to keep ~50 mL of the solvent. The white solids were filtered and dried in vacuum oven to afford compound 140 (180 mg) as white powder. Method B; Rt: 1.00 min. m/z: 431 (M–H)$^-$ Exact mass: 432.09. $^1$H NMR (400 MHz, DMSO-d$_6$) δ ppm 1.07 (d, J=6.8 Hz, 3H), 2.44 (s, 3H), 3.76-3.87 (m, 1H), 3.84 (s, 3H), 7.38 (s, 1H), 7.52 (t, J=9.1 Hz, 1H), 8.01 (ddd, J=9.2, 4.8, 2.9 Hz, 1H), 8.10-8.35 (m, 1H), 8.22 (dd, J=5.9, 2.6 Hz, 1H), 10.30 (br. s, 1H).

Compound 141: N-(3-Bromo-4-fluorophenyl)-1,5-dimethyl-4-{[(1R)-2,2,2-trifluoro-1-methylethyl]sulfamoyl}-1H-pyrrole-2-carboxamide

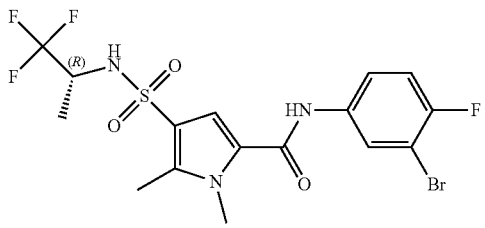

Compound 141 (210 mg) as white powder was synthesized similarly as described for compound 140 using 3-bromo-4-fluoroaniline (0.20 g, 1.07 mmol) instead of 5-amino-2-fluorobenzonitrile. Method B; Rt: 1.11 min. m/z: 484 (M–H)⁻ Exact mass: 485.00. ¹H NMR (400 MHz, DMSO-$d_6$) δ ppm 1.07 (d, J=7.0 Hz, 3H), 2.43 (s, 3H), 3.74-3.89 (m, 1H), 3.83 (s, 3H), 7.29-7.40 (m, 2H), 7.70 (ddd, J=9.0, 4.4, 2.6 Hz, 1H), 8.13 (dd, J=6.4, 2.6 Hz, 1H), 8.18 (br. s., 1H), 10.13 (s, 1H).

Compound 142: N-[4-Fluoro-3-(trifluoromethyl)phenyl]-1,5-dimethyl-4-{[(1R)-2,2,2-trifluoro-1-methylethyl]sulfamoyl}-1H-pyrrole-2-carboxamide

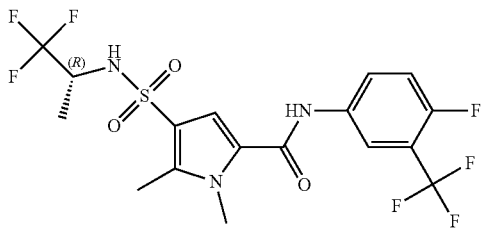

Compound 142 (187 mg) as white powder was synthesized similarly as described for compound 140 using 4-fluoro-3-(trifluoromethyl)aniline (0.19 g, 1.07 mmol) instead of 5-amino-2-fluorobenzonitrile. Method B; Rt: 1.14 min. m/z: 474 (M–H)⁻ Exact mass: 475.08. ¹H NMR (400 MHz, DMSO-$d_6$) δ ppm 1.07 (d, J=7.0 Hz, 3H), 2.44 (s, 3H), 3.76-3.85 (m, 1H), 3.84 (s, 3H), 7.39 (s, 1H), 7.49 (br. t, J=9.8, 9.8 Hz, 1H), 8.00-8.08 (m, 1H), 8.10-8.30 (m, 1H), 8.19 (dd, J=6.6, 2.6 Hz, 1H), 10.28 (s, 1H).

Compound 143: N-(3-Chloro-2,4-difluorophenyl)-1,5-dimethyl-4-{[(1R)-2,2,2-trifluoro-1-methylethyl]sulfamoyl}-1H-pyrrole-2-carboxamide

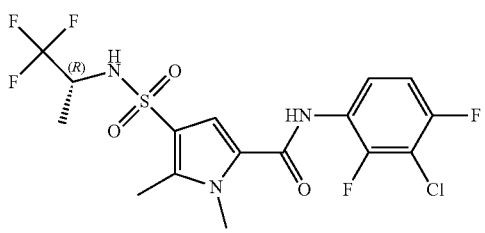

Compound 143 (147 mg) as white powder was synthesized similarly as described for compound 140 using 3-chloro-2,4-difluoroaniline (0.17 g, 1.07 mmol) instead of 5-amino-2-fluorobenzonitrile. The reaction mixture was stirred at 60° C. for 2 hours more. Method B; Rt: 1.07 min. m/z: 458 (M–H)⁻ Exact mass: 459.04. ¹H NMR (400 MHz, DMSO-$d_6$) δ ppm 1.09 (d, J=7.0 Hz, 3H), 2.44 (s, 3H), 3.82 (s, 3H), 3.76-3.91 (m, 1H), 7.34 (td, J=9.0, 2.0 Hz, 1H), 7.35 (s, 1H), 7.52 (td, J=8.7, 5.8 Hz, 1H), 8.20 (br. s., 1H), 10.05 (s, 1H).

Synthesis of ethyl 4-chlorosulfonyl-1,3-dimethyl-pyrrole-2-carboxylate (step 1)

Ethyl 1,3-dimethylpyrrole-2-carboxylate (10.7 g, 61.0 mmol) was added drop wise to chlorosulfonic acid (33.3 mL, 500 mmol) at 0° C. under nitrogen atmosphere. The reaction mixture was warmed to room temperature and allowed to stir 2 hours. The resulting mixture was added drop wise to a stirred, temperature controlled ice-water mixture (200 mL) keeping the temperature under 5° C. A white precipitation was formed. The obtained aqueous suspension was extracted using dichloromethane (3×100 mL). The combined extracts were washed with Brine and dried on sodium sulphate, filtered and concentrated in vacuo yielding ethyl 4-chlorosulfonyl-1,3-dimethyl-pyrrole-2-carboxylate (13.96 g) as a brown powder which was used as such. Method B; Rt: 1.11 min. m/z: 264 (M–H)⁻ Exact mass: 265.02.

Synthesis of Ethyl 1,3-dimethyl-4-[[(1R)-2,2,2-trifluoro-1-methyl-ethyl]sulfamoyl]pyrrole-2-carboxylate (step 2)

In a pressure tube, ethyl 4-chlorosulfonyl-1,3-dimethyl-pyrrole-2-carboxylate (4.65 g, 17.5 mmol) was dissolved in acetonitrile (30 mL). To this was added diisopropylethylamine (7.54 mL, 43.8 mmol) followed by (R)-1,1,1-trifluoro-2-propylamine (2.97 g, 26.3 mmol) and the tube was closed and resulting mixture was heated at 80° C. overnight. Then the mixture was cooled to room temperature and concentrated. The resulting brown sticky oil was dissolved in dichloromethane (100 mL) and this was washed with hydrochloric acid (1N, 2×30 mL). The organics were dried on sodium sulphate, filtered and concentrated in vacuo yielding brown oil (5.12 g). The brown oil was purified using silica gel column chromatography (gradient elution: ethyl acetate: heptane from 0 to 80%). The desired fractions were combined and evaporated to dryness to afford ethyl 1,3-dimethyl-4-[[(1R)-2,2,2-trifluoro-1-methyl-ethyl]sulfamoyl]pyrrole-2-carboxylate (3.05 g) as light yellow powder. Method B; Rt: 0.96 min. m/z: 341 (M–H)⁻ Exact mass: 342.09.

Synthesis of 1,3-dimethyl-4-[[(1R)-2,2,2-trifluoro-1-methyl-ethyl]sulfamoyl]pyrrole-2-carboxylic acid (Step 3)

Ethyl 1,3-dimethyl-4-[[(1R)-2,2,2-trifluoro-1-methyl-ethyl]sulfamoyl]pyrrole-2-carboxylate (3.05 g, 8.46 mmol) was dissolved in ethanol (50 mL) and sodium hydroxide in water (1 M, 42.3 mL, 42.3 mmol) was added. The reaction mixture was stirred at 80° C. for 18 hours. The reaction mixture was allowed to reach room temperature and was concentrated to keep ~20 mL solvent. The solution was diluted with aqueous hydrochloride (1 M, 42.3 mL, 42.3 mmol) and extracted with Me-THF (3×30 mL). The combined organic layers were washed with Brine, dried (Na₂SO₄) and concentrated to dryness to afford 1,3-dimethyl-4-[[(1R)-2,2,2-trifluoro-1-methyl-ethyl]sulfamoyl]pyrrole-2-carboxylic acid (2.71 g). Method B; Rt: 0.45 min. m/z: 313 (M–H)⁻ Exact mass: 314.05.

Compound 144: N-(3,4-Difluorophenyl)-1,3-dimethyl-4-{[(1R)-2,2,2-trifluoro-1-methylethyl]sulfamoyl}-1H-pyrrole-2-carboxamide (step 4)

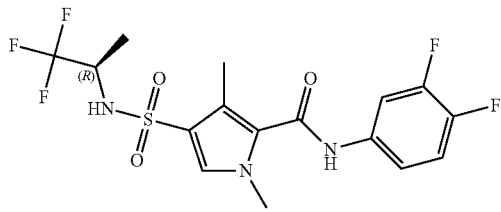

1,3-dimethyl-4-[[(1R)-2,2,2-trifluoro-1-methyl-ethyl]sulfamoyl]pyrrole-2-carboxylic acid (450 mg, 1.43 mmol) and 3,4-difluoroaniline (0.37 g, 2.86 mmol) and HATU (0.73 g, 1.91 mmol) were dissolved in DMF (1.92 mL, 24.7 mmol) containing diisopropylethylamine (0.82 mL, 4.77 mmol). The reaction mixture was stirred at 40° C. for 42 hours and allowed to reach room temperature. The reaction mixtures were purified using silica gel column chromatography (gradient elution: ethyl acetate in heptane from 10 to 70%). The desired fractions were combined and evaporated to keep ~50 mL of the solvent. The white solids were filtered and dried overnight in vacuum oven at 50° C. to afford compound 144 (470 mg) as white powder. Method B; Rt: 1.01 min. m/z: 424 (M–H)⁻ Exact mass: 425.08. ¹H NMR (400 MHz, DMSO-d₆) δ ppm 1.11 (d, J=6.8 Hz, 3H), 2.29 (s, 3H), 3.72 (s, 3H), 3.82 (quin, J=7.5 Hz, 1H), 7.37-7.46 (m, 2H), 7.50 (s, 1H), 7.73-7.92 (m, 1H), 8.16 (br. s., 1H), 10.31 (s, 1H).

Compound 145: N-(3-Chloro-4-fluorophenyl)-1,3-dimethyl-4-{[(1R)-2,2,2-trifluoro-1-methylethyl]sulfamoyl}-1H-pyrrole-2-carboxamide

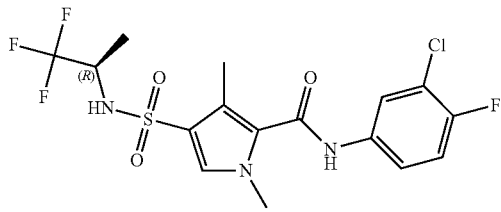

Compound 145 (452 mg) as white powder was synthesized similarly as described for compound 144 using 3-chloro-4-fluoroaniline instead of 3,4-difluoroaniline. Method B; Rt: 1.06 min. m/z: 440 (M–H)⁻ Exact mass: 441.05. ¹H NMR (400 MHz, DMSO-d₆) δ ppm 1.11 (d, J=6.8 Hz, 3H), 2.30 (s, 3H), 3.72 (s, 3H), 3.83 (quin, J=6.6 Hz, 1H), 7.41 (t, J=9.1 Hz, 1H), 7.50 (s, 1H), 7.55-7.71 (m, 1H), 7.98 (dd, J=6.7, 2.1 Hz, 1H), 8.16 (br. s., 1H), 10.29 (s, 1H).

Compound 146: N-(3,4-Difluorophenyl)-1,3-dimethyl-4-{[(1S)-2,2,2-trifluoro-1-methylethyl]sulfamoyl}-1H-pyrrole-2-carboxamide

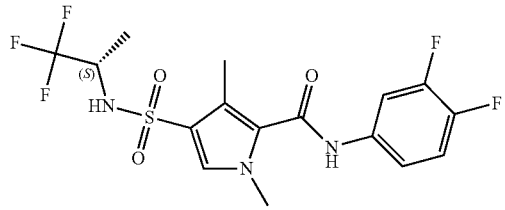

Compound 146 (353 mg) as white powder was synthesized similarly as described for compound 144 using (S)-1,1,1-trifluoro-2-propylamine (1.50 g, 13.3 mmol) instead of (R)-1,1,1-trifluoro-2-propylamine in Step 2 (resulting in 1,3-dimethyl-4-[[(1S)-2,2,2-trifluoro-1-methyl-ethyl]sulfamoyl]pyrrole-2-carboxylic acid as intermediate). Method B; Rt: 1.01 min. m/z: 424 (M–H)⁻ Exact mass: 425.08. ¹H NMR (400 MHz, DMSO-d₆) δ ppm 1.11 (d, J=6.8 Hz, 3H), 2.29 (s, 3H), 3.72 (s, 3H), 3.76-3.87 (m, 1H), 7.34-7.46 (m, 2H), 7.49 (s, 1H), 7.74-7.91 (m, 1H), 8.16 (br. s., 1H), 10.31 (s, 1H).

Compound 147: N-(3-Chloro-4-fluorophenyl)-1,3-dimethyl-4-{[(1S)-2,2,2-trifluoro-1-methylethyl]sulfamoyl}-1H-pyrrole-2-carboxamide

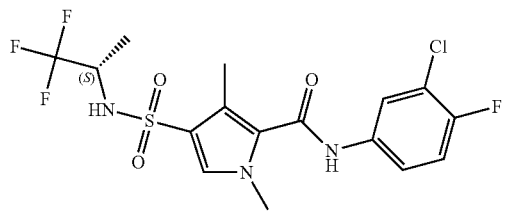

Compound 147 (443 mg) as white powder was synthesized similarly as described for compound 144 using (S)-1,1,1-trifluoro-2-propylamine (1.50 g, 13.3 mmol) instead of (R)-1,1,1-trifluoro-2-propylamine in Step 2 (resulting in 1,3-dimethyl-4-[[(1S)-2,2,2-trifluoro-1-methyl-ethyl]sulfamoyl]pyrrole-2-carboxylic acid as intermediate) and 3-chloro-4-fluoroaniline instead of 3,4-difluoroaniline in Step 4. Method B; Rt: 1.06 min. m/z: 440 (M–H)⁻ Exact mass: 441.05. ¹H NMR (400 MHz, DMSO-d₆) δ ppm 1.11 (d, J=7.0 Hz, 3H), 2.30 (s, 3H), 3.72 (s, 3H), 3.83 (quin, J=7.2 Hz, 1H), 7.41 (t, J=9.1 Hz, 1H), 7.50 (s, 1H), 7.62 (ddd, J=9.0, 4.2, 2.6 Hz, 1H), 7.98 (dd, J=6.8, 2.4 Hz, 1H), 8.17 (br. s., 1H), 10.29 (s, 1H).

Compound 148: N-(3,4-Difluorophenyl)-1,3-dimethyl-4-[(3-methyloxetan-3-yl)sulfamoyl]-1H-pyrrole-2-carboxamide

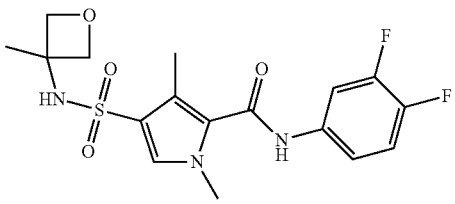 [SMILES: Cc1c(S(=O)(=O)NC2(C)COC2)cn(C)c1C(=O)Nc1ccc(F)c(F)c1]

Compound 148 was synthesized similarly as described for compound 144 using 3-methyl-3-oxetanamine instead of (R)-1,1,1-trifluoro-2-propylamine in Step 2. In Step 4, the desired fractions were evaporated to afford oil which was purified again using silica gel column chromatography (gradient elution: ethyl acetate in heptane from 40 to 70%). The desired fractions were combined and evaporated to afford compound 148 (475 mg) as white powder. Method B; Rt: 0.86 min. m/z: 398 (M−H)⁻ Exact mass: 399.11. ¹H NMR (400 MHz, DMSO-d$_6$) δ ppm 1.53 (s, 3H), 2.32 (s, 3H), 3.72 (s, 3H), 4.13 (d, J=6.4 Hz, 2H), 4.62 (d, J=5.9 Hz, 2H), 7.36-7.51 (m, 3H), 7.62-8.16 (m, 2H), 10.32 (br. s., 1H).

Compound 149: N-(3-Chloro-4-fluorophenyl)-1,3-dimethyl-4-[(3-methyloxetan-3-yl)sulfamoyl]-1H-pyrrole-2-carboxamide

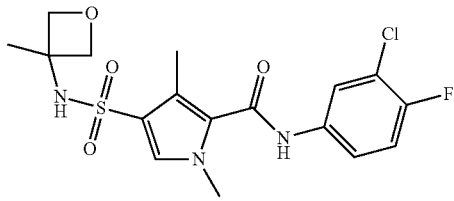 [SMILES: Cc1c(S(=O)(=O)NC2(C)COC2)cn(C)c1C(=O)Nc1ccc(F)c(Cl)c1]

Compound 149 was synthesized as compound 144 using 3-methyl-3-oxetanamine instead of (R)-1,1,1-trifluoro-2-propylamine in Step 2 and 3-chloro-4-fluoroaniline instead of 3,4-difluoroaniline in Step 4. In Step 4, the desired fractions were evaporated to afford oil which solidified while standing. The powder was triturated in warm CH$_2$Cl$_2$ (10 mL) and allowed to reach room temperature. The white solids were filtered and washed with CH$_2$Cl$_2$ (5 mL) and petroleum ether (5 mL) and dried in vacuum oven at 50° C. to afford compound 149 (435 mg) as white powder. Method B; Rt: 0.92 min. m/z: 414 (M−H)⁻ Exact mass: 415.08. ¹H NMR (400 MHz, DMSO-d$_6$) δ ppm 1.53 (s, 3H), 2.32 (s, 3H), 3.72 (s, 3H), 4.12 (d, J=6.4 Hz, 2H), 4.62 (d, J=5.9 Hz, 2H), 7.41 (t, J=9.1 Hz, 1H), 7.47 (s, 1H), 7.62 (ddd, J=9.0, 4.4, 2.6 Hz, 1H), 7.91 (br. s., 1H), 7.99 (dd, J=6.8, 2.6 Hz, 1H), 10.29 (br. s., 1H).

Compound 150: N-(3-Cyano-4-fluorophenyl)-1,3-dimethyl-4-{[(1R)-2,2,2-trifluoro-1-methylethyl]sulfamoyl}-1H-pyrrole-2-carboxamide

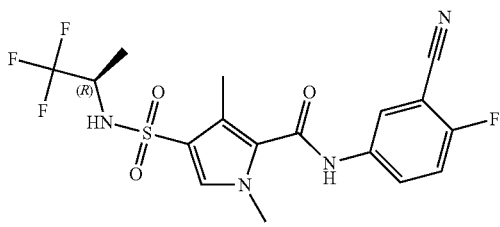

Compound 150 (416 mg) as white powder was synthesized as compound 144 using 5-amino-2-fluorobenzonitrile instead of 3,4-difluoroaniline and the reaction time was 20 hours instead of 42 hours in Step 4. Method C; Rt: 1.68 min. m/z: 431 (M−H)⁻ Exact mass: 432.09. ¹H NMR (400 MHz, DMSO-d$_6$) δ ppm 1.11 (d, J=7.0 Hz, 3H), 2.31 (s, 3H), 3.73 (s, 3H), 3.83 (quin, J=7.2 Hz, 1H), 7.52 (br. s, 1H), 7.54 (t, J=9.1 Hz, 1H), 7.97 (ddd, J=9.2, 4.9, 2.6 Hz, 1H), 8.09-8.27 (m, 1H), 8.18 (dd, J=5.7, 2.6 Hz, 1H), 10.42 (br. s., 1H).

Compound 151: N-(3-Cyano-4-fluorophenyl)-1,3-dimethyl-4-{[(1S)-2,2,2-trifluoro-1-methylethyl]sulfamoyl}-1H-pyrrole-2-carboxamide

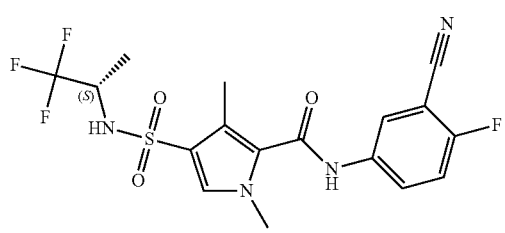

Compound 151 (420 mg) as white powder was synthesized similarly as described for compound 144 using (S)-1,1,1-trifluoro-2-propylamine (1.50 g, 13.3 mmol) instead of (R)-1,1,1-trifluoro-2-propylamine in Step 2 and 5-amino-2-fluorobenzonitrile instead of 3,4-difluoroaniline and the reaction time was 20 hours instead of 42 hours in Step 4. Method B; Rt: 0.96 min. m/z: 431 (M−H)⁻ Exact mass: 432.09. ¹H NMR (400 MHz, DMSO-d$_6$) δ ppm 1.11 (d, J=6.8 Hz, 3H), 2.31 (s, 3H), 3.73 (s, 3H), 3.83 (quin, J=7.2 Hz, 1H), 7.51 (s, 1H), 7.54 (t, J=9.2 Hz, 1H), 7.97 (ddd, J=9.2, 4.9, 2.9 Hz, 1H), 8.09-8.27 (m, 1H), 8.18 (dd, J=5.9, 2.6 Hz, 1H), 10.42 (br. s., 1H).

Compound 152: N-(3-Cyano-4-fluorophenyl)-1,3-dimethyl-4-[(3-methyloxetan-3-yl)sulfamoyl]-1H-pyrrole-2-carboxamide

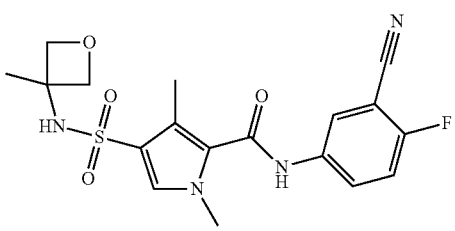 [SMILES: Cc1c(S(=O)(=O)NC2(C)COC2)cn(C)c1C(=O)Nc1ccc(F)c(C#N)c1]

Compound 152 was synthesized similarly as described for compound 144 using 3-methyl-3-oxetanamine instead of (R)-1,1,1-trifluoro-2-propylamine in Step 2 and 5-amino-2-fluorobenzonitrile instead of 3,4-difluoroaniline in Step 4. In Step 4, the desired fractions were evaporated to afford light yellow oil which was purified again using silica gel column chromatography (gradient elution: ethyl acetate in heptane from 40 to 70%). The desired fractions were combined and evaporated to afford compound 152 (332 mg) as white powder. Method B; Rt: 0.80 min. m/z: 405 (M−H)⁻ Exact mass: 406.11. ¹H NMR (400 MHz, DMSO-d$_6$) δ ppm 1.53 (s, 3H), 2.34 (s, 3H), 3.73 (s, 3H), 4.13 (d, J=6.4 Hz, 2H), 4.62 (d, J=5.9 Hz, 2H), 7.48 (s, 1H), 7.54 (t, J=9.1 Hz, 1H), 7.92 (br. s., 1H), 7.98 (ddd, J=9.2, 4.9, 2.9 Hz, 1H), 8.19 (dd, J=5.8, 2.8 Hz, 1H), 10.43 (br. s., 1H).

Compound 153: N-[4-Fluoro-3-(trifluoromethyl)phenyl]-1,3-dimethyl-4-{[(1R)-2,2,2-trifluoro-1-methylethyl]sulfamoyl}-1H-pyrrole-2-carboxamide

Compound 154: 1-Methyl-4-{[(1S)-2,2,2-trifluoro-1-methylethyl]sulfamoyl}-N-(2,3,4-trifluorophenyl)-1H-pyrrole-2-carboxamide

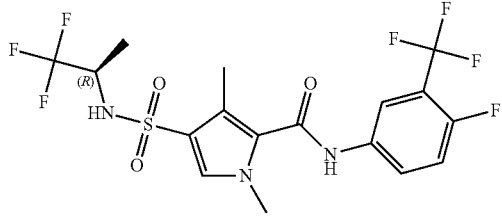

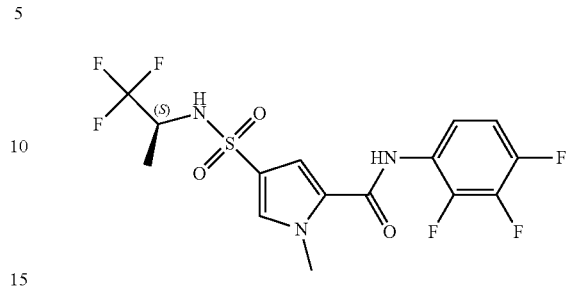

Compound 153 (270 mg) as beige solid was synthesized similarly as described for compound 144 using 1,3-dimethyl-4-[[(1R)-2,2,2-trifluoro-1-methyl-ethyl]sulfamoyl]pyrrole-2-carboxylic acid (260 mg, 0.83 mmol) and 4-fluoro-3-(trifluoromethyl)aniline (0.31 g, 1.65 mmol) instead of 3,4-difluoroaniline in Step 4. Method B; Rt: 1.10 min. m/z: 474 (M−H)⁻ Exact mass: 475.08. ¹H NMR (400 MHz, DMSO-$d_6$) δ ppm 1.12 (d, J=6.8 Hz, 3H), 2.32 (s, 3H), 3.73 (s, 3H), 3.84 (quin, J=7.3 Hz, 1H), 7.48-7.56 (m, 2H), 7.91-8.00 (m, 1H), 8.12-8.24 (m, 2H), 10.41 (s, 1H).

Synthesis of methyl 1-methyl-4-[[(1S)-2,2,2-trifluoro-1-methyl-ethyl]sulfamoyl]pyrrole-2-carboxylate In a pressure tube methyl 4-chlorosulfonyl-1-methyl-pyrrole-2-carboxylate (15 g, 63.11 mmol) was dissolved in 100 mL of dry acetonitrile. To this was added (S)-1,1,1-trifluoro-2-propylamine (8.56 g, 75.74 mmol) followed by diisopropylethylamine (27.19 mL, 157.79 mmol). The pressure tube was flushed with nitrogen and closed. The mixture was stirred in a pre-heated oil bath at 80° C. for 15 hours. Then it was cooled to room temperature and concentrated in vacuo. The obtained residue was dissolved in dichloromethane (400 mL) and this was washed with HCl (1M/aq/2×100 mL). The obtained organics were dried on $Na_2SO_4$, filtered and concentrated in vacuo resulting in Methyl 1-methyl-4-[[(1S)-2,2,2-trifluoro-1-methyl-ethyl]sulfamoyl]pyrrole-2-carboxylate as a beige powder (17.5 g) which was used as such. Method B; Rt: 0.83 min. m/z: 313.1 (M−H)⁻ Exact mass: 314.05.

Synthesis of 1-methyl-4-[[(1S)-2,2,2-trifluoro-1-methyl-ethyl]sulfamoyl]pyrrole-2-carboxylic acid Methyl 1-methyl-4-[[(1S)-2,2,2-trifluoro-1-methyl-ethyl]sulfamoyl]pyrrole-2-carboxylate (6.6 g, 19.7 mmol) was dissolved in tetrahydrofuran (56 mL). To this was added lithium hydroxide (1.655 g, 69.1 mmol) in distilled water (7.5 mL) followed by methanol (3 mL). The resulting mixture was stirred overnight. The mixture was concentrated until only water remained and extra distilled water (15 mL) was added. The mixture was neutralised with hydrochloric acid (1M, aq). The resulting mixture was extracted using 2-methyltetrahydrofuran (3×20 mL). The combined extracts were dried on sodium sulphate, filtered and concentrated in vacuo yielding 1-methyl-4-[[(1S)-2,2,2-trifluoro-1-methyl-ethyl]sulfamoyl]pyrrole-2-carboxylic acid (5.34 g). Method B; Rt: 0.45 min. m/z: 299.0 (M−H)⁻ Exact mass: 300.04.

1-methyl-4-[[(1S)-2,2,2-trifluoro-1-methyl-ethyl]sulfamoyl]pyrrole-2-carboxylic acid (500 mg, 1.67 mmol) was dissolved in of N,N-dimethylformamide (1 mL). Then HATU (0.76 g, 2 mmol) was added and this mixture was stirred for 20 minutes. Then diisopropylethylamine (0.86 mL, 5 mmol) was added followed by 2,3,4-trifluoroaniline (0.49 g, 3.33 mmol). The reaction mixture was stirred at 50° C. for 5 hours. Then this mixture was cooled to room temperature and injected directly onto a silica plug. The mixture was purified by silica gel column chromatography using gradient elution from heptane to EtOAc. (100:0 to 0:100) yielding compound 154 as a white powder (253 mg) Method B; Rt: 0.99 min. m/z: 428.1 (M−H)⁻ Exact mass: 429.06. ¹H NMR (400 MHz, DMSO-$d_6$) δ ppm, 1.09 (d, J=7.0 Hz, 3H), 3.90 (s, 3H), 3.91-4.02 (m, 1H), 7.24-7.48 (m, 3H), 7.65 (d, J=1.8 Hz, 1H), 7.76-8.97 6 (br.s, 1H), 9.58-11.00 (br.s, 1H).

Compound 155: N-(3-Bromo-2,4-difluorophenyl)-1-methyl-4-{[(1S)-2,2,2-trifluoro-1-methylethyl]sulfamoyl}-1H-pyrrole-2-carboxamide

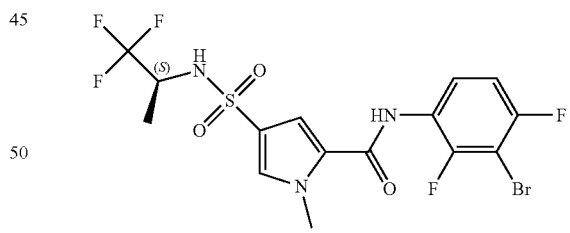

Compound 155 (314 mg) was prepared similarly as described for compound 154 using 3-bromo-2,4-difluoroaniline (0.69 g, 3.33 mmol) instead of 2,3,4-trifluoroaniline resulting in white powder. Method B; Rt: 1.04 min. m/z: 490.03 (M−H)⁻ Exact mass: 491.0. ¹H NMR (400 MHz, DMSO-$d_6$) δ ppm 1.09 (d, J=7.0 Hz, 3H), 3.90 (s, 3H), 3.91-4.02 (m, 1H), 7.23-7.39 (m, 2H), 7.57 (td, J=8.7, 5.9 Hz, 1H), 7.64 (d, J=1.5 Hz, 1H), 8.18 (br. s., 1H), 10.12 (br. s., 1H).

Compound 156: N-(3-Chloro-2,4-difluorophenyl)-1-methyl-4-{[(1S)-2,2,2-trifluoro-1-methylethyl]sulfamoyl}-1H-pyrrole-2-carboxamide

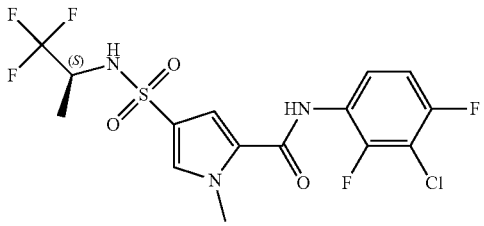

Compound 156 (289 mg) was prepared similarly as compound 154 using 3-chloro-2,4-difluoro-aniline (0.54 g, 3.33 mmol) instead of 2,3,4-trifluoroaniline resulting in white powder. Method B; Rt: 1.03 min. m/z: 444.11 (M−H)⁻ Exact mass: 445.03. ¹H NMR (400 MHz, DMSO-d₆) δ ppm 1.09 (d, J=6.8 Hz, 3H), 3.90 (s, 3H), 3.91-4.00 (m, 1H), 7.29-7.43 (m, 2H), 7.53 (td, J=8.7, 5.9 Hz, 1H), 7.64 (d, J=1.8 Hz, 1H), 8.17 (br. s., 1H), 10.14 (br. s., 1H).

Compound 157: N-(3-cyano-4-fluoro-phenyl)-1-methyl-4-[[(1R)-2,2,2-trifluoro-1-methylethyl]sulfamoyl]pyrrole-2-carboxamide

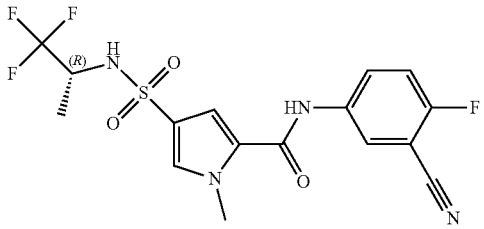

Prepared similarly as described for compound 123 using 5-amino-2-fluoro-benzonitrile (580.5 mg, 4.14 mmol) instead of 3-chloro-4-fluoro-aniline, resulting in compound 157 as a white powder (136 mg). Method B; Rt: 0.96 min. m/z: 417.13 (M−H)⁻ Exact mass: 418.07. ¹H NMR (400 MHz, DMSO-d₆) δ ppm 1.08 (d, J=6.8 Hz, 3H), 3.82-4.00 (m, 4H), 7.36 (d, J=2.0 Hz, 1H), 7.43-7.59 (m, 1H), 7.65 (d, J=1.5 Hz, 1H), 7.96-8.04 (m, 1H), 8.05-8.33 (m, 2H), 10.38 (br. s., 1H).

Compound 158: N-(3-Cyanophenyl)-1-methyl-4-{[(1R)-2,2,2-trifluoro-1-methylethyl]-sulfamoyl}-1H-pyrrole-2-carboxamide

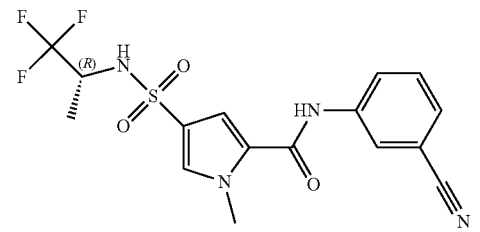

To methyl 1-methyl-4-[[(1R)-2,2,2-trifluoro-1-methylethyl]sulfamoyl]pyrrole-2-carboxylate (5.0 g, 15.91 mmol, prepared as in the synthesis for compound 122) dissolved in dioxane (59 mL) and water (10 mL) was added LiOH (2.34 g, 55.68 mmol) and the reaction mixture stirred 16 h. The mixture was concentrated in vacuo. The residue was dissolved in water and acidified with 1N HCl solution till pH~3. The mixture was stirred at room temperature for 30'. The product was filtered off and dried in vacuo to become a pale yellow solid of 1-methyl-4-[[(1R)-2,2,2-trifluoro-1-methylethyl]sulfamoyl]pyrrole-2-carboxylic acid (3.95 g). This acid (700 mg, 2.33 mmol), 3-aminobenzonitrile (347.8 mg, 2.91 mmol), HATU (1108 mg, 2.914 mmol) and DIPEA (1.2 mL, 6.99 mmol) was dissolved in DMF (7 mL) and the mixture was stirred at room temperature for 16 h. The mixture was poured in 100 mL ice water and was extracted with EtOAc. The organic layer was separated, washed with brine, dried (MgSO₄), filtered and concentrated in vacuo. The residue was purified on a silica using a gradient eluent Heptane-EtOAc 100-0→50-50. The product fractions were collected and concentrated in vacuo. The product was crystallized from 2-propanol, filtered off and dried in vacuo, yielding compound 158 (518 mg) as a white solid. Method B; Rt: 0.93 min. m/z: 399.1 (M−H)⁻ Exact mass: 400.08 ¹H NMR (600 MHz, DMSO-d₆) δ ppm 1.08 (d, J=7.04 Hz, 3H) 3.86-4.00 (m, 4H) 7.39 (d, J=1.91 Hz, 1H) 7.50-7.61 (m, 2H) 7.66 (d, J=1.61 Hz, 1H) 7.99 (dt, J=7.56, 2.02 Hz, 1H) 8.12-8.21 (m, 2H) 10.35 (s, 1H).

Compound 159: N-[2-Fluoro-3-(trifluoromethyl)phenyl]-1-methyl-4-{[(1R)-2,2,2-trifluoro-1-methylethyl]sulfamoyl}-1H-pyrrole-2-carboxamide

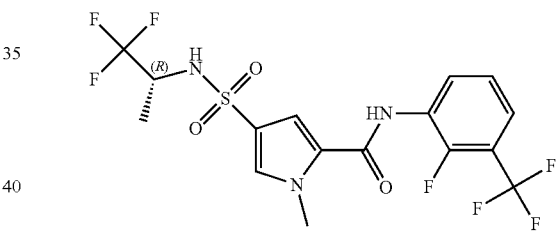

Compound 159 (582 mg) was prepared similarly as described for compound 158 using 3-amino-2-fluorobenzotrifluoride (0.387 mL, 2.91 mmol) instead of 3-aminobenzonitrile resulting in a white solid. Method B; Rt: 1.06 min. m/z: 460.1 (M−H)⁻ Exact mass: 461.06. ¹H NMR (400 MHz, DMSO-d₆) δ ppm 1.10 (d, J=6.8 Hz, 3H), 3.87-3.98 (m, 4H), 7.37-7.47 (m, 2H), 7.61-7.67 (m, 2H), 7.88 (t, J=7.2 Hz, 1H), 8.19 6 (d, J=8.4 Hz, 1H), 10.21 (s, 1H).

Compound 160: N-(3-Cyano-2-fluorophenyl)-1-methyl-4-{[(1R)-2,2,2-trifluoro-1-methylethyl]sulfamoyl}-1H-pyrrole-2-carboxamide

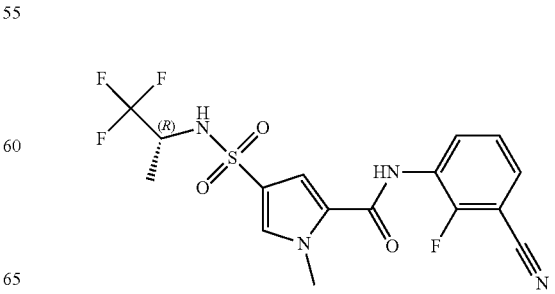

Compound 160 (202 mg) was prepared similarly as described for compound 158 using 3-amino-2-fluorobenzonitrile (396.7 mg, 2.91 mmol) instead of 3-aminobenzonitrile resulting in a white solid. Method B; Rt: 0.92 min. m/z: 417.1 (M−H)⁻ Exact mass: 418.07. ¹H NMR (400 MHz, DMSO-d₆) δ ppm 1.10 (d, J=7.0 Hz, 3H), 3.89-3.99 (m, 4H), 7.38 (d, J=2.0 Hz, 1H), 7.43 (t, J=7.9 Hz, 1H), 7.67 (d, J=1.8 Hz, 1H), 6 7.78 (ddd, J=7.8, 5.9, 1.5 Hz, 1H), 7.88-7.93 (m, 1H), 8.19 (d, J=8.6 Hz, 1H), 10.26 (s, 1H).

Compound 161: N-[3-(1,1-Difluoroethyl)-4-fluorophenyl]-1-methyl-4-[(3-methyloxetan-3-yl)sulfamoyl]-1H-pyrrole-2-carboxamide

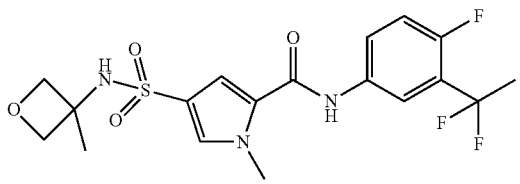 [SMILES: Cn1cc(S(=O)(=O)NC2(C)COC2)cc1C(=O)Nc1ccc(F)c(C(C)(F)F)c1]

Synthesis of 2-(1,1-difluoroethyl)-1-fluoro-4-nitro-benzene 1-(2-fluoro-5-nitrophenyl)ethanone (19 g, 103.7 mmol) was dissolved in dichloromethane (300 mL) The mixture was stirred at −78° C. under N₂-atmosphere. Diethylamino) sulfur trifluoride (33.4 g, 207 mmol) was added to the mixture via cannula over a period of 30 min. The reaction mixture was stirred at 35° C. for 16 h. The cold reaction mixture was poured into ice water (200 mL). The aqueous layer was extracted with dichloromethane (80 mL) twice. The combined organic layers were washed with water, dried over sodium sulfate and evaporated to dryness to provide a yellow oil. The crude product was purified by column chromatography to provide a yellow oil (13 g).

Synthesis of 3-(1,1-difluoroethyl)-4-fluoro-aniline 2-(1,1-difluoroethyl)-1-fluoro-4-nitrobenzene (13 g, 63.37 mmol) was dissolved in methanol (65 mL) and water (65 mL). Iron powder (10.6 g) and HCl (25 mL) were added. The mixture was stirred at room temperature for 45 min. The reaction mixture was then filtered through celite, the filtrate was washed with saturated solution of sodium carbonate and dried over sodium sulfate and evaporated to dryness to provide a yellow oil. The crude product was purified by column chromatography to provide a yellow oil (5845 mg).

Synthesis of 5-[[3-(1,1-difluoroethyl)-4-fluoro-phenyl]carbamoyl]-1-methyl-pyrrole-3-sulfonyl chloride 3-(1,1-difluoroethyl)-4-fluoro-aniline (1099.8 mg, 6.28 mmol) dissolved in toluene (10 mL) was added dropwise during 5' to a solution of 4-chlorosulfonyl-1-methyl-pyrrole-2-carbonyl chloride (1520 mg, 6.28 mmol) in toluene (100 mL) at reflux. The reaction mixture was refluxed 90 minutes and then concentrated in vacuo, yielding a brown powder which was used as such (2566 mg) Method A; Rt: 2.01 min. m/z: 378.9 (M−H)⁻ Exact mass: 380.02.

3-methyloxetan-3-amine (390 mg, 4.47 mmol) was added to a solution of 5-[[3-(1,1-difluoroethyl)-4-fluoro-phenyl] carbamoyl]-1-methyl-pyrrole-3-sulfonyl chloride (605 mg, 1.49 mmol) in CH₃CN (50 mL) and stirred 17 hr. Water was added until crystallisation began. The white powder was filtered off and dried overnight in vacuo at 50° C., resulting in compound 161 (514 mg); Method A; Rt: 1.70 min. m/z: 430.1 (M−H)⁻ Exact mass: 431.11. ¹H NMR (400 MHz, DMSO-d₆) δ ppm 1.55 (s, 3H), 1.95-2.06 (m, 3H), 3.92 (s, 3H), 4.14 (d, J=6.4 Hz, 2H), 4.60 (d, J=5.9 Hz, 2H), 7.35 (d, J=2.0 Hz, 2H), 7.59 (d, J=1.8 Hz, 1H), 7.85-7.92 (m, 1H), 7.93-8.02 (m, 2H), 10.23 (s, 1H).

Compound 162: 4-(tert-Butylsulfamoyl)-N-[3-(1,1-difluoroethyl)-4-fluorophenyl]-1-methyl-1H-pyrrole-2-carboxamide

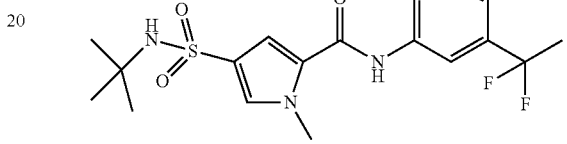

tert-butylamine (400.6 mg, 5.48 mmol) was added to a solution of 5-[[3-(1,1-difluoroethyl)-4-fluoro-phenyl]carbamoyl]-1-methyl-pyrrole-3-sulfonyl chloride (622 mg, 1.53 mmol) in CH₃CN (50 mL) and stirred 17 hr. Water was added until crystallisation began. The white powder was filtered off and dried overnight in vacuo at 50° C., resulting in compound 162 (355 mg). Method A; Rt: 1.91 min. m/z: 416.1 (M−H)⁻ Exact mass: 417.13. ¹H NMR (400 MHz, DMSO-d₆) δ ppm 1.17 (s, 9H), 1.93-2.08 (m, 3H), 3.91 (s, 3H), 7.11 (s, 1H), 7.27-7.37 (m, 2H), 7.52 (d, J=1.5 Hz, 1H), 7.85-7.93 6 (m, 1H), 7.96-8.02 (m, 1H), 10.21 (s, 1H).

Compound 163: N-(3,5-Dichloro-4-fluorophenyl)-1-methyl-4-[(2,2,2-trifluoro-1,1-dimethylethyl)sulfamoyl]-1H-pyrrole-2-carboxamide

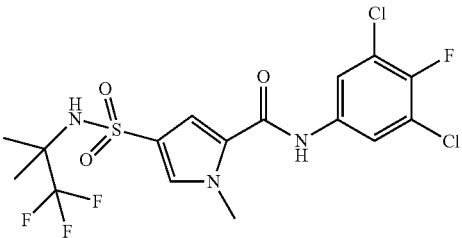 [SMILES: Cn1cc(S(=O)(=O)NC(C)(C)C(F)(F)F)cc1C(=O)Nc1cc(Cl)c(F)c(Cl)c1]

3,5-dichloro-4-fluoroaniline (1534 mg, 18.52 mmol) dissolved in toluene (10 mL) was added to 4-chlorosulfonyl-1-methyl-pyrrole-2-carbonyl chloride (2063 mg, 8.52 mmol) in toluene (125 mL) at reflux and refluxed 2 hours. The reaction mixture was filtered while still hot and concentrated yielding a crude beige powder (2833 mg, 5-[(3,5-dichloro-4-fluoro-phenyl)carbamoyl]-1-methyl-pyrrole-3-sulfonyl chloride) which was used as such. ¹H NMR (400 MHz, ACETONITRILE-d₃) δ ppm 3.96 (s, 3H), 7.39 (d, J=2.0 Hz, 1H), 7.71-7.77 (m, 3H), 8.78 (br. s., 1H)

2,2,2-trifluoro-1,1-dimethyl-ethylamine (692 mg, 5.45 mmol) was added to 5-[(3,5-dichloro-4-fluoro-phenyl)carbamoyl]-1-methyl-pyrrole-3-sulfonyl chloride (700.2 mg, 1.82 mmol) and DIPEA (0.47 mL, 2.72 mmol) dissolved in CH₃CN (66 mL) and refluxed overnight. The reaction mixture was concentrated. The residue was dissolved in EtOAc, washed with 1M HCl, dried over sodium sulphate, filtered and concentrated. The residue was purified by column chromatography on silica using a gradient from 10 till 100% EtOAc in heptane. The obtained powder was recrystallized from methanol (25 mL), upon addition of water and further purified by Prep HPLC (Stationary phase: RP XBridge Prep C18 OBD-10 µm, 30×150 mm), Mobile phase: 0.25% NH₄HCO₃ solution in water, MeOH), yielding a white powder which was dried in vacuo at 50° C. during 6 hours. Method A; Rt: 2.13 min. m/z: 473.9 (M–H)⁻ Exact mass: 475.01. ¹H NMR (400 MHz, DMSO-d₆) δ ppm 1.36 (s, 6H), 3.92 (s, 3H), 7.34 (d, J=2.0 Hz, 1H), 7.61 (d, J=1.5 Hz, 1H), 7.95 (d, J=6.2 Hz, 2H), 8.07 (s, 1H), 6 10.30 (s, 1H).

Compound 164: N-(3-Chloro-4,5-difluorophenyl)-4-[(3,3-difluorocyclobutyl)sulfamoyl]-1-methyl-1H-pyrrole-2-carboxamide

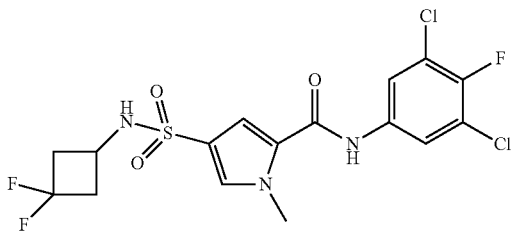 [SMILES: Cn1cc(S(=O)(=O)NC2CC(F)(F)C2)cc1C(=O)Nc1cc(Cl)c(F)c(Cl)c1]

A mixture of 5-[(3-chloro-4,5-difluoro-phenyl)carbamoyl]-1-methyl-pyrrole-3-sulfonyl chloride (561.7 mg, 1.15 mmol) (prepared as in the synthesis for compound 57) 3,3-difluorocyclobutanamine hydrochloride (248.5 mg, 1.73 mmol) DIPEA (0.6 mL, 3.46 mmol) in CH₃CN (22 mL) was stirred overnight at room temperature. The reaction mixture was concentrated. The residue was subjected to column chromatography on silica using a gradient from 10 till 100% EtOAc in heptane. The product fractions were partially concentrated until product crystallized. The white crystals were filtered off and dried overnight in vacuo at 50° C., resulting in compound 164 (175 mg) Method A: Rt: 1.86 min m/z: 438.0 (M–H)⁻ Exact mass: 439.04. ¹H NMR (400 MHz, DMSO-d₆) δ ppm 2.36-2.58 (m, 2H), 2.72-2.90 (m, 2H), 3.48-3.63 (m, 1H), 3.92 (s, 3H), 7.34 (d, J=1.8 Hz, 1H), 7.63 (d, J=1.8 6 Hz, 1H), 7.75-7.88 (m, 3H), 10.29 (s, 1H)¹H NMR (400 MHz, ACETONITRILE-d₃) δ ppm 2.40-2.58 (m, 2H), 2.74-2.89 (m, 2H), 3.59-3.72 (m, 1H), 3.93 (s, 3H), 5.84 (d, J=1.0 Hz, 1H), 7.13 3 (d, J=1.8 Hz, 1H), 7.36 (d, J=1.8 Hz, 1H), 7.56-7.61 (m, 1H), 7.61-7.69 (m, 1H), 8.63 (s, 1H).

Compound 165: N-(3-chloro-4,5-difluoro-phenyl)-1-methyl-4-[[1-methyl-1-(trifluoro-methyl)propyl]sulfamoyl]pyrrole-2-carboxamide

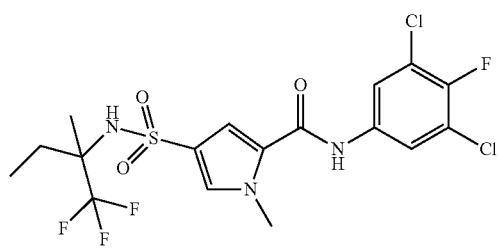 [SMILES: CCC(C)(NS(=O)(=O)c1cc(C(=O)Nc2cc(Cl)c(F)c(Cl)c2)n(C)c1)C(F)(F)F]

A mixture of 5-[(3-chloro-4,5-difluoro-phenyl)carbamoyl]-1-methyl-pyrrole-3-sulfonyl chloride (1034 mg. 12 mmol) (prepared as in the synthesis for compound 57) 1,1,1-trifluoro-2-methyl-butan-2-amine hydrochloride (754 mg, 4.25 mmol) DIPEA (1.14 mL, 36.58 mmol) in CH₃CN (31 mL) was refluxed 2 days. The reaction mixture was concentrated. The residue was dissolved in EtOAc (100 mL), washed with 1M HCl, dried over sodium sulphate, filtered and concentrated. The residue was subjected to column chromatography on silica using a gradient from 10 till 100% EtOAc in heptane. The product fractions were concentrated yielding compound 165 (300.1 mg) as a white solid. The racemic mixture 165 was separated in enantiomers 165a and 165b by Prep SFC (Stationary phase: Chiralpak Diacel AD 20×250 mm), Mobile phase: CO₂, iPrOH with 0.2% iPrNH₂), the desired fractions were collected, evaporated, dissolved in MeOH and evaporated again, yielding 165a (first eluding, white solid, 45 mg). Method A: Rt: 2.10 min m/z: 472.0 (M–H)⁻ Exact mass: 473.06. ¹H NMR (400 MHz, DMSO-d₆) δ ppm 0.79 (t, J=7.3 Hz, 3H), 1.37 (s, 3H), 1.45-1.59 (m, 1H), 1.73-1.87 (m, 1H), 3.92 (s, 3H), 7.34 (d, J=1.8 Hz, 1H), 7.59 (d, J=1.8 Hz, 1H), 7.76-7.86 (m, 2H), 7.90 (s, 1H), 10.31 (s, 1H) and 165b (second eluding, 40 mg, white solid). Method A: Rt: 2.10 min m/z: 472.0 (M–H)⁻ Exact mass: 473.06. ¹H NMR (400 MHz, DMSO-d₆) δ ppm 0.79 (t, J=7.3 Hz, 3H), 1.37 (s, 3H), 1.46-1.59 (m, 1H), 1.74-1.87 (m, 1H), 3.92 (s, 3H), 7.34 (d, J=1.8 Hz, 1H), 7.59 (d, J=1.8 Hz, 1H), 7.76-7.86 (m, 2H), 7.90 (s, 1H), 10.31 (s, 1H).

Compound 166: N-(3-Chloro-4,5-difluorophenyl)-4-[(3,3-difluorocyclopentyl)sulfamoyl]-1-methyl-1H-pyrrole-2-carboxamide

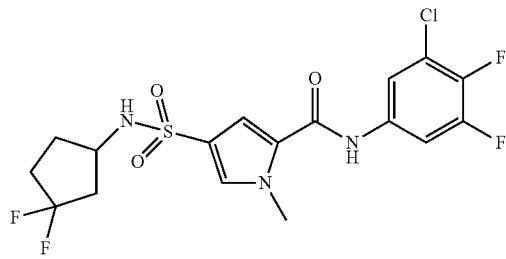 [SMILES: Cn1cc(S(=O)(=O)NC2CCC(F)(F)C2)cc1C(=O)Nc1cc(F)c(F)c(Cl)c1]

A mixture of 5-[(3-chloro-4,5-difluoro-phenyl)carbamoyl]-1-methyl-pyrrole-3-sulfonyl chloride (1496 mg. 3.07 mmol) (prepared as in the synthesis for compound 57) 3,3-difluorocyclopentanamine (819 mg, 6.76 mmol) DIPEA (0.79 mL, 4.61 mmol) in CH₃CN (23 mL) was refluxed 1 hour. The reaction mixture was concentrated. The residue was dissolved in EtOAc (100 mL), washed with 1M HCl, dried over sodium sulphate, filtered and concentrated. The residue was subjected to column chromatography on silica using a gradient from 10 till 100% EtOAc in heptane. The product fractions were partially concentrated until the product started to crystallize. The white crystals were filtered off and dried overnight in vacuo at 50° C., resulting in compound 166 (856.3 mg) Method A: Rt: 1.87 min m/z: 452.0 (M–H)⁻ Exact mass: 453.05. ¹H NMR (400 MHz, DMSO-d₆) δ ppm 1.56-1.75 (m, 1H), 1.87-2.07 (m, 3H), 2.07-2.23 (m, 1H), 2.24-2.40 (m, 1H), 3.55-3.70 (m, 1H), 3.92 (s, 3H), 7.34 (d, J=2.0 Hz, 1H), 7.62 (d, J=1.5 Hz, 1H), 7.65 (d, J=6.8

Hz, 1H), 7.77-7.86 (m, 2H), 10.31 (s, 1H) Differential scanning calorimetry: From 30 to 300° C. at 10° C./min: peak at 198.05° C.

The racemic mixture 166 was separated in enantiomers 166a and 166b by Prep SFC (Stationary phase: Chiralpak Diacel AD 20×250 mm), Mobile phase: $CO_2$, MeOH-iPrOH (50-50) with 0.2% iPrNH$_2$), the desired fractions were collected, evaporated, dissolved in MeOH and evaporated again, The residues were dissolved in methanol (20 mL) and crystallized upon addition of water. The white powders were filtered off and dried overnight in vacuo at 50° C., resulting in compound 166a (285.5 mg, first eluding enantiomer), 166b (296 mg, second eluding enantiomer) Method A: Rt: 1.96 min m/z: 452.0 (M−H)⁻ Exact mass: 453.05. $^1$H NMR (400 MHz, DMSO-d$_6$) δ ppm 1.58-1.73 (m, 1H), 1.88-2.07 (m, 3H), 2.07-2.23 (m, 1H), 2.24-2.41 (m, 1H), 3.57-3.69 (m, 1H), 3.92 (s, 3H), 7.34 (d, J=1.8 Hz, 1H), 7.62 (d, J=1.5 Hz, 1H), 7.65 (d, J=6.6 Hz, 1H), 7.75-7.87 (m, 2H), 10.31 (s, 1H).

Compound 167: 4-(Bicyclo[1.1.1]pent-1-ylsulfamoyl)-N-(3-chloro-4,5-difluorophenyl)-1-methyl-1H-pyrrole-2-carboxamide

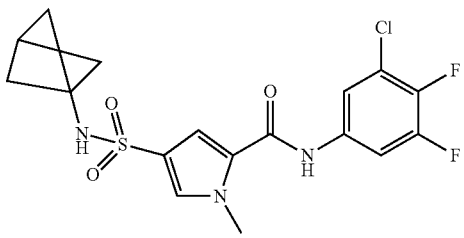 [SMILES: Cn1cc(S(=O)(=O)NC23CC4CC42C3)cc1C(=O)Nc1cc(F)c(F)c(Cl)c1]

Compound 167 was prepared similarly as described for compound 164 using bicyclo[1.1.1]pentan-1-amine hydrochloride instead of 3,3-difluorocyclobutanamine hydrochloride. The product fractions after column chromatography were concentrated and the residue dissolved in hot methanol (25 mL). The product crystallized upon addition of a small amount of water. The white powder was filtered off and dried overnight in vacuo at 50° C., resulting in compound 167 (226 mg) Method A: Rt: 1.89 min m/z: 414.0 (M−H)⁻ 416.0 (M+H)⁺ Exact mass: 415.06. $^1$H NMR (400 MHz, DMSO-d$_6$) δ ppm 1.81 (s, 6H), 2.31 (s, 1H), 3.93 (s, 3H), 7.34 (d, J=2.0 Hz, 1H), 7.58 (d, J=1.5 Hz, 1H), 7.77-7.86 (m, 2H), 8.22 (s, 1H), 10.29 (s, 1H).

Compound 168: N-(3-Chloro-4,5-difluorophenyl)-1-methyl-4-[(3,3,3-trifluoropropyl)sulfamoyl]-1H-pyrrole-2-carboxamide

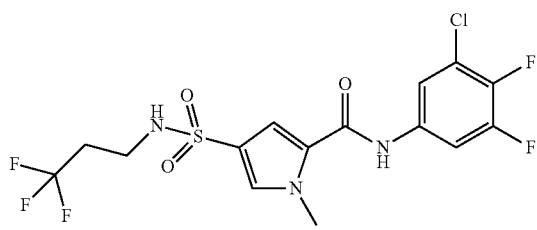 [SMILES: Cn1cc(S(=O)(=O)NCCC(F)(F)F)cc1C(=O)Nc1cc(F)c(F)c(Cl)c1]

Compound 168 was prepared similarly as described for compound 164 using 3,3,3-trifluoropropylamine instead of 3,3-difluorocyclobutanamine hydrochloride but was stirred 3 hours at room temperature. Water was added until the product start to crystallize. The white powder was filtered off and dried overnight in vacuo at 50° C. Method A: Rt: 1.95 min m/z: 444.0 (M−H)⁻ Exact mass: 445.03 $^1$H NMR (400 MHz, DMSO-d$_6$) δ ppm 2.40-2.55 (m, 2H), 2.95-3.05 (m, 2H), 3.92 (s, 3H), 7.35 (d, J=2.0 Hz, 1H), 7.52 (t, J=5.9 Hz, 1H), 7.65 (d, J=1.8 6 Hz, 1H), 7.76-7.86 (m, 2H), 10.31 (s, 1H).

Compound 169: N-(3-Chloro-4,5-difluorophenyl)-1-methyl-4-[(3,3,3-trifluoro-1-methylpropyl)sulfamoyl]-1H-pyrrole-2-carboxamide

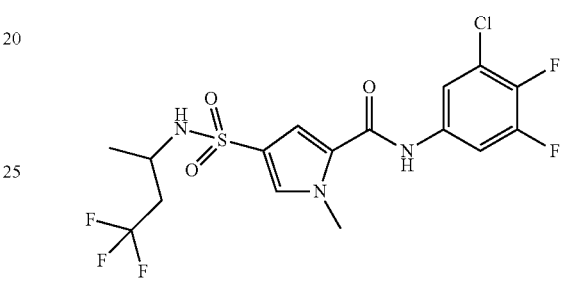

Compound 169 was prepared similarly as compound 164 using 4,4,4-trifluorobutan-2-amine hydrochloride instead of 3,3-difluorocyclobutanamine hydrochloride. Water was added until the product starts to crystallize. The white powder was filtered off and dried overnight in vacuo at 50° C., resulting in compound 169 (542 mg). Method A: Rt: 1.91 min m/z: 458.0 (M−H)⁻ Exact mass: 459.04. $^1$H NMR (400 MHz, DMSO-d$_6$) δ ppm 1.06 (d, J=6.8 Hz, 3H), 2.32-2.47 (m, 2H), 3.43-3.55 (m, 1H), 3.92 (s, 3H), 7.34 (d, J=1.8 Hz, 1H), 7.55 (d, J=7.9 Hz, 1H), 7.62 (d, J=1.8 Hz, 1H), 7.76-7.86 (m, 2H), 10.30 (s, 1H). The racemic compound 169 (492 mg) was separated in enantiomers 169a and 169b by Prep SFC (Stationary phase: Chiralpak Diacel AD 20×250 mm), Mobile phase: $CO_2$, MeOH with 0.2% iPrNH$_2$), the desired fractions were collected, evaporated, solved in MeOH and evaporated again. The residue was crystallized from 25 mL methanol upon addition of water, filtered off and dried overnight in vacuo at 50° C. yielding white crystals, resulting in compound 169a (first eluding enantiomer, 144 mg) and 169b (second eluding enantiomer, 135 mg).

Compound 170: N-(3-Cyano-4-fluorophenyl)-3-fluoro-1-methyl-4-{[(1R)-2,2,2-trifluoro-1-methylethyl]sulfamoyl}-1H-pyrrole-2-carboxamide

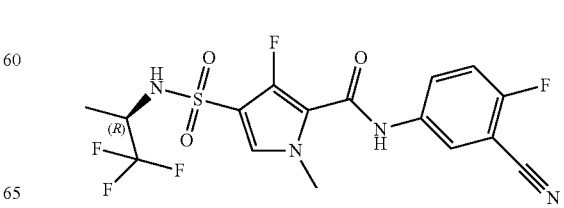

Ethyl 4-chlorosulfonyl-3-fluoro-1-methyl-pyrrole-2-carboxylate (prepared similarly as described in the synthesis of 3-fluoro-1-methyl-4-[(3-methyloxetan-3-yl)sulfamoyl]pyrrole-2-carboxylic acid for compound 74, from 5-ethoxycarbonyl-4-fluoro-1-methyl-pyrrole-3-sulfonic acid (heating 60 minutes at 80° C. in thionylchloride instead of 30 minutes at 80° C.; 4880 mg, 19.4 mmol) was dissolved in $CH_3CN$ (50 mL), DIPEA (10.04 mL, 58.27 mmol) was added followed by (2R)-1,1,1-trifluoropropan-2-amine (3295 mg, 29.14 mmol) and the mixture was refluxed for 3 hours. The reaction mixture was concentrated. The residue was dissolved in EtOAc (200 mL), washed with water, dried over sodium sulphate, filtered and concentrated. The residue was purified by column chromatography on silica using a gradient from 5 till 100% EtOAc in heptane. The product fractions were concentrated in vacuo yielding ethyl 3-fluoro-1-methyl-4-[[(1R)-2,2,2-trifluoro-1-methyl-ethyl]sulfamoyl]pyrrole-2-carboxylate as a light brown semisolid which was used as such (1705 mg). Method A: Rt 1.68 min, m/z: 345 (M−H)⁻ 347.0 (M+H)⁺ Exact mass: 346.06. A mixture of ethyl 3-fluoro-1-methyl-4-[[(1R)-2,2,2-trifluoro-1-methyl-ethyl]sulfamoyl]pyrrole-2-carboxylate (1705 mg, 4.92 mmol), LiOH (354 mg, 14.77 mmol) THF (17 mL) and water (4 mL) was stirred overnight. The reaction mixture was concentrated, the residue dissolved in water (50 mL) and the solution was neutralised with HCl 1M (14.77 mL, 14.77 mmol). The mixture was extracted with Me-THF (2×100 mL). The organic layer was dried over sodium sulphate, filtered and concentrated resulting in 3-fluoro-1-methyl-4-[[(1R)-2,2,2-trifluoro-1-methyl-ethyl]sulfamoyl]pyrrole-2-carboxylic acid (1533 mg) as a powder, which was used as such. Method A: Rt: 0.88 m/z: 317 (M−H)⁻ Exact mass: 318.03. $^1H$ NMR (400 MHz, DMSO-$d_6$) δ ppm 1.15 (d, J=7.0 Hz, 3H), 3.82 (s, 3H), 3.88-4.04 (m, 1H), 7.56 (d, J=4.8 Hz, 1H), 8.56 (d, J=8.8 Hz, 1H), 13.13 (br. s., 1H). Compound 170 (531 mg) was synthesized similarly as described for compound 94 using 3-fluoro-1-methyl-4-[[(1R)-2,2,2-trifluoro-1-methyl-ethyl]sulfamoyl]pyrrole-2-carboxylic acid (601.7 mg 1.89 mmol) instead of 3-fluoro-1-methyl-4-[(3-methyloxetan-3-yl)sulfamoyl]pyrrole-2-carboxylic acid and 5-amino-2-fluorobenzonitrile (531 mg, 3.78 mmol) instead of 4-fluoro-3-methylaniline and the reaction mixture was stirred overnight at 65° C. The column fractions were concentrated and the residue was crystallized by dissolving in 100 mL warm methanol upon addition of water. The crystals were filtered off and dried overnight in vacuo at 50° C. Method A: Rt: 1.66 min m/z: 435 (M−H)⁻ Exact mass: 436.06. $^1H$ NMR (400 MHz, DMSO-$d_6$) δ ppm 1.18 (d, J=6.8 Hz, 3H), 3.81 (s, 3H), 3.91-4.05 (m, 1H), 7.50-7.59 (m, 2H), 7.96 (ddd, J=9.2, 5.0, 2.8 Hz, 1H), 8.17 (dd, J=5.8, 2.8 Hz, 1H), 8.62 (d, J=8.8 Hz, 1H), 10.36 (s, 1H). Differential scanning calorimetry: From 30 to 300° C. at 10° C./min: peak at 190.99° C.

Alternative Synthesis of Compound 170:

Sodium hydride (6.99 g, 183 mmol) was added portionwise to ethyl 3-fluoropyrrole-2-carboxylate (23.9 g, 152 mmol), iodomethane (25.9 g, 183 mmol) in DMF (238 mL) under nitrogen in an icebath and stirred overnight at room temperature. The reaction mixture was acidified with 1M HCl and concentrated. The residue was dissolved in water/EtOAc. The organic layer was dried over $Na_2SO_4$, filtered and concentrated. The obtained residue was dissolved in $CH_3CN$ (150 mL), washed with heptane and concentrated at 60° C. and 40 mbar yielding a brown liquid which was submitted to silica gel column chromatography using a gradient from 10 to 25% EtOAc in heptane. The product fractions were concentrated resulting in ethyl 3-fluoro-1-methyl-pyrrole-2-carboxylate as a clear oil (14.0 g). Chlorosulfonic acid (9.97 g, 85.6 mmol) dissolved in dichloromethane (50 mL) was added to ethyl 3-fluoro-1-methyl-pyrrole-2-carboxylate (14.0 g, 81.5 mmol) dissolved in dichloromethane (250 mL) in an icebath and stirred 30 minutes. The formed light beige crystals were filtered off and dried overnight in vacuo at 50° C., resulting in 5-ethoxycarbonyl-4-fluoro-1-methyl-pyrrole-3-sulfonic acid (14.3 g). $^1H$ NMR (400 MHz, DMSO-$d_6$) δ ppm 1.26 (t, J=7.2 Hz, 3H), 3.72 (s, 3H), 4.23 (q, J=7.0 Hz, 2H), 7.02 (d, J=5.1 Hz, 1H). Method D: Rt: 0.88 min. m/z: 250.0 (M−H)⁻ Exact mass: 251.0. 5-ethoxycarbonyl-4-fluoro-1-methyl-pyrrole-3-sulfonic acid (20.3 g, 80.7 mmol) in $SOCl_2$ (80 mL, 1.1 mol) was stirred 2 hours at 80° C. The reaction mixture was concentrated. The obtained dark green solid was subjected to silica gel column chromatography using a gradient from 10 to 50% EtOAc in heptane. The product fractions were concentrated yielding ethyl 4-chlorosulfonyl-3-fluoro-1-methyl-pyrrole-2-carboxylate (18.9 g) as light yellow crystals which was used as such. Ethyl 4-chlorosulfonyl-3-fluoro-1-methyl-pyrrole-2-carboxylate (18.9 g, 70.1 mmol) (2R)-1,1,1-trifluoropropan-2-amine (11.89 g, 105.2 mmol) $NaHCO_3$ (17.7 g, 210 mmol) in acetonitrile (150 mL) with molecular sieves 4A (15 g) and was refluxed overnight. The reaction mixture was filtered and concentrated. The residue was dissolved in EtOAc and washed with 1 M HCl. The organic layer was dried over sodium sulphate, filtered and concentrated. The residue was purified via silica gel column chromatography (2×) using a gradient from 10 to 100% EtOAc in heptane, resulting in ethyl 3-fluoro-1-methyl-4-[[(1R)-2,2,2-trifluoro-1-methyl-ethyl]sulfamoyl]pyrrole-2-carboxylate as a white powder which was dried overnight at 50° C. in vacuo (19.1 g in total). Method D: Rt: 1.77 min. m/z: 345.0 (M−H)⁻ Exact mass: 346.1. $^1H$ NMR (400 MHz, DMSO-$d_6$) δ ppm 1.15 (d, J=7.0 Hz, 3H), 1.28 (t, J=7.2 Hz, 3H), 3.83 (s, 3H), 3.90-4.03 (m, 1H), 4.28 (q, J=7.2 Hz, 2H), 7.60 (d, J=4.8 Hz, 1H), 8.60 (d, J=8.8 Hz, 1H). To ethyl 3-fluoro-1-methyl-4-[[(1R)-2,2,2-trifluoro-1-methyl-ethyl]sulfamoyl]pyrrole-2-carboxylate (10.0 g, 28.9 mmol) and 5-amino-2-fluoro-benzonitrile (5.11 g, 37.6 mmol)) dissolved in dry THF (200 mL) at 5° C. under nitrogen atmosphere, lithium bis(trimethylsilyl)amide in toluene (115.6 mL, 1 M, 115.6 mmol) was added. The mixture was stirred 4 hours allowing to reach room temperature. The reaction mixture was quenched with $NH_4Cl$ (250 mL) solution and extracted with EtOAc (500 mL), diluted with brine (200 mL) and extracted again with EtOAc (300 mL). The combined organic layers were dried over sodium sulphate, filtered and concentrated. The residue was purified by silica gel column chromatography with a gradient from 10 to 100% EtOAc in heptane. The product fractions were concentrated and the solid residue was crystallised from warm methanol (300 mL) upon addition of water. The pink crystals were filtered off and dried in vacuo at 50° C. overnight. The compound was repeatedly purified by silica gel chromatography (using 10 to 100% EtOAc in heptane and using dichloromethane). The resulting product was crystallised once more from hot methanol (500 mL) and the product crystallised upon addition of water. The white powder was filtered off and dried overnight in vacuo at 50° C., resulting in compound 170 (9.28 g). Method D: Rt: 1.86 min m/z: 435.3 (M−H)⁻ Exact mass: 436.1. Differential scanning calorimetry: From 30 to 300° C. at 10° C./min: peak at 192.2° C. $[α]_{589}^{20}$=−23.2° (c 0.504 w/v %, DMF).

Compound 171: N-(3-Cyano-4-fluorophenyl)-3-fluoro-1-methyl-4-[(1-methylethyl)sulfamoyl]-1H-pyrrole-2-carboxamide

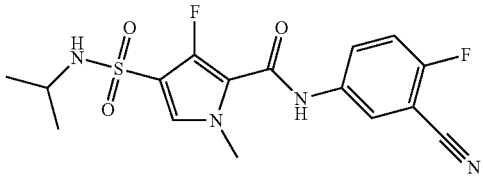 [SMILES: CC(C)NS(=O)(=O)c1cn(C)c(C(=O)Nc2ccc(F)c(C#N)c2)c1F]

Intermediate ethyl 3-fluoro-4-(isopropylsulfamoyl)-1-methyl-pyrrole-2-carboxylate was made similarly as described for ethyl 3-fluoro-1-methyl-4-[[(1R)-2,2,2-trifluoro-1-methyl-ethyl]sulfamoyl]pyrrole-2-carboxylate starting from 5-ethoxycarbonyl-4-fluoro-1-methyl-pyrrole-3-sulfonic acid (1220 mg, 4.86 mmol), converting it to the sulphonyl chloride with thionyl chloride (heating at 80° C. during 1 hour) and reaction with isopropylamine (1160 mg, 19.42 mmol) resulting in ethyl 3-fluoro-4-(isopropylsulfamoyl)-1-methyl-pyrrole-2-carboxylate (1169 mg) as a white powder. $^1$H NMR (400 MHz, DMSO-$d_6$) δ ppm 1.03 (d, J=6.6 Hz, 6H), 1.28 (t, J=7.2 Hz, 3H), 3.26-3.37 (m, 1H), 3.82 (s, 3H), 4.27 (q, J=7.2 Hz, 2H), 7.52 (d, J=4.6 Hz, 1H), 7.56 (d, J=7.3 Hz, 1H) Method A: Rt: 1.48 min m/z: 291 (M−H)$^-$ Exact mass: 292.09. Intermediate 3-fluoro-4-(isopropylsulfamoyl)-1-methyl-pyrrole-2-carboxylic acid was made similarly as for compound 170 using ethyl 3-fluoro-4-(isopropylsulfamoyl)-1-methyl-pyrrole-2-carboxylate (1169 mg, 4.0 mmol) The reaction mixture was concentrated. The residue was dissolved in water (75 mL) and neutralised with HCl 1M (12.0 mL, 12.0 mmol). The product crystallized and was filtered off. The white powder was dried overnight in vacuo at 50° C., resulting in 3-fluoro-4-(isopropylsulfamoyl)-1-methyl-pyrrole-2-carboxylic acid (856 mg) Method A: Rt: 0.75 min m/z: 263.0 (M−H)$^-$ Exact mass: 264.06. $^1$H NMR (400 MHz, DMSO-$d_6$) δ ppm 1.02 (d, J=6.6 Hz, 6H), 3.22-3.38 (m, 1H), 3.81 (s, 3H), 7.47 (d, J=4.8 Hz, 1H), 7.54 (d, J=7.5 Hz, 1H), 13.06 (s, 1H). Compound 171 was made similarly as compound 170 using 3-fluoro-4-(isopropylsulfamoyl)-1-methyl-pyrrole-2-carboxylic acid (594 mg, 2.25 mmol) resulting in compound 171 (670 mg) as a white powder. Method A: Rt: 1.59 min m/z: 381 (M−H)$^-$ Exact mass: 382.09. $^1$H NMR (400 MHz, DMSO-$d_6$) δ ppm 1.05 (d, J=6.6 Hz, 6H), 3.26-3.42 (m, 1H), 3.80 (s, 3H), 7.48 (d, J=4.6 Hz, 1H), 7.53 (t, J=9.1 Hz, 1H), 7.59 (d, J=7.3 Hz, 1H), 7.96 (ddd, J=9.2, 4.9, 2.6 Hz, 1H), 8.17 (dd, J=5.8, 2.8 Hz, 1H), 10.32 (s, 1H) Differential scanning calorimetry: From 30 to 300° C. at 10° C./min: peak at 204.47° C.

Compound 172: N-(3-Chloro-2,4-difluorophenyl)-1-methyl-4-[(1-methylethyl)sulfamoyl]-1H-pyrrole-2-carboxamide

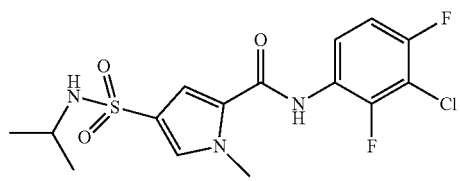 [SMILES: CC(C)NS(=O)(=O)c1cc(C(=O)Nc2ccc(F)c(Cl)c2F)n(C)c1]

4-(isopropylsulfamoyl)-1-methyl-pyrrole-2-carboxylic acid (250 mg, 1.02 mmol was dissolved in CH$_3$CN (15 mL). Triethylamine (0.56 mL), 3-chloro-2,4-difluoroaniline (183 mg, 1.12 mmol) and HATU (463 mg, 1.22 mmol) were added. The reaction mixture was stirred at room temperature for 1 h, next at 50° C. for 80 h and then for 24 h at 75° C. The solution was allowed to cool down. The solvent was evaporated leaving a yellow oil which was dissolved in CH$_2$Cl$_2$/MeOH (2 mL, 95:5) and purified by Flash Chromatography on silica using a gradient of EtOAc-heptane 0/100 to 100/0]. The desired fractions were combined and the solvent was evaporated leaving a brown stable foam which was dissolved in a boiling mixture of diisopropyl ether (3 mL) and CH$_3$CN (0.5 mL). The solution was allowed to cool while stirring. The precipitate was filtered off, washed once with its own filtrate and with of diisopropyl ether (2 mL). The product was collected as a white solid and dried in vacuo at 50° C., resulting in compound 172 (60 mg). Method B: Rt: 0.98 min m/z: 390.1 (M−H)$^-$ Exact mass: 391.06. $^1$H NMR (360 MHz, DMSO-$d_6$) δ ppm 1.02 (d, J=6.6 Hz, 6H), 3.26 (dd, J=13.4, 6.8 Hz, 1H), 3.89 (s, 3H), 7.25 (d, J=6.6 Hz, 1H), 7.28-7.39 (m, 2H), 7.48-7.59 (m, 2H), 10.16 (s, 1H).

Compound 173: N-(3-Chloro-2-fluorophenyl)-1-methyl-4-[(1-methylethyl)sulfamoyl]-1H-pyrrole-2-carboxamide

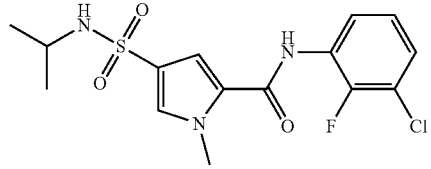 [SMILES: CC(C)NS(=O)(=O)c1cc(C(=O)Nc2cccc(Cl)c2F)n(C)c1]

4-(isopropylsulfamoyl)-1-methyl-pyrrole-2-carboxylic acid (0.75 g, 3.05 mmol) was dissolved in N,N-dimethylformamide (2 mL). HATU (1.27 g, 3.35 mmol) was added and the mixture was stirred for 20 minutes. DIPEA (1.31 mL, 7.61 mmol) was added followed by 3-chloro-2-fluoroaniline (0.44 g, 3.05 mmol). The reaction mixture was stirred at 50° C. for 16 hours. Then this mixture was purified by silica gel column chromatography using gradient elution from heptane to EtOAc. (100:0 to 0:100). The desired fractions were concentrated in vacuo and the obtained residue was crystallized out of MeOH/water. The precipitate was collected on a glass filter and dried in a vacuum oven at 55° C. for 24 hours yielding compound 173 (477 mg) as a white powder. Method B: Rt: 0.97 min m/z: 372.1 (M−H)$^-$ Exact mass: 373.07. $^1$H NMR (400 MHz, DMSO-$d_6$) δ ppm 1.03 (d, J=6.6 Hz, 6H), 3.21-3.30 (m, 1H), 3.90 (s, 3H), 7.18-7.27 (m, 2H), 7.32 (d, J=1.8 Hz, 1H), 7.44 (ddd, J=8.2, 6.8, 1.5 Hz, 1H), 7.50 (ddd, J=8.1, 6.8, 1.8 Hz, 1H), 7.55 (d, J=1.8 Hz, 1H), 10.12 (s, 1H).

Compound 174: N-(3-Chloro-4-fluorophenyl)-1-methyl-4-[(1-methylethyl)sulfamoyl]-1H-pyrrole-2-carboxamide

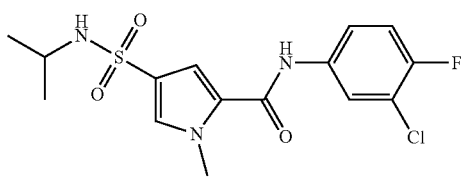 [SMILES: CC(C)NS(=O)(=O)c1cc(C(=O)Nc2ccc(F)c(Cl)c2)n(C)c1]

Compound 174 (681 mg) was prepared similarly as described for compound 173 using 3-chloro-4-fluoroaniline (0.44 g, 3.05 mmol) instead of 3-chloro-2-fluoroaniline resulting in a white powder. Method B: Rt: 1.02 min m/z: 372.1 (M–H)⁻ Exact mass: 373.07. ¹H NMR (400 MHz, DMSO-d₆) δ ppm 1.02 (d, J=6.6 Hz, 6H), 3.19-3.29 (m, 1H), 3.92 (s, 3H), 7.20 (br. s., 1H), 7.32 (d, J=1.8 Hz, 1H), 7.39 (t, J=9.1 Hz, 1H), 7.55 (d, J=1.8 Hz, 1H), 7.66 (ddd, J=9.0, 4.2, 2.6 Hz, 1H), 8.02 (dd, J=6.8, 2.6 Hz, 1H 10.22 (br. s., 1H).

Compound 175: N-(3-Cyano-4-fluorophenyl)-1-methyl-4-[(1-methylethyl)sulfamoyl]-1H-pyrrole-2-carboxamide

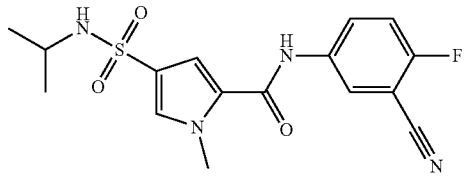 [SMILES: CC(C)NS(=O)(=O)c1cc(C(=O)Nc2ccc(F)c(C#N)c2)n(C)c1]

Compound 175 (576 mg) was prepared similarly as described for compound 173 using 5-amino-2-fluorobenzonitrile (0.41 g, 3.05 mmol) instead of 3-chloro-2-fluoroaniline resulting in a white powder. Method B: Rt: 0.91 min m/z: 363.2 (M–H)⁻ Exact mass: 364.10. ¹H NMR (400 MHz, DMSO-d₆) δ ppm 1.02 (d, J=6.6 Hz, 6H), 3.18-3.29 (m, 1H), 3.92 (s, 3H), 7.22 (d, J=5.5 Hz, 1H), 7.34 (d, J=2.0 Hz, 1H), 7.49-7.56 (m, 1H), 7.57 (d, J=1.8 Hz, 1H), 7.89-8.10 (m, 1H), 8.15-8.27 (m, 1H), 10.37 (br. s., 1H).

Compound 176: N-(3-Cyano-2-fluorophenyl)-1-methyl-4-[(1-methylethyl)sulfamoyl]-1H-pyrrole-2-carboxamide

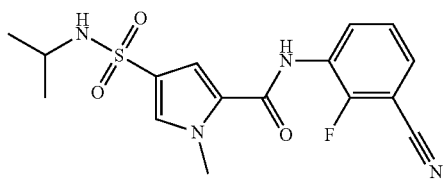 [SMILES: CC(C)NS(=O)(=O)c1cc(C(=O)Nc2cccc(C#N)c2F)n(C)c1]

Compound 176 (294 mg) was prepared similarly as described for compound 173 using 3-cyano-2-fluoroaniline (0.41 g, 3.05 mmol) instead of 3-chloro-2-fluoroaniline resulting in a white powder. Method B: Rt: 0.85 min m/z: 363.1 (M–H)⁻ Exact mass: 364.10. ¹H NMR (400 MHz, DMSO-d₆) δ ppm 1.03 (d, J=6.4 Hz, 6H), 3.18-3.30 (m, 1H), 3.79-3.97 (m, 3H), 7.22 (d, J=6.8 Hz, 1H), 7.34 (d, J=2.0 Hz, 1H), 7.37-7.48 (m, 1H), 7.57 (d, J=1.8 Hz, 1H), 7.71-7.81 (m, 1H), 7.83-7.98 (m, 1H), 10.25 (br. s., 1H).

Compound 177: N-(3-Cyanophenyl)-1-methyl-4-[(1-methylethyl)sulfamoyl]-1H-pyrrole-2-carboxamide

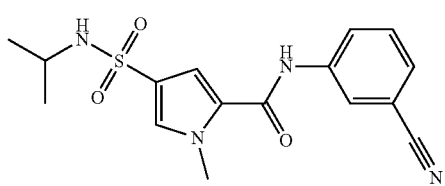 [SMILES: CC(C)NS(=O)(=O)c1cc(C(=O)Nc2cccc(C#N)c2)n(C)c1]

Compound 177 (629 mg) was prepared similarly as described for compound 173 using 3-aminobenzonitrile (0.36 g, 3.05 mmol) instead of 3-chloro-2-fluoroaniline resulting in a white powder. Method A: Rt: 1.49 min m/z: 345.1 (M–H)⁻ Exact mass: 346.11. ¹H NMR (400 MHz, DMSO-d₆) δ ppm 1.02 (d, J=6.6 Hz, 6H), 3.20-3.30 (m, 1H), 3.93 (s, 3H), 7.21 (br. s., 1H), 7.36 (d, J=1.8 Hz, 1H), 7.48-7.61 (m, 3H), 7.94-8.04 (m, 1H), 8.11-8.26 (m, 1H), 10.34 (br. s., 1H).

Compound 178: N-(3-Cyano-2,4-difluorophenyl)-1-methyl-4-[(1-methylethyl)sulfamoyl]-1H-pyrrole-2-carboxamide

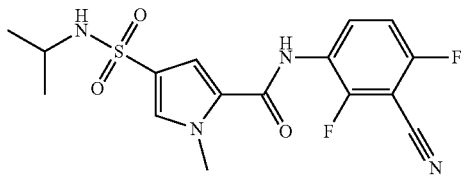 [SMILES: CC(C)NS(=O)(=O)c1cc(C(=O)Nc2ccc(F)c(C#N)c2F)n(C)c1]

Compound 178 (244 mg) was prepared similarly as described for compound 173 using 3-amino-2,6-difluorobenzonitrile (0.47 g, 3.05 mmol) instead of 3-chloro-2-fluoroaniline resulting in a white powder. Method B: Rt: 0.89 min m/z: 381.1 (M–H)⁻ Exact mass: 382.09. ¹H NMR (400 MHz, DMSO-d₆) δ ppm 1.03 (d, J=6.6 Hz, 6H), 3.20-3.29 (m, 1H), 3.90 (s, 3H), 7.22 (d, J=6.8 Hz, 1H), 7.32 (d, J=1.8 Hz, 1H), 7.45 (td, J=8.9, 1.5 Hz, 1H), 7.56 (d, J=1.8 Hz, 1H), 7.94 (td, J=8.9, 6.2 Hz, 1H), 10.25 (br. s., 1H).

Compound 179: N-[4-Fluoro-3-(trifluoromethyl)phenyl]-1,3-dimethyl-4-[(3-methyloxetan-3-yl)sulfamoyl]-1H-pyrrole-2-carboxamide

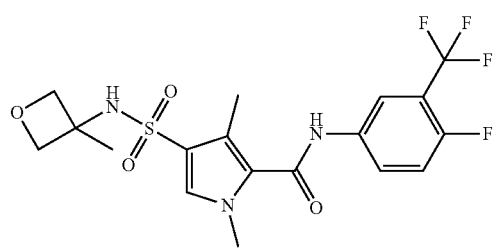 [SMILES: Cc1c(S(=O)(=O)NC2(C)COC2)cn(C)c1C(=O)Nc1ccc(F)c(C(F)(F)F)c1]

Compound 179 was prepared similarly as described for compound 144 using 3-methyl-3-oxetanamine (2.29 g, 26.3 mmol) instead of (R)-1,1,1-trifluoro-2-propylamine in Step 2 and, in step 4, 1,3-dimethyl-4-[(3-methyloxetan-3-yl)sulfamoyl]pyrrole-2-carboxylic acid (155 mg, 0.54 mmol), 4-fluoro-3-(trifluoromethyl)aniline (0.2 g, 1.08 mmol) and HATU (0.25 g, 0.65 mmol) were dissolved in DMF (0.72 mL) containing DIPEA (0.23 mL, 1.34 mmol). The reaction mixture was stirred at 40° C. for 42 hours and allowed to reach room temperature. The reaction mixture was purified using silica gel column chromatography (ethyl acetate in heptane from 10 to 70%). The desired fractions were combined and evaporated to afford light yellow oil. The yellow oil was purified using silica gel column chromatography (ethyl acetate in heptane from 40 to 70%) yielding compound 179 (93 mg) as white powder which was dried in vacuum oven at 50° C. Method B: Rt: 0.97 min m/z: 448.1 (M−H)⁻ Exact mass: 449.10. ¹H NMR (400 MHz, DMSO-d₆) δ ppm 1.54 (s, 3H), 2.34 (s, 3H), 3.73 (s, 3H), 4.13 (d, J=6.4 Hz, 2H), 4.63 (d, J=5.9 Hz, 2H), 7.48 (s, 1H), 7.52 (t, J=9.8 Hz, 1H), 7.89-8.00 (m, 2H), 8.20 (dd, J=6.6, 2.6 Hz, 1H), 10.42 (br. s., 1H).

Compound 180: N-(3-Cyanophenyl)-3-fluoro-1-methyl-4-{[(1R)-2,2,2-trifluoro-1-methylethyl]sulfamoyl}-1H-pyrrole-2-carboxamide

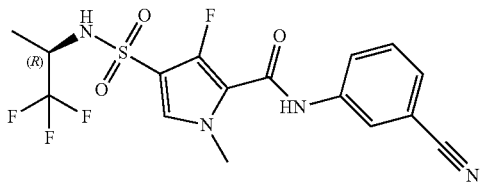

Compound 180 was prepared similarly as described for compound 170 using 3-amino-benzonitrile (138 mg, 1.16 mmol) instead of 5-amino-2-fluorobenzonitrile. The column fractions were concentrated and the residue was crystallized by dissolving in 10 mL warm methanol upon addition of water. The crystals were filtered off and dried overnight in vacuo at 50° C. resulting in a white powder (121 mg). Method A: Rt: 1.72 min m/z: 417.0 (M−H)⁻ Exact mass: 418.07. ¹H NMR (360 MHz, DMSO-d₆) δ ppm 1.18 (d, J=7.0 Hz, 3H), 3.81 (s, 3H), 3.91-4.05 (m, 1H), 7.54-7.61 (m, 3H), 7.89-7.96 (m, 1H), 8.14 (d, J=1.1 Hz, 1H), 8.64 (d, J=8.4 Hz, 1H), 10.40 (s, 1H).

Compound 181: N-(3-Cyano-2,4-difluorophenyl)-3-fluoro-1-methyl-4-{[(1R)-2,2,2-trifluoro-1-methylethyl]sulfamoyl}-1H-pyrrole-2-carboxamide

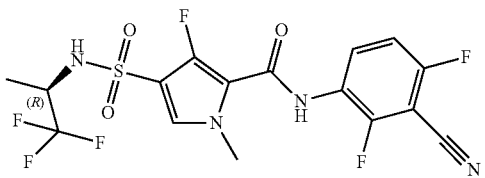

Compound 181 was prepared similarly as described for compound 180 using 3-amino-2,6-difluorobenzonitrile (143 mg, 0.928 mmol) instead of 3-aminobenzonitrile resulting in a white powder (79 mg). Method A: Rt: 1.77 min m/z: 453.0 (M−H)⁻ Exact mass: 454.05. ¹H NMR (360 MHz, DMSO-d₆) δ ppm 1.18 (d, J=7.0 Hz, 3H), 3.81 (s, 3H), 3.92-4.04 (m, 1H), 7.43-7.51 (m, 1H), 7.59 (d, J=4.4 Hz, 1H), 7.98-8.08 (m, 1H), 8.66 (d, J=8.8 Hz, 1H), 10.06 (s, 1H).

Compound 182: N-(3-Cyano-2-fluorophenyl)-3-fluoro-1-methyl-4-{[(1R)-2,2,2-trifluoro-1-methylethyl]sulfamoyl}-1H-pyrrole-2-carboxamide

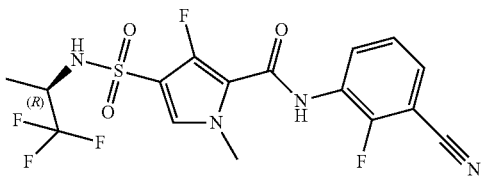

Compound 182 was prepared similarly as described for compound 180 using 3-amino-2-fluorobenzonitrile (127.5 mg, 0.936 mmol) instead of 3-aminobenzonitrile resulting in a white powder (66 mg). Method A: Rt: 1.78 min m/z: 435.1 (M−H)⁻ Exact mass: 436.06. ¹H NMR (360 MHz, DMSO-d₆) δ ppm 1.18 (d, J=7.0 Hz, 3H), 3.82 (s, 3H), 3.91-4.06 (m, 1H), 7.43 (t, J=7.7 Hz, 1H), 7.59 (d, J=4.4 Hz, 1H), 7.78 (ddd, J=7.8, 5.9, 1.6 Hz, 1H), 8.03 (td, J=8.0, 1.6 Hz, 1H), 8.66 (d, J=8.8 Hz, 1H), 10.06 (s, 1H).

Compound 183: 3-Fluoro-1-methyl-4-{[(1R)-2,2,2-trifluoro-1-methylethyl]sulfamoyl}-N-(2,3,4-trifluorophenyl)-1H-pyrrole-2-carboxamide

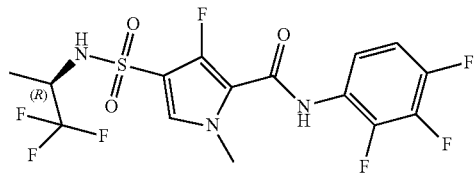

Compound 183 was prepared similarly as described for compound 180 using 2,3,4-trifluoroaniline (136.8 mg, 0.911 mmol) instead of 3-aminobenzonitrile resulting in a white powder (79 mg). Method A: Rt: 1.89 min m/z: 446.0 (M−H)⁻ Exact mass: 447.05. ¹H NMR (400 MHz, DMSO-d₆) δ ppm 1.19 (d, J=7.0 Hz, 3H), 3.81 (s, 3H), 3.91-4.04 (m, 1H), 7.29-7.39 (m, 1H), 7.42-7.50 (m, 1H), 7.56 (d, J=4.6 Hz, 1H), 8.61 (d, J=8.8 Hz, 1H), 9.93 (s, 1H).

Compound 184: N-(3-Bromo-2,4-difluorophenyl)-3-fluoro-1-methyl-4-{[(1R)-2,2,2-trifluoro-1-methylethyl]sulfamoyl}-1H-pyrrole-2-carboxamide

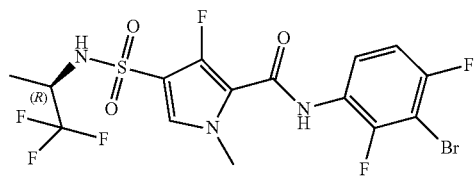

Compound 184 was prepared similarly as described for compound 180 using 3-bromo-2,4-difluoroaniline (194.9 mg, 0.937 mmol) instead of 3-aminobenzene resulting in a white powder (115 mg). Method A: Rt: 1.98 min m/z: 508.0 (M−H)⁻ Exact mass: 506.97. ¹H NMR (400 MHz, DMSO-d₆) δ ppm 1.19 (d, J=7.0 Hz, 3H), 3.81 (s, 3H), 3.90-4.04 (m, 1H), 7.27-7.35 (m, 1H), 7.56 (d, J=4.4 Hz, 1H), 7.64-7.73 (m, 1H), 8.61 (d, J=8.8 Hz, 1H), 9.86 (s, 1H).

Compound 185: N-(3-Chloro-2,4-difluorophenyl)-3-fluoro-1-methyl-4-{[(1R)-2,2,2-trifluoro-1-methylethyl]sulfamoyl}-1H-pyrrole-2-carboxamide

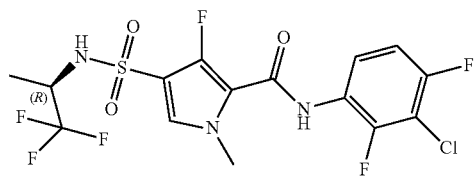

Compound 185 was prepared similarly as described for 180 using 3-chloro-2,4-difluoroaniline (150.9 mg, 0.923 mmol) instead of 3-aminobenzene resulting in a white powder (115 mg). Method A: Rt: 1.97 min m/z: 462.0 (M–H)⁻ Exact mass: 463.02. ¹H NMR (400 MHz, DMSO-d₆) δ ppm 1.19 (d, J=6.8 Hz, 3H), 3.81 (s, 3H), 3.92-4.04 (m, 1H), 7.35 (td, J=8.9, 2.0 Hz, 1H), 7.56 (d, J=4.6 Hz, 1H), 7.65 (td, J=8.7, 5.8 Hz, 1H), 8.61 (d, J=8.6 Hz, 1H), 9.88 (s, 1H).

Compound 186: N-(3-Cyano-4-fluorophenyl)-3-fluoro-1-methyl-4-{[(1R)-1-methyl-propyl]sulfamoyl}-1H-pyrrole-2-carboxamide

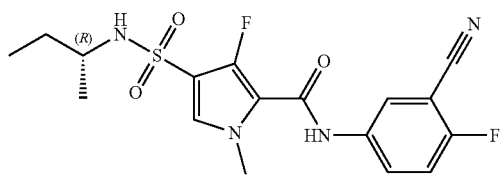

Intermediate ethyl 3-fluoro-1-methyl-4-[[(1R)-1-methyl-propyl]sulfamoyl]pyrrole-2-carboxylate was made similarly as described for compound 170 using 5-ethoxycarbonyl-4-fluoro-1-methyl-pyrrole-3-sulfonic acid (541.4 mg, 2.155 mmol), converting it to the corresponding sulphonylchloride with thionylchloride (heating at 80° C. during 90°) and reacting this with (R)-(–)-2-aminobutane (238.8 mg, 3.233 mmol) resulting in ethyl 3-fluoro-1-methyl-4-[[(1R)-1-methylpropyl]sulfamoyl]pyrrole-2-carboxylate (354 mg) as a white powder. ¹H NMR (400 MHz, DMSO-d₆) δ ppm 0.76 (t, J=7.4 Hz, 3H), 0.98 (d, J=6.6 Hz, 3H), 1.28 (t, J=7.0 Hz, 3H), 1.31-1.40 (m, 2H), 3.01-3.18 (m, 1H), 3.81 (s, 3H), 4.27 (q, J=7.2 Hz, 2H), 7.47-7.57 (m, 2H). To ethyl 3-fluoro-1-methyl-4-[[(1R)-1-methylpropyl]sulfamoyl]pyrrole-2-carboxylate (354 mg, 1.156 mmol) and 5-amino-2-fluoro-benzonitrile (201.7 mg, 1.483 mmol) in dry THF (20 mL) at 0° C., lithium bis(trimethylsilyl)amide in THF (4.62 mL, 4.62 mmol) was added. The mixture was stirred 1 hour at 0° C. The reaction mixture was quenched with NH₄Cl solution (30 mL) and extracted with EtOAc (50 mL), diluted with brine (50 mL) and extracted again with EtOAc (50 mL). The combine organic layers were dried over sodium sulphate, filtered and concentrated. The residue (dissolved in 1 mL DMF) was purified by column chromatography on silica using a gradient from 10 till 100% EtOAc in heptane. The product fractions were concentrated and the solid residue was crystallized from 50 mL warm methanol upon addition of water. The white crystals were filtered off and dried in vacuo at 50° C. overnight, resulting in compound 186 (306 mg) Method A: Rt: 1.83 min m/z: 395.1 (M–H)⁻ Exact mass: 396.11. ¹H NMR (400 MHz, DMSO-d₆) δ ppm 0.78 (t, J=7.4 Hz, 3H), 1.01 (d, J=6.6 Hz, 3H), 1.31-1.44 (m, 2H), 3.06-3.20 (m, 1H), 3.80 (s, 3H), 7.47 (d, J=4.6 Hz, 1H), 7.50-7.58 (m, 2H), 7.96 (ddd, J=9.2, 4.8, 2.9 Hz, 1H), 8.17 (dd, J=5.7, 2.6 Hz, 1H), 10.31 (s, 1H).

Compound 187: N-(3-Cyano-4-fluorophenyl)-4-[(3,3-difluoro-1-methylcyclobutyl)sulfamoyl]-3-fluoro-1-methyl-1H-pyrrole-2-carboxamide

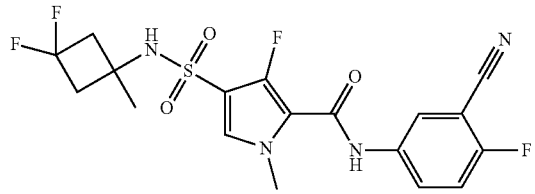 [SMILES: Cn1cc(S(=O)(=O)NC2(C)CC(F)(F)C2)c(F)c1C(=O)Nc1ccc(F)c(C#N)c1]

Compound 187 (290 mg) was prepared similarly as described for compound 186 using 3,3-difluoro-1-methyl-cyclobutanamine hydrochloride (509.4 mg, 3.232 mmol) instead of (R)-(–)-2-aminobutane resulting in a white powder. Method A: Rt: 1.84 min m/z: 443.1 (M–H)⁻ Exact mass: 444.09. ¹H NMR (400 MHz, DMSO-d₆) δ ppm 1.42 (s, 3H), 2.47-2.62 (m, 2H), 2.80-2.97 (m, 2H), 3.81 (s, 3H), 7.49-7.58 (m, 2H), 7.96 (ddd, J=9.2, 5.0, 2.8 Hz, 1H), 8.16 (dd, J=5.7, 2.6 Hz, 1H), 8.22 (s, 1H), 10.33 (s, 1H).

Compound 188: N-(3-Cyano-4-fluorophenyl)-3-fluoro-1-methyl-4-{[(1S)-2,2,2-trifluoro-1-methyl-ethyl]sulfamoyl}-1H-pyrrole-2-carboxamide

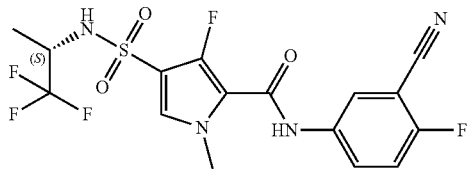

Compound 188 (409 mg) was prepared similarly as described for compound 186 using (2S)-1,1,1-trifluoropropan-2-amine instead of (R)-(–)-2-aminobutane resulting in a white powder. Method A: Rt: 1.89 min m/z: 435.0 (M–H)⁻ Exact mass: 436.06. ¹H NMR (400 MHz, DMSO-d₆) δ ppm 1.18 (d, J=7.0 Hz, 3H), 3.81 (s, 3H), 3.92-4.05 (m, 1H), 7.50-7.59 (m, 2H), 7.96 (ddd, J=9.2, 4.9, 2.9 Hz, 1H), 8.17 (dd, J=5.7, 2.6 Hz, 1H), 8.62 (d, J=8.8 Hz, 1H), 10.36 (s, 1H). Differential scanning calorimetry: peak at 190.92° C.

Compound 189: N-(3-Chloro-4,5-difluorophenyl)-1-methyl-4-{[1-(trifluoromethyl)-cyclobutyl]sulfamoyl}-1H-pyrrole-2-carboxamide

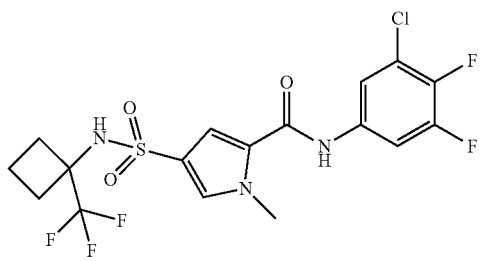 [SMILES: Cn1cc(S(=O)(=O)NC2(C(F)(F)F)CCC2)cc1C(=O)Nc1cc(F)c(F)c(Cl)c1]

5-[(3-chloro-4,5-difluoro-phenyl)carbamoyl]-1-methyl-pyrrole-3-sulfonyl chloride (470.2 mg, 0.966 mmol) 1-trifluoromethyl)cyclobutan-1-amine (268.7 mg, 1.932 mmol DIPEA (0.518 mL, 2.99 mmol) was dissolved in CH₃CN and refluxed over weekend. The reaction mixture was concentrated. The residue was dissolved in EtOAc (100 mL), washed with 1M HCl, dried over sodium sulphate, filtered and concentrated. The residue was purified by column chromatography on a silica using a gradient from 10 till 100% EtOAc in heptane. The product fractions were concentrated yielding a beige powder. This powder was repurified by Prep HPLC (Stationary phase: RP XBridge Prep C18 OBD-10 μm, 30×150 mm), Mobile phase: 0.25% NH₄HCO₃ solution in water, CH₃CN), yielding a white powder which was dried in vacuo at 50° C., resulting in compound 189 (32.9 mg). Method B: Rt: 1.18 min m/z: 470.0 (M–H)⁻ Exact mass: 471.04. ¹H NMR (400 MHz, DMSO-d₆) δ ppm 1.71-1.87 (m, 2H), 2.24-2.36 (m, 2H), 2.39-2.48 (m, 2H), 3.93 (s, 3H), 7.37 (d, J=2.0 Hz, 1H), 7.64 (d, J=1.8 Hz, 1H), 7.76-7.87 (m, 2H), 8.37 (s, 1H), 10.33 (s, 1H).

Compound 190: 4-(tert-Butylsulfamoyl)-N-(3-cyano-4-fluorophenyl)-1-methyl-1H-pyrrole-2-carboxamide

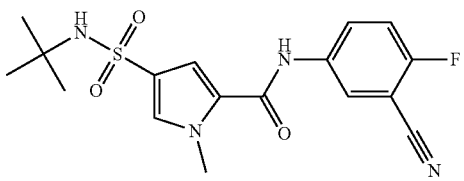 [SMILES: Cn1cc(S(=O)(=O)NC(C)(C)C)cc1C(=O)Nc1ccc(F)c(C#N)c1]

methyl 4-chlorosulfonyl-1-methyl-pyrrole-2-carboxylate (5 g, 1.04 mmol) was dissolved in acetonitrile (100 mL). To this was added diisopropylethylamine (9.06 mL, 52.6 mmol) followed by Tert-Butylamine (3.23 g, 44.2 mmol) and the resulting mixture was refluxed for 2 hours. Then the mixture was cooled to room temperature and concentrated in vacuo. The resulting residue was dissolved in dichloromethane (250 mL) and was washed with HCl (2×150 mL). The organics were dried on sodium sulphate, filtered and concentrated in vacuo yielding a powder of methyl 4-(tert-butylsulfamoyl)-1-methyl-pyrrole-2-carboxylate which was used as such (6.07 g) Method B: Rt: 1.52 min m/z: 273.0 (M–H)⁻ Exact mass: 274.10. ¹H NMR (360 MHz, DMSO-d₆) δ ppm 1.13 (s, 9H), 3.77 (s, 3H), 3.88 (s, 3H) 7.00 (d, J=1.8 Hz, 1H), 7.18 (s, 1H), 7.60 (d, J=2.2 Hz, 1H). methyl 4-(tert-butylsulfamoyl)-1-methyl-pyrrole-2-carboxylate (11.269 g, 41.077 mmol) was dissolved in THF (120 mL). To this was added lithium hydroxide (1.476 g, 1.5 eq) in distilled water (16 mL) and a turbid mixture was obtained. Then MeOH (6 mL) was added and the mixture became clear. The resulting mixture was stirred for 18 hours. Then it was concentrated until water remained and distilled water (30 mL) was added. The mixture was neutralized using an exact amount of hydrochloric acid (1M/aq/61.6 mL, 61.62 mmol). The resulting mixture was extracted using 2-methyltetrahydrofuran. The combined extracts were dried on MgSO₄, filtered and concentrated under reduced pressure resulting in 4-(tert-butylsulfamoyl)-1-methyl-pyrrole-2-carboxylic acid as a white powder which was used without further purifications for the next step (10.62 g). Method B: Rt: 0.83 min m/z: 258.9 (M–H)– Exact mass: 260.08. Compound 190 (2140 mg) was prepared similarly as described for compound 158 using 5-amino-2-fluorobenzonitrile (1348 mg, 9.604 mmol) and 4-(tert-butylsulfamoyl)-1-methyl-pyrrole-2-carboxylic acid and stirring at 50° C. instead of room temperature, resulting in a white solid. Method B: Rt: 0.96 min m/z: 377.1 (M–H)⁻ Exact mass: 378.12. ¹H NMR (400 MHz, DMSO-d₆) δ ppm 1.17 (s, 9H) 3.91 (s, 3H) 7.14 (s, 1H) 7.34 (d, J=1.76 Hz, 1H) 7.48-7.56 (m, 2H) 7.98-8.05 (m, 1H) 8.22 (dd, J=5.83, 2.75 Hz, 1H) 10.34 (s, 1H).

Compound 191: 4-(tert-Butylsulfamoyl)-N-(3-cyanophenyl)-1-methyl-1H-pyrrole-2-carboxamide

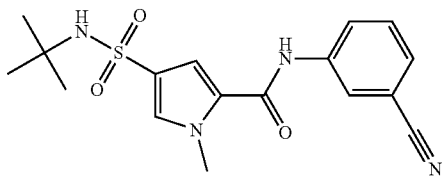 [SMILES: Cn1cc(S(=O)(=O)NC(C)(C)C)cc1C(=O)Nc1cccc(C#N)c1]

Compound 191 (758 mg) was prepared similarly as described for compound 190 using 3-aminobenzonitrile (458.4 mg, 3.84 mmol) instead of 5-amino-2-fluorobenzonitrile resulting in a white solid. Method B: Rt: 0.92 min m/z: 359.1 (M–H)⁻ Exact mass: 360.13. ¹H NMR (400 MHz, DMSO-d₆) δ ppm 1.18 (s, 9H) 3.92 (s, 3H) 7.13 (s, 1H) 7.36 (s, 1H) 7.51-7.59 (m, 3H) 7.99 (d, J=7.04 Hz, 1H) 8.19 (s, 1H) 10.31 (s, 1H).

Compound 192: 4-(tert-Butylsulfamoyl)-N-(3-cyano-2-fluorophenyl)-1-methyl-1H-pyrrole-2-carboxamide

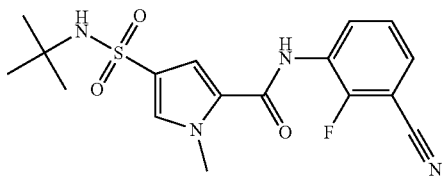 [SMILES: Cn1cc(S(=O)(=O)NC(C)(C)C)cc1C(=O)Nc1cccc(C#N)c1F]

Compound 192 (733 mg) was prepared similarly as described for compound 190 using 3-amino-2-fluorobenzonitrile (522.9 mg, 3.842 mmol) instead of 5-amino-2-fluorobenzonitrile resulting in a white solid. Method B: Rt: 0.90 min m/z: 377.1 (M–H)⁻ Exact mass: 378.12. ¹H NMR (400 MHz, DMSO-d₆) δ ppm 1.18 (s, 9H) 3.89 (s, 3H) 7.15 (s, 1H) 7.34 (d, J=2.0 Hz, 1H) 7.42 (t, J=7.9 Hz, 1H) 7.55 (d, J=1.76 Hz, 1H) 7.77 (ddd, J=7.7, 5.9, 1.8 Hz, 1H) 7.90 (td, J=7.90, 1.5 Hz, 1H) 10.23 (s, 1H).

Compound 193: 4-(tert-Butylsulfamoyl)-N-(3-chloro-2-fluorophenyl)-1-methyl-1H-pyrrole-2-carboxamide

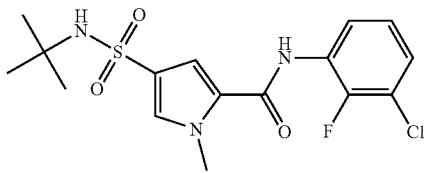 [SMILES: Cn1cc(S(=O)(=O)NC(C)(C)C)cc1C(=O)Nc1cccc(Cl)c1F]

Compound 193 (787 mg) was prepared similarly as described compound 190 using 3-chloro-2-fluoroaniline (0.435 mL, 3.84 mmol) resulting in a white solid. Method B: Rt: 1.02 min m/z: 386.1 (M−H)⁻ Exact mass: 387.08. ¹H NMR (400 MHz, DMSO-d₆) δ ppm 1.18 (s, 9H) 3.89 (s, 3H) 7.14 (s, 1H) 7.20-7.26 (m, 1H) 7.32 (d, J=1.76 Hz, 1H) 7.41-7.46 (m, 1H) 7.48-7.54 (m, 2H) 10.10 (s, 1H).

Compound 194: 4-(tert-Butylsulfamoyl)-N-(3-chloro-2,4-difluorophenyl)-1-methyl-1H-pyrrole-2-carboxamide

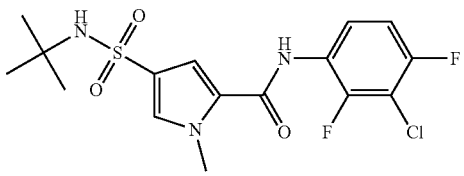 [SMILES: Cn1cc(S(=O)(=O)NC(C)(C)C)cc1C(=O)Nc1ccc(F)c(Cl)c1F]

Compound 194 (708 mg) was prepared similarly as described for compound 190 using 3-chloro-2,4-difluoroaniline (628.3, 3.84 mmol) resulting in a white solid. Method B: Rt: 1.03 min m/z: 404.1 (M−H)⁻ Exact mass: 405.07. ¹H NMR (400 MHz, DMSO-d₆) δ ppm 1.18 (s, 9H) 3.89 (s, 3H) 7.15 (s, 1H) 7.30-7.37 (m, 2H) 7.48-7.58 (m, 2H) 10.11 (s, 1H).

Compound 195: 4-(tert-Butylsulfamoyl)-N-(3-chloro-4-fluorophenyl)-1-methyl-1H-pyrrole-2-carboxamide

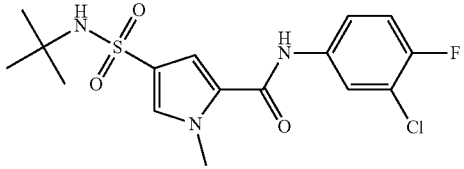 [SMILES: Cn1cc(S(=O)(=O)NC(C)(C)C)cc1C(=O)Nc1ccc(F)c(Cl)c1]

Compound 195 (705 mg) was prepared similarly as described for compound 190 using 3-chloro-4-fluoroaniline (559.2 mg, 3.842 mmol) resulting in a white solid. Method A: Rt: 1.95 min m/z: 386.0 (M−H)⁻ Exact mass: 387.08. ¹H NMR (400 MHz, DMSO-d₆) δ ppm 1.17 (s, 9H), 3.91 (s, 3H), 7.12 (s, 1H), 7.32 (d, J=2.0 Hz, 1H), 7.39 (t, J=9.1 Hz, 1H), 7.53 (d, J=1.8 Hz, 1H), 7.63-7.70 (m, 1H), 8.02 (dd, J=6.8, 2.6 Hz, 1H), 10.19 (s, 1H).

Compound 196: N-(3-Cyano-2,4-difluorophenyl)-1-methyl-4-{[(1S)-2,2,2-trifluoro-1-methylethyl]sulfamoyl}-1H-pyrrole-2-carboxamide

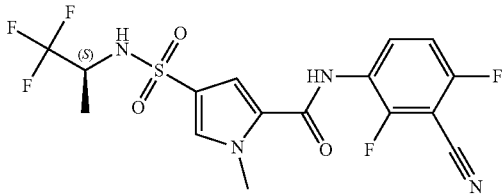

Methyl 1-methyl-4-[[(1S)-2,2,2-trifluoro-1-methyl-ethyl]sulfamoyl]pyrrole-2-carboxylate (0.7 g, 2.23 mmol) was dissolved in THF (10 mL) under nitrogen. To this was added 3-amino-2,6-difluorobenzonitrile (0.45 g, 2.9 mmol) and the mixture was cooled in an ice-water bath while stirred under nitrogen. To this was added drop wise lithium bis(trimethylsilyl)amide 1M in toluene (6.68 mL, 6.68 mmol) over a period of 10 minutes. The resulting mixture was stirred for 1 hour while cooling was continued. The mixture was quenched with saturated ammonium chloride (25 mL) and the resulting mixture was extracted using EtOAc (3×25 mL). The combined extracts were washed with brine (20 mL), dried on Na₂SO₄, filtered and concentrated in vacuo. The obtained residue was dissolved in 2 mL dichloromethane and this was loaded on a dry silica plug. This was purified by column chromatography using gradient elution from heptane to EtOAc. (100:0 to 0:100). The desired fractions were collected and concentrated in vacuo yielding a powder. This powder was recrystallized out of MeOH/water. The obtained crystals were collected on a filter, rinsed with water followed by diisopropylether and dried in a vacuo at 55° C. for 24 hours resulting in N-(3-Cyano-2,4-difluorophenyl)-1-methyl-4-{[(1S)-2,2,2-trifluoro-1-methylethyl]sulfamoyl}-1H-pyrrole-2-carboxamide (563 mg) as a powder. Method A: Rt: 1.75 min m/z: 435.0 (M−H)⁻ Exact mass: 436.06. ¹H NMR (400 MHz, DMSO-d₆) δ ppm 1.09 (d, J=6.8 Hz, 3H), 3.80-4.06 (m, 4H), 7.36 (d, J=2.0 Hz, 1H), 7.40-7.51 (m, 1H), 7.66 (d, J=1.5 Hz, 1H), 7.85-8.02 (m, 1H), 8.54 (br. s, 1H), 10.14 (br. s, 1H).

Compound 197: N-(3-Cyanophenyl)-1-methyl-4-{[(1S)-2,2,2-trifluoro-1-methylethyl]-sulfamoyl}-1H-pyrrole-2-carboxamide

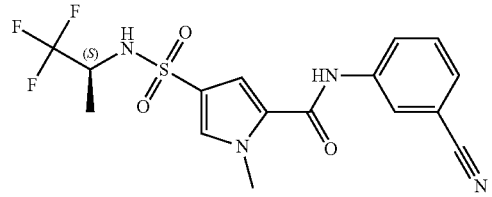

Compound 197 (697.6 mg) was prepared similarly as described for compound 196 using 3-aminobenzonitrile (342 mg, 2.895 mmol) instead of 3-amino-2,6-difluorobenzonitrile resulting in N-(3-cyanophenyl)-1-methyl-4-[[(1S)-2,2,2-trifluoro-1-methyl-ethyl]sulfamoyl]pyrrole-2-carboxamide as a solid. Method B: Rt: 0.93 min m/z: 399.1 (M−H)⁻ Exact mass: 400.08. ¹H NMR (400 MHz, DMSO-d₆) δ ppm 1.08 (d, J=6.8 Hz, 3H) 3.93 (s, 4H) 7.39 (d, J=1.9 Hz, 1H) 7.52-7.60 (m, 2H) 7.65 (d, J=1.9 Hz, 1H) 7.99 (dt, J=6.9, 2.3 Hz, 1H) 8.20 (br. s, 1H) 8.17-8.20 (m, 1H) 10.35 (br. s., 1H).

Compound 198: N-(3-Cyano-2-fluorophenyl)-1-methyl-4-{[(1S)-2,2,2-trifluoro-1-methylethyl]sulfamoyl}-1H-pyrrole-2-carboxamide

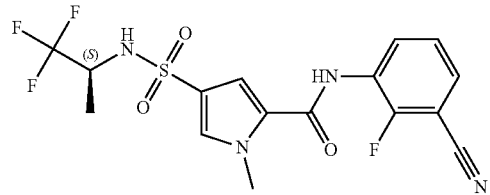

Compound 198 (691 mg) was prepared similarly as described for compound 196 using 3-amino-2-fluoro-benzonitrile (394 mg, 2.895 mmol) instead of 3-amino-2,6-difluorobenzonitrile resulting in as a solid. Method B: Rt: 0.91 min m/z: 417.1 (M−H)⁻ Exact mass: 418.07. ¹H NMR (400 MHz, DMSO-d₆) δ ppm 1.03-1.18 (m, 3H), 3.84-4.03 (m, 4H), 7.38 (d, J=2.0 Hz, 1H), 7.42 (t, J=7.9 Hz, 1H), 7.66 (d, J=1.8 Hz, 1H), 7.77 (ddd, J=7.6, 6.0, 1.5 Hz, 1H), 7.91 (td, J=7.8, 1.5 Hz, 1H), 7.99-9.14 (m, 1H), 10.26 (br. s., 1H).

Compound 199: 3-Chloro-N-(3-cyano-4-fluorophenyl)-1-methyl-4-{[(1R)-2,2,2-trifluoro-1-methylethyl]sulfamoyl}-1H-pyrrole-2-carboxamide

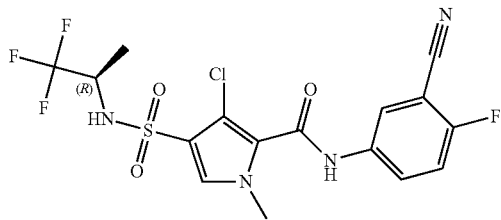

Sodium hydride (3.46 g, 90.2 mmol, 60% dispersion in oil) was added portion wise, over a period of 10 minutes, to a solution of methyl 3-chloro-1H-pyrrole-2-carboxylate (12 g, 75.2 mmol), iodomethane (12.8 g, 90.2 mmol) and DMF (120 mL) at 0° C. under nitrogen in an ice bath. The ice bath was removed and the reaction mixture was stirred 3 hours at room temperature. The reaction mixture was acidified with aqueous hydrochloric acid (15.04 mL, 1 M) and concentrated. The residue was dissolved in water (100 mL)/ethyl acetate (300 mL). The organic layer was dried over Na₂SO₄, filtered and concentrated. The residue was dissolved in acetonitrile (150 mL), washed with heptane (100 mL) and concentrated at 70° C. yielding methyl 3-chloro-1-methyl-pyrrole-2-carboxylate (12.0 g) as yellow liquid which was used as such. ¹H NMR (400 MHz, CHLOROFORM-d) δ ppm 3.87 (s, 3H), 3.88 (s, 3H), 6.13 (d, J=2.9 Hz, 1H), 6.69 (d, J=2.9 Hz, 1H) Methyl 3-chloro-1-methyl-pyrrole-2-carboxylate (5.0 g, 25.1 mmol) was added drop wise to chlorosulfonic acid (11 mL) at 0° C. under nitrogen atmosphere. The reaction mixture was warmed to room temperature and allowed to stir 2 hours. The resulting mixture was added drop wise to a stirred, temperature controlled ice-water mixture (200 mL) keeping the temperature under 5° C. A white precipitation was formed. The obtained aqueous suspension was extracted using dichloromethane (3×100 mL). The combined organic extracts were washed with Brine and dried on sodium sulphate, filtered and concentrated in vacuo yielding methyl 3-chloro-4-chlorosulfonyl-1-methyl-pyrrole-2-carboxylate (5.56 g) as light green powder which was used as such. ¹H NMR (400 MHz, CHLOROFORM-d) δ ppm 3.94 (s, 3H), 3.98 (s, 3H), 7.46 (s, 1H). In a microwave tube methyl 3-chloro-4-chlorosulfonyl-1-methyl-pyrrole-2-carboxylate (1.5 g, 5.51 mmol) was dissolved in acetonitrile (10 mL). To this was added DIPEA (1.42 mL, 0.75 g/mL, 8.27 mmol) followed by (R)-1,1,1-trifluoro-2-propylamine (0.94 g, 8.27 mmol) and molecular sieves and the tube was closed and resulting mixture was heated at 80° C. 30 minutes under microwave irradiation. The reaction mixture was concentrated and the resulting brown sticky oil was dissolved in dichloromethane (50 mL) and this was washed with HCl (1N, 2×10 mL) and Brine (5 mL) and dried on sodium sulphate. The solids were filtered off and the filtrate was concentrated in vacuo yielding brown oil. The brown oil was purified using silica gel column chromatography (ethyl acetate in heptane from 0 to 100%) to afford methyl 3-chloro-1-methyl-4-[[(1R)-2,2,2-trifluoro-1-methyl-ethyl]sulfamoyl]pyrrole-2-carboxylate (660 mg) as white powder which was used as such. Method B: Rt: 0.88 min m/z: 347 (M−H)⁻ Exact mass: 348.02. ¹H NMR (400 MHz, DMSO-d₆) δ ppm 1.15 (d, J=7.0 Hz, 3H), 3.83 (s, 3H), 3.86 (s, 3H), 3.89-4.02 (m, 1H), 7.76 (s, 1H), 8.51 (d, J=8.8 Hz, 1H). Methyl 3-chloro-1-methyl-4-[[(1R)-2,2,2-trifluoro-1-methyl-ethyl]sulfamoyl]pyrrole-2-carboxylate (660 mg, 1.89 mmol) and 5-amino-2-fluorobenzonitrile (332 mg, 2.37 mmol) were dissolved in dry tetrahydrofuran (30 mL) under nitrogen. The reaction mixture was cooled to 0° C. and lithium bis(trimethylsilyl)amide in tetrahydrofuran (5.46 mL, 5.46 mmol, 1M) was added over a period of 2 minutes. The resulting mixture was stirred for 2 minutes while cooling was continued. The mixture was quenched with saturated aqueous ammonium chloride (15 mL) and the resulting mixture was extracted using ethyl acetate (3×30 mL). The combined extracts were washed with Brine (10 mL), dried on Na₂SO₄, filtered and concentrated in vacuo to afford a red powder. The obtained residue was triturated in a refluxing mixture of CH₂Cl₂/EtOAc/methanol (10/5/5 mL). The solids were filtered to afford a dark pink powder which was recrystallized from methanol/water (7/0.5 mL) to afford compound 199 as a powder (325 mg) Method B: Rt: 0.99 min m/z: 451.0 (M−H)⁻ Exact mass: 452.03. ¹H NMR (400 MHz, DMSO-d₆) δ ppm 1.19 (d, J=6.8 Hz, 3H), 3.78 (s, 3H), 3.91-4.05 (m, 1H), 7.56 (t, J=9.1 Hz, 1H), 7.69 (s, 1H), 7.98 (ddd, J=9.2, 4.8, 2.8 Hz, 1H), 8.19 (dd, J=5.8, 2.8 Hz, 1H), 8.51 (d, J=8.8 Hz, 1H), 10.68 (s, 1H). Differential scanning calorimetry: From 30 to 300° C. at 10° C./min: peak at 190.1° C.

Alternative Procedure for the Synthesis of methyl 3-chloro-1-methyl-4-[[(1R)-2,2,2-trifluoro-1-methylethyl]sulfamoyl]pyrrole-2-carboxylate Methyl 3-chloro-4-chlorosulfonyl-1-methyl-pyrrole-2-carboxylate (1 g, 3.68 mmol) was dissolved in hot acetonitrile (5 mL), molecular sieves (about 100 mg) were added and the reaction mixture was stirred. In a separate vessel (R)-1,1,1-trifluoro-2-propylamine (623 mg, 5.51 mmol) was dissolved in acetonitrile (5 mL), molecular sieves (about 100 mg) was added. This suspension was added to the reaction mixture and then NaHCO₃ (926 mg, 11.0 mmol) was added. The vessel was closed and it was stirred overnight at 80° C. The volatiles were removed under reduced pressure and the obtained residue was purified by silica gel chromatography, using a gradient from heptane to EtOAc, yielding methyl 3-chloro-1-methyl-4-[[(1R)-2,2,2-trifluoro-1-methyl-ethyl]sulfamoyl]pyrrole-2-carboxylate (1.04 g) as a white powder.

Compound 200: N-(3-Cyano-4-fluorophenyl)-4-{[2,2-difluoro-1-methylethyl]sulfamoyl}-1-methyl-1H-pyrrole-2-carboxamide

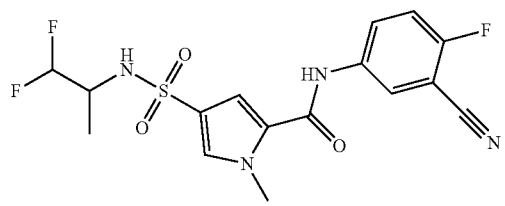 [SMILES: CC(NS(=O)(=O)c1cc(C(=O)Nc2ccc(F)c(C#N)c2)n(C)c1)C(F)F]

5-amino-2-fluoro-benzonitrile (5.62 g, 41.3 mmol) was added to a solution of 4-chlorosulfonyl-1-methyl-pyrrole-2-carbonyl chloride (described in the synthesis of compound 3) (10 g, 41.3 mmol), toluene (300 mL) at reflux. The reaction mixture was refluxed 4 hours and filtered warm. The filtrate was concentrated to dryness to afford a yellow powder which was dried over weekend in vacuo. The yellow powder was triturated in warm ethyl acetate (50 mL) and filtered and washed with dichloromethane. The filtrate was concentrated to dryness and the residue was purified using silica gel column chromatography (ethyl acetate in heptane from 0 to 100%) to afford 5-[(3-cyano-4-fluoro-phenyl)carbamoyl]-1-methyl-pyrrole-3-sulfonyl chloride (5.05 g) as off white powder. 5-[(3-cyano-4-fluoro-phenyl)carbamoyl]-1-methyl-pyrrole-3-sulfonyl chloride (1.00 g, 2.93 mmol) was dissolved in a solution of 1,1-difluoropropan-2-amine (417 mg, 4.39 mmol, synthesized according of PCT Int. Appl., 2012049277) in THF (17 mL) dried on molecular sieves and stirred at 60° C. for 20 hours. The reaction mixture was filtered and the filtrate was evaporated to dryness. The residue was purified using silica gel column chromatography (ethyl acetate in heptane from 10 to 70%) to afford crude compound 200 as white powder. Compound 200 was purified by Prep SFC (Stationary phase: Chiralpak Diacel AD 20×250 mm), Mobile phase: $CO_2$, methanol with 0.2% $iPrNH_2$), the desired fractions were collected, evaporated, solved in methanol and evaporated again, yielding compound 200 a (192 mg) as white powder. Method A: Rt: 1.67 min m/z: 399.1 (M–H)⁻ Exact mass: 400.08 $^1$H NMR (400 MHz, DMSO-$d_6$) δ ppm 0.99 (d, J=7.0 Hz, 3H), 3.42-3.56 (m, 1H), 3.93 (s, 3H), 5.90 (td, J=56.1, 2.6 Hz, 1H), 7.36 (d, J=2.0 Hz, 1H), 7.53 (t, J=9.2 Hz, 1H), 7.64 (d, J=1.8 Hz, 1H), 7.83 (br. s., 1H), 8.01 (ddd, J=9.2, 4.8, 2.6 Hz, 1H), 8.21 (dd, J=5.7, 2.6 Hz, 1H), 10.37 (s, 1H). And compound 200b (190 mg) as white powder. Method A: Rt: 1.67 min m/z: 399.0 (M–H)⁻ Exact mass: 400.08. $^1$H NMR (400 MHz, DMSO-$d_6$) δ ppm 0.99 (d, J=7.0 Hz, 3H), 3.42-3.57 (m, 1H), 3.93 (s, 3H), 5.90 (td, J=56.1, 2.6 Hz, 1H), 7.36 (d, J=1.8 Hz, 1H), 7.53 (t, J=9.1 Hz, 1H), 7.64 (d, J=1.8 Hz, 1H), 7.77 (br. s., 1H), 8.01 (ddd, J=9.2, 4.9, 2.9 Hz, 1H), 8.21 (dd, J=5.9, 2.6 Hz, 1H), 10.37 (br. s., 1H).

Compound 201: N-(3-Chloro-4,5-difluorophenyl)-1,3-dimethyl-4-[(3-methyloxetan-3-yl)sulfamoyl]-1H-pyrrole-2-carboxamide

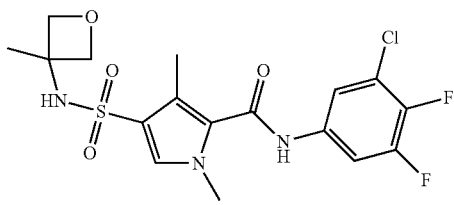 [SMILES: Cc1c(S(=O)(=O)NC2(C)COC2)cn(C)c1C(=O)Nc1cc(F)c(F)c(Cl)c1]

Compound 201 (69 mg) as white powder was prepared similarly as described for compound 179 using 3-chloro-4,5-difluoro-aniline (0.18 g, 1.08 mmol) instead of 4-fluoro-3-(trifluoromethyl)aniline. The reaction was stirred at 50° C. for 92 hours. Method B: Rt: 0.98 min m/z: 432.1 (M–H)⁻ Exact mass: 433.07. $^1$H NMR (400 MHz, DMSO-$d_6$) δ ppm 1.53 (s, 3H), 2.32 (s, 3H), 3.72 (s, 3H), 4.12 (d, J=6.4 Hz, 2H), 4.61 (d, J=5.9 Hz, 2H), 7.49 (s, 1H), 7.71-7.81 (m, 2H), 7.93 (br. s., 1H), 10.40 (br. s., 1H).

Compound 243: N-(3-Chloro-2,4-difluorophenyl)-1,3-dimethyl-4-[(3-methyloxetan-3-yl)sulfamoyl]-1H-pyrrole-2-carboxamide

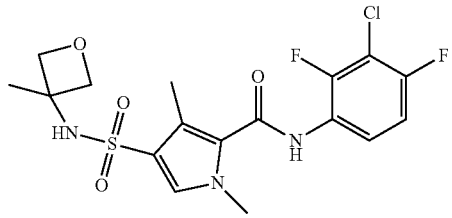 [SMILES: Cc1c(S(=O)(=O)NC2(C)COC2)cn(C)c1C(=O)Nc1ccc(F)c(Cl)c1F]

1,3-dimethyl-4-(N-(3-methyloxetan-3-yl)sulfamoyl)-1H-pyrrole-2-carboxylic acid (500 mg, 1.73 mmol), 3-chloro-2,4-difluoroaniline (0.57 g, 3.47 mmol) and HATU (0.88 g, 2.31 mmol) were dissolved in DMF (2 mL) containing DIPEA (0.69 mL, 3.98 mmol). The reaction mixture was stirred at 65° C. for 28 hours and at room temperature for 60 hours. The reaction mixture was purified using silica gel column chromatography (ethyl acetate in heptane from 10 to 70%). The desired fractions were combined and evaporated to afford a light brown oil which solidified while standing. The solid was recrystallized from ethanol (5 mL) to afford a white solid which was filtered and washed with ethanol (1 mL). The white solid was dried overnight in vacuo, resulting in compound 243 (318 mg) as off white solid. Method D: Rt: 1.73 min m/z: 432.0 (M–H)⁻ Exact mass: 433.1. $^1$H NMR (400 MHz, DMSO-$d_6$) δ ppm 1.52 (s, 3H), 2.37 (s, 3H), 3.73 (s, 3H), 4.11 (d, J=6.4 Hz, 2H), 4.61 (d, J=5.9 Hz, 2H), 7.35 (td, J=9.0, 2.0 Hz, 1H), 7.47 (s, 1H), 7.67 (td, J=8.7, 5.8 Hz, 1H), 7.91 (br. s., 1H), 10.03 (br. s., 1H).

Compound 202: N-(3-Chloro-4,5-difluorophenyl)-1,3-dimethyl-4-{[(1R)-2,2,2-trifluoro-1-methylethyl]sulfamoyl}-1H-pyrrole-2-carboxamide

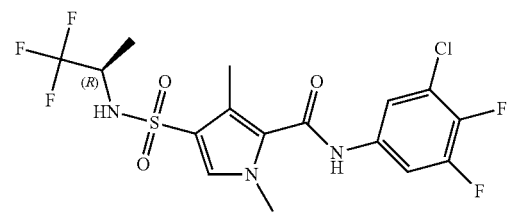

Compound 202 was prepared similarly as described for compound 144. In Step 4, 1,3-dimethyl-4-[[(1R)-2,2,2-trifluoro-1-methyl-ethyl]sulfamoyl]pyrrole-2-carboxylic acid (260 mg, 0.83 mmol) was used and 3-chloro-4,5-difluoro-aniline (0.27 g, 1.65 mmol) instead of 3,4-difluoroaniline was used. This reaction was performed at 50° C. for 92 hours. The desired fractions were combined and evaporated to afford a powder which was recrystallized from $CH_2Cl_2$. The white crystals were filtered and washed with $CH_2Cl_2$ and dried overnight in vacuum oven at 50° C. to afford a white solid (170 mg). Method B: Rt: 1.12 min m/z: 458.0 (M–H)⁻ Exact mass: 459.04. $^1$H NMR (400 MHz, DMSO-$d_6$) δ ppm 1.11 (d, J=6.8 Hz, 3H), 2.30 (s, 3H), 3.72 (s, 3H), 3.78-3.90 (m, 1H), 7.53 (s, 1H), 7.66-7.84 (m, 2H), 8.18 (br. s., 1H), 10.39 (s, 1H).

Compound 203: N-(2,3-Difluorophenyl)-1-methyl-4-{[(1R)-2,2,2-trifluoro-1-methyl-ethyl]sulfamoyl}-1H-pyrrole-2-carboxamide

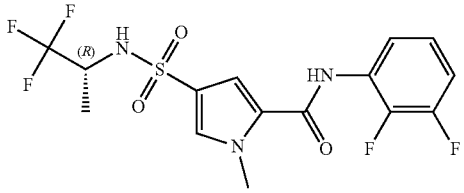

Into a 100 mL round bottom flask equipped with a magnetic stir bar was placed methyl 1-methyl-4-[[(1R)-2,2,2-trifluoro-1-methyl-ethyl]sulfamoyl]pyrrole-2-carboxylate (0.9 g, 2.86 mmol), anhydrous THF (40 mL), and 2,3-difluoroaniline (490 mg, 3.72 mmol). The vial was sealed and placed into an ice-water bath and to it was added LHMDS (8.6 mL of a 1M solution in THF/ethylbenzene) slowly via syringe (approx rate of 2 mL/min). Conversion to product seen after 30 min at 0° C. Sat. aq. ammonium chloride was added to quench the reaction. This was diluted with ethyl acetate (100 mL) and the mixture partitioned with ethyl acetate (3×100 mL). The organic layers were combined, dried (magnesium sulfate), the solids were removed by filtration and the solvents of the filtrate were removed under reduced pressure. The crude was partially purified via silica column chromatography using a heptane to ethylacetate gradient. The solvent of the best fractions were removed under reduced pressure and the compound was recrystallized from ether/heptane to afford compound 203 as a white solid (395 mg). Method A: Rt: 1.75 min m/z: 410.1 (M−H)⁻ Exact mass: 411.07. ¹H NMR (400 MHz, DMSO-d₆) δ ppm 1.10 (d, J=7.0 Hz, 3H), 3.85-4.00 (m, 1H), 3.91 (s, 3H), 7.16-7.40 (m, 4H), 7.65 (d, J=1.8 Hz, 1H), 8.17 (d, J=7.7 Hz, 1H), 10.15 (s, 1H). Differential scanning calorimetry: From 30 to 300° C. at 10° C./min: peak at 157.94° C.

Compound 204: N-(3-Chloro-2,6-difluorophenyl)-1-methyl-4-{[(1R)-2,2,2-trifluoro-1-methylethyl]sulfamoyl}-1H-pyrrole-2-carboxamide

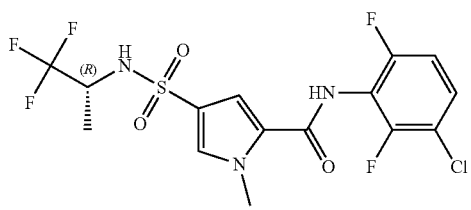

Compound 204 was prepared similarly as described for compound 203 using 3-chloro-2,6-difluoro-aniline (627.7 mg, 3.72 mmol) and the crude was recrystallized in diisopropyl ether/heptane to afford a white solid (423 mg) Method A: Rt: 1.79 min m/z: 444.0 (M−H)− Exact mass: 445.03. ¹H NMR (400 MHz, DMSO-d₆) δ ppm 1.12 (d, J=6.8 Hz, 3H), 3.84-4.01 (m, 1H), 3.91 (s, 3H), 7.31 (t, J=8.8 Hz, 1H), 7.41 (s, 1H), 7.57-7.66 (m, 1H), 7.69 (s, 1H), 8.21 (d, J=8.1 Hz, 1H), 10.17 (s, 1H).

Compound 205: N-(3-Bromo-4,5-difluorophenyl)-1-methyl-4-{[(1R)-2,2,2-trifluoro-1-methylethyl]sulfamoyl}-1H-pyrrole-2-carboxamide

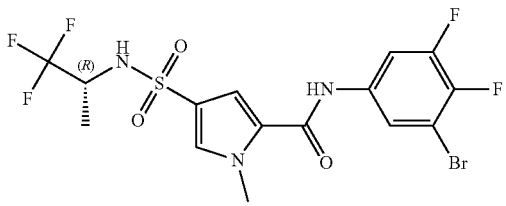

Compound 205 (893 mg) was prepared similarly as described for compound 158 using 3-bromo-4,5-difluoroaniline (970 mg, 4.663 mmol) instead of 3-aminobenzonitrile and stirring at 60° C. during 18 h. The obtained residue was warmed with CH₂Cl₂/heptanes and the white solid collected by filtration. Method A: Rt: 1.79 min m/z: 489.9 (M−H)− Exact mass: 488.98. ¹H NMR (400 MHz, DMSO-d₆) δ ppm 1.08 (d, J=7.0 Hz, 3H), 3.84-3.99 (m, 1H), 3.92 (s, 3H), 7.36 (d, J=1.8 Hz, 1H), 7.67 (d, J=1.5 Hz, 1H), 7.80-7.93 (m, 2H), 8.19 (br. s., 1H), 10.30 (s, 1H). Differential scanning calorimetry: From 30 to 300° C. at 10° C./min: peak at 196.72° C.

Compound 206: N-(3-Bromo-2-fluorophenyl)-1-methyl-4-{[(1R)-2,2,2-trifluoro-1-methylethyl]sulfamoyl}-1H-pyrrole-2-carboxamide

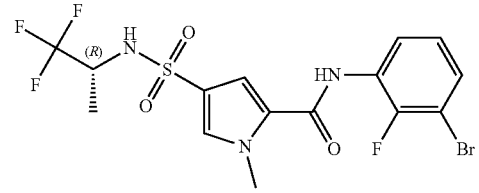

Compound 206 (637 mg) was prepared similarly as described for compound 158 using 3-bromo-2-fluoroaniline (886 mg, 4.663 mmol) instead of 3-aminobenzonitrile and stirring at 60° C. during 18 h. The residue was warmed with heptane, 1 drop EtOAc added precipitation occurs. A white solid was filtered off and dried in vacuo. Method A: Rt: 1.88 min m/z: 470.0 (M−H)⁻ Exact mass: 470.99. ¹H NMR (400 MHz, DMSO-d₆) δ ppm 1.09 (d, J=6.8 Hz, 3H), 3.85-4.00 (m, 1H), 3.90 (s, 3H), 7.18 (td, J=8.0, 1.3 Hz, 1H), 7.36 (d, J=2.0 Hz, 1H), 7.50-7.60 (m, 2H), 7.65 (d, J=1.8 Hz, 1H), 8.17 (br. s., 1H), 10.11 (br. s., 1H) Differential scanning calorimetry: From 30 to 300° C. at 10° C./min: peak at 216.73° C.

Compound 207: N-(3-chloro-4,5-difluoro-phenyl)-4-[(2-fluoro-1,1-dimethyl-ethyl)sulfamoyl]-1-methyl-pyrrole-2-carboxamide

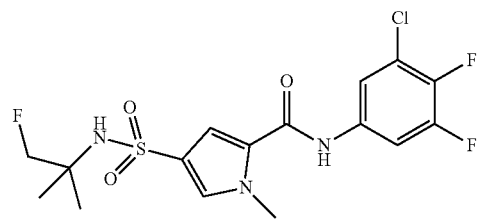 [SMILES: Cn1cc(S(=O)(=O)NC(C)(C)CF)cc1C(=O)Nc1cc(F)c(F)c(Cl)c1]

5-[(3-chloro-4,5-difluoro-phenyl)carbamoyl]-1-methyl-pyrrole-3-sulfonyl chloride (212.7 mg, 0.437 mmol) [112433-52-0], 1-fluoro-2-methyl-propan-2-amine hydrochloride (69.7 mg, 0.546 mmol) and Et₃N (0.152 mL, 1.09 mmol) was dissolved in CH₃CN (35.4 mL, 678.73 mmol) stirred overnight and concentrated. The residue was dissolved in DMF (2 mL) and purified by column chromatography on silica using a gradient from 10 till 100% EtOAc in heptane. The product fractions were concentrated. The residue was crystallized from methanol (10 mL) upon addition of water. The white crystals of were filtered off and dried overnight in vacuo at 50° C., resulting in compound 207 (93 mg). Method A: Rt: 2.02 min m/z: 422.0 (M−H)⁻ Exact mass: 423.06. ¹H NMR (400 MHz, DMSO-d₆) δ ppm 1.17 (d, J=1.8 Hz, 6H), 3.91 (s, 3H), 4.23 (d, J=1.0 Hz, 2H), 7.34 (d, J=2.0 Hz, 1H), 7.42 (s, 1H), 7.58 (d, J=1.8 Hz, 1H), 7.76-7.86 (m, 2H), 10.29 (s, 1H).

Compound 208: N-(3-Chloro-2,4-difluorophenyl)-1,3-dimethyl-4-[(1-methylethyl)sulfamoyl]-1H-pyrrole-2-carboxamide

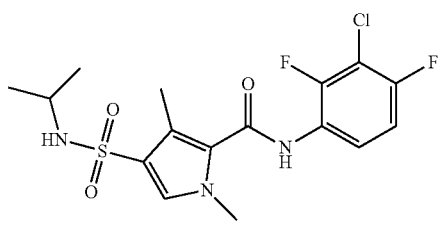 [SMILES: Cc1c(S(=O)(=O)NC(C)C)cn(C)c1C(=O)Nc1ccc(F)c(Cl)c1F]

Compound 208 was prepared from ethyl 4-[tert-butoxycarbonyl(isopropyl)sulfamoyl]-1,3-dimethyl-pyrrole-2-carboxylate and 3-chloro-2,4-difluoroaniline using LiHMDS in THF, followed by removal of the Boc-protection by treatment with HCl in iPrOH/CH₂Cl₂, resulting in compound 208 (266 mg). Method B: Rt: 1.02 min m/z: 404.1 (M−H)⁻ Exact mass: 405.1. ¹H NMR (400 MHz, DMSO-d₆) δ ppm 1.02 (d, J=6.6 Hz, 6H), 2.34 (s, 3H), 3.14-3.25 (m, 1H), 3.73 (s, 3H), 7.20 (d, J=7.5 Hz, 1H), 7.35 (td, J=9.0, 2.1 Hz, 1H), 7.44 (s, 1H), 7.66 (td, J=8.7, 5.8 Hz, 1H), 9.99 (s, 1H).

Compound 209: N-(3-Chloro-2,4-difluorophenyl)-1,3-dimethyl-4-{[(1S)-2,2,2-trifluoro-1-methylethyl]sulfamoyl}-1H-pyrrole-2-carboxamide

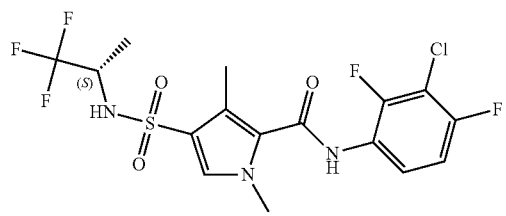

Compound 209 was prepared similarly as described for compound 146, using 3-chloro-2,4-difluoroaniline instead of 3,4-difluoroaniline. Compound 209 was recrystallized from EtOH, resulting in a white powder (211 mg). Method D: Rt: 1.97 min m/z: 458.0 (M−H)⁻ Exact mass: 459.0. ¹H NMR (400 MHz, DMSO-d₆) δ ppm 1.11 (d, J=6.8 Hz, 3H), 2.35 (s, 3H), 3.73 (s, 3H), 3.76-3.90 (m, 1H), 7.36 (td, J=9.0, 2.0 Hz, 1H), 7.52 (s, 1H), 7.66 (td, J=8.7, 5.8 Hz, 1H), 8.16 (br. d, J=7.3 Hz, 1H), 10.02 (s, 1H).

Compound 210: N-(3-Chloro-2,4-difluorophenyl)-1,3-dimethyl-4-{[(1R)-2,2,2-trifluoro-1-methylethyl]sulfamoyl}-1H-pyrrole-2-carboxamide

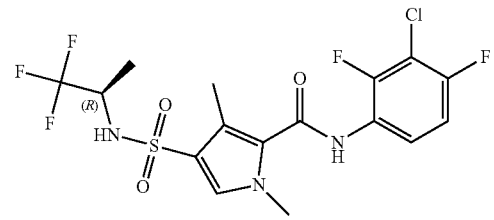

Compound 210 was prepared similarly as described for compound 144 using 3-chloro-2,4-difluoroaniline instead of 3,4-difluoroaniline. The obtained solid was recrystallized from ethanol (5 mL) to afford compound 210 (206 mg) as a white solid. Method D: Rt: 1.97 min m/z: 458.0 (M−H)⁻ Exact mass: 459.0. ¹H NMR (400 MHz, DMSO-d₆) δ ppm 1.11 (d, J=6.8 Hz, 3H), 2.35 (s, 3H), 3.73 (s, 3H), 3.76-3.89 (m, 1H), 7.36 (td, J=9.0, 2.0 Hz, 1H), 7.52 (s, 1H), 7.66 (td, J=8.7, 5.7 Hz, 1H), 8.16 (d, J=8.6 Hz, 1H), 10.02 (s, 1H).

Compound 211: 4-(tert-Butylsulfamoyl)-N-(3,4-difluorophenyl)-3-fluoro-1-methyl-1H-pyrrole-2-carboxamide

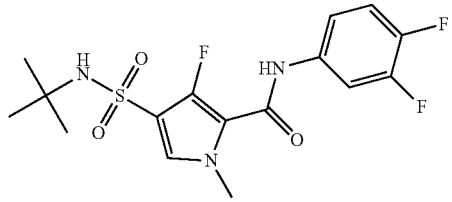 [SMILES: Cn1cc(S(=O)(=O)NC(C)(C)C)c(F)c1C(=O)Nc1ccc(F)c(F)c1]

Compound 211 (516 mg, white crystals) was prepared similarly as described for compound 214, using 3,4-difluoroaniline instead of 5-amino-2-fluoro-benzonitrile.
Method D: Rt: 1.96 min m/z: 388.1 (M−H)⁻ Exact mass: 389.1. ¹H NMR (400 MHz, DMSO-d₆) δ ppm 1.20 (s, 9H), 3.79 (s, 3H), 7.35-7.48 (m, 4H), 7.77-7.86 (m, 1H), 10.19 (s, 1H). Differential scanning calorimetry: From 30 to 300° C. at 10° C./min: peak at: 184.9° C.

Compound 212: 4-(tert-Butylsulfamoyl)-N-(3-chloro-2,4-difluorophenyl)-3-fluoro-1-methyl-1H-pyrrole-2-carboxamide

Compound 212 (396 mg, white crystals) was prepared similarly as described for compound 214, using 3-chloro-2,4-difluoro-aniline instead of 5-amino-2-fluoro-benzonitrile. Method D: Rt: 2.05 min m/z: 422.1 (M−H)⁻ Exact mass: 423.1

$^1$H NMR (400 MHz, DMSO-$d_6$) δ ppm 1.20 (s, 9H), 3.80 (s, 3H), 7.34 (d, J=2.0 Hz, 1H), 7.45-7.50 (m, 2H), 7.60-7.70 (m, 1H), 9.80 (br. s., 1H). Differential scanning calorimetry: From 30 to 300° C. at 10° C./min: peak at: 230.3° C.

Compound 213: 4-(tert-Butylsulfamoyl)-3-fluoro-1-methyl-N-(2,3,4-trifluorophenyl)-1H-pyrrole-2-carboxamide

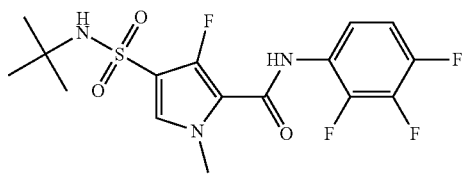 [SMILES: Cn1cc(S(=O)(=O)NC(C)(C)C)c(F)c1C(=O)Nc1ccc(F)c(F)c1F]

Compound 213 (25 mg, white crystals) was prepared similarly as described for compound 214, using 2,3,4-trifluoroaniline instead of 5-amino-2-fluoro-benzonitrile.

Method D: Rt: 1.97 min m/z: 406.1 (M−H)⁻ Exact mass: 407.1. $^1$H NMR (400 MHz, DMSO-$d_6$) δ ppm 1.20 (s, 9H), 3.80 (s, 3H), 7.27-7.39 (m, 1H), 7.41-7.51 (m, 3H), 9.85 (br. s, 1H). Differential scanning calorimetry: From 30 to 300° C. at 10° C./min: peak at: 223.3° C.

Compound 214: 4-(tert-Butylsulfamoyl)-N-(3-cyano-4-fluorophenyl)-3-fluoro-1-methyl-1H-pyrrole-2-carboxamide

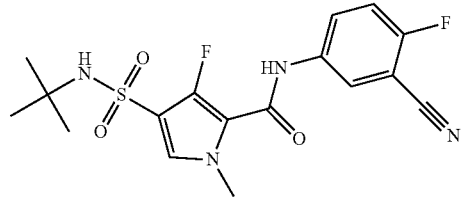 [SMILES: Cn1cc(S(=O)(=O)NC(C)(C)C)c(F)c1C(=O)Nc1ccc(F)c(C#N)c1]

A mixture of ethyl 4-chlorosulfonyl-3-fluoro-1-methyl-pyrrole-2-carboxylate (purified by column chromatography with 10 to 50% EtOAc in heptane, 1.50 g, 5.6 mmol), tert-butylamine (934 mg, 12.8 mmol) and acetonitrile (75 mL) was stirred 2 hours and then concentrated. The residue was dissolved in EtOAc (150 mL) washed with water, dried over sodium sulphate, filtered and concentrated yielding ethyl 4-(tert-butylsulfamoyl)-3-fluoro-1-methyl-pyrrole-2-carboxylate (1.65 g) as light yellow crystals. $^1$H NMR (400 MHz, DMSO-$d_6$) δ ppm 1.17 (s, 9H), 1.28 (t, J=7.0 Hz, 3H), 3.82 (s, 3H), 4.27 (q, J=7.1 Hz, 2H), 7.45 (s, 1H), 7.51 (d, J=4.8 Hz, 1H). Method D: Rt: 1.79 min m/z: 305.1 (M−H)⁻ Exact mass: 306.1. A mixture of ethyl 4-(tert-butylsulfamoyl)-3-fluoro-1-methyl-pyrrole-2-carboxylate (1.65 g, 5.4 mmol), lithium hydroxide (386 mg, 16.1 mmol), THF (20 mL) and water (5 mL) was stirred overnight. The reaction mixture was concentrated and the obtained residue was dissolved in water (50 mL) and neutralised with HCl (1M in H₂O). The formed white crystals were filtered off and dried in vacuo at 50° C. during 4 hours, resulting in 4-(tert-butylsulfamoyl)-3-fluoro-1-methyl-pyrrole-2-carboxylic acid (1.1 g). $^1$H NMR (400 MHz, DMSO-$d_6$) δ ppm 1.16 (s, 9H), 3.81 (s, 3H), 7.42 (s, 1H), 7.46 (d, J=4.8 Hz, 1H), 13.02 (br. s, 1H) Method B: Rt: 0.43 min m/z: 277.1 (M−H)⁻ Exact mass: 278.1.

4-(tert-butylsulfamoyl)-3-fluoro-1-methyl-pyrrole-2-carboxylic acid (100 mg, 0.359 mmol), HATU (170.781 mg, 0.449 mmol), Et₃N (0.15 mL, 0.728 g/mL, 1.078 mmol), 5-amino-2-fluoro-benzonitrile (97.8 mg, 0.72 mmol) in DMF (1 mL) was stirred overnight at 65° C. The solution was cooled to room temperature and, as such, subjected to silica gel (120 g) column chromatography using a gradient from 10 to 100% EtOAc in heptane. The product fractions were concentrated and the obtained residue was dissolved in warm methanol (10 mL). Water was added until crystallisation began. The crystals were filtered off and dried overnight in vacuo at 50° C., resulting in compound 214 (94 mg). Method D: Rt: 1.87 min m/z: 395.1 (M−H)⁻ Exact mass: 396.1. $^1$H NMR (400 MHz, DMSO-$d_6$) δ ppm 1.20 (s, 9H), 3.80 (s, 3H), 7.44-7.49 (m, 2H), 7.53 (t, J=9.1 Hz, 1H), 7.92-8.00 (m, 1H), 8.17 (dd, J=5.7, 2.6 Hz, 1H), 10.29 (s, 1H). Differential scanning calorimetry: From 30 to 300° C. at 10° C./min: peak at: 198.3° C.

Compound 215: N-(3-Chloro-2,4-difluorophenyl)-3-fluoro-1-methyl-4-[(3-methyloxetan-3-yl)sulfamoyl]-1H-pyrrole-2-carboxamide

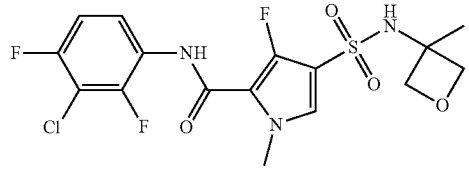 [SMILES: Cn1cc(S(=O)(=O)NC2(C)COC2)c(F)c1C(=O)Nc1ccc(F)c(Cl)c1F]

Compound 215 (94 mg, white solid) was prepared from 3-chloro-2,4-difluoro-aniline and 3-fluoro-1-methyl-4-[(3-methyloxetan-3-yl)sulfamoyl]pyrrole-2-carboxylic acid similarly as described for the synthesis of compound 214 from 5-amino-2-fluoro-benzonitrile and 4-(tert-butylsulfamoyl)-3-fluoro-1-methyl-pyrrole-2-carboxylic acid. Method D: Rt: 1.80 min m/z: 436.1 (M−H)⁻ Exact mass: 437.0. $^1$H NMR (400 MHz, DMSO-$d_6$) δ ppm 1.56 (s, 3H), 3.81 (s, 3H), 4.18 (d, J=6.4 Hz, 2H), 4.65 (d, J=6.2 Hz, 2H), 7.35 (td, J=9.0, 2.0 Hz, 1H), 7.53 (d, J=4.4 Hz, 1H), 7.64 (td, J=8.7, 5.8 Hz, 1H), 8.32 (s, 1H), 9.87 (s, 1H).

Compound 216: 3-Cyano-N-(3-cyano-4-fluorophenyl)-1-methyl-4-[(1-methylethyl)sulfamoyl]-1H-pyrrole-2-carboxamide

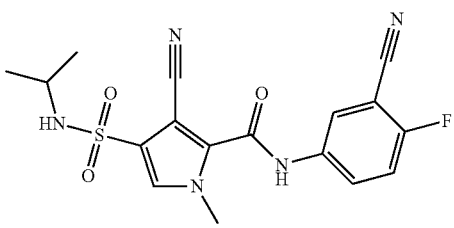 [SMILES: CC(C)NS(=O)(=O)c1cn(C)c(C(=O)Nc2ccc(F)c(C#N)c2)c1C#N]

Compound 171 (60 mg, 0.16 mmol) and potassium cyanide (102 mg, 1.6 mmol) were dissolved in acetonitrile (2 mL, 38.3 mmol) and heated at 130° C. for 8.5 hours by microwave irradiation. The reaction mixture was filtered, decalite was added to the filtrate and the suspension was evaporated to dryness. The solid was purified using silica gel column chromatography (ethyl acetate in heptane from 10 to 100%) to afford compound 216 as a yellow powder. Method B: Rt: 0.90 min m/z: 388.1 (M−H)⁻ Exact mass: 389.1. $^1$H NMR (400 MHz, DMSO-d$_6$) δ ppm 1.07 (d, J=6.4 Hz, 6H), 3.35-3.46 (m, 1H), 3.85 (s, 3H), 7.58 (t, J=9.1 Hz, 1H), 7.72 (s, 1H), 7.74 (br. s., 1H), 7.94 (ddd, J=9.1, 4.8, 2.8 Hz, 1H), 8.18 (dd, J=5.7, 2.6 Hz, 1H), 11.15 (br. s., 1H).

Compound 217: 3-Chloro-N-(3,4-difluorophenyl)-1-methyl-4-{[(1R)-2,2,2-trifluoro-1-methylethyl]sulfamoyl}-1H-pyrrole-2-carboxamide

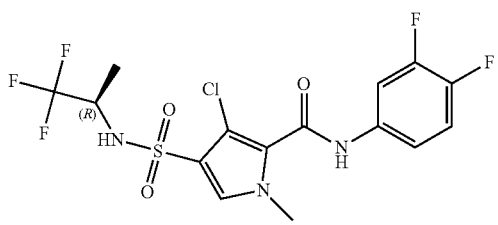

Methyl 3-chloro-4-chlorosulfonyl-1-methyl-pyrrole-2-carboxylate (4 g, 14.7 mmol) was dispensed in acetonitrile (20 mL), (R)-1,1,1-trifluoro-2-propylamine (2493 mg, 22.1 mmol), Hunig's base (3.8 mL, 22.1 mmol) and molecular sieves (100 mg) were added and the reaction mixture was heated overnight at 80° C. The reaction mixture was cooled down, filtered and evaporated to dryness. The obtained residue was purified by silica gel column chromatography using a heptane to EtOAc gradient yielding methyl 3-chloro-1-methyl-4-[[(1R)-2,2,2-trifluoro-1-methyl-ethyl]sulfamoyl]pyrrole-2-carboxylate (1.76 g) as a white powder. Methyl 3-chloro-1-methyl-4-[[(1R)-2,2,2-trifluoro-1-methyl-ethyl]sulfamoyl]pyrrole-2-carboxylate (590 mg, 1.69 mmol) and 3,4-difluoroaniline (286 mg, 2.2 mmol) were dissolved in THF (10 mL) and cooled to 0° C. Lithium bis(trimethylsilyl)amide (1M in THF), 5.08 mL, 1 M, 5.08 mmol) was added and the reaction mixture was allowed to reach room temperature. The volatiles were removed under reduced pressure to keep +/−5 mL. The residue was partitioned between CH$_2$Cl$_2$ and water. The water layer was neutralised using aqueous hydrochloric acid (1M) to form a white precipitate. The white solids were filtered and washed with water. The organic layer was loaded on a silica gel cartridge and a gradient from heptane to EtOAc was applied. The desired fractions were evaporated to keep +/−50 mL. A white precipitate was formed. The white solid was filtered and washed with heptane to afford a second solid fraction. The two solids were combined and recrystallized from methanol (5 mL) to afford compound 217 (255 mg) as a white powder. The filtrate was concentrated to dryness and recrystallized from ethyl acetate (6 mL) heptane (20 mL) to afford more compound 217 (185 mg) as a white powder which was dried in vacuo. Method B: Rt: 1.06 min m/z: 444.1 (M−H)⁻ Exact mass: 445.0. $^1$H NMR (400 MHz, DMSO-d$_6$) δ ppm 1.19 (d, J=6.8 Hz, 3H), 3.77 (s, 3H), 3.89-4.06 (m, 1H), 7.38-7.50 (m, 2H), 7.66 (s, 1H), 7.78-7.91 (m, 1H), 8.49 (br. s., 1H), 10.56 (br. s., 1H). Differential scanning calorimetry: From 30 to 300° C. at 10° C./min: peak at: 203.9° C. (EtOAc/heptane).

Compound 218: 3-Chloro-N-(3-chloro-2,4-difluorophenyl)-1-methyl-4-{[(1R)-2,2,2-trifluoro-1-methylethyl]sulfamoyl}-1H-pyrrole-2-carboxamide

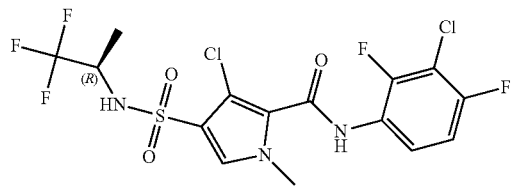

Compound 218 was prepared similarly as described for the synthesis of compound 217 using 3-chloro-2,4-difluoro-aniline instead of 3,4-difluoroaniline. After partitioning between CH$_2$Cl$_2$ and water, the water layer was neutralised using aqueous hydrochloric acid (1M) to form a white precipitate. The water layer was extracted with CH$_2$Cl$_2$ (2×50 mL) and EtOAc (2×150 mL). The combined organic layers were washed with brine and dried (Na$_2$SO$_4$) and concentrated to dryness. The obtained brown powder was recrystallized from ethyl acetate (20 mL) resulting in compound 218 (576 mg) as a powder which was dried in vacuo. Method B: Rt: 1.13 min m/z: 478.0 (M−H)⁻ Exact mass: 479.0. $^1$H NMR (400 MHz, DMSO-d$_6$) δ ppm 1.19 (d, J=7.0 Hz, 3H), 3.79 (s, 3H), 3.90-4.05 (m, 1H), 7.37 (td, J=9.0, 2.0 Hz, 1H), 7.69 (s, 1H), 7.66-7.76 (m, 1H), 8.50 (br. s., 1H), 10.24 (s, 1H). Differential scanning calorimetry: From 30 to 300° C. at 10° C./min: peak at 213.0° C.

Compound 219: 3-Chloro-N-(3-chloro-2,4-difluorophenyl)-1-methyl-4-{[1-(trifluoro-methyl)cyclobutyl]sulfamoyl}-1H-pyrrole-2-carboxamide

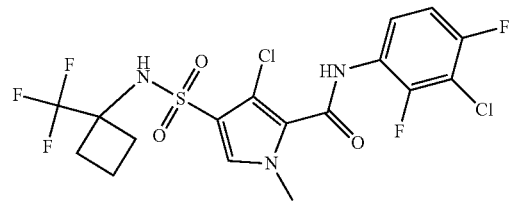 [SMILES: Cn1cc(S(=O)(=O)NC2(C(F)(F)F)CCC2)c(Cl)c1C(=O)Nc1ccc(F)c(Cl)c1F]

Compound 219 (136 mg) was prepared similarly as described for the synthesis of compound 221 using 3-chloro-2,4-difluoro-aniline instead of 5-amino-2-fluorobenzonitrile. $^1$H NMR (400 MHz, DMSO-d$_6$) δ ppm 1.75-1.87 (m, 2H), 2.24-2.35 (m, 2H), 2.41-2.47 (m, 2H), 3.80 (s, 3H), 7.37 (td, J=9.0, 2.1 Hz, 1H), 7.68 (s, 1H), 7.69-7.75 (m, 1H), 8.60 (br. s., 1H), 10.22 (s, 1H). Method D: Rt: 2.14 min m/z: 504.0 (M−H)⁻ Exact mass: 505.0. Differential scanning calorimetry: From 30 to 300° C. at 10° C./min: peak at 237.3° C.

Compound 220: 4-(tert-Butylsulfamoyl)-3-chloro-N-(3-chloro-4-fluorophenyl)-1-methyl-1H-pyrrole-2-carboxamide

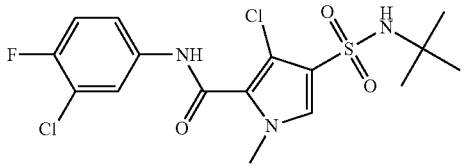 [SMILES: Cn1cc(S(=O)(=O)NC(C)(C)C)c(Cl)c1C(=O)Nc1ccc(F)c(Cl)c1]

Compound 220 (614 mg) was prepared similarly as described for the synthesis of compound 226 using 3-chloro-4-fluoro-aniline instead of 5-amino-2-fluorobenzonitrile. Method D: Rt: 2.07 min m/z: 420.1 (M−H)⁻ Exact mass: 421.0. ¹H NMR (400 MHz, DMSO-d₆) δ ppm 1.18 (s, 9H), 3.76 (s, 3H), 7.34 (s, 1H), 7.42 (t, J=9.1 Hz, 1H), 7.59 (s, 1H), 7.60-7.67 (m, 1H), 7.98 (dd, J=6.7, 2.5 Hz, 1H), 10.48 (s, 1H). Differential scanning calorimetry: From 30 to 300° C. at 10° C./min: peak at 195.9° C.

Compound 221: 3-Chloro-N-(3-cyano-4-fluorophenyl)-1-methyl-4-{[1-(trifluoro-methyl)cyclobutyl]sulfamoyl}-1H-pyrrole-2-carboxamide

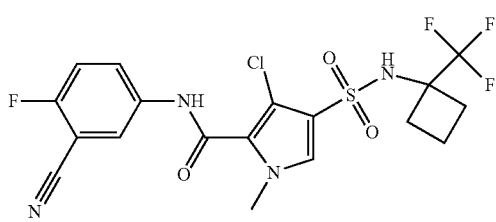 [SMILES: Cn1cc(S(=O)(=O)NC2(C(F)(F)F)CCC2)c(Cl)c1C(=O)Nc1ccc(F)c(C#N)c1]

Methyl 3-chloro-4-chlorosulfonyl-1-methyl-pyrrole-2-carboxylate (2000 mg, 7.35 mmol) was dispensed in acetonitrile (15 mL) in a microwave tube, 1-(trifluoromethyl)cyclobutan-1-amine (1.53 mg, 11.0 mmol) and Hunig's base (1.9 mL, 11.03 mmol) were added and the tube was sealed and heated at 85° C. for 8 hours. The solids were filtered off and the filtrate was evaporated to dryness. The residue was purified on silica gel using a heptane to EtOAc gradient yielding methyl 3-chloro-1-methyl-4-[[1-(trifluoromethyl)cyclobutyl]sulfamoyl]pyrrole-2-carboxylate as an off-white powder (382 mg). Methyl 3-chloro-1-methyl-4-[[1-(trifluoromethyl)cyclobutyl]sulfamoyl]pyrrole-2-carboxylate (150 mg, 0.4 mmol) and 5-amino-2-fluorobenzonitrile (0.52 mmol) were dissolved in dry THF and cooled to 0° C. Lithium bis(trimethylsilyl)amide (1.24 mL, 1 M in THF, 1.24 mmol) was added dropwise and the reaction mixture was allowed to reach room temperature. After 1 hour lithium bis(trimethyl-silyl)amide (0.5 mL, 1 M in THF, 0.5 mmol) was added and the reaction mixture was stirred for another hour. The volatiles were removed under reduced pressure and the residue was purified on silica gel using a heptane to EtOAc gradient. The collected fractions were evaporated to dryness and the residue was crystallized from a heptane/EtOAc mixture yielding compound 221 (91 mg) as off-white powder. Method D: Rt: 1.95 min m/z: 477.1 (M−H)⁻ Exact mass: 478.0. ¹H NMR (400 MHz, DMSO-d₆) δ ppm 1.75-1.88 (m, 2H), 2.25-2.37 (m, 2H), 2.41-2.48 (m, 2H), 3.79 (s, 3H), 7.56 (t, J=9.1 Hz, 1H), 7.68 (s, 1H), 7.99 (ddd, J=9.2, 4.8, 2.6 Hz, 1H), 8.20 (dd, J=5.7, 2.6 Hz, 1H), 8.61 (s, 1H), 10.67 (s, 1H).

Compound 222: 3-Chloro-N-(3-chloro-4-fluorophenyl)-1-methyl-4-{[(1R)-2,2,2-trifluoro-1-methylethyl]sulfamoyl}-1H-pyrrole-2-carboxamide

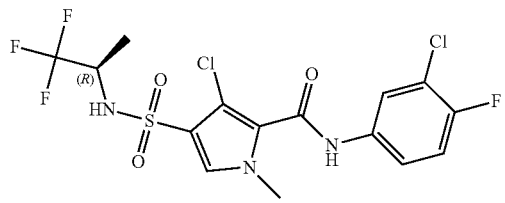

Compound 222 was prepared similarly as described for the synthesis of compound 217 using 3-chloro-4-fluoro-aniline instead of 3,4-difluoroaniline. After partitioning between CH₂Cl₂ and water, the water layer was neutralised using aqueous hydrochloric acid (1M) to form a white precipitate. The water layer was extracted with CH₂Cl₂ (4×50 mL). The combined organic layers were washed with brine and dried (Na₂SO₄) and concentrated to keep (15 mL). The white solid was filtered and washed with heptane to afford compound 222 (632 mg) as off white powder. Method B: Rt: 1.12 min m/z: 460.1 (M−H)⁻ Exact mass: 461.0. ¹H NMR (400 MHz, DMSO-d₆) δ ppm 1.19 (d, J=6.8 Hz, 3H), 3.77 (s, 3H), 3.92-4.04 (m, 1H), 7.43 (t, J=9.0 Hz, 1H), 7.63 (ddd, J=9.0, 4.2, 2.6 Hz, 1H), 7.67 (s, 1H), 7.99 (dd, J=6.8, 2.6 Hz, 1H), 8.14 (br. s., 1H), 10.56 (br. s., 1H). Differential scanning calorimetry: From 30 to 300° C. at 10° C./min: peak at 218.8° C.

Compound 223: 4-(tert-Butylsulfamoyl)-3-chloro-N-(3,4-difluorophenyl)-1-methyl-1H-pyrrole-2-carboxamide

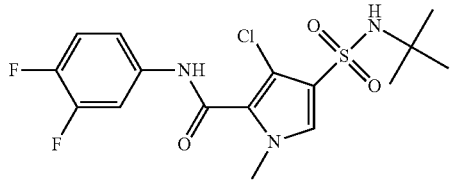 [SMILES: Cn1cc(S(=O)(=O)NC(C)(C)C)c(Cl)c1C(=O)Nc1ccc(F)c(F)c1]

Compound 223 (579 mg) was prepared similarly as described for the synthesis of compound 226 using 3,4-difluoroaniline instead of 5-amino-2-fluorobenzonitrile. ¹H NMR (400 MHz, DMSO-d₆) δ ppm 1.18 (s, 9H), 3.76 (s, 3H), 7.34 (s, 1H), 7.39-7.50 (m, 2H), 7.59 (s, 1H), 7.78-7.91 (m, 1H), 10.50 (Br. s., 1H). Method D: Rt: 1.99 min m/z: 404.1 (M−H)⁻ Exact mass: 405.1.

Compound 224: 4-(tert-Butylsulfamoyl)-3-chloro-N-(3-chloro-2,4-difluorophenyl)-1-methyl-1H-pyrrole-2-carboxamide

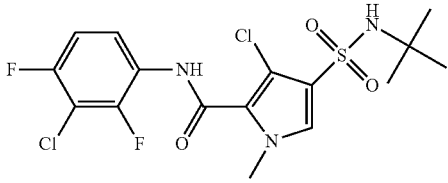 [SMILES: Cn1cc(S(=O)(=O)NC(C)(C)C)c(Cl)c1C(=O)Nc1ccc(F)c(Cl)c1F]

Compound 224 (405 mg) was prepared similarly as described for the synthesis of compound 226 using 3-chloro-2,4-difluoroaniline instead of 5-amino-2-fluorobenzonitrile. Method B: Rt: 1.16 min m/z: 438.1 (M−H)⁻ Exact mass: 439.0. ¹H NMR (400 MHz, DMSO-d₆) δ ppm 1.18 (s, 9H), 3.78 (s, 3H), 7.31-7.40 (m, 2H), 7.61 (s, 1H), 7.65-7.75 (m, 1H), 10.16 (br. s., 1H). Differential scanning calorimetry: From 30 to 300° C. at 10° C./min: peak at 241.6° C.

Compound 225: 3-Chloro-N-(3-cyano-4-fluorophenyl)-1-methyl-4-{[(1S)-2,2,2-trifluoro-1-methylethyl]sulfamoyl}-1H-pyrrole-2-carboxamide

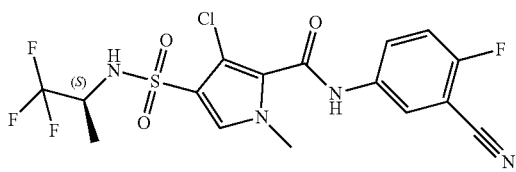

Compound 225 was prepared similarly as described for compound 199, using (S)-1,1,1-trifluoro-2-propylamine instead of (R)-1,1,1-trifluoro-2-propylamine. Method D: Rt: 1.86 min m/z: 451.0 (M−H)⁻ Exact mass: 452.0. ¹H NMR (400 MHz, DMSO-d₆) δ ppm 1.19 (d, J=7.0 Hz, 3H), 3.78 (s, 3H), 3.92-4.05 (m, 1H), 7.56 (t, J=9.1 Hz, 1H), 7.68 (s, 1H), 7.98 (ddd, J=9.1, 4.8, 2.8 Hz, 1H), 8.19 (dd, J=5.7, 2.6 Hz, 1H), 8.51 (br. s., 1H), 10.67 (s, 1H).

Compound 226: 4-(tert-Butylsulfamoyl)-3-chloro-N-(3-cyano-4-fluorophenyl)-1-methyl-1H-pyrrole-2-carboxamide

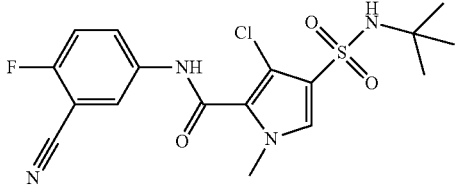 [SMILES: Cn1cc(S(=O)(=O)NC(C)(C)C)c(Cl)c1C(=O)Nc1ccc(F)c(C#N)c1]

Methyl 3-chloro-4-chlorosulfonyl-1-methyl-pyrrole-2-carboxylate (4 g, 14.7 mmol) was dispensed in acetonitrile (25 mL) and tert-butylamine (4388 mg, 58.8 mmol) was added. The reaction mixture was stirred for 30 minutes at room temperature. The solids were filtered off and the filtrate was evaporated to dryness. The residue was purified on silica using a heptane to EtOAc gradient yielding methyl 4-(tert-butylsulfamoyl)-3-chloro-1-methyl-pyrrole-2-carboxylate (3.57 g) as a white powder after trituration in CH₂Cl₂ and diisopropylether. ¹H NMR (400 MHz, DMSO-d₆) δ ppm 1.14 (s, 9H), 3.82 (s, 3H), 3.86 (s, 3H), 7.35 (s, 1H), 7.69 (s, 1H). Methyl 4-(tert-butylsulfamoyl)-3-chloro-1-methyl-pyrrole-2-carboxylate (500 mg, 1.619 mmol) and 5-amino-2-fluorobenzonitrile (295.4 mg, 2.11 mmol) were dissolved in THF (10 mL) and cooled to 0° C. Lithium bis(trimethylsilyl)amide (5 mL, 1 M in toluene, 5 mmol) was added and the reaction mixture was allowed to reach room temperature. More lithium bis(trimethylsilyl)amide (1 mL, 1M in THF, 1 mmol) was added and the reaction mixture was stirred for 30 minutes more. The volatiles were removed under reduced pressure and the residue was partitioned between CH₂Cl₂ and water. The organic layer was loaded on a silica cartridge and a gradient form heptane to EtOAc was applied. The desired fractions were evaporated to dryness and the residue was crystallized from a EtOAc/heptane mixture. The precipitate was filtered off, triturated with diisopropylether and dried, yielding compound 226 (513 mg) as a white powder. Method B: Rt: 1.01 min m/z: 411.2 (M−H)⁻ Exact mass: 412.1. ¹H NMR (400 MHz, DMSO-d₆) δ ppm 1.18 (s, 9H), 3.77 (s, 3H), 7.36 (s, 1H), 7.55 (t, J=9.1 Hz, 1H), 7.61 (s, 1H), 7.99 (ddd, J=9.2, 4.8, 2.8 Hz, 1H), 8.19 (dd, J=5.8, 2.8 Hz, 1H), 10.61 (s, 1H). Differential scanning calorimetry: From 30 to 300° C. at 10° C./min: peak at 207.0° C.

Compound 227: N-(3-Cyano-4-fluorophenyl)-1-methyl-4-{[1-(trifluoromethyl)cyclo-propyl]sulfamoyl}-1H-pyrrole-2-carboxamide

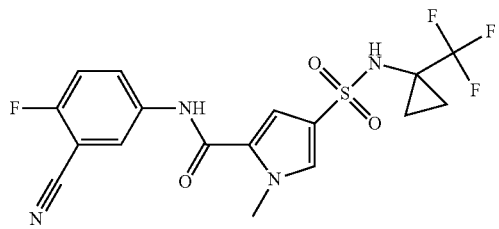 [SMILES: Cn1cc(S(=O)(=O)NC2(C(F)(F)F)CC2)cc1C(=O)Nc1ccc(F)c(C#N)c1]

5-[(3-cyano-4-fluoro-phenyl)carbamoyl]-1-methyl-pyrrole-3-sulfonyl chloride (600 mg, 1.76 mmol) was mixed with 1-trifluoromethyl-1-cyclopropylamine (329 mg, 2.63 mmol), acetonitrile (10 mL), molecular sieves and Hunig's base (0.91 mL, 0.75 g/mL, 5.27 mmol) in a microwave vial (20 mL) and stirred at 100° C. for 1 hour and next at 110° C. for 1 hour under MW-irradiation. The reaction mixture was filtered and the filtrate concentrated to dryness. The obtained residue was purified using silica gel column chromatography (ethyl acetate in heptane from 10 to 70%) and further by preparative HPLC (Stationary phase: Uptisphere C18 ODB—10 μm, 200 g, 5 cm, Mobile phase: 0.25% NH₄HCO₃ solution in water, CH₃CN), resulting in compound 227 (63 mg) after concentration and drying in vacuo at 50° C.

Method B: Rt: 0.98 min m/z: 429.1 (M−H)⁻ Exact mass: 430.1. ¹H NMR (400 MHz, DMSO-d₆) δ ppm 1.09-1.21 (m, 4H), 3.91 (s, 3H), 7.31 (d, J=2.0 Hz, 1H), 7.53 (t, J=9.1 Hz, 1H), 7.56-7.58 (m, 1H), 8.01 (ddd, J=9.2, 5.0, 2.8 Hz, 1H), 8.21 (dd, J=5.8, 2.8 Hz, 1H), 8.74 (br. s., 1H), 10.36 (br. s., 1H).

Compound 228: N-(3-Cyano-4-fluorophenyl)-1-methyl-4-{[3-(trifluoromethyl)tetrahydrofuran-3-yl]sulfamoyl}-1H-pyrrole-2-carboxamide

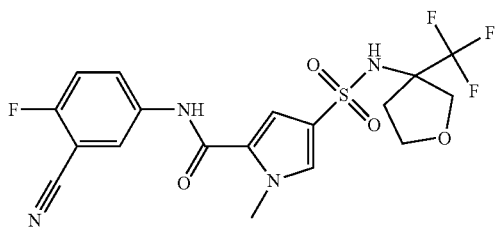 [SMILES: Cn1cc(S(=O)(=O)NC2(C(F)(F)F)CCOC2)cc1C(=O)Nc1ccc(F)c(C#N)c1]

Compound 228 (153 mg) was prepared similarly as described for compound 227, using 3-(trifluoromethyl)tetrahydrofuran-3-amine hydrochloride instead of 1-trifluoromethyl-1-cyclopropylamine. Racemic compound 228 was separated in enantiomers by Prep SFC (Stationary phase: Chiralpak Daicel IC 20×250 mm, Mobile phase: $CO_2$, 12-50% MeOH with 0.4% iPrNH$_2$), resulting in compound 228a (first eluding) and 228b (second eluding, 41 mg). 228a was further purified by Prep HPLC (Stationary phase: RP XBridge Prep C18 OBD-10 μm, 30×150 mm, Mobile phase: 0.25% $NH_4HCO_3$ solution in water, $CH_3CN$) resulting in compound 228a (28 mg) as white solid. 228a: Method D: Rt: 1.79 min m/z: 459.0 (M−H)⁻ Exact mass: 460.1.

¹H NMR (400 MHz, DMSO-d$_6$) δ ppm 2.18 (dt, J=13.8, 8.1 Hz, 1H), 2.42-2.49 (m, 1H), 3.60 (q, J=7.8 Hz, 1H), 3.83 (td, J=8.3, 4.4 Hz, 1H), 3.92 (s, 3H), 3.91-3.96 (m, 1H), 4.04-4.10 (m, 1H), 7.35 (d, J=2.0 Hz, 1H), 7.53 (t, J=9.1 Hz, 1H), 7.60 (d, J=1.8 Hz, 1H), 8.01 (ddd, J=9.2, 4.8, 2.9 Hz, 1H), 8.21 (dd, J=5.8, 2.8 Hz, 1H), 8.49 (br. s., 1H), 10.39 (s, 1H). 228b: Method D: Rt: 1.79 min m/z: 459.0 (M−H)⁻ Exact mass: 460.1. ¹H NMR (400 MHz, DMSO-d$_6$) δ ppm 2.20 (dt, J=13.8, 8.1 Hz, 1H), 2.43-2.49 (m, 1H), 3.60 (q, J=7.7 Hz, 1H), 3.79-3.88 (m, 1H), 3.92 (s, 3H), 3.91-3.96 (m, 1H), 4.04-4.10 (m, 1H), 7.35 (d, J=2.0 Hz, 1H), 7.53 (t, J=9.1 Hz, 1H), 7.62 (d, J=1.8 Hz, 1H), 8.01 (ddd, J=9.3, 4.9, 2.8 Hz, 1H), 8.21 (dd, J=5.7, 2.6 Hz, 1H), 8.46 (br. s., 1H), 10.38 (s, 1H).

Synthesis of
3-(trifluoromethyl)tetrahydrofuran-3-amine
hydrochloride

A mixture of 3-oxotetrahydrofuran (30 g, 348.5 mmol), benzylamine (39.2 g, 365.8 mmol), $MgSO_4$ (21 g, 174.5 mmol) and $CH_2Cl_2$ (200 mL) was stirred at 28° C. for 24 hours. The mixture was filtrated. The filtrate was concentrated in vacuo and the obtained residue (63.1 g) was used directly in the next step. The obtained residue (63 g) was dissolved in acetonitrile (600 mL). Trifluoroacetic acid (45 g, 394 mmol), potassium hydrogen fluoride (22.5 g, 288 mmol) and DMF (60 mL) were added to the mixture at 0° C. The mixture was stirred at 0° for 10 minutes. (trifluoromethyl)trimethylsilane (77 g, 541 mmol) was added to the reaction mixture and the mixture was stirred at ambient temperature for 12 h. Saturated aqueous $Na_2CO_3$ (200 mL) was added and the mixture was stirred for 5 min. The mixture was diluted with water (500 mL), and extracted with ethyl acetate (3×300 mL). The combined organic layers were washed with water and brine, dried over $Na_2SO_4$ and evaporated under reduced pressure. The obtained residue was dissolved in 2M HCl/MeOH and the solvent was evaporated.

The resulting hydrochloride salt was crystallized from $CH_3CN$ to provide N-benzyl-3-(trifluoromethyl)tetrahydrofuran-3-amine (30.5 g). A mixture of N-benzyl-3-(trifluoromethyl)tetrahydrofuran-3-amine (30.5 g), palladium on alumina (1.5 g) and MeOH was stirred under $H_2$ (20 psi) atmosphere at 28° C. for 12 hours.

The mixture was filtered and the filtrate was concentrated in vacuo resulting in 3-(trifluoromethyl)tetrahydrofuran-3-amine hydrochloride (20.5 g). ¹H NMR (400 MHz, DMSO-d$_6$) δ ppm 2.21-2.43 (m, 2H) 3.83-4.16 (m, 4H) 9.68 (br. s., 3H).

Compound 229: N-(3,4-Difluorophenyl)-3-fluoro-1-methyl-4-{[(1R)-2,2,2-trifluoro-1-methylethyl]sulfamoyl}-1H-pyrrole-2-carboxamide

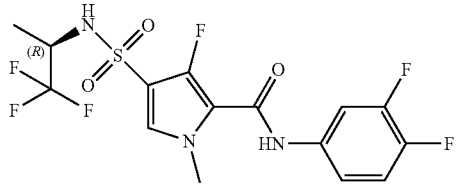

To ethyl 3-fluoro-1-methyl-4-[[(1R)-2,2,2-trifluoro-1-methyl-ethyl]sulfamoyl]pyrrole-2-carboxylate (¹H NMR (400 MHz, DMSO-d$_6$) δ ppm 1.15 (d, J=7.0 Hz, 3H), 1.28 (t, J=7.0 Hz, 3H), 3.83 (s, 3H), 3.90-4.02 (m, 1H), 4.28 (q, J=7.0 Hz, 2H), 7.60 (d, J=4.6 Hz, 1H), 8.59 (d, J=8.8 Hz, 1H); 1.10 g, 3.18 mmol) and 3,4-difluoroaniline (534 mg, 4.14 mmol) dissolved in THF (47 mL) under nitrogen atmosphere, at 0° C., lithium bis(trimethylsilyl)amide (12.7 mL, 1 M in toluene, 12.72 mmol) was added. The mixture was stirred 1 hour at 0° C. and further overnight at room temperature. The reaction mixture was quenched with $NH_4Cl$ (30 mL) solution and extracted with EtOAc (50 mL), diluted with brine (50 mL) and extracted again with EtOAc (50 mL). The combined organic layers were dried over sodium sulphate, filtered and concentrated. The residue (dissolved in 1 mL DMF) was purified by column chromatography on silica (120 g) with a gradient from 10 till 100% EtOAc in heptane. The product fractions were concentrated and the solid residue was crystallized from warm methanol (20 mL) upon addition of water. The white crystals were filtered off and dried in vacuo at 50° C. overnight, resulting in compound 229 (945 mg). Method D: Rt: 1.93 min m/z: 428.1 (M−H)⁻ Exact mass: 429.1. ¹H NMR (400 MHz, DMSO-d$_6$) δ ppm 1.18 (d, J=7.0 Hz, 3H), 3.80 (s, 3H), 3.91-4.04 (m, 1H), 7.37-7.48 (m, 2H), 7.54 (d, J=4.4 Hz, 1H), 7.76-7.86 (m, 1H), 8.59 (d, J=8.6 Hz, 1H), 10.26 (s, 1H).

Compound 230: N-(3-Bromo-4-fluorophenyl)-3-fluoro-1-methyl-4-[(1-methylethyl)sulfamoyl]-1H-pyrrole-2-carboxamide

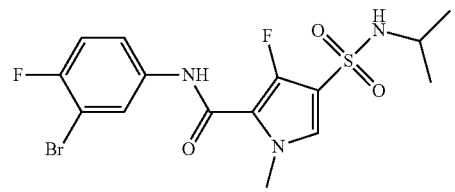

3-fluoro-4-(isopropylsulfamoyl)-1-methyl-pyrrole-2-carboxylic acid (153 mg, 0.579 mmol), HATU (275 mg, 0.724 mmol), Et₃N (0.242 mL, 1.74 mmol), 3-bromo-4-fluoro-aniline (220 mg, 1.16 mmol) and DMF (1.1 mL) were stirred overnight at 65° C. The solution was subjected to column chromatography on a 120 g Reveleris silica gel cartridge using a gradient from 10 till 100% EtOAc in heptane. The product fractions were concentrated. The residue was dissolved in warm methanol (50 mL). Water was added until crystallisation began. The white crystals were filtered off and dried overnight in vacuo at 50° C. Method D: Rt: 2.04 min m/z: 436.2 (M−H)⁻ Exact mass: 437.0. ¹H NMR (400 MHz, DMSO-d₆) δ ppm 1.05 (d, J=6.6 Hz, 6H), 3.31-3.40 (m, 1H), 3.79 (s, 3H), 7.37 (t, J=8.8 Hz, 1H), 7.45 (d, J=4.4 Hz, 1H), 7.57 (d, J=7.3 Hz, 1H), 7.64 (ddd, J=9.0, 4.4, 2.6 Hz, 1H), 8.08 (dd, J=6.4, 2.4 Hz, 1H), 10.18 (s, 1H). Differential scanning calorimetry: From 30 to 300° C. at 10° C./min: peak at 200.9° C.

Compound 231: N-(3-Cyano-2,4-difluorophenyl)-3-fluoro-1-methyl-4-[(1-methyl-ethyl)sulfamoyl]-1H-pyrrole-2-carboxamide

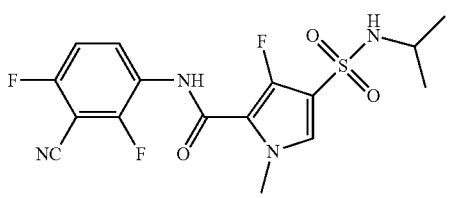 [SMILES: CC(C)NS(=O)(=O)c1cn(C)c(C(=O)Nc2ccc(F)c(C#N)c2F)c1F]

Compound 231 (88 mg) was prepared similarly as described for compound 230, using 3-amino-2,6-difluoro-benzonitrile instead of 3-bromo-4-fluoro-aniline. Method D: Rt: 1.86 min m/z: 399.3 (M−H)⁻ Exact mass: 400.1. ¹H NMR (400 MHz, DMSO-d₆) δ ppm 1.06 (d, J=6.4 Hz, 6H), 3.31-3.40 (m, 1H), 3.81 (s, 3H), 7.41-7.52 (m, 2H), 7.61 (d, J=7.3 Hz, 1H), 8.03 (td, J=8.9, 6.2 Hz, 1H), 9.96 (s, 1H).

Compound 232: N-(3,4-Difluorophenyl)-3-fluoro-1-methyl-4-[(1-methylethyl)sulfamoyl]-1H-pyrrole-2-carboxamide

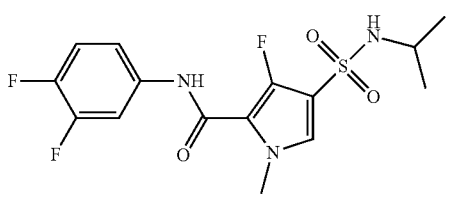 [SMILES: CC(C)NS(=O)(=O)c1cn(C)c(C(=O)Nc2ccc(F)c(F)c2)c1F]

Compound 232 (144 mg) was prepared similarly as described for compound 230, using 3,4-difluoroaniline instead of 3-bromo-4-fluoro-aniline. Method D: Rt: 1.95 min m/z: 374.3 (M−H)⁻ Exact mass: 375.1. ¹H NMR (400 MHz, DMSO-d₆) δ ppm 1.05 (d, J=6.6 Hz, 6H), 3.31-3.41 (m, 1H), 3.79 (s, 3H), 7.35-7.49 (m, 3H), 7.57 (d, J=7.3 Hz, 1H), 7.76-7.87 (m, 1H), 10.22 (s, 1H). Differential scanning calorimetry: From 30 to 300° C. at 10° C./min: peak at 195.8° C.

Compound 233: 3-Fluoro-1-methyl-4-[(1-methyl-ethyl)sulfamoyl]-N-(2,3,4-trifluorophenyl)-1H-pyrrole-2-carboxamide

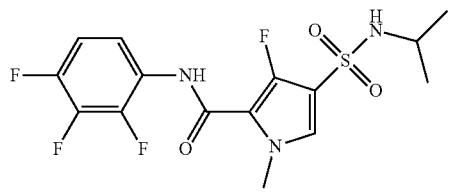 [SMILES: CC(C)NS(=O)(=O)c1cn(C)c(C(=O)Nc2ccc(F)c(F)c2F)c1F]

Compound 233 (89 mg) was prepared similarly as described for compound 230, using 2,3,4-trifluoroaniline instead of 3-bromo-4-fluoro-aniline. Method D: Rt: 1.95 min m/z: 392.3 (M−H)⁻ Exact mass: 393.1. ¹H NMR (400 MHz, DMSO-d₆) δ ppm 1.06 (d, J=6.6 Hz, 6H), 3.31-3.40 (m, 1H), 3.80 (s, 3H), 7.28-7.39 (m, 1H), 7.41-7.51 (m, 2H), 7.59 (d, J=7.3 Hz, 1H), 9.87 (s, 1H). Differential scanning calorimetry: From 30 to 300° C. at 10° C./min: peak at 214.3° C.

Compound 234: N-(3-Chloro-2,4-difluorophenyl)-3-fluoro-1-methyl-4-[(1-methyl-ethyl)sulfamoyl]-1H-pyrrole-2-carboxamide

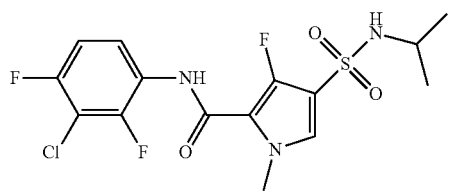 [SMILES: CC(C)NS(=O)(=O)c1cn(C)c(C(=O)Nc2ccc(F)c(Cl)c2F)c1F]

Compound 234 (95 mg) was prepared similarly as described for compound 230, using 3-chloro-2,4-difluoro-aniline instead of 3-bromo-4-fluoro-aniline. Method D: Rt: 2.03 min m/z: 408.3 (M−H)⁻ Exact mass: 409.0. ¹H NMR (400 MHz, DMSO-d₆) δ ppm 1.06 (d, J=6.4 Hz, 6H), 3.31-3.40 (m, 1H), 3.81 (s, 3H), 7.35 (td, J=9.0, 2.1 Hz, 1H), 7.48 (d, J=4.6 Hz, 1H), 7.59 (d, J=7.3 Hz, 1H), 7.65 (td, J=8.7, 5.8 Hz, 1H), 9.83 (s, 1H).

Compound 235: N-(3-Chloro-4-fluorophenyl)-3-fluoro-1-methyl-4-[(1-methylethyl)sulfamoyl]-1H-pyrrole-2-carboxamide

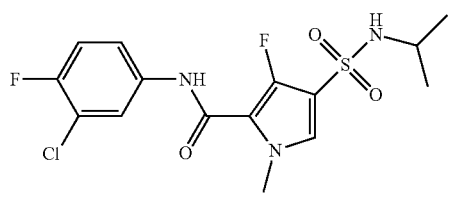

Compound 235 (156 mg) was prepared similarly as described for compound 230, using 3-chloro-4-fluoro-aniline instead of 3-bromo-4-fluoro-aniline. Method D: Rt: 2.03 min m/z: 390.3 (M−H)⁻ Exact mass: 391.1. ¹H NMR (400 MHz, DMSO-d₆) δ ppm 1.05 (d, J=6.6 Hz, 6H), 3.31-3.40

(m, 1H), 3.80 (s, 3H), 7.40 (t, J=9.1 Hz, 1H), 7.45 (d, J=4.6 Hz, 1H), 7.54-7.64 (m, 2H), 7.96 (dd, J=6.8, 2.4 Hz, 1H), 10.19 (s, 1H). Differential scanning calorimetry: From 30 to 300° C. at 10° C./min: peak at 201.9° C.

Compound 236: N-(3-Chloro-2,4-difluorophenyl)-4-{[2,2-difluorocyclopentyl]sulfamoyl}-1-methyl-1H-pyrrole-2-carboxamide

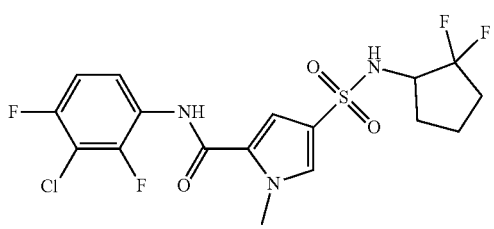 [SMILES: Cn1cc(S(=O)(=O)NC2CCCC2(F)F)cc1C(=O)Nc1ccc(F)c(Cl)c1F]

5-[(3-chloro-2,4-difluoro-phenyl)carbamoyl]-1-methyl-pyrrole-3-sulfonyl chloride (532.5 mg, 1.442 mmol), 2,2-difluorocyclopentan-1-amine hydrochloride (261 mg, 1.66 mmol) and Et₃N (0.501 mL, 3.61 mmol) in acetonitrile (50 mL) was stirred and refluxed 2 hours. The reaction mixture was concentrated and the obtained residue was dissolved in EtOAc (50 mL) washed with HCl 1M, dried over sodium sulphate, filtered and concentrated. The obtained residue was subjected to silica gel column chromatography using a gradient from 10 till 100% EtOAc in heptane. The product fractions were concentrated resulting in compound 236 (518 mg) as a white solid.

Racemic compound 236 was separated in its enantiomers 236a (first eluding) and 236b (second eluding) via Prep SFC (Stationary phase: Chiralpak Diacel AD 20×250 mm, Mobile phase: CO₂, 30% EtOH-iPrOH (50-50) with 0.2% iPrNH₂)

236a: Method D: Rt: 1.98 min m/z: 452.3 (M−H)⁻ Exact mass: 453.1. ¹H NMR (400 MHz, DMSO-d₆) δ ppm 1.41-1.72 (m, 3H), 1.76-1.87 (m, 1H), 1.90-2.18 (m, 2H), 3.61-3.78 (m, 1H), 3.89 (s, 3H), 7.31-7.38 (m, 2H), 7.53 (td, J=8.7, 5.9 Hz, 1H), 7.58 (d, J=1.5 Hz, 1H), 7.81 (d, J=8.8 Hz, 1H), 10.12 (s, 1H).

236b: Method D: Rt: 1.98 min m/z: 452.3 (M−H)⁻ Exact mass: 453.1. ¹H NMR (400 MHz, DMSO-d₆) δ ppm 1.40-1.74 (m, 3H), 1.75-1.89 (m, 1H), 1.90-2.18 (m, 2H), 3.62-3.78 (m, 1H), 3.89 (s, 3H), 7.29-7.39 (m, 2H), 7.48-7.61 (m, 2H), 7.81 (d, J=8.1 Hz, 1H), 10.12 (s, 1H).

Compound 237: N-(3-Cyano-4-fluorophenyl)-1-methyl-4-[(2,2,2-trifluoro-1,1-di-methylethyl)sulfamoyl]-1H-pyrrole-2-carboxamide

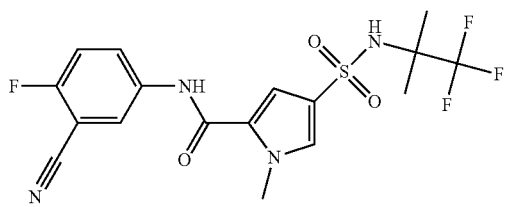 [SMILES: Cn1cc(S(=O)(=O)NC(C)(C)C(F)(F)F)cc1C(=O)Nc1ccc(F)c(C#N)c1]

5-[(3-cyano-4-fluoro-phenyl)carbamoyl]-1-methyl-pyrrole-3-sulfonyl chloride (0.25 g, 0.73 mmol) was dissolved in acetonitrile (6 mL) and dried with molecular sieves 4A powder over a period of 30 minutes in a pressure tube. 2,2,2-trifluoro-1,1-dimethyl-ethylamine (139 mg, 1.1 mmol) and sodium bicarbonate (307.3 mg, 3.66 mmol) were dispersed in acetonitrile (2 mL), dried with molecular sieves 4A powder over a period of 30 minutes and the resulting mixture was added to the pressure tube, which was flushed with nitrogen, capped and stirred in a heating block at 80° C. for 24 hours. Then the reaction mixture was filtered and rinsed using dichloromethane (50 mL). The filtrate was concentrated in vacuo and the obtained residue was purified using silica gel column chromatography (gradient elution: EtOAc-heptane 0:100 to 100:0). The desired fractions were concentrated under reduced pressure and the obtained powder was dried in a vacuum oven at 55° C. for 24 hours yielding compound 237 (213 mg). Method D: Rt: 1.89 min m/z: 431.1 (M−H)⁻ Exact mass: 432.1. ¹H NMR (400 MHz, DMSO-d₆) δ ppm 1.36 (s, 6H), 3.93 (s, 3H), 7.35 (d, J=2.0 Hz, 1H), 7.53 (t, J=9.1 Hz, 1H), 7.59 (d, J=1.8 Hz, 1H), 7.84-8.15 (m, 2H), 8.21 (dd, J=5.9, 2.6 Hz, 1H), 10.38 (br. s., 1H).

Compound 238: N-(3-Cyano-4-fluorophenyl)-1-methyl-4-[(3,3,3-trifluoro-1-methyl-propyl)sulfamoyl]-1H-pyrrole-2-carboxamide

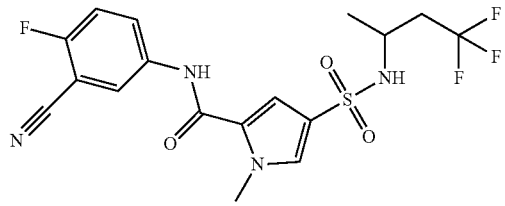 [SMILES: CC(CC(F)(F)F)NS(=O)(=O)c1cc(C(=O)Nc2ccc(F)c(C#N)c2)n(C)c1]

Compound 238 (206 mg) was prepared similarly as described for compound 237, using 4,4,4-trifluorobutan-2-amine instead of 2,2,2-trifluoro-1,1-dimethyl-ethylamine and 48 hours reaction time instead of 24 hours. Method D: Rt: 1.86 min m/z: 431.1 (M−H)⁻ Exact mass: 432.1. ¹H NMR (400 MHz, DMSO-d₆) δ ppm 1.06 (d, J=6.6 Hz, 3H), 2.29-2.47 (m, 2H), 3.50 (sxt, J=6.6 Hz, 1H), 3.93 (s, 3H), 7.36 (d, J=2.0 Hz, 1H), 7.40-7.88 (m, 3H), 8.01 (ddd, J=9.2, 5.0, 2.8 Hz, 1H), 8.22 (dd, J=5.8, 2.8 Hz, 1H), 10.38 (br. s., 1H).

Compound 239: N-(3-Cyano-4-fluorophenyl)-1-methyl-4-{[(1S)-1-(trifluoromethyl)-propyl]sulfamoyl}-1H-pyrrole-2-carboxamide

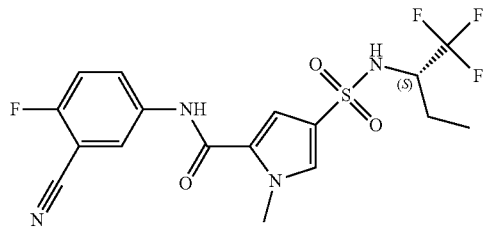

Compound 239 (236 mg) was prepared similarly as described for compound 237, using (S)-1-trifluoromethyl-propylamine instead of 2,2,2-trifluoro-1,1-dimethyl-ethylamine. Method D: Rt: 1.89 min m/z: 431.1 (M–H)⁻ Exact mass: 432.1. ¹H NMR (400 MHz, DMSO-$d_6$) δ ppm 0.70 (t, J=7.4 Hz, 3H), 1.32-1.51 (m, 1H), 1.56-1.74 (m, 1H), 3.68-3.85 (m, 1H), 3.95 (s, 3H), 7.37 (d, J=2.0 Hz, 1H), 7.53 (t, J=9.1 Hz, 1H), 7.64 (d, J=1.8 Hz, 1H), 8.02 (ddd, J=9.2, 5.0, 2.8 Hz, 1H), 8.06-8.33 (m, 2H), 10.37 (br. s., 1H).

Compound 240: N-(3-Cyano-4-fluorophenyl)-1-methyl-4-{[(1R)-1-(trifluoromethyl)-propyl]sulfamoyl}-1H-pyrrole-2-carboxamide

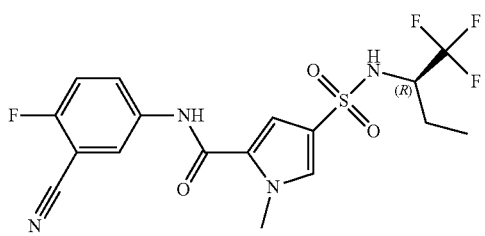

Compound 240 (244 mg) was prepared similarly as described for compound 237, using (R)-1-trifluoromethyl-propylamine instead of 2,2,2-trifluoro-1,1-dimethyl-ethyl-amine Method D: Rt: 1.89 min m/z: 431.1 (M–H)⁻ Exact mass: 432.1. ¹H NMR (400 MHz, DMSO-$d_6$) δ ppm 0.70 (t, J=7.4 Hz, 3H), 1.35-1.53 (m, 1H), 1.55-1.73 (m, 1H), 3.62-3.83 (m, 1H), 3.92 (s, 3H), 7.37 (d, J=1.8 Hz, 1H), 7.53 (t, J=9.1 Hz, 1H), 7.63 (d, J=1.5 Hz, 1H), 8.02 (ddd, J=9.2, 4.8, 2.9 Hz, 1H), 8.06-8.51 (m, 2H), 10.37 (br. s., 1H).

Compound 241: N-(3-Cyano-4-fluorophenyl)-1-methyl-4-{[1-(trifluoromethyl)cyclo-butyl]sulfamoyl}-1H-pyrrole-2-carboxamide

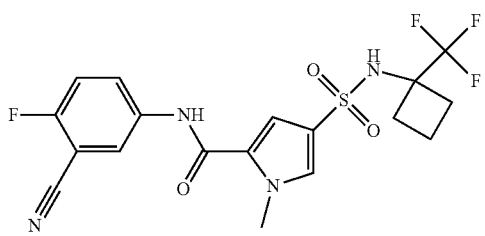 [SMILES: Cn1cc(S(=O)(=O)NC2(C(F)(F)F)CCC2)cc1C(=O)Nc1ccc(F)c(C#N)c1]

Compound 241 (119 mg) was prepared similarly as described for compound 237, using 1-trifluoromethyl-cyclobutylamine instead of 2,2,2-trifluoro-1,1-dimethyl-ethyl-amine and 48 hours reaction time instead of 24 hours. Method D: Rt: 1.91 min m/z: 443.1 (M–H)⁻ Exact mass: 444.1. ¹H NMR (400 MHz, DMSO-$d_6$) δ ppm 1.67-1.90 (m, 2H), 2.23-2.36 (m, 2H), 2.39-2.48 (m, 2H), 3.94 (s, 3H), 7.39 (d, J=1.8 Hz, 1H), 7.53 (t, J=9.1 Hz, 1H), 7.63 (d, J=1.8 Hz, 1H), 8.02 (ddd, J=9.2, 5.0, 2.8 Hz, 1H), 8.22 (dd, J=5.8, 2.8 Hz, 1H), 8.37 (br. s., 1H), 10.39 (br. s., 1H).

Compound 242: N-(3-Cyano-4-fluorophenyl)-4-{[2-fluoro-1-(fluoromethyl)ethyl]sulfamoyl}-1-methyl-1H-pyrrole-2-carboxamide

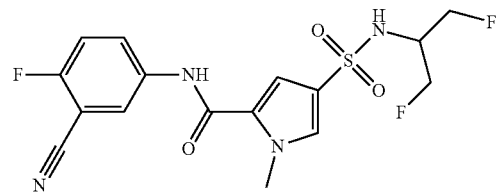 [SMILES: Cn1cc(S(=O)(=O)NC(CF)CF)cc1C(=O)Nc1ccc(F)c(C#N)c1]

Compound 242 (162 mg) was prepared similarly as described for compound 237, using 1,3-difluoropropan-2-amine hydrochloride instead of 2,2,2-trifluoro-1,1-dimethyl-ethylamine.

Method D: Rt: 1.70 min m/z: 399.0 (M–H)⁻ Exact mass: 400.1. ¹H NMR (400 MHz, DMSO-$d_6$) δ ppm 3.50-3.76 (m, 1H), 3.92 (s, 3H), 4.26-4.54 (m, 4H), 7.37 (d, J=2.0 Hz, 1H), 7.53 (t, J=9.1 Hz, 1H), 7.63 (d, J=1.5 Hz, 1H), 7.73-8.17 (m, 2H), 8.22 (dd, J=5.8, 2.8 Hz, 1H), 10.38 (br. s., 1H).

Compound 244: N-(3-cyano-4-fluoro-phenyl)-1-methyl-4-[(1-methylcyclopropyl)-sulfamoyl]pyrrole-2-carboxamide

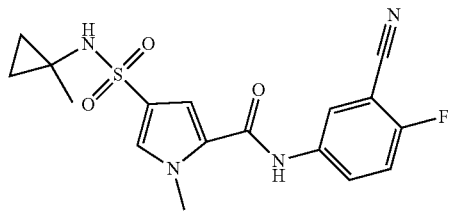 [SMILES: Cn1cc(S(=O)(=O)NC2(C)CC2)cc1C(=O)Nc1ccc(F)c(C#N)c1]

Compound 244 (144 mg) was prepared similarly as described for compound 237, using (1-methylcyclopropyl)amine hydrochloride instead of 2,2,2-trifluoro-1,1-dimethyl-ethylamine. Method B: Rt: 0.93 min m/z: 375.1 (M–H)⁻ Exact mass: 376.1. ¹H NMR (400 MHz, DMSO-$d_6$) δ ppm 0.30-0.47 (m, 2H), 0.63-0.73 (m, 2H), 1.18 (s, 3H), 3.93 (s, 3H), 7.33 (d, J=2.0 Hz, 1H), 7.53 (t, J=9.1 Hz, 1H), 7.56 (d, J=1.5 Hz, 1H), 7.68 (s, 1H), 8.02 (ddd, J=9.2, 5.0, 2.8 Hz, 1H), 8.22 (dd, J=5.9, 2.6 Hz, 1H), 10.36 (s, 1H).

Compound 245: N-(3-cyano-4-fluoro-phenyl)-4-[(3,3-difluoro-1-methyl-cyclobutyl)sulfamoyl]-1-methyl-1H-pyrrole-2-carboxamide

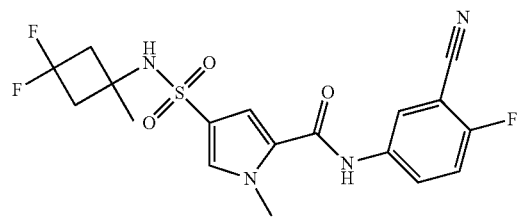 [SMILES: Cn1cc(S(=O)(=O)NC2(C)CC(F)(F)C2)cc1C(=O)Nc1ccc(F)c(C#N)c1]

Compound 245 (243 mg) was prepared similarly as described for compound 237, using 3,3-difluoro-1-methylcyclobutanamine hydrochloride instead of 2,2,2-trifluoro-1,1-dimethyl-ethylamine. Method B: Rt: 0.99 min m/z: 425.2 (M−H)⁻ Exact mass: 426.1. ¹H NMR (400 MHz, DMSO-d₆) δ ppm 1.39 (s, 3H), 2.40-2.57 (m, 2H), 2.74-2.95 (m, 2H), 3.93 (s, 3H), 7.35 (d, J=2.0 Hz, 1H), 7.53 (t, J=9.1 Hz, 1H), 7.61 (d, J=1.8 Hz, 1H), 7.87 (br. s., 1H), 8.01 (ddd, J=9.2, 4.8, 2.9 Hz, 1H), 8.21 (dd, J=5.7, 2.6 Hz, 1H), 10.37 (br. s., 1H).

Compound 246: N-(3-cyano-4-fluoro-phenyl)-1-methyl-4-{[1-methyl-1-(trifluoro-methyl)propyl]sulfamoyl}-1H-pyrrole-2-carboxamide

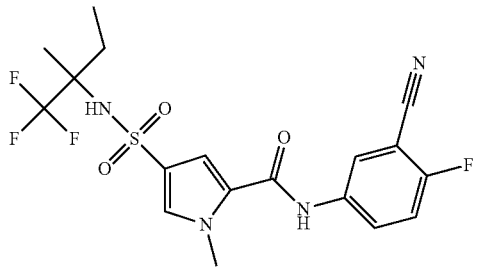 [SMILES: CCC(C)(NS(=O)(=O)c1cc(C(=O)Nc2ccc(F)c(C#N)c2)n(C)c1)C(F)(F)F]

Compound 246 (130 mg) was prepared similarly as described for compound 237, using 1,1,1-trifluoro-2-methylbutan-2-amine hydrochloride instead of 2,2,2-trifluoro-1,1-dimethyl-ethylamine and 48 hours reaction time instead of 24 hours.

Method B: Rt: 1.05 min m/z: 445.2 (M−H)⁻ Exact mass: 446.1. ¹H NMR (400 MHz, DMSO-d₆) δ ppm 0.79 (t, J=7.4 Hz, 3H), 1.37 (s, 3H), 1.46-1.58 (m, 1H), 1.73-1.89 (m, 1H), 3.92 (s, 3H), 7.35 (d, J=1.8 Hz, 1H), 7.53 (t, J=9.1 Hz, 1H), 7.58 (d, J=1.8 Hz, 1H), 7.89 (br. s., 1H), 8.02 (ddd, J=9.2, 4.9, 2.9 Hz, 1H), 8.21 (dd, J=5.8, 2.8 Hz, 1H), 10.37 (s, 1H).

Compound 247: N-(3-cyano-4-fluoro-phenyl)-1-methyl-4-{[4-(trifluoromethyl)tetrahydropyran-4-yl]sulfamoyl}-1H-pyrrole-2-carboxamide

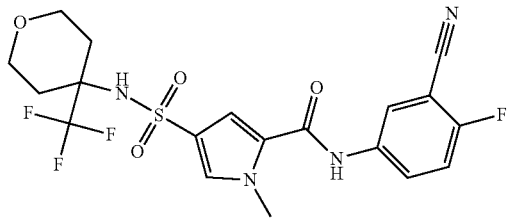 [SMILES: Cn1cc(S(=O)(=O)NC2(C(F)(F)F)CCOCC2)cc1C(=O)Nc1ccc(F)c(C#N)c1]

Compound 247 (23 mg) was prepared similarly as described for compound 237, using 4-(trifluoromethyl)oxan-4-amine hydrochloride instead of 2,2,2-trifluoro-1,1-dimethyl-ethylamine and 48 hours reaction time instead of 24 hours. An extra purification was performed via Prep HPLC (Stationary phase: RP XBridge Prep C18 OBD-10 μm, 30×150 mm, Mobile phase: 0.25% NH₄HCO₃ solution in water, MeOH). Method B: Rt: 0.96 min m/z: 473.1 (M−H)⁻ Exact mass: 474.1. ¹H NMR (400 MHz, DMSO-d₆) δ ppm 1.64-1.79 (m, 2H), 2.11 (d, J=13.4 Hz, 2H), 3.50 (t, J=11.4 Hz, 2H), 3.70-3.81 (m, 2H), 3.93 (s, 3H), 7.36 (d, J=1.8 Hz, 1H), 7.53 (t, J=9.1 Hz, 1H), 7.57-7.65 (m, 1H), 7.92 (br. s., 1H), 8.02 (ddd, J=9.2, 4.8, 2.9 Hz, 1H), 8.22 (dd, J=5.8, 2.8 Hz, 1H), 10.41 (br. s., 1H).

Compound 248: N-(3-cyano-4-fluoro-phenyl)-4-{[1-ethyl-1-(trifluoromethyl)propyl]sulfamoyl}-1-methyl-1H-pyrrole-2-carboxamide

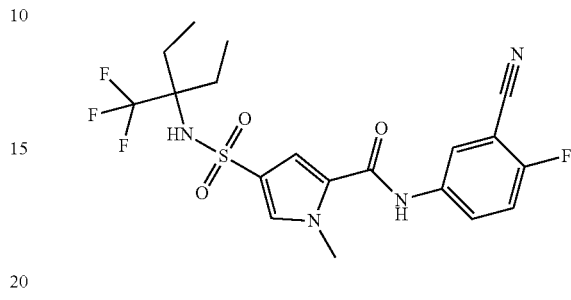

Compound 248 (40 mg) was prepared similarly as described for compound 237, using 3-(trifluoromethyl)pentan-3-amine hydrochloride instead of 2,2,2-trifluoro-1,1-dimethyl-ethylamine. Method B: Rt: 1.11 min m/z: 459.2 (M−H)⁻ Exact mass: 460.1

¹H NMR (400 MHz, DMSO-d₆) δ ppm 0.82 (t, J=7.4 Hz, 6H), 1.70-1.83 (m, 2H), 1.84-1.97 (m, 2H), 3.92 (s, 3H), 7.34 (d, J=1.8 Hz, 1H), 7.47-7.61 (m, 2H), 7.73 (br. s., 1H), 8.02 (ddd, J=9.2, 4.8, 2.9 Hz, 1H), 8.21 (dd, J=5.7, 2.6 Hz, 1H), 10.38 (br. s., 1H).

Compound 249: N-(3-cyano-4-fluoro-phenyl)-4-[(2-fluoro-1,1-dimethyl-ethyl)sulfamoyl]-1-methyl-1H-pyrrole-2-carboxamide

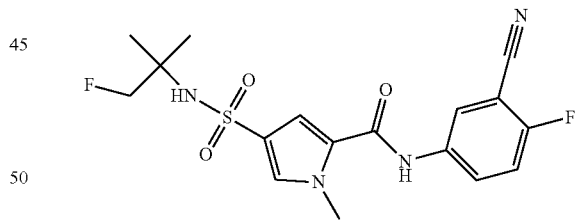

Compound 249 (178 mg) was prepared similarly as described for compound 237, using 1-fluoro-2-methylpropan-2-amine instead of 2,2,2-trifluoro-1,1-dimethyl-ethylamine Method B: Rt: 0.94 min m/z: 395.1 (M−H)⁻ Exact mass: 396.1. ¹H NMR (400 MHz, DMSO-d₆) δ ppm 1.13-1.20 (m, 6H), 3.92 (s, 3H), 4.24 (d, J=47.5 Hz, 2H), 7.35 (d, J=2.0 Hz, 1H), 7.41 (br. s., 1H), 7.53 (t, J=9.1 Hz, 1H), 7.58 (d, J=1.8 Hz, 1H), 8.01 (ddd, J=9.2, 4.9, 2.6 Hz, 1H), 8.22 (dd, J=5.9, 2.6 Hz, 1H), 10.36 (br. s., 1H).

Compound 250: N-(3-Bromophenyl)-3-chloro-1-methyl-4-{[(1R)-2,2,2-trifluoro-1-methylethyl]sulfamoyl}-1H-pyrrole-2-carboxamide

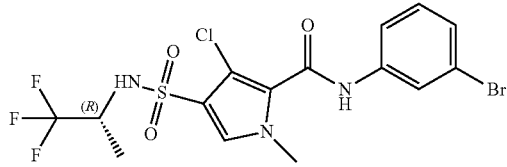

3-bromoaniline (92 mg, 0.53 mmol) and methyl 3-chloro-1-methyl-4-[[(1R)-2,2,2-trifluoro-1-methyl-ethyl]sulfamoyl]pyrrole-2-carboxylate (143 mg, 0.41 mmol) were dissolved in THF (10 mL). Lithium bis(trimethylsilyl)amide (1M in THF) (1.23 mL, 1 M, 1.23 mmol) was added and the reaction mixture was stirred overnight. The reaction mixture was quenched with sat. NH$_4$Cl (aq) (5 mL). The aqueous layer was extracted with CH$_2$Cl$_2$ (2×5 mL). The combined organic layers were evaporated to dryness and the residue was purified on silica using a heptane to EtOAc gradient. The obtained products was crystallized from CH$_2$Cl$_2$, triturated with diisopropylether and dried yielding, compound 250 (156 mg) as a white powder. Method D: Rt: 2.05 min m/z: 487.9 (M−H)⁻ Exact mass: 489.0. ¹H NMR (400 MHz, DMSO-d$_6$) δ ppm 1.19 (d, J=7.0 Hz, 3H), 3.77 (s, 3H), 3.91-4.01 (m, 1H), 7.29-7.37 (m, 2H), 7.61-7.69 (m, 2H), 7.97-8.04 (m, 1H), 8.48 (s, 1H), 10.51 (s, 1H). Differential scanning calorimetry: From 30 to 300° C. at 10° C./min: peak at 197.9° C.

Compound 251: N-(3-Bromophenyl)-3-fluoro-1-methyl-4-[(3-methyloxetan-3-yl)sulfamoyl]-1H-pyrrole-2-carboxamide

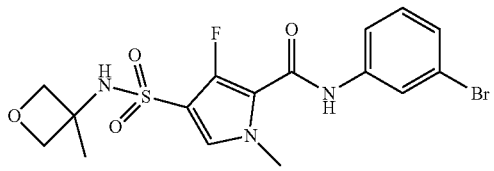 [SMILES: Cn1cc(S(=O)(=O)NC2(C)COC2)c(F)c1C(=O)Nc1cccc(Br)c1]

3-fluoro-1-methyl-4-[(3-methyloxetan-3-yl)sulfamoyl]pyrrole-2-carb oxy c acid (250 mg, 0.855 mmol), HATU (407 mg, 1.07 mmol), Et$_3$N (0.36 mL, 2.57 mmol) and 3-bromoaniline (294 mg, 1.71 mmol) in DMF (4 mL) were stirred 4 hours at 65° C. The solution was subjected to column chromatography on a 120 g silica gel Reveleris cartridge using a gradient from 10 till 100% EtOAc in heptane. The product fractions were concentrated and compound 251 was crystallized by dissolving the obtained liquid residue in methanol (30 mL) upon addition of water. The white crystals were filtered off and dried overnight in vacuo at 50° C. Method D: Rt: 1.81 min m/z: 446.0 (M−H)⁻ Exact mass: 447.0. ¹H NMR (400 MHz, DMSO-d$_6$) δ ppm 1.56 (s, 3H), 3.80 (s, 3H), 4.17 (d, J=6.4 Hz, 2H), 4.65 (d, J=6.2 Hz, 2H), 7.26-7.35 (m, 2H), 7.50 (d, J=4.6 Hz, 1H), 7.62 (dt, J=6.5, 2.4 Hz, 1H), 7.96-8.01 (m, 1H), 8.30 (s, 1H), 10.19 (s, 1H). Differential scanning calorimetry: From 30 to 300° C. at 10° C./min: peak at 193.4° C.

Compound 252: N-(3-chloro-2,4-difluoro-phenyl)-4-[(2,2-difluoro-1-methyl-ethyl)sulfamoyl]-1-methyl-1H-pyrrole-2-carboxamide

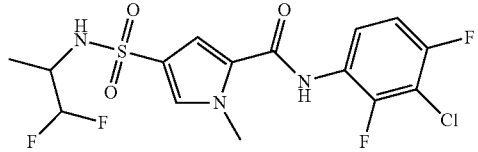 [SMILES: CC(NS(=O)(=O)c1cc(C(=O)Nc2ccc(F)c(Cl)c2F)n(C)c1)C(F)F]

5-[(3-chloro-2,4-difluoro-phenyl)carbamoyl]-1-methyl-pyrrole-3-sulfonyl chloride (0.25 g, 0.68 mmol) was dissolved in acetonitrile (6 mL) in a pressure tube and this was dried with powdered molecular sieves (4 Å) over a period of 30 minutes. Another tube was loaded with 1,1-difluoropropan-2-amine (1.0 mmol) and sodium bicarbonate (284 mg, 3.39 mmol) and this was dispersed in acetonitrile (2 mL) and dried with powdered molecular sieves (4 Å) over a period of 30 minutes. This was added to the pressure tube which was flushed with nitrogen, capped and stirred in a heating block at 80° C. for 24 hours. Then the reaction mixture was filtered and rinsed using dichloromethane (50 mL). The filtrate was concentrated in vacuo and the obtained residue was purified using silica gel column chromatography (gradient elution: EtOAc-heptane 0:100 to 100:0). The obtained powder was dried in a vacuum oven at 55° C. for 24 hours yielding compound 252 (204 mg) as a white powder. Method B: Rt: 1.00 min m/z: 426.1 (M−H)⁻ Exact mass: 427.0. ¹H NMR (400 MHz, DMSO-d$_6$) δ ppm 1.01 (d, J=7.0 Hz, 3H), 3.39-3.59 (m, 1H), 3.92 (s, 3H), 5.91 (td, J=55.9, 2.4 Hz, 1H), 7.29-7.39 (m, 2H), 7.46-7.58 (m, 1H), 7.63 (d, J=1.5 Hz, 1H), 7.85 (br. s., 1H), 10.14 (br. s., 1H).

Compound 253: N-(3-chloro-2,4-difluoro-phenyl)-1-methyl-4-{[1-(trifluoromethyl)-cyclopropyl]sulfamoyl}-1H-pyrrole-2-carboxamide

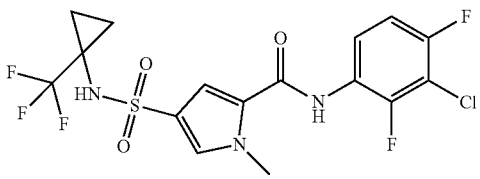 [SMILES: Cn1cc(S(=O)(=O)NC2(C(F)(F)F)CC2)cc1C(=O)Nc1ccc(F)c(Cl)c1F]

Compound 253 (104 mg) was prepared similarly as described for compound 252, using 1-trifluoromethyl-1-cyclopropylamine instead of 1,1-difluoropropan-2-amine and 48 hours reaction time instead of 24 hours. An extra purification was performed via Prep HPLC (Stationary phase: RP XBridge Prep C18 OBD-10 μm, 30×150 mm, Mobile phase: 0.25% NH$_4$HCO$_3$ solution in water, MeOH). Method B: Rt: 1.05 min m/z: 456.1 (M−H)⁻ Exact mass: 457.0. ¹H NMR (400 MHz, DMSO-d$_6$) δ ppm 1.07-1.24 (m, 4H), 3.89 (s, 3H), 7.29 (d, J=1.8 Hz, 1H), 7.35 (td, J=9.0, 1.9 Hz, 1H), 7.46-7.56 (m, 1H), 7.57 (d, J=1.8 Hz, 1H), 8.65 (br. s, 1H), 10.13 (br. s., 1H).

Compound 254: N-(3-chloro-2,4-difluoro-phenyl)-1-methyl-4-[(2,2,2-trifluoro-1,1-dimethyl-ethyl)sulfamoyl]-1H-pyrrole-2-carboxamide

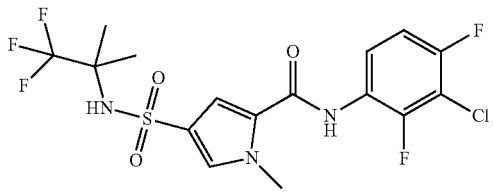 [SMILES: Cn1cc(S(=O)(=O)NC(C)(C)C(F)(F)F)cc1C(=O)Nc1ccc(F)c(Cl)c1F]

Compound 254 (75 mg) was prepared similarly as described for compound 252, using 2,2,2-trifluoro-1,1-dimethyl-ethylamine instead of 1,1-difluoropropan-2-amine. An extra purification was performed via Prep HPLC (Stationary phase: RP XBridge Prep C18 OBD-10 μm, 30×150 mm, Mobile phase: 0.25% NH$_4$HCO$_3$ solution in water, MeOH). Method B: Rt: 1.09 min m/z: 458.1 (M−H)⁻ Exact mass: 459.0. $^1$H NMR (400 MHz, DMSO-d$_6$) δ ppm 1.37 (s, 6H), 3.90 (s, 3H), 7.28-7.42 (m, 2H), 7.47-7.57 (m, 1H), 7.59 (d, J=1.8 Hz, 1H), 8.08 (br. s., 1H), 10.16 (br. s., 1H).

Compound 255: N-(3-chloro-2,4-difluoro-phenyl)-1-methyl-4-[(1-methylcyclopropyl)-sulfamoyl]-1H-pyrrole-2-carboxamide

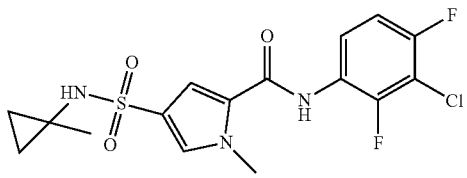 [SMILES: Cn1cc(S(=O)(=O)NC2(C)CC2)cc1C(=O)Nc1ccc(F)c(Cl)c1F]

Compound 255 (211 mg) was prepared similarly as described for compound 252, using (1-methylcyclopropyl)amine hydrochloride instead of 1,1-difluoropropan-2-amine. Method B: Rt: 1.00 min m/z: 402.1 (M−H)⁻ Exact mass: 403.1. $^1$H NMR (400 MHz, DMSO-d$_6$) δ ppm 0.36-0.44 (m, 2H), 0.66-0.75 (m, 2H), 1.20 (s, 3H), 3.90 (s, 3H), 7.30 (d, J=2.0 Hz, 1H), 7.34 (td, J=8.9, 2.0 Hz, 1H), 7.48-7.55 (m, 1H), 7.56 (d, J=1.5 Hz, 1H), 7.67 (br. s., 1H), 10.13 (br. s., 1H).

Compound 256: N-(3-chloro-2,4-difluoro-phenyl)-4-[(3,3-difluoro-1-methyl-cyclo-butyl)sulfamoyl]-1-methyl-1H-pyrrole-2-carboxamide

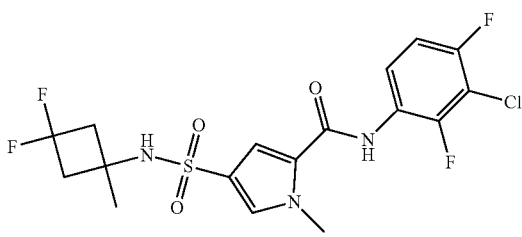 [SMILES: Cn1cc(S(=O)(=O)NC2(C)CC(F)(F)C2)cc1C(=O)Nc1ccc(F)c(Cl)c1F]

Compound 256 (258 mg) was prepared similarly as described for compound 252, using 3,3-difluoro-1-methyl-cyclobutanamine instead of 1,1-difluoropropan-2-amine. Method B: Rt: 1.05 min m/z: 452.1 (M−H)⁻ Exact mass: 453.1. $^1$H NMR (400 MHz, DMSO-d$_6$) δ ppm 1.41 (s, 3H), 2.43-2.57 (m, 2H), 2.73-2.94 (m, 2H), 3.90 (s, 3H), 7.30-7.40 (m, 2H), 7.48-7.57 (m, 1H), 7.60 (d, J=1.8 Hz, 1H), 7.87 (br. s., 1H), 10.14 (br. s., 1H).

Compound 257: N-(3-chloro-2,4-difluoro-phenyl)-1-methyl-4-{[1-methyl-1-(trifluoro-methyl)propyl]sulfamoyl}-1H-pyrrole-2-carboxamide

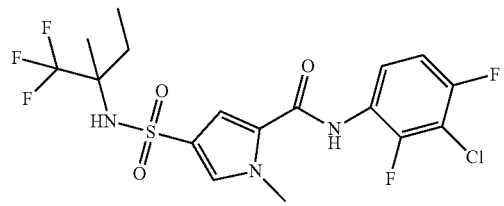 [SMILES: CCC(C)(NS(=O)(=O)c1cc(C(=O)Nc2ccc(F)c(Cl)c2F)n(C)c1)C(F)(F)F]

Compound 257 (71 mg) was prepared similarly as described for compound 252, using 1,1,1-trifluoro-2-methylbutan-2-amine hydrochloride instead of 1,1-difluoropropan-2-amine and 48 h reaction time instead of 24 h. An extra purification was performed via Prep HPLC (Stationary phase: RP XBridge Prep C18 OBD-10 μm, 30×150 mm, Mobile phase: 0.25% NH$_4$HCO$_3$ solution in water, MeOH). Method B: Rt: 1.13 min m/z: 472.1 (M−H)⁻ Exact mass: 473.1. $^1$H NMR (400 MHz, DMSO-d$_6$) δ ppm 0.81 (t, J=7.3 Hz, 3H), 1.38 (s, 3H), 1.53 (dq, J=14.0, 7.2 Hz, 1H), 1.73-1.89 (m, 1H), 3.89 (s, 3H), 7.29-7.39 (m, 2H), 7.47-7.56 (m, 1H), 7.57 (d, J=1.8 Hz, 1H), 7.89 (br. s., 1H), 10.14 (br. s., 1H).

Compound 258: N-(3-chloro-2,4-difluoro-phenyl)-1-methyl-4-[[4-(trifluoromethyl)-tetrahydropyran-4-yl]sulfamoyl]-1H-pyrrole-2-carboxamide

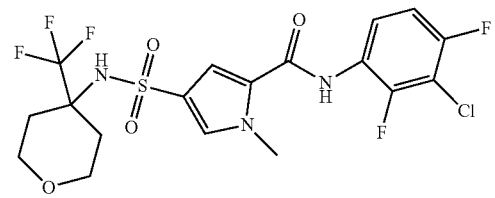 [SMILES: Cn1cc(S(=O)(=O)NC2(C(F)(F)F)CCOCC2)cc1C(=O)Nc1ccc(F)c(Cl)c1F]

Compound 258 (29 mg) was prepared similarly as described for compound 252, using 4-(trifluoromethyl)oxan-4-amine hydrochloride instead of 1,1-difluoropropan-2-amine and 48 h reaction time instead of 24 h. An extra purification was performed via Prep HPLC (Stationary phase: RP XBridge Prep C18 OBD-10 μm, 30×150 mm, Mobile phase: 0.25% NH$_4$HCO$_3$ solution in water, MeOH). Method B: Rt: 1.03 min m/z: 500.1 (M−H)⁻ Exact mass: 501.1. $^1$H NMR (400 MHz, DMSO-d$_6$) δ ppm 1.64-1.78 (m, 2H), 2.06-2.18 (m, 2H), 3.51 (t, J=11.4 Hz, 2H), 3.71-3.82 (m, 2H), 3.90 (s, 3H), 7.27-7.41 (m, 2H), 7.49-7.57 (m, 1H), 7.57-7.61 (m, 1H), 7.91 (br. s., 1H), 10.17 (br. s., 1H).

Compound 259: N-(3-chloro-2,4-difluoro-phenyl)-4-[[1-ethyl-1-(trifluoromethyl)-propyl]sulfamoyl]-1-methyl-1H-pyrrole-2-carboxamide

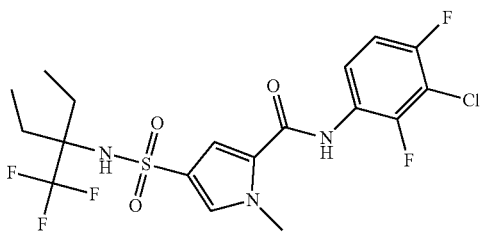 [SMILES: CCC(CC)(NS(=O)(=O)c1cc(C(=O)Nc2ccc(F)c(Cl)c2F)n(C)c1)C(F)(F)F]

Compound 259 (114 mg) was prepared similarly as described for compound 252, using 3-(trifluoromethyl)pentan-3-amine hydrochloride instead of 1,1-difluoropropan-2-amine. Method B: Rt: 1.16 min m/z: 486.1 (M–H)⁻ Exact mass: 487.1. ¹H NMR (400 MHz, DMSO-d₆) δ ppm 0.84 (t, J=7.4 Hz, 6H), 1.68-2.02 (m, 4H), 3.90 (s, 3H), 7.29-7.41 (m, 2H), 7.47-7.54 (m, 1H), 7.55 (d, J=1.5 Hz, 1H), 7.62-7.94 (m, 1H), 10.14 (br. s., 1H).

Compound 260: N-(3-chloro-2,4-difluoro-phenyl)-1-methyl-4-[(3,3,3-trifluoro-1-methylpropyl)sulfamoyl]-1H-pyrrole-2-carboxamide

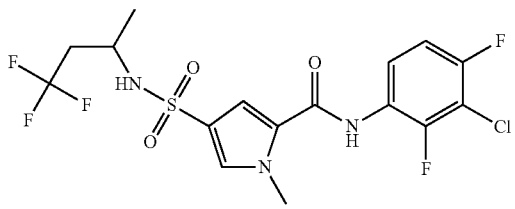 [SMILES: CC(CC(F)(F)F)NS(=O)(=O)c1cc(C(=O)Nc2ccc(F)c(Cl)c2F)n(C)c1]

Compound 260 (252 mg) was prepared similarly as described for compound 252, using 4,4,4-trifluorobutan-2-amine instead of 1,1-difluoropropan-2-amine. Method B: Rt: 1.06 min m/z: 458.1 (M–H)⁻ Exact mass: 459.0. ¹H NMR (400 MHz, DMSO-d₆) δ ppm 1.08 (d, J=6.6 Hz, 3H), 2.24-2.49 (m, 2H), 3.50 (sxt, J=6.5 Hz, 1H), 3.92 (s, 3H), 7.20-7.41 (m, 2H), 7.42-7.81 (m, 3H), 10.13 (br. s., 1H).

Compound 261: N-(3-chloro-2,4-difluoro-phenyl)-4-[(2-fluoro-1,1-dimethyl-ethyl)sulfamoyl]-1-methyl-1H-pyrrole-2-carboxamide

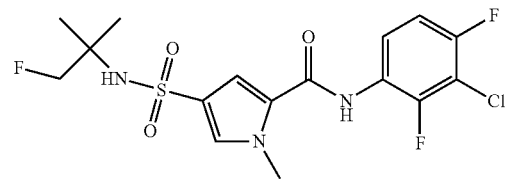 [SMILES: Cn1cc(S(=O)(=O)NC(C)(C)CF)cc1C(=O)Nc1ccc(F)c(Cl)c1F]

Compound 261 (143 mg) was prepared similarly as described for compound 252, using 1-fluoro-2-methylpropan-2-amine instead of 1,1-difluoropropan-2-amine. The desired fractions were concentrated under reduced pressure yielding a powder. An extra purification was performed via Prep HPLC (Stationary phase: RP XBridge Prep C18 OBD-10 μm, 30×150 mm, Mobile phase: 0.25% NH₄HCO₃ solution in water, MeOH). Method B: Rt: 1.03 min m/z: 422.1 (M–H)⁻ Exact mass: 423.1. ¹H NMR (400 MHz, DMSO-d₆) δ ppm 1.13-1.22 (m, 6H), 3.90 (s, 3H), 4.24 (d, J=47.3 Hz, 2H), 7.29-7.37 (m, 2H), 7.41 (br. s., 1H), 7.49-7.55 (m, 1H), 7.56 (d, J=1.8 Hz 1H), 10.13 (br. s., 1H).

Compound 262: N-(3-chloro-2,4-difluoro-phenyl)-1-methyl-4-{[(1S)-1-(trifluoro-methyl)propyl]sulfamoyl}-1H-pyrrole-2-carboxamide

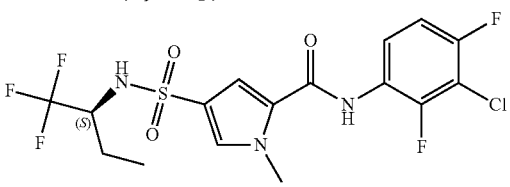

Compound 262 (227 mg) was prepared similarly as described for compound 252, using (S)-1-trifluoromethyl-propylamine instead of 1,1-difluoropropan-2-amine.
Method B: Rt: 1.08 min m/z: 458.1 (M–H)⁻ Exact mass: 459.0. ¹H NMR (400 MHz, DMSO-d₆) δ ppm 0.73 (t, J=7.5 Hz, 3H), 1.38-1.52 (m, 1H), 1.58-1.73 (m, 1H), 3.62-3.84 (m, 1H), 3.89 (s, 3H), 7.28-7.40 (m, 2H), 7.45-7.58 (m, 1H), 7.63 (d, J=1.5 Hz, 1H), 8.15 (br. s., 1H), 10.12 (br. s, 1H).

Compound 263: N-(3-chloro-2,4-difluoro-phenyl)-1-methyl-4-{[1-(trifluoromethyl)-cyclobutyl]sulfamoyl}-1H-pyrrole-2-carboxamide

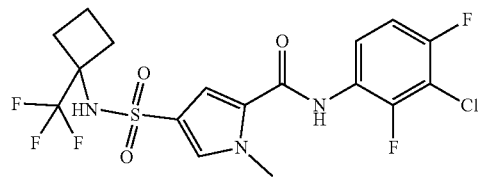 [SMILES: Cn1cc(S(=O)(=O)NC2(C(F)(F)F)CCC2)cc1C(=O)Nc1ccc(F)c(Cl)c1F]

Compound 263 (154 mg) was prepared similarly as described for compound 252, using 1-trifluoromethyl-cyclobutylamine instead of 1,1-difluoropropan-2-amine and 48 h reaction time instead of 24 h. An extra purification was performed via Prep HPLC (Stationary phase: RP XBridge Prep C18 OBD-10 μm, 30×150 mm, Mobile phase: 0.25% NH₄HCO₃ solution in water, MeOH). Method B: Rt: 1.10 min m/z: 470.1 (M–H)⁻ Exact mass: 471.0. ¹H NMR (400 MHz, DMSO-d₆) δ ppm 1.71-1.92 (m, 2H), 2.21-2.37 (m, 2H), 2.39-2.49 (m, 2H), 3.91 (s, 3H), 7.25-7.43 (m, 2H), 7.46-7.58 (m, 1H), 7.62 (d, J=1.8 Hz, 1H), 8.38 (br. s., 1H), 10.16 (br. s., 1H).

Compound 264: N-(3-chloro-2,4-difluoro-phenyl)-4-{[2-fluoro-1-(fluoromethyl)-ethyl]sulfamoyl}-1-methyl-1H-pyrrole-2-carboxamide

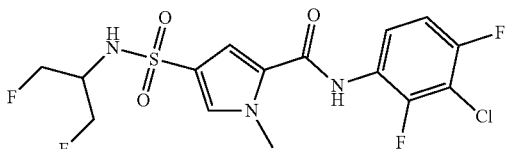

Compound 264 (231 mg) was prepared similarly as described for compound 252, using 1,3-difluoropropan-2-amine hydrochloride instead of 1,1-difluoropropan-2-amine. Method B: Rt: 0.96 min m/z: 426.1 (M−H)⁻ Exact mass: 427.0. ¹H NMR (400 MHz, DMSO-d₆) δ ppm 3.53-3.75 (m, 1H), 3.89 (s, 3H), 4.28-4.53 (m, 4H), 7.24-7.41 (m, 2H), 7.45-7.58 (m, 1H), 7.62 (d, J=1.8 Hz, 1H), 8.04 (br. s., 1H), 10.02 (br. s, 1H).

Compound 265: N-(3-chloro-2,4-difluoro-phenyl)-1-methyl-4-{[(1R)-1-(trifluoro-methyl)propyl]sulfamoyl}-1H-pyrrole-2-carboxamide

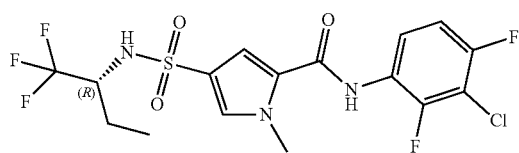

Compound 265 (241 mg) was prepared similarly as described for compound 252, using (R)-1,1,1-trifluoro-2-butylamine instead of 1,1-difluoropropan-2-amine and 48 hours reaction time instead of 24 h. Method B: Rt: 1.09 min m/z: 458.1 (M−H)⁻ Exact mass: 459.0. ¹H NMR (400 MHz, DMSO-d₆) δ ppm 0.73 (t, J=7.5 Hz, 3H), 1.38-1.52 (m, 1H), 1.58-1.73 (m, 1H), 3.67-3.83 (m, 1H), 3.89 (s, 3H), 7.29-7.39 (m, 2H), 7.45-7.58 (m, 1H), 7.63 (d, J=1.5 Hz, 1H), 8.16 (br. s., 1H), 10.13 (br. s., 1H).

Compound 266: N-(3-chloro-2,4-difluoro-phenyl)-1-methyl-4-{[3-(trifluoromethyl)-tetrahydrofuran-3-yl]sulfamoyl}-1H-pyrrole-2-carboxamide

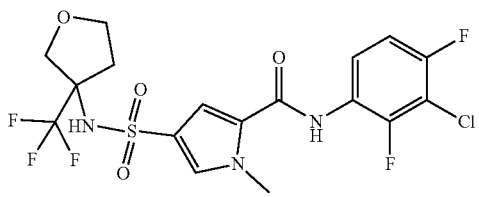 [SMILES: Cn1cc(S(=O)(=O)NC2(C(F)(F)F)CCOC2)cc1C(=O)Nc1ccc(F)c(Cl)c1F]

Compound 266 (140 mg) was prepared similarly as described for compound 252, using 3-(trifluoromethyl)tetrahydrofuran-3-amine hydrochloride instead of 1,1-difluoropropan-2-amine. An extra purification was performed via Prep HPLC (Stationary phase: RP XBridge Prep C18 OBD-10 μm, 30×150 mm, Mobile phase: 0.25% NH₄HCO₃ solution in water, MeOH). Method B: Rt: 1.03 min m/z: 486.1 (M−H)⁻ Exact mass: 487.0. ¹H NMR (400 MHz, DMSO-d₆) δ ppm 2.19 (dt, J=13.8, 8.1 Hz, 1H), 2.40-2.48 (m, 1H), 3.62 (q, J=7.8 Hz, 1H), 3.79-3.87 (m, 1H), 3.89 (s, 3H), 3.95 (d, J=10.1 Hz, 1H), 4.01-4.11 (m, 1H), 7.27-7.41 (m, 2H), 7.49-7.57 (m, 1H), 7.60 (d, J=1.8 Hz, 1H), 8.52 (br. s., 1H), 10.15 (br. s., 1H).

Compound 267: 3-chloro-N-(3,4-difluorophenyl)-1-methyl-4-{[1-(trifluoromethyl)-cyclobutyl]sulfamoyl}-1H-pyrrole-2-carboxamide

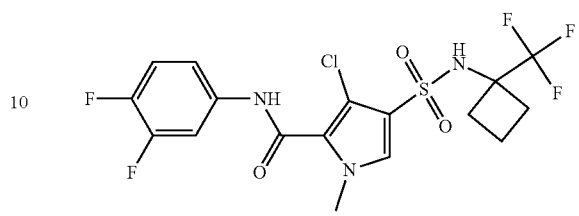

Methyl 3-chloro-1-methyl-4-[[1-(trifluoromethyl)cyclobutyl]sulfamoyl]pyrrole-2-carboxylate (83 mg, 0.22 mmol) and 3,4-difluoroaniline (37 mg, 0.29 mmol) were dissolved in dry THF (10 mL) and cooled to 0° C. Lithium bis(trimethylsilyl)amide (1M in THF) (0.66 mL, 1 M, 0.66 mmol) was added dropwise and the reaction mixture was allowed to reach room temperature. The volatiles were removed under reduced pressure and the residue was purified on silica using a heptane to EtOAc gradient and further by preparative HPLC (Stationary phase: RP XBridge Prep C18 OBD-10 μm, 30×150 mm, Mobile phase: 0.25% NH₄HCO₃ solution in water, CH₃CN);—resulting in compound 267 (60 mg). Method B: Rt: 1.11 min m/z: 470.1 (M−H)⁻ Exact mass: 471.0.

¹H NMR (400 MHz, DMSO-d₆) δ ppm 1.74-1.91 (m, 2H), 2.24-2.36 (m, 2H), 2.41-2.50 (m, 2H), 3.78 (s, 3H), 7.38-7.51 (m, 2H), 7.65 (s, 1H), 7.80-7.90 (m, 1H), 8.59 (br. s., 1H), 10.55 (s, 1H).

Compound 268: 3-chloro-N-(3-chloro-4-fluoro-phenyl)-1-methyl-4-{[1-(trifluoro-methyl)cyclobutyl]sulfamoyl}-1H-pyrrole-2-carboxamide

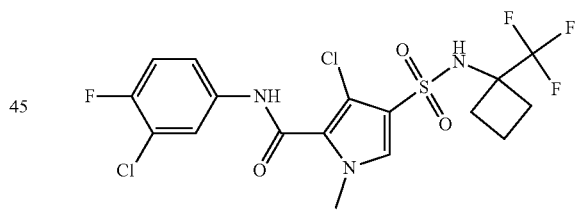

Methyl 3-chloro-1-methyl-4-[[1-(trifluoromethyl)cyclobutyl]sulfamoyl]pyrrole-2-carboxylate (155 mg, 0.2 mmol) and 3-chloro-4-fluoro-aniline (38 mg, 0.26 mmol) were dissolved in dry THF (10 mL) and cooled to 0° C. Lithium bis(trimethylsilyl)amide (1M in THF) (0.6 mL, 1 M, 0.6 mmol) was added dropwise and the reaction mixture was allowed to reach room temperature. After 1 hour more lithium bis(trimethylsilyl)amide (1M in THF) (0.6 mL, 1 M, 0.6 mmol) was added and the reaction mixture was stirred for another hour. The volatiles were removed under reduced pressure and the residue was purified on silica using a heptane to EtOAc gradient and further Preparative HPLC (Stationary phase: RP XBridge Prep C18 OBD-10 μm, 30×150 mm, Mobile phase: 0.25% NH₄HCO₃ solution in water, CH₃CN)—resulting in compound 268 (23 mg). Method B: Rt: 1.17 min m/z: 486.0 (M−H)⁻ Exact mass: 487.0. ¹H NMR (400 MHz, DMSO-d₆) δ ppm 1.72-1.88 (m, 2H), 2.20-2.36 (m, 2H), 2.41-2.53 (m, 2H), 3.78 (s, 3H), 7.43 (t, J=9.1 Hz, 1H), 7.58-7.69 (m, 2H), 7.99 (dd, J=6.8, 2.4 Hz, 1H), 8.61 (br. s., 1H), 10.53 (s, 1H).

Compound 269: 3-Chloro-N-(3-cyano-4-fluorophenyl)-1-methyl-4-[(1-methylethyl)sulfamoyl]-1H-pyrrole-2-carboxamide

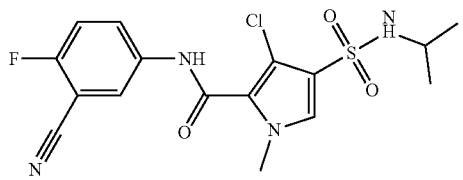 [SMILES: CC(C)NS(=O)(=O)c1cn(C)c(C(=O)Nc2ccc(F)c(C#N)c2)c1Cl]

Methyl 3-chloro-4-chlorosulfonyl-1-methyl-pyrrole-2-carboxylate (1.5 g, 5.51 mmol) was dissolved in acetonitrile (8 mL) and dried on molecular sieves. NaHCO$_3$ (1389 mg, 16.54 mmol) was added. Isopropylamine (493.71 mg, 8.27 mmol) was dissolved in acetonitrile (2 mL) and dried on molecular sieves. The two suspensions were combined and heated at 70° C. for 2 hours. The reaction mixture was filtered and washed with acetonitrile and evaporated to dryness to afford a crude residue (1.68 g). The crude was purified using silica gel column chromatography (ethyl acetate in heptane from 0 to 100%) to afford methyl 3-chloro-4-(isopropylsulfamoyl)-1-methyl-pyrrole-2-carboxylate (1.62 g). Method D: Rt: 1.62 min m/z: 293.0 (M−H)$^−$ Exact mass: 294.0. Methyl 3-chloro-4-(isopropylsulfamoyl)-1-methyl-pyrrole-2-carboxylate (500 mg, 1.7 mmol) and 5-amino-2-fluorobenzonitrile (0.26 g, 1.86 mmol) were dissolved in dry THF under a blanket of nitrogen. The reaction mixture was cooled to 0° C. and lithium bis(trimethylsilyl)amide (1M in toluene) (5.09 mL, 1 M, 5.09 mmol) was added over a period of 2 minutes. The resulting mixture was stirred for 2 minutes while cooling was continued. The mixture was quenched with saturated ammonium chloride (50 mL) and extracted using EtOAc (2×100 mL). The combined extracts were washed with brine (50 mL), dried on Na$_2$SO$_4$, filtered and concentrated in vacuo to afford a dark brown powder which was purified using silica gel column chromatography (ethyl acetate in heptane from 0 to 100%) and further via Prep HPLC (Stationary phase: RP XBridge Prep C18 OBD-10 μm, 30×150 mm, Mobile phase: 0.25% NH$_4$HCO$_3$ solution in water, CH$_3$CN) yielding compound 269 (449 mg). Method B: Rt: 0.94 min m/z: 397.1 (M−H)$^−$ Exact mass: 398.1. $^1$H NMR (400 MHz, DMSO-d$_6$) δ ppm 1.05 (d, J=6.6 Hz, 6H), 3.24-3.38 (m, 1H), 3.77 (s, 3H), 7.49 (br. d, J=6.8 Hz, 1H), 7.55 (t, J=9.1 Hz, 1H), 7.62 (s, 1H), 7.99 (ddd, J=9.2, 4.8, 2.8 Hz, 1H), 8.20 (dd, J=5.8, 2.8 Hz, 1H), 10.67 (br. s., 1H).

Compound 270: 3-Chloro-N-(3-cyano-4-fluorophenyl)-1-methyl-4-[(2,2,2-trifluoro-1,1-dimethylethyl)sulfamoyl]-1H-pyrrole-2-carboxamide

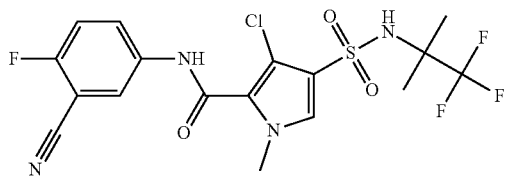 [SMILES: Cn1cc(S(=O)(=O)NC(C)(C)C(F)(F)F)c(Cl)c1C(=O)Nc1ccc(F)c(C#N)c1]

Compound 270 was prepared similarly as described for compound 269, using 3 equiv 2,2,2-trifluoro-1,1-dimethylethylamine, instead of 1.5 equiv isopropylamine (heating was continued for more then 44 hours at 80° C. instead of 2 hours at 70° C.). Method B: Rt: 1.04 min m/z: 465.1 (M−H)$^−$ Exact mass: 466.0. $^1$H NMR (400 MHz, DMSO-d$_6$) δ ppm 1.38 (s, 6H), 3.78 (s, 3H), 7.56 (t, J=9.1 Hz, 1H), 7.66 (s, 1H), 7.99 (ddd, J=9.1, 4.8, 2.8 Hz, 1H), 8.20 (dd, J=5.7, 2.6 Hz, 1H), 8.34 (br. s., 1H), 10.64 (br. s., 1H).

Compound 271: 3-Chloro-N-(3-cyano-4-fluorophenyl)-1-methyl-4-{[1-(trifluoro-methyl)cyclopropyl]sulfamoyl}-1H-pyrrole-2-carboxamide

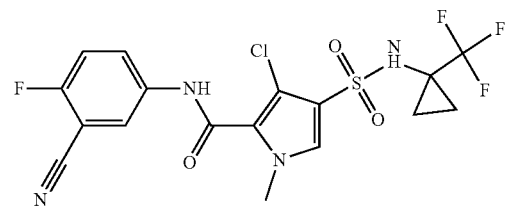 [SMILES: Cn1cc(S(=O)(=O)NC2(C(F)(F)F)CC2)c(Cl)c1C(=O)Nc1ccc(F)c(C#N)c1]

Compound 271 was prepared similarly as described for compound 270, using 1-(trifluoromethyl)cyclopropanamine instead of 2,2,2-trifluoro-1,1-dimethyl-ethylamine. Method B: Rt: 1.01 min m/z: 463.1 (M−H)$^−$ Exact mass: 464.1. Differential scanning calorimetry: From 30 to 300° C. at 10° C./min: peak at 209.5° C. $^1$H NMR (400 MHz, DMSO-d$_6$) δ ppm 1.10-1.25 (m, 4H), 3.78 (s, 3H), 7.56 (t, J=9.1 Hz, 1H), 7.65 (s, 1H), 7.98 (ddd, J=9.1, 4.8, 2.8 Hz, 1H), 8.19 (dd, J=5.8, 2.8 Hz, 1H), 9.01 (br. s., 1H), 10.67 (br. s., 1H).

Compound 272: 3-chloro-N-(2-cyano-4-fluoro-3-methyl-phenyl)-1-methyl-4-[[(1R)-2,2,2-trifluoro-1-methyl-ethyl]sulfamoyl]pyrrole-2-carboxamide

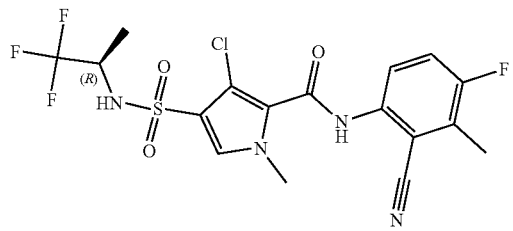

Compound 272 was prepared similarly as described for compound 250, using 6-amino-3-fluoro-2-methyl-benzonitrile instead of 3-bromoaniline. Differential scanning calorimetry: From 30 to 300° C. at 10° C./min: peak at 235.1° C. Method B: Rt: 1.05 min m/z: 465.1 (M−H)$^−$ Exact mass: 466.0. $^1$H NMR (400 MHz, DMSO-d$_6$) δ ppm 1.19 (d, J=6.8 Hz, 3H), 2.43 (d, J=2.2 Hz, 3H), 3.81 (s, 3H), 3.91-4.05 (m, 1H), 7.50 (dd, J=8.8, 4.8 Hz, 1H), 7.59 (t, J=9.0 Hz, 1H), 7.70 (s, 1H), 8.49 (d, J=6.6 Hz, 1H), 10.44 (br. s., 1H).

Compound 273: 3-chloro-N-(2-cyano-4-fluoro-phenyl)-1-methyl-4-[[(1R)-2,2,2-trifluoro-1-methyl-ethyl]sulfamoyl]pyrrole-2-carboxamide

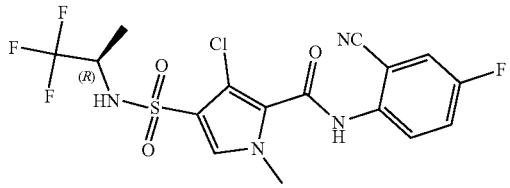

Compound 273 was prepared similarly as described for compound 250, using 2-amino-5-fluorobenzonitrile instead of 3-bromoaniline. Method D: Rt: 1.82 min m/z: 451.0 (M−H)⁻ Exact mass: 452.0. Differential scanning calorimetry: From 30 to 300° C. at 10° C./min: peak at 200.7° C. ¹H NMR (400 MHz, DMSO-d₆) δ ppm 1.19 (d, J=6.8 Hz, 3H), 3.81 (s, 3H), 3.91-4.06 (m, 1H), 7.61-7.69 (m, 2H), 7.70 (s, 1H), 7.87-7.95 (m, 1H), 8.50 (d, J=8.6 Hz, 1H), 10.49 (s, 1H).

Compound 274: 3-chloro-N-[4-fluoro-3-(trifluoromethyl)phenyl]-1-methyl-4-[[(1R)-2,2,2-trifluoro-1-methyl-ethyl]sulfamoyl]pyrrole-2-carboxamide

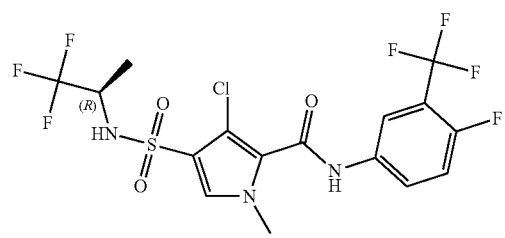

Compound 274 was prepared similarly as described for compound 250, using 4-fluoro-3-(trifluoromethyl)aniline instead of 3-bromoaniline. Method B: Rt: 1.15 min m/z: 494.1 (M−H)⁻ Exact mass: 495.0. Differential scanning calorimetry: From 30 to 300° C. at 10° C./min: peak at 189.8° C. ¹H NMR (400 MHz, DMSO-d₆) δ ppm 1.19 (d, J=6.8 Hz, 3H), 3.78 (s, 3H), 3.91-4.04 (m, 1H), 7.54 (t, J=9.8 Hz, 1H), 7.68 (s, 1H), 7.91-8.02 (m, 1H), 8.19 (dd, J=6.4, 2.4 Hz, 1H), 8.49 (br. s., 1H), 10.67 (s, 1H).

Compound 275: 3-chloro-N-(2-fluoro-6-methyl-phenyl)-1-methyl-4-[[(1R)-2,2,2-trifluoro-1-methyl-ethyl]sulfamoyl]pyrrole-2-carboxamide

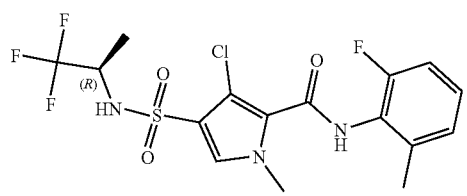

Compound 275 was prepared similarly as described for compound 250, using 2-fluoro-6-methylaniline instead of 3-bromoaniline. Method B: Rt: 0.99 min m/z: 440.1 (M−H)⁻ Exact mass: 441.1. ¹H NMR (400 MHz, DMSO-d₆) δ ppm 1.14-1.29 (m, 3H), 2.28 (s, 3H), 3.76 (s, 3H), 3.91-4.03 (m, 1H), 7.08-7.18 (m, 2H), 7.22-7.32 (m, 1H), 7.65 (s, 1H), 8.45 (br. s., 1H), 9.85 (s, 1H).

Compound 276: 3-chloro-N-(3-cyano-2,4-difluoro-phenyl)-1-methyl-4-[[(1R)-2,2,2-trifluoro-1-methyl-ethyl]sulfamoyl]pyrrole-2-carboxamide

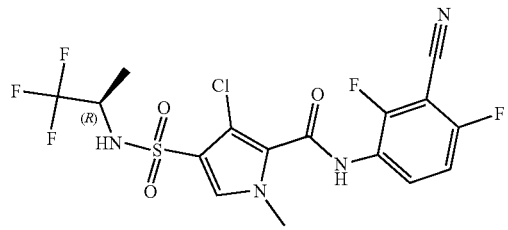

Compound 276 was prepared similarly as described for compound 250, using 3-amino-2,6-difluorobenzonitrile instead of 3-bromoaniline. Differential scanning calorimetry: From 30 to 300° C. at 10° C./min: peak at 217.6° C. Method B: Rt: 1.03 min m/z: 469.1 (M−H)⁻ Exact mass: 470.0. ¹H NMR (400 MHz, DMSO-d₆) δ ppm 1.19 (d, J=6.8 Hz, 3H), 3.79 (s, 3H), 3.91-4.04 (m, 1H), 7.47 (dt, J=8.9, 1.5 Hz, 1H), 7.70 (s, 1H), 8.09 (td, J=9.0, 6.2 Hz, 1H), 8.50 (br. s., 1H), 10.36 (br. s., 1H).

Compound 277: 3-chloro-N-(2,3-dichloro-4-fluoro-phenyl)-1-methyl-4-[[(1R)-2,2,2-trifluoro-1-methyl-ethyl]sulfamoyl]pyrrole-2-carboxamide

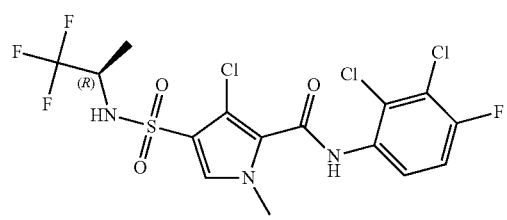

Compound 277 was prepared similarly as described for compound 250, using 2,3-dichloro-4-fluoroaniline instead of 3-bromoaniline. Differential scanning calorimetry: From 30 to 300° C. at 10° C./min: peak at 206.0° C. Method B: Rt: 1.20 min m/z: 496.0 (M−H)⁻ Exact mass: 495.0. ¹H NMR (400 MHz, DMSO-d₆) δ ppm 1.19 (d, J=6.8 Hz, 3H), 3.81 (s, 3H), 3.91-4.03 (m, 1H), 7.52 (t, J=8.9 Hz, 1H), 7.70 (s, 1H), 7.76 (dd, J=9.1, 5.4 Hz, 1H), 8.49 (br. s., 1H), 10.08 (br. s., 1H).

Compound 278: 3-chloro-N-[3-(difluoromethyl)-2,4-difluoro-phenyl]-1-methyl-4-[[(1R)-2,2,2-trifluoro-1-methyl-ethyl]sulfamoyl]pyrrole-2-carboxamide

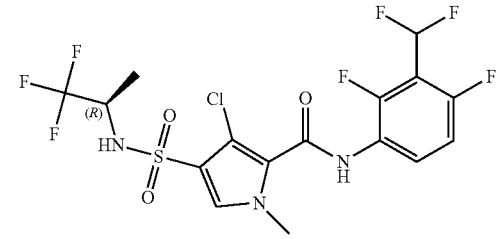

Diethylaminosulfur trifluoride (23.4 mL) was added to the solution of 2,6-difluoro-3-nitro-benzaldehyde (18 g, 96.21 mmol) in dichloromethane (180 mL) at −78° C. under N$_2$ atmosphere. The mixture was stirred for 1 hour and then warmed to 25° C. for 4 hours. The mixture was poured into aqueous NaHCO$_3$/ice and the aqueous phase was extracted twice with ethyl acetate. The combined organic layers were dried and concentrated in vacuo, resulting in crude 2-(difluoromethyl)-1,3-difluoro-4-nitro-benzene (15 g). 2-(difluoromethyl)-1,3-difluoro-4-nitro-benzene (10 g, 47.8 mmol) was stirred in water (100 mL) and ethanol (100 mL). Fe (16.0 g, 286.8 mmol) and ammonium chloride (15.34 g, 286.8 mmol) were added at 0° C. The mixture was stirred at 70° C. for 2 hours, filtered off and the filtrate was concentrated in vacuo. The residue was dissolved in water (20 mL) and extracted with ethyl acetate (3×50 mL). The combined organic layers were washed with brine and dried over Na$_2$SO$_4$. The solvent was removed in vacuo and the obtained residue was dissolved in ethyl acetate (5 mL), and then HCl/ethylacetate (2 mL) was added. The mixture was stirred at 20° C. for 20 minutes. The volatiles were removed in vacuo, resulting in 3-(difluoromethyl)-2,4-difluoro-aniline hydrochloride (5.1 g). Compound 278 was prepared similarly as described for compound 250, using 3-(difluoromethyl)-2,4-difluoro-aniline hydrochloride instead of 3-bromoaniline. Differential scanning calorimetry: From 30 to 300° C. at 10° C./min: peak at 189.5° C. Method B: Rt: 1.07 min m/z: 494.1 (M−H)⁻ Exact mass: 495.0. $^1$H NMR (400 MHz, DMSO-d$_6$) δ ppm 1.19 (d, J=6.8 Hz, 3H), 3.79 (s, 3H), 3.97 (br. s., 1H), 7.32 (t, J=9.8 Hz, 1H), 7.35 (t, J=52.0 Hz, 1H), 7.68 (s, 1H), 7.87-7.98 (m, 1H), 8.48 (br. s., 1H), 10.19 (br. s., 1H).

Compound 279: 3-chloro-N-[3-(difluoromethyl)-4-fluoro-phenyl]-1-methyl-4-[[(1R)-2,2,2-trifluoro-1-methyl-ethyl]sulfamoyl]pyrrole-2-carboxamide

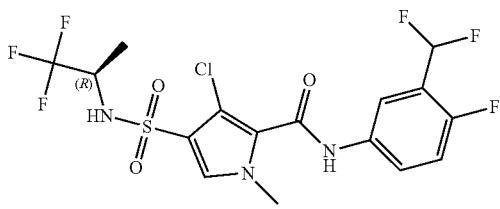

Compound 279 was prepared similarly as described for compound 250, using 3-(difluoromethyl)-4-fluoro-aniline instead of 3-bromoaniline. Differential scanning calorimetry: From 30 to 300° C. at 10° C./min: peak at 190.4° C. Method B: Rt: 1.06 min m/z: 476.1 (M−H)⁻ Exact mass: 477.0. $^1$H NMR (400 MHz, DMSO-d$_6$) δ ppm 1.19 (d, J=6.8 Hz, 3H), 3.77 (s, 3H), 3.90-4.06 (m, 1H), 7.24 (t, J=54.4 Hz, 1H), 7.39 (t, J=9.7 Hz, 1H), 7.67 (s, 1H), 7.80-7.88 (m, 1H), 8.01-8.08 (m, 1H), 8.49 (d, J=7.0 Hz, 1H), 10.58 (s, 1H).

Compound 280: N-(3-bromophenyl)-3-fluoro-1-methyl-4-[[(1R)-2,2,2-trifluoro-1-methyl-ethyl]sulfamoyl]pyrrole-2-carboxamide

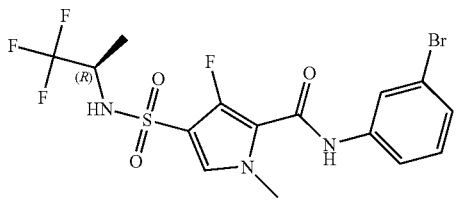

Compound 280 (344 mg) was prepared similarly as described for compound 229, using 3-bromoaniline instead of 3,4-difluoroaniline. Method D: Rt: 2.02 min m/z: 472.0 (M−H)⁻ Exact mass: 473.0. $^1$H NMR (400 MHz, DMSO-d$_6$) δ ppm 1.18 (d, J=7.0 Hz, 3H), 3.80 (s, 3H), 3.91-4.04 (m, 1H), 7.27-7.35 (m, 2H), 7.54 (d, J=4.4 Hz, 1H), 7.59-7.65 (m, 1H), 7.96-8.01 (m, 1H), 8.59 (d, J=8.6 Hz, 1H), 10.21 (s, 1H). Differential scanning calorimetry: From 30 to 300° C. at 10° C./min: peak at 216.8° C.

Compound 281: N-(3-cyano-4-fluoro-phenyl)-3-fluoro-1-methyl-4-[[1-(trifluoro-methyl)cyclopentyl]sulfamoyl]pyrrole-2-carboxamide

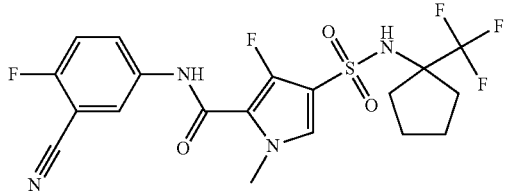 [SMILES: Cn1cc(S(=O)(=O)NC2(C(F)(F)F)CCCC2)c(F)c1C(=O)Nc1ccc(F)c(C#N)c1]

A mixture of ethyl 4-chlorosulfonyl-3-fluoro-1-methyl-pyrrole-2-carboxylate (302 mg, 1.04 mmol), 1-(trifluoromethyl)cyclopentanamine (216 mg, 1.4 mmol) NaHCO$_3$ (261 mg, 3.1 mmol) acetonitrile (20 mL) and molecular sieves 4A (1000 mg) was refluxed overnight. The reaction mixture was filtered and concentrated. The residue was purified by silica gel column chromatography using a gradient from 10 to 100% EtOAc in heptane. The product fractions were concentrated yielding ethyl 3-fluoro-1-methyl-4-[[1-(trifluoromethyl)cyclopentyl]sulfamoyl]pyrrole-2-carboxylate (60.5 mg) as a light yellow powder. Lithium bis(trimethylsilyl)amide in toluene (0.59 mL, 1 M, 0.59 mmol) was added to ethyl 3-fluoro-1-methyl-4-[[1-(trifluoromethyl)cyclopentyl]sulfamoyl]pyrrole-2-carboxylate (57 mg, 0.148 mmol) and 5-amino-2-fluoro-benzonitrile (26.1 mg, 0.19 mmol) in THF (10 mL) at room temperature under nitrogen. The reaction mixture was stirred 1 hour, quenched with NH$_4$Cl (25 mL) solution, diluted with brine (25 mL) and extracted with EtOAc (50 mL). The organic layer was dried over magnesium sulphate, filtered and concentrated. The residue was purified by silica gel column chromatography using a gradient from 10 to 100% EtOAc in heptane. The product fractions were concentrated. The residue was dissolved in hot methanol (10 mL). The product crystallised upon addition of water. Compound 281 (30.5 mg) was filtered off and dried overnight in vacuo at 50° C. Method D: Rt: 2.02 min m/z: 475.3 (M−H)⁻ Exact mass: 476.1. $^1$H NMR (400 MHz, DMSO-d$_6$) δ ppm 1.42-1.54 (m, 2H), 1.58-1.71 (m, 2H), 1.72-1.85 (m, 2H), 2.21-2.32 (m, 2H), 3.81 (s, 3H), 7.50-7.57 (m, 2H), 7.97 (ddd, J=9.2, 4.8, 2.9 Hz, 1H), 8.17 (dd, J=5.8, 2.8 Hz, 1H), 8.32 (s, 1H), 10.33 (s, 1H). Differential scanning calorimetry: From 30 to 300° C. at 10° C./min: peak at 187.0° C.

Compound 282: 3-chloro-N-(3-cyano-4-fluoro-phenyl)-1,5-dimethyl-4-[[(1R)-2,2,2-trifluoro-1-methyl-ethyl]sulfamoyl]pyrrole-2-carboxamide

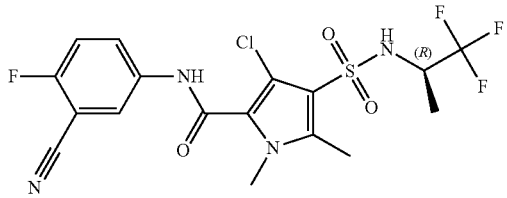

Ethyl 4-chlorosulfonyl-1,5-dimethyl-pyrrole-2-carboxylate (600 mg, 2.26 mmol) was dissolved in acetonitrile (4 mL), dried on molecular sieves and NaHCO$_3$ (569 mg, 6.77 mmol) was added. (R)-1,1,1-trifluoro-2-propylamine (766 mg, 6.77 mmol) was dissolved in acetonitrile (1 mL) and dried on molecular sieves. The two suspensions were combined and heated at 80° C. for 4 hours. The reaction mixture was filtered, washed with acetonitrile and evaporated to dryness to afford a yellow sticky powder (730 mg) which was purified using silica gel column chromatography resulting in ethyl 1,5-dimethyl-4-[[(1R)-2,2,2-trifluoro-1-methyl-ethyl]sulfamoyl]pyrrole-2-carboxylate (600 mg) as colorless sticky powder. Ethyl 1,5-dimethyl-4-[[(1R)-2,2,2-trifluoro-1-methyl-ethyl]sulfamoyl]pyrrole-2-carboxylate (402 mg, 1.17 mmol) was dissolved in HOAc (10 mL) and N-Chlorosuccinimide (156.8 mg, 1.17 mmol) was added. The reaction mixture was heated at 40° C. over weekend. The reaction mixture was evaporated to dryness and the residue was purified using silica gel column chromatography (first ethylacetate in heptane from 0 to 100%, then again using methanol in CH$_2$Cl$_2$ from 0.1 to 0.5%) to afford ethyl 3-chloro-1,5-dimethyl-4-[[(1R)-2,2,2-trifluoro-1-methyl-ethyl]sulfamoyl]pyrrole-2-carboxylate (177 mg). Method D: Rt: 1.89 min m/z: 375.3 (M−H)$^-$ Exact mass: 376.0. Lithium bis(trimethylsilyl)amide in toluene (0.934 mL, 1 M, 0.934 mmol) was added to ethyl 3-chloro-1,5-dimethyl-4-[[(1R)-2,2,2-trifluoro-1-methyl-ethyl]sulfamoyl]pyrrole-2-carboxylate (88 mg, 0.234 mmol) and 5-amino-2-fluoro-benzonitrile (41.3 mg, 0.30 mmol) dissolved in THF (5 mL) and stirred overnight. The reaction mixture was quenched with NH$_4$Cl solution (5 mL) and diluted with brine (5 mL) then extracted with EtOAc (20 mL). The organic layer was dried over magnesium sulphate, filtered and concentrated. The obtained residue was dissolved in DMF (1 mL) and purified by silica gel column chromatography using a gradient from 10 to 100% EtOAc in heptane. The product fractions were concentrated and the residue dissolved in hot methanol (10 mL). Water was added until crystallisation began. Compound 282 (44 mg) was filtered off and dried overnight in vacuo at 50° C. Method D: Rt: 1.89 min m/z: 465.0 (M−H)$^-$ Exact mass: 466.0. $^1$H NMR (400 MHz, DMSO-d$_6$) δ ppm 1.17 (d, J=6.8 Hz, 3H), 2.49 (s, 3H), 3.64 (s, 3H), 3.87-4.00 (m, 1H), 7.56 (t, J=9.1 Hz, 1H), 7.98 (ddd, J=9.2, 4.9, 2.6 Hz, 1H), 8.20 (dd, J=5.7, 2.6 Hz, 1H), 8.40 (d, J=9.0 Hz, 1H), 10.71 (s, 1H). Differential scanning calorimetry: From 30 to 300° C. at 10° C./min: peak at 240.0° C.

Compound 283: N-(3-cyano-4-fluoro-5-methyl-phenyl)-3-fluoro-1-methyl-4-[[(1R)-2,2,2-trifluoro-1-methyl-ethyl]sulfamoyl]pyrrole-2-carboxamide

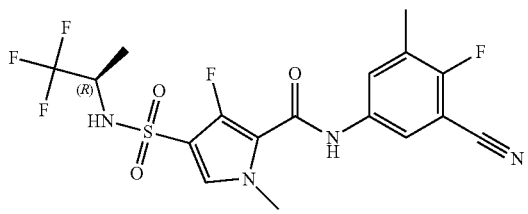

2-fluoro-3-methylbenzonitrile (18 g, 133 mmol) was added to a solution of potassium nitrate (13.5 g, 133 mmol) in sulfuric acid (250 mL) cooled at 0° C., the mixture was allowed to stir at room temperature for 40 minutes. The reaction mixture was poured into ice water and the pale yellow precipitate was filtered off and dried in the vacuum oven yielding crude 2-fluoro-3-methyl-5-nitro-benzonitrile (18 g). Crude 2-fluoro-3-methyl-5-nitro-benzonitrile (18 g) was stirred in MeOH (210 mL) and water (70 mL). Fe powder (16.7 g) and HCl (36 mL, 5 equiv) were added and the mixture was stirred at room temperature for 2 hours. The reaction mixture was then filtered through celite and after removal of organic solvent, the mixture was adjusted to pH 9 with saturated solution of sodium carbonate and extracted with CH$_2$Cl$_2$ twice. The combined organic layers were dried over sodium sulfate and evaporated to dryness to provide an yellow oil. The crude product was purified by column chromatography to provide 5-amino-2-fluoro-3-methyl-benzonitrile (5.1 g) as a pale yellow solid. Compound 283 (123 mg) was prepared similarly as described for compound 229, using 5-amino-2-fluoro-3-methyl-benzonitrile instead of 3,4-difluoroaniline. Method D: Rt: 1.95 min m/z: 449.3 (M−H)$^-$ Exact mass: 450.1. $^1$H NMR (600 MHz, DMSO-d$_6$) δ ppm 1.18 (d, J=7.0 Hz, 3H), 2.30 (d, J=1.8 Hz, 3H), 3.80 (s, 3H), 3.98 (dq, J=15.2, 7.6 Hz, 1H), 7.57 (d, J=4.3 Hz, 1H), 7.87 (dd, J=6.5, 2.3 Hz, 1H), 7.97 (dd, J=5.2, 2.6 Hz, 1H), 8.64 (d, J=8.7 Hz, 1H), 10.31 (s, 1H). Differential scanning calorimetry: From 30 to 300° C. at 10° C./min: peak at 214.8° C.

Compound 284: N-(3-cyano-4-fluoro-phenyl)-3-fluoro-1-methyl-4-[[(1S)-1-(trifluoro-methyl)propyl]sulfamoyl]pyrrole-2-carboxamide

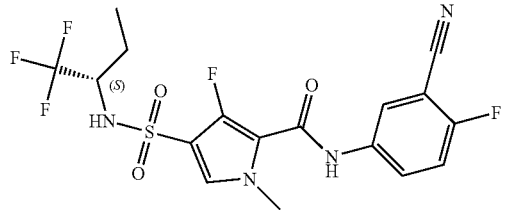

Compound 284 was prepared similarly as described for compound 281 using (S)-1-trifluoromethyl-propylamine instead of 1-(trifluoromethyl)cyclopentanamine. Method D: Rt: 1.92 min m/z: 449.3 (M−H)$^-$ Exact mass: 450.1. $^1$H NMR (400 MHz, DMSO-d$_6$) δ ppm 0.80 (t, J=7.4 Hz, 3H), 1.43-1.56 (m, 1H), 1.62-1.74 (m, 1H), 3.70-3.79 (m, 1H), 3.80 (s, 3H), 7.50-7.57 (m, 2H), 7.94-7.99 (m, 1H), 8.17 (dd, J=5.7, 2.6 Hz, 1H), 8.58 (d, J=8.6 Hz, 1H), 10.33 (s, 1H). Differential scanning calorimetry: From 30 to 300° C. at 10° C./min: peak at 177.3° C.

Compound 285: 3-fluoro-N-(4-fluorophenyl)-1-methyl-4-[[(1R)-2,2,2-trifluoro-1-methyl-ethyl]sulfamoyl]pyrrole-2-carboxamide

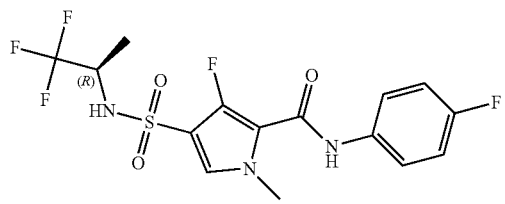

Compound 285 (105 mg) was prepared similarly as described for compound 229, using 4-fluoroaniline instead of 3,4-difluoroaniline. Method D: Rt: 1.87 min m/z: 410.3 (M−H)⁻ Exact mass: 411.1. ¹H NMR (400 MHz, DMSO-$d_6$) δ ppm 1.18 (d, J=7.0 Hz, 3H), 3.80 (s, 3H), 3.91-4.03 (m, 1H), 7.14-7.22 (m, 2H), 7.51 (d, J=4.4 Hz, 1H), 7.65-7.72 (m, 2H), 8.57 (d, J=8.8 Hz, 1H), 10.12 (s, 1H). Differential scanning calorimetry: From 30 to 300° C. at 10° C./min: peak at 212.9° C.

Compound 286: N-[3-(difluoromethyl)-4-fluoro-phenyl]-3-fluoro-1-methyl-4-[[(1R)-2,2,2-trifluoro-1-methyl-ethyl]sulfamoyl]pyrrole-2-carboxamide

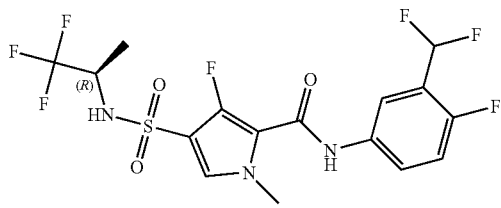

Compound 286 (130 mg) was prepared similarly as described for compound 229, using 3-(difluoromethyl)-4-fluoro-aniline instead of 3,4-difluoroaniline. Method D: Rt: 1.93 min m/z: 460.0 (M−H)⁻ Exact mass: 461.1. ¹H NMR (400 MHz, DMSO-$d_6$) δ ppm 1.18 (d, J=6.8 Hz, 3H), 3.81 (s, 3H), 3.92-4.03 (m, 1H), 7.07-7.41 (m, 2H), 7.54 (d, J=4.4 Hz, 1H), 7.78-7.84 (m, 1H), 8.01 (dd, J=6.3, 2.5 Hz, 1H), 8.60 (d, J=8.8 Hz, 1H), 10.28 (s, 1H). Differential scanning calorimetry: From 30 to 300° C. at 10° C./min: peak at 198.8° C.

Compound 287: N-[3-(difluoromethyl)-2,4-difluoro-phenyl]-3-fluoro-1-methyl-4-[[(1R)-2,2,2-trifluoro-1-methyl-ethyl]sulfamoyl]pyrrole-2-carboxamide

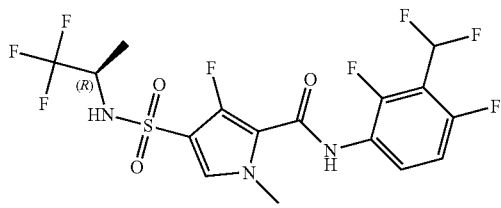

Compound 287 (80 mg) was prepared similarly as described for compound 229, using 3-(difluoromethyl)-2,4-difluoro-aniline instead of 3,4-difluoroaniline. Method D: Rt: 1.95 min m/z: 478.3 (M−H)⁻ Exact mass: 479.1. ¹H NMR (400 MHz, DMSO-$d_6$) δ ppm 1.19 (d, J=7.0 Hz, 3H), 3.81 (s, 3H), 3.92-4.04 (m, 1H), 7.19-7.48 (m, 2H), 7.56 (d, J=4.6 Hz, 1H), 7.82-7.91 (m, 1H), 8.62 (d, J=8.8 Hz, 1H), 9.84 (s, 1H).

Compound 288: N-(3-cyano-4-fluoro-phenyl)-3-fluoro-1-methyl-4-[[(1R)-1-(trifluoro-methyl)propyl]sulfamoyl]pyrrole-2-carboxamide

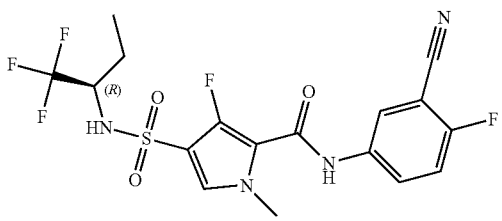

Compound 288 was prepared similarly as described for compound 281 using (R)-1-trifluoromethyl-propylamine instead of 1-(trifluoromethyl)cyclopentanamine. Method D: Rt: 1.92 min m/z: 449.0 (M−H)⁻ Exact mass: 450.1. ¹H NMR (400 MHz, DMSO-$d_6$) δ ppm 0.80 (t, J=7.3 Hz, 3H), 1.43-1.56 (m, 1H), 1.62-1.74 (m, 1H), 3.70-3.79 (m, 1H), 3.80 (s, 3H), 7.50-7.57 (m, 2H), 7.97 (ddd, J=9.2, 4.8, 2.6 Hz, 1H), 8.17 (dd, J=5.7, 2.6 Hz, 1H), 8.58 (d, J=8.6 Hz, 1H), 10.34 (s, 1H). Differential scanning calorimetry: From 30 to 300° C. at 10° C./min: peak at 175.7° C.

Compound 289: 3-chloro-N-(3-cyano-4-fluoro-phenyl)-1-methyl-4-[[(1S)-1-(trifluoro-methyl)propyl]sulfamoyl]pyrrole-2-carboxamide

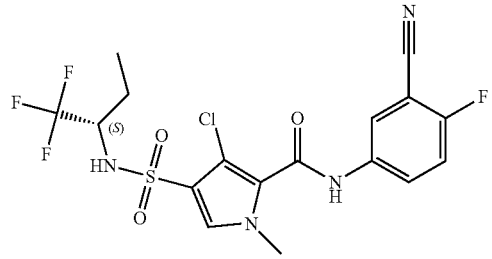

Methyl 3-chloro-4-chlorosulfonyl-1-methyl-pyrrole-2-carboxylate (1000 mg, 3.68 mmol) was dissolved in CH₃CN (18 mL) in a pressure tube and this was dried with powdered molecular sieves (4 Å) over a period of 30 minutes. Another tube was loaded with (S)-1-trifluoromethyl-propylamine (700.7 mg, 5.51 mmol) and NaHCO₃ (926 mg, 11.03 mmol) and this was dispersed in acetonitrile (2 mL) and dried with powdered molecular sieves (4 Å) over a period of 30 minutes. This was added to the pressure tube which was flushed with nitrogen, capped and stirred in a heating block at 80° C. for 48 hours and next 1 hour at 125° C. by microwave irradiation. The reaction mixture was filtered and concentrated. The residue was dissolved in CH₂Cl₂ (5 mL) filtered and subjected to silica gel column chromatography using a gradient from 10 to 100% EtOAc in heptane. The product fractions were concentrated yielding methyl 3-chloro-1-methyl-4-[[(1S)-1-(trifluoromethyl)propyl]sulfamoyl]pyrrole-2-carboxylate (829 mg) as a white solidified resin. Lithium bis(trimethylsilyl)amide in toluene (1.844 mL, 1 M, 1.84 mmol) was added to methyl 3-chloro-1-methyl-4-[[(1S)-1-(trifluoromethyl)propyl]sulfamoyl]pyrrole-2-carboxylate (167.2 mg, 0.461 mmol) and 5-amino-2-fluoro-benzonitrile (81.6 mg, 0.599 mmol) dissolved in THF (2 mL) and stirred overnight. The reaction mixture was quenched with NH₄Cl solution (5 mL) and diluted with brine (5 mL) then extracted with EtOAc (20 mL). The organic layer was dried over magnesium sulphate, filtered and concentrated. The residue was purified by column chromatography using a gradient from 10 to 100% EtOAc in heptane. The product fractions were concentrated and the residue dissolved in methanol (10 mL). Water was added until crystallisation began. Compound 289 (160 mg) was filtered off and dried overnight in vacuo at 50° C. Method D: Rt: 1.92 min m/z: 465.0 (M–H)⁻ Exact mass: 466.0. $^1$H NMR (400 MHz, DMSO-d₆) δ ppm 0.81 (t, J=7.4 Hz, 3H), 1.46-1.59 (m, 1H), 1.61-1.73 (m, 1H), 3.72-3.82 (m, 4H), 7.56 (t, J=9.1 Hz, 1H), 7.66 (s, 1H), 7.99 (ddd, J=9.2, 4.9, 2.6 Hz, 1H), 8.20 (dd, J=5.7, 2.6 Hz, 1H), 8.49 (d, J=8.6 Hz, 1H), 10.65 (s, 1H). Differential scanning calorimetry: From 30 to 300° C. at 10° C./min: peak at 184.8° C.

Compound 290: 3-chloro-N-(3-cyano-4-fluoro-phenyl)-1-methyl-4-[[(1R)-1-(trifluoro-methyl)propyl]sulfamoyl]pyrrole-2-carboxamide

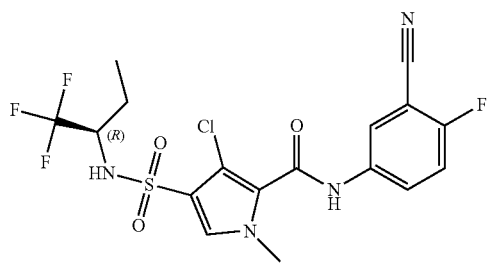

Compound 290 (133 mg) was prepared similarly as described for compound 289 using (R)-1,1,1-trifluoro-2-butylamine instead of (S)-1-trifluoromethyl-propylamine. Method D: Rt: 1.95 min m/z: 465.3 (M–H)⁻ Exact mass: 466.0. $^1$H NMR (400 MHz, DMSO-d₆) δ ppm 0.81 (t, J=7.4 Hz, 3H), 1.45-1.59 (m, 1H), 1.61-1.73 (m, 1H), 3.71-3.82 (m, 4H), 7.56 (t, J=9.1 Hz, 1H), 7.66 (s, 1H), 7.99 (ddd, J=9.2, 4.8, 2.6 Hz, 1H), 8.20 (dd, J=5.7, 2.6 Hz, 1H), 8.49 (d, J=8.8 Hz, 1H), 10.65 (s, 1H). Differential scanning calorimetry: From 30 to 300° C. at 10° C./min: peak at 183.8° C.

Compound 291: 3-chloro-N-(3-cyano-4-fluoro-phenyl)-1-isopropyl-4-[[(1R)-2,2,2-trifluoro-1-methyl-ethyl]sulfamoyl]pyrrole-2-carboxamide

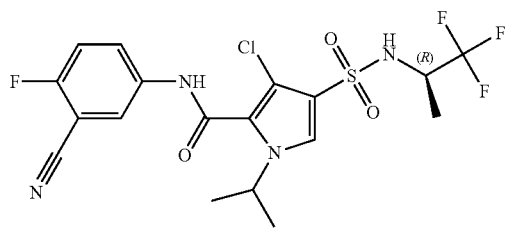

Methyl 3-chloro-1H-pyrrole-2-carboxylate (2 g, 12.5 mmol) was dissolved in DMF (20 mL) under N₂ atmosphere. NaH (60% dispersion in mineral oil) [(601.6 mg, 15.0 mmol) was added portion wise and the mixture was stirred for 10 minutes at room temperature. 2-iodopropane (1.5 mL, 15.0 mmol) was added dropwise and the mixture was stirred at room temperature for 16 hours. The mixture was quenched with water and the mixture was extracted with EtOAc. The organic layer was washed with brine, dried (MgSO₄), filtered and concentrated in vacuo. The residue was purified by silica gel chromatography using gradient eluent Heptane-EtOAc; 100-0→50-50. The product fractions were collected and concentrated in vacuo resulting in methyl 3-chloro-1-isopropyl-pyrrole-2-carboxylate (1.2 g) as an oil. Methyl 3-chloro-1-isopropyl-pyrrole-2-carboxylate (1.2 g, 5.95 mmol) was added drop wise to chlorosulfonic acid (1.99 mL, 29.9 mmol) at 0° C. under nitrogen atmosphere. The reaction mixture was warmed to room temperature and allowed to stir for 1 hour. The resulting mixture was added dropwise to a stirred, temperature controlled ice-water mixture (100 mL) keeping the temperature under 5° C. A white suspension was formed. The obtained aqueous suspension was extracted using Me-THF (2×50 mL). The combined extracts were washed with Brine and dried on sodium sulphate, filtered and concentrated in vacuo yielding methyl 3-chloro-4-chlorosulfonyl-1-isopropyl-pyrrole-2-carboxylate (1.7 g) which was used as such in the next step. Methyl 3-chloro-4-chlorosulfonyl-1-isopropyl-pyrrole-2-carboxylate (1.7 g, 5.66 mmol) was dissolved in hot acetonitrile (3 mL), molecular sieves (~0.7 g) were added and the reaction mixture was stirred. In a separate vessel (R)-1,1,1-trifluoro-2-propylamine (960.7 mg, 8.5 mmol) was dissolved in acetonitrile (2 mL), molecular sieves (~0.7 g) were added. This suspension was added to the reaction mixture and then NaHCO₃ (1.43 g, 17.0 mmol) was added. The vessel was closed and it was stirred overnight at 80° C. The reaction mixture was filtered and the solids were washed with acetonitrile (2×50 mL). The organic fractions were combined and concentrated in vacuo. The mixture was concentrated and purified by silica gel chromatography using gradient eluent heptane-EtOAc; 100-0→50-50. The product fractions were combined and concentrated in vacuo resulting in methyl 3-chloro-1-isopropyl-4-[[(1R)-2,2,2-trifluoro-1-methyl-ethyl]sulfamoyl]pyrrole-2-carboxylate (907 mg) as a fluffy solid. Methyl 3-chloro-1-isopropyl-4-[[(1R)-2,2,2-trifluoro-1-methyl-ethyl]sulfamoyl]pyrrole-2-carboxylate (450 mg, 1.194 mmol) and 5-amino-2-fluorobenzonitrile 201 mg, 1.43 mmol) was dissolved in THF (dried on molecular sieves) (10.1 mL, 124.7 mmol). lithium bis(trimethylsilyl)amide (1M in THF) (3.58 mL, 1 M, 3.583 mmol) was added drop wise and the reaction mixture was stirred for 1 hour at room temperature. The mixture was quenched with sat. NH₄Cl-sol. The organic layer was separated, dried (MgSO₄), filtered and concentrated in vacuo. The product was purified by silica gel chromatography using gradient eluent Heptane-EtOAc; 100-0→50-50. The product fractions were collected and concentrated in vacuo. The product was crystallized from 2-propanol, filtered and dried under vacuum to resulting in compound 291 (58 mg) as a pale yellow solid. The filtrate was concentrated in vacuo and further purified by preparative HPLC, resulting in more compound 291 (247 mg). Method B: Rt: 1.10 min m/z: 479.1 (M–H)⁻ Exact mass: 480.1. $^1$H NMR (400 MHz, DMSO-d₆) δ ppm 1.18 (d, J=6.8 Hz, 3H) 1.42 (d, J=6.6 Hz, 6H) 4.00-4.09 (m, 1H) 4.71 (quin, J=6.7 Hz, 1H) 7.56 (t, J=9.1 Hz, 1H) 7.78 (s, 1H) 7.95-8.00 (m, 1H) 8.20 (dd, J=5.6, 2.5 Hz, 1H) 8.47 (d, J=8.6 Hz, 1H) 10.91 (s, 1H).

Compound 292: 3-bromo-N-(3-cyano-4-fluoro-phenyl)-1-methyl-4-[[(1R)-2,2,2-trifluoro-1-methylethyl]sulfamoyl]pyrrole-2-carboxamide

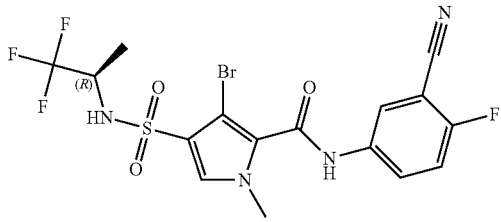

Methyl 3-bromo-1-methyl-pyrrole-2-carboxylate (5 g, 22.93 mmol) was added drop wise to chlorosulfonic acid (13.4 g, 114.7 mmol) at 0° C. The reaction mixture was warmed to room temperature and allowed to stir for 1 hour. The resulting mixture was added dropwise to a stirred ice-water mixture (300 mL) keeping the temperature below 5° C. An off white precipitation was formed. The solids were filtered and washed with water (20 mL), triturated with diisopropylether and dried in vacuum oven overnight, resulting in methyl 3-bromo-4-chlorosulfonyl-1-methyl-pyrrole-2-carboxylate (3.9 g).

Methyl 3-bromo-4-chlorosulfonyl-1-methyl-pyrrole-2-carboxylate (3.9 g, 12.32 mmol) was dissolved in hot acetonitrile (20 mL) in a pressure vessel (100 mL), molecular sieves (10 g) were added and the reaction mixture was stirred. In a separate vessel (R)-1,1,1-trifluoro-2-propylamine (2.09 g, 18.5 mmol) was dissolved in acetonitrile (20 mL), molecular sieves (5 g) were added. This suspension was added to the reaction mixture and then NaHCO$_3$ (3.1 g, 36.96 mmol) was added. The vessel was closed and it was stirred overnight at 80° C. The reaction mixture was filtered and the volatiles were removed under reduced pressure. The residue was purified on silica using a heptane to EtOAc gradient. The fractions containing the product were evaporated to dryness resulting in methyl 3-bromo-1-methyl-4-[[(1R)-2,2,2-trifluoro-1-methylethyl]sulfamoyl]pyrrole-2-carboxylate (4.24 g) as a white powder. Methyl 3-bromo-1-methyl-4-[[(1R)-2,2,2-trifluoro-1-methyl-ethyl]sulfamoyl]pyrrole-2-carboxylate (150 mg, 0.38 mmol) and 5-amino-2-fluorobenzonitrile (69.6 mg, 0.5 mmol) were dissolved in dry THF (5 mL). Lithium bis(trimethylsilyl)amide (1M in THF) (1.14 mL, 1 M, 1.14 mmol) was added and the reaction mixture was stirred overnight at room temperature. The reaction mixture was quenched with sat. NH$_4$Cl (5 mL). The organic layer was removed and the aqueous layer extracted with CH$_2$Cl$_2$ (2×5 mL). The combined organic layers were evaporated to dryness and the residue was purified on silica using a heptane to EtOAc gradient resulting in compound 292 (146 mg) as a light pink powder after trituration in CH$_2$Cl$_2$/diisopropylether. Method B: Rt: 1.00 min m/z: 496.9 (M−H)$^−$ Exact mass: 498.0. $^1$H NMR (400 MHz, DMSO-d$_6$) δ ppm 1.20 (d, J=7.0 Hz, 3H), 3.77 (s, 3H), 4.01 (br. s., 1H), 7.57 (t, J=9.1 Hz, 1H), 7.71 (s, 1H), 7.98 (ddd, J=9.2, 4.9, 2.6 Hz, 1H), 8.19 (dd, J=5.7, 2.6 Hz, 1H), 8.44 (br. s., 1H), 10.74 (s, 1H). Differential scanning calorimetry: From 30 to 300° C. at 10° C./min: peak at 189.2° C.

Compound 293: 3-cyano-N-(3-cyano-4-fluoro-phenyl)-1-methyl-4-[[(1R)-2,2,2-trifluoro-1-methylethyl]sulfamoyl]pyrrole-2-carboxamide

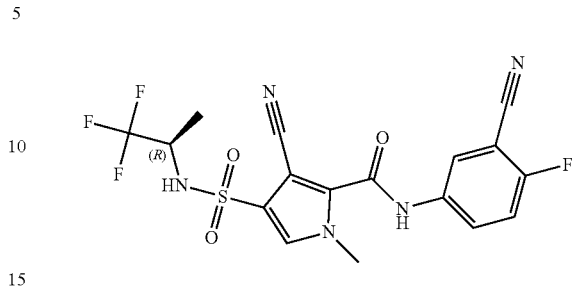

A microwave vial was charged with compound 292 (94 mg, 0.189 mmol) and zinc cyanide (13.6 mg, 0.113 mmol) in DMF (0.8 mL). The mixture was purged with N$_2$ for 5 minutes. tetrakis(triphenylphosphine)palladium(0) (10.9 mg, 0.00945 mmol) was added and the vial capped. The mixture was heated at 160° C. for 30 minutes by microwave irradiation. The mixture was concentrated in vacuo. A purification was performed via Preparative HPLC (Stationary phase: RP XBridge Prep C18 OBD-10 μm, 30×150 mm, Mobile phase: 0.25% NH$_4$HCO$_3$ solution in water, CH$_3$CN). The product fractions were collected and concentrated in vacuo. The residue was dissolved in MeOH and concentrated again resulting in compound 293 (8.3 mg) as a white solid. Method B: Rt: 0.97 min m/z: 442.1 (M−H)$^−$ Exact mass: 443.1. $^1$H NMR (400 MHz, DMSO-d$_6$) δ ppm 1.22 (d, J=6.8 Hz, 3H) 3.85 (s, 3H) 4.01-4.12 (m, 1H) 7.60 (t, J=9.0 Hz, 1H) 7.82 (s, 1H) 7.95 (ddd, J=9.1, 4.8, 2.8 Hz, 1H) 8.19 (dd, J=5.7, 2.6 Hz, 1H) 8.80 (br. s., 1H) 11.18 (br. s., 1H).

Compound 294: N-(3-cyano-4-fluoro-phenyl)-1-methyl-4-[[(1R)-1-methylpropyl]-sulfamoyl]pyrrole-2-carboxamide

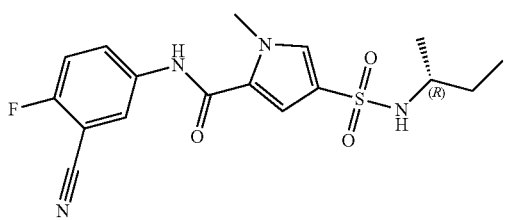

5-[(3-cyano-4-fluoro-phenyl)carbamoyl]-1-methyl-pyrrole-3-sulfonyl chloride (200 mg, 0.59 mmol) was dissolved in acetonitrile (6 mL) in a pressure tube and this was dried with powdered molecular sieves (4 Å) over a period of 30 minutes. Another tube was loaded with (R)-(−)-2-aminobutane (64.2 mg, 0.88 mmol) and NaHCO$_3$ (245.81 mg, 2.93 mmol) and this was dispersed in acetonitrile (4 mL) and dried with powdered molecular sieves (4 Å) over a period of 30 minutes. This was added to the pressure tube which was flushed with nitrogen, capped and stirred in a heating block at 80° C. for 2 hours. Then the reaction mixture was filtered over a small path of dicalite and rinsed using dichloromethane (50 mL). The filtrate was concentrated in vacuo and the obtained residue was purified using silica gel column chromatography (gradient elution: EtOAc-heptane 0:100 to 100:0), resulting in compound 294 (136 mg).

Method B: Rt: 1.00 min m/z: 377.1 (M−H)⁻ Exact mass: 378.1. ¹H NMR (400 MHz, DMSO-d₆) δ ppm 0.76 (t, J=7.4 Hz, 3H), 0.91-0.99 (m, 3H), 1.29-1.41 (m, 2H), 3.01-3.15 (m, 1H), 3.92 (s, 3H), 7.17 (d, J=7.5 Hz, 1H), 7.35 (d, J=1.8 Hz, 1H), 7.49-7.59 (m, 2H), 8.02 (ddd, J=9.2, 4.9, 2.9 Hz, 1H), 8.19-8.25 (m, 1H), 10.36 (s, 1H).

Compound 295: 3-chloro-N-(3-cyano-4-fluoro-phenyl)-1-methyl-4-[[(1R)-1-methyl-propyl]sulfamoyl]pyrrole-2-carboxamide

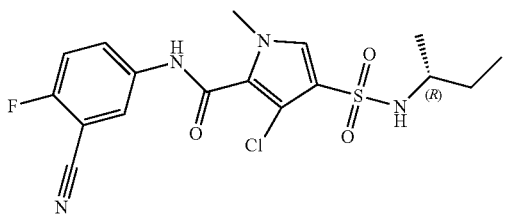

Compound 295 (515 mg) was prepared similarly as described for compound 289 using (S)-(+)-2-aminobutane instead of (S)-1-trifluoromethyl-propylamine, stirring at 70° C. for 2 hours for the formation of methyl 3-chloro-1-methyl-4-[[(1R)-1-methylpropyl]sulfamoyl]pyrrole-2-carboxylate instead of 80° C. for 48 hours as described for methyl 3-chloro-1-methyl-4-[[(1S)-1-(trifluoromethyl)propyl]sulfamoyl]pyrrole-2-carboxylate. Method B: Rt: 1.01 min m/z: 411.1 (M−H)⁻ Exact mass: 412.1. ¹H NMR (400 MHz, DMSO-d₆) δ ppm 0.79 (t, J=7.4 Hz, 3H), 1.00 (d, J=6.6 Hz, 3H), 1.31-1.45 (m, 2H), 3.03-3.18 (m, 1H), 3.77 (s, 3H), 7.42 (d, J=7.9 Hz, 1H), 7.55 (t, J=9.1 Hz, 1H), 7.60 (s, 1H), 7.98 (ddd, J=9.1, 4.9, 2.8 Hz, 1H), 8.19 (dd, J=5.8, 2.8 Hz, 1H), 10.64 (br. s., 1H).

Compound 296: N-(3-cyano-4-fluoro-phenyl)-4-[(3-hydroxy-1,1-dimethyl-propyl)sulfamoyl]-1-methyl-pyrrole-2-carboxamide

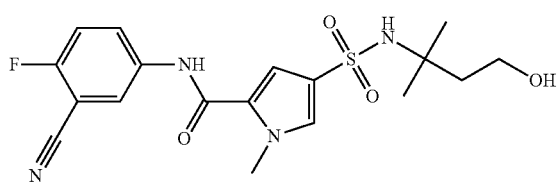 [SMILES: Cn1cc(S(=O)(=O)NC(C)(C)CCO)cc1C(=O)Nc1ccc(F)c(C#N)c1]

Compound 296 was prepared similarly as described for compound 294 using 3-amino-3-methylbutan-1-ol instead of (R)-(−)-2-aminobutane. Method B: Rt: 0.85 min m/z: 407.1 (M−H)⁻ Exact mass: 408.1. ¹H NMR (400 MHz, DMSO-d₆) δ ppm 1.13-1.20 (m, 6H), 1.67 (t, J=7.0 Hz, 2H), 3.48 (t, J=6.9 Hz, 2H), 3.91 (s, 3H), 4.45 (br. s., 1H), 7.07 (br. s., 1H), 7.34 (d, J=2.0 Hz, 1H), 7.49-7.57 (m, 2H), 8.02 (ddd, J=9.2, 5.0, 2.8 Hz, 1H), 8.22 (dd, J=5.8, 2.8 Hz, 1H), 10.25-10.51 (m, 1H).

Synthesis of (2S)-3,3-difluorobutan-2-amine hydrochloride (S)-2-((tert-butoxycarbonyl)amino)propanoic acid (39 g, 206 mmol), N,O-dimethyl-hydroxylamine hydrochloride (24 g, 246 mmol), HATU (117 g, 308 mmol) and N,N-diisopropylethylamine (66.3 g, 513 mmol) were dissolved in DMF (500 mL) and stirred at room temperature for 16 hours. The reaction mixture was poured into water (500 mL) and the formed precipitate was filtered off. The filter cake was washed with water (1 L) and dried to give tert-butyl N-[(1S)-2-[methoxy(methyl)amino]-1-methyl-2-oxo-ethyl]carbamate (36 g) as a white powder. tert-butyl N-[(1S)-2-[methoxy(methyl)amino]-1-methyl-2-oxo-ethyl]carbamate (35 g, 151 mmol) was dissolved in THF (500 mL) and cooled to 0° C. Methylmagnesium bromide (3.0 M in diethyl ether, 140 mL) was added and the reaction mixture was stirred 16 hours at room temperature. The reaction mixture was poured into water (100 mL) and evaporated to dryness. The residue was dissolved in EtOAc, washed with water, dried over Na₂SO₄, filtered and evaporated to dryness yielding tert-butyl N-[1S)-1-methyl-2-oxo-propyl]carbamate (22 g) as a white powder. To a cooled (−78° C.) solution of tert-butyl N-[(1S)-1-methyl-2-oxo-propyl]carbamate (12 g, 64.1 mmol) in CH₂Cl₂ (200 mL) bis(2-methoxyethyl)-aminosulfur trifluoride (18.9 g, 117.5 mmol) was added. The reaction mixture was allowed to warm to room temperature and stirred overnight. The reaction mixture was poured into water and extracted with CH₂Cl₂. The organic layer was washed with water, dried over Na₂SO₄, filtered and evaporated to dryness. The obtained residue was purified by silica gel chromatography yielding tert-butyl N-[(1S)-2,2-difluoro-1-methyl-propyl]carbamate (5.8 g) as a pale yellow solid. Tert-butyl N-[(1S)-2,2-difluoro-1-methyl-propyl]carbamate (5.8 g, 27.7 mmol) was dissolved in EtOAc (100 mL). HCl (g) was bubbled through for 30 minutes and then the volatiles were removed under reduced pressure yielding (2S)-3,3-difluorobutan-2-amine hydrochloride (3.8 g) ¹H NMR (400 MHz, DMSO-d₆) δ ppm 8.69 (br. s., 3H), 3.76-3.63 (m, 1H), 1.72 (t, J=19.7 Hz, 3H), 1.28 (d, J=6.8 Hz, 3H).

Compound 297: N-(3-cyano-4-fluoro-phenyl)-4-[[(1S)-2,2-difluoro-1-methyl-propyl]sulfamoyl]-1-methyl-pyrrole-2-carboxamide

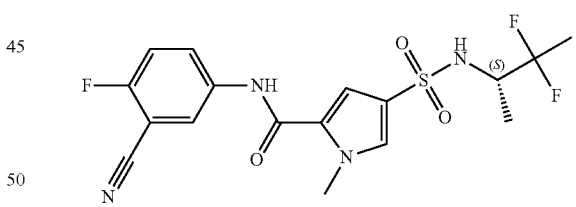

Compound 297 was prepared similarly as described for compound 294 using (2S)-3,3-difluorobutan-2-amine hydrochloride instead of (R)-(−)-2-aminobutane. Method D: Rt: 1.79 min m/z: 413.0 (M−H)⁻ Exact mass: 414.1. ¹H NMR (400 MHz, DMSO-d₆) δ ppm 0.97 (d, J=6.8 Hz, 3H), 1.57 (t, J=19.1 Hz, 3H), 3.42-3.56 (m, 1H), 3.93 (s, 3H), 7.36 (d, J=1.8 Hz, 1H), 7.53 (t, J=9.2 Hz, 1H), 7.63 (d, J=1.5 Hz, 1H), 7.78 (d, J=9.0 Hz, 1H), 8.01 (ddd, J=9.2, 4.8, 2.9 Hz, 1H), 8.22 (dd, J=5.8, 2.8 Hz, 1H), 10.36 (s, 1H).

Synthesis of (2R)-3,3-difluorobutan-2-amine (R)-2-((tert-butoxycarbonyl)amino)propanoic acid (30 g, 159 mmol), N,O-dimethyl-hydroxylamine hydrochloride (17.5 g, 178 mmol), HATU (74 g, 195 mmol) and N,N- diisopropylethylamine (30 g, 232 mmol) were dissolved in DMF (300 mL) and stirred at room temperature for 15 hours. The reaction mixture was concentrated under vacuum and the residue was dissolved in $CH_2Cl_2$ (500 mL) and washed with brine (3×200 mL). The organic layer was dried over $Na_2SO_4$ and concentrated in vacuo. The residue was purified via silica gel chromatography using petroleum ether: EtOAc 2:1 as eluent yielding tert-butyl N-[(1R)-2-[methoxy(methyl)amino]-1-methyl-2-oxo-ethyl]carbamate (28.9 g). Tert-butyl N-[(1R)-2-[methoxy(methyl)amino]-1-methyl-2-oxo-ethyl]carbamate was dissolved in THF (300 mL) and cooled to 0° C. Methylmagnesium bromide 3.0 m in diethyl ether (85 mL, 255 mmol) was added drop wise and the reaction mixture was stirred 15 hours at room temperature. The reaction mixture was quenched with sat. $NH_4Cl$ and extracted with $CH_2Cl_2$ (3×100 mL). The combined organic layers were dried over $Na_2SO_4$, filtered and evaporated to dryness. The obtained residue was purified via silica gel chromatography yielding tert-butyl N-[(1R)-1-methyl-2-oxo-propyl]carbamate (18.9 g). To a cooled (−78° C.) solution of tert-butyl N-[(1R)-1-methyl-2-oxo-propyl]carbamate (10 g, 53.4 mmol) in $CH_2Cl_2$ (200 mL) bis(2-methoxyethyl)aminosulfur trifluoride (18.9 g, 117.5 mmol) was added drop wise and stirring was continued for 2 hours at −78° C. The reaction mixture was allowed to warm to room temperature and stirred overnight. The reaction mixture was quenched with sat. $NaHCO_3$ and extracted with EtOAc. The combined organic layers were washed with brine, dried over $MgSO_4$, filtered and evaporated to dryness. The residue was purified by silica gel chromatography using a gradient from petroleum ether to petroleum ether:EtOAc 1:1 yielding tert-butyl N-[(1R)-2,2-difluoro-1-methyl-propyl]carbamate (6.77 g). Tert-butyl N-[(1R)-2,2-difluoro-1-methyl-propyl]carbamate (6.77 g) was dissolved in EtOAc (50 mL). HCl in EtOAc was added at 0° C. and the reaction mixture was stirred for 4 hours at room temperature. The formed precipitate was filtered off and dried under high vacuum yielding (2R)-3,3-difluorobutan-2-amine hydrochloride (3.5 g).

Compound 298: N-(3-cyano-4-fluoro-phenyl)-4-[[(1R)-2,2-difluoro-1-methyl-propyl]-sulfamoyl]-1-methyl-pyrrole-2-carboxamide

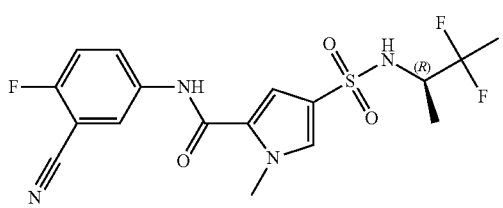

Compound 298 was prepared similarly as described for compound 294 using (2R)-3,3-difluorobutan-2-amine hydrochloride instead of (R)-(−)-2-aminobutane. Method D: Rt: 1.79 min m/z: 413.0 (M−H)⁻ Exact mass: 414.1. $^1H$ NMR (400 MHz, DMSO-$d_6$) δ ppm 0.97 (d, J=7.0 Hz, 3H), 1.57 (t, J=19.1 Hz, 3H), 3.43-3.57 (m, 1H), 3.93 (s, 3H), 7.36 (d, J=2.0 Hz, 1H), 7.53 (t, J=9.1 Hz, 1H), 7.63 (d, J=1.5 Hz, 1H), 7.78 (d, J=9.0 Hz, 1H), 8.01 (ddd, J=9.2, 4.8, 2.9 Hz, 1H), 8.22 (dd, J=5.8, 2.8 Hz, 1H), 10.36 (s, 1H).

Compound 299: N-(3-cyano-4-fluoro-phenyl)-3-fluoro-1,5-dimethyl-4-[[(1R)-2,2,2-trifluoro-1-methyl-ethyl]sulfamoyl]pyrrole-2-carboxamide

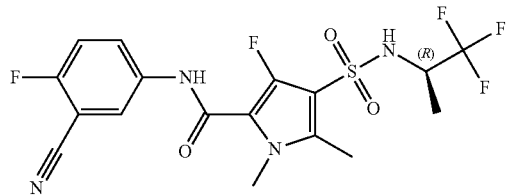

$Br_2$ (510 mg, 3.191 mmol) dissolved in HOAc (20 mL) was added to ethyl 3-fluoro-1-methyl-4-[[(1R)-2,2,2-trifluoro-1-methyl-ethyl]sulfamoyl]pyrrole-2-carboxylate (1050 mg, 3.03 mmol) and the solution was refluxed for 1 hour. More $Br_2$ (0.25 equiv) was added and the solution was refluxed for 1 hour more. More $Br_2$ (0.3 equiv) was added and the reaction mixture was allowed to reach room temperature overnight. The reaction mixture was concentrated and the obtained residue was dissolved in EtOAc (50 mL) washed with $NaHCO_3$ solution, dried over magnesium sulphate, filtered and concentrated, resulting in ethyl 5-bromo-3-fluoro-1-methyl-4-[[(1R)-2,2,2-trifluoro-1-methyl-ethyl]sulfamoyl]pyrrole-2-carboxylate (1.19 g) as a white powder. Method D: Rt: 1.92 min m/z: 423.2 (M−H)⁻ Exact mass: 424.0. $^1H$ NMR (400 MHz, DMSO-$d_6$) δ ppm 1.19 (d, J=7.0 Hz, 3H), 1.28 (t, J=7.2 Hz, 3H), 3.87 (s, 3H), 3.94-4.07 (m, 1H), 4.28 (q, J=7.0 Hz, 2H), 8.88 (d, J=8.8 Hz, 1H). A solution ethyl 5-bromo-3-fluoro-1-methyl-4-[[(1R)-2,2,2-trifluoro-1-methyl-ethyl]sulfamoyl]pyrrole-2-carboxylate (963 mg, 2.265 mmol), tetraethyltin (852.8 mg, 4.53 mmol) in DMF (7 mL), was flushed with nitrogen during 5 minutes. Tetrakis(triphenylphosphine)palladium(0) (261.7 mg, 0.226 mmol) was added and the reaction mixture was heated at 140° C. during 30 minutes by microwave irradiation. The reaction mixture was concentrated and the obtained residue was purified by silica gel column chromatography using a gradient from 10 to 100% EtOAc in heptane. The product fractions were concentrated yielding ethyl 3-fluoro-1,5-dimethyl-4-[[(1R)-2,2,2-trifluoro-1-methyl-ethyl]sulfamoyl]pyrrole-2-carboxylate (769 mg) as a white fluffy powder. Method D: Rt: 1.89 min m/z: 359.3 (M−H)⁻ Exact mass: 360.1. $^1H$ NMR (400 MHz, DMSO-$d_6$) δ ppm 1.14 (d, J=6.8 Hz, 3H), 1.27 (t, J=7.2 Hz, 3H), 2.42 (s, 3H), 3.76 (s, 3H), 3.86-3.98 (m, 1H), 4.26 (q, J=7.0 Hz, 2H), 8.54 (d, J=8.8 Hz, 1H). Lithium bis(trimethylsilyl)amide in toluene (1.66 mL, 1 M, 1.66 mmol) was added to ethyl 3-fluoro-1,5-dimethyl-4-[[(1R)-2,2,2-trifluoro-1-methyl-ethyl]sulfamoyl]pyrrole-2-carboxylate (149.6 mg, 0.415 mmol) and 5-amino-2-fluoro-benzonitrile (73.5 mg, 0.54 mmol) dissolved in THF (2 mL) and stirred overnight. The reaction mixture was quenched with $NH_4Cl$ solution (5 mL) and diluted with brine (5 mL) then extracted with EtOAc (20 mL). The organic layer was dried over magnesium sulphate, filtered and concentrated. The residue was dissolved in DMF (1 mL) and purified by silica gel column chromatography using a gradient from 10 to 100% EtOAc in heptane. The product fractions were concentrated and the residue dissolved in methanol (2 mL). Water was added until crystallisation began. The powder was filtered off and dried overnight in vacuo at 50° C., resulting in compound 299 (76 mg). Method D: Rt: 1.88 min m/z: 449.1 (M−H)⁻ Exact mass: 450.1. $^1H$ NMR (400 MHz, DMSO-$d_6$) δ ppm 1.17 (d, J=6.8 Hz, 3H), 2.44 (s, 3H), 3.70 (s, 3H), 3.85-3.99 (m, 1H), 7.53 (t, J=9.1 Hz, 1H), 7.95 (ddd, J=9.2, 4.8, 2.9 Hz, 1H), 8.17 (dd, J=5.7, 2.6 Hz, 1H), 8.55 (d, J=8.8 Hz, 1H), 10.35 (s, 1H). Differential scanning calorimetry: From 30 to 300° C. at 10° C./min: peak at 177.5° C.

Compound 300: 5-bromo-3-chloro-N-(3-cyano-4-fluoro-phenyl)-1-methyl-4-[[(1R)-2,2,2-trifluoro-1-methyl-ethyl]sulfamoyl]pyrrole-2-carboxamide

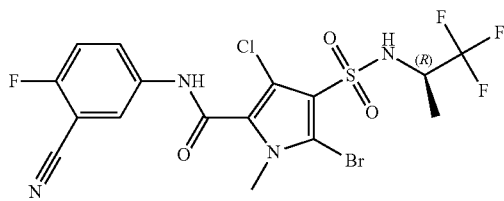

Compound 199 (1100 mg, 2.43 mmol), DMF (15 mL), N-bromosuccinimide (449.8 mg, 2.5 mmol) were stirred at room temperature for 64 hours. The reaction mixture was poured into water (150 mL). The pink solids were filtered, washed with water and purified using silica gel column chromatography (ethyl acetate in heptane from 0 to 40%) resulting in compound 300 (348 mg). Method B: Rt: 1.07 min m/z: 530.9 (M−H)⁻ Exact mass: 531.9. ¹H NMR (400 MHz, DMSO-d₆) δ ppm 1.20 (d, J=6.8 Hz, 3H), 3.73 (s, 3H), 3.89-4.09 (m, 1H), 7.57 (t, J=9.1 Hz, 1H), 7.97 (ddd, J=9.1, 4.8, 2.8 Hz, 1H), 8.20 (dd, J=5.7, 2.6 Hz, 1H), 8.77 (br. s., 1H), 10.88 (br. s., 1H).

Compound 301: 5-bromo-N-(3-cyano-4-fluoro-phenyl)-3-fluoro-1-methyl-4-[[(1R)-2,2,2-trifluoro-1-methyl-ethyl]sulfamoyl]pyrrole-2-carboxamide

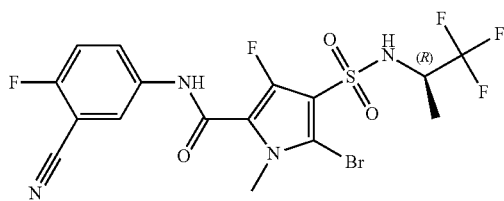

A mixture of ethyl 5-bromo-3-fluoro-1-methyl-4-[[(1R)-2,2,2-trifluoro-1-methyl-ethyl]sulfamoyl]pyrrole-2-carboxylate (174 mg, 0.409 mmol), Lithium hydroxide (29.4 mg, 1.23 mmol), THF (20 mL) and water (distilled, 20 mL) was stirred overnight. More LiOH was added (3 equiv) and the reaction mixture was stirred for 4 hours. The reaction mixture was concentrated, the obtained residue dissolved in water (50 mL) and the solution was neutralised with HCl (1 M in H₂O). The formed white powder was filtered off and dried in vacuo at 50° C., resulting in 5-bromo-3-fluoro-1-methyl-4-[[(1R)-2,2,2-trifluoro-1-methyl-ethyl]sulfamoyl] pyrrole-2-carboxylic acid (111 mg). Method D: Rt: 1.05 min m/z: 397.0 (M−H)⁻ Exact mass: 397.9. 5-bromo-3-fluoro-1-methyl-4-[[(1R)-2,2,2-trifluoro-1-methyl-ethyl]sulfamoyl]pyrrole-2-carboxylic acid (106.9 mg, 0.269 mmol), HATU (127.9 mg, 0.336 mmol) and 5-amino-2-fluoro-benzonitrile (73.3 mg, 0.538 mmol) were dissolved in DMF (1 mL), Et₃N (0.112 mL, 0.808 mmol) was added and the reaction mixture was stirred over weekend at 55° C. The solution was subjected to silica gel column chromatography using a gradient from 10 to 100% EtOAc in heptane. The product fractions were concentrated. The residue was dissolved in methanol (2 mL). Water was added until crystallisation began. The white powder was filtered off and dried overnight in vacuo at 50° C., resulting in compound 301 (54 mg). Method D: Rt: 1.99 min m/z: 515.2 (M−H)⁻ Exact mass: 516.0. ¹H NMR (400 MHz, DMSO-d₆) δ ppm 1.22 (d, J=7.0 Hz, 3H), 3.80 (s, 3H), 3.95-4.07 (m, 1H), 7.55 (t, J=9.1 Hz, 1H), 7.95 (ddd, J=9.2, 4.8, 2.9 Hz, 1H), 8.17 (dd, J=5.7, 2.6 Hz, 1H), 8.91 (d, J=8.8 Hz, 1H), 10.55 (s, 1H).

Compound 302: 3-chloro-N-(3-cyano-4-fluoro-phenyl)-5-cyclopropyl-1-methyl-4-[[(1R)-2,2,2-trifluoro-1-methyl-ethyl]sulfamoyl]pyrrole-2-carboxamide

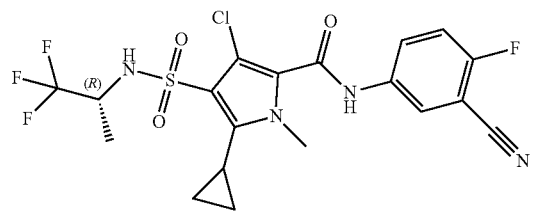

Compound 300 (130 mg, 0.24 mmol) and potassium cyclopropyltrifluoroborate (54.3 mg, 0.37 mmol) were dissolved in dimethoxyethane (1.5 mL) and distilled water (0.4 mL). The mixture was degassed with N₂ for 5 minutes. Cs₂CO₃ (239 mg, 0.73 mmol) was added and the mixture was degassed with N₂. Tetrakis(triphenylphosphine)palladium(0) (28.3 mg, 0.024 mmol) was added and the mixture was degassed with N₂. The vial was capped and the mixture was heated at 90° C. for 30 minutes under microwave irradiation, next at 120° C. for 30 minutes under microwave irradiation and at 140° C. in MW for 30 minutes under microwave irradiation. The mixture was cooled and EtOAc was added. The organic layer was separated. The water layer was made acidic with HCl (1M) and extracted with ethyl acetate (5 mL), The combined organic layers were dried (MgSO₄), filtered and concentrated in vacuo. The product was purified using silica gel column chromatography using gradient eluent Heptane-EtOAc; 100-0→0-50 and further via preparative HPLC (Stationary phase: RP XBridge Prep C18 OBD-10 μm, 30×150 mm, Mobile phase: 0.25% NH₄HCO₃ solution in water, CH₃CN), resulting in compound 302 (10 mg). Method B: Rt: 1.10 min m/z: 491.0 (M−H)⁻ Exact mass: 492.1. ¹H NMR (400 MHz, DMSO-d₆) δ ppm 0.73-0.91 (m, 2H), 1.03-1.15 (m, 2H), 1.22 (d, J=6.8 Hz, 3H), 1.72-1.83 (m, 1H), 3.74 (s, 3H), 3.93-4.09 (m, 1H), 7.56 (t, J=9.1 Hz, 1H), 7.97 (ddd, J=9.1, 4.8, 2.8 Hz, 1H), 8.19 (dd, J=5.8, 2.8 Hz, 1H), 8.29 (br. s., 1H), 10.73 (br. s., 1H).

Compound 303: N-(3-cyano-4-fluoro-phenyl)-3-isopropyl-1-methyl-4-[[(1R)-2,2,2-trifluoro-1-methyl-ethyl]sulfamoyl]pyrrole-2-carboxamide

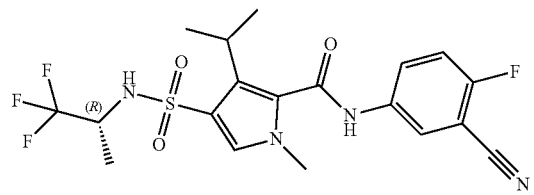

A microwave vial was charged with methyl 3-bromo-1-methyl-4-[[(1R)-2,2,2-trifluoro-1-methyl-ethyl]sulfamoyl]pyrrole-2-carboxylate (500 mg, 1.27 mmol) and potassium isopropenyltrifluoroborate (291 mg, 1.9 mmol). Toluene (6.5 mL) and distilled water, (0.65 mL) were added and the mixture was purged with N₂ for 5 minutes. Pd(OAc)₂ (57.1 mg, 0.254 mmol) and butyldi-1-adamantylphosphine (137 mg, 0.382 mmol) were added under N₂ and then Cs₂CO₃ (1243 mg, 3.82 mmol) was added. The vial was capped and the mixture was heated at 110° C. for 16 hour. The mixture was cooled and Me-THF was added. The organic layer was separated, dried (MgSO₄), filtered and concentrated in vacuo. The residue was purified by silica gel column chromatography using gradient eluent Heptane-EtOAc; 100-0 to 70-30. The product fractions were collected and concentrated in vacuo resulting in methyl 3-isopropenyl-1-methyl-4-[[(1R)-2,2,2-trifluoro-1-methyl-ethyl]sulfamoyl]pyrrole-2-carboxylate (350 mg) as a semi solid. Methyl 3-isopropenyl-1-methyl-4-[[(1R)-2,2,2-trifluoro-1-methyl-ethyl]sulfamoyl]pyrrole-2-carboxylate (350 mg, 0.988 mmol) was dissolved in THF (50 mL), Pd/C (10%) (158 mg) was added under N₂-atmosphere and the reaction mixture was stirred under Hz-atmosphere until 1 eq. H₂ was absorbed. The catalyst was removed by filtration over dicalite under nitrogen atmosphere, and the solvent was removed in vacuo, resulting in crude methyl 3-isopropyl-1-methyl-4-[[(1R)-2,2,2-trifluoro-1-methyl-ethyl]sulfamoyl]pyrrole-2-carboxylate (352 mg). Methyl 3-isopropyl-1-methyl-4-[[(1R)-2,2,2-trifluoro-1-methyl-ethyl]sulfamoyl]pyrrole-2-carboxylate (175 mg, 0.491 mmol) and 5-amino-2-fluorobenzonitrile (89.61 mg, 0.638 mmol) were dissolved in THF (3.9 mL) dried on molecular sieves. Lithium bis(trimethylsilyl)amide (1M in THF, 1.5 mL, 1.5 mmol) was added drop wise and the reaction mixture was stirred 1 hour at room temperature. The mixture was quenched with sat. NH₄Cl-sol. The organic layer was separated, dried (MgSO₄), filtered and concentrated in vacuo. The product was purified by silica gel column chromatography using gradient eluent Heptane-EtOAc; 100-0 to 50-50 and further by prep HPLC (Stationary phase: RP)(Bridge Prep C18 OBD-10 µm, 30×150 mm, Mobile phase: 0.25% NH₄HCO₃ solution in water, CH₃CN). The product fractions were collected and concentrated in vacuo. The residue was dissolved in MeOH and concentrated in vacuo again resulting in compound 303 (77 mg) as a light yellow solid. Method B: Rt: 1.06 min m/z: 459.1 (M−H)⁻ Exact mass: 460.1. ¹H NMR (400 MHz, DMSO-d₆) δ ppm 1.16 (d, J=6.8 Hz, 3H) 1.18-1.30 (m, 6H) 3.32-3.41 (m, 1H) 3.64 (s, 3H) 3.75-3.90 (m, 1H) 7.39 (s, 1H) 7.56 (t, J=9.1 Hz, 1H) 7.90-8.02 (m, 1H) 8.12-8.25 (m, 2H) 10.81 (s, 1H).

Compound 304: N-(3-cyano-4-fluoro-phenyl)-5-cyclopropyl-3-fluoro-1-methyl-4-[[(1R)-2,2,2-trifluoro-1-methyl-ethyl]sulfamoyl]pyrrole-2-carboxamide

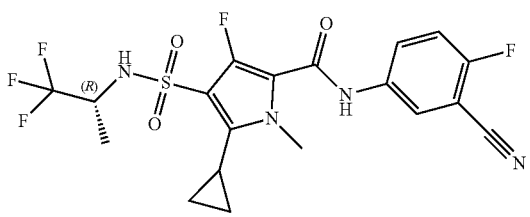

Nitrogen was flushed through a mixture of compound 301 (44.4 mg, 0.086 mmol) potassium cyclopropyltrifluoroborate (38.3 mg, 0.26 mmol) Cs₂CO₃ (84 mg, 0.26 mmol) in dimethoxyethane (2 mL) and distilled water (0.2 mL) during 5 minutes. tetrakis(triphenylphosphine)palladium(0) (19.9 mg, 0.0172 mmol) was added and the reaction mixture was heated at 140° C. during 30 minutes. The reaction mixture was concentrated. The residue was dissolved in EtOAc (10 mL) and water (5 mL) The organic layer was dried over magnesium sulphate, filtered and concentrated. The residue was subjected to silica gel column chromatography using a gradient from 10 to 100% EtOAc in heptane. The product fractions were concentrated and the residue was dissolved in methanol (2 mL). Water was added until crystallisation began. The white powder was filtered off and dried in vacuo at 50° C., resulting in compound 304 (21 mg). Method D: Rt: 1.98 min m/z: 475.1 (M−H)⁻ Exact mass: 476.1. ¹H NMR (400 MHz, DMSO-d₆) δ ppm 0.82-0.91 (m, 2H), 1.04-1.10 (m, 2H), 1.23 (d, J=7.0 Hz, 3H), 1.71-1.81 (m, 1H), 3.81 (s, 3H), 3.90-4.03 (m, 1H), 7.54 (t, J=9.1 Hz, 1H), 7.95 (ddd, J=9.2, 4.8, 2.9 Hz, 1H), 8.17 (dd, J=5.7, 2.6 Hz, 1H), 8.47 (d, J=8.4 Hz, 1H), 10.37 (s, 1H). Differential scanning calorimetry: From 30 to 300° C. at 10° C./min: peak at 161.4° C.

Compound 305: 3-chloro-N-(3-cyano-4-fluoro-phenyl)-1-cyclopropyl-4-[[(1R)-2,2,2-trifluoro-1-methyl-ethyl]sulfamoyl]pyrrole-2-carboxamide

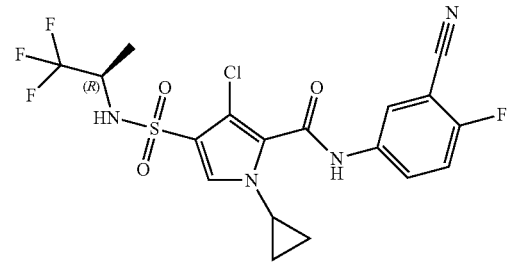

A flask (250 mL) was charged with methyl 3-chloro-1H-pyrrole-2-carboxylate (2 g, 12.53 mmol), cyclopropylboronic acid (2.153 g, 25.07 mmol), Na₂CO₃ (2.66 g, 25.07 mmol) in dichloroethane (50 mL). 2,2'-bipyridine (1.98 g, 12.53 mmol) and copper(II) acetate (2.3 g, 12.53 mmol) were added and the mixture was vigourously stirred on air and heated at 70° C. for 2 hours. The mixture was cooled and washed with water/NH₄OH. The organic layer was separated, dried (MgSO₄), filtered and concentrated in vacuo. The residue was purified by silica gel chromatography using gradient eluent Heptane-EtOAc; 100-0→70-30. The product fractions were collected and concentrated in vacuo resulting in methyl 3-chloro-1-cyclopropyl-pyrrole-2-carboxylate (1.15 g) as a yellow oil. Chlorosulfonic acid (0.46 mL, 6.91 mmol) dissolved in dichloromethane (1 mL) was added to methyl 3-chloro-1-cyclopropyl-pyrrole-2-carboxylate (1.15 g, 5.76 mmol) in CH₂Cl₂ (17.7 mL, 275.9 mmol) in an ice bath and stirred 30 minutes. The reaction was further stirred at room temperature for 1 hour, the precipitate was filtered off washed with diisopropylether and used as such in the next step (0.7 g after drying in vacuo). The precipatate (0.7 g) was added to SOCl₂ (0.7 g, 2.503 mmol) and the mixture was stirred at 80° C. for 30 minutes. The mixture was cooled and stirred at room temperature for 16 hours and concentrated in vacuo. To the residue ice was added and the mixture was extracted with Me-THF. The organic layer was separated, dried (MgSO₄), filtered and concentrated in vacuo. The residue was purified by silica gel chromatography using gradient eluent Heptane-EtOAc; 100-0→70-30. The product fractions were collected and concentrated in vacuo resulting in methyl 3-chloro-4-chlorosulfonyl-1-cyclopropyl-pyrrole-2-carboxylate (359 mg) as an oil which solidified on standing. Methyl 3-chloro-4-chlorosulfonyl-1-cyclopropyl-pyrrole-2-carboxylate (359 mg, 1.20 mmol) was dissolved in hot acetonitrile (3 mL), molecular sieves (about 0.7 g) were added and the reaction mixture was stirred. In a separate vessel (R)-1,1,1-trifluoro-2-propylamine (204.2 mg, 1.81 mmol) was dissolved in acetonitrile (2 mL), molecular sieves (about 0.7 g) was added. This suspension was added to the reaction mixture and then NaHCO₃ (303.5 mg, 3.61 mmol) was added. The vessel was closed and it was stirred overnight at 80° C. The reaction mixture was filtered and the solids were washed with acetonitrile (2×50 mL). The organic fractions were combined and concentrated in vacuo. The mixture was concentrated and purified by silica gel chromatography (solid phase, 40 g) using gradient eluent heptane-EtOAc; 100-0→50-50. The product fractions were combined and concentrated in vacuo to resulting in methyl 3-chloro-1-cyclopropyl-4-[[(1R)-2,2,2-trifluoro-1-methyl-ethyl]sulfamoyl]pyrrole-2-carboxylate (281 mg) as an oil which solidified on standing.

Methyl 3-chloro-1-cyclopropyl-4-[[(1R)-2,2,2-trifluoro-1-methyl-ethyl]sulfamoyl]pyrrole-2-carboxylate (100 mg, 0.267 mmol) and 5-amino-2-fluorobenzonitrile (48.681 mg, 0.347 mmol) were dissolved in THF (2.1 mL, 25.8 mmol). Lithium bis(trimethylsilyl)amide (1M in THF) (0.8 mL, 1 M, 0.8 mmol) was added dropwise at room temperature. The mixture was stirred at room temperature for 1 hour. The mixture was quenched with sat. NH₄Cl-sol. The organic layer was separated, dried (MgSO₄), filtered and concentrated in vacuo. A purification was performed via Preparative HPLC (Stationary phase: RP XBridge Prep C18 OBD-10 μm, 30×150 mm, Mobile phase: 0.25% NH₄HCO₃ solution in water, CH₃CN). The product fractions were collected and concentrated in vacuo. The residue was dissolved in MeOH and concentrated in vacuo again to obtain compound 305 (80 mg) as a white solid. Method B: Rt: 1.06 min m/z: 477.0 (M−H)⁻ Exact mass: 478.0. ¹H NMR (400 MHz, DMSO-d₆) δ ppm 0.85-1.05 (m, 4H), 1.17 (d, J=7.0 Hz, 3H), 3.61-3.76 (m, 1H), 3.93-4.12 (m, 1H), 7.53-7.60 (m, 2H), 7.95-6 8.01 (m, 1H), 8.17-8.23 (m, 1H), 8.49 (d, J=8.6 Hz, 1H), 10.86 (s, 1H).

Compound 306: 3-chloro-N-(3-cyano-4-fluoro-phenyl)-1-methyl-4-[(3-methyloxetan-3-yl)sulfamoyl]pyrrole-2-carboxamide

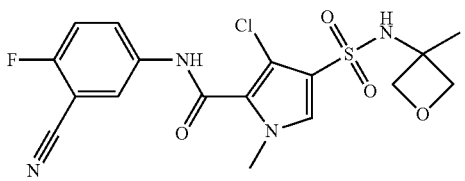 [SMILES: Cn1cc(S(=O)(=O)NC2(C)COC2)c(Cl)c1C(=O)Nc1ccc(F)c(C#N)c1]

Compound 306 (179 mg) was prepared in two steps from methyl 3-chloro-4-chlorosulfonyl-1-methyl-pyrrole-2-carboxylate similarly as described for compound 269, using 3 equiv 3-methyl-3-oxetanamine, instead of 1.5 equiv isopropylamine in the first step. Method B: Rt: 0.86 min m/z: 425.1 (M−H)⁻ Exact mass: 426.1. ¹H NMR (400 MHz, DMSO-d₆) δ ppm 1.53 (s, 3H), 3.77 (s, 3H), 4.15 (d, J=6.6 Hz, 2H), 4.66 (d, J=5.9 Hz, 2H), 7.55 (t, J=9.1 Hz, 1H), 7.66 (s, 1H), 7.78-8.76 (m, 1H), 7.98 (ddd, J=9.2, 4.8, 2.9 Hz, 1H), 8.19 (dd, J=5.8, 2.8 Hz, 1H), 10.65 (br. s., 1H).

Compound 307: 3-chloro-N-(3-cyano-4-fluoro-phenyl)-4-(cyclopentylsulfamoyl)-1-methyl-pyrrole-2-carboxamide

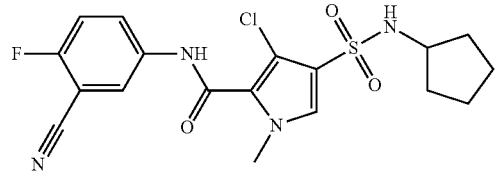 [SMILES: Cn1cc(S(=O)(=O)NC2CCCC2)c(Cl)c1C(=O)Nc1ccc(F)c(C#N)c1]

Compound 307 (241 mg) was prepared in two steps from methyl 3-chloro-4-chlorosulfonyl-1-methyl-pyrrole-2-carboxylate similarly as described for compound 269, using 3 equiv cyclopentylamine, instead of 1.5 equiv isopropylamine in the first step. Method B: Rt: 1.05 min m/z: 423.1 (M−H)⁻ Exact mass: 424.1. ¹H NMR (400 MHz, DMSO-d₆) δ ppm 1.34-1.51 (m, 4H), 1.51-1.77 (m, 4H), 3.41-3.52 (m, 1H), 3.77 (s, 3H), 7.52-7.59 (m, 2H), 7.61 (br. s, 1H), 7.91-8.07 (m, 1H), 8.14-8.27 (m, 1H), 10.65 (br. s., 1H).

Compound 308: 3-bromo-N-(4-fluoro-3-methyl-phenyl)-1-methyl-4-[[(1R)-2,2,2-trifluoro-1-methyl-ethyl]sulfamoyl]pyrrole-2-carboxamide

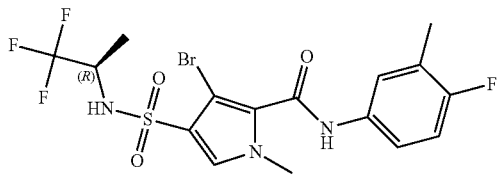

Compound 308 can be prepared similarly as described for compound 292, using 4-fluoro-3-methyl-aniline instead of 5-amino-2-fluorobenzonitrile. Method B: Rt: 1.07 min m/z: 486.0 (M−H)⁻ Exact mass: 487.0. ¹H NMR (400 MHz, DMSO-d₆) δ ppm 1.20 (d, J=6.8 Hz, 3H), 2.23 (d, J=1.8 Hz, 3H), 3.75 (s, 3H), 3.93-4.07 (m, 1H), 7.13 (t, J=9.1 Hz, 1H), 7.47-7.55 (m, 1H), 7.59-7.65 (m, 1H), 7.67 (s, 1H), 8.39 (br. s., 1H), 10.36 (s, 1H).

Compound 309: N-(3-cyano-4-fluoro-phenyl)-3-fluoro-5-(methoxymethyl)-1-methyl-4-[[(1R)-2,2,2-trifluoro-1-methyl-ethyl]sulfamoyl]pyrrole-2-carboxamide

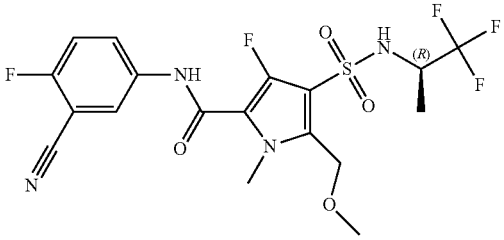

Nitrogen was bubbled through a mixture of compound 301 (prepared similarly as described in the synthesis of 301, but on a larger scale, 100.1 mg, 0.194 mmol) potassium trifluoro(methoxymethyl)borate (88.6 mg, 0.58 mmol), $Cs_2CO_3$ (189.9 mg, 0.58 mmol), DME (3 mL, 29.0 mmol), water (distilled, 0.25 mL) during 5 minutes. Then tetrakis(triphenylphosphine)palladium(0) (44.9 mg, 0.039 mmol) was added and the reaction mixture was heated at 140° C. during 30 minutes by microwave irradiation. The reaction mixture was further heated by microwave irradiation for 60 min at 160° C. and next the reaction mixture was concentrated. The residue was dissolved in EtOAc (50 mL) and water (50 mL) The organic layer was dried over magnesium sulphate, filtered and concentrated. The obtained residue was purified by silica gel column chromatography using a gradient from 10 till 100% EtOAc in heptane. The product fractions were concentrated and further purified by prep HPLC (Stationary phase: RP XBridge Prep C18 ODB—5 μm, 30×250 mm, Mobile phase: 0.25% $NH_4HCO_3$ solution in water, $CH_3CN$) yielding compound 309 (20 mg) as a white powder after drying overnight in vacuo at 50° C. Method D: Rt: 1.91 min m/z: 479.1 (M–H)⁻ Exact mass: 480.1. Differential scanning calorimetry: From 30 to 300° C. at 10° C./min: peak at 180.7° C. ¹H NMR (400 MHz, DMSO-$d_6$) δ ppm 1.16 (d, J=7.0 Hz, 3H), 3.31 (s, 3H), 3.77 (s, 3H), 3.90-4.02 (m, 1H), 4.64-4.73 (m, 2H), 7.55 (t, J=9.1 Hz, 1H), 7.96 (ddd, J=9.2, 4.9, 2.6 Hz, 1H), 8.18 (dd, J=5.7, 2.6 Hz, 1H), 8.69 (d, J=8.4 Hz, 1H), 10.54 (s, 1H).

Compound 310: 5-cyano-N-(3-cyano-4-fluoro-phenyl)-3-fluoro-1-methyl-4-[[(1R)-2,2,2-trifluoro-1-methyl-ethyl]sulfamoyl]pyrrole-2-carboxamide

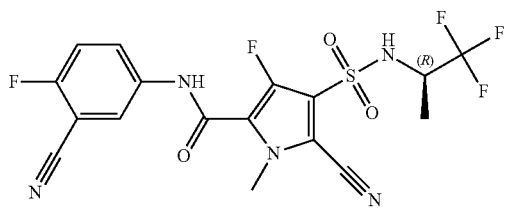

Compound 301 (prepared similarly as described in the synthesis of 301, but on a larger scale, 185.6 mg, 0.346 mmol), copper (I) cyanide (93.04 mg, 1.04 mmol), DMF (2 mL, 25.8 mmol) was heated 110 minutes at 160° C. under microwave irradiation. This was diluted with EtOAc (50 mL) washed with ammonia, dried over magnesium sulphate, filtered and concentrated. The residue was purified by silica gel chromatography with EtOAc/heptane gradient from 10 to 50%. The product fractions were concentrated. The residue was dissolved in methanol (5 mL) and the product crystallised upon addition of water. The white powder was filtered off and dried overnight in vacuo at 50° C., resulting in compound 310 (45 mg). Method D: Rt: 1.91 min m/z: 460.3 (M–H)⁻ Exact mass: 461.1. Differential scanning calorimetry: From 30 to 300° C. at 10° C./min: peak at 211.4° C. ¹H NMR (400 MHz, DMSO-$d_6$) δ ppm 1.24 (d, J=7.0 Hz, 3H), 3.94 (s, 3H), 4.04-4.15 (m, 1H), 7.57 (t, J=9.1 Hz, 1H), 7.93-7.99 (m, 1H), 8.17 (dd, J=5.7, 2.6 Hz, 1H), 9.32 (d, J=8.6 Hz, 1H), 10.87 (s, 1H).

Compound 311: N-(3-cyano-4-fluoro-phenyl)-3-fluoro-1-methyl-4-[[(1R)-2,2,2-trifluoro-1-methyl-ethyl]sulfamoyl]-5-vinyl-pyrrole-2-carboxamide

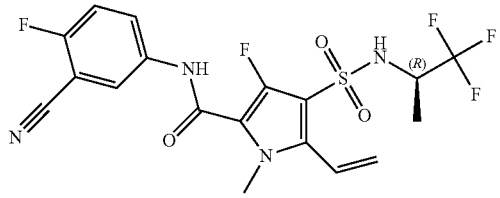

Nitrogen was flushed through a mixture of compound 301 (prepared similarly as described in the synthesis of 301, but on a larger scale, 446 mg, 0.87 mmol) potassium vinyltrifluoroborate (348.0 mg, 2.60 mmol), $Cs_2CO_3$ (846.5 mg, 2.60 mmol), DME (7 mL), water (1 mL) during 5 minutes. Tetrakis(triphenylphosphine)palladium(0) (200.1 mg, 0.17 mmol) was added and the reaction mixture was heated at 140° C. during 30 minutes by microwave irradiation. The reaction mixture was concentrated. The obtained residue was dissolved in EtOAc (50 mL) and water (25 mL). The organic layer was dried over magnesium sulphate, filtered and concentrated. The residue was subjected to silica gel column chromatography using a gradient from 10 till 100% EtOAc in heptane. The product fractions were concentrated and the obtained residue was dissolved in methanol (10 mL). Water was added until crystallisation began. The white powder was filtered off and dried in vacuo at 50° C., resulting in compound 311 (297 mg). Method D: Rt: 1.94 min m/z: 461.1 (M–H)⁻ Exact mass: 462.1. Differential scanning calorimetry: From 30 to 300° C. at 10° C./min: peak at 195.8° C. ¹H NMR (400 MHz, DMSO-$d_6$) δ ppm 1.17 (d, J=6.8 Hz, 3H), 3.77 (s, 3H), 3.87-3.98 (m, 1H), 5.78-5.82 (m, 1H), 5.84 (s, 1H), 6.80-6.91 (m, 1H), 7.55 (t, J=9.1 Hz, 1H), 7.96 (ddd, J=9.2, 4.8, 2.6 Hz, 1H), 8.19 (dd, J=5.7, 2.6 Hz, 1H), 8.66 (d, J=8.8 Hz, 1H), 10.51 (s, 1H).

Compound 312: N-(2,4-difluorophenyl)-3-fluoro-1-methyl-4-[[(1R)-2,2,2-trifluoro-1-methyl-ethyl]sulfamoyl]pyrrole-2-carboxamide

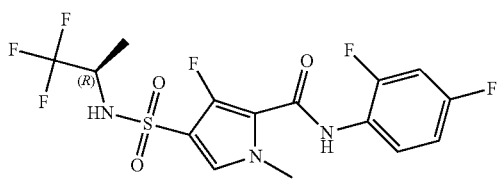

$Et_3N$ (0.19 mL, 1.35 mmol) was added to 3-fluoro-1-methyl-4-[[(1R)-2,2,2-trifluoro-1-methyl-ethyl]sulfamoyl]pyrrole-2-carboxylic acid (146 mg, 0.46 mmol), HATU (218 mg, 0.57 mmol) 2,4-difluoroaniline (119.8 mg, 0.92 mmol) in DMF (1 mL, 12.92 mmol) and stirred at 65° C. overnight. The solution was directly charged on a silica gel column and purified by column chromatography using a gradient from 10 till 100% EtOAc in heptane. The product fractions were concentrated and the residue was crystallised from methanol (10 mL) upon addition of water. The white crystals were filtered off and dried at 50° C. overnight, resulting in compound 312 (105 mg). Method D: Rt: 1.88 min m/z:

428.0 (M–H)⁻ Exact mass: 429.1. Differential scanning calorimetry: From 30 to 300° C. at 10° C./min: peak at 179.4° C. ¹H NMR (400 MHz, DMSO-d₆) δ ppm 1.18 (d, J=7.0 Hz, 3H), 3.81 (s, 3H), 3.91-4.03 (m, 1H), 7.07-7.14 (m, 1H), 7.31-7.39 (m, 1H), 7.54 (d, J=4.6 Hz, 1H), 7.63-7.72 (m, 1H), 8.59 (d, J=8.8 Hz, 1H), 9.69 (s, 1H).

Compound 313: N-(3-chloro-5-cyano-4-fluoro-phenyl)-3-fluoro-1-methyl-4-[[(1R)-2,2,2-trifluoro-1-methyl-ethyl]sulfamoyl]pyrrole-2-carboxamide

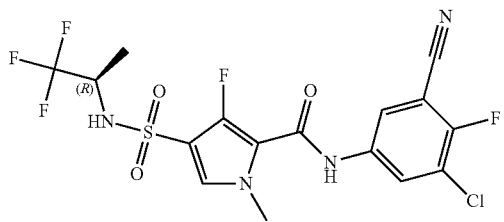

To a solution of 3-chloro-2-fluoro-5-nitro-benzoic acid (9 g, 40.99 mmol) in DMF (150 mL), HATU (31.17 g, 82.0 mmol) and DIPEA (15.89 g, 123.0 mmol) were added The reaction was stirred at room temperature for 10 minutes. NH₄Cl (3.29 g, 61.5 mmol) was added and the mixture was stirred overnight. Water was added and the mixture was extracted with ethyl acetate. The organic layer was collected, washed with brine, dried and evaporated. The crude was purified by column chromatography over silica gel (petrol ether/ethyl acetate=1/1) resulting in 3-chloro-2-fluoro-5-nitro-benzamide (3 g). To a solution of 3-chloro-2-fluoro-5-nitro-benzamide (3 g) in CH₃CN (50 mL), POCl₃ was added (6.86 g, 44.74 mmol) dropwise. The mixture was stirred at 80° C. overnight. The mixture was evaporated and NaHCO₃ solution was added to adjust the pH to 7-8. CH₂Cl₂ was added and the organic layer was collected, dried and evaporated resulting in 3-chloro-2-fluoro-5-nitro-benzonitrile (1.6 g). A mixture of 3-chloro-2-fluoro-5-nitro-benzonitrile (1.5 g, 7.48 mmol) in ethyl acetate (40 mL) was hydrogenated at room temperature with Pd/C (0.3 g) as a catalyst. After uptake of H₂, the catalyst was filtered off and the filtrate was evaporated. The crude compound was purified by high-performance liquid chromatography (Column: ADIKMA Diamonsil(2) C₁₈, 150*25*5 um, Flow rate: 35 mL/min, Mobile Phase A: Purified water (containing 0.5% HCl), Mobile Phase B: CH₃CN, Gradient: 53-83% (% B). NaHCO₃ solution was added to adjust the pH to 8. The desired fraction was collected and the solvent was concentrated in vacuo resulting in 5-amino-3-chloro-2-fluoro-benzonitrile (253 mg).

Compound 313 (118 mg) was prepared similarly as described for compound 312 using 5-amino-3-chloro-2-fluoro-benzonitrile instead of 2,4-difluoroaniline. Method D: Rt: 2.01 min m/z: 469.0 (M–H)⁻ Exact mass: 470.0. Differential scanning calorimetry: From 30 to 300° C. at 10° C./min: peak at 205.4° C. ¹H NMR (400 MHz, DMSO-d₆) δ ppm 1.18 (d, J=7.0 Hz, 3H), 3.81 (s, 3H), 3.92-4.04 (m, 1H), 7.58 (d, J=4.4 Hz, 1H), 8.08 (dd, J=5.1, 2.6 Hz, 1H), 8.21 (dd, J=6.7, 2.5 Hz, 1H), 8.64 (d, J=8.4 Hz, 1H), 10.40 (s, 1H).

Compound 314: 5-chloro-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide

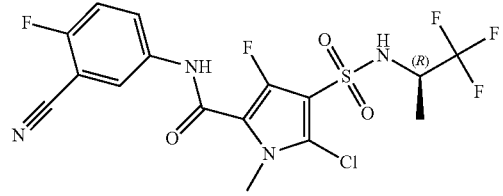

NCS (20.0 mg, 0.15 mmol) was added to compound 181 (synthesized similarly as described for compound 181, but on a larger scale, 68 mg, 0.15 mmol) acetonitrile (1 mL, 19.15 mmol) DMF (1 mL) and stirred over weekend. More NCS (0.75 eq) was added and the reaction mixture was stirred overnight. The reaction mixture was charged directly on a silica gel column and purified using a gradient from 10 till 100% EtOAc in heptane. The product fractions were concentrated. The obtained residue was dissolved in methanol (5 mL) and the product crystallised upon addition of water. The white powder was filtered off and dried overnight in vacuo at 50° C., resulting in compound 314 (9.6 mg). Method B: Rt: 1.05 min m/z: 486.9 (M–H)⁻ Exact mass: 488.0.
¹H NMR (400 MHz, DMSO-d₆) δ ppm 1.22 (d, J=7.0 Hz, 3H), 3.80 (s, 3H), 3.95-4.15 (m, 1H), 7.47 (td, J=9.0, 1.4 Hz, 1H), 8.03 (td, J=8.9, 6.2 Hz, 1H), 8.96 (d, J=8.8 Hz, 1H), 10.22 (s, 1H).

Compound 315: 5-bromo-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide

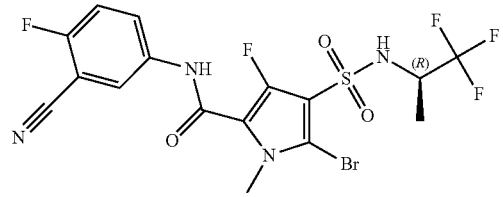

Compound 181 (synthesized similarly as described for compound 181, but on a larger scale, 221 mg, 0.486 mmol) and NBS (129.9 mg, 0.73 mmol) were dissolved in DMF (1.5 mL) and acetonitrile (1.5 mL) and stirred overnight. Extra NBS (50 mg) was added and the mixture was stirred for 30 minutes. The reaction mixture was subjected directly to column chromatography on a silica gel column chromatography system using a gradient from 10 till 100% EtOAc in heptane. The product fractions were concentrated. The residue was crystallised from methanol (10 mL) upon addition of water. The white crystals were filtered off and dried overnight in vacuo at 50° C., resulting in compound 315 (125 mg). Method D: Rt: 1.93 min m/z: 533.0 (M–H)⁻ Exact mass: 534.0. Differential scanning calorimetry: From 30 to 300° C. at 10° C./min: peak at 197.6° C. ¹H NMR (360 MHz, DMSO-d₆) δ ppm 1.22 (d, J=7.0 Hz, 3H), 3.81 (s, 3H), 3.95-4.08 (m, 1H), 7.48 (s, 1H), 7.98-8.07 (m, 1H), 8.95 (d, J=8.8 Hz, 1H), 10.28 (s, 1H).

Compound 316: 3-cyano-N-(3-cyano-4-fluoro-phenyl)-1,5-dimethyl-4-[[(1R)-2,2,2-trifluoro-1-methyl-ethyl]sulfamoyl]pyrrole-2-carboxamide

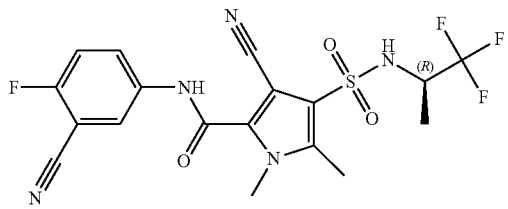

Ethyl 3-fluoro-1,5-dimethyl-4-[[(1R)-2,2,2-trifluoro-1-methyl-ethyl]sulfamoyl]pyrrole-2-carboxylate (211 mg, 0.59 mmol), potassium cyanide (190.9 mg, 2.93 mmol), DMA (5 mL, 54.0 mmol), 18-crown-6 (156.6 mg, 0.59 mmol) were heated at 165° C. during 6 hours and further overnight at 150° C. The reaction mixture was concentrated. The obtained residue was dissolved in water/EtOAc (10/20 mL) The organic layer was dried over magnesium sulphate, filtered and concentrated. The obtained residue was purified by silica gel column chromatography using a gradient from 10 till 100% EtOAc in heptane. The product fractions were concentrated yielding ethyl 3-cyano-1,5-dimethyl-4-[[(1R)-2,2,2-trifluoro-1-methyl-ethyl]sulfamoyl]pyrrole-2-carboxylate (27 mg) as a clear oil which was used as such. Method D: Rt: 1.74 min m/z: 366.0 (M−H)⁻ Exact mass: 367.1. Lithium bis(trimethylsilyl)amide in toluene (0.296 mL, 1 M, 0.296 mmol) was added to a mixture of ethyl 3-cyano-1,5-dimethyl-4-[[(1R)-2,2,2-trifluoro-1-methyl-ethyl]sulfamoyl]pyrrole-2-carboxylate (27 mg, 0.07 mmol) and 5-amino-2-fluoro-benzonitrile (13.1 mg, 0.10 mmol) in THF (2 mL) and stirred overnight. The reaction mixture was quenched with NH₄Cl solution (5 mL) and diluted with brine (5 mL), then extracted with EtOAc (20 mL). The organic layer was dried over magnesium sulphate, filtered and concentrated. The residue was dissolved in DMF (1 mL) and purified by silica gel column chromatography using a gradient from 10 till 100% EtOAc in heptane. The product fractions were concentrated and the residue dissolved in methanol (2 mL). Water was added until crystallisation began. The crystals were filtered off and dried in vacuo at 50° C., resulting in compound 316 (8 mg). Method D: Rt: 1.78 min m/z: 456.1 (M−H)⁻ Exact mass: 457.1. ¹H NMR (360 MHz, DMSO-d₆) δ ppm 1.20 (d, J=6.8 Hz, 3H), CH₃ overlapping DMSO signal, 3.72 (s, 3H), 3.93-4.05 (m, 1H), 7.59 (t, J=9.1 Hz, 1H), 7.94 (ddd, J=9.1, 4.8, 2.8 Hz, 1H), 8.20 (dd, J=5.7, 2.6 Hz, 1H), 8.75 (d, J=9.0 Hz, 1H), 11.16 (s, 1H).

Compound 317: N-(3-cyano-4-fluoro-phenyl)-4-[[(1R)-2,2-difluoro-1-methyl-propyl]sulfamoyl]-3-fluoro-1-methyl-pyrrole-2-carboxamide

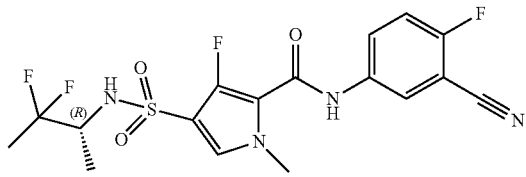

Ethyl 4-chlorosulfonyl-3-fluoro-1-methyl-pyrrole-2-carboxylate (725 mg, 2.54 mmol), (2R)-3,3-difluorobutan-2-amine hydrochloride (415.7 mg), NaHCO₃ (853 mg, 10.2 mmol), acetonitrile (10 mL) and molecular sieves 4A (3000 mg) were heated at 80° C. for 18 hours in a pressure tube. The reaction mixture was filtered and the solids on filter were washed with acetonitrile (2×10 mL). The filtrate was concentrated. The residue (1 g) was subjected to silica gel column chromatography using a gradient from 0 till 100% EtOAc in heptane. The product fractions were concentrated in vacuo at 50° C. yielding ethyl 4-[[(1R)-2,2-difluoro-1-methyl-propyl]sulfamoyl]-3-fluoro-1-methyl-pyrrole-2-carboxylate (882 mg) as a white powder. Ethyl 4-[[(1R)-2,2-difluoro-1-methyl-propyl]sulfamoyl]-3-fluoro-1-methyl-pyrrole-2-carboxylate (150 mg, 0.42 mmol) and 5-amino-2-fluorobenzonitrile (75.9 mg, 0.54 mmol) were dissolved in THF (5 mL). Lithium bis(trimethylsilyl)amide (1.67 mL, 1 M, 1.67 mmol) was added drop wise and the reaction mixture was stirred at room temperature for 30 minutes. The reaction mixture was quenched with sat. NH₄Cl (aq, 5 mL). The organic layer was removed and the aqueous layer extracted with CH₂Cl₂ (2×5 mL). The combined organic layers were evaporated to dryness and the residue was purified by silica gel chromatography (ethyl acetate in heptane 0 to 100% and again with ethyl acetate in heptane 0 to 60%). The desired fractions were evaporated to dryness, the resulting residue was dissolved in refluxing isopropanol (7 mL) and sonicated to afford a suspension. The white solids were filtered and washed with isopropanol (1 mL) to afford compound 317 (115 mg) as off white powder. ¹H NMR (400 MHz, DMSO-d₆) δ ppm 1.07 (d, J=6.8 Hz, 3H), 1.58 (t, J=19.1 Hz, 3H), 3.45-3.61 (m, 1H), 3.81 (s, 3H), 7.48-7.54 (m, 1H), 7.54 (t, J=9.2 Hz, 1H), 7.96 (ddd, J=9.2, 4.9, 2.6 Hz, 1H), 8.04-8.37 (m, 1H), 8.17 (dd, J=5.7, 2.6 Hz, 1H), 10.32 (br. s., 1H). Method B: Rt: 0.98 min m/z: 431.1 (M−H)⁻ Exact mass: 432.1.

Compound 318: N-(3-cyano-4-fluoro-phenyl)-4-[[(1S)-2,2-difluoro-1-methyl-propyl]sulfamoyl]-3-fluoro-1-methyl-pyrrole-2-carboxamide

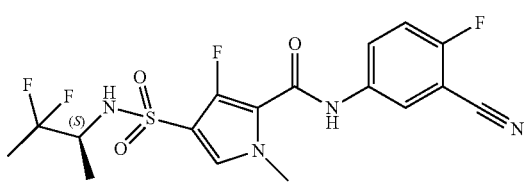

Compound 318 (111 mg) was prepared similarly as described for compound 317, using (2S)-3,3-difluorobutan-2-amine hydrochloride instead of (2R)-3,3-difluorobutan-2-amine hydrochloride. Method B: Rt: 0.98 min m/z: 431.1 (M−H)⁻ Exact mass: 432.1.

¹H NMR (400 MHz, DMSO-d₆) δ ppm 1.07 (d, J=6.8 Hz, 3H), 1.58 (t, J=19.1 Hz, 3H), 3.48-3.61 (m, 1H), 3.82 (s, 3H), 7.52 (d, J=4.6 Hz, 1H), 7.54 (t, J=9.2 Hz, 1H), 7.96 (ddd, J=9.2, 4.9, 2.9 Hz, 1H), 8.10-8.28 (m, 1H), 8.17 (dd, J=5.8, 2.8 Hz, 1H), 10.34 (br. s., 1H). Differential scanning calorimetry: From 30 to 300° C. at 10° C./min: peak at 167.9° C.

Compound 319: N-(3-cyano-4-fluoro-phenyl)-3-fluoro-1-methyl-4-[[1-(trifluoromethyl)cyclobutyl]sulfamoyl]pyrrole-2-carboxamide

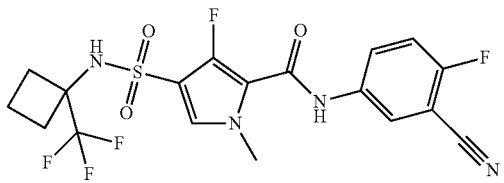 [SMILES: Cn1cc(S(=O)(=O)NC2(C(F)(F)F)CCC2)c(F)c1C(=O)Nc1ccc(F)c(C#N)c1]

A mixture ethyl 4-chlorosulfonyl-3-fluoro-1-methyl-pyrrole-2-carboxylate (640 mg, 2.20 mmol) 1-(trifluoromethyl)cyclobutan-1-amine (1710 mg, 12.29 mmol), NaHCO$_3$ (553 mg, 6.58 mmol), acetonitrile (12.8 mL, 245.1 mmol) and molecular sieves 4A (250 mg) was stirred and refluxed in total for 5 days (After 2 days another 4 equiv of 1-(trifluoromethyl)cyclobutan-1-amine were added). The reaction mixture was filtered while still hot. The filtrate was concentrated. and the obtained residue was purified by column chromatography by silica gel chromatography using a gradient from 10 to 100% EtOAc in heptane. The product fractions were concentrated in vacuo at 50° C. yielding ethyl 3-fluoro-1-methyl-4-[[1-(trifluoromethyl)cyclobutyl]sulfamoyl]pyrrole-2-carboxylate (631 mg) as white crystals. Method D: Rt: 1.90 min m/z: 371.3 (M−H)$^-$ Exact mass: 372.1. A solution of ethyl 3-fluoro-1-methyl-4-[[1-(trifluoromethyl)cyclobutyl]sulfamoyl]pyrrole-2-carboxylate (624 mg, 1.68 mmol), LiOH (120.4 mg, 5.03 mmol) in THF (10 mL) and water (distilled, 10 mL) was stirred overnight. HCl (1M in H$_2$O) (5.03 mL, 1 M, 5.03 mmol) was added and THF distilled off. The white precipitate was filtered off and dried overnight in vacuo at 50° C., resulting in 3-fluoro-1-methyl-4-[[1-(trifluoromethyl)cyclobutyl]sulfamoyl]pyrrole-2-carboxylic acid (412 mg) Method D: Rt: 1.04 min m/z: 343.0 (M−H)$^-$ Exact mass: 344.0. $^1$H NMR (400 MHz, DMSO-d$_6$) δ ppm 1.82 (quin, J=8.1 Hz, 2H), 2.26-2.35 (m, 2H), 2.39-2.48 (m, 2H), 3.82 (s, 3H), 7.53 (d, J=4.8 Hz, 1H), 8.67 (s, 1H), 13.12 (br. s., 1H). Et$_3$N (0.23 mL, 1.62 mmol) was added to a mixture of 3-fluoro-1-methyl-4-[[1-(trifluoromethyl)cyclobutyl]sulfamoyl]pyrrole-2-carboxylic acid (186 mg, 0.54 mmol), HATU (257 mg, 0.676 mmol) and 5-amino-2-fluoro-benzonitrile (147.323 mg, 1.082 mmol) in DMF (2 mL) and the mixture was stirred 4 hours at 65° C. The reaction mixture was purified directly by silica gel column chromatography using a gradient from 10 till 100% EtOAc in heptane. The product fractions were concentrated in vacuo yielding a white powder which was dried overnight in vacuo at 50° C. This powder was dissolved in warm methanol (25 mL) and water was added until crystallisation began. The white crystals were filtered off and dried in vacuo at 50° C. overnight, resulting in compound 319 (157 mg). Method D: Rt: 1.96 min m/z: 461.3 (M−H)$^-$ Exact mass: 462.1. $^1$H NMR (400 MHz, DMSO-d$_6$) δ ppm 1.78-1.91 (m, 2H), 2.28-2.37 (m, 2H), 2.41-2.48 (m, 2H), 3.82 (s, 3H), 7.50-7.58 (m, 2H), 7.97 (ddd, J=9.2, 4.9, 2.6 Hz, 1H), 8.17 (dd, J=5.8, 2.8 Hz, 1H), 8.71 (s, 1H), 10.36 (s, 1H).

Biological Examples—Anti-HBV Activity of Compounds of Formula (ID)

The anti-HBV activity was measured using a stable transfected cell line, HepG2.2.15. This cell line was described to secrete relatively consistent high levels of HBV virion particles, which have been shown to cause both acute and chronic infection and disease in chimpanzees. For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| Co. No. | HepG2 2.15 EC$_{50}$ (μM) | HepG2 117 EC$_{50}$ (μM) | HepG2 4 days CC$_{50}$ (μM) |
| --- | --- | --- | --- |
| 1 | 0.42 | 3.10 | >25 |
| 2 | 0.03 | 0.06 | >25 |
| 3 | 0.07 | 0.10 | >25 |
| 4 | 0.10 | 0.06 | >25 |
| 5 | 0.03 | 0.02 | >25 |
| 6 | 0.02 | 0.02 | >25 |
| 7 | 0.12 | 0.10 | >25 |
| 8 | 0.02 | 0.02 | >25 |
| 9 | 0.01 | 0.03 | >25 |
| 10 | 0.11 | 0.08 | >25 |
| 11 | 0.03 | 0.02 | >25 |
| 12 | 0.12 | 0.06 | >25 |
| 13 | 0.46 | 0.14 | >25 |
| 13a | 0.35 | 0.20 | >25 |
| 13b | 1.01 | 0.46 | >25 |
| 14 | 0.04 | 0.02 | >25 |
| 15 | 0.16 | 0.13 | >25 |
| 16 | 0.06 | 0.03 | >25 |
| 17 | 0.03 | 0.02 | >25 |
| 18 | <0.02 | 0.03 | >25 |
| 19 | 0.06 | 0.08 | >25 |
| 20 | 0.07 | 0.06 | >25 |
| 21 | 0.22 | 0.84 | >25 |
| 22 | 0.08 | 0.07 | >25 |
| 23 | 0.02 | 0.13 | >25 |
| 24 | 0.20 | 0.30 | >25 |
| 25 | 0.34 | 0.23 | >25 |
| 26 | 0.14 | 0.26 | >25 |
| 27 | 0.04 | 0.06 | >25 |
| 28 | 0.10 | 0.14 | >25 |
| 29 | 0.15 | 0.21 | >25 |
| 30 | 0.45 | 0.33 | >25 |
| 31 | 0.13 | 0.39 | >25 |
| 32 | 0.18 | 0.34 | >25 |
| 33 | 0.03 | 0.04 | >25 |
| 34 | 0.03 | <0.02 | >25 |
| 35 | 0.03 | 0.02 | >25 |
| 36 | 0.08 | 0.04 | >25 |
| 37 | 0.73 | 0.38 | >25 |
| 38 | 0.05 | 0.02 | >25 |
| 39 | 0.05 | 0.04 | >25 |
| 40 | 0.20 | 0.12 | >25 |
| 41 | 0.52 | 0.33 | >25 |
| 42 | 0.54 | 0.72 | >25 |
| 43 | 0.11 | 0.13 | >25 |
| 44 | 0.37 | 0.26 | >25 |
| 45 | 0.32 | 0.34 | >25 |

TABLE 1-continued

| Co. No. | HepG2 2.15 EC$_{50}$ (μM) | HepG2 117 EC$_{50}$ (μM) | HepG2 4 days CC$_{50}$ (μM) |
|---|---|---|---|
| 46 | 0.12 | 0.17 | >25 |
| 47 | 0.10 | 0.10 | >25 |
| 48 | 0.05 | 0.06 | >25 |
| 49 | 0.07 | 0.02 | >25 |
| 50 | 0.07 | 0.05 | >25 |
| 51 | >1 | >1 | >25 |
| 52 | 0.26 | 0.33 | >25 |
| 53 | 0.26 | 0.18 | >25 |
| 54 | 0.20 | 0.25 | >25 |
| 55 | 0.21 | 0.11 | >25 |
| 56 | 0.02 | <0.02 | >25 |
| 57 | 0.06 | 0.05 | >25 |
| 58 | 0.09 | 0.06 | >25 |
| 59 | 0.03 | 0.03 | >25 |
| 60 | 0.02 | 0.03 | 24.1 |
| 61 |  | >1 | >25 |
| 62 | 0.27 | 0.14 | >25 |
| 63 | 0.06 | 0.04 | >25 |
| 64 | 0.13 | 0.05 | >25 |
| 65 | 0.01 | 0.01 | >25 |
| 66 | 0.03 | 0.03 | >25 |
| 67 | 0.02 | 0.03 | >25 |
| 68 | 0.07 | 0.07 | >25 |
| 69 | 0.03 | 0.07 | >25 |
| 70 | 0.02 | 0.04 | >25 |
| 71 | 0.10 | 0.13 | >25 |
| 72 | 0.01 | 0.01 | >25 |
| 73 |  | 0.10 | 14.1 |
| 74 | 0.02 | 0.02 | >25 |
| 75 | 0.18 | 0.18 | >25 |
| 76 | 0.18 | 0.13 | >25 |
| 77 | 0.07 | 0.18 | >25 |
| 78 | 0.02 | 0.03 | >25 |
| 79 | 0.53 | 0.46 | >25 |
| 80 | 0.04 | 0.09 | >25 |
| 81 | 0.01 | 0.05 | >25 |
| 82 | 0.17 | 0.49 | >25 |
| 83 | >1 | 1.35 | >25 |
| 84 | 0.46 | 0.61 | >25 |
| 85 | 0.03 | 0.05 | >25 |
| 86 | 0.37 | 0.35 | >25 |
| 87 | 0.96 | >1 | >25 |
| 88 | 0.02 | 0.03 | >25 |
| 89 | 0.02 | 0.02 | >25 |
| 90 | 0.05 | 0.03 | >25 |
| 91 | 0.06 | 0.04 | >25 |
| 92 | 0.04 | 0.03 | >25 |
| 93 | 0.03 | 0.03 | >25 |
| 94 | 0.009 | 0.01 | >25 |
| 95 | 0.13 | 0.06 | >25 |
| 96 | 0.01 | 0.03 | 23.7 |
| 97 | 0.03 | 0.03 | >25 |
| 98 | 0.81 | 0.54 | >25 |
| 99 | 0.13 | 0.10 | >25 |
| 100 | 0.06 | 0.05 | 12.2 |
| 101 | 0.03 | 0.03 | >25 |
| 102 | 0.06 | 0.06 | >25 |
| 103 | 0.05 | 0.02 | >25 |
| 104 | 0.02 | 0.02 | >25 |
| 105 | 0.03 | 0.02 | >25 |
| 106 | 0.01 | 0.01 | >25 |
| 107 | 0.01 | 0.01 | >25 |
| 108 |  | 0.01 | >25 |
| 109 | 0.24 | 0.10 | >25 |
| 110 | 0.02 | 0.03 | >25 |
| 111 | 0.007 | 0.007 | >25 |
| 112 | 0.06 | 0.09 | >25 |
| 113 | 0.03 | 0.02 | >25 |
| 114 | 0.10 | 0.05 | >25 |
| 115 | 0.30 | 0.11 | >25 |
| 116 | 0.03 | 0.02 | >25 |
| 117 | 0.007 | 0.01 | >25 |
| 118 | 0.05 | 0.02 | >25 |
| 119 | 0.03 | 0.01 | >25 |
| 120 | 0.03 | 0.03 | >25 |
| 121 | 0.05 | 0.04 | >25 |
| 122 | 0.07 | >1 | 13.1 |
| 123 | 0.04 | 0.04 | >25 |
| 124 | 0.04 | 0.04 | >25 |
| 125 | 0.19 | 0.08 | 16.7 |
| 126 | 0.59 | 0.23 | >25 |
| 127 | 0.05 | 0.19 | >25 |
| 128 | 0.15 | 0.09 | >25 |
| 129 | 0.17 | 0.08 | >25 |
| 130 | 0.09 | 0.15 | >25 |
| 131 | 0.01 | 0.01 | >25 |
| 132 | 0.08 | 0.07 | >25 |
| 133 | 0.04 | 0.08 | >25 |
| 134 | 0.18 | 0.13 | >25 |
| 135 | 0.02 | 0.26 | >25 |
| 136 | 0.06 | 0.06 | >25 |
| 137 | 0.03 | 0.04 | 16.5 |
| 138 | 0.10 | 0.03 | >25 |
| 139 | 0.05 | 0.03 | >25 |
| 140 | 0.10 | 0.06 | >25 |
| 141 | 0.04 | 0.15 | >25 |
| 142 | 0.15 | 0.42 | >25 |
| 143 | 0.05 | 0.15 | >25 |
| 144 | 0.05 | 0.07 | >25 |
| 145 | 0.04 | 0.03 | >25 |
| 146 | 0.07 | 0.04 | >25 |
| 147 | 0.08 | 0.04 | >25 |
| 148 | 0.11 | 0.07 | >25 |
| 149 | 0.04 | 0.03 | >25 |
| 150 | 0.09 | 0.06 | >25 |
| 151 | 0.08 | 0.07 | >25 |
| 152 | 0.24 | 0.08 | >25 |
| 153 | 0.27 | 0.15 | >25 |
| 154 | 0.13 | 0.08 | >25 |
| 155 | 0.03 | 0.05 | >25 |
| 156 | 0.04 | 0.03 | >25 |
| 157 | 0.08 | 0.05 | >25 |
| 158 | 0.12 | 0.36 | >25 |
| 159 | 0.09 | 0.81 | >25 |
| 160 | 0.16 | 0.13 | >25 |
| 161 | >1 | 0.91 | >25 |
| 162 | >1 | 0.89 | >25 |
| 163 | 0.18 | 0.11 | 14.3 |
| 164 | 0.13 | 0.13 | >25 |
| 165a | 0.15 | 0.04 | 9.3 |
| 165b | 0.12 | 0.02 | 4.8 |
| 166 | 0.14 | 0.12 | >25 |
| 166a | 0.14 | 0.10 | 17.9 |
| 166b | 0.31 | 0.17 | 21.3 |
| 167 | 0.12 | 0.31 | >25 |
| 168 | 0.12 | 0.32 | >25 |
| 169 | 0.12 | 0.07 | 11.2 |
| 169a | 0.14 | 0.05 | 16.1 |
| 169b | 0.04 | 0.03 | 17.1 |
| 170 | <0.005 | 0.005 | >100 |
| 171 | 0.02 | 0.02 | >25 |
| 172 | 0.10 | 0.08 | >25 |
| 173 | 0.21 | 0.32 | >25 |
| 174 | 0.08 | 0.04 | >25 |
| 175 | 0.07 | 0.13 | >25 |
| 176 | 0.50 | 0.37 | >25 |
| 177 | 0.33 | 0.26 | >25 |
| 178 | 0.04 | 0.09 | >25 |
| 179 | 0.30 | 0.27 | >25 |
| 180 | 0.01 | 0.02 | >25 |
| 181 | 0.008 | 0.006 | >25 |
| 182 | 0.01 | 0.03 | >25 |
| 183 | 0.02 | 0.01 | >25 |
| 184 | 0.008 | 0.006 | >25 |
| 185 | 0.006 | 0.005 | >25 |
| 186 | 0.008 | 0.005 | >25 |
| 187 | 0.008 | 0.006 | >25 |
| 188 | 0.04 | 0.03 | >25 |
| 189 | 0.007 | 0.007 | 11.3 |
| 190 | 0.09 | 0.10 | >25 |
| 191 | 0.18 | 0.16 | >25 |
| 192 | 0.57 | 0.19 | >25 |

TABLE 1-continued
| Co. No. | HepG2 2.15 EC$_{50}$ (μM) | HepG2 117 EC$_{50}$ (μM) | HepG2 4 days CC$_{50}$ (μM) |
|---|---|---|---|
| 193 | 0.14 | 0.11 | >25 |
| 194 | 0.09 | 0.05 | >25 |
| 195 | 0.04 | 0.04 | >25 |
| 196 | 0.10 | 0.08 | >25 |
| 197 | 0.12 | 0.09 | >25 |
| 198 | 0.15 | 0.08 | >25 |
| 199 | 0.006 | 0.008 | >25 |
| 200a | 0.10 | 0.05 | >25 |
| 200b | 0.09 | 0.10 | >25 |
| 201 | 0.07 | 0.02 | >25 |
| 202 | 0.03 | 0.02 | >25 |
| 203 | 0.38 | 0.47 | >25 |
| 204 | 0.65 | 0.62 | >25 |
| 205 | 0.08 | 0.03 | 13.0 |
| 206 | 0.03 | 0.09 | >25 |
| 207 | 0.05 | 0.14 | >25 |
| 208 | 0.20 | 0.66 | >25 |
| 209 | 0.09 | 0.09 | >25 |
| 210 | 0.05 | 0.05 | >25 |
| 211 | 0.04 | 0.04 | >25 |
| 212 | 0.09 | 0.04 | >25 |
| 213 | 0.21 | 0.31 | >25 |
| 214 | 0.06 | 0.02 | >25 |
| 215 | 0.02 | 0.010 | >25 |
| 216 | 0.18 | 0.46 | >25 |
| 217 | 0.005 | 0.005 | >25 |
| 218 | 0.009 | 0.007 | >25 |
| 219 | 0.01 | 0.009 | >25 |
| 220 | 0.10 | 0.04 | >25 |
| 221 | 0.007 | 0.006 | >25 |
| 222 | 0.004 | 0.009 | >25 |
| 223 | 0.12 | 0.09 | >25 |
| 224 | 0.22 | 0.26 | >25 |
| 225 | 0.07 | 0.07 | >25 |
| 226 | 0.19 | 0.21 | >25 |
| 227 | 0.02 | 0.04 | >25 |
| 228a | 0.03 | 0.03 | >25 |
| 228b | 0.03 | 0.03 | >25 |
| 229 | 0.004 | 0.004 | >25 |
| 230 | 0.008 | 0.03 | >25 |
| 231 | 0.04 | 0.03 | >25 |
| 232 | 0.02 | 0.02 | >25 |
| 233 | 0.09 | 0.16 | >25 |
| 234 | 0.02 | 0.03 | >25 |
| 235 | 0.01 | 0.01 | >25 |
| 236a | 0.02 | 0.05 | >25 |
| 236b | 0.06 | 0.05 | >25 |
| 237 | 0.08 | 0.10 | >25 |
| 238 | 0.10 | 0.11 | >25 |
| 239 | 0.02 | 0.01 | >25 |
| 240 | 0.02 | 0.05 | >25 |
| 241 | 0.01 | 0.01 | >25 |
| 242 | 0.20 | 0.30 | >25 |
| 243 | 0.11 | 0.10 | >25 |
| 244 | 0.14 | 0.53 | >25 |
| 245 | 0.04 | 0.04 | >25 |
| 246 | 0.05 | 0.06 | >25 |
| 247 | 0.03 | 0.03 | >25 |
| 248 | 0.03 | 0.07 | >25 |
| 249 | 0.07 | 0.18 | 1.7 |
| 250 | 0.007 | 0.40 | 20.0 |
| 251 | 0.01 | 0.06 | >25 |
| 252 | 0.05 | 0.08 | >25 |
| 253 | 0.01 | 0.01 | >25 |
| 254 | 0.05 | 0.05 | >25 |
| 255 | 0.09 | 0.10 | >25 |
| 256 | 0.02 | 0.03 | >25 |
| 257 | 0.08 | 0.09 | >25 |
| 258 | 0.03 | 0.02 | >25 |
| 259 | 0.05 | 0.05 | >25 |
| 260 | 0.07 | 0.09 | >25 |
| 261 | 0.04 | 0.13 | >25 |
| 262 | 0.02 | 0.02 | >25 |
| 263 | 0.005 | 0.008 | >25 |
| 264 | 0.09 | 0.13 | >25 |
| 265 | 0.01 | 0.03 | >25 |
| 266 | 0.02 | 0.03 | >25 |
| 267 | 0.006 | 0.009 | >25 |
| 268 | 0.005 | 0.006 | >25 |
| 269 | 0.05 | 0.07 | >25 |
| 270 | 0.06 | 0.11 | >25 |
| 271 | 0.009 | 0.02 | >25 |
| 272 | 0.30 | 0.76 | >25 |
| 273 | 0.42 | 0.70 | >25 |
| 274 | 0.02 | 0.04 | 19.4 |
| 275 | 0.60 | 0.70 | >25 |
| 276 | 0.01 | 0.01 | >25 |
| 277 | 0.03 | 0.04 | >25 |
| 278 | 0.006 | 0.01 | >25 |
| 279 | <0.004 | 0.005 | >25 |
| 280 | 0.005 | 0.06 | >25 |
| 281 | <0.004 | 0.007 | >25 |
| 282 | <0.005 | 0.005 | >25 |
| 283 | 0.02 | 0.03 | >25 |
| 284 |  | 0.009 | >25 |
| 285 |  | 0.007 | >25 |
| 286 |  | 0.005 | 21.9 |
| 287 | 0.004 | 0.005 | >25 |
| 288 | 0.007 | 0.01 | >25 |
| 289 | 0.04 | 0.05 | >25 |
| 290 |  | 0.02 | >25 |
| 291 | 0.42 | 0.39 | >25 |
| 292 |  | 0.03 | 15.5 |
| 293 | 0.02 | 0.05 | >25 |
| 294 | 0.04 | 0.10 | >25 |
| 295 | 0.02 | 0.03 | >25 |
| 296 | 0.10 | 0.23 | >25 |
| 297 | 0.04 | 0.09 | 22.6 |
| 298 | 0.02 | 0.05 | 23.7 |
| 299 |  | 0.009 | >25 |
| 300 |  | 0.008 | 14.2 |
| 301 |  | 0.007 | >25 |
| 302 |  | 0.03 | >25 |
| 303 | >12.5 |  | >25 |
| 304 |  | 0.01 | >25 |
| 305 | 0.17 | 0.35 | >25 |
| 306 | 0.03 | 0.06 | >25 |
| 307 |  | 0.03 | >25 |
| 308 |  | 0.01 | >25 |
| 309 | 0.53 | 0.32 | >25 |
| 310 | 0.07 | 0.16 | >25 |
| 311 |  | 0.06 | >25 |
| 312 |  | 0.06 | >25 |
| 313 | 0.02 | 0.05 | >25 |
| 314 |  | 0.007 | >25 |
| 315 |  | 0.007 | >25 |
| 316 | 0.05 | 0.05 | >25 |
| 317 |  | 0.006 | >25 |
| 318 |  | 0.019 | >25 |
| 319 |  | <0.004 | >25 |
The invention claimed is:
1. A method of treating Hepatitis B virus infection in a subject in need thereof comprising administering to said subject a therapeutically effective amount of a compound of Formula (ID)
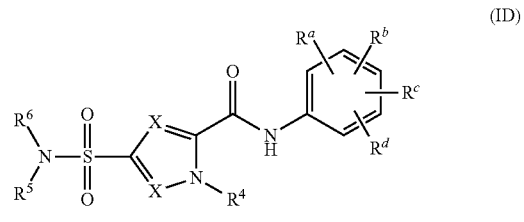

or a stereoisomer or tautomeric form thereof, wherein:
each X is independently $CR^7$;
$R^a$, $R^b$ and $R^c$ are each independently selected from the group consisting of hydrogen, fluoro, bromo, chloro, —$CHF_2$, —$CF_2$-methyl, —$CH_2F$, —$CF_3$, —$OCF_3$, —CN, $C_1$-$C_3$alkyl and $C_3$-$C_4$cycloalkyl;
$R^d$ is hydrogen or fluoro;
$R^4$ is hydrogen, $C_1$-$C_3$alkyl or $C_3$-$C_4$cycloalkyl;
$R^5$ is hydrogen;
$R^6$ is selected from the group consisting of $C_2$-$C_6$alkyl, $C_1$-$C_4$alkyl-$R^8$ optionally substituted with one or more fluoro, $C_1$-$C_4$alkyl-$R^9$ optionally substituted with one or more fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally substituted with one or more substituents each independently selected from the group consisting of hydrogen, —OH, fluoro, oxo, $R^9$, $R^{10}$ and $C_1$-$C_4$alkyl optionally substituted with $R^{10}$;
$R^7$ is selected from the group consisting of hydrogen, —CN, fluoro, chloro, bromo, —$CHF_2$, —$CF_2$—methyl, —$CH_2F$, —$CF_3$, $C_1$-$C_3$alkyl optionally substituted with methoxy, $C_2$-$C_3$alkenyl and $C_3$-$C_4$cycloalkyl;
$R^8$ is a 3-7 membered saturated ring optionally containing one or more heteroatoms each independently selected from the group consisting of O, S and N, such 3-7 membered saturated ring optionally substituted with one or more $C_1$-$C_4$alkyl optionally substituted with $R^{10}$;
$R^9$ is selected from the group consisting of $C_1$-$C_4$alkyloxy, —$SO_2$-methyl, —C(=O)—$OR^{11}$ and —C(=O)—$N(R^{11})_2$;
$R^{10}$ is selected from the group consisting of —CN, —OH, fluoro, —$CHF_2$, —$CH_2F$ and —$CF_3$;
$R^{11}$ is hydrogen or $C_1$-$C_3$alkyl;
or a pharmaceutically acceptable salt or a solvate thereof wherein such compound is not

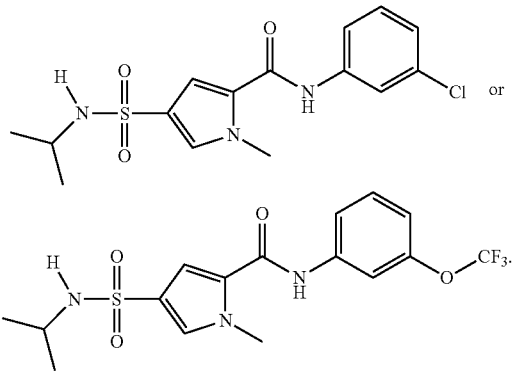

2. The method of claim 1, wherein
$R^a$ is —CN;
$R^b$, $R^c$ and $R^d$ are each independently selected from the group consisting of hydrogen and fluoro;
$R^4$ is $C_1$-$C_3$alkyl;
$R^6$ is selected from the group consisting of $C_2$-$C_6$alkyl, optionally substituted with one or more fluoro; and
$R^7$ is hydrogen.

3. The method of claim 1, wherein the compound is selected from the group consisting of:
N-(4-fluoro-3-methyl-phenyl)-4-(isopropylsulfamoyl)-1H-pyrrole-2-carboxamide;
N-(4-fluoro-3-methyl-phenyl)-4-(isopropylsulfamoyl)-1-methyl-pyrrole-2-carboxamide;
N-(4-fluoro-3-methyl-phenyl)-4-[[(1R)-2-hydroxy-1-methyl-ethyl]sulfamoyl]-1-methyl-pyrrole-2-carboxamide;
N-(4-fluoro-3-methyl-phenyl)-1-methyl-4-[[(3S)-tetrahydrofuran-3-yl]sulfamoyl]pyrrole-2-carboxamide;
N-(4-fluoro-3-methyl-phenyl)-1-methyl-4-[(3-methyloxetan-3-yl)sulfamoyl]pyrrole-2-carboxamide;
N-(4-fluoro-3-methyl-phenyl)-1-methyl-4-[[(1R)-1-methylpropyl]sulfamoyl]pyrrole-2-carboxamide;
N-(4-fluoro-3-methyl-phenyl)-1-methyl-4-[(3-methyloxetan-3-yl)methylsulfamoyl]pyrrole-2-carboxamide;
N-(4-fluoro-3-methyl-phenyl)-1-methyl-4-[[(1S)-2,2,2-trifluoro-1-methyl-ethyl]sulfamoyl]pyrrole-2-carboxamide;
N-(4-fluoro-3-methyl-phenyl)-1-methyl-4-[[(1R)-2,2,2-trifluoro-1-methyl-ethyl]sulfamoyl]pyrrole-2-carboxamide;
N-(4-fluoro-3-methyl-phenyl)-4-[[3-(hydroxymethyl)oxetan-3-yl]sulfamoyl]-1-methyl-pyrrole-2-carboxamide;
N-(4-fluoro-3-methyl-phenyl)-1-methyl-4-[(3-methyltetrahydrofuran-3-yl)sulfamoyl]pyrrole-2-carboxamide;
N-(4-fluoro-3-methyl-phenyl)-4-[[1-(hydroxymethyl)cyclopropyl]sulfamoyl]-1-methyl-pyrrole-2-carboxamide;
N-(4-fluoro-3-methyl-phenyl)-1-methyl-4-[(1-methyl-5-oxo-pyrrolidin-3-yl)sulfamoyl]pyrrole-2-carboxamide;
N-(4-fluoro-3-methy-phenyl)-4-[[3-(2-hydroxyethyl)oxetan-3-yl]sulfamoyl]-1-methyl-pyrrole-2-carboxamide;
N-(4-fluoro-3-methy-phenyl)-4-[(3-hydroxycyclobutyl)sulfamoyl]-1-methyl-pyrrole-2-carboxamide;
4-(tert-butylsulfamoyl)-N-(4-fluoro-3-methyl-phenyl)-1-methyl-pyrrole-2-carboxamide
4-[[3-(cyanomethyl)oxetan-3-yl]sulfamoyl]-N-(4-fluoro-3-methy-phenyl)-1-methyl-pyrrole-2-carboxamide;
4-[[1-(cyanomethyl)cyclopropyl]sulfamoyl]-N-(4-fluoro-3-methyl-phenyl)-1-methyl-pyrrole-2-carboxamide;
4-(tert-butylsulfamoyl)-N-(3,4-difluorophenyl)-1-methyl-pyrrole-2-carboxamide;
N-(3,4-difluorophenyl)-1-methyl-4-[(3-methyloxetan-3-yl)sulfamoyl]pyrrole-2-carboxamide;
N-(3,4-difluorophenyl)-1-methyl-4-[[(3S)-tetrahydrofuran-3-yl]sulfamoyl]pyrrole-2-carboxamide;
N-(3,4-difluorophenyl)-4-(isopropylsulfamoyl)-1-methyl-pyrrole-2-carboxamide;
N-(3,4-difluorophenyl)-1-methyl-4-[[(1R)-1-methylpropyl]sulfamoyl]pyrrole-2-carboxamide;
N-(3,4-difluorophenyl)-4-[[(1R)-2-hydroxy-1-methyl-ethyl]sulfamoyl]-1-methyl-pyrrole-2-carboxamide;
N-(3,4-difluorophenyl)-4-[(3-hydroxycyclobutyl)sulfamoyl]-1-methyl-pyrrole-2-carboxamide;
1-methyl-4-[[(3S)-tetrahydrofuran-3-yl]sulfamoyl]-N-(3,4,5-trifluorophenyl)pyrrole-2-carboxamide;
1-methyl-4-[(3-methyloxetan-3-yl)sulfamoyl]-N-(3,4,5-trifluorophenyl)pyrrole-2-carboxamide;
1-methyl-4-[(3-methyloxetan-3-yl)sulfamoyl]-N-[3-(trifluoromethyl)phenyl]pyrrole-2-carboxamide;
1-ethyl-N-(4-fluoro-3-methyl-phenyl)-4-(isopropylsulfamoyl)pyrrole-2-carboxamide;

1-ethyl-N-(4-fluoro-3-methyl-phenyl)-4-[[(3S)-tetrahydrofuran-3-yl]sulfamoyl]pyrrole-2-carboxamide;
N-(4-fluoro-3,5-dimethyl-phenyl)-1-methyl-4-[[(3S)-tetrahydrofuran-3-yl]sulfamoyl]pyrrole-2-carboxamide;
N-(3-fluoro-5-methyl-phenyl)-1-methyl-4-[[(3S)-tetrahydrofuran-3-yl]sulfamoyl]pyrrole-2-carboxamide;
N-(3,4-difluoro-5-methyl-phenyl)-4-(isopropylsulfamoyl)-1-methyl-pyrrole-2-carboxamide;
N-(3,4-difluoro-5-methyl-phenyl)-1-methyl-4-[[(1R)-1-methylpropyl]sulfamoyl]pyrrole-2-carboxamide;
N-(3,4-difluoro-5-methyl-phenyl)-1-methyl-4-[(3-methyloxetan-3-yl)sulfamoyl]pyrrole-2-carboxamide;
N-(3,4-difluoro-5-methyl-phenyl)-4-[[(1R)-2-hydroxy-1-methyl-ethyl]sulfamoyl]-1-methyl-pyrrole-2-carboxamide;
N-(3,4-difluoro-5-methyl-phenyl)-1-methyl-4-[[(3S)-tetrahydrofuran-3-yl]sulfamoyl]pyrrole-2-carboxamide;
4-(tert-butylsulfamoyl)-N-(3,4-difluoro-5-methyl-phenyl)-1-methyl-pyrrole-2-carboxamide;
N-[3-(difluoromethyl)-4-fluoro-phenyl]-1-methyl-4-[(3-methyloxetan-3-yl)sulfamoyl]pyrrole-2-carboxamide;
N-[3-(difluoromethyl)-4-fluoro-phenyl]-4-[[(1R)-2-hydroxy-1-methyl-ethyl]sulfamoyl]-1-methyl-pyrrole-2-carboxamide;
N-[4-fluoro-3-(trifluoromethyl)phenyl]-4-[[(1R)-2-hydroxy-1-methyl-ethyl]sulfamoyl]-1-methyl-pyrrole-2-carboxamide;
N-[4-fluoro-3-(trifluoromethyl)phenyl]-1-methyl-4-[[(3S)-tetrahydrofuran-3-yl]sulfamoyl]pyrrole-2-carboxamide;
N-[4-fluoro-3-(trifluoromethyl)phenyl]-1-methyl-4-[(3-methyloxetan-3-yl)sulfamoyl]pyrrole-2-carboxamide;
N-[4-fluoro-3-(trifluoromethyl)phenyl]-4-(isopropylsulfamoyl)-1-methyl-pyrrole-2-carboxamide;
N-[3-fluoro-5-(trifluoromethyl)phenyl]-1-methyl-4-[(3-methyloxetan-3-yl)sulfamoyl]pyrrole-2-carboxamide;
N-(3-bromo-4,5-difluoro-phenyl)-4-(isopropylsulfamoyl)-1-methyl-pyrrole-2-carboxamide;
N-(3-bromo-4,5-difluoro-phenyl)-1-methyl-4-[[(1R)-1-methylpropyl]sulfamoyl]pyrrole-2-carboxamide;
N-(3-bromo-4,5-difluoro-phenyl)-1-methyl-4-[(3-methyloxetan-3-yl)sulfamoyl]pyrrole-2-carboxamide;
methyl 2-[[5-[(4-fluoro-3-methyl-phenyl)carbamoyl]-1-methyl-pyrrol-3-yl]sulfonylamino]-2-methyl-propanoate;
N-(3-cyano-4-fluorophenyl)-1-methyl-4-[(3-methyloxetan-3-yl)sulfamoyl]-1H-pyrrole-2-carboxamide;
N-[4-cyano-3-(trifluoromethyl)phenyl]-1-methyl-4-[(3-methyloxetan-3-yl)sulfamoyl]-1H-pyrrole-2-carboxamide;
N-(3-cyano-4,5-difluoro-phenyl)-4-(isopropylsulfamoyl)-1-methyl-pyrrole-2-carboxamide;
4-(tert-butylsulfamoyl)-N-(3-cyano-5-fluoro-phenyl)-1-methyl-pyrrole-2-carboxamide;
N-(3-cyano-5-fluoro-phenyl)-1-methyl-4-[(3-methyloxetan-3-yl)sulfamoyl]pyrrole-2-carboxamide;
N-(3-cyanophenyl)-1-methyl-4-[(3-methyloxetan-3-yl)sulfamoyl]pyrrole-2-carboxamide;
N-(2,6-dideuterio-4-fluoro-3-methyl-phenyl)-1-methyl-4-[(3-methyloxetan-3-yl)sulfamoyl]pyrrole-2-carboxamide;
N-(3-chloro-4,5-difluoro-phenyl)-4-(isopropylsulfamoyl)-1-methyl-pyrrole-2-carboxamide;
4-(tert-butylsulfamoyl)-N-(3-chloro-4,5-difluoro-phenyl)-1-methyl-pyrrole-2-carboxamide;
N-(3-chloro-4,5-difluoro-phenyl)-1-methyl-4-[(3-methyloxetan-3-yl)sulfamoyl]pyrrole-2-carboxamide;
N-(3-chloro-4,5-difluoro-phenyl)-1-methyl-4-[[(1R)-2,2,2-trifluoro-1-methyl-ethyl]sulfamoyl]pyrrole-2-carboxamide;
2-[[5-[(4-fluoro-3-methyl-phenyl)carbamoyl]-1-methyl-pyrrol-3-yl]sulfonylamino]-2-methyl-propanoic acid;
4-[[1,1-dimethyl-2-(methylamino)-2-oxo-ethyl]sulfamoyl]-N-(4-fluoro-3-methyl-phenyl)-1-methyl-pyrrole-2-carboxamide;
4-[[2-(dimethylamino)-1,1-dimethyl-2-oxo-ethyl]sulfamoyl]-N-(4-fluoro-3-methyl-phenyl)-1-methyl-pyrrole-2-carboxamide;
4-[(2-amino-1,1-dimethyl-2-oxo-ethyl)sulfamoyl]-N-(4-fluoro-3-methyl-phenyl)-1-methyl-pyrrole-2-carboxamide;
N-(3-chloro-4,5-difluoro-phenyl)-4-[(3,3-difluoro-1-methyl-cyclobutyl)sulfamoyl]-1-methyl-pyrrole-2-carboxamide;
N-(3-chloro-4,5-difluoro-phenyl)-4-(1,1-dimethylpropylsulfamoyl)-1-methyl-pyrrole-2-carboxamide;
4-tert-butylsulfamoyl)-N-(2,6-dideuterio-4-fluoro-3-methyl-phenyl)-1-methyl-pyrrole-2-carboxamide;
4-(tert-butylsulfamoyl)-1-methyl-N-(3,4,5-trifluorophenyl)pyrrole-2-carboxamide;
N-(4-fluoro-3-methyl-phenyl)-1-methyl-4-[[2,2,2-trideuterio-1,1-bis(trideuteriomethyl)ethyl]sulfamoyl]pyrrole-2-carboxamide;
N-(2,6-dideuterio-4-fluoro-3-methyl-phenyl)-1-methyl-4-[[2,2,2-trideuterio-1,1-bis(trideuteriomethyl)ethyl]sulfamoyl]pyrrole-2-carboxamide;
4-(tert-butylsulfamoyl)-N-(2,6-dideuterio-3,4,5-trifluoro-phenyl)-1-methyl-pyrrole-2-carboxamide;
N-(3-chloro-4,5-difluoro-phenyl)-1-methyl-4-[[1-(trifluoromethyl)-cyclopropyl]sulfamoyl]pyrrole-2-carboxamide;
N-(3-chloro-4,5-difluoro-phenyl)-1-methyl-4-[[2,2,2-trifluoro-1-(methoxymethyl)-1-methyl-ethyl]sulfamoyl]pyrrole-2-carboxamide;
N-(3,4-difluorophenyl)-3-fluoro-1-methyl-4-[(3-methyloxetan-3-yl)sulfamoyl]pyrrole-2-carboxamide;
N-(3,5-Dichloro-4-fluorophenyl)-1-methyl-4-[(3-methyloxetan-3-yl)sulfamoyl]-1H-pyrrole-2-carboxamide;
4-(tert-Butylsulfamoyl)-N-(3,5-dichloro-4-fluorophenyl)-1-methyl-1H-pyrrole-2-carboxamide;
N-(4-Chloro-3-methylphenyl)-1-methyl-4-[(3-methyloxetan-3-yl)sulfamoyl]-1H-pyrrole-2-carboxamide;
N-(3-Chloro-4-fluorophenyl)-1-methyl-4-[(3-methyloxetan-3-yl)sulfamoyl]-1H-pyrrole-2-carboxamide;
N-[4-Fluoro-3-methyl-5-(trifluoromethyl)phenyl]-1-methyl-4-[(3-methyloxetan-3-yl)sulfamoyl]-1H-pyrrole-2-carboxamide;
N-(4-Fluoro-3,5-dimethylphenyl)-1-methyl-4-[(3-methyloxetan-3-yl)sulfamoyl]-1H-pyrrole-2-carboxamide;
N-(3-Bromo-4-fluorophenyl)-1-methyl-4-[(3-methyloxetan-3-yl)sulfamoyl]-1H-pyrrole-2-carboxamide;
1-Methyl-4-[(3-methyloxetan-3-yl)sulfamoyl]-N-[3-methyl-5-(trifluoromethyl)phenyl]-1H-pyrrole-2-carboxamide;
N-(4-Cyano-3-methylphenyl)-1-methyl-4-[(3-methyloxetan-3-ylsulfamoyl]-1H-pyrrole-2-carboxamide;
N-(4-Chloro-3-fluorophenyl)-1-methyl-4-[(3-methyloxetan-3-yl)sulfamoyl]-1H-pyrrole-2-carboxamide;
N-(2,4-Difluoro-3-methylphenyl)-1-methyl-4-[(3-methyloxetan-3-yl)sulfamoyl]-1H-pyrrole-2-carboxamide;
N-[4-Fluoro-3-(trifluoromethoxy)phenyl]-1-methyl-4-[(3-methyloxetan-3-yl)sulfamoyl]-1H-pyrrole-2-carboxamide;

N-(3-Chloro-5-cyanophenyl)-1-methyl-4-[(3-methyloxetan-3-yl)sulfamoyl]-1H-pyrrole-2-carboxamide;

N-(4-Fluoro-3-methylphenyl)-1,3,5-trimethyl-4-[(3-methyloxetan-3-yl)sulfamoyl]-1H-pyrrole-2-carboxamide;

N-(4-Fluoro-3-methylphenyl)-1,5-dimethyl-4-[(3-methyloxetan-3-yl)sulfamoyl]-1H-pyrrole-2-carboxamide;

N-(4-Fluoro-3-methylphenyl)-1,3-dimethyl-4-[(3-methyloxetan-3-yl)sulfamoyl]-1H-pyrrole-2-carboxamide;

N-(3,4-Difluorophenyl)-1-methyl-4-[(3-methyltetrahydrofuran-3-yl)sulfamoyl]-1H-pyrrole-2-carboxamide;

N-(3,4-Difluorophenyl)-1-methyl-4-{[(1R)-2,2,2-trifluoro-1-methylethyl]sulfamoyl}-1H-pyrrole-2-carboxamide;

N-(3,4-Difluorophenyl)-1-methyl-4-{[(1S)-2,2,2-trifluoro-1-methylethyl]sulfamoyl}-1H-pyrrole-2-carboxamide;

3-Fluoro-N-(4-fluoro-3-methylphenyl)-1-methyl-4-[(3-methyloxetan-3-yl)sulfamoyl]-1H-pyrrole-2-carboxamide;

N-(3,4-Difluorophenyl)-1-methyl-4-[(2,2,2-trifluoro-1,1-dimethylethyl)sulfamoyl]-1H-pyrrole-2-carboxamide;

N-(3-Chloro-4,5-difluorophenyl)-1-methyl-4-[(2,2,2-trifluoro-1,1-dimethylethyl)sulfamoyl]-1H-pyrrole-2-carboxamide;

N-(4-Fluoro-3-methylphenyl)-1-methyl-4-{[(1R)-1-methyl-2-(methylsulfonyl)ethyl]sulfamoyl}-1H-pyrrole-2-carboxamide;

4-(tert-Butylsulfamoyl)-N-[4-fluoro-3-(trifluoromethoxy)phenyl]-1-methyl-1H-pyrrole-2-carboxamide;

N-(2,4-Difluoro-3-methylphenyl)-1-methyl-4-[(1-methylethyl)sulfamoyl]-1H-pyrrole-2-carboxamide;

N-(3-Bromo-4,5-difluorophenyl)-1-methyl-4-{[(1S)-2,2,2-trifluoro-1-methylethyl]sulfamoyl}-1H-pyrrole-2-carboxamide;

N-(3-Bromo-4-fluorophenyl)-1-methyl-4-{[(1S)-2,2,2-trifluoro-1-methylethyl]sulfamoyl}-1H-pyrrole-2-carboxamide;

N-(3-Cyano-4-fluorophenyl)-1-methyl-4-{[(1S)-2,2,2-trifluoro-1-methylethyl]sulfamoyl}-1H-pyrrole-2-carboxamide;

N-(3-Chloro-4,5-difluorophenyl)-1-methyl-4-{[(1S)-2,2,2-trifluoro-1-methylethyl]sulfamoyl}-1H-pyrrole-2-carboxamide;

N-(3,4-Difluoro-5-methylphenyl)-1-methyl-4-{[(1S)-2,2,2-trifluoro-1-methylethyl]sulfamoyl}-1H-pyrrole-2-carboxamide;

N-(3-Chloro-4-fluorophenyl)-1-methyl-4-{[(1S)-2,2,2-trifluoro-1-methylethyl]sulfamoyl}-1H-pyrrole-2-carboxamide;

N-(3-Bromo-4-fluorophenyl)-3-fluoro-1-methyl-4-[(3-methyloxetan-3-yl)sulfamoyl]-1H-pyrrole-2-carboxamide;

N-[3-(Difluoromethyl)-4-fluorophenyl]-3-fluoro-1-methyl-4-[(3-methyloxetan-3-yl)sulfamoyl]-1H-pyrrole-2-carboxamide;

N-(3-Chloro-4-fluorophenyl)-3-fluoro-1-methyl-4-[(3-methyloxetan-3-yl)sulfamoyl]-1H-pyrrole-2-carboxamide;

3-Fluoro-1-methyl-4-[(3-methyloxetan-3-yl)sulfamoyl]-N-(2,4,5-trifluorophenyl)-1H-pyrrole-2-carboxamide;

N-(2,4-Difluoro-3-methylphenyl)-3-fluoro-1-methyl-4-[(3-methyloxetan-3-yl)sulfamoyl]-1H-pyrrole-2-carboxamide;

N-(3-Chloro-4,5-difluorophenyl)-3-fluoro-1-methyl-4-[(3-methyloxetan-3-yl)sulfamoyl]-1H-pyrrole-2-carboxamide;

4-(tert-butylsulfamoyl)-N-(2,4-difluoro-3-methyl-phenyl)-1-methyl-pyrrole-2-carboxamide;

N-(3-cyano-4-fluoro-phenyl)-3-fluoro-1-methyl-4-[(3-methyloxetan-3-yl)sulfamoyl]pyrrole-2-carboxamide;

4-[(1-Carbamoylcyclopropyl)sulfamoyl]-N-(3-chloro-4,5-difluorophenyl)-1-methyl-1H-pyrrole-2-carboxamide;

N-(3-Chloro-4,5-difluorophenyl)-1-methyl-4-{[1-(methylcarbamoyl)cyclopropyl]sulfamoyl}-1H-pyrrole-2-carboxamide;

N-(2,4-Difluoro-3-methylphenyl)-1-methyl-4-{[(1R)-2,2,2-trifluoro-1-methylethyl]sulfamoyl}-1H-pyrrole-2-carboxamide;

N-(2,4-Difluoro-3-methylphenyl)-1-methyl-4-{[1-(trifluoromethyl)cyclopropyl]sulfamoyl}-1H-pyrrole-2-carboxamide;

N-(2,4-Difluoro-3-methylphenyl)-1-methyl-4-[(2,2,2-trifluoro-1,1-dimethylethyl)sulfamoyl]-1H-pyrrole-2-carboxamide;

N-(2,4-Difluoro-3-methylphenyl)-1-methyl-4-{[(1S)-2,2,2-trifluoro-1-methylethyl]sulfamoyl}-1H-pyrrole-2-carboxamide;

N-(3-Chloro-2,4-difluorophenyl)-1-methyl-4-{[(1R)-2,2,2-trifluoro-1l-methylethyl]sulfamoyl}-1H-pyrrole-2-carboxamide;

N-(3-Chloro-2,4-difluorophenyl)-1-methyl-4-[(3-methyloxetan-3-yl)sulfamoyl]-1H-pyrrole-2-carboxamide;

1-methyl-4-[[(1R)-2,2,2-trifluoro-1-methyl-ethyl]sulfamoyl]-N-[3-(trifluoromethyl)phenyl]pyrrole-2-carboxamide;

N-(3-Chloro-4-fluorophenyl)-1-methyl-4-{[(1R)-2,2,2-trifluoro-1-methylethyl]sulfamoyl}-1H-pyrrole-2-carboxamide;

N-(3-Bromo-4-fluorophenyl)-1-methyl-4-{[(1R)-2,2,2-trifluoro-1-methylethyl]sulfamoyl}-1H-pyrrole-2-carboxamide;

N-[4-Fluoro-3-(trifluoromethyl)phenyl]-1-methyl-4-{[(1R)-2,2,2-trifluoro-1-methylethyl]sulfamoyl}-1H-pyrrole-2-carboxamide;

N-(3-Cyano-4-fluorophenyl)-4-[(2,2-difluoroethyl)sulfamoyl]-1-methyl-1H-pyrrole-2-carboxamide;

N-(3-Bromo-4-fluorophenyl)-4-[(2,2-difluoroethyl)sulfamoyl]-1-methyl-1H-pyrrole-2-carboxamide;

N-(3-Chloro-4-fluorophenyl)-4-[(2,2-difluoroethyl)sulfamoyl]-1-methyl-1H-pyrrole-2-carboxamide;

4-[(2,2-Difluoroethyl)sulfamoyl]-N-(3,4-difluorophenyl)-1-methyl-1H-pyrrole-2-carboxamide;

N-(3-Chloro-4,5-difluorophenyl)-4-[(2,2-difluoroethyl)sulfamoyl]-1-methyl-1H-pyrrole-2-carboxamide;

N-(3-Chloro-4-fluorophenyl)-1-methyl-4-[(2,2,2-trifluoroethyl)sulfamoyl]-1H-pyrrole-2-carboxamide;

N-(3,4-Difluorophenyl)-1-methyl-4-[(2,2,2-trifluoroethyl)sulfamoyl]-1H-pyrrole-2-carboxamide;

N-(3-Chloro-4,5-difluorophenyl)-1-methyl-4-[(2,2,2-trifluoroethyl)sulfamoyl]-1H-pyrrole-2-carboxamide;

N-(3-Cyano-4-fluorophenyl)-1-methyl-4-[(2,2,2-trifluoroethyl)sulfamoyl]-1H-pyrrole-2-carboxamide;

N-(3-Bromo-4-fluorophenyl)-1-methyl-4-[(2,2,2-trifluoroethyl)sulfamoyl]-1H-pyrrole-2-carboxamide;

N-(3-Chloro-4,5-difluorophenyl)-1,5-dimethyl-4-[(3-methyloxetan-3-yl)sulfamoyl]-1H-pyrrole-2-carboxamide;

N-(3-Chloro-4,5-difluorophenyl)-1,5-dimethyl-4-{[(1R)-2,2,2-trifluoro-1-methylethyl]sulfamoyl}-1H-pyrrole-2-carboxamide;

N-(3-Chloro-4-fluorophenyl)-1,5-dimethyl-4-{[(1R)-2,2,2-trifluoro-1l-methylethyl]sulfamoyl}-1H-pyrrole-2-carboxamide;

N-(3,4-Difluorophenyl)-1,5-dimethyl-4-{[(1R)-2,2,2-trifluoro-1-methylethyl]sulfamoyl}-1H-pyrrole-2-carboxamide;

N-(3-Cyano-4-fluorophenyl)-1,5-dimethyl-4-{[(1R)-2,2,2-trifluoro-1-methylethyl]sulfamoyl}-1H-pyrrole-2-carboxamide;

N-(3-Bromo-4-fluorophenyl)-1,5-dimethyl-4-{[(1R)-2,2,2-trifluoro-1l-methylethyl]sulfamoyl}-1H-pyrrole-2-carboxamide;

N-[4-Fluoro-3-(trifluoromethyl)phenyl]-1,5-dimethyl-4-{[(1R)-2,2,2-trifluoro-1-methylethyl]sulfamoyl}-1H-pyrrole-2-carboxamide;

N-(3-Chloro-2,4-difluorophenyl)-1,5-dimethyl-4-{[(1R)-2,2,2-trifluoro-1-methylethyl]sulfamoyl}-1H-pyrrole-2-carboxamide;

N-(3,4-Difluorophenyl)-1,3-dimethyl-4-{[(1R)-2,2,2-trifluoro-1-methylethyl]sulfamoyl}-1H-pyrrole-2-carboxamide;

N-(3-Chloro-4-fluorophenyl)-1,3-dimethyl-4-{[(1R)-2,2,2-trifluoro-1l-methylethyl]sulfamoyl}-1H-pyrrole-2-carboxamide;

N-(3,4-Difluorophenyl)-1,3-dimethyl-4-{[(1S)-2,2,2-trifluoro-1-methylethyl]sulfamoyl}-1H-pyrrole-2-carboxamide;

N-(3-Chloro-4-fluorophenyl)-1,3-dimethyl-4-{[(1S)-2,2,2-trifluoro-1-methylethyl]sulfamoyl}-1H-pyrrole-2-carboxamide;

N-(3,4-Difluorophenyl)-1,3-dimethyl-4-[(3-methyloxetan-3-yl)sulfamoyl]-1H-pyrrole-2-carboxamide;

N-(3-Chloro-4-fluorophenyl)-1,3-dimethyl-4-[(3-methyloxetan-3-yl)sulfamoyl]-1H-pyrrole-2-carboxamide;

N-(3-Cyano-4-fluorophenyl)-1,3-dimethyl-4-{[(1R)-2,2,2-trifluoro-1-methylethyl]sulfamoyl}-1H-pyrrole-2-carboxamide;

N-(3-Cyano-4-fluorophenyl)-1,3-dimethyl-4-{[(1S)-2,2,2-trifluoro-1-methylethyl]sulfamoyl}-1H-pyrrole-2-carboxamide;

N-(3-Cyano-4-fluorophenyl)-1,3-dimethyl-4-[(3-methyloxetan-3-yl)sulfamoyl]-1H-pyrrole-2-carboxamide;

N-[4-Fluoro-3-(trifluoromethyl)phenyl]-1,3-dimethyl-4-{[(1R)-2,2,2-trifluoro-1-methylethyl]sulfamoyl}-1H-pyrrole-2-carboxamide;

1-Methyl-4-{[(1S)-2,2,2-trifluoro-1-methylethyl]sulfamoyl}-N-(2,3,4-trifluorophenyl)-1H-pyrrole-2-carboxamide;

N-(3-Bromo-2,4-difluorophenyl)-1-methyl-4-{[(1S)-2,2,2-trifluoro-1-methylethyl]sulfamoyl}-1H-pyrrole-2-carboxamide;

N-(3-Chloro-2,4-difluorophenyl)-1-methyl-4-{[(1S)-2,2,2-trifluoro-1-methylethyl]sulfamoyl}-1H-pyrrole-2-carboxamide;

N-(3-cyano-4-fluoro-phenyl)-1-methyl-4-[[(1R)-2,2,2-trifluoro-1-methylethyl]sulfamoyl]pyrrole-2-arboxamide;

N-(3-Cyanophenyl)-1-methyl-4-{[(1R)-2,2,2-trifluoro-1-methylethyl]sulfamoyl}-1H-pyrrole-2-carboxamide;

N-[2-Fluoro-3-(trifluoromethyl)phenyl]-1-methyl-4-{[(1R)-2,2,2-trifluoro-1-methylethyl]sulfamoyl}-1H-pyrrole-2-carboxamide;

N-(3-Cyano-2-fluorophenyl)-1-methyl-4-{[(1R)-2,2,2-trifluoro-1-methylethyl]sulfamoyl}-1H-pyrrole-2-carboxamide;

N-[3-(1,1-Difluoroethyl)-4-fluorophenyl]-1-methyl-4-[(3-methyloxetan-3-yl)sulfamoyl]-1H-pyrrole-2-carboxamide;

4-(tert-Butylsulfamoyl)-N-[3-(1,1-difluoroethyl)-4-fluorophenyl]-1-methyl-1H-pyrrole-2-carboxamide;

N-(3,5-Dichloro-4-fluorophenyl)-1-methyl-4-[(2,2,2-trifluoro-1,1-dimethylethyl)sulfamoyl]-1H-pyrrole-2-carboxamide;

N-(3-Chloro-4,5-difluorophenyl)-4-[(3,3-difluorocyclobutyl)sulfamoyl]-1-methyl-1H-pyrrole-2-carboxamide;

N-(3-chloro-4,5-difluoro-phenyl)-1-methyl-4-[[1-methyl-1-(trifluoro-methyl)propyl]sulfamoyl]pyrrole-2-carboxamide;

N-(3-Chloro-4,5-difluorophenyl)-4-[(3,3-difluorocyclopentyl)sulfamoyl]-1-methyl-1H-pyrrole-2-carboxamide;

4-(Bicyclo[1.1.1]pent-1-ylsulfamoyl)-N-(3-chloro-4,5-difluorophenyl)-1-methyl-1H-pyrrole-2-carboxamide;

N-(3-Chloro-4,5-difluorophenyl)-1-methyl-4-[(3,3,3-trifluoropropyl)sulfamoyl]-1H-pyrrole-2-carboxamide;

N-(3-Chloro-4,5-difluorophenyl)-1-methyl-4-[(3,3,3-trifluoro-1-methylpropyl)sulfamoyl]-1H-pyrrole-2-carboxamide;

N-(3-Cyano-4-fluorophenyl)-3-fluoro-1-methyl-4-{[(1R)-2,2,2-trifluoro-1-methylethyl]sulfamoyl}-1H-pyrrole-2-carboxamide;

N-(3-Cyano-4-fluorophenyl)-3-Fluoro-1-methyl-4-[(1-methylethyl)sulfamoyl]-1H-pyrrole-2-carboxamide;

N-(3-Chloro-2,4-difluorophenyl)-1-methyl-4-[(1-methylethyl)sulfamoyl]-1H-pyrrole-2-carboxamide;

N-(3-Chloro-2-fluorophenyl)-1-methyl-4-[(1-methylethyl)sulfamoyl]-1H-pyrrole-2-carboxamide;

N-(3-Chloro-4-fluorophenyl)-1-methyl-4-[(1-methylethyl)sulfamoyl]-1H-pyrrole-2-carboxamide;

N-(3-Cyano-4-fluorophenyl)-1-methyl-4-[(1-methylethyl)sulfamoyl]-1H-pyrrole-2-carboxamide;

N-(3-Cyano-2-fluorophenyl)-1-methyl-4-[(1-methylethyl)sulfamoyl]-1H-pyrrole-2-carboxamide;

N-(3-Cyanophenyl)-1-methyl-4-[(1-methylethyl)sulfamoyl]-1H-pyrrole-2-carboxamide;

N-(3-Cyano-2,4-difluorophenyl)-1-methyl-4-[(1-methylethyl)sulfamoyl]-1H-pyrrole-2-carboxamide;

N-[4-Fluoro-3-(trifluoromethyl)phenyl]-1,3-dimethyl-4-[(3-methyloxetan-3-yl)sulfamoyl]-1H-pyrrole-2-carboxamide;

N-(3-Cyanophenyl)-3-fluoro-1-methyl-4-{[(1R)-2,2,2-trifluoro-1-methylethyl]sulfamoyl}-1H-pyrrole-2-carboxamide;

N-(3-Cyano-2,4-difluorophenyl)-3-fluoro-1-methyl-4-{[(1R)-2,2,2-trifluoro-1-methylethyl]sulfamoyl}-1H-pyrrole-2-carboxamide;

N-(3-Cyano-2-fluorophenyl)-3-fluoro-1-methyl-4-{[(1R)-2,2,2-trifluoro-1-methylethyl]sulfamoyl}-1H-pyrrole-2-carboxamide;

3-Fluoro-1-methyl-4-{[(1R)-2,2,2-trifluoro-1-methylethyl]sulfamoyl}-N-(2,3,4-trifluorophenyl)-1H-pyrrole-2-carboxamide;

N-(3-Bromo-2,4-difluorophenyl)-3-fluoro-1-methyl-4-{[(1R)-2,2,2-trifluoro-1-methylethyl]sulfamoyl}-1H-pyrrole-2-carboxamide;

N-(3-Chloro-2,4-difluorophenyl)-3-fluoro-1-methyl-4-{[(1R)-2,2,2-trifluoro-1-methylethyl]sulfamoyl}-1H-pyrrole-2-carboxamide;

N-(3-Cyano-4-fluorophenyl)-3-fluoro-1-methyl-4-{[(1R)-1-methylpropyl]sulfamoyl}-1H-pyrrole-2-carboxamide;

N-(3-Cyano-4-fluorophenyl)-4-[(3,3-difluoro-1-methylcyclobutyl)sulfamoyl]-3-fluoro-1-methyl-1H-pyrrole-2-carboxamide;

N-(3-Cyano-4-fluorophenyl)-3-fluoro-1-methyl-4-{[(1S)-2,2,2-trifluoro-1-methylethyl]sulfamoyl}-1H-pyrrole-2-carboxamide;

N-(3-Chloro-4,5-difluorophenyl)-1-methyl-4-{[1-(trifluoromethyl)cyclobutyl]sulfamoyl}-1H-pyrrole-2-carboxamide;

4-(tert-Butylsulfamoyl)-N-(3-cyano-4-fluorophenyl)-1-methyl-1H-pyrrole-2-carboxamide;

4-(tert-Butylsulfamoyl)-N-(3-cyanophenyl)-1-methyl-1H-pyrrole-2-carboxamide;

4-(tert-Butylsulfamoyl)-N-(3-cyano-2-fluorophenyl)-1-methyl-1H-pyrrole-2-carboxamide;

4-(tert-Butylsulfamoyl)-N-(3-chloro-2-fluorophenyl)-1-methyl-1H-pyrrole-2-carboxamide;

4-(tert-Butylsulfamoyl)-N-(3-chloro-2,4-difluorophenyl)-1-methyl-1H-pyrrole-2-carboxamide;

4-(tert-Butylsulfamoyl)-N-(3-chloro-4-fluorophenyl)-1-methyl-1H-pyrrole-2-carboxamide;

N-(3-Cyano-2,4-difluorophenyl)-1-methyl-4-{[(1S)-2,2,2-trifluoro-1-methylethyl]sulfamoyl}-1H-pyrrole-2-carboxamide;

N-(3-Cyanophenyl)-1-methyl-4-{[(1S)-2,2,2-trifluoro-1-methylethyl]sulfamoyl}-1H-pyrrole-2-carboxamide;

N-(3-Cyano-2-fluorophenyl)-1-methyl-4-{[(1S)-2,2,2-trifluoro-1-methylethyl]sulfamoyl}-1H-pyrrole-2-carboxamide;

3-Chloro-N-(3-cyano-4-fluorophenyl)-1-methyl-4-{[(1R)-2,2,2-trifluoro-1-methylethyl]sulfamoyl}-1H-pyrrole-2-carboxamide;

N-(3-Cyano-4-fluorophenyl)-4-{[2,2-difluoro-1-methylethyl]sulfamoyl}-1-methyl-1H-pyrrole-2-carboxamide;

N-(3-Chloro-4,5-difluorophenyl)-1,3-dimethyl-4-[(3-methyloxetan-3-yl)sulfamoyl]-1H-pyrrole-2-carboxamide;

N-(3-Chloro-4,5-difluorophenyl)-1,3-dimethyl-4-{[(1R)-2,2,2-trifluoro-1-methylethyl]sulfamoyl}-1H-pyrrole-2-carboxamide;

N-(2,3-Difluorophenyl)-1-methyl-4-{[(1R)-2,2,2-trifluoro-1-methylethyl]sulfamoyl}-1H-pyrrole-2-carboxamide;

N-(3-Chloro-2,6-difluorophenyl)-1-methyl-4-{[(1R)-2,2,2-trifluoro-1l-methylethyl]sulfamoyl}-1H-pyrrole-2-carboxamide;

N-(3-Bromo-4,5-difluorophenyl)-1-methyl-4-{[(1R)-2,2,2-trifluoro-1l-methylethyl]sulfamoyl}-1H-pyrrole-2-carboxamide;

N-(3-Bromo-2-fluorophenyl)-1-methyl-4-{[(1R)-2,2,2-trifluoro-1-methylethyl]sulfamoyl}-1H-pyrrole-2-carboxamide;

N-(3-chloro-4,5-difluoro-phenyl)-4-[(2-fluoro-1,1-dimethyl-ethyl)sulfamoyl]-1-methyl-pyrrole-2-carboxamide;

N-(3-Chloro-2,4-difluorophenyl)-1,3-dimethyl-4-[(1-methylethyl)sulfamoyl]-1H-pyrrole-2-carboxamide;

N-(3-Chloro-2,4-difluorophenyl)-1,3-dimethyl-4-{[(1S)-2,2,2-trifluoro-1-methylethyl]sulfamoyl}-1H-pyrrole-2-carboxamide;

N-(3-Chloro-2,4-difluorophenyl)-1,3-dimethyl-4-{[(1R)-2,2,2-trifluoro-1-methylethyl]sulfamoyl}-1H-pyrrole-2-carboxamide;

4-(tert-Butylsulfamoyl)-N-(3,4-difluorophenyl)-3-fluoro-1-methyl-1H-pyrrole-2-carboxamide;

4-(tert-Butylsulfamoyl)-N-(3-chloro-2,4-difluorophenyl)-3-fluoro-1-methyl-1H-pyrrole-2-carboxamide;

4-(tert-Butylsulfamoyl)-3-fluoro-1-methyl-N-(2,3,4-trifluorophenyl)-1H-pyrrole-2-carboxamide;

4-(tert-Butylsulfamoyl)-N-(3-cyano-4-fluorophenyl)-3-fluoro-1-methyl-1H-pyrrole-2-carboxamide;

N-(3-Chloro-2,4-difluorophenyl)-3-fluoro-1-methyl-4-[(3-methyloxetan-3-yl)sulfamoyl]-1H-pyrrole-2-carboxamide;

3-Cyano-N-(3-cyano-4-fluorophenyl)-1-methyl-4-[(1-methylethyl)sulfamoyl]-1H-pyrrole-2-carboxamide;

3-Chloro-N-(3,4-difluorophenyl)-1-methyl-4-{[(1R)-2,2,2-trifluoro-1-methylethyl]sulfamoyl}-1H-pyrrole-2-carboxamide;

3-Chloro-N-(3-chloro-2,4-difluorophenyl)-1-methyl-4-{[(1R)-2,2,2-trifluoro-1-methylethyl]sulfamoyl}-1H-pyrrole-2-carboxamide;

3-Chloro-N-(3-chloro-2,4-difluorophenyl)-1-methyl-4-{[1-(trifluoro-methyl)cyclobutyl]sulfamoyl}-1H-pyrrole-2-carboxamide;

4-(tert-Butylsulfamoyl)-3-chloro-N-(3-chloro-4-fluorophenyl)-1-methyl-1H-pyrrole-2-carboxamide;

3-Chloro-N-(3-cyano-4-fluorophenyl)-1-methyl-4-{[1-(trifluoromethyl)cyclobutyl]sulfamoyl}-1H-pyrrole-2-carboxamide;

3-Chloro-N-(3-chloro-4-fluorophenyl)-1-methyl-4-{[(1R)-2,2,2-trifluoro-1-methylethyl]sulfamoyl}-1H-pyrrole-2-carboxamide;

4-(tert-Butylsulfamoyl)-3-chloro-N-(3,4-difluorophenyl)-1-methyl-1H-pyrrole-2-carboxamide;

4-(tert-Butylsulfamoyl)-3-chloro-N-(3-chloro-2,4-difluorophenyl)-1-methyl-1H-pyrrole-2-carboxamide;

3-Chloro-N-(3-cyano-4-fluorophenyl)-1-methyl-4-{[(1S)-2,2,2-trifluoro-1-methylethyl]sulfamoyl}-1H-pyrrole-2-carboxamide;

4-(tert-Butylsulfamoyl)-3-chloro-N-(3-cyano-4-fluorophenyl)-1-methyl-1H-pyrrole-2-carboxamide;

N-(3-Cyano-4-fluorophenyl)-1-methyl-4-{[1-(trifluoromethyl)cyclopropyl]sulfamoyl}-1H-pyrrole-2-carboxamide;

N-(3-Cyano-4-fluorophenyl)-1-methyl-4-{[3-(trifluoromethyl)tetrahydrofuran-3-yl]sulfamoyl}-1H-pyrrole-2-carboxamide;

N-(3,4-Difluorophenyl)-3-fluoro-1-methyl-4-{[(1R)-2,2,2-trifluoro-1-methylethyl]sulfamoyl}-1H-pyrrole-2-carboxamide;

N-(3-Bromo-4-fluorophenyl)-3-fluoro-1-methyl-4-[(1-methylethyl)sulfamoyl]-1H-pyrrole-2-carboxamide;

N-(3-Cyano-2,4-difluorophenyl)-3-fluoro-1-methyl-4-[(1-methylethyl)sulfamoyl]-1H-pyrrole-2-carboxamide;

N-(3,4-Difluorophenyl)-3-fluoro-1-methyl-4-[(1-methylethyl)sulfamoyl]-1H-pyrrole-2-carboxamide;

3-Fluoro-1-methyl-4-[(1-methylethyl)sulfamoyl]-N-(2,3,4-trifluorophenyl)-1H-pyrrole-2-carboxamide;

N-(3-Chloro-2,4-difluorophenyl)-3-fluoro-1-methyl-4-[(1-methylethyl)sulfamoyl]-1H-pyrrole-2-carboxamide;

N-(3-Chloro-4-fluorophenyl)-3-fluoro-1-methyl-4-[(1-methylethyl)sulfamoyl]-1H-pyrrole-2-carboxamide;

N-(3-Chloro-2,4-difluorophenyl)-4-{[2,2-difluorocyclopentyl]sulfamoyl}-1-methyl-1H-pyrrole-2-carboxamide;

N-(3-Cyano-4-fluorophenyl)-1-methyl-4-[(2,2,2-trifluoro-1,1-dimethylethyl)sulfamoyl]-1H-pyrrole-2-carboxamide;
N-(3-Cyano-4-fluorophenyl)-1-methyl-4-[(3,3,3-trifluoro-1-methylpropyl)sulfamoyl]-1H-pyrrole-2-carboxamide;
N-(3-Cyano-4-fluorophenyl)-1-methyl-4-{[(1S)-1-(trifluoromethyl)propyl]sulfamoyl}-1H-pyrrole-2-carboxamide;
N-(3-Cyano-4-fluorophenyl)-1-methyl-4-{[(1R)-1-(trifluoromethyl)propyl]sulfamoyl}-1H-pyrrole-2-carboxamide;
N-(3-Cyano-4-fluorophenyl)-1-methyl-4-{[1-(trifluoromethyl)cyclobutyl]sulfamoyl}-1H-pyrrole-2-carboxamide;
N-(3-Cyano-4-fluorophenyl)-4-{[2-fluoro-1-(fluor(methyl)ethyl]sulfamoyl}-1-methyl-1H-pyrrole-2-carboxamide;
N-(3-Chloro-2,4-difluorophenyl)-1,3-dimethyl-4-[(3-methyloxetan-3-yl)sulfamoyl]-1H-pyrrole-2-carboxamide;
N-(3-cyano-4-fluoro-phenyl)-1-methyl-4-[(1-methylcyclopropyl)sulfamoyl]pyrrole-2-carboxamide;
N-(3-cyano-4-fluoro-phenyl)-4-[(3,3-difluoro-1-methylcyclobutyl)sulfamoyl]-1-methyl-1H-pyrrole-2-carboxamide;
N-(3-cyano-4-fluoro-phenyl)-1-methyl-4-{[1-methyl-1-(trifluoromethyl)propyl]sulfamoyl}-1H-pyrrole-2-carboxamide;
N-(3-cyano-4-fluoro-phenyl)-1-methyl-4-{[4-(trifluoromethyl)tetrahydropyran-4-yl]sulfamoyl}-1H-pyrrole-2-carboxamide;
N-(3-cyano-4-fluoro-phenyl)-4-{[1-ethyl-1-(trifluoromethyl)propyl]sulfamoyl}-1-methyl-1H-pyrrole-2-carboxamide;
N-(3-cyano-4-fluoro-phenyl)-4-[(2-fluoro-1,1-dimethylethyl)sulfamoyl]-1-methyl-1H-pyrrole-2-carboxamide;
N-(3-Bromophenyl)-3-chloro-1-methyl-4-{[(1R)-2,2,2-trifluoro-1-methylethyl]sulfamoyl}-1H-pyrrole-2-carboxamide;
N-(3-Bromophenyl)-3-fluoro-1-methyl-4-[(3-methyloxetan-3-yl)sulfamoyl]-1H-pyrrole-2-carboxamide;
N-(3-chloro-2,4-difluoro-phenyl)-4-[(2,2-difluoro-1-methyl-ethyl)sulfamoyl]-1-methyl-1H-pyrrole-2-carboxamide;
N-(3-chloro-2,4-difluoro-phenyl)-1-methyl-4-{[1-(trifluoromethyl)cyclopropyl]sulfamoyl}-1H-pyrrole-2-carboxamide;
N-(3-chloro-2,4-difluoro-phenyl)-1-methyl-4-[(2,2,2-trifluoro-1,1-dimethyl-ethyl)sulfamoyl]-1H-pyrrole-2-carboxamide;
N-(3-chloro-2,4-difluoro-phenyl)-1-methyl-4-[(1-methylcyclopropyl)sulfamoyl]-1H-pyrrole-2-carboxamide;
N-(3-chloro-2,4-difluoro-phenyl)-4-[(3,3-difluoro-1-methyl-cyclobutyl)sulfamoyl]-1-methyl-1H-pyrrole-2-carboxamide;
N-(3-chloro-2,4-difluoro-phenyl)-1-methyl-4-{[1-methyl-1-(trifluoromethyl)propyl]sulfamoyl}-1H-pyrrole-2-carboxamide;
N-(3-chloro-2,4-difluoro-phenyl)-1-methyl-4-[[4-(trifluoromethyl)tetrahydropyran-4-yl]sulfamoyl]-1H-pyrrole-2-carboxamide;
N-(3-chloro-2,4-difluoro-phenyl)-4-[[1-ethyl-1-(trifluoromethyl)propyl]sulfamoyl]-1-methyl-1H-pyrrole-2-carboxamide;
N-(3-chloro-2,4-difluoro-phenyl)-1-methyl-4-[(3,3,3-trifluoro-1-methylpropyl)sulfamoyl]-1H-pyrrole-2-carboxamide;
N-(3-chloro-2,4-difluoro-phenyl)-4-[(2-fluoro-1,1-dimethyl-ethyl)sulfamoyl]-1-methyl-1H-pyrrole-2-carboxamide;
N-(3-chloro-2,4-difluoro-phenyl)-1-methyl-4-{[(1S)-1-(trifluoromethyl)propyl]sulfamoyl}-1H-pyrrole-2-carboxamide;
N-(3-chloro-2,4-difluoro-phenyl)-1-methyl-4-{[1-(trifluoromethyl)cyclobutyl]sulfamoyl}-1H-pyrrole-2-carboxamide;
N-(3-chloro-2,4-difluoro-phenyl)-4-{[2-fluoro-1-(fluoromethyl)ethyl]sulfamoyl}-1-methyl-1H-pyrrole-2-carboxamide;
N-(3-chloro-2,4-difluoro-phenyl)-1-methyl-4-{[(1R)-1-(trifluoromethyl)propyl]sulfamoyl}-1H-pyrrole-2-carboxamide;
N-(3-chloro-2,4-difluoro-phenyl)-1-methyl-4-{[3-(trifluoromethyl)tetrahydrofuran-3-yl]sulfamoyl}-1H-pyrrole-2-carboxamide;
3-chloro-N-(3,4-difluorophenyl)-1-methyl-4-{[1-(trifluoromethyl)cyclobutyl]sulfamoyl}-1H-pyrrole-2-carboxamide;
3-chloro-N-(3-chloro-4-fluoro-phenyl)-1-methyl-4-{[1-(trifluoromethyl)cyclobutyl]sulfamoyl}-1H-pyrrole-2-carboxamide;
3-Chloro-N-(3-cyano-4-fluorophenyl)-1-methyl-4-[(1-methylethyl)sulfamoyl]-1H-pyrrole-2-carboxamide;
3-Chloro-N-(3-cyano-4-fluorophenyl)-1-methyl-4-[(2,2,2-trifluoro-1,1-dimethylethyl)sulfamoyl]-1H-pyrrole-2-carboxamide;
3-Chloro-N-(3-cyano-4-fluorophenyl)-1-methyl-4-{[1-(trifluoromethyl)cyclopropyl]sulfamoyl}-1H-pyrrole-2-carboxamide;
3-chloro-N-(2-cyano-4-fluoro-3-methyl-phenyl)-1-methyl-4-[[(1R)-2,2,2-trifluoro-1-methyl-ethyl]sulfamoyl]pyrrole-2-carboxamide;
3-chloro-N-(2-cyano-4-fluoro-phenyl)-1-methyl-4-[[(1R)-2,2,2-trifluoro-1-methyl-ethyl]sulfamoyl]pyrrole-2-carboxamide;
3-chloro-N-[4-fluoro-3-(trifluoromethyl)phenyl]-1-methyl-4-[[(1R)-2,2,2-trifluoro-1-methyl-ethyl]sulfamoyl]pyrrole-2-carboxamide;
3-chloro-N-(2-fluoro-6-methyl-phenyl)-1-methyl-4-[[(1R)-2,2,2-trifluoro-1-methyl-ethyl]sulfamoyl]pyrrole-2-carboxamide;
3-chloro-N-(3-cyano-2,4-difluoro-phenyl)-1-methyl-4-[[(1R)-2,2,2-trifluoro-1-methyl-ethyl]sulfamoyl]pyrrole-2-carboxamide;
3-chloro-N-(2,3-dichloro-4-fluoro-phenyl)-1-methyl-4-[[(1R)-2,2,2-trifluoro-1-methyl-ethyl]sulfamoyl]pyrrole-2-carboxamide;
3-chloro-N-[3-(difluoromethyl)-2,4-difluoro-phenyl]-1-methyl-4-[[(1R)-2,2,2-trifluoro-1-methyl-ethyl]sulfamoyl]pyrrole-2-carboxamide;
3-chloro-N-[3-(difluoromethyl)-4-fluoro-phenyl]-1-methyl-4-[[(1R)-2,2,2-trifluoro-1-methyl-ethyl]sulfamoyl]pyrrole-2-carboxamide;
N-(3-bromophenyl)-3-fluoro-1l-methyl-4-[[(1R)-2,2,2-trifluoro-1-methyl-ethyl]sulfamoyl]pyrrole-2-carboxamide;
N-(3-cyano-4-fluoro-phenyl)-3-fluoro-1-methyl-4-[[1-(trifluoro-methyl)cyclopentyl]sulfamoyl]pyrrole-2-carboxamide;

3-chloro-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-5-methyl-phenyl)-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1S)-1-(trifluoro-methyl)propyl]sulfamoyl]pyrrole-2-carboxamide;

3-fluoro-N-(4-fluorophenyl)-1-methyl-4-[[(1R)-2,2,2-trifluoro-1-methyl-ethyl]sulfamoyl]pyrrole-2-carboxamide;

N-[3-(difluoromethyl)-4-fluoro-phenyl]-3-fluoro-1-methyl-4-[[(1R)-2,2,2-trifluoro-1-methyl-ethyl]sulfamoyl]pyrrole-2-carboxamide;

N-[3-(difluoromethyl)-2,4-difluoro-phenyl]-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1R)-1-(trifluoro-methyl)propyl]sulfamoyl]pyrrole-2-carboxamide;

3-chloro-N-(3-cyano-4-fluoro-phenyl)-1-methyl-4-[[(1S)-1-(trifluoro-methyl)propyl]sulfamoyl]pyrrole-2-carboxamide;

3-chloro-N-(3-cyano-4-fluoro-phenyl)-1-methyl-4-[[(1R)-1-(trifluoro-methyl)propyl]sulfamoyl]pyrrole-2-carboxamide;

3-chloro-N-(3-cyano-4-fluoro-phenyl)-1-isopropyl-4-[[(1R)-2,2,2-trifluoro-1l-methyl-ethyl]sulfamoyl]pyrrole-2-carboxamide;

3-bromo-N-(3-cyano-4-fluoro-phenyl)-1-methyl-4-[[(1R)-2,2,2-trifluoro-1-methyl-ethyl]sulfamoyl]pyrrole-2-carboxamide;

3-cyano-N-(3-cyano-4-fluoro-phenyl)-1-methyl-4-[[(1R)-2,2,2-trifluoro-1-methyl-ethyl]sulfamoyl]pyrrole-2-carboxamide;

N-(3-cyano-4-fluoro-phenyl)-1-methyl-4-[[(1R)-1-methylpropyl]sulfamoyl]pyrrole-2-carboxamide;

3-chloro-N-(3-cyano-4-fluoro-phenyl)-1-methyl-4-[[(1R)-1-methylpropyl]sulfamoyl]pyrrole-2-carboxamide;

N-(3-cyano-4-fluoro-phenyl)-4-[(3-hydroxy-1,1-dimethyl-propyl)sulfamoyl]-1-methyl-pyrrole-2-carboxamide;

N-(3-cyano-4-fluoro-phenyl)-4-[[(1S)-2,2-difluoro-1-methyl-propyl]sulfamoyl]-1-methyl-pyrrole-2-carboxamide;

N-(3-cyano-4-fluoro-phenyl)-4-[[(1R)-2,2-difluoro-1-methyl-propyl]sulfamoyl]-1-methyl-pyrrole-2-carboxamide;

N-(3-cyano-4-fluoro-phenyl)-3-fluoro-1,5-dimethyl-4-[[(1R)-2,2,2-trifluoro-1-methyl-ethyl]sulfamoyl]pyrrole-2-carboxamide;

5-bromo-3-chloro-N-(3-cyano-4-fluoro-phenyl)-1-methyl-4-[[(1R)-2,2,2-trifluoro-1-methyl-ethyl]sulfamoyl]pyrrole-2-carboxamide;

5-bromo-N-(3-cyano-4-fluoro-phenyl)-3-fluoro-1-methyl-4-[[(1R)-2,2,2-trifluoro-1-methyl-ethyl]sulfamoyl]pyrrole-2-carboxamide;

3-chloro-N-(3-cyano-4-fluoro-phenyl)-5-cyclopropyl-1-methyl-4-[[(1R)-2,2,2-trifluoro-1-methyl-ethyl]sulfamoyl]pyrrole-2-carboxamide;

N-(3-cyano-4-fluoro-phenyl)-3-isopropyl-1-methyl-4-[[(1R)-2,2,2-trifluoro-1-methyl-ethyl]sulfamoyl]pyrrole-2-carboxamide;

N-(3-cyano-4-fluoro-phenyl)-5-cyclopropyl-3-fluoro-1-methyl-4-[[(1R)-2,2,2-trifluoro-1-methyl-ethyl]sulfamoyl]pyrrole-2-carboxamide;

3-chloro-N-(3-cyano-4-fluoro-phenyl)-1-cyclopropyl-4-[[(1R)-2,2,2-trifluoro-1-methyl-ethyl]sulfamoyl]pyrrole-2-carboxamide;

3-chloro-N-(3-cyano-4-fluoro-phenyl)-1-methyl-4-[(3-methyloxetan-3-yl)sulfamoyl]pyrrole-2-carboxamide;

3-bromo-N-(3-cyano-4-fluoro-phenyl)-4-(cyclopentylsulfamoyl)-1-methyl-pyrrole-2-carboxamide;

3-bromo-N-(4-fluoro-3-methyl-phenyl)-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-5-(methoxymethyl)-1-methyl-4-[[(1R)-2,2,2-trifluoro-1-methyl-ethyl]sulfamoyl]pyrrole-2-carboxamide;

5-cyano-N-(3-cyano-4-fluoro-phenyl)-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1R)-2,2,2-trifluoro-1l-methyl-ethyl]sulfamoyl]-5-vinyl-pyrrole-2-carboxamide;

N-(2,4-difluorophenyl)-3-fluoro-1-methyl-4-[[(1R)-2,2,2-trifluoro-1-methyl-ethyl]sulfamoyl]pyrrole-2-carboxamide;

N-(3-chloro-5-cyano-4-fluoro-phenyl)-3-fluoro-1-methyl-4-[[(1R)-2,2,2-trifluoro-1-methyl-ethyl]sulfamoyl]pyrrole-2-carboxamide;

5-chloro-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide;

5-bromo-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide;

3-cyano-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-phenyl)-4-[[(1R)-2,2-difluoro-1-methyl-propyl]sulfamoyl]-3-fluoro-1-methyl-pyrrole-2-carboxamide;

N-(3-cyano-4-fluoro-phenyl)-4-[[(1S)-2,2-difluoro-1-methyl-propyl]sulfamoyl]-3-fluoro-1-methyl-pyrrole-2-carboxamide; and N-(3-cyano-4-fluoro-phenyl)-3-fluoro-1-methyl-4-[[1-(trifluoromethyl)cyclobutyl]sulfamoyl]pyrrole-2-carboxamide.

4. The method of claim 1, wherein the compound is selected from the group consisting of:

N-(4-fluoro-3-methyl-phenyl)-1-methyl-4-[[(1S)-2,2,2-trifluoro-1-methyl-ethyl]sulfamoyl]pyrrole-2-carboxamide;

N-(4-fluoro-3-methyl-phenyl)-1-methyl-4-[[(1R)-2,2,2-trifluoro-1-methyl-ethyl]sulfamoyl]pyrrole-2-carboxamide;

N-(3,4-Difluorophenyl)-1-methyl-4-{[(1R)-2,2,2-trifluoro-1-methylethyl]sulfamoyl}-1H-pyrrole-2-carboxamide;

N-(3,4-Difluorophenyl)-1-methyl-4-{[(1S)-2,2,2-trifluoro-1-methylethyl]sulfamoyl}-1H-pyrrole-2-carboxamide;

N-(3,4-Difluorophenyl)-1-methyl-4-[(2,2,2-trifluoro-1,1-dimethylethyl)sulfamoyl]-1H-pyrrole-2-carboxamide;

N-(3-Bromo-4-fluorophenyl)-1-methyl-4-{[(1S)-2,2,2-trifluoro-1-methylethyl]sulfamoyl}-1H-pyrrole-2-carboxamide;

N-(3-Cyano-4-fluorophenyl)-1-methyl-4-{[(1S)-2,2,2-trifluoro-1-methylethyl]sulfamoyl}-1H-pyrrole-2-carboxamide;

N-(3-Chloro-4-fluorophenyl)-1-methyl-4-{[(1S)-2,2,2-trifluoro-1-methylethyl]sulfamoyl}-1H-pyrrole-2-carboxamide;

N-(3-Chloro-4-fluorophenyl)-1-methyl-4-{[(1R)-2,2,2-trifluoro-1-methylethyl]sulfamoyl}-1H-pyrrole-2-carboxamide;

N-(3-Bromo-4-fluorophenyl)-1-methyl-4-{[(1R)-2,2,2-trifluoro-1-methylethyl]sulfamoyl}-1H-pyrrole-2-carboxamide;

N-(3-cyano-4-fluoro-phenyl)-1-methyl-4-[[(1R)-2,2,2-trifluoro-1-methylethyl]sulfamoyl]pyrrole-2-carboxamide;

N-(3-Cyano-4-fluorophenyl)-1-methyl-4-[(2,2,2-trifluoro-1,1-dimethylethyl)sulfamoyl]-1H-pyrrole-2-carboxamide;

N-(3-Cyano-4-fluorophenyl)-1-methyl-4-{[(1S)-1-(trifluoromethyl)propyl]sulfamoyl}-1H-pyrrole-2-carboxamide;

N-(3-Cyano-4-fluorophenyl)-1-methyl-4-{[(1R)-1-(trifluoromethyl)propyl]sulfamoyl}-1H-pyrrole-2-carboxamide;

N-(3-cyano-4-fluoro-phenyl)-1-methyl-4-{[1-methyl-1-(trifluoromethyl)propyl]sulfamoyl}-1H-pyrrole-2-carboxamide;

N-(3-cyano-4-fluoro-phenyl)-4-{[1-ethyl-1-(trifluoromethyl)propyl]sulfamoyl}-1-methyl-1H-pyrrole-2-carboxamide;

N-(3-cyano-4-fluoro-phenyl)-4-[(2-fluoro-1,1-dimethylethyl)sulfamoyl]-1-methyl-1H-pyrrole-2-carboxamide;

N-(3-cyano-4-fluoro-phenyl)-4-[[(1S)-2,2-difluoro-1-methyl-propyl]sulfamoyl]-1-methyl-pyrrole-2-carboxamide;

N-(3-cyano-4-fluoro-phenyl)-4-[[(1R)-2,2-difluoro-1-methyl-propyl]sulfamoyl]-1-methyl-pyrrole-2-carboxamide;

N-(3-Chloro-4-fluorophenyl)-1,5-dimethyl-4-{[(1R)-2,2,2-trifluoro-1-methylethyl]sulfamoyl}-1H-pyrrole-2-carboxamide;

N-(3,4-Difluorophenyl)-1,5-dimethyl-4-{[(1R)-2,2,2-trifluoro-1-methylethyl]sulfamoyl}-1H-pyrrole-2-carboxamide;

N-(3-Cyano-4-fluorophenyl)-1,5-dimethyl-4-{[(1R)-2,2,2-trifluoro-1-methylethyl]sulfamoyl}-1H-pyrrole-2-carboxamide;

N-(3-Bromo-4-fluorophenyl)-1,5-dimethyl-4-{[(1R)-2,2,2-trifluoro-1-methylethyl]sulfamoyl}-1H-pyrrole-2-carboxamide;

N-(3,4-Difluorophenyl)-1,3-dimethyl-4-{[(1R)-2,2,2-trifluoro-1-methylethyl]sulfamoyl}-1H-pyrrole-2-carboxamide;

N-(3-Chloro-4-fluorophenyl)-1,3-dimethyl-4-{[(1R)-2,2,2-trifluoro-1-methylethyl]sulfamoyl}-1H-pyrrole-2-carboxamide;

N-(3,4-Difluorophenyl)-1,3-dimethyl-4-{[(1S)-2,2,2-trifluoro-1-methylethyl]sulfamoyl}-1H-pyrrole-2-carboxamide;

N-(3-Chloro-4-fluorophenyl)-1,3-dimethyl-4-{[(1S)-2,2,2-trifluoro-1-methylethyl]sulfamoyl}-1H-pyrrole-2-carboxamide;

N-(3-Cyano-4-fluorophenyl)-1,3-dimethyl-4-{[(1R)-2,2,2-trifluoro-1-methylethyl]sulfamoyl}-1H-pyrrole-2-carboxamide;

N-(3-Cyano-4-fluorophenyl)-1,3-dimethyl-4-{[(1S)-2,2,2-trifluoro-1-methylethyl]sulfamoyl}-1H-pyrrole-2-carboxamide;

N-(3-Cyano-4-fluorophenyl)-3-fluoro-1-methyl-4-{[(1R)-2,2,2-trifluoro-1-methylethyl]sulfamoyl}-1H-pyrrole-2-carboxamide;

N-(3-Cyano-2-fluorophenyl)-3-fluoro-1-methyl-4-{[(1R)-2,2,2-trifluoro-1-methylethyl]sulfamoyl}-1H-pyrrole-2-carboxamide;

N-(3-Cyano-4-fluorophenyl)-3-fluoro-1-methyl-4-{[(1S)-2,2,2-trifluoro-1-methylethyl]sulfamoyl}-1H-pyrrole-2-carboxamide;

3-Chloro-N-(3-cyano-4-fluorophenyl)-1-methyl-4-{[(1R)-2,2,2-trifluoro-1-methylethyl]sulfamoyl}-1H-pyrrole-2-carboxamide;

3-Chloro-N-(3,4-difluorophenyl)-1-methyl-4-{[(1R)-2,2,2-trifluoro-1-methylethyl]sulfamoyl}-1H-pyrrole-2-carboxamide;

3-Chloro-N-(3-chloro-4-fluorophenyl)-1-methyl-4-{[(1R)-2,2,2-trifluoro-1-methylethyl]sulfamoyl}-1H-pyrrole-2-carboxamide;

3-Chloro-N-(3-cyano-4-fluorophenyl)-1-methyl-4-{[(1S)-2,2,2-trifluoro-1-methylethyl]sulfamoyl}-1H-pyrrole-2-carboxamide;

N-(3,4-Difluorophenyl)-3-fluoro-1-methyl-4-{[(1R)-2,2,2-trifluoro-1-methylethyl]sulfamoyl}-1H-pyrrole-2-carboxamide;

3-Chloro-N-(3-cyano-4-fluorophenyl)-1-methyl-4-[(2,2,2-trifluoro-1,1-dimethylethyl)sulfamoyl]-1H-pyrrole-2-carboxamide;

3-chloro-N-[3-(difluoromethyl)-4-fluoro-phenyl]-1-methyl-4-[[(1R)-2,2,2-trifluoro-1-methyl-ethyl]sulfamoyl]pyrrole-2-carboxamide;

3-chloro-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1S)-1-(trifluoro-methyl)propyl]sulfamoyl]pyrrole-2-carboxamide;

N-[3-(difluoromethyl)-4-fluoro-phenyl]-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1R)-1-(trifluoro-methyl)propyl]sulfamoyl]pyrrole-2-carboxamide;

3-chloro-N-(3-cyano-4-fluoro-phenyl)-1-methyl-4-[[(1S)-1-(trifluoro-methyl)propyl]sulfamoyl]pyrrole-2-carboxamide;

3-chloro-N-(3-cyano-4-fluoro-phenyl)-1-methyl-4-[[(1R)-1-(trifluoro-methyl)propyl]sulfamoyl]pyrrole-2-carboxamide;

3-bromo-N-(3-cyano-4-fluoro-phenyl)-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1,5-dimethyl-4-[[(1R)-2,2,2-trifluoro-1-methyl-ethyl]sulfamoyl]pyrrole-2-carboxamide;

N-(3-cyano-4-fluoro-phenyl)-4-[[(1R)-2,2-difluoro-1-methyl-propyl]sulfamoyl]-3-fluoro-1-methyl-pyrrole-2-carboxamide;

N-(3-cyano-4-fluoro-phenyl)-4-[[(1S)-2,2-difluoro-1-methyl-propyl]sulfamoyl]-3-fluoro-1-methyl-pyrrole-2-carboxamide;

N-(3-chloro-4,5-difluoro-phenyl)-1-methyl-4-[[(1R)-2,2,2-trifluoro-1-methyl-ethyl]sulfamoyl]pyrrole-2-carboxamide;

N-(3,4-Difluorophenyl)-1-methyl-4-{[(1S)-2,2,2-trifluoro-1-methylethyl]sulfamoyl}-1H-pyrrole-2-carboxamide;
N-(3-Chloro-4,5-difluorophenyl)-1-methyl-4-[(2,2,2-trifluoro-1,1-dimethylethyl)sulfamoyl]-1H-pyrrole-2-carboxamide;
N-(3-Bromo-4,5-difluorophenyl)-1-methyl-4-{[(1S)-2,2,2-trifluoro-1-methylethyl]sulfamoyl}-1H-pyrrole-2-carboxamide;
N-(3-Chloro-4,5-difluorophenyl)-1-methyl-4-{[(1S)-2,2,2-trifluoro-1-methylethyl]sulfamoyl}-1H-pyrrole-2-carboxamide;
N-(3,4-Difluoro-5-methylphenyl)-1-methyl-4-{[(1S)-2,2,2-trifluoro-1-methylethyl]sulfamoyl}-1H-pyrrole-2-carboxamide;
N-(3-Chloro-2,4-difluorophenyl)-1-methyl-4-{[(1R)-2,2,2-trifluoro-1l-methylethyl]sulfamoyl}-1H-pyrrole-2-carboxamide;
N-(3-Chloro-4,5-difluorophenyl)-1,5-dimethyl-4-{[(1R)-2,2,2-trifluoro-1-methylethyl]sulfamoyl}-1H-pyrrole-2-carboxamide;
N-(3-Chloro-2,4-difluorophenyl)-1,5-dimethyl-4-{[(1R)-2,2,2-trifluoro-1-methylethyl]sulfamoyl}-1H-pyrrole-2-carboxamide;
N-(3-Chloro-2,4-difluorophenyl)-1-methyl-4-{[(1S)-2,2,2-trifluoro-1-methylethyl]sulfamoyl}-1H-pyrrole-2-carboxamide;
N-(3-Cyanophenyl)-3-fluoro-1-methyl-4-{[(1R)-2,2,2-trifluoro-1-methylethyl]sulfamoyl}-1H-pyrrole-2-carboxamide;
N-(3-Cyano-2,4-difluorophenyl)-3-fluoro-1-methyl-4-{[(1R)-2,2,2-trifluoro-1-methylethyl]sulfamoyl}-1H-pyrrole-2-carboxamide;
3-Fluoro-1-methyl-4-{[(1R)-2,2,2-trifluoro-1-methylethyl]sulfamoyl}-N-(2,3,4-trifluorophenyl)-1H-pyrrole-2-carboxamide;
N-(3-Bromo-2,4-difluorophenyl)-3-fluoro-1-methyl-4-{[(1R)-2,2,2-trifluoro-1-methylethyl]sulfamoyl}-1H-pyrrole-2-carboxamide;
N-(3-Chloro-2,4-difluorophenyl)-3-fluoro-1-methyl-4-{[(1R)-2,2,2-trifluoro-1-methylethyl]sulfamoyl}-1H-pyrrole-2-carboxamide;
N-(3-Cyano-2,4-difluorophenyl)-1-methyl-4-{[(1S)-2,2,2-trifluoro-1-methylethyl]sulfamoyl}-1H-pyrrole-2-carboxamide;
3-Chloro-N-(3-chloro-2,4-difluorophenyl)-1-methyl-4-{[(1R)-2,2,2-trifluoro-1-methylethyl]sulfamoyl}-1H-pyrrole-2-carboxamide
N-(3-Bromophenyl)-3-chloro-1-methyl-4-{[(1R)-2,2,2-trifluoro-1-methylethyl]sulfamoyl}-1H-pyrrole-2-carboxamide;
N-(3-chloro-2,4-difluoro-phenyl)-1-methyl-4-[(2,2,2-trifluoro-1,1-dimethyl-ethyl)sulfamoyl]-1H-pyrrole-2-carboxamide;
N-(3-chloro-2,4-difluoro-phenyl)-1-methyl-4-{[(1R)-1-(trifluoromethyl)propyl]sulfamoyl}-1H-pyrrole-2-carboxamide;
3-chloro-N-(3-cyano-2,4-difluoro-phenyl)-1-methyl-4-[[(1R)-2,2,2-trifluoro-1-methyl-ethyl]sulfamoyl]pyrrole-2-carboxamide;
3-chloro-N-[3-(difluoromethyl)-2,4-difluoro-phenyl]-1-methyl-4-[[(1R)-2,2,2-trifluoro-1-methyl-ethyl]sulfamoyl]pyrrole-2-carboxamide;
N-(3-bromophenyl)-3-fluoro-1l-methyl-4-[[(1R)-2,2,2-trifluoro-1-methyl-ethyl]sulfamoyl]pyrrole-2-carboxamide;
3-fluoro-N-(4-fluorophenyl)-1-methyl-4-[[(1R)-2,2,2-trifluoro-1-methyl-ethyl]sulfamoyl]pyrrole-2-carboxamide; and
N-[3-(difluoromethyl)-2,4-difluoro-phenyl]-3-fluoro-1-methyl-4-[[(1R)-2,2,2-trifluoro-1-methyl-ethyl]sulfamoyl]pyrrole-2-carboxamide.

5. The method of claim 1, wherein the compound is selected from the group consisting of:
N-(4-fluoro-3-methyl-phenyl)-1-methyl-4-[[(1S)-2,2,2-trifluoro-1-methyl-ethyl]sulfamoyl]pyrrole-2-carboxamide;
N-(4-fluoro-3-methyl-phenyl)-1-methyl-4-[[(1R)-2,2,2-trifluoro-1-methyl-ethyl]sulfamoyl]pyrrole-2-carboxamide;
N-(3,4-Difluorophenyl)-1-methyl-4-{[(1R)-2,2,2-trifluoro-1-methylethyl]sulfamoyl}-1H-pyrrole-2-carboxamide;
N-(3,4-Difluorophenyl)-1-methyl-4-{[(1S)-2,2,2-trifluoro-1-methylethyl]sulfamoyl}-1H-pyrrole-2-carboxamide;
N-(3,4-Difluorophenyl)-1-methyl-4-[(2,2,2-trifluoro-1,1-dimethylethyl)sulfamoyl]-1H-pyrrole-2-carboxamide;
N-(3-Bromo-4-fluorophenyl)-1-methyl-4-{[(1S)-2,2,2-trifluoro-1-methylethyl]sulfamoyl}-1H-pyrrole-2-carboxamide;
N-(3-Cyano-4-fluorophenyl)-1-methyl-4-{[(1S)-2,2,2-trifluoro-1-methylethyl]sulfamoyl}-1H-pyrrole-2-carboxamide;
N-(3-Chloro-4-fluorophenyl)-1-methyl-4-{[(1S)-2,2,2-trifluoro-1-methylethyl]sulfamoyl}-1H-pyrrole-2-carboxamide;
N-(3-Chloro-4-fluorophenyl)-1-methyl-4-{[(1R)-2,2,2-trifluoro-1-methylethyl]sulfamoyl}-1H-pyrrole-2-carboxamide;
N-(3-Bromo-4-fluorophenyl)-1-methyl-4-{[(1R)-2,2,2-trifluoro-1-methylethyl]sulfamoyl}-1H-pyrrole-2-carboxamide;
N-(3-cyano-4-fluoro-phenyl)-1-methyl-4-[[(1R)-2,2,2-trifluoro-1-methylethyl]sulfamoyl]pyrrole-2-carboxamide;
N-(3-Cyano-4-fluorophenyl)-1-methyl-4-[(2,2,2-trifluoro-1,1-dimethylethyl)sulfamoyl]-1H-pyrrole-2-carboxamide;
N-(3-Cyano-4-fluorophenyl)-1-methyl-4-{[(1S)-1-(trifluoromethyl)propyl]sulfamoyl}-1H-pyrrole-2-carboxamide;
N-(3-Cyano-4-fluorophenyl)-1-methyl-4-{[(1R)-1-(trifluoromethyl)propyl]sulfamoyl}-1H-pyrrole-2-carboxamide;
N-(3-cyano-4-fluoro-phenyl)-1-methyl-4-{[1-methyl-1-(trifluoromethyl)propyl]sulfamoyl}-1H-pyrrole-2-carboxamide;
N-(3-cyano-4-fluoro-phenyl)-4-{[1-ethyl-1-(trifluoromethyl)propyl]sulfamoyl}-1-methyl-1H-pyrrole-2-carboxamide;
N-(3-cyano-4-fluoro-phenyl)-4-[(2-fluoro-1,1-dimethyl-ethyl)sulfamoyl]-1-methyl-1H-pyrrole-2-carboxamide;
N-(3-cyano-4-fluoro-phenyl)-4-[[(1S)-2,2-difluoro-1-methyl-propyl]sulfamoyl]-1-methyl-pyrrole-2-carboxamide;
N-(3-cyano-4-fluoro-phenyl)-4-[[(1R)-2,2-difluoro-1-methyl-propyl]sulfamoyl]-1-methyl-pyrrole-2-carboxamide;
N-(3-Chloro-4-fluorophenyl)-1,5-dimethyl-4-{[(1R)-2,2,2-trifluoro-1-methylethyl]sulfamoyl}-1H-pyrrole-2-carboxamide;

N-(3,4-Difluorophenyl)-1,5-dimethyl-4-{[(1R)-2,2,2-trifluoro-1-methylethyl]sulfamoyl}-1H-pyrrole-2-carboxamide;

N-(3-Cyano-4-fluorophenyl)-1,5-dimethyl-4-{[(1R)-2,2,2-trifluoro-1-methylethyl]sulfamoyl}-1H-pyrrole-2-carboxamide;

N-(3-Bromo-4-fluorophenyl)-1,5-dimethyl-4-{[(1R)-2,2,2-trifluoro-1l-methylethyl]sulfamoyl}-1H-pyrrole-2-carboxamide;

N-(3,4-Difluorophenyl)-1,3-dimethyl-4-{[(1R)-2,2,2-trifluoro-1-methylethyl]sulfamoyl}-1H-pyrrole-2-carboxamide;

N-(3-Chloro-4-fluorophenyl)-1,3-dimethyl-4-{[(1R)-2,2,2-trifluoro-1l-methylethyl]sulfamoyl}-1H-pyrrole-2-carboxamide;

N-(3,4-Difluorophenyl)-1,3-dimethyl-4-{[(1S)-2,2,2-trifluoro-1-methylethyl]sulfamoyl}-1H-pyrrole-2-carboxamide;

N-(3-Chloro-4-fluorophenyl)-1,3-dimethyl-4-{[(1S)-2,2,2-trifluoro-1-methylethyl]sulfamoyl}-1H-pyrrole-2-carboxamide;

N-(3-Cyano-4-fluorophenyl)-1,3-dimethyl-4-{[(1R)-2,2,2-trifluoro-1-methylethyl]sulfamoyl}-1H-pyrrole-2-carboxamide;

N-(3-Cyano-4-fluorophenyl)-1,3-dimethyl-4-{[(1S)-2,2,2-trifluoro-1-methylethyl]sulfamoyl}-1H-pyrrole-2-carboxamide;

N-(3-Cyano-4-fluorophenyl)-3-fluoro-1-methyl-4-{[(1R)-2,2,2-trifluoro-1-methylethyl]sulfamoyl}-1H-pyrrole-2-carboxamide;

N-(3-Cyano-2-fluorophenyl)-3-fluoro-1-methyl-4-{[(1R)-2,2,2-trifluoro-1-methylethyl]sulfamoyl}-1H-pyrrole-2-carboxamide;

N-(3-Cyano-4-fluorophenyl)-3-fluoro-1-methyl-4-{[(1S)-2,2,2-trifluoro-1-methylethyl]sulfamoyl}-1H-pyrrole-2-carboxamide;

3-Chloro-N-(3-cyano-4-fluorophenyl)-1-methyl-4-{[(1R)-2,2,2-trifluoro-1-methylethyl]sulfamoyl}-1H-pyrrole-2-carboxamide;

3-Chloro-N-(3,4-difluorophenyl)-1-methyl-4-{[(1R)-2,2,2-trifluoro-1-methylethyl]sulfamoyl}-1H-pyrrole-2-carboxamide;

3-Chloro-N-(3-chloro-4-fluorophenyl)-1-methyl-4-{[(1R)-2,2,2-trifluoro-1-methylethyl]sulfamoyl}-1H-pyrrole-2-carboxamide;

3-Chloro-N-(3-cyano-4-fluorophenyl)-1-methyl-4-{[(1S)-2,2,2-trifluoro-1-methylethyl]sulfamoyl}-1H-pyrrole-2-carboxamide;

N-(3,4-Difluorophenyl)-3-fluoro-1-methyl-4-{[(1R)-2,2,2-trifluoro-1-methylethyl]sulfamoyl}-1H-pyrrole-2-carboxamide;

3-Chloro-N-(3-cyano-4-fluorophenyl)-1-methyl-4-[(2,2,2-trifluoro-1,1-dimethylethyl)sulfamoyl]-1H-pyrrole-2-carboxamide;

3-chloro-N-[3-(difluoromethyl)-4-fluoro-phenyl]-1-methyl-4-[[(1R)-2,2,2-trifluoro-1-methyl-ethyl]sulfamoyl]pyrrole-2-carboxamide;

3-chloro-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1S)-1-(trifluoro-methyl)propyl]sulfamoyl]pyrrole-2-carboxamide;

N-[3-(difluoromethyl)-4-fluoro-phenyl]-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1R)-1-(trifluoro-methyl)propyl]sulfamoyl]pyrrole-2-carboxamide;

3-chloro-N-(3-cyano-4-fluoro-phenyl)-1-methyl-4-[[(1S)-1-(trifluoro-methyl)propyl]sulfamoyl]pyrrole-2-carboxamide;

3-chloro-N-(3-cyano-4-fluoro-phenyl)-1-methyl-4-[[(1R)-1-(trifluoro-methyl)propyl]sulfamoyl]pyrrole-2-carboxamide;

3-bromo-N-(3-cyano-4-fluoro-phenyl)-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1,5-dimethyl-4-[[(1R)-2,2,2-trifluoro-1-methyl-ethyl]sulfamoyl]pyrrole-2-carboxamide;

N-(3-cyano-4-fluoro-phenyl)-4-[[(1R)-2,2-difluoro-1-methyl-propyl]sulfamoyl]-3-fluoro-1-methyl-pyrrole-2-carboxamide; and N-(3-cyano-4-fluoro-phenyl)-4-[[(1S)-2,2-difluoro-1-methyl-propyl]sulfamoyl]-3-fluoro-1-methyl-pyrrole-2-carboxamide.

6. The method of claim 1, wherein the compound is selected from the group consisting of:

N-(4-fluoro-3-methyl-phenyl)-1-methyl-4-[[(1S)-2,2,2-trifluoro-1-methyl-ethyl]sulfamoyl]pyrrole-2-carboxamide;

N-(4-fluoro-3-methyl-phenyl)-1-methyl-4-[[(1R)-2,2,2-trifluoro-1-methyl-ethyl]sulfamoyl]pyrrole-2-carboxamide;

N-(3,4-Difluorophenyl)-1-methyl-4-{[(1R)-2,2,2-trifluoro-1-methylethyl]sulfamoyl}-1H-pyrrole-2-carboxamide;

N-(3,4-Difluorophenyl)-1-methyl-4-{[(1S)-2,2,2-trifluoro-1-methylethyl]sulfamoyl}-1H-pyrrole-2-carboxamide;

N-(3,4-Difluorophenyl)-1-methyl-4-[(2,2,2-trifluoro-1,1-dimethylethyl)sulfamoyl]-1H-pyrrole-2-carboxamide;

N-(3-Bromo-4-fluorophenyl)-1-methyl-4-{[(1S)-2,2,2-trifluoro-1-methylethyl]sulfamoyl}-1H-pyrrole-2-carboxamide;

N-(3-Cyano-4-fluorophenyl)-1-methyl-4-{[(1S)-2,2,2-trifluoro-1-methylethyl]sulfamoyl}-1H-pyrrole-2-carboxamide;

N-(3-Chloro-4-fluorophenyl)-1-methyl-4-{[(1S)-2,2,2-trifluoro-1-methylethyl]sulfamoyl}-1H-pyrrole-2-carboxamide;

N-(3-Chloro-4-fluorophenyl)-1-methyl-4-{[(1R)-2,2,2-trifluoro-1-methylethyl]sulfamoyl}-1H-pyrrole-2-carboxamide;

N-(3-Bromo-4-fluorophenyl)-1-methyl-4-{[(1R)-2,2,2-trifluoro-1-methylethyl]sulfamoyl}-1H-pyrrole-2-carboxamide;

N-(3-cyano-4-fluoro-phenyl)-1-methyl-4-[[(1R)-2,2,2-trifluoro-1-methylethyl]sulfamoyl]pyrrole-2-carboxamide;

N-(3-Cyano-4-fluorophenyl)-1-methyl-4-[(2,2,2-trifluoro-1,1-dimethylethyl)sulfamoyl]-1H-pyrrole-2-carboxamide;

N-(3-Cyano-4-fluorophenyl)-1-methyl-4-{[(1S)-1-(trifluoromethyl)propyl]sulfamoyl}-1H-pyrrole-2-carboxamide;

N-(3-Cyano-4-fluorophenyl)-1-methyl-4-{[(1R)-1-(trifluoromethyl)propyl]sulfamoyl}-1H-pyrrole-2-carboxamide;

N-(3-cyano-4-fluoro-phenyl)-1-methyl-4-{[1-methyl-1-(trifluoromethyl)propyl]sulfamoyl}-1H-pyrrole-2-carboxamide;

N-(3-cyano-4-fluoro-phenyl)-4-{[1-ethyl-1-(trifluoromethyl)propyl]sulfamoyl}-1-methyl-1H-pyrrole-2-carboxamide;

N-(3-cyano-4-fluoro-phenyl)-4-[(2-fluoro-1,1-dimethylethyl)sulfamoyl]-1-methyl-1H-pyrrole-2-carboxamide;

N-(3-cyano-4-fluoro-phenyl)-4-[[(1S)-2,2-difluoro-1-methyl-propyl]sulfamoyl]-1-methyl-pyrrole-2-carboxamide; and N-(3-cyano-4-fluoro-phenyl)-4-[[(1R)-2,2-difluoro-1-methyl-propyl]sulfamoyl]-1-methyl-pyrrole-2-carboxamide.

7. The method of claim 1, further comprising administering an effective amount of at least one additional therapeutic agent.

8. The method of claim 7, wherein the at least one additional therapeutic agent is an anti-HBV agent.

9. The method of claim 7, wherein the at least one additional therapeutic agent is an immunomodulator.

10. The method of claim 9, wherein the immunomodulator is an interferon or Toll-like receptor agonist.

11. The method of claim 7, wherein the at least one additional therapeutic agent is selected from the group consisting of pegylated interferon-α, Toll-like receptor 7 and/or 8 agonists, lamivudine, adefovir and combinations thereof.

12. The method of claim 7, wherein the at least one additional therapeutic agent is administered simultaneous to, separate from or sequential with the compound of claim 1.

13. A method of treating Hepatitis B virus infection in a subject in need thereof comprising administering to said subject a pharmaceutical composition comprising a pharmaceutically acceptable carrier and further comprising a compound of Formula (ID)

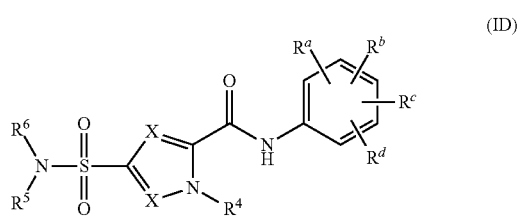

(ID)

or a stereoisomer or tautomeric form thereof, wherein:
each X is independently $CR^7$;
$R^a$, $R^b$ and $R^c$ are each independently selected from the group consisting of hydrogen, fluoro, bromo, chloro, —$CHF_2$, —$CF_2$-methyl, —$CH_2F$, —$CF_3$, —$OCF_3$, —CN, $C_1$-$C_3$alkyl and $C_3$-$C_4$cycloalkyl;
$R^d$ is hydrogen or fluoro;
$R^4$ is hydrogen, $C_1$-$C_3$alkyl or $C_3$-$C_4$cycloalkyl;
$R^5$ is hydrogen;
$R^6$ is selected from the group consisting of $C_2$-$C_6$alkyl, $C_1$-$C_4$alkyl-$R^8$ optionally substituted with one or more fluoro, $C_1$-$C_4$alkyl-$R^9$ optionally substituted with one or more fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally substituted with one or more substituents each independently selected from the group consisting of hydrogen, —OH, fluoro, oxo, $R^9$, $R^{10}$ and $C_1$-$C_4$alkyl optionally substituted with $R^{10}$;

$R^7$ is selected from the group consisting of hydrogen, —CN, fluoro, chloro, bromo, —$CHF_2$, —$CF_2$—methyl, —$CH_2F$, —$CF_3$, $C_1$-$C_3$alkyl optionally substituted with methoxy, $C_2$-$C_3$alkenyl and $C_3$-$C_4$cycloalkyl;
$R^8$ is a 3-7 membered saturated ring optionally containing one or more heteroatoms each independently selected from the group consisting of O, S and N, such 3-7 membered saturated ring optionally substituted with one or more $C_1$-$C_4$alkyl optionally substituted with $R^{10}$;
$R^9$ is selected from the group consisting of $C_1$-$C_4$alkyloxy, —$SO_2$-methyl, —C(=O)—$OR^{11}$ and —C(=O)—N($R^{11}$)$_2$;
$R^{10}$ is selected from the group consisting of —CN, —OH, fluoro, —$CHF_2$, —$CH_2F$ and —$CF_3$;
$R^{11}$ is hydrogen or $C_1$-$C_3$alkyl;
or a pharmaceutically acceptable salt or a solvate thereof wherein such compound is not

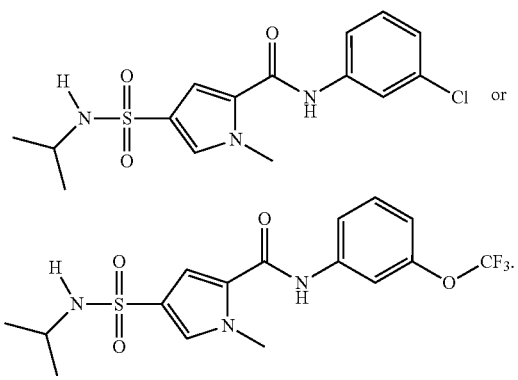

14. The method of claim 13, wherein
$R^a$ is —CN;
$R^b$, $R^c$ and $R^d$ are each independently selected from the group consisting of hydrogen and fluoro;
$R^4$ is $C_1$-$C_3$alkyl;
$R^6$ is selected from the group consisting of $C_2$-$C_6$alkyl, optionally substituted with one or more fluoro; and
$R^7$ is hydrogen.

15. The method of claim 13, wherein the compound is selected from the group consisting of:
N-(4-fluoro-3-methyl-phenyl)-4-(isopropylsulfamoyl)-1H-pyrrole-2-carboxamide;
N-(4-fluoro-3-methy-phenyl)-4-(isopropylsulfamoyl)-1-methyl-pyrrole-2-carboxamide;
N-(4-fluoro-3-methyl-phenyl)-4-[[(1R)-2-hydroxy-1-methyl-ethyl]sulfamoyl]-1-methyl-pyrrole-2-carboxamide;
N-(4-fluoro-3-methyl-phenyl)-1-methyl-4-[[(3S)-tetrahydrofuran-3-yl]sulfamoyl]pyrrole-2-carboxamide;
N-(4-fluoro-3-methyl-phenyl)-1-methyl-4-[(3-methyloxetan-3-yl)sulfamoyl]pyrrole-2-carboxamide;
N-(4-fluoro-3-methyl-phenyl)-1-methyl-4-[[(1R)-1-methylpropyl]sulfamoyl]pyrrole-2-carboxamide;
N-(4-fluoro-3-methyl-phenyl)-1-methyl-4-[(3-methyloxetan-3-yl)methylsulfamoyl]pyrrole-2-carboxamide;
N-(4-fluoro-3-methyl-phenyl)-1-methyl-4-[[(1S)-2,2,2-trifluoro-1-methyl-ethyl]sulfamoyl]pyrrole-2-carboxamide;
N-(4-fluoro-3-methyl-phenyl)-1-methyl-4-[[(1R)-2,2,2-trifluoro-1-methyl-ethyl]sulfamoyl]pyrrole-2-carboxamide;

N-(4-fluoro-3-methyl-phenyl)-4-[[3-(hydroxymethyl)oxetan-3-yl]sulfamoyl]-1-methyl-pyrrole-2-carboxamide;
N-(4-fluoro-3-methyl-phenyl)-1-methyl-4-[(3-methyltetrahydrofuran-3-yl)sulfamoyl]pyrrole-2-carboxamide;
N-(4-fluoro-3-methyl-phenyl)-4-[[1-(hydroxymethyl)cyclopropyl]sulfamoyl]-1-methyl-pyrrole-2-carboxamide;
N-(4-fluoro-3-methyl-phenyl)-1-methyl-4-[(1-methyl-5-oxo-pyrrolidin-3-yl)sulfamoyl]pyrrole-2-carboxamide;
N-(4-fluoro-3-methyl-phenyl)-4-[[3-(2-hydroxyethyl)oxetan-3-yl]sulfamoyl]-1-methyl-pyrrole-2-carboxamide;
N-(4-fluoro-3-methyl-phenyl)-4-[(3-hydroxycyclobutyl)sulfamoyl]-1-methyl-pyrrole-2-carboxamide;
4-(tert-butylsulfamoyl)-N-(4-fluoro-3-methyl-phenyl)-1-methyl-pyrrole-2-carboxamide
4-[[3-(cyanomethyl)oxetan-3-yl]sulfamoyl]-N-(4-fluoro-3-methy-phenyl)-1-methyl-pyrrole-2-carboxamide;
4-[[1-(cyanomethyl)cyclopropyl]sulfamoyl]-N-(4-fluoro-3-methy-phenyl)-1-methyl-pyrrole-2-carboxamide;
4-(tert-butylsulfamoyl)-N-(3,4-difluorophenyl)-1-methyl-pyrrole-2-carboxamide;
N-(3,4-difluorophenyl)-1-methyl-4-[(3-methyloxetan-3-yl)sulfamoyl]pyrrole-2-carboxamide;
N-(3,4-difluorophenyl)-1-methyl-4-[[(3S)-tetrahydrofuran-3-yl]sulfamoyl]pyrrole-2-carboxamide;
N-(3,4-difluorophenyl)-4-(isopropylsulfamoyl)-1-methyl-pyrrole-2-carboxamide;
N-(3,4-difluorophenyl)-1-methyl-4-[[(1R)-1-methylpropyl]sulfamoyl]pyrrole-2-carboxamide;
N-(3,4-difluorophenyl)-4-[[(1R)-2-hydroxy-1-methyl-ethyl]sulfamoyl]-1-methyl-pyrrole-2-carboxamide;
N-(3,4-difluorophenyl)-4-[(3-hydroxycyclobutyl)sulfamoyl]-1-methyl-pyrrole-2-carboxamide;
1-methyl-4-[[(3S)-tetrahydrofuran-3-yl]sulfamoyl]-N-(3,4,5-trifluorophenyl)pyrrole-2-carboxamide;
1-methyl-4-[(3-methyloxetan-3-yl)sulfamoyl]-N-(3,4,5-trifluorophenyl)pyrrole-2-carboxamide;
1-methyl-4-[(3-methyloxetan-3-yl)sulfamoyl]-N-[3-(trifluoromethyl)phenyl]pyrrole-2-carboxamide;
1-ethyl-N-(4-fluoro-3-methyl-phenyl)-4-(isopropylsulfamoyl)pyrrole-2-carboxamide;
1-ethyl-N-(4-fluoro-3-methyl-phenyl)-4-[[(3S)-tetrahydrofuran-3-yl]sulfamoyl]pyrrole-2-carboxamide;
N-(4-fluoro-3,5-dimethyl-phenyl)-1-methyl-4-[[(3S)-tetrahydrofuran-3-yl]sulfamoyl]pyrrole-2-carboxamide;
N-(3-fluoro-5-methyl-phenyl)-1-methyl-4-[[(3S)-tetrahydrofuran-3-yl]sulfamoyl]pyrrole-2-carboxamide;
N-(3,4-difluoro-5-methyl-phenyl)-4-(isopropylsulfamoyl)-1-methyl-pyrrole-2-carboxamide;
N-(3,4-difluoro-5-methyl-phenyl)-1-methyl-4-[[(1R)-1-methylpropyl]sulfamoyl]pyrrole-2-carboxamide;
N-(3,4-difluoro-5-methyl-phenyl)-1-methyl-4-[(3-methyloxetan-3-yl)sulfamoyl]pyrrole-2-carboxamide;
N-(3,4-difluoro-5-methyl-phenyl)-4-[[(1R)-2-hydroxy-1-methyl-ethyl]sulfamoyl]-1-methyl-pyrrole-2-carboxamide;
N-(3,4-difluoro-5-methyl-phenyl)-1-methyl-4-[[(3S)-tetrahydrofuran-3-yl]sulfamoyl]pyrrole-2-carboxamide;
4-(tert-butylsulfamoyl)-N-(3,4-difluoro-5-methyl-phenyl)-1-methyl-pyrrole-2-carboxamide;
N-[3-(difluoromethyl)-4-fluoro-phenyl]-1-methyl-4-[(3-methyloxetan-3-yl)sulfamoyl]pyrrole-2-carboxamide;
N-[3-(difluoromethyl)-4-fluoro-phenyl]-4-[[(1R)-2-hydroxy-1-methyl-ethyl]sulfamoyl]-1-methyl-pyrrole-2-carboxamide;
N-[4-fluoro-3-(trifluoromethyl)phenyl]-4-[[(1R)-2-hydroxy-1-methyl-ethyl]sulfamoyl]-1-methyl-pyrrole-2-carboxamide;
N-[4-fluoro-3-(trifluoromethyl)phenyl]-1-methyl-4-[[(3S)-tetrahydrofuran-3-yl]sulfamoyl]pyrrole-2-carboxamide;
N-[4-fluoro-3-(trifluoromethyl)phenyl]-1-methyl-4-[(3-methyloxetan-3-yl)sulfamoyl]pyrrole-2-carboxamide;
N-[4-fluoro-3-(trifluoromethyl)phenyl]-4-(isopropylsulfamoyl)-1-methyl-pyrrole-2-carboxamide;
N-[3-fluoro-5-(trifluoromethyl)phenyl]-1-methyl-4-[(3-methyloxetan-3-yl)sulfamoyl]pyrrole-2-carboxamide;
N-(3-bromo-4,5-difluoro-phenyl)-4-(isopropylsulfamoyl)-1-methyl-pyrrole-2-carboxamide;
N-(3-bromo-4,5-difluoro-phenyl)-1-methyl-4-[[(1R)-1-methylpropyl]sulfamoyl]pyrrole-2-carboxamide;
N-(3-bromo-4,5-difluoro-phenyl)-1-methyl-4-[(3-methyloxetan-3-yl)sulfamoyl]pyrrole-2-carboxamide;
methyl 2-[[5-[(4-fluoro-3-methyl-phenyl)carbamoyl]-1-methyl-pyrrol-3-yl]sulfonylamino]-2-methyl-propanoate;
N-(3-cyano-4-fluorophenyl)-1-methyl-4-[(3-methyloxetan-3-yl)sulfamoyl]-1H-pyrrole-2-carboxamide;
N-[4-cyano-3-(trifluoromethyl)phenyl]-1-methyl-4-[(3-methyloxetan-3-yl)sulfamoyl]-1H-pyrrole-2-carboxamide;
N-(3-cyano-4,5-difluoro-phenyl)-4-(isopropylsulfamoyl)-1-methyl-pyrrole-2-carboxamide;
4-(tert-butylsulfamoyl)-N-(3-cyano-5-fluoro-phenyl)-1-methyl-pyrrole-2-carboxamide;
N-(3-cyano-5-fluoro-phenyl)-1-methyl-4-[(3-methyloxetan-3-yl)sulfamoyl]pyrrole-2-carboxamide;
N-(3-cyanophenyl)-1-methyl-4-[(3-methyloxetan-3-yl)sulfamoyl]pyrrole-2-carboxamide;
N-(2,6-dideuterio-4-fluoro-3-methyl-phenyl)-1-methyl-4-[(3-methyloxetan-3-yl)sulfamoyl]pyrrole-2-carboxamide;
N-(3-chloro-4,5-difluoro-phenyl)-4-(isopropylsulfamoyl)-1-methyl-pyrrole-2-carboxamide;
4-(tert-butylsulfamoyl)-N-(3-chloro-4,5-difluoro-phenyl)-1-methyl-pyrrole-2-carboxamide;
N-(3-chloro-4,5-difluoro-phenyl)-1-methyl-4-[(3-methyloxetan-3-yl)sulfamoyl]pyrrole-2-carboxamide;
N-(3-chloro-4,5-difluoro-phenyl)-1-methyl-4-[[(1R)-2,2,2-trifluoro-1-methyl-ethyl]sulfamoyl]pyrrole-2-carboxamide;
2-[[5-[(4-fluoro-3-methyl-phenyl)carbamoyl]-1-methyl-pyrrol-3-yl]sulfonylamino]-2-methyl-propanoic acid;
4-[[1,1-dimethyl-2-(methylamino)-2-oxo-ethyl]sulfamoyl]-N-(4-fluoro-3-methyl-phenyl)-1-methyl-pyrrole-2-carboxamide;
4-[[2-(dimethylamino)-1,1-dimethyl-2-oxo-ethyl]sulfamoyl]-N-(4-fluoro-3-methyl-phenyl)-1-methyl-pyrrole-2-carboxamide;
4-[2-amino-1,1-dimethyl-2-oxo-ethyl)sulfamoyl]-N-(4-fluoro-3-methyl-phenyl)-1-methyl-pyrrole-2-carboxamide;
N-(3-chloro-4,5-difluoro-phenyl)-4-[(3,3-difluoro-1-methyl-cyclobutyl)sulfamoyl]-1-methyl-pyrrole-2-carboxamide;
N-(3-chloro-4,5-difluoro-phenyl)-4-(1,1-dimethylpropyl-sulfamoyl)-1-methyl-pyrrole-2-carboxamide;
4-tert-butylsulfamoyl)-N-(2,6-dideuterio-4-fluoro-3-methyl-phenyl)-1-methyl-pyrrole-2-carboxamide;
4-(tert-butylsulfamoyl)-1-methyl-N-(3,4,5-trifluorophenyl)pyrrole-2-carboxamide;

N-(4-fluoro-3-methyl-phenyl)-1-methyl-4-[[2,2,2-trideuterio-1,1-bis(trideuteriomethyl)ethyl]sulfamoyl]pyrrole-2-carboxamide;
N-(2,6-dideuterio-4-fluoro-3-methyl-phenyl)-1-methyl-4-[[2,2,2-trideuterio-1,1-bis(trideuteriomethyl)ethyl]sulfamoyl]pyrrole-2-carboxamide;
4-tert-butylsulfamoyl)-N-(2,6-dideuterio-3,4,5-trifluorophenyl)-1-methyl-pyrrole-2-carboxamide;
N-(3-chloro-4,5-difluoro-phenyl)-1-methyl-4-[[1-(trifluoromethyl)-cyclopropyl]sulfamoyl]pyrrole-2-carboxamide;
N-(3-chloro-4,5-difluoro-phenyl)-1-methyl-4-[[2,2,2-trifluoro-1-(methoxymethyl)-1-methyl-ethyl]sulfamoyl]pyrrole-2-carboxamide;
N-(3,4-difluorophenyl)-3-fluoro-1-methyl-4-[(3-methyloxetan-3-yl)sulfamoyl]pyrrole-2-carboxamide;
N-(3,5-Dichloro-4-fluorophenyl)-1-methyl-4-[(3-methyloxetan-3-yl)sulfamoyl]-1H-pyrrole-2-carboxamide;
4-(tert-Butylsulfamoyl)-N-(3,5-dichloro-4-fluorophenyl)-1-methyl-1H-pyrrole-2-carboxamide;
N-(4-Chloro-3-methylphenyl)-1-methyl-4-[(3-methyloxetan-3-yl)sulfamoyl]-1H-pyrrole-2-carboxamide;
N-(3-Chloro-4-fluorophenyl)-1-methyl-4-[(3-methyloxetan-3-yl)sulfamoyl]-1H-pyrrole-2-carboxamide;
N-[4-Fluoro-3-methyl-5-(trifluoromethyl)phenyl]-1-methyl-4-[(3-methyloxetan-3-yl)sulfamoyl]-1H-pyrrole-2-carboxamide;
N-(4-Fluoro-3,5-dimethylphenyl)-1-methyl-4-[(3-methyloxetan-3-yl)sulfamoyl]-1H-pyrrole-2-carboxamide;
N-(3-Bromo-4-fluorophenyl)-1-methyl-4-[(3-methyloxetan-3-yl)sulfamoyl]-1H-pyrrole-2-carboxamide;
1-Methyl-4-[(3-methyloxetan-3-yl)sulfamoyl]-N-[3-methyl-5-(trifluoromethyl)phenyl]-1H-pyrrole-2-carboxamide;
N-(4-Cyano-3-methylphenyl)-1-methyl-4-[(3-methyloxetan-3-ylsulfamoyl]-1H-pyrrole-2-carboxamide;
N-(4-Chloro-3-fluorophenyl)-1-methyl-4-[(3-methyloxetan-3-yl)sulfamoyl]-1H-pyrrole-2-carboxamide;
N-(2,4-Difluoro-3-methylphenyl)-1-methyl-4-[(3-methyloxetan-3-yl)sulfamoyl]-1H-pyrrole-2-carboxamide;
N-[4-Fluoro-3-(trifluoromethoxy)phenyl]-1-methyl-4-[(3-methyloxetan-3-yl)sulfamoyl]-1H-pyrrole-2-carboxamide;
N-(3-Chloro-5-cyanophenyl)-1-methyl-4-[(3-methyloxetan-3-yl)sulfamoyl]-1H-pyrrole-2-carboxamide;
N-(4-Fluoro-3-methylphenyl)-1,3,5-trimethyl-4-[(3-methyloxetan-3-yl)sulfamoyl]-1H-pyrrole-2-carboxamide;
N-(4-Fluoro-3-methylphenyl)-1,5-dimethyl-4-[(3-methyloxetan-3-yl)sulfamoyl]-1H-pyrrole-2-carboxamide;
N-(4-Fluoro-3-methylphenyl)-1,3-dimethyl-4-[(3-methyloxetan-3-yl)sulfamoyl]-1H-pyrrole-2-carboxamide;
N-(3,4-Difluorophenyl)-1-methyl-4-[(3-methyltetrahydrofuran-3-yl)sulfamoyl]-1H-pyrrole-2-carboxamide;
N-(3,4-Difluorophenyl)-1-methyl-4-{[(1R)-2,2,2-trifluoro-1-methylethyl]sulfamoyl}-1H-pyrrole-2-carboxamide;
N-(3,4-Difluorophenyl)-1-methyl-4-{[(1S)-2,2,2-trifluoro-1-methylethyl]sulfamoyl}-1H-pyrrole-2-carboxamide;
3-Fluoro-N-(4-fluoro-3-methylphenyl)-1-methyl-4-[(3-methyloxetan-3-yl)sulfamoyl]-1H-pyrrole-2-carboxamide;
N-(3,4-Difluorophenyl)-1-methyl-4-[(2,2,2-trifluoro-1,1-dimethylethyl)sulfamoyl]-1H-pyrrole-2-carboxamide;
N-(3-Chloro-4,5-difluorophenyl)-1-methyl-4-[(2,2,2-trifluoro-1,1-dimethylethyl)sulfamoyl]-1H-pyrrole-2-carboxamide;
N-(4-Fluoro-3-methylphenyl)-1-methyl-4-{[(1R)-1-methyl-2-(methylsulfonyl)ethyl]sulfamoyl}-1H-pyrrole-2-carboxamide;
4-(tert-Butylsulfamoyl)-N-[4-fluoro-3-(trifluoromethoxy)phenyl]-1-methyl-1H-pyrrole-2-carboxamide;
N-(2,4-Difluoro-3-methylphenyl)-1-methyl-4-[(1-methylethyl)sulfamoyl]-1H-pyrrole-2-carboxamide;
N-(3-Bromo-4,5-difluorophenyl)-1-methyl-4-{[(1S)-2,2,2-trifluoro-1-methylethyl]sulfamoyl}-1H-pyrrole-2-carboxamide;
N-(3-Bromo-4-fluorophenyl)-1-methyl-4-{[(1S)-2,2,2-trifluoro-1-methylethyl]sulfamoyl}-1H-pyrrole-2-carboxamide;
N-(3-Cyano-4-fluorophenyl)-1-methyl-4-{[(1S)-2,2,2-trifluoro-1-methylethyl]sulfamoyl}-1H-pyrrole-2-carboxamide;
N-(3-Chloro-4,5-difluorophenyl)-1-methyl-4-{[(1S)-2,2,2-trifluoro-1-methylethyl]sulfamoyl}-1H-pyrrole-2-carboxamide;
N-(3,4-Difluoro-5-methylphenyl)-1-methyl-4-{[(1S)-2,2,2-trifluoro-1-methylethyl]sulfamoyl}-1H-pyrrole-2-carboxamide;
N-(3-Chloro-4-fluorophenyl)-1-methyl-4-{[(1S)-2,2,2-trifluoro-1-methylethyl]sulfamoyl}-1H-pyrrole-2-carboxamide;
N-(3-Bromo-4-fluorophenyl)-3-fluoro-1-methyl-4-[(3-methyloxetan-3-yl)sulfamoyl]-1H-pyrrole-2-carboxamide;
N-[3-(Difluoromethyl)-4-fluorophenyl]-3-fluoro-1-methyl-4-[(3-methyloxetan-3-yl)sulfamoyl]-1H-pyrrole-2-carboxamide;
N-(3-Chloro-4-fluorophenyl)-3-fluoro-1-methyl-4-[(3-methyloxetan-3-yl)sulfamoyl]-1H-pyrrole-2-carboxamide;
3-Fluoro-1-methyl-4-[(3-methyloxetan-3-yl)sulfamoyl]-N-(2,4,5-trifluorophenyl)-1H-pyrrole-2-carboxamide;
N-(2,4-Difluoro-3-methylphenyl)-3-fluoro-1-methyl-4-[(3-methyloxetan-3-yl)sulfamoyl]-1H-pyrrole-2-carboxamide;
N-(3-Chloro-4,5-difluorophenyl)-3-fluoro-1-methyl-4-[(3-methyloxetan-3-yl)sulfamoyl]-1H-pyrrole-2-carboxamide;
4-(tert-butylsulfamoyl)-N-(2,4-difluoro-3-methyl-phenyl)-1-methyl-pyrrole-2-carboxamide;
N-(3-cyano-4-fluoro-phenyl)-3-fluoro-1-methyl-4-[(3-methyloxetan-3-yl)sulfamoyl]pyrrole-2-carboxamide;
4-[(1-Carbamoylcyclopropyl)sulfamoyl]-N-(3-chloro-4,5-difluorophenyl)-1-methyl-1H-pyrrole-2-carboxamide;
N-(3-Chloro-4,5-difluorophenyl)-1-methyl-4-{[1-(methylcarbamoyl)cyclopropyl]sulfamoyl}-1H-pyrrole-2-carboxamide;
N-(2,4-Difluoro-3-methylphenyl)-1-methyl-4-{[(1R)-2,2,2-trifluoro-1-methylethyl]sulfamoyl}-1H-pyrrole-2-carboxamide;
N-(2,4-Difluoro-3-methylphenyl)-1-methyl-4-{[1-(trifluoromethyl)cyclopropyl]sulfamoyl}-1H-pyrrole-2-carboxamide;
N-(2,4-Difluoro-3-methylphenyl)-1-methyl-4-[(2,2,2-trifluoro-1,1-dimethylethyl)sulfamoyl]-1H-pyrrole-2-carboxamide;

N-(2,4-Difluoro-3-methylphenyl)-1-methyl-4-{[(1S)-2,2,2-trifluoro-1-methylethyl]sulfamoyl}-1H-pyrrole-2-carboxamide;

N-(3-Chloro-2,4-difluorophenyl)-1-methyl-4-{[(1R)-2,2,2-trifluoro-1l-methylethyl]sulfamoyl}-1H-pyrrole-2-carboxamide;

N-(3-Chloro-2,4-difluorophenyl)-1-methyl-4-[(3-methyloxetan-3-yl)sulfamoyl]-1H-pyrrole-2-carboxamide;

1-methyl-4-[[(1R)-2,2,2-trifluoro-1-methyl-ethyl]sulfamoyl]-N-[3-(trifluoromethyl)phenyl]pyrrole-2-carboxamide;

N-(3-Chloro-4-fluorophenyl)-1-methyl-4-{[(1R)-2,2,2-trifluoro-1-methylethyl]sulfamoyl}-1H-pyrrole-2-carboxamide;

N-(3-Bromo-4-fluorophenyl)-1-methyl-4-{[(1R)-2,2,2-trifluoro-1-methylethyl]sulfamoyl}-1H-pyrrole-2-carboxamide;

N-[4-Fluoro-3-(trifluoromethyl)phenyl]-1-methyl-4-{[(1R)-2,2,2-trifluoro-1-methylethyl]sulfamoyl}-1H-pyrrole-2-carboxamide;

N-(3-Cyano-4-fluorophenyl)-4-[(2,2-difluoroethyl)sulfamoyl]-1-methyl-1H-pyrrole-2-carboxamide;

N-(3-Bromo-4-fluorophenyl)-4-[(2,2-difluoroethyl)sulfamoyl]-1-methyl-1H-pyrrole-2-carboxamide;

N-(3-Chloro-4-fluorophenyl)-4-[(2,2-difluoroethyl)sulfamoyl]-1-methyl-1H-pyrrole-2-carboxamide;

4-[(2,2-Difluoroethyl)sulfamoyl]-N-(3,4-difluorophenyl)-1-methyl-1H-pyrrole-2-carboxamide;

N-(3-Chloro-4,5-difluorophenyl)-4-[(2,2-difluoroethyl)sulfamoyl]-1-methyl-1H-pyrrole-2-carboxamide;

N-(3-Chloro-4-fluorophenyl)-1-methyl-4-[(2,2,2-trifluoroethyl)sulfamoyl]-1H-pyrrole-2-carboxamide;

N-(3,4-Difluorophenyl)-1-methyl-4-[(2,2,2-trifluoroethyl)sulfamoyl]-1H-pyrrole-2-carboxamide;

N-(3-Chloro-4,5-difluorophenyl)-1-methyl-4-[(2,2,2-trifluoroethyl)sulfamoyl]-1H-pyrrole-2-carboxamide;

N-(3-Cyano-4-fluorophenyl)-1-methyl-4-[(2,2,2-trifluoroethyl)sulfamoyl]-1H-pyrrole-2-carboxamide;

N-(3-Bromo-4-fluorophenyl)-1-methyl-4-[(2,2,2-trifluoroethyl)sulfamoyl]-1H-pyrrole-2-carboxamide;

N-(3-Chloro-4,5-difluorophenyl)-1,5-dimethyl-4-[(3-methyloxetan-3-yl)sulfamoyl]-1H-pyrrole-2-carboxamide;

N-(3-Chloro-4,5-difluorophenyl)-1,5-dimethyl-4-{[(1R)-2,2,2-trifluoro-1-methylethyl]sulfamoyl}-1H-pyrrole-2-carboxamide;

N-(3-Chloro-4-fluorophenyl)-1,5-dimethyl-4-{[(1R)-2,2,2-trifluoro-1l-methylethyl]sulfamoyl}-1H-pyrrole-2-carboxamide;

N-(3,4-Difluorophenyl)-1,5-dimethyl-4-{[(1R)-2,2,2-trifluoro-1-methylethyl]sulfamoyl}-1H-pyrrole-2-carboxamide;

N-(3-Cyano-4-fluorophenyl)-1,5-dimethyl-4-{[(1R)-2,2,2-trifluoro-1-methylethyl]sulfamoyl}-1H-pyrrole-2-carboxamide;

N-(3-Bromo-4-fluorophenyl)-1,5-dimethyl-4-{[(1R)-2,2,2-trifluoro-1l-methylethyl]sulfamoyl}-1H-pyrrole-2-carboxamide;

N-[4-Fluoro-3-(trifluoromethyl)phenyl]-1,5-dimethyl-4-{[(1R)-2,2,2-trifluoro-1-methylethyl]sulfamoyl}-1H-pyrrole-2-carboxamide;

N-(3-Chloro-2,4-difluorophenyl)-1,5-dimethyl-4-{[(1R)-2,2,2-trifluoro-1-methylethyl]sulfamoyl}-1H-pyrrole-2-carboxamide;

N-(3,4-Difluorophenyl)-1,3-dimethyl-4-{[(1R)-2,2,2-trifluoro-1-methylethyl]sulfamoyl}-1H-pyrrole-2-carboxamide;

N-(3-Chloro-4-fluorophenyl)-1,3-dimethyl-4-{[(1R)-2,2,2-trifluoro-1l-methylethyl]sulfamoyl}-1H-pyrrole-2-carboxamide;

N-(3,4-Difluorophenyl)-1,3-dimethyl-4-{[(1S)-2,2,2-trifluoro-1-methylethyl]sulfamoyl}-1H-pyrrole-2-carboxamide;

N-(3-Chloro-4-fluorophenyl)-1,3-dimethyl-4-{[(1S)-2,2,2-trifluoro-1-methylethyl]sulfamoyl}-1H-pyrrole-2-carboxamide;

N-(3,4-Difluorophenyl)-1,3-dimethyl-4-[(3-methyloxetan-3-yl)sulfamoyl]-1H-pyrrole-2-carboxamide;

N-(3-Chloro-4-fluorophenyl)-1,3-dimethyl-4-[(3-methyloxetan-3-yl)sulfamoyl]-1H-pyrrole-2-carboxamide;

N-(3-Cyano-4-fluorophenyl)-1,3-dimethyl-4-{[(1R)-2,2,2-trifluoro-1-methylethyl]sulfamoyl}-1H-pyrrole-2-carboxamide;

N-(3-Cyano-4-fluorophenyl)-1,3-dimethyl-4-{[(1S)-2,2,2-trifluoro-1-methylethyl]sulfamoyl}-1H-pyrrole-2-carboxamide;

N-(3-Cyano-4-fluorophenyl)-1,3-dimethyl-4-[(3-methyloxetan-3-yl)sulfamoyl]-1H-pyrrole-2-carboxamide;

N-[4-Fluoro-3-(trifluoromethyl)phenyl]-1,3-dimethyl-4-{[(1R)-2,2,2-trifluoro-1-methylethyl]sulfamoyl}-1H-pyrrole-2-carboxamide;

1-Methyl-4-{[(1S)-2,2,2-trifluoro-1-methylethyl]sulfamoyl}-N-(2,3,4-trifluorophenyl)-1H-pyrrole-2-carboxamide;

N-(3-Bromo-2,4-difluorophenyl)-1-methyl-4-{[(1S)-2,2,2-trifluoro-1-methylethyl]sulfamoyl}-1H-pyrrole-2-carboxamide;

N-(3-Chloro-2,4-difluorophenyl)-1-methyl-4-{[(1S)-2,2,2-trifluoro-1-methylethyl]sulfamoyl}-1H-pyrrole-2-carboxamide;

N-(3-cyano-4-fluoro-phenyl)-1-methyl-4-[[(1R)-2,2,2-trifluoro-1-methylethyl]sulfamoyl]pyrrole-2-carboxamide;

N-(3-Cyanophenyl)-1-methyl-4-{[(1R)-2,2,2-trifluoro-1-methylethyl]sulfamoyl}-1H-pyrrole-2-carboxamide;

N-[2-Fluoro-3-(trifluoromethyl)phenyl]-1-methyl-4-{[(1R)-2,2,2-trifluoro-1-methylethyl]sulfamoyl}-1H-pyrrole-2-carboxamide;

N-(3-Cyano-2-fluorophenyl)-1-methyl-4-{[(1R)-2,2,2-trifluoro-1-methylethyl]sulfamoyl}-1H-pyrrole-2-carboxamide;

N-[3-(1,1-Difluoroethyl)-4-fluorophenyl]-1-methyl-4-[(3-methyloxetan-3-yl)sulfamoyl]-1H-pyrrole-2-carboxamide;

4-(tert-Butylsulfamoyl)-N-[3-(1,1-difluoroethyl)-4-fluorophenyl]-1-methyl-1H-pyrrole-2-carboxamide;

N-(3,5-Dichloro-4-fluorophenyl)-1-methyl-4-[(2,2,2-trifluoro-1,1-dimethylethyl)sulfamoyl]-1H-pyrrole-2-carboxamide;

N-(3-Chloro-4,5-difluorophenyl)-4-[(3,3-difluorocyclobutyl)sulfamoyl]-1-methyl-1H-pyrrole-2-carboxamide;

N-(3-chloro-4,5-difluoro-phenyl)-1-methyl-4-[[1-methyl-1-(trifluoro-methyl)propyl]sulfamoyl]pyrrole-2-carboxamide;

N-(3-Chloro-4,5-difluorophenyl)-4-[(3,3-difluorocyclopentyl)sulfamoyl]-1-methyl-1H-pyrrole-2-carboxamide;

4-(Bicyclo[1.1.1]pent-1-ylsulfamoyl)-N-(3-chloro-4,5-difluorophenyl)-1-methyl-1H-pyrrole-2-carboxamide;

N-(3-Chloro-4,5-difluorophenyl)-1-methyl-4-[(3,3,3-trifluoropropyl)sulfamoyl]-1H-pyrrole-2-carboxamide;

N-(3-Chloro-4,5-difluorophenyl)-1-methyl-4-[(3,3,3-trifluoro-1-methylpropyl)sulfamoyl]-1H-pyrrole-2-carboxamide;
N-(3-Cyano-4-fluorophenyl)-3-fluoro-1-methyl-4-{[(1R)-2,2,2-trifluoro-1-methylethyl]sulfamoyl}-1H-pyrrole-2-carboxamide;
N-(3-Cyano-4-fluorophenyl)-3-fluoro-1-methyl-4-[(1-methylethyl)sulfamoyl]-1H-pyrrole-2-carboxamide;
N-(3-Chloro-2,4-difluorophenyl)-1-methyl-4-[(1-methylethyl)sulfamoyl]-1H-pyrrole-2-carboxamide;
N-(3-Chloro-2-fluorophenyl)-1-methyl-4-[(1-methylethyl)sulfamoyl]-1H-pyrrole-2-carboxamide;
N-(3-Chloro-4-fluorophenyl)-1-methyl-4-[(1-methylethyl)sulfamoyl]-1H-pyrrole-2-carboxamide;
N-(3-Cyano-4-fluorophenyl)-1-methyl-4-[(1-methylethyl)sulfamoyl]-1H-pyrrole-2-carboxamide;
N-(3-Cyano-2-fluorophenyl)-1-methyl-4-[(1-methylethyl)sulfamoyl]-1H-pyrrole-2-carboxamide;
N-(3-Cyanophenyl)-1-methyl-4-[(1-methylethyl)sulfamoyl]-1H-pyrrole-2-carboxamide;
N-(3-Cyano-2,4-difluorophenyl)-1-methyl-4-[(1-methylethyl)sulfamoyl]-1H-pyrrole-2-carboxamide;
N-[4-Fluoro-3-(trifluoromethyl)phenyl]-1,3-dimethyl-4-[(3-methyloxetan-3-yl)sulfamoyl]-1H-pyrrole-2-carboxamide;
N-(3-Cyanophenyl)-3-fluoro-1-methyl-4-{[(1R)-2,2,2-trifluoro-1-methylethyl]sulfamoyl}-1H-pyrrole-2-carboxamide;
N-(3-Cyano-2,4-difluorophenyl)-3-fluoro-1-methyl-4-{[(1R)-2,2,2-trifluoro-1-methylethyl]sulfamoyl}-1H-pyrrole-2-carboxamide;
N-(3-Cyano-2-fluorophenyl)-3-fluoro-1-methyl-4-{[(1R)-2,2,2-trifluoro-1-methylethyl]sulfamoyl}-1H-pyrrole-2-carboxamide;
3-Fluoro-1-methyl-4-{[(1R)-2,2,2-trifluoro-1-methylethyl]sulfamoyl}-N-(2,3,4-trifluorophenyl)-1H-pyrrole-2-carboxamide;
N-(3-Bromo-2,4-difluorophenyl)-3-fluoro-1-methyl-4-{[(1R)-2,2,2-trifluoro-1-methylethyl]sulfamoyl}-1H-pyrrole-2-carboxamide;
N-(3-Chloro-2,4-difluorophenyl)-3-fluoro-1-methyl-4-{[(1R)-2,2,2-trifluoro-1-methylethyl]sulfamoyl}-1H-pyrrole-2-carboxamide;
N-(3-Cyano-4-fluorophenyl)-3-fluoro-1-methyl-4-{[(1R)-1-methylpropyl]sulfamoyl}-1H-pyrrole-2-carboxamide;
N-(3-Cyano-4-fluorophenyl)-4-[(3,3-difluoro-1-methylcyclobutyl)sulfamoyl]-3-fluoro-1-methyl-1H-pyrrole-2-carboxamide;
N-(3-Cyano-4-fluorophenyl)-3-fluoro-1-methyl-4-{[(1S)-2,2,2-trifluoro-1-methylethyl]sulfamoyl}-1H-pyrrole-2-carboxamide;
N-(3-Chloro-4,5-difluorophenyl)-1-methyl-4-{[1-(trifluoromethyl)cyclobutyl]sulfamoyl}-1H-pyrrole-2-carboxamide;
4-(tert-Butylsulfamoyl)-N-(3-cyano-4-fluorophenyl)-1-methyl-1H-pyrrole-2-carboxamide;
4-(tert-Butylsulfamoyl)-N-(3-cyanophenyl)-1-methyl-1H-pyrrole-2-carboxamide;
4-(tert-Butylsulfamoyl)-N-(3-cyano-2-fluorophenyl)-1-methyl-1H-pyrrole-2-carboxamide;
4-(tert-Butylsulfamoyl)-N-(3-chloro-2-fluorophenyl)-1-methyl-1H-pyrrole-2-carboxamide;
4-(tert-Butylsulfamoyl)-N-(3-chloro-2,4-difluorophenyl)-1-methyl-1H-pyrrole-2-carboxamide;
4-(tert-Butylsulfamoyl)-N-(3-chloro-4-fluorophenyl)-1-methyl-1H-pyrrole-2-carboxamide;
N-(3-Cyano-2,4-difluorophenyl)-1-methyl-4-{[(1S)-2,2,2-trifluoro-1-methylethyl]sulfamoyl}-1H-pyrrole-2-carboxamide;
N-(3-Cyanophenyl)-1-methyl-4-{[(1S)-2,2,2-trifluoro-1-methylethyl]sulfamoyl}-1H-pyrrole-2-carboxamide;
N-(3-Cyano-2-fluorophenyl)-1-methyl-4-{[(1S)-2,2,2-trifluoro-1-methylethyl]sulfamoyl}-1H-pyrrole-2-carboxamide;
3-Chloro-N-(3-cyano-4-fluorophenyl)-1-methyl-4-{[(1R)-2,2,2-trifluoro-1-methylethyl]sulfamoyl}-1H-pyrrole-2-carboxamide;
N-(3-Cyano-4-fluorophenyl)-4-{[2,2-difluoro-1-methylethyl]sulfamoyl}-1-methyl-1H-pyrrole-2-carboxamide;
N-(3-Chloro-4,5-difluorophenyl)-1,3-dimethyl-4-[(3-methyloxetan-3-yl)sulfamoyl]-1H-pyrrole-2-carboxamide;
N-(3-Chloro-4,5-difluorophenyl)-1,3-dimethyl-4-{[(1R)-2,2,2-trifluoro-1-methylethyl]sulfamoyl}-1H-pyrrole-2-carboxamide;
N-(2,3-Difluorophenyl)-1-methyl-4-{[(1R)-2,2,2-trifluoro-1-methylethyl]sulfamoyl}-1H-pyrrole-2-carboxamide;
N-(3-Chloro-2,6-difluorophenyl)-1-methyl-4-{[(1R)-2,2,2-trifluoro-1l-methylethyl]sulfamoyl}-1H-pyrrole-2-carboxamide;
N-(3-Bromo-4,5-difluorophenyl)-1-methyl-4-{[(1R)-2,2,2-trifluoro-1l-methylethyl]sulfamoyl}-1H-pyrrole-2-carboxamide;
N-(3-Bromo-2-fluorophenyl)-1-methyl-4-{[(1R)-2,2,2-trifluoro-1-methylethyl]sulfamoyl}-1H-pyrrole-2-carboxamide;
N-(3-chloro-4,5-difluoro-phenyl)-4-[(2-fluoro-1,1-dimethyl-ethyl)sulfamoyl]-1-methyl-pyrrole-2-carboxamide;
N-(3-Chloro-2,4-difluorophenyl)-1,3-dimethyl-4-[(1-methylethyl)sulfamoyl]-1H-pyrrole-2-carboxamide;
N-(3-Chloro-2,4-difluorophenyl)-1,3-dimethyl-4-{[(1S)-2,2,2-trifluoro-1-methylethyl]sulfamoyl}-1H-pyrrole-2-carboxamide;
N-(3-Chloro-2,4-difluorophenyl)-1,3-dimethyl-4-{[(1R)-2,2,2-trifluoro-1-methylethyl]sulfamoyl}-1H-pyrrole-2-carboxamide;
4-(tert-Butylsulfamoyl)-N-(3,4-difluorophenyl)-3-fluoro-1-methyl-1H-pyrrole-2-carboxamide;
4-(tert-Butylsulfamoyl)-N-(3-chloro-2,4-difluorophenyl)-3-fluoro-1-methyl-1H-pyrrole-2-carboxamide;
4-(tert-Butylsulfamoyl)-3-fluoro-1-methyl-N-(2,3,4-trifluorophenyl)-1H-pyrrole-2-carboxamide;
4-(tert-Butylsulfamoyl)-N-(3-cyano-4-fluorophenyl)-3-fluoro-1-methyl-1H-pyrrole-2-carboxamide;
N-(3-Chloro-2,4-difluorophenyl)-3-fluoro-1-methyl-4-[(3-methyloxetan-3-yl)sulfamoyl]-1H-pyrrole-2-carboxamide;
3-Cyano-N-(3-cyano-4-fluorophenyl)-1-methyl-4-[(1-methylethyl)sulfamoyl]-1H-pyrrole-2-carboxamide;
3-Chloro-N-(3,4-difluorophenyl)-1-methyl-4-{[(1R)-2,2,2-trifluoro-1-methylethyl]sulfamoyl}-1H-pyrrole-2-carboxamide;
3-Chloro-N-(3-chloro-2,4-difluorophenyl)-1-methyl-4-{[(1R)-2,2,2-trifluoro-1-methylethyl]sulfamoyl}-1H-pyrrole-2-carboxamide;
3-Chloro-N-(3-chloro-2,4-difluorophenyl)-1-methyl-4-{[1-(trifluoro-methyl)cyclobutyl]sulfamoyl}-1H-pyrrole-2-carboxamide;
4-(tert-Butylsulfamoyl)-3-chloro-N-(3-chloro-4-fluorophenyl)-1-methyl-1H-pyrrole-2-carboxamide;

3-Chloro-N-(3-cyano-4-fluorophenyl)-1-methyl-4-{[1-(trifluoromethyl)cyclobutyl]sulfamoyl}-1H-pyrrole-2-carboxamide;
3-Chloro-N-(3-chloro-4-fluorophenyl)-1-methyl-4-{[(1R)-2,2,2-trifluoro-1-methylethyl]sulfamoyl}-1H-pyrrole-2-carboxamide;
4-(tert-Butylsulfamoyl)-3-chloro-N-(3,4-difluorophenyl)-1-methyl-1H-pyrrole-2-carboxamide;
4-(tert-Butylsulfamoyl)-3-chloro-N-(3-chloro-2,4-difluorophenyl)-1-methyl-1H-pyrrole-2-carboxamide;
3-Chloro-N-(3-cyano-4-fluorophenyl)-1-methyl-4-{[(1S)-2,2,2-trifluoro-1-methylethyl]sulfamoyl}-1H-pyrrole-2-carboxamide;
4-(tert-Butylsulfamoyl)-3-chloro-N-(3-cyano-4-fluorophenyl)-1-methyl-1H-pyrrole-2-carboxamide;
N-(3-Cyano-4-fluorophenyl)-1-methyl-4-{[1-(trifluoromethyl)cyclopropyl]sulfamoyl}-1H-pyrrole-2-carboxamide;
N-(3-Cyano-4-fluorophenyl)-1-methyl-4-{[3-(trifluoromethyl)tetrahydrofuran-3-yl]sulfamoyl}-1H-pyrrole-2-carboxamide;
N-(3,4-Difluorophenyl)-3-fluoro-1-methyl-4-{[(1R)-2,2,2-trifluoro-1-methylethyl]sulfamoyl}-1H-pyrrole-2-carboxamide;
N-(3-Bromo-4-fluorophenyl)-3-fluoro-1-methyl-4-[(1-methylethyl)sulfamoyl]-1H-pyrrole-2-carboxamide;
N-(3-Cyano-2,4-difluorophenyl)-3-fluoro-1-methyl-4-[(1-methylethyl)sulfamoyl]-1H-pyrrole-2-carboxamide;
N-(3,4-Difluorophenyl)-3-fluoro-1-methyl-4-[(1-methylethyl)sulfamoyl]-1H-pyrrole-2-carboxamide;
3-Fluoro-1-methyl-4-[(1-methylethyl)sulfamoyl]-N-(2,3,4-trifluorophenyl)-1H-pyrrole-2-carboxamide;
N-(3-Chloro-2,4-difluorophenyl)-3-fluoro-1-methyl-4-[(1-methylethyl)sulfamoyl]-1H-pyrrole-2-carboxamide;
N-(3-Chloro-4-fluorophenyl)-3-fluoro-1-methyl-4-[(1-methylethyl)sulfamoyl]-1H-pyrrole-2-carboxamide;
N-(3-Chloro-2,4-difluorophenyl)-4-{[2,2-difluorocyclopentyl]sulfamoyl}-1-methyl-1H-pyrrole-2-carboxamide;
N-(3-Cyano-4-fluorophenyl)-1-methyl-4-[(2,2,2-trifluoro-1,1-dimethylethyl)sulfamoyl]-1H-pyrrole-2-carboxamide;
N-(3-Cyano-4-fluorophenyl)-1-methyl-4-[(3,3,3-trifluoro-1-methylpropyl)sulfamoyl]-1H-pyrrole-2-carboxamide;
N-(3-Cyano-4-fluorophenyl)-1-methyl-4-{[(1S)-1-(trifluoromethyl)propyl]sulfamoyl}-1H-pyrrole-2-carboxamide;
N-(3-Cyano-4-fluorophenyl)-1-methyl-4-{[(1R)-1-(trifluoromethyl)propyl]sulfamoyl}-1H-pyrrole-2-carboxamide;
N-(3-Cyano-4-fluorophenyl)-1-methyl-4-{[1-(trifluoromethyl)cyclobutyl]sulfamoyl}-1H-pyrrole-2-carboxamide;
N-(3-Cyano-4-fluorophenyl)-4-{[2-fluoro-1-(fluoromethyl)ethyl]sulfamoyl}-1-methyl-1H-pyrrole-2-carboxamide;
N-(3-Chloro-2,4-difluorophenyl)-1,3-dimethyl-4-[(3-methyloxetan-3-yl)sulfamoyl]-1H-pyrrole-2-carboxamide;
N-(3-cyano-4-fluoro-phenyl)-1-methyl-4-[(1-methylcyclopropyl)sulfamoyl]pyrrole-2-carboxamide;
N-(3-cyano-4-fluoro-phenyl)-4-[(3,3-difluoro-1-methyl-cyclobutyl)sulfamoyl]-1-methyl-1H-pyrrole-2-carboxamide;
N-(3-cyano-4-fluoro-phenyl)-1-methyl-4-{[1-methyl-1-(trifluoromethyl)propyl]sulfamoyl}-1H-pyrrole-2-carboxamide;
N-(3-cyano-4-fluoro-phenyl)-1-methyl-4-{[4-(trifluoromethyl)tetrahydropyran-4-yl]sulfamoyl}-1H-pyrrole-2-carboxamide;
N-(3-cyano-4-fluoro-phenyl)-4-{[1-ethyl-1-(trifluoromethyl)propyl]sulfamoyl}-1-methyl-1H-pyrrole-2-carboxamide;
N-(3-cyano-4-fluoro-phenyl)-4-[(2-fluoro-1,1-dimethyl-ethyl)sulfamoyl]-1-methyl-1H-pyrrole-2-carboxamide;
N-(3-Bromophenyl)-3-chloro-1-methyl-4-{[(1R)-2,2,2-trifluoro-1-methylethyl]sulfamoyl}-1H-pyrrole-2-carboxamide;
N-(3-Bromophenyl)-3-fluoro-1-methyl-4-[(3-methyloxetan-3-yl)sulfamoyl]-1H-pyrrole-2-carboxamide;
N-(3-chloro-2,4-difluoro-phenyl)-4-[(2,2-difluoro-1-methyl-ethyl)sulfamoyl]-1-methyl-1H-pyrrole-2-carboxamide;
N-(3-chloro-2,4-difluoro-phenyl)-1-methyl-4-{[1-(trifluoromethyl)cyclopropyl]sulfamoyl}-1H-pyrrole-2-carboxamide;
N-(3-chloro-2,4-difluoro-phenyl)-1-methyl-4-[(2,2,2-trifluoro-1,1-dimethyl-ethyl)sulfamoyl]-1H-pyrrole-2-carboxamide;
N-(3-chloro-2,4-difluoro-phenyl)-1-methyl-4-[(1-methylcyclopropyl)sulfamoyl]-1H-pyrrole-2-carboxamide;
N-(3-chloro-2,4-difluoro-phenyl)-4-[(3,3-difluoro-1-methyl-cyclobutyl)sulfamoyl]-1-methyl-1H-pyrrole-2-carboxamide;
N-(3-chloro-2,4-difluoro-phenyl)-1-methyl-4-{[1-methyl-1-(trifluoromethyl)propyl]sulfamoyl}-1H-pyrrole-2-carboxamide;
N-(3-chloro-2,4-difluoro-phenyl)-1-methyl-4-[[4-(trifluoromethyl)tetrahydropyran-4-yl]sulfamoyl]-1H-pyrrole-2-carboxamide;
N-(3-chloro-2,4-difluoro-phenyl)-4-[[1-ethyl-1-(trifluoromethyl)propyl]sulfamoyl]-1-methyl-1H-pyrrole-2-carboxamide;
N-(3-chloro-2,4-difluoro-phenyl)-1-methyl-4-[(3,3,3-trifluoro-1-methylpropyl)sulfamoyl]-1H-pyrrole-2-carboxamide;
N-(3-chloro-2,4-difluoro-phenyl)-4-[(2-fluoro-1,1-dimethyl-ethyl)sulfamoyl]-1-methyl-1H-pyrrole-2-carboxamide;
N-(3-chloro-2,4-difluoro-phenyl)-1-methyl-4-{[(1S)-1-(trifluoromethyl)propyl]sulfamoyl}-1H-pyrrole-2-carboxamide;
N-(3-chloro-2,4-difluoro-phenyl)-1-methyl-4-{[1-(trifluoromethyl)cyclobutyl]sulfamoyl}-1H-pyrrole-2-carboxamide;
N-(3-chloro-2,4-difluoro-phenyl)-4-{[2-fluoro-1-(fluoromethyl)ethyl]sulfamoyl}-1-methyl-1H-pyrrole-2-carboxamide;
N-(3-chloro-2,4-difluoro-phenyl)-1-methyl-4-{[(1R)-1-(trifluoromethyl)propyl]sulfamoyl}-1H-pyrrole-2-carboxamide;
N-(3-chloro-2,4-difluoro-phenyl)-1-methyl-4-{[3-(trifluoromethyl)tetrahydrofuran-3-yl]sulfamoyl}-1H-pyrrole-2-carboxamide;
3-chloro-N-(3,4-difluorophenyl)-1-methyl-4-{[1-(trifluoromethyl)cyclobutyl]sulfamoyl}-1H-pyrrole-2-carboxamide;
3-chloro-N-(3-chloro-4-fluoro-phenyl)-1-methyl-4-{[1-(trifluoromethyl)cyclobutyl]sulfamoyl}-1H-pyrrole-2-carboxamide;

3-Chloro-N-(3-cyano-4-fluorophenyl)-1-methyl-4-[(1-methylethyl)sulfamoyl]-1H-pyrrole-2-carboxamide;

3-Chloro-N-(3-cyano-4-fluorophenyl)-1-methyl-4-[(2,2,2-trifluoro-1,1-dimethylethyl)sulfamoyl]-1H-pyrrole-2-carboxamide;

3-Chloro-N-(3-cyano-4-fluorophenyl)-1-methyl-4-{[1-(trifluoromethyl)cyclopropyl]sulfamoyl}-1H-pyrrole-2-carboxamide;

3-chloro-N-(2-cyano-4-fluoro-3-methyl-phenyl)-1-methyl-4-[[(1R)-2,2,2-trifluoro-1-methyl-ethyl]sulfamoyl]pyrrole-2-carboxamide;

3-chloro-N-(2-cyano-4-fluoro-phenyl)-1-methyl-4-[[(1R)-2,2,2-trifluoro-1-methyl-ethyl]sulfamoyl]pyrrole-2-carboxamide;

3-chloro-N-[4-fluoro-3-(trifluoromethyl)phenyl]-1-methyl-4-[[(1R)-2,2,2-trifluoro-1-methyl-ethyl]sulfamoyl]pyrrole-2-carboxamide;

3-chloro-N-(2-fluoro-6-methyl-phenyl)-1-methyl-4-[[(1R)-2,2,2-trifluoro-1-methyl-ethyl]sulfamoyl]pyrrole-2-carboxamide, 3-chloro-N-(3-cyano-2,4-difluoro-phenyl)-1-methyl-4-[[(1R)-2,2,2-trifluoro-1-methyl-ethyl]sulfamoyl]pyrrole-2-carboxamide;

3-chloro-N-(2,3-dichloro-4-fluoro-phenyl)-1-methyl-4-[[(1R)-2,2,2-trifluoro-1-methyl-ethyl]sulfamoyl]pyrrole-2-carboxamide;

3-chloro-N-[3-(difluoromethyl)-2,4-difluoro-phenyl]-1-methyl-4-[[(1R)-2,2,2-trifluoro-1-methyl-ethyl]sulfamoyl]pyrrole-2-carboxamide;

3-chloro-N-[3-(difluoromethyl)-4-fluoro-phenyl]-1-methyl-4-[[(1R)-2,2,2-trifluoro-1-methyl-ethyl]sulfamoyl]pyrrole-2-carboxamide;

N-(3-bromophenyl)-3-fluoro-1l-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[1-(trifluoro-methyl)cyclopentyl]sulfamoyl]pyrrole-2-carboxamide;

3-chloro-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-5-methyl-phenyl)-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1S)-1-(trifluoro-methyl)propyl]sulfamoyl]pyrrole-2-carboxamide;

3-fluoro-N-(4-fluorophenyl)-1-methyl-4-[[(1R)-2,2,2-trifluoro-1-methyl-ethyl]sulfamoyl]pyrrole-2-carboxamide;

N-[3-(difluoromethyl)-4-fluoro-phenyl]-3-fluoro-1-methyl-4-[[(1R)-2,2,2-trifluoro-1-methyl-ethyl]sulfamoyl]pyrrole-2-carboxamide;

N-[3-(difluoromethyl)-2,4-difluoro-phenyl]-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1R)-1-(trifluoro-methyl)propyl]sulfamoyl]pyrrole-2-carboxamide;

3-chloro-N-(3-cyano-4-fluoro-phenyl)-1-methyl-4-[[(1S)-1-(trifluoromethyl)propyl]sulfamoyl]pyrrole-2-carboxamide;

3-chloro-N-(3-cyano-4-fluoro-phenyl)-1-methyl-4-[[(1R)-1-(trifluoromethyl)propyl]sulfamoyl]pyrrole-2-carboxamide;

3-chloro-N-(3-cyano-4-fluoro-phenyl)-1-isopropyl-4-[[(1R)-2,2,2-trifluoro-1l-methyl-ethyl]sulfamoyl]pyrrole-2-carboxamide;

3-bromo-N-(3-cyano-4-fluoro-phenyl)-1-methyl-4-[[(1R)-2,2,2-trifluoro-1-methyl-ethyl]sulfamoyl]pyrrole-2-carboxamide;

3-cyano-N-(3-cyano-4-fluoro-phenyl)-1-methyl-4-[[(1R)-2,2,2-trifluoro-1-methyl-ethyl]sulfamoyl]pyrrole-2-carboxamide;

N-(3-cyano-4-fluoro-phenyl)-1-methyl-4-[[(1R)-1-methylpropyl]sulfamoyl]pyrrole-2-carboxamide;

3-chloro-N-(3-cyano-4-fluoro-phenyl)-1-methyl-4-[[(1R)-1-methylpropyl]sulfamoyl]pyrrole-2-carboxamide;

N-(3-cyano-4-fluoro-phenyl)-4-[(3-hydroxy-1,1-dimethyl-propyl)sulfamoyl]-1-methyl-pyrrole-2-carboxamide;

N-(3-cyano-4-fluoro-phenyl)-4-[[(1S)-2,2-difluoro-1-methyl-propyl]sulfamoyl]-1-methyl-pyrrole-2-carboxamide;

N-(3-cyano-4-fluoro-phenyl)-4-[[(1R)-2,2-difluoro-1-methyl-propyl]sulfamoyl]-1-methyl-pyrrole-2-carboxamide;

N-(3-cyano-4-fluoro-phenyl)-3-fluoro-1,5-dimethyl-4-[[(1R)-2,2,2-trifluoro-1-methyl-ethyl]sulfamoyl]pyrrole-2-carboxamide;

5-bromo-3-chloro-N-(3-cyano-4-fluoro-phenyl)-1-methyl-4-[[(1R)-2,2,2-trifluoro-1-methyl-ethyl]sulfamoyl]pyrrole-2-carboxamide;

5-bromo-N-(3-cyano-4-fluoro-phenyl)-3-fluoro-1-methyl-4-[[(1R)-2,2,2-trifluoro-1-methyl-ethyl]sulfamoyl]pyrrole-2-carboxamide;

3-chloro-N-(3-cyano-4-fluoro-phenyl)-5-cyclopropyl-1-methyl-4-[[(1R)-2,2,2-trifluoro-1-methyl-ethyl]sulfamoyl]pyrrole-2-carboxamide;

N-(3-cyano-4-fluoro-phenyl)-3-isopropyl-1-methyl-4-[[(1R)-2,2,2-trifluoro-1-methyl-ethyl]sulfamoyl]pyrrole-2-carboxamide;

N-(3-cyano-4-fluoro-phenyl)-5-cyclopropyl-3-fluoro-1-methyl-4-[[(1R)-2,2,2-trifluoro-1-methyl-ethyl]sulfamoyl]pyrrole-2-carboxamide;

3-chloro-N-(3-cyano-4-fluoro-phenyl)-1-cyclopropyl-4-[[(1R)-2,2,2-trifluoro-1-methyl-ethyl]sulfamoyl]pyrrole-2-carboxamide;

3-chloro-N-(3-cyano-4-fluoro-phenyl)-1-methyl-4-[(3-methyloxetan-3-yl)sulfamoyl]pyrrole-2-carboxamide;

3-bromo-N-(3-cyano-4-fluoro-phenyl)-4-(cyclopentylsulfamoyl)-1-methyl-pyrrole-2-carboxamide;

3-bromo-N-(4-fluoro-3-methyl-phenyl)-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-5-(methoxymethyl)-1-methyl-4-[[(1R)-2,2,2-trifluoro-1-methyl-ethyl]sulfamoyl]pyrrole-2-carboxamide;

5-cyano-N-(3-cyano-4-fluoro-phenyl)-3-fluoro-1-methyl-4-[[(1R)-2,2,2-trifluoro-1-methyl-ethyl]sulfamoyl]pyrrole-2-carboxamide;

N-(3-cyano-4-fluoro-phenyl)-3-fluoro-1-methyl-4-[[(1R)-2,2,2-trifluoro-1l-methyl-ethyl]sulfamoyl]-5-vinyl-pyrrole-2-carboxamide;

N-(2,4-difluorophenyl)-3-fluoro-1-methyl-4-[[(1R)-2,2,2-trifluoro-1-methyl-ethyl]sulfamoyl]pyrrole-2-carboxamide;

N-(3-chloro-5-cyano-4-fluoro-phenyl)-3-fluoro-1-methyl-4-[[(1R)-2,2,2-trifluoro-1-methyl-ethyl]sulfamoyl]pyrrole-2-carboxamide;

5-chloro-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide;

5-bromo-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide;

3-cyano-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-phenyl)-4-[[(1R)-2,2-difluoro-1-methyl-propyl]sulfamoyl]-3-fluoro-1-methyl-pyrrole-2-carboxamide;

N-(3-cyano-4-fluoro-phenyl)-4-[[(1S)-2,2-difluoro-1-methyl-propyl]sulfamoyl]-3-fluoro-1-methyl-pyrrole-2-carboxamide; and N-(3-cyano-4-fluoro-phenyl)-3-fluoro-1-methyl-4-[[1-(trifluoromethyl)cyclobutyl]sulfamoyl]pyrrole-2-carboxamide.

16. A method of treating Hepatitis B virus infection in a subject in need thereof comprising administering to said subject a product comprising a Hepatitis B virus inhibitor as a combined preparation for simultaneous, separate or sequential administration to the subject with a compound of Formula (ID)

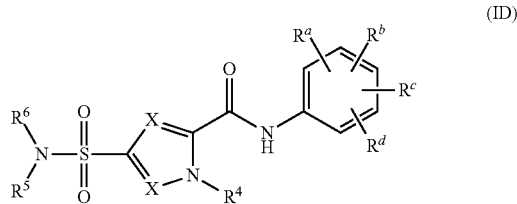

or a stereoisomer or tautomeric form thereof, wherein:

each X is independently $CR^7$;

$R^a$, $R^b$ and $R^c$ are each independently selected from the group consisting of hydrogen, fluoro, bromo, chloro, —$CHF_2$, —$CF_2$-methyl, —$CH_2F$, —$CF_3$, —$OCF_3$, —CN, $C_1$-$C_3$alkyl and $C_3$-$C_4$cycloalkyl;

$R^d$ is hydrogen or fluoro;

$R^4$ is hydrogen, $C_1$-$C_3$alkyl or $C_3$-$C_4$cycloalkyl;

$R^5$ is hydrogen;

$R^6$ is selected from the group consisting of $C_2$-$C_6$alkyl, $C_1$-$C_4$alkyl-$R^8$ optionally substituted with one or more fluoro, $C_1$-$C_4$alkyl-$R^9$ optionally substituted with one or more fluoro, and a 3-7 membered mono or polycyclic saturated ring optionally containing one or more heteroatoms each independently selected from the group consisting of O, S and N, such 3-7 membered saturated ring or $C_2$-$C_6$alkyl optionally substituted with one or more substituents each independently selected from the group consisting of hydrogen, —OH, fluoro, oxo, $R^9$, $R^{10}$ and $C_1$-$C_4$alkyl optionally substituted with $R^{10}$;

$R^7$ is selected from the group consisting of hydrogen, —CN, fluoro, chloro, bromo, —$CHF_2$, —$CF_2$—methyl, —$CH_2F$, —$CF_3$, $C_1$-$C_3$alkyl optionally substituted with methoxy, $C_2$-$C_3$alkenyl and $C_3$-$C_4$cycloalkyl;

$R^8$ is a 3-7 membered saturated ring optionally containing one or more heteroatoms each independently selected from the group consisting of O, S and N, such 3-7 membered saturated ring optionally substituted with one or more $C_1$-$C_4$alkyl optionally substituted with $R^{10}$;

$R^9$ is selected from the group consisting of $C_1$-$C_4$alkyloxy, —$SO_2$-methyl, —C(=O)—$OR^{11}$ and —C(=O)—$N(R^{11})_2$;

$R^{10}$ is selected from the group consisting of —CN, —OH, fluoro, —$CHF_2$, —$CH_2F$ and —$CF_3$;

$R^{11}$ is hydrogen or $C_1$-$C_3$alkyl;

or a pharmaceutically acceptable salt or a solvate thereof wherein such compound is not

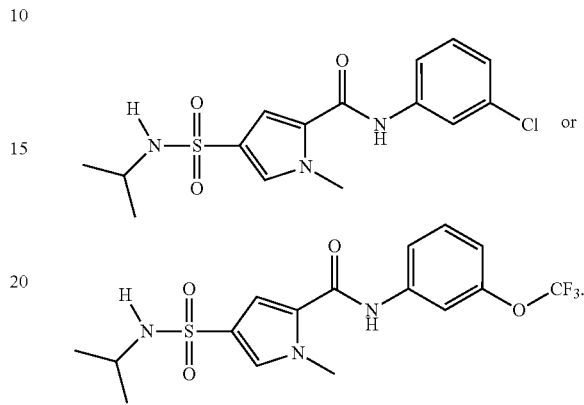

17. The method of claim 16, wherein $R^a$ is —CN;

$R^b$, $R^c$ and $R^d$ are each independently selected from the group consisting of hydrogen and fluoro;

$R^4$ is $C_1$-$C_3$alkyl;

$R^6$ is selected from the group consisting of $C_2$-$C_6$alkyl, optionally substituted with one or more fluoro; and $R^7$ is hydrogen.

18. The method of claim 16, wherein the compound is selected from the group consisting of:

N-(4-fluoro-3-methyl-phenyl)-4-(isopropylsulfamoyl)-1H-pyrrole-2-carboxamide;

N-(4-fluoro-3-methyl-phenyl)-4-(isopropylsulfamoyl)-1-methyl-pyrrole-2-carboxamide;

N-(4-fluoro-3-methyl-phenyl)-4-[[(1R)-2-hydroxy-1-methyl-ethyl]sulfamoyl]-1-methyl-pyrrole-2-carboxamide;

N-(4-fluoro-3-methyl-phenyl)-1-methyl-4-[[(3S)-tetrahydrofuran-3-yl]sulfamoyl]pyrrole-2-carboxamide;

N-(4-fluoro-3-methyl-phenyl)-1-methyl-4-[(3-methyloxetan-3-yl)sulfamoyl]pyrrole-2-carboxamide;

N-(4-fluoro-3-methyl-phenyl)-1-methyl-4-[[(1R)-1-methylpropyl]sulfamoyl]pyrrole-2-carboxamide;

N-(4-fluoro-3-methyl-phenyl)-1-methyl-4-[(3-methyloxetan-3-yl)methylsulfamoyl]pyrrole-2-carboxamide;

N-(4-fluoro-3-methyl-phenyl)-1-methyl-4-[[(1S)-2,2,2-trifluoro-1-methyl-ethyl]sulfamoyl]pyrrole-2-carboxamide;

N-(4-fluoro-3-methyl-phenyl)-1-methyl-4-[[(1R)-2,2,2-trifluoro-1-methyl-ethyl]sulfamoyl]pyrrole-2-carboxamide;

N-(4-fluoro-3-methyl-phenyl)-4-[[3-(hydroxymethyl)oxetan-3-yl]sulfamoyl]-1-methyl-pyrrole-2-carboxamide;

N-(4-fluoro-3-methyl-phenyl)-1-methyl-4-[(3-methyltetrahydrofuran-3-yl)sulfamoyl]pyrrole-2-carboxamide;

N-(4-fluoro-3-methyl-phenyl)-4-[[1-(hydroxymethyl)cyclopropyl]sulfamoyl]-1-methyl-pyrrole-2-carboxamide;

N-(4-fluoro-3-methyl-phenyl)-1-methyl-4-[(1-methyl-5-oxo-pyrrolidin-3-yl)sulfamoyl]pyrrole-2-carboxamide;

N-(4-fluoro-3-methyl-phenyl)-4-[[3-(2-hydroxyethyl)ox-etan-3-yl]sulfamoyl]-1-methyl-pyrrole-2-carboxamide;
N-(4-fluoro-3-methy-phenyl)-4-[(3-hydroxycyclobutyl)sulfamoyl]-1-methyl-pyrrole-2-carboxamide;
4-(tert-butylsulfamoyl)-N-(4-fluoro-3-methyl-phenyl)-1-methyl-pyrrole-2-carboxamide
4-[[3-(cyanomethyl)oxetan-3-yl]sulfamoyl]-N-(4-fluoro-3-methy-phenyl)-1-methyl-pyrrole-2-carboxamide;
4-[[1-(cyanomethyl)cyclopropyl]sulfamoyl]-N-(4-fluoro-3-methyl-phenyl)-1-methyl-pyrrole-2-carboxamide;
4-(tert-butylsulfamoyl)-N-(3,4-difluorophenyl)-1-methyl-pyrrole-2-carboxamide;
N-(3,4-difluorophenyl)-1-methyl-4-[(3-methyloxetan-3-yl)sulfamoyl]pyrrole-2-carboxamide;
N-(3,4-difluorophenyl)-1-methyl-4-[[(3S)-tetrahydrofuran-3-yl]sulfamoyl]pyrrole-2-carboxamide;
N-(3,4-difluorophenyl)-4-(isopropylsulfamoyl)-1-methyl-pyrrole-2-carboxamide;
N-(3,4-difluorophenyl)-1-methyl-4-[[(1R)-1-methylpropyl]sulfamoyl]pyrrole-2-carboxamide;
N-(3,4-difluorophenyl)-4-[[(1R)-2-hydroxy-1-methyl-ethyl]sulfamoyl]-1-methyl-pyrrole-2-carboxamide;
N-(3,4-difluorophenyl)-4-[(3-hydroxycyclobutyl)sulfamoyl]-1-methyl-pyrrole-2-carboxamide;
1-methyl-4-[[(3S)-tetrahydrofuran-3-yl]sulfamoyl]-N-(3,4,5-trifluorophenyl)pyrrole-2-carboxamide;
1-methyl-4-[(3-methyloxetan-3-yl)sulfamoyl]-N-(3,4,5-trifluorophenyl)pyrrole-2-carboxamide;
1-methyl-4-[(3-methyloxetan-3-yl)sulfamoyl]-N-[3-(trifluoromethyl)phenyl]pyrrole-2-carboxamide;
1-ethyl-N-(4-fluoro-3-methyl-phenyl)-4-(isopropylsulfamoyl)pyrrole-2-carboxamide;
1-ethyl-N-(4-fluoro-3-methyl-phenyl)-4-[[(3S)-tetrahydrofuran-3-yl]sulfamoyl]pyrrole-2-carboxamide;
N-(4-fluoro-3,5-dimethyl-phenyl)-1-methyl-4-[[(3S)-tetrahydrofuran-3-yl]sulfamoyl]pyrrole-2-carboxamide;
N-(3-fluoro-5-methyl-phenyl)-1-methyl-4-[[(3S)-tetrahydrofuran-3-yl]sulfamoyl]pyrrole-2-carboxamide;
N-(3,4-difluoro-5-methyl-phenyl)-4-(isopropylsulfamoyl)-1-methyl-pyrrole-2-carboxamide;
N-(3,4-difluoro-5-methyl-phenyl)-1-methyl-4-[[(1R)-1-methylpropyl]sulfamoyl]pyrrole-2-carboxamide;
N-(3,4-difluoro-5-methyl-phenyl)-1-methyl-4-[(3-methyloxetan-3-yl)sulfamoyl]pyrrole-2-carboxamide;
N-(3,4-difluoro-5-methyl-phenyl)-4-[[(1R)-2-hydroxy-1-methyl-ethyl]sulfamoyl]-1-methyl-pyrrole-2-carboxamide;
N-(3,4-difluoro-5-methyl-phenyl)-1-methyl-4-[[(3S)-tetrahydrofuran-3-yl]sulfamoyl]pyrrole-2-carboxamide;
4-(tert-butylsulfamoyl)-N-(3,4-difluoro-5-methyl-phenyl)-1-methyl-pyrrole-2-carboxamide;
N-[3-(difluoromethyl)-4-fluoro-phenyl]-1-methyl-4-[(3-methyloxetan-3-yl)sulfamoyl]pyrrole-2-carboxamide;
N-[3-(difluoromethyl)-4-fluoro-phenyl]-4-[[(1R)-2-hydroxy-1-methyl-ethyl]sulfamoyl]-1-methyl-pyrrole-2-carboxamide;
N-[4-fluoro-3-(trifluoromethyl)phenyl]-4-[[(1R)-2-hydroxy-1-methyl-ethyl]sulfamoyl]-1-methyl-pyrrole-2-carboxamide;
N-[4-fluoro-3-(trifluoromethyl)phenyl]-1-methyl-4-[[(3S)-tetrahydrofuran-3-yl]sulfamoyl]pyrrole-2-carboxamide;
N-[4-fluoro-3-(trifluoromethyl)phenyl]-1-methyl-4-[(3-methyloxetan-3-yl)sulfamoyl]pyrrole-2-carboxamide;
N-[4-fluoro-3-(trifluoromethyl)phenyl]-4-(isopropylsulfamoyl)-1-methyl-pyrrole-2-carboxamide;
N-[3-fluoro-5-(trifluoromethyl)phenyl]-1-methyl-4-[(3-methyloxetan-3-yl)sulfamoyl]pyrrole-2-carboxamide;
N-(3-bromo-4,5-difluoro-phenyl)-4-(isopropylsulfamoyl)-1-methyl-pyrrole-2-carboxamide;
N-(3-bromo-4,5-difluoro-phenyl)-1-methyl-4-[[(1R)-1-methylpropyl]sulfamoyl]pyrrole-2-carboxamide;
N-(3-bromo-4,5-difluoro-phenyl)-1-methyl-4-[(3-methyloxetan-3-yl)sulfamoyl]pyrrole-2-carboxamide;
methyl 2-[[5-[(4-fluoro-3-methyl-phenyl)carbamoyl]-1-methyl-pyrrol-3-yl]sulfonylamino]-2-methyl-propanoate;
N-(3-cyano-4-fluorophenyl)-1-methyl-4-[(3-methyloxetan-3-yl)sulfamoyl]-1H-pyrrole-2-carboxamide;
N-[4-cyano-3-(trifluoromethyl)phenyl]-1-methyl-4-[(3-methyloxetan-3-yl)sulfamoyl]-1H-pyrrole-2-carboxamide;
N-(3-cyano-4,5-difluoro-phenyl)-4-(isopropylsulfamoyl)-1-methyl-pyrrole-2-carboxamide;
4-(tert-butylsulfamoyl)-N-(3-cyano-5-fluoro-phenyl)-1-methyl-pyrrole-2-carboxamide;
N-(3-cyano-5-fluoro-phenyl)-1-methyl-4-[(3-methyloxetan-3-yl)sulfamoyl]pyrrole-2-carboxamide;
N-(3-cyanophenyl)-1-methyl-4-[(3-methyloxetan-3-yl)sulfamoyl]pyrrole-2-carboxamide;
N-(2,6-dideuterio-4-fluoro-3-methyl-phenyl)-1-methyl-4-[(3-methyloxetan-3-yl)sulfamoyl]pyrrole-2-carboxamide;
N-(3-chloro-4,5-difluoro-phenyl)-4-(isopropylsulfamoyl)-1-methyl-pyrrole-2-carboxamide;
4-(tert-butylsulfamoyl)-N-(3-chloro-4,5-difluoro-phenyl)-1-methyl-pyrrole-2-carboxamide;
N-(3-chloro-4,5-difluoro-phenyl)-1-methyl-4-[(3-methyloxetan-3-yl)sulfamoyl]pyrrole-2-carboxamide;
N-(3-chloro-4,5-difluoro-phenyl)-1-methyl-4-[[(1R)-2,2,2-trifluoro-1-methyl-ethyl]sulfamoyl]pyrrole-2-carboxamide;
2-[[5-[(4-fluoro-3-methyl-phenyl)carbamoyl]-1-methyl-pyrrol-3-yl]sulfonylamino]-2-methyl-propanoic acid;
4-[[1,1-dimethyl-2-(methylamino)-2-oxo-ethyl]sulfamoyl]-N-(4-fluoro-3-methyl-phenyl)-1-methyl-pyrrole-2-carboxamide;
4-[[2-(dimethylamino)-1,1-dimethyl-2-oxo-ethyl]sulfamoyl]-N-(4-fluoro-3-methyl-phenyl)-1-methyl-pyrrole-2-carboxamide;
4-[2-amino-1,1-dimethyl-2-oxo-ethyl)sulfamoyl]-N-(4-fluoro-3-methyl-phenyl)-1-methyl-pyrrole-2-carboxamide;
N-(3-chloro-4,5-difluoro-phenyl)-4-[(3,3-difluoro-1-methyl-cyclobutyl)sulfamoyl]-1-methyl-pyrrole-2-carboxamide;
N-(3-chloro-4,5-difluoro-phenyl)-4-(1,1-dimethylpropylsulfamoyl)-1-methyl-pyrrole-2-carboxamide;
4-tert-butylsulfamoyl)-N-(2,6-dideuterio-4-fluoro-3-methyl-phenyl)-1-methyl-pyrrole-2-carboxamide;
4-(tert-butylsulfamoyl)-1-methyl-N-(3,4,5-trifluorophenyl)pyrrole-2-carboxamide;
N-(4-fluoro-3-methyl-phenyl)-1-methyl-4-[[2,2,2-trideuterio-1,1-bis(trideuteriomethyl)ethyl]sulfamoyl]pyrrole-2-carboxamide;
N-(2,6-dideuterio-4-fluoro-3-methyl-phenyl)-1-methyl-4-[[2,2,2-trideuterio-1,1-bis(trideuteriomethyl)ethyl]sulfamoyl]pyrrole-2-carboxamide;
4-(tert-butylsulfamoyl)-N-(2,6-dideuterio-3,4,5-trifluoro-phenyl)-1-methyl-pyrrole-2-carboxamide;
N-(3-chloro-4,5-difluoro-phenyl)-1-methyl-4-[[1-(trifluoromethyl)-cyclopropyl]sulfamoyl]pyrrole-2-carboxamide;

N-(3-chloro-4,5-difluoro-phenyl)-1-methyl-4-[[2,2,2-trifluoro-1-(methoxymethyl)-1-methyl-ethyl]sulfamoyl]pyrrole-2-carboxamide;

N-(3,4-difluorophenyl)-3-fluoro-1-methyl-4-[(3-methyloxetan-3-yl)sulfamoyl]pyrrole-2-carboxamide;

N-(3,5-Dichloro-4-fluorophenyl)-1-methyl-4-[(3-methyloxetan-3-yl)sulfamoyl]-1H-pyrrole-2-carboxamide;

4-(tert-Butylsulfamoyl)-N-(3,5-dichloro-4-fluorophenyl)-1-methyl-1H-pyrrole-2-carboxamide;

N-(4-Chloro-3-methylphenyl)-1-methyl-4-[(3-methyloxetan-3-yl)sulfamoyl]-1H-pyrrole-2-carboxamide;

N-(3-Chloro-4-fluorophenyl)-1-methyl-4-[(3-methyloxetan-3-yl)sulfamoyl]-1H-pyrrole-2-carboxamide;

N-[4-Fluoro-3-methyl-5-(trifluoromethyl)phenyl]-1-methyl-4-[(3-methyloxetan-3-yl)sulfamoyl]-1H-pyrrole-2-carboxamide;

N-(4-Fluoro-3,5-dimethylphenyl)-1-methyl-4-[(3-methyloxetan-3-yl)sulfamoyl]-1H-pyrrole-2-carboxamide;

N-(3-Bromo-4-fluorophenyl)-1-methyl-4-[(3-methyloxetan-3-yl)sulfamoyl]-1H-pyrrole-2-carboxamide;

1-Methyl-4-[(3-methyloxetan-3-yl)sulfamoyl]-N-[3-methyl-5-(trifluoromethyl)phenyl]-1H-pyrrole-2-carboxamide;

N-(4-Cyano-3-methylphenyl)-1-methyl-4-[(3-methyloxetan-3-ylsulfamoyl]-1H-pyrrole-2-carboxamide;

N-(4-Chloro-3-fluorophenyl)-1-methyl-4-[(3-methyloxetan-3-yl)sulfamoyl]-1H-pyrrole-2-carboxamide;

N-(2,4-Difluoro-3-methylphenyl)-1-methyl-4-[(3-methyloxetan-3-yl)sulfamoyl]-1H-pyrrole-2-carboxamide;

N-[4-Fluoro-3-(trifluoromethoxy)phenyl]-1-methyl-4-[(3-methyloxetan-3-yl)sulfamoyl]-1H-pyrrole-2-carboxamide;

N-(3-Chloro-5-cyanophenyl)-1-methyl-4-[(3-methyloxetan-3-yl)sulfamoyl]-1H-pyrrole-2-carboxamide;

N-(4-Fluoro-3-methylphenyl)-1,3,5-trimethyl-4-[(3-methyloxetan-3-yl)sulfamoyl]-1H-pyrrole-2-carboxamide;

N-(4-Fluoro-3-methylphenyl)-1,5-dimethyl-4-[(3-methyloxetan-3-yl)sulfamoyl]-1H-pyrrole-2-carboxamide;

N-(4-Fluoro-3-methylphenyl)-1,3-dimethyl-4-[(3-methyloxetan-3-yl)sulfamoyl]-1H-pyrrole-2-carboxamide;

N-(3,4-Difluorophenyl)-1-methyl-4-[(3-methyltetrahydrofuran-3-yl)sulfamoyl]-1H-pyrrole-2-carboxamide;

N-(3,4-Difluorophenyl)-1-methyl-4-{[(1R)-2,2,2-trifluoro-1-methylethyl]sulfamoyl}-1H-pyrrole-2-carboxamide;

N-(3,4-Difluorophenyl)-1-methyl-4-{[(1S)-2,2,2-trifluoro-1-methylethyl]sulfamoyl}-1H-pyrrole-2-carboxamide;

3-Fluoro-N-(4-fluoro-3-methylphenyl)-1-methyl-4-[(3-methyloxetan-3-yl)sulfamoyl]-1H-pyrrole-2-carboxamide;

N-(3,4-Difluorophenyl)-1-methyl-4-[(2,2,2-trifluoro-1,1-dimethylethyl)sulfamoyl]-1H-pyrrole-2-carboxamide;

N-(3-Chloro-4,5-difluorophenyl)-1-methyl-4-[(2,2,2-trifluoro-1,1-dimethylethyl)sulfamoyl]-1H-pyrrole-2-carboxamide;

N-(4-Fluoro-3-methylphenyl)-1-methyl-4-{[(1R)-1-methyl-2-(methylsulfonyl)ethyl]sulfamoyl}-1H-pyrrole-2-carboxamide;

4-(tert-Butylsulfamoyl)-N-[4-fluoro-3-(trifluoromethoxy)phenyl]-1-methyl-1H-pyrrole-2-carboxamide;

N-(2,4-Difluoro-3-methylphenyl)-1-methyl-4-[(1-methylethyl)sulfamoyl]-1H-pyrrole-2-carboxamide;

N-(3-Bromo-4,5-difluorophenyl)-1-methyl-4-{[(1S)-2,2,2-trifluoro-1-methylethyl]sulfamoyl}-1H-pyrrole-2-carboxamide;

N-(3-Bromo-4-fluorophenyl)-1-methyl-4-{[(1S)-2,2,2-trifluoro-1-methylethyl]sulfamoyl}-1H-pyrrole-2-carboxamide;

N-(3-Cyano-4-fluorophenyl)-1-methyl-4-{[(1S)-2,2,2-trifluoro-1-methylethyl]sulfamoyl}-1H-pyrrole-2-carboxamide;

N-(3-Chloro-4,5-difluorophenyl)-1-methyl-4-{[(1S)-2,2,2-trifluoro-1-methylethyl]sulfamoyl}-1H-pyrrole-2-carboxamide;

N-(3,4-Difluoro-5-methylphenyl)-1-methyl-4-{[(1S)-2,2,2-trifluoro-1-methylethyl]sulfamoyl}-1H-pyrrole-2-carboxamide;

N-(3-Chloro-4-fluorophenyl)-1-methyl-4-{[(1S)-2,2,2-trifluoro-1-methylethyl]sulfamoyl}-1H-pyrrole-2-carboxamide;

N-(3-Bromo-4-fluorophenyl)-3-fluoro-1-methyl-4-[(3-methyloxetan-3-yl)sulfamoyl]-1H-pyrrole-2-carboxamide;

N-[3-(Difluoromethyl)-4-fluorophenyl]-3-fluoro-1-methyl-4-[(3-methyloxetan-3-yl)sulfamoyl]-1H-pyrrole-2-carboxamide;

N-(3-Chloro-4-fluorophenyl)-3-fluoro-1-methyl-4-[(3-methyloxetan-3-yl)sulfamoyl]-1H-pyrrole-2-carboxamide;

3-Fluoro-1-methyl-4-[(3-methyloxetan-3-yl)sulfamoyl]-N-(2,4,5-trifluorophenyl)-1H-pyrrole-2-carboxamide;

N-(2,4-Difluoro-3-methylphenyl)-3-fluoro-1-methyl-4-[(3-methyloxetan-3-yl)sulfamoyl]-1H-pyrrole-2-carboxamide;

N-(3-Chloro-4,5-difluorophenyl)-3-fluoro-1-methyl-4-[(3-methyloxetan-3-yl)sulfamoyl]-1H-pyrrole-2-carboxamide;

4-(tert-butylsulfamoyl)-N-(2,4-difluoro-3-methyl-phenyl)-1-methyl-pyrrole-2-carboxamide;

N-(3-cyano-4-fluoro-phenyl)-3-fluoro-1-methyl-4-[(3-methyloxetan-3-yl)sulfamoyl]pyrrole-2-carboxamide;

4-[(1-Carbamoylcyclopropyl)sulfamoyl]-N-(3-chloro-4,5-difluorophenyl)-1-methyl-1H-pyrrole-2-carboxamide;

N-(3-Chloro-4,5-difluorophenyl)-1-methyl-4-{[1-(methylcarbamoyl)cyclopropyl]sulfamoyl}-1H-pyrrole-2-carboxamide;

N-(2,4-Difluoro-3-methylphenyl)-1-methyl-4-{[(1R)-2,2,2-trifluoro-1-methylethyl]sulfamoyl}-1H-pyrrole-2-carboxamide;

N-(2,4-Difluoro-3-methylphenyl)-1-methyl-4-{[1-(trifluoromethyl)cyclopropyl]sulfamoyl}-1H-pyrrole-2-carboxamide;

N-(2,4-Difluoro-3-methylphenyl)-1-methyl-4-[(2,2,2-trifluoro-1,1-dimethylethyl)sulfamoyl]-1H-pyrrole-2-carboxamide;

N-(2,4-Difluoro-3-methylphenyl)-1-methyl-4-{[(1S)-2,2,2-trifluoro-1-methylethyl]sulfamoyl}-1H-pyrrole-2-carboxamide;

N-(3-Chloro-2,4-difluorophenyl)-1-methyl-4-{[(1R)-2,2,2-trifluoro-1l-methylethyl]sulfamoyl}-1H-pyrrole-2-carboxamide;

N-(3-Chloro-2,4-difluorophenyl)-1-methyl-4-[(3-methyloxetan-3-yl)sulfamoyl]-1H-pyrrole-2-carboxamide;

1-methyl-4-[[(1R)-2,2,2-trifluoro-1-methyl-ethyl]sulfamoyl]-N-[3-(trifluoromethyl)phenyl]pyrrole-2-carboxamide;

N-(3-Chloro-4-fluorophenyl)-1-methyl-4-{[(1R)-2,2,2-trifluoro-1-methylethyl]sulfamoyl}-1H-pyrrole-2-carboxamide;
N-(3-Bromo-4-fluorophenyl)-1-methyl-4-{[(1R)-2,2,2-trifluoro-1-methylethyl]sulfamoyl}-1H-pyrrole-2-carboxamide;
N-[4-Fluoro-3-(trifluoromethyl)phenyl]-1-methyl-4-{[(1R)-2,2,2-trifluoro-1-methylethyl]sulfamoyl}-1H-pyrrole-2-carboxamide;
N-(3-Cyano-4-fluorophenyl)-4-[(2,2-difluoroethyl)sulfamoyl]-1-methyl-1H-pyrrole-2-carboxamide;
N-(3-Bromo-4-fluorophenyl)-4-[(2,2-difluoroethyl)sulfamoyl]-1-methyl-1H-pyrrole-2-carboxamide;
N-(3-Chloro-4-fluorophenyl)-4-[(2,2-difluoroethyl)sulfamoyl]-1-methyl-1H-pyrrole-2-carboxamide;
4-[(2,2-Difluoroethyl)sulfamoyl]-N-(3,4-difluorophenyl)-1-methyl-1H-pyrrole-2-carboxamide;
N-(3-Chloro-4,5-difluorophenyl)-4-[(2,2-difluoroethyl)sulfamoyl]-1-methyl-1H-pyrrole-2-carboxamide;
N-(3-Chloro-4-fluorophenyl)-1-methyl-4-[(2,2,2-trifluoroethyl)sulfamoyl]-1H-pyrrole-2-carboxamide;
N-(3,4-Difluorophenyl)-1-methyl-4-[(2,2,2-trifluoroethyl)sulfamoyl]-1H-pyrrole-2-carboxamide;
N-(3-Chloro-4,5-difluorophenyl)-1-methyl-4-[(2,2,2-trifluoroethyl)sulfamoyl]-1H-pyrrole-2-carboxamide;
N-(3-Cyano-4-fluorophenyl)-1-methyl-4-[(2,2,2-trifluoroethyl)sulfamoyl]-1H-pyrrole-2-carboxamide;
N-(3-Bromo-4-fluorophenyl)-1-methyl-4-[(2,2,2-trifluoroethyl)sulfamoyl]-1H-pyrrole-2-carboxamide;
N-(3-Chloro-4,5-difluorophenyl)-1,5-dimethyl-4-[(3-methyloxetan-3-yl)sulfamoyl]-1H-pyrrole-2-arboxamide;
N-(3-Chloro-4,5-difluorophenyl)-1,5-dimethyl-4-{[(1R)-2,2,2-trifluoro-1-methylethyl]sulfamoyl}-1H-pyrrole-2-carboxamide;
N-(3-Chloro-4-fluorophenyl)-1,5-dimethyl-4-{[(1R)-2,2,2-trifluoro-1l-methylethyl]sulfamoyl}-1H-pyrrole-2-carboxamide;
N-(3,4-Difluorophenyl)-1,5-dimethyl-4-{[(1R)-2,2,2-trifluoro-1-methylethyl]sulfamoyl}-1H-pyrrole-2-carboxamide;
N-(3-Cyano-4-fluorophenyl)-1,5-dimethyl-4-{[(1R)-2,2,2-trifluoro-1-methylethyl]sulfamoyl}-1H-pyrrole-2-carboxamide;
N-(3-Bromo-4-fluorophenyl)-1,5-dimethyl-4-{[(1R)-2,2,2-trifluoro-1l-methylethyl]sulfamoyl}-1H-pyrrole-2-carboxamide;
N-[4-Fluoro-3-(trifluoromethyl)phenyl]-1,5-dimethyl-4-{[(1R)-2,2,2-trifluoro-1-methylethyl]sulfamoyl}-1H-pyrrole-2-carboxamide;
N-(3-Chloro-2,4-difluorophenyl)-1,5-dimethyl-4-{[(1R)-2,2,2-trifluoro-1-methylethyl]sulfamoyl}-1H-pyrrole-2-carboxamide;
N-(3,4-Difluorophenyl)-1,3-dimethyl-4-{[(1R)-2,2,2-trifluoro-1-methylethyl]sulfamoyl}-1H-pyrrole-2-carboxamide;
N-(3-Chloro-4-fluorophenyl)-1,3-dimethyl-4-{[(1R)-2,2,2-trifluoro-1l-methylethyl]sulfamoyl}-1H-pyrrole-2-carboxamide;
N-(3,4-Difluorophenyl)-1,3-dimethyl-4-{[(1S)-2,2,2-trifluoro-1-methylethyl]sulfamoyl}-1H-pyrrole-2-carboxamide;
N-(3-Chloro-4-fluorophenyl)-1,3-dimethyl-4-{[(1S)-2,2,2-trifluoro-1-methylethyl]sulfamoyl}-1H-pyrrole-2-carboxamide;
N-(3,4-Difluorophenyl)-1,3-dimethyl-4-[(3-methyloxetan-3-yl)sulfamoyl]-1H-pyrrole-2-carboxamide;
N-(3-Chloro-4-fluorophenyl)-1,3-dimethyl-4-[(3-methyloxetan-3-yl)sulfamoyl]-1H-pyrrole-2-carboxamide;
N-(3-Cyano-4-fluorophenyl)-1,3-dimethyl-4-{[(1R)-2,2,2-trifluoro-1-methylethyl]sulfamoyl}-1H-pyrrole-2-carboxamide;
N-(3-Cyano-4-fluorophenyl)-1,3-dimethyl-4-{[(1S)-2,2,2-trifluoro-1-methylethyl]sulfamoyl}-1H-pyrrole-2-carboxamide;
N-(3-Cyano-4-fluorophenyl)-1,3-dimethyl-4-[(3-methyloxetan-3-yl)sulfamoyl]-1H-pyrrole-2-carboxamide;
N-[4-Fluoro-3-(trifluoromethyl)phenyl]-1,3-dimethyl-4-{[(1R)-2,2,2-trifluoro-1-methylethyl]sulfamoyl}-1H-pyrrole-2-carboxamide;
1-Methyl-4-{[(1S)-2,2,2-trifluoro-1-methylethyl]sulfamoyl}-N-(2,3,4-trifluorophenyl)-1H-pyrrole-2-carboxamide;
N-(3-Bromo-2,4-difluorophenyl)-1-methyl-4-{[(1S)-2,2,2-trifluoro-1-methylethyl]sulfamoyl}-1H-pyrrole-2-carboxamide;
N-(3-Chloro-2,4-difluorophenyl)-1-methyl-4-{[(1S)-2,2,2-trifluoro-1-methylethyl]sulfamoyl}-1H-pyrrole-2-carboxamide;
N-(3-cyano-4-fluoro-phenyl)-1-methyl-4-[[(1R)-2,2,2-trifluoro-1-methylethyl]sulfamoyl]pyrrole-2-carboxamide;
N-(3-Cyanophenyl)-1-methyl-4-{[(1R)-2,2,2-trifluoro-1-methylethyl]sulfamoyl}-1H-pyrrole-2-carboxamide;
N-[2-Fluoro-3-(trifluoromethyl)phenyl]-1-methyl-4-{[(1R)-2,2,2-trifluoro-1-methylethyl]sulfamoyl}-1H-pyrrole-2-carboxamide;
N-(3-Cyano-2-fluorophenyl)-1-methyl-4-{[(1R)-2,2,2-trifluoro-1-methylethyl]sulfamoyl}-1H-pyrrole-2-carboxamide;
N-[3-(1,1-Difluoroethyl)-4-fluorophenyl]-1-methyl-4-[(3-methyloxetan-3-yl)sulfamoyl]-1H-pyrrole-2-carboxamide;
4-(tert-Butylsulfamoyl)-N-[3-(1,1-difluoroethyl)-4-fluorophenyl]-1-methyl-1H-pyrrole-2-carboxamide;
N-(3,5-Dichloro-4-fluorophenyl)-1-methyl-4-[(2,2,2-trifluoro-1,1-dimethylethyl)sulfamoyl]-1H-pyrrole-2-carboxamide;
N-(3-Chloro-4,5-difluorophenyl)-4-[(3,3-difluorocyclobutyl)sulfamoyl]-1-methyl-1H-pyrrole-2-carboxamide;
N-(3-chloro-4,5-difluoro-phenyl)-1-methyl-4-[[1-methyl-1-(trifluoro-methyl)propyl]sulfamoyl]pyrrole-2-carboxamide;
N-(3-Chloro-4,5-difluorophenyl)-4-[(3,3-difluorocyclopentyl)sulfamoyl]-1-methyl-1H-pyrrole-2-carboxamide;
4-(Bicyclo[1.1.1]pent-1-ylsulfamoyl)-N-(3-chloro-4,5-difluorophenyl)-1-methyl-1H-pyrrole-2-carboxamide;
N-(3-Chloro-4,5-difluorophenyl)-1-methyl-4-[(3,3,3-trifluoropropyl)sulfamoyl]-1H-pyrrole-2-carboxamide;
N-(3-Chloro-4,5-difluorophenyl)-1-methyl-4-[(3,3,3-trifluoro-1-methylpropyl)sulfamoyl]-1H-pyrrole-2-carboxamide;
N-(3-Cyano-4-fluorophenyl)-3-fluoro-1-methyl-4-{[(1R)-2,2,2-trifluoro-1-methylethyl]sulfamoyl}-1H-pyrrole-2-carboxamide;
N-(3-Cyano-4-fluorophenyl)-3-fluoro-1-methyl-4-[(1-methylethyl)sulfamoyl]-1H-pyrrole-2-carboxamide;
N-(3-Chloro-2,4-difluorophenyl)-1-methyl-4-[(1-methylethyl)sulfamoyl]-1H-pyrrole-2-carboxamide;
N-(3-Chloro-2-fluorophenyl)-1-methyl-4-[(1-methylethyl)sulfamoyl]-1H-pyrrole-2-carboxamide;

N-(3-Chloro-4-fluorophenyl)-1-methyl-4-[(1-methyl-ethyl)sulfamoyl]-1H-pyrrole-2-carboxamide;
N-(3-Cyano-4-fluorophenyl)-1-methyl-4-[(1-methyl-ethyl)sulfamoyl]-1H-pyrrole-2-carboxamide;
N-(3-Cyano-2-fluorophenyl)-1-methyl-4-[(1-methyl-ethyl)sulfamoyl]-1H-pyrrole-2-carboxamide;
N-(3-Cyanophenyl)-1-methyl-4-[(1-methylethyl)sulfamoyl]-1H-pyrrole-2-carboxamide;
N-(3-Cyano-2,4-difluorophenyl)-1-methyl-4-[(1-methyl-ethyl)sulfamoyl]-1H-pyrrole-2-carboxamide;
N-[4-Fluoro-3-(trifluoromethyl)phenyl]-1,3-dimethyl-4-[(3-methyloxetan-3-yl)sulfamoyl]-1H-pyrrole-2-carboxamide;
N-(3-Cyanophenyl)-3-fluoro-1-methyl-4-{[(1R)-2,2,2-trifluoro-1-methylethyl]sulfamoyl}-1H-pyrrole-2-carboxamide;
N-(3-Cyano-2,4-difluorophenyl)-3-fluoro-1-methyl-4-{[(1R)-2,2,2-trifluoro-1-methylethyl]sulfamoyl}-1H-pyrrole-2-carboxamide;
N-(3-Cyano-2-fluorophenyl)-3-fluoro-1-methyl-4-{[(1R)-2,2,2-trifluoro-1-methylethyl]sulfamoyl}-1H-pyrrole-2-carboxamide;
3-Fluoro-1-methyl-4-{[(1R)-2,2,2-trifluoro-1-methylethyl]sulfamoyl}-N-(2,3,4-trifluorophenyl)-1H-pyrrole-2-carboxamide;
N-(3-Bromo-2,4-difluorophenyl)-3-fluoro-1-methyl-4-{[(1R)-2,2,2-trifluoro-1-methylethyl]sulfamoyl}-1H-pyrrole-2-carboxamide;
N-(3-Chloro-2,4-difluorophenyl)-3-fluoro-1-methyl-4-{[(1R)-2,2,2-trifluoro-1-methylethyl]sulfamoyl}-1H-pyrrole-2-carboxamide;
N-(3-Cyano-4-fluorophenyl)-3-fluoro-1-methyl-4-{[(1R)-1-methylpropyl]sulfamoyl}-1H-pyrrole-2-carboxamide;
N-(3-Cyano-4-fluorophenyl)-4-[(3,3-difluoro-1-methylcyclobutyl)sulfamoyl]-3-fluoro-1-methyl-1H-pyrrole-2-carboxamide;
N-(3-Cyano-4-fluorophenyl)-3-fluoro-1-methyl-4-{[(1S)-2,2,2-trifluoro-1-methylethyl]sulfamoyl}-1H-pyrrole-2-carboxamide;
N-(3-Chloro-4,5-difluorophenyl)-1-methyl-4-{[1-(trifluoromethyl)cyclobutyl]sulfamoyl}-1H-pyrrole-2-carboxamide;
4-(tert-Butylsulfamoyl)-N-(3-cyano-4-fluorophenyl)-1-methyl-1H-pyrrole-2-carboxamide;
4-(tert-Butylsulfamoyl)-N-(3-cyanophenyl)-1-methyl-1H-pyrrole-2-carboxamide;
4-(tert-Butylsulfamoyl)-N-(3-cyano-2-fluorophenyl)-1-methyl-1H-pyrrole-2-carboxamide;
4-(tert-Butylsulfamoyl)-N-(3-chloro-2-fluorophenyl)-1-methyl-1H-pyrrole-2-carboxamide;
4-(tert-Butylsulfamoyl)-N-(3-chloro-2,4-difluorophenyl)-1-methyl-1H-pyrrole-2-carboxamide;
4-(tert-Butylsulfamoyl)-N-(3-chloro-4-fluorophenyl)-1-methyl-1H-pyrrole-2-carboxamide;
N-(3-Cyano-2,4-difluorophenyl)-1-methyl-4-{[(1S)-2,2,2-trifluoro-1-methylethyl]sulfamoyl}-1H-pyrrole-2-carboxamide;
N-(3-Cyanophenyl)-1-methyl-4-{[(1S)-2,2,2-trifluoro-1-methylethyl]sulfamoyl}-1H-pyrrole-2-carboxamide;
N-(3-Cyano-2-fluorophenyl)-1-methyl-4-{[(1S)-2,2,2-trifluoro-1-methylethyl]sulfamoyl}-1H-pyrrole-2-carboxamide;
3-Chloro-N-(3-cyano-4-fluorophenyl)-1-methyl-4-{[(1R)-2,2,2-trifluoro-1-methylethyl]sulfamoyl}-1H-pyrrole-2-carboxamide;
N-(3-Cyano-4-fluorophenyl)-4-{[2,2-difluoro-1-methylethyl]sulfamoyl}-1-methyl-1H-pyrrole-2-carboxamide;
N-(3-Chloro-4,5-difluorophenyl)-1,3-dimethyl-4-[(3-methyloxetan-3-yl)sulfamoyl]-1H-pyrrole-2-carboxamide;
N-(3-Chloro-4,5-difluorophenyl)-1,3-dimethyl-4-{[(1R)-2,2,2-trifluoro-1-methylethyl]sulfamoyl}-1H-pyrrole-2-carboxamide;
N-(2,3-Difluorophenyl)-1-methyl-4-{[(1R)-2,2,2-trifluoro-1-methylethyl]sulfamoyl}-1H-pyrrole-2-carboxamide;
N-(3-Chloro-2,6-difluorophenyl)-1-methyl-4-{[(1R)-2,2,2-trifluoro-1l-methylethyl]sulfamoyl}-1H-pyrrole-2-carboxamide;
N-(3-Bromo-4,5-difluorophenyl)-1-methyl-4-{[(1R)-2,2,2-trifluoro-1l-methylethyl]sulfamoyl}-1H-pyrrole-2-carboxamide;
N-(3-Bromo-2-fluorophenyl)-1-methyl-4-{[(1R)-2,2,2-trifluoro-1-methylethyl]sulfamoyl}-1H-pyrrole-2-carboxamide;
N-(3-chloro-4,5-difluoro-phenyl)-4-[(2-fluoro-1,1-dimethyl-ethyl)sulfamoyl]-1-methyl-pyrrole-2-carboxamide;
N-(3-Chloro-2,4-difluorophenyl)-1,3-dimethyl-4-[(1-methylethyl)sulfamoyl]-1H-pyrrole-2-carboxamide;
N-(3-Chloro-2,4-difluorophenyl)-1,3-dimethyl-4-{[(1S)-2,2,2-trifluoro-1-methylethyl]sulfamoyl}-1H-pyrrole-2-carboxamide;
N-(3-Chloro-2,4-difluorophenyl)-1,3-dimethyl-4-{[(1R)-2,2,2-trifluoro-1-methylethyl]sulfamoyl}-1H-pyrrole-2-carboxamide;
4-(tert-Butylsulfamoyl)-N-(3,4-difluorophenyl)-3-fluoro-1-methyl-1H-pyrrole-2-carboxamide;
4-(tert-Butylsulfamoyl)-N-(3-chloro-2,4-difluorophenyl)-3-fluoro-1-methyl-1H-pyrrole-2-carboxamide;
4-(tert-Butylsulfamoyl)-3-fluoro-1-methyl-N-(2,3,4-trifluorophenyl)-1H-pyrrole-2-carboxamide;
4-(tert-Butylsulfamoyl)-N-(3-cyano-4-fluorophenyl)-3-fluoro-1-methyl-1H-pyrrole-2-carboxamide;
N-(3-Chloro-2,4-difluorophenyl)-3-fluoro-1-methyl-4-[(3-methyloxetan-3-yl)sulfamoyl]-1H-pyrrole-2-carboxamide;
3-Cyano-N-(3-cyano-4-fluorophenyl)-1-methyl-4-[(1-methylethyl)sulfamoyl]-1H-pyrrole-2-carboxamide;
3-Chloro-N-(3,4-difluorophenyl)-1-methyl-4-{[(1R)-2,2,2-trifluoro-1-methylethyl]sulfamoyl}-1H-pyrrole-2-carboxamide;
3-Chloro-N-(3-chloro-2,4-difluorophenyl)-1-methyl-4-{[(1R)-2,2,2-trifluoro-1-methylethyl]sulfamoyl}-1H-pyrrole-2-carboxamide;
3-Chloro-N-(3-chloro-2,4-difluorophenyl)-1-methyl-4-{[1-(trifluoro-methyl)cyclobutyl]sulfamoyl}-1H-pyrrole-2-carboxamide;
4-(tert-Butylsulfamoyl)-3-chloro-N-(3-chloro-4-fluorophenyl)-1-methyl-1H-pyrrole-2-carboxamide;
3-Chloro-N-(3-cyano-4-fluorophenyl)-1-methyl-4-{[1-(trifluoromethyl)cyclobutyl]sulfamoyl}-1H-pyrrole-2-carboxamide;
3-Chloro-N-(3-chloro-4-fluorophenyl)-1-methyl-4-{[(1R)-2,2,2-trifluoro-1-methylethyl]sulfamoyl}-1H-pyrrole-2-carboxamide;
4-(tert-Butylsulfamoyl)-3-chloro-N-(3,4-difluorophenyl)-1-methyl-1H-pyrrole-2-carboxamide;
4-(tert-Butylsulfamoyl)-3-chloro-N-(3-chloro-2,4-difluorophenyl)-1-methyl-1H-pyrrole-2-carboxamide;

3-Chloro-N-(3-cyano-4-fluorophenyl)-1-methyl-4-{[(1S)-2,2,2-trifluoro-1-methylethyl]sulfamoyl}-1H-pyrrole-2-carboxamide;

4-(tert-Butylsulfamoyl)-3-chloro-N-(3-cyano-4-fluorophenyl)-1-methyl-1H-pyrrole-2-carboxamide;

N-(3-Cyano-4-fluorophenyl)-1-methyl-4-{[1-(trifluoromethyl)cyclopropyl]sulfamoyl}-1H-pyrrole-2-carboxamide;

N-(3-Cyano-4-fluorophenyl)-1-methyl-4-{[3-(trifluoromethyl)tetrahydrofuran-3-yl]sulfamoyl}-1H-pyrrole-2-carboxamide;

N-(3,4-Difluorophenyl)-3-fluoro-1-methyl-4-{[(1R)-2,2,2-trifluoro-1-methylethyl]sulfamoyl}-1H-pyrrole-2-carboxamide;

N-(3-Bromo-4-fluorophenyl)-3-fluoro-1-methyl-4-[(1-methylethyl)sulfamoyl]-1H-pyrrole-2-carboxamide;

N-(3-Cyano-2,4-difluorophenyl)-3-fluoro-1-methyl-4-[(1-methylethyl)sulfamoyl]-1H-pyrrole-2-carboxamide;

N-(3,4-Difluorophenyl)-3-fluoro-1-methyl-4-[(1-methylethyl)sulfamoyl]-1H-pyrrole-2-carboxamide;

3-Fluoro-1-methyl-4-[(1-methylethyl)sulfamoyl]-N-(2,3,4-trifluorophenyl)-1H-pyrrole-2-carboxamide;

N-(3-Chloro-2,4-difluorophenyl)-3-fluoro-1-methyl-4-[(1-methylethyl)sulfamoyl]-1H-pyrrole-2-carboxamide;

N-(3-Chloro-4-fluorophenyl)-3-fluoro-1-methyl-4-[(1-methylethyl)sulfamoyl]-1H-pyrrole-2-carboxamide;

N-(3-Chloro-2,4-difluorophenyl)-4-{[2,2-difluorocyclopentyl]sulfamoyl}-1-methyl-1H-pyrrole-2-carboxamide;

N-(3-Cyano-4-fluorophenyl)-1-methyl-4-[(2,2,2-trifluoro-1,1-dimethylethyl)sulfamoyl]-1H-pyrrole-2-carboxamide;

N-(3-Cyano-4-fluorophenyl)-1-methyl-4-[(3,3,3-trifluoro-1-methylpropyl)sulfamoyl]-1H-pyrrole-2-carboxamide;

N-(3-Cyano-4-fluorophenyl)-1-methyl-4-{[(1S)-1-(trifluoromethyl)propyl]sulfamoyl}-1H-pyrrole-2-carboxamide;

N-(3-Cyano-4-fluorophenyl)-1-methyl-4-{[(1R)-1-(trifluoromethyl)propyl]sulfamoyl}-1H-pyrrole-2-carboxamide;

N-(3-Cyano-4-fluorophenyl)-1-methyl-4-{[1-(trifluoromethyl)cyclobutyl]sulfamoyl}-1H-pyrrole-2-carboxamide;

N-(3-Cyano-4-fluorophenyl)-4-{[2-fluoro-1-(fluor(methyl)ethyl]sulfamoyl}-1-methyl-1H-pyrrole-2-carboxamide;

N-(3-Chloro-2,4-difluorophenyl)-1,3-dimethyl-4-[(3-methyloxetan-3-yl)sulfamoyl]-1H-pyrrole-2-carboxamide;

N-(3-cyano-4-fluoro-phenyl)-1-methyl-4-[(1-methylcyclopropyl)sulfamoyl]pyrrole-2-carboxamide;

N-(3-cyano-4-fluoro-phenyl)-4-[(3,3-difluoro-1-methyl-cyclobutyl)sulfamoyl]-1-methyl-1H-pyrrole-2-carboxamide;

N-(3-cyano-4-fluoro-phenyl)-1-methyl-4-{[1-methyl-1-(trifluoromethyl)propyl]sulfamoyl}-1H-pyrrole-2-carboxamide;

N-(3-cyano-4-fluoro-phenyl)-1-methyl-4-{[4-(trifluoromethyl)tetrahydropyran-4-yl]sulfamoyl}-1H-pyrrole-2-carboxamide;

N-(3-cyano-4-fluoro-phenyl)-4-{[1-ethyl-1-(trifluoromethyl)propyl]sulfamoyl}-1-methyl-1H-pyrrole-2-carboxamide;

N-(3-cyano-4-fluoro-phenyl)-4-[(2-fluoro-1,1-dimethyl-ethyl)sulfamoyl]-1-methyl-1H-pyrrole-2-carboxamide;

N-(3-Bromophenyl)-3-chloro-1-methyl-4-{[(1R)-2,2,2-trifluoro-1-methylethyl]sulfamoyl}-1H-pyrrole-2-carboxamide;

N-(3-Bromophenyl)-3-fluoro-1-methyl-4-[(3-methyloxetan-3-yl)sulfamoyl]-1H-pyrrole-2-carboxamide;

N-(3-chloro-2,4-difluoro-phenyl)-4-[(2,2-difluoro-1-methyl-ethyl)sulfamoyl]-1-methyl-1H-pyrrole-2-carboxamide;

N-(3-chloro-2,4-difluoro-phenyl)-1-methyl-4-{[1-(trifluoromethyl)cyclopropyl]sulfamoyl}-1H-pyrrole-2-carboxamide;

N-(3-chloro-2,4-difluoro-phenyl)-1-methyl-4-[(2,2,2-trifluoro-1,1-dimethyl-ethyl)sulfamoyl]-1H-pyrrole-2-carboxamide;

N-(3-chloro-2,4-difluoro-phenyl)-1-methyl-4-[(1-methylcyclopropyl)sulfamoyl]-1H-pyrrole-2-carboxamide;

N-(3-chloro-2,4-difluoro-phenyl)-4-[(3,3-difluoro-1-methyl-cyclobutyl)sulfamoyl]-1-methyl-1H-pyrrole-2-carboxamide;

N-(3-chloro-2,4-difluoro-phenyl)-1-methyl-4-{[1-methyl-1-(trifluoromethyl)propyl]sulfamoyl}-1H-pyrrole-2-carboxamide;

N-(3-chloro-2,4-difluoro-phenyl)-1-methyl-4-{[4-(trifluoromethyl)tetrahydropyran-4-yl]sulfamoyl}-1H-pyrrole-2-carboxamide;

N-(3-chloro-2,4-difluoro-phenyl)-4-[[1-ethyl-1-(trifluoromethyl)propyl]sulfamoyl]-1-methyl-1H-pyrrole-2-carboxamide;

N-(3-chloro-2,4-difluoro-phenyl)-1-methyl-4-[(3,3,3-trifluoro-1-methylpropyl)sulfamoyl]-1H-pyrrole-2-carboxamide;

N-(3-chloro-2,4-difluoro-phenyl)-4-[(2-fluoro-1,1-dimethyl-ethyl)sulfamoyl]-1-methyl-1H-pyrrole-2-carboxamide;

N-(3-chloro-2,4-difluoro-phenyl)-1-methyl-4-{[(1S)-1-(trifluoromethyl)propyl]sulfamoyl}-1H-pyrrole-2-carboxamide;

N-(3-chloro-2,4-difluoro-phenyl)-1-methyl-4-{[1-(trifluoromethyl)cyclobutyl]sulfamoyl}-1H-pyrrole-2-carboxamide;

N-(3-chloro-2,4-difluoro-phenyl)-4-{[2-fluoro-1-(fluoromethyl)ethyl]sulfamoyl}-1-methyl-1H-pyrrole-2-carboxamide;

N-(3-chloro-2,4-difluoro-phenyl)-1-methyl-4-{[(1R)-1-(trifluoromethyl)propyl]sulfamoyl}-1H-pyrrole-2-carboxamide;

N-(3-chloro-2,4-difluoro-phenyl)-1-methyl-4-{[3-(trifluoromethyl)tetrahydrofuran-3-yl]sulfamoyl}-1H-pyrrole-2-carboxamide;

3-chloro-N-(3,4-difluorophenyl)-1-methyl-4-{[1-(trifluoromethyl)cyclobutyl]sulfamoyl}-1H-pyrrole-2-carboxamide;

3-chloro-N-(3-chloro-4-fluoro-phenyl)-1-methyl-4-{[1-(trifluoromethyl)cyclobutyl]sulfamoyl}-1H-pyrrole-2-carboxamide;

3-Chloro-N-(3-cyano-4-fluorophenyl)-1-methyl-4-[(1-methylethyl)sulfamoyl]-1H-pyrrole-2-carboxamide;

3-Chloro-N-(3-cyano-4-fluorophenyl)-1-methyl-4-[(2,2,2-trifluoro-1,1-dimethylethyl)sulfamoyl]-1H-pyrrole-2-carboxamide;

3-Chloro-N-(3-cyano-4-fluorophenyl)-1-methyl-4-{[1-(trifluoromethyl)cyclopropyl]sulfamoyl}-1H-pyrrole-2-carboxamide;

3-chloro-N-(2-cyano-4-fluoro-3-methyl-phenyl)-1-methyl-4-[[(1R)-2,2,2-trifluoro-1-methyl-ethyl]sulfamoyl]pyrrole-2-carboxamide;
3-chloro-N-(2-cyano-4-fluoro-phenyl)-1-methyl-4-[[(1R)-2,2,2-trifluoro-1-methyl-ethyl]sulfamoyl]pyrrole-2-carboxamide;
3-chloro-N-[4-fluoro-3-(trifluoromethyl)phenyl]-1-methyl-4-[[(1R)-2,2,2-trifluoro-1-methyl-ethyl]sulfamoyl]pyrrole-2-carboxamide;
3-chloro-N-(2-fluoro-6-methyl-phenyl)-1-methyl-4-[[(1R)-2,2,2-trifluoro-1-methyl-ethyl]sulfamoyl]pyrrole-2-carboxamide;
3-chloro-N-(3-cyano-2,4-difluoro-phenyl)-1-methyl-4-[[(1R)-2,2,2-trifluoro-1-methyl-ethyl]sulfamoyl]pyrrole-2-carboxamide;
3-chloro-N-(2,3-dichloro-4-fluoro-phenyl)-1-methyl-4-[[(1R)-2,2,2-trifluoro-1-methyl-ethyl]sulfamoyl]pyrrole-2-carboxamide;
3-chloro-N-[3-(difluoromethyl)-2,4-difluoro-phenyl]-1-methyl-4-[[(1R)-2,2,2-trifluoro-1-methyl-ethyl]sulfamoyl]pyrrole-2-carboxamide;
3-chloro-N-[3-(difluoromethyl)-4-fluoro-phenyl]-1-methyl-4-[[(1R)-2,2,2-trifluoro-1-methyl-ethyl]sulfamoyl]pyrrole-2-carboxamide;
N-(3-bromophenyl)-3-fluoro-1l-methyl-4-[[(1R)-2,2,2-trifluoro-1-methyl-ethyl]sulfamoyl]pyrrole-2-carboxamide;
N-(3-cyano-4-fluoro-phenyl)-3-fluoro-1-methyl-4-[[1-(trifluoro-methyl)cyclopentyl]sulfamoyl]pyrrole-2-carboxamide;
3-chloro-N-(3-cyano-4-fluoro-phenyl)-1,5-dimethyl-4-[[(1R)-2,2,2-trifluoro-1-methyl-ethyl]sulfamoyl]pyrrole-2-carboxamide;
N-(3-cyano-4-fluoro-5-methyl-phenyl)-3-fluoro-1-methyl-4-[[(1R)-2,2,2-trifluoro-1-methyl-ethyl]sulfamoyl]pyrrole-2-carboxamide;
N-(3-cyano-4-fluoro-phenyl)-3-fluoro-1-methyl-4-[[(1S)-1-(trifluoro-methyl)propyl]sulfamoyl]pyrrole-2-carboxamide;
3-fluoro-N-(4-fluorophenyl)-1-methyl-4-[[(1R)-2,2,2-trifluoro-1-methyl-ethyl]sulfamoyl]pyrrole-2-arboxamide;
N-[3-(difluoromethyl)-4-fluoro-phenyl]-3-fluoro-1-methyl-4-[[(1R)-2,2,2-trifluoro-1-methyl-ethyl]sulfamoyl]pyrrole-2-carboxamide;
N-[3-(difluoromethyl)-2,4-difluoro-phenyl]-3-fluoro-1-methyl-4-[[(1R)-2,2,2-trifluoro-1-methyl-ethyl]sulfamoyl]pyrrole-2-carboxamide;
N-(3-cyano-4-fluoro-phenyl)-3-fluoro-1-methyl-4-[[(1R)-1-(trifluoro-methyl)propyl]sulfamoyl]pyrrole-2-carboxamide;
3-chloro-N-(3-cyano-4-fluoro-phenyl)-1-methyl-4-[[(1S)-1-(trifluoro-methyl)propyl]sulfamoyl]pyrrole-2-carboxamide;
3-chloro-N-(3-cyano-4-fluoro-phenyl)-1-methyl-4-[[(1R)-1-(trifluoro-methyl)propyl]sulfamoyl]pyrrole-2-carboxamide;
3-chloro-N-(3-cyano-4-fluoro-phenyl)-1-isopropyl-4-[[(1R)-2,2,2-trifluoro-1l-methyl-ethyl]sulfamoyl]pyrrole-2-carboxamide;
3-bromo-N-(3-cyano-4-fluoro-phenyl)-1-methyl-4-[[(1R)-2,2,2-trifluoro-1-methyl-ethyl]sulfamoyl]pyrrole-2-carboxamide;
3-cyano-N-(3-cyano-4-fluoro-phenyl)-1-methyl-4-[[(1R)-2,2,2-trifluoro-1-methyl-ethyl]sulfamoyl]pyrrole-2-carboxamide;
N-(3-cyano-4-fluoro-phenyl)-1-methyl-4-[[(1R)-1-methylpropyl]sulfamoyl]pyrrole-2-carboxamide;
3-chloro-N-(3-cyano-4-fluoro-phenyl)-1-methyl-4-[[(1R)-1-methylpropyl]sulfamoyl]pyrrole-2-carboxamide;
N-(3-cyano-4-fluoro-phenyl)-4-[(3-hydroxy-1,1-dimethyl-propyl)sulfamoyl]-1-methyl-pyrrole-2-carboxamide;
N-(3-cyano-4-fluoro-phenyl)-4-[[(1S)-2,2-difluoro-1-methyl-propyl]sulfamoyl]-1-methyl-pyrrole-2-carboxamide;
N-(3-cyano-4-fluoro-phenyl)-4-[[(1R)-2,2-difluoro-1-methyl-propyl]sulfamoyl]-1-methyl-pyrrole-2-carboxamide;
N-(3-cyano-4-fluoro-phenyl)-3-fluoro-1,5-dimethyl-4-[[(1R)-2,2,2-trifluoro-1-methyl-ethyl]sulfamoyl]pyrrole-2-carboxamide;
5-bromo-3-chloro-N-(3-cyano-4-fluoro-phenyl)-1-methyl-4-[[(1R)-2,2,2-trifluoro-1-methyl-ethyl]sulfamoyl]pyrrole-2-carboxamide;
5-bromo-N-(3-cyano-4-fluoro-phenyl)-3-fluoro-1-methyl-4-[[(1R)-2,2,2-trifluoro-1-methyl-ethyl]sulfamoyl]pyrrole-2-carboxamide;
3-chloro-N-(3-cyano-4-fluoro-phenyl)-5-cyclopropyl-1-methyl-4-[[(1R)-2,2,2-trifluoro-1-methyl-ethyl]sulfamoyl]pyrrole-2-carboxamide;
N-(3-cyano-4-fluoro-phenyl)-3-isopropyl-1-methyl-4-[[(1R)-2,2,2-trifluoro-1-methyl-ethyl]sulfamoyl]pyrrole-2-carboxamide;
N-(3-cyano-4-fluoro-phenyl)-5-cyclopropyl-3-fluoro-1-methyl-4-[[(1R)-2,2,2-trifluoro-1-methyl-ethyl]sulfamoyl]pyrrole-2-carboxamide;
3-chloro-N-(3-cyano-4-fluoro-phenyl)-1-cyclopropyl-4-[[(1R)-2,2,2-trifluoro-1-methyl-ethyl]sulfamoyl]pyrrole-2-carboxamide,
3-chloro-N-(3-cyano-4-fluoro-phenyl)-1-methyl-4-[(3-methyloxetan-3-yl)sulfamoyl]pyrrole-2-carboxamide;
3-bromo-N-(3-cyano-4-fluoro-phenyl)-4-(cyclopentylsulfamoyl)-1-methyl-pyrrole-2-carboxamide;
3-bromo-N-(4-fluoro-3-methyl-phenyl)-1-methyl-4-[[(1R)-2,2,2-trifluoro-1-methyl-ethyl]sulfamoyl]pyrrole-2-carboxamide;
N-(3-cyano-4-fluoro-phenyl)-3-fluoro-5-(methoxymethyl)-1-methyl-4-[[(1R)-2,2,2-trifluoro-1-methyl-ethyl]sulfamoyl]pyrrole-2-carboxamide;
5-cyano-N-(3-cyano-4-fluoro-phenyl)-3-fluoro-1-methyl-4-[[(1R)-2,2,2-trifluoro-1-methyl-ethyl]sulfamoyl]pyrrole-2-carboxamide;
N-(3-cyano-4-fluoro-phenyl)-3-fluoro-1-methyl-4-[[(1R)-2,2,2-trifluoro-1l-methyl-ethyl]sulfamoyl]-5-vinyl-pyrrole-2-carboxamide;
N-(2,4-difluorophenyl)-3-fluoro-1-methyl-4-[[(1R)-2,2,2-trifluoro-1-methyl-ethyl]sulfamoyl]pyrrole-2-carboxamide;
N-(3-chloro-5-cyano-4-fluoro-phenyl)-3-fluoro-1-methyl-4-[[(1R)-2,2,2-trifluoro-1-methyl-ethyl]sulfamoyl]pyrrole-2-carboxamide;
5-chloro-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide;
5-bromo-N-(3-cyano-2,4-difluoro-phenyl)-3-fluoro-1-methyl-4-[[(1R)-2,2,2-trifluoro-1-methyl-ethyl]sulfamoyl]pyrrole-2-carboxamide;
3-cyano-N-(3-cyano-4-fluoro-phenyl)-1,5-dimethyl-4-[[(1R)-2,2,2-trifluoro-1-methyl-ethyl]sulfamoyl]pyrrole-2-carboxamide;

N-(3-cyano-4-fluoro-phenyl)-4-[[(1R)-2,2-difluoro-1-methyl-propyl]sulfamoyl]-3-fluoro-1-methyl-pyrrole-2-carboxamide;
N-(3-cyano-4-fluoro-phenyl)-4-[[(1S)-2,2-difluoro-1-methyl-propyl]sulfamoyl]-3-fluoro-1-methyl-pyrrole-2-carboxamide; and
N-(3-cyano-4-fluoro-phenyl)-3-fluoro-1-methyl-4-[[1-(trifluoromethyl)cyclobutyl]sulfamoyl]pyrrole-2-carboxamide.

* * * * *